United States Patent
Mooney et al.

(10) Patent No.: US 12,274,744 B2
(45) Date of Patent: Apr. 15, 2025

(54) BIOMATERIALS FOR MODULATING IMMUNE RESPONSES

(71) Applicant: President and Fellows of Harvard College, Cambridge, MA (US)

(72) Inventors: David J. Mooney, Sudbury, MA (US); Aileen Weiwei Li, Norcross, GA (US); Omar Abdel-Rahman Ali, Oakland, CA (US); Ting-Yu Shih, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 585 days.

(21) Appl. No.: 16/263,098

(22) Filed: Jan. 31, 2019

(65) Prior Publication Data

US 2019/0216910 A1    Jul. 18, 2019

Related U.S. Application Data

(63) Continuation of application No. PCT/US2017/045022, filed on Aug. 2, 2017.

(60) Provisional application No. 62/473,699, filed on Mar. 20, 2017, provisional application No. 62/460,652, filed on Feb. 17, 2017, provisional application No. 62/370,211, filed on Aug. 2, 2016.

(51) Int. Cl.
| | |
|---|---|
| *A61K 39/39* | (2006.01) |
| *A61K 9/00* | (2006.01) |
| *A61K 9/50* | (2006.01) |
| *A61K 39/00* | (2006.01) |
| *A61K 47/02* | (2006.01) |
| *A61K 47/34* | (2017.01) |
| *A61P 35/00* | (2006.01) |

(52) U.S. Cl.
CPC ............ *A61K 39/39* (2013.01); *A61K 9/0019* (2013.01); *A61K 9/5031* (2013.01); *A61K 39/0011* (2013.01); *A61K 39/001106* (2018.08); *A61K 39/00119* (2018.08); *A61K 47/02* (2013.01); *A61K 47/34* (2013.01); *A61P 35/00* (2018.01); *A61K 2039/5154* (2013.01); *A61K 2039/54* (2013.01); *A61K 2039/545* (2013.01); *A61K 2039/55522* (2013.01); *A61K 2039/55555* (2013.01); *A61K 2039/55561* (2013.01); *A61K 2039/572* (2013.01); *A61K 2039/6056* (2013.01); *A61K 2039/812* (2018.08); *A61K 2039/876* (2018.08)

(58) Field of Classification Search
CPC ...... A61K 39/001106; A61K 39/00119; A61K 9/0019; A61K 9/5031; A61K 39/39; A61K 47/02; A61K 47/34; A61P 35/00
See application file for complete search history.

(56) References Cited

U.S. PATENT DOCUMENTS

| | | |
|---|---|---|
| 3,773,919 A | 11/1973 | Boswell et al. |
| 4,465,827 A | 8/1984 | Kawasaki et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 5,906,826 A | 5/1999 | Emery et al. |
| 5,951,976 A | 9/1999 | Segal |
| 6,129,716 A | 10/2000 | Steer |
| 6,160,084 A | 12/2000 | Langer et al. |
| 6,187,762 B1 | 2/2001 | Mandeville, III et al. |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,352,694 B1 | 3/2002 | June et al. |
| 6,403,374 B1 | 6/2002 | Tsien et al. |
| 6,429,199 B1 | 8/2002 | Krieg et al. |
| 6,511,511 B1 | 1/2003 | Slivka et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 6,858,222 B2 | 2/2005 | Nelson et al. |

(Continued)

FOREIGN PATENT DOCUMENTS

| | | |
|---|---|---|
| AU | 2014200405 A1 | 2/2014 |
| AU | 2018201930 A1 | 4/2018 |

(Continued)

OTHER PUBLICATIONS

Lungu et al. ("Linear and Branched PEIs (Polyethylenimines) and Their Property Space", Int J Mol Sci. Apr. 13, 2016;17(4):55) (Year: 2016).*

(Continued)

*Primary Examiner* — Amy E Juedes
*Assistant Examiner* — Peter Johansen
(74) *Attorney, Agent, or Firm* — McCarter & English, LLP; Maria Laccotripe Zacharakis; Maneesh Gulati

(57) ABSTRACT

The provided herein are methods and compositions for eliciting an immune response to an antigen, such as cancer and microbial antigens.

10 Claims, 65 Drawing Sheets
Specification includes a Sequence Listing.

(56) References Cited

U.S. PATENT DOCUMENTS

| | | |
|---|---|---|
| 6,974,698 B1 | 12/2005 | Miller et al. |
| 7,015,205 B1 | 3/2006 | Wallack et al. |
| 7,157,566 B2 | 1/2007 | Tsien et al. |
| 7,186,413 B2 | 3/2007 | Bouhadir et al. |
| 7,192,693 B2 | 3/2007 | Bryant et al. |
| 7,244,714 B1 | 7/2007 | Gonda et al. |
| 7,357,936 B1 | 4/2008 | Garcon |
| 7,410,953 B2 | 8/2008 | Kawasaki |
| 7,427,602 B1 | 9/2008 | Shea et al. |
| 7,569,850 B2 | 8/2009 | Noy et al. |
| 7,575,759 B2 | 8/2009 | Murphy et al. |
| 7,592,326 B2 | 9/2009 | Karaolis |
| 7,687,241 B2 | 3/2010 | Chen |
| 7,709,458 B2 | 5/2010 | Karaolis et al. |
| 7,790,699 B2 | 9/2010 | Melvik et al. |
| 8,067,237 B2 | 11/2011 | Mooney et al. |
| 8,188,058 B2 | 5/2012 | Hackam et al. |
| 8,273,373 B2 | 9/2012 | Alsberg et al. |
| 8,354,119 B2 | 1/2013 | Geistlich et al. |
| 8,367,628 B2 | 2/2013 | Goodwin et al. |
| 8,535,719 B2 | 9/2013 | Badylak et al. |
| 8,709,464 B2 | 4/2014 | Ma et al. |
| 8,728,456 B2 | 5/2014 | Sands et al. |
| 8,883,308 B2 | 11/2014 | Polshettiwar et al. |
| 8,932,583 B2 | 1/2015 | Mooney et al. |
| 9,012,399 B2 | 4/2015 | Cao et al. |
| 9,132,210 B2 | 9/2015 | Mooney et al. |
| 9,139,809 B2 | 9/2015 | Porcelli et al. |
| 9,150,631 B2 | 10/2015 | Super et al. |
| 9,370,558 B2 | 6/2016 | Ali et al. |
| 9,381,235 B2 | 7/2016 | Sands et al. |
| 9,446,107 B2 | 9/2016 | Mooney et al. |
| 9,486,512 B2 | 11/2016 | Kim et al. |
| 9,591,360 B2 | 3/2017 | Jennings et al. |
| 9,610,328 B2 | 4/2017 | Mooney et al. |
| 9,675,561 B2 | 6/2017 | Bencherif et al. |
| 9,770,535 B2 | 9/2017 | Mooney et al. |
| 9,821,045 B2 | 11/2017 | Ali et al. |
| 9,937,249 B2 | 4/2018 | Kim et al. |
| 10,045,947 B2 | 8/2018 | Bencherif et al. |
| 10,080,789 B2 | 9/2018 | Sands et al. |
| 10,137,184 B2 | 11/2018 | Mooney et al. |
| 10,149,897 B2 | 12/2018 | Mooney et al. |
| 10,258,677 B2 | 4/2019 | Mooney et al. |
| 11,059,050 B2 | 7/2021 | Kang et al. |
| 11,684,638 B2 | 6/2023 | Prabha et al. |
| 2002/0045672 A1 | 4/2002 | Harris et al. |
| 2002/0131853 A1 | 9/2002 | Nagasawa |
| 2002/0131953 A1 | 9/2002 | Takashima et al. |
| 2002/0150604 A1 | 10/2002 | Yi et al. |
| 2003/0075822 A1 | 4/2003 | Slivka et al. |
| 2003/0082806 A1 | 5/2003 | Berenson et al. |
| 2003/0095994 A1 | 5/2003 | Geistlich et al. |
| 2003/0100527 A1 | 5/2003 | Krieg et al. |
| 2003/0194397 A1 | 10/2003 | Mishra |
| 2003/0232895 A1 | 12/2003 | Omidian et al. |
| 2003/0235557 A1 | 12/2003 | Gaiger et al. |
| 2004/0028745 A1 | 2/2004 | Bouhadir et al. |
| 2004/0043034 A1 | 3/2004 | Jensenius et al. |
| 2004/0058883 A1 | 3/2004 | Phillips et al. |
| 2004/0063206 A1 | 4/2004 | Rowley et al. |
| 2004/0136968 A1 | 7/2004 | Zheng et al. |
| 2004/0151764 A1 | 8/2004 | Zamora |
| 2004/0213795 A1 | 10/2004 | Collins et al. |
| 2004/0220111 A1 | 11/2004 | Kleinman et al. |
| 2004/0228858 A1 | 11/2004 | Hanson et al. |
| 2004/0242469 A1 | 12/2004 | Lee et al. |
| 2004/0242482 A1 | 12/2004 | Gehring et al. |
| 2005/0002915 A1 | 1/2005 | Atala et al. |
| 2005/0037330 A1 | 2/2005 | Fischer et al. |
| 2005/0053667 A1 | 3/2005 | Irvine et al. |
| 2005/0079159 A1 | 4/2005 | Shastri et al. |
| 2005/0090008 A1 | 4/2005 | Segura et al. |
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2005/0202394 A1 | 9/2005 | Dobson |
| 2006/0083712 A1 | 4/2006 | Anversa |
| 2006/0141018 A1 | 6/2006 | Cochrum et al. |
| 2006/0264380 A1 | 11/2006 | Hellstrom et al. |
| 2006/0292134 A1 | 12/2006 | Stohs |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0113929 A1 | 5/2008 | Lipford et al. |
| 2008/0138416 A1 | 6/2008 | Rauh et al. |
| 2008/0152624 A1 | 6/2008 | Paludan et al. |
| 2008/0159993 A1 | 7/2008 | Stauss et al. |
| 2008/0206308 A1 | 8/2008 | Jabbari et al. |
| 2008/0233181 A1 | 9/2008 | Nagy et al. |
| 2008/0268019 A1 | 10/2008 | Badylak et al. |
| 2008/0268052 A1 | 10/2008 | Voytik-Harbin et al. |
| 2008/0279812 A1 | 11/2008 | Boyd et al. |
| 2009/0017096 A1 | 1/2009 | Lowman et al. |
| 2009/0041825 A1 | 2/2009 | Kotov et al. |
| 2009/0061014 A1 | 3/2009 | Messersmith et al. |
| 2009/0192079 A1 | 7/2009 | Santos et al. |
| 2009/0238853 A1 | 9/2009 | Liu et al. |
| 2009/0252752 A1 | 10/2009 | Tahara et al. |
| 2009/0297551 A1 | 12/2009 | Sattentau et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055102 A1 | 3/2010 | Langermann |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0159008 A1 | 6/2010 | Barron et al. |
| 2010/0174346 A1 | 7/2010 | Boyden et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0008443 A1 | 1/2011 | Alsberg et al. |
| 2011/0020216 A1 | 1/2011 | Mooney et al. |
| 2011/0117170 A1 | 5/2011 | Cao et al. |
| 2011/0159023 A1 | 6/2011 | Langermann |
| 2011/0207166 A1 | 8/2011 | Vaiselbuh |
| 2011/0223255 A1 | 9/2011 | Thiesen et al. |
| 2011/0253643 A1 | 10/2011 | Polshettiwar et al. |
| 2011/0256184 A1 | 10/2011 | Lei et al. |
| 2011/0300186 A1 | 12/2011 | Hellstrom et al. |
| 2012/0040011 A9 | 2/2012 | Boons et al. |
| 2012/0100182 A1 | 4/2012 | Mooney et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0207795 A1* | 8/2012 | Zink ............... A61K 9/0019 977/773 |
| 2012/0256336 A1* | 10/2012 | Yano ............... C01B 33/18 977/773 |
| 2012/0264599 A1 | 10/2012 | Komatsu et al. |
| 2012/0294888 A1 | 11/2012 | Kishimoto et al. |
| 2012/0329791 A1 | 12/2012 | Ashwell et al. |
| 2013/0029030 A1 | 1/2013 | Larsen |
| 2013/0035283 A1 | 2/2013 | Super et al. |
| 2013/0045246 A1 | 2/2013 | Edwards et al. |
| 2013/0052117 A1 | 2/2013 | Imai et al. |
| 2013/0072547 A1 | 3/2013 | Hackam et al. |
| 2013/0145488 A1 | 6/2013 | Wang et al. |
| 2013/0177536 A1 | 7/2013 | Mooney et al. |
| 2013/0202707 A1 | 8/2013 | Ali et al. |
| 2013/0225502 A1 | 8/2013 | Sugiyama et al. |
| 2013/0251784 A1 | 9/2013 | Kim et al. |
| 2013/0302396 A1 | 11/2013 | Mooney et al. |
| 2013/0331343 A1 | 12/2013 | Cao et al. |
| 2014/0072510 A1 | 3/2014 | Shea et al. |
| 2014/0079752 A1 | 3/2014 | Huebsch et al. |

(56) References Cited

U.S. PATENT DOCUMENTS

| | | | |
|---|---|---|---|
| 2014/0112990 | A1 | 4/2014 | Bencherif et al. |
| 2014/0178964 | A1 | 6/2014 | Mooney et al. |
| 2014/0193488 | A1 | 7/2014 | Kim et al. |
| 2014/0205653 | A1 | 7/2014 | Dubensky, Jr. et al. |
| 2014/0227327 | A1 | 8/2014 | Bencherif et al. |
| 2014/0227723 | A1 | 8/2014 | Ingber et al. |
| 2014/0234423 | A1 | 8/2014 | Sands et al. |
| 2015/0024026 | A1 | 1/2015 | Mooney et al. |
| 2015/0030669 | A1 | 1/2015 | Platscher et al. |
| 2015/0072009 | A1 | 3/2015 | Kim et al. |
| 2015/0080321 | A1 | 3/2015 | Li et al. |
| 2015/0094518 | A1 | 4/2015 | Wu et al. |
| 2015/0202291 | A1 | 7/2015 | Bosch et al. |
| 2015/0352201 | A1 | 12/2015 | Scheinberg et al. |
| 2015/0359928 | A1 | 12/2015 | Gu et al. |
| 2015/0366956 | A1 | 12/2015 | Mooney et al. |
| 2016/0033511 | A1 | 2/2016 | Pannell et al. |
| 2016/0060360 | A1 | 3/2016 | Moore et al. |
| 2016/0120984 | A1 | 5/2016 | Navale et al. |
| 2016/0129053 | A1 | 5/2016 | Brass et al. |
| 2016/0220668 | A1 | 8/2016 | Mooney et al. |
| 2016/0228543 | A1 | 8/2016 | Mooney et al. |
| 2016/0271298 | A1 | 9/2016 | Mooney et al. |
| 2016/0279219 | A1 | 9/2016 | Mooney et al. |
| 2016/0279220 | A1 | 9/2016 | Mooney et al. |
| 2016/0296611 | A1 | 10/2016 | Ali et al. |
| 2017/0042995 | A1 | 2/2017 | Ali et al. |
| 2017/0182138 | A1 | 6/2017 | Kim et al. |
| 2017/0246281 | A1 | 8/2017 | Super et al. |
| 2017/0362307 | A1 | 12/2017 | Ingber et al. |
| 2017/0368169 | A1 | 12/2017 | Loew et al. |
| 2018/0021253 | A1 | 1/2018 | Sandeep et al. |
| 2018/0117171 | A1 | 5/2018 | Mooney et al. |
| 2018/0164298 | A1 | 6/2018 | Ali et al. |
| 2018/0243231 | A1 | 8/2018 | Bencherif et al. |
| 2018/0289789 | A1 | 10/2018 | Ali et al. |
| 2018/0298047 | A1 | 10/2018 | Cheng et al. |
| 2018/0320157 | A1 | 11/2018 | Super et al. |
| 2018/0326073 | A1 | 11/2018 | Mooney et al. |
| 2018/0344821 | A1 | 12/2018 | Kim et al. |
| 2018/0371058 | A1 | 12/2018 | Watters et al. |
| 2019/0060525 | A1 | 2/2019 | Shah et al. |
| 2019/0076373 | A1 | 3/2019 | Bencherif et al. |
| 2019/0125849 | A1 | 5/2019 | Mooney et al. |
| 2019/0183992 | A1 | 6/2019 | Sands et al. |
| 2019/0290696 | A1 | 9/2019 | De Miroschedji |
| 2019/0292517 | A1 | 9/2019 | Cheung et al. |
| 2019/0367550 | A1 | 12/2019 | Cheng et al. |
| 2020/0024339 | A1 | 1/2020 | Springer et al. |
| 2020/0206333 | A1 | 7/2020 | Shah et al. |
| 2020/0276290 | A1 | 9/2020 | Ali et al. |
| 2020/0297854 | A1 | 9/2020 | Ingber et al. |
| 2021/0170007 | A1 | 6/2021 | Super et al. |
| 2021/0205233 | A1 | 7/2021 | Bencherif et al. |
| 2021/0284776 | A1 | 9/2021 | Wang et al. |
| 2022/0047778 | A1 | 2/2022 | Shah et al. |
| 2022/0107308 | A1 | 4/2022 | Ali et al. |
| 2022/0192986 | A1 | 6/2022 | Huebsch et al. |
| 2022/0339274 | A1 | 10/2022 | Najibi et al. |
| 2023/0000961 | A1 | 1/2023 | Kim et al. |
| 2023/0085214 | A1 | 3/2023 | Wang et al. |
| 2023/0340404 | A1 | 10/2023 | Cheung et al. |
| 2023/0404936 | A1 | 12/2023 | Bencherif et al. |

FOREIGN PATENT DOCUMENTS

| | | | |
|---|---|---|---|
| CN | 1487839 | A | 4/2004 |
| CN | 1527697 | A | 9/2004 |
| CN | 1757662 | A | 4/2006 |
| CN | 101584612 | A | 11/2009 |
| CN | 101655611 | A | 2/2010 |
| CN | 101829361 | A | 9/2010 |
| CN | 102000689 | A | 4/2011 |
| CN | 102006891 | A | 4/2011 |
| CN | 102170903 | A | 8/2011 |
| CN | 102947341 | A | 2/2013 |
| CN | 103237885 | A | 8/2013 |
| CN | 104244929 | A | 12/2014 |
| CN | 104411331 | A | 3/2015 |
| EP | 0562862 | A1 | 9/1993 |
| EP | 1452191 | A2 | 9/2004 |
| EP | 1561481 | A2 | 8/2005 |
| EP | 1712238 | A1 | 10/2006 |
| EP | 1975230 | A1 | 10/2008 |
| EP | 2254602 | A2 | 12/2010 |
| JP | 2000-503884 | A | 4/2000 |
| JP | 2001-049018 | A | 2/2001 |
| JP | 2001-524136 | A | 11/2001 |
| JP | 2003-506401 | A | 2/2003 |
| JP | 2003-180815 | A | 7/2003 |
| JP | 2004-159849 | A | 6/2004 |
| JP | 2004-520043 | A | 7/2004 |
| JP | 2005-160669 | A | 6/2005 |
| JP | 2005-168760 | A | 6/2005 |
| JP | 2005-170816 | A | 6/2005 |
| JP | 2005-528401 | A | 9/2005 |
| JP | 2007-500673 | A | 1/2007 |
| JP | 2007-503881 | A | 3/2007 |
| JP | 2007-505827 | A | 3/2007 |
| JP | 2007-528848 | A | 10/2007 |
| JP | 2008-515503 | A | 5/2008 |
| JP | 2008-528114 | A | 7/2008 |
| JP | 2009-519042 | A | 5/2009 |
| JP | 2009-521406 | A | 6/2009 |
| JP | 2009-540921 | A | 11/2009 |
| JP | 2010-502824 | A | 1/2010 |
| JP | 2010-508976 | A | 3/2010 |
| JP | 2010-227012 | A | 10/2010 |
| JP | 2010-228961 | A | 10/2010 |
| JP | 2011-511684 | A | 4/2011 |
| JP | 2011-511834 | A | 4/2011 |
| JP | 2012-062236 | A | 3/2012 |
| JP | 2013-531043 | A | 8/2013 |
| JP | 2015-503626 | A | 2/2015 |
| JP | 2015-516398 | A | 6/2015 |
| JP | 2015-134766 | A | 7/2015 |
| JP | 2018-117680 | A | 8/2018 |
| JP | 2019-522486 | A | 8/2019 |
| WO | WO-1996/02555 | A1 | 2/1996 |
| WO | WO-1996/16086 | A1 | 5/1996 |
| WO | WO-1998/12228 | A1 | 3/1998 |
| WO | WO-1998/16266 | A1 | 4/1998 |
| WO | WO-1999/44583 | A2 | 9/1999 |
| WO | WO-1999/51259 | A2 | 10/1999 |
| WO | WO-1999/52356 | A1 | 10/1999 |
| WO | WO-2000/50006 | A2 | 8/2000 |
| WO | WO-2007/150020 | A1 | 12/2000 |
| WO | WO-2001/10421 | A1 | 2/2001 |
| WO | WO-2001/35932 | A2 | 5/2001 |
| WO | WO-2001/37810 | A2 | 5/2001 |
| WO | WO-2002/16557 | A2 | 2/2002 |
| WO | WO-2002/40071 | A1 | 5/2002 |
| WO | WO-2002/058723 | A2 | 8/2002 |
| WO | WO-2002/092054 | A2 | 11/2002 |
| WO | WO-2003/020161 | A2 | 3/2003 |
| WO | WO-2003/020884 | A2 | 3/2003 |
| WO | WO-2003/070291 | A1 | 8/2003 |
| WO | WO-2003/088905 | A2 | 10/2003 |
| WO | WO-2004/006990 | A2 | 1/2004 |
| WO | WO-2004/029230 | A2 | 4/2004 |
| WO | WO-2004/030706 | A2 | 4/2004 |
| WO | WO-2004/031371 | A2 | 4/2004 |
| WO | WO-2004/089413 | A1 | 10/2004 |
| WO | WO-2005/013896 | A2 | 2/2005 |
| WO | WO-2005/013933 | A1 | 2/2005 |
| WO | WO-2005/020849 | A2 | 3/2005 |
| WO | WO-2005/025614 | A2 | 3/2005 |
| WO | WO-2005/026318 | A2 | 3/2005 |
| WO | WO-2005/037190 | A2 | 4/2005 |
| WO | WO-2005/037293 | A1 | 4/2005 |
| WO | WO-2005/046748 | A1 | 5/2005 |
| WO | WO-2005/072088 | A2 | 8/2005 |
| WO | WO-2005/104755 | A2 | 11/2005 |
| WO | WO-2006/039045 | A2 | 4/2006 |

(56) References Cited

FOREIGN PATENT DOCUMENTS

| | | |
|---|---|---|
| WO | WO-2006/040128 A1 | 4/2006 |
| WO | WO-2006/078987 A2 | 7/2006 |
| WO | WO-2006/113407 A2 | 10/2006 |
| WO | WO-2006/119619 A1 | 11/2006 |
| WO | WO-2006/136905 A2 | 12/2006 |
| WO | WO-2007/001332 A2 | 1/2007 |
| WO | WO-2007/030901 A1 | 3/2007 |
| WO | WO-2007/039150 A2 | 4/2007 |
| WO | WO-2007/042554 A2 | 4/2007 |
| WO | WO-2007/051120 A2 | 5/2007 |
| WO | WO-2007/063075 A1 | 6/2007 |
| WO | WO-2007/064152 A1 | 6/2007 |
| WO | WO-2007/068489 A2 | 6/2007 |
| WO | WO-2007/070660 A2 | 6/2007 |
| WO | WO-2007/078196 A1 | 7/2007 |
| WO | WO-2007/087585 A1 | 8/2007 |
| WO | WO-2007/089870 A2 | 8/2007 |
| WO | WO-2007/107739 A1 | 9/2007 |
| WO | WO-2007/149161 A2 | 12/2007 |
| WO | WO-2008/008266 A2 | 1/2008 |
| WO | WO-2008/018707 A1 | 2/2008 |
| WO | WO-2008/031525 A1 | 3/2008 |
| WO | WO-2008/043157 A1 | 4/2008 |
| WO | WO-2008/057600 A2 | 5/2008 |
| WO | WO-2008/109852 A2 | 9/2008 |
| WO | WO-2008/114149 A2 | 9/2008 |
| WO | WO-2008/148761 A1 | 12/2008 |
| WO | WO-2008/157394 A2 | 12/2008 |
| WO | WO-2009/002401 A2 | 12/2008 |
| WO | WO-2009/005769 A2 | 1/2009 |
| WO | WO-2009/018500 A1 | 2/2009 |
| WO | WO-2009/024775 A1 | 2/2009 |
| WO | WO-2009/072767 A2 | 6/2009 |
| WO | WO-2009/074341 A1 | 6/2009 |
| WO | WO-2009/100716 A2 | 8/2009 |
| WO | WO-2009/102465 A2 | 8/2009 |
| WO | WO-2009/146456 A1 | 12/2009 |
| WO | WO-2009/155583 A1 | 12/2009 |
| WO | WO-2010/078209 A2 | 7/2010 |
| WO | WO-2010/120749 A2 | 10/2010 |
| WO | WO-2011/014871 A1 | 2/2011 |
| WO | WO-2011/043834 A1 | 4/2011 |
| WO | WO-2011/043835 A1 | 4/2011 |
| WO | WO-2011/063336 A2 | 5/2011 |
| WO | WO-2011/109834 A2 | 9/2011 |
| WO | WO-2011/130753 A2 | 10/2011 |
| WO | WO-2011/150240 A1 | 12/2011 |
| WO | WO-2011/151431 A1 | 12/2011 |
| WO | WO-2011/163669 A2 | 12/2011 |
| WO | WO-2012/009611 A2 | 1/2012 |
| WO | WO-2012/019049 A1 | 2/2012 |
| WO | WO-2012/048165 A2 | 4/2012 |
| WO | WO-2012/064697 A2 | 5/2012 |
| WO | WO-2012/148684 A1 | 11/2012 |
| WO | WO-2012/149358 A1 | 11/2012 |
| WO | WO-2012/167230 A1 | 12/2012 |
| WO | WO-2013/012924 A2 | 1/2013 |
| WO | WO-2013/106852 A1 | 7/2013 |
| WO | WO-2013/158673 A1 | 10/2013 |
| WO | WO-2013/172967 A1 | 11/2013 |
| WO | WO-2013/190555 A1 | 12/2013 |
| WO | WO-2014/063128 A1 | 4/2014 |
| WO | WO-2014/189805 A1 | 11/2014 |
| WO | WO-2014/190229 A1 | 11/2014 |
| WO | WO-2015/066535 A1 | 5/2015 |
| WO | WO-2015/077354 A1 | 5/2015 |
| WO | WO-2015095811 A2 * 6/2015 ......... A61K 39/0011 | |
| WO | 2015/148775 A1 | 10/2015 |
| WO | WO-2015/154078 A1 | 10/2015 |
| WO | WO-2015/168379 A2 | 11/2015 |
| WO | WO-2016/004068 A1 | 1/2016 |
| WO | WO-2016/123573 A1 | 8/2016 |
| WO | WO-2016/161372 A1 | 10/2016 |
| WO | 2017/136837 A1 | 8/2017 |
| WO | WO-2017/143024 A2 | 8/2017 |
| WO | WO-2018/013797 A1 | 1/2018 |
| WO | WO-2018/026884 A1 | 2/2018 |
| WO | 2018/144966 A1 | 8/2018 |
| WO | 2018/148650 A1 | 8/2018 |
| WO | 2018/170414 A1 | 9/2018 |
| WO | 2018/213631 A1 | 11/2018 |
| WO | 2018/227205 A1 | 12/2018 |
| WO | 2020/061129 A1 | 3/2020 |
| WO | 2021/155297 A1 | 8/2021 |

OTHER PUBLICATIONS

Sahdev et al. "Biomaterials for nanoparticle vaccine delivery systems", Pharm Res. Oct. 2014;31(10):2563-82. (Year: 2014).*

Xia et al. "Polyethyleneimine Coating Enhances the Cellular Uptake of Mesoporous Silica Nanoparticles and Allows Safe Delivery of siRNA and DNA Constructs", ACS Nano. Oct. 27, 2009; 3(10): 3273-3286 (Year: 2009).*

Chen et al. "Improved antigen cross-presentation by polyethyleneimine-based nanoparticles", Int J Nanomedicine. 2011; 6: 77-84. (Year: 2011).*

U.S. Appl. No. 16/121,988, filed Sep. 5, 2018, 2019-0183992, Published.

U.S. Appl. No. 17/501,821, filed Oct. 14, 2021, Pending.

U.S. Appl. No. 17/381,031, filed Jul. 20, 2021, Pending.

U.S. Appl. No. 13/877,572, filed Nov. 19, 2013, 2014-0079752, Published.

U.S. Appl. No. 17/522,297, filed Nov. 9, 2021, Pending.

U.S. Appl. No. 15/935,392, filed Mar. 26, 2018, 2018-0344821, Allowed.

U.S. Appl. No. 16/075,937, filed Aug. 6, 2018, 2019-0060525, Published.

Abrahams et al., Expression and secretion of antiviral factors by trophoblast cells following stimulation by the TLR-3 agonist, Poly(I : C). Hum Reprod. Sep. 2006;21(9):2432-9.

Agache et al., Mechanical properties and Young's modulus of human skin in vivo. Arch Dermatol Res. 1980;269(3):221-32.

Agrawal et al., Cutting edge: different Toll-like receptor agonists instruct dendritic cells to induce distinct Th responses via differential modulation of extracellular signal-regulated kinase-mitogen-activated protein kinase and c-Fos. J Immunol. Nov. 15, 2003;171(10):4984-9.

Aguado et al., Improving viability of stem cells during syringe needle flow through the design of hydrogel cell carriers. Tissue Eng Part A. Apr. 2012;18(7-8):806-15.

Aharoni et al., New findings and old controversies in the research of multiple sclerosis and its model experimental autoimmune encephalomyelitis. Expert Rev Clin Immunol. May 2013;9(5):423-40.

Akira et al., Pathogen recognition and innate immunity. Cell. Feb. 24, 2006;124(4):783-801.

Akira et al., Toll-like receptors: critical proteins linking innate and acquired immunity. Nat Immunol. Aug. 2001;2(8):675-80.

Akpalo et al., Fibrin-polyethylene oxide interpenetrating polymer networks: new self-supported biomaterials combining the properties of both protein gel and synthetic polymer. Acta Biomater. Jun. 2011;7(6):2418-27.

Aldhous, Print Me a Heart and a Set of Arteries. New Scientist. 2006;2547:19.

Ali et al., Biomaterial-based vaccine induces regression of established intracranial glioma in rats. Pharm Res. May 2011;28(5):1074-80.

Ali et al., Controlled Local Delivery of GM-CSF From Polymer-Based Vaccines Enhances Anti-Tumor Immune Responses by Priming Host Dendritic Cells. 2007 AACR Annual Meeting. 2007;48:652, Abstract #2736.

Ali et al., Converging Cell Therapy with Biomaterials. Cell Transplantation from Laboratory to Clinic. 2006:591-609.

Ali et al., Identification of immune factors regulating antitumor immunity using polymeric vaccines with multiple adjuvants. Cancer Res. Mar. 15, 2014;74(6):1670-81.

Ali et al., In situ regulation of DC subsets and T cells mediates tumor regression in mice. Sci Transl Med. Nov. 25, 2009;1(8):8ra19, 1-10.

(56) References Cited

OTHER PUBLICATIONS

Ali et al., Infection-mimicking materials to program dendritic cells in situ. Nat Mater. Feb. 2009;8(2):151-8.
Ali et al., Inflammatory cytokines presented from polymer matrices differentially generate and activate DCs in situ.. Adv Funct Mater. Aug. 1, 2013;23(36):4621-4628.
Ali et al., Relationship of vaccine efficacy to the kinetics of DC and T-cell responses induced by PLG-based cancer vaccines. Biomater. 2011;1(1):66-75.
Ali et al., Sustained GM-CSF and PEI condensed pDNA presentation increases the level and duration of gene expression in dendritic cells. J Control Release. Dec. 18, 2008;132(3):273-8.
Ali et al., The efficacy of intracranial PLG-based vaccines is dependent on direct implantation into brain tissue. J Control Release. Sep. 25, 2011;154(3):249-57.
Allen et al., Regulation of satellite cells during skeletal muscle growth and development. Proc Soc Exp Biol Med. Jun. 1990;194(2):81-6.
Allen et al., Regulation of skeletal muscle satellite cell proliferation by bovine pituitary fibroblast growth factor. Exp Cell Res. May 1984;152(1):154-60.
Almarza et al., Evaluation of three growth factors in combinations of two for temporomandibular joint disc tissue engineering. Arch Oral Biol. Mar. 2006;51(3):215-21.
Alsberg et al., Cell-interactive alginate hydrogels for bone tissue engineering. J Dent Res. Nov. 2001;80(11):2025-9.
Alsberg et al., Engineering growing tissues. Proc Natl Acad Sci U S A. Sep. 17, 2002;99(19):12025-30.
Alsberg et al., Regulating bone formation via controlled scaffold degradation. J Dent Res. Nov. 2003;82(11):903-8.
Ambrosini et al., Astrocytes produce dendritic cell-attracting chemokines in vitro and in multiple sclerosis lesions. J Neuropathol Exp Neurol. Aug. 2005;64(8):706-15.
American Diabetes Association, Standards of Medical Care in Diabetes—2013. Diabetes Care. 2013;36(S1):S11-S66.
Anderson et al., Biomaterial microarrays: rapid, microscale screening of polymer-cell interaction. Biomaterials. Aug. 2005;26(23):4892-7.
Anderson et al., Nanoliter-scale synthesis of arrayed biomaterials and application to human embryonic stem cells. Nat Biotechnol. Jul. 2004;22(7):863-6.
Anderson et al., The NOD mouse: a model of immune dysregulation. Annu Rev Immunol. 2005;23:447-85.
Anderson, A role for nitric oxide in muscle repair: nitric oxide-mediated activation of muscle satellite cells. Mol Biol Cell. May 2000;11(5):1859-74.
Annabi et al., Controlling the porosity and microarchitecture of hydrogels for tissue engineering. Tissue Eng Part B Rev. Aug. 2010;16(4):371-83.
Annual Review. 2008:122-131.
Arany et al., At the edge of translation—materials to program cells for directed differentiation. Oral Dis. Apr. 2011;17(3):241-51.
Aschner et al., Metabolic memory for vascular disease in diabetes. Diabetes Technol Ther. Jun. 2012;14 Suppl 1:S68-74.
Atala et al., Endoscopic treatment of vesicoureteral reflux with a chondrocyte-alginate suspension. J Urol. Aug. 1994; 152(2 Pt 2):641-3.
Aubin et al., Directed 3D cell alignment and elongation in microengineered hydrogels. Biomaterials. Sep. 2010;31(27):6941-6951.
Augst et al., Alginate hydrogels as biomaterials. Macromol Biosci. Aug. 7, 2006;6(8):623-33.
Babensee et al., Host response to tissue engineered devices. Advanced Drug Delivery Reviews. Aug. 3, 1998;33(1-2):111-139.
Bachelder et al., Acid-degradable polyurethane particles for protein-based vaccines: biological evaluation and in vitro analysis of particle degradation products. Mol Pharm. Sep.-Oct. 2008;5(5):876-84.

Bachem et al., Superior antigen cross-presentation and XCR1 expression define human CD11c+CD141+ cells as homologues of mouse CD8+ dendritic cells. J Exp Med. Jun. 7, 2010;207(6):1273-81.
Badovinac et al., Regulation of CD8+ T cells undergoing primary and secondary responses to infection in the same host. J Immunol. May 15, 2003;170(10):4933-42.
Bakri et al., Pharmacokinetics of intravitreal bevacizumab (Avastin). Ophthalmology. May 2007;114(5):855-9.
Balakrishna et al., Structural correlates of antibacterial and membrane-permeabilizing activities in acylpolyamines. Antimicrob Agents Chemother. Mar. 2006;50(3):852-61.
Banchereau et al., Dendritic cells and the control of immunity. Nature. Mar. 19, 1998;392(6673):245-52.
Bar-Cohen et al., Electroactive Polymer Actuators and Sensors. MRS Bullet. 2008;33(3):173-181.
Bar-Or et al., Induction of antigen-specific tolerance in multiple sclerosis after immunization with DNA encoding myelin basic protein in a randomized, placebo-controlled phase 1/2 trial. Arch Neurol. Oct. 2007;64(10):1407-15.
Barbero et al., Growth factor supplemented matrigel improves ectopic skeletal muscle formation—a cell therapy approach. J Cell Physiol. Feb. 2001;186(2):183-92.
Barbucci et al., Hyaluronic acid hydrogel in the treatment of osteoarthritis. Biomaterials. Dec. 2002;23(23):4503-13.
Barrio et al., A two-dimensional numerical study of spatial pattern formation in interacting Turing systems. Bull Math Biol. May 1999;61(3):483-505.
Bartholomew et al., Mesenchymal stem cells suppress lymphocyte proliferation in vitro and prolong skin graft survival in vivo. Exp Hematol. Jan. 2002;30(1):42-8.
Baskin et al., Copper-free click chemistry for dynamic in vivo imaging. Proc Natl Acad Sci U S A. Oct. 23, 2007;104(43):16793-7.
Bates, Improved muscle regeneration by combining VEGF with IGF1. Regen Med. Nov. 2010;5(6):853-4.
Beaucage et al., The Functionalization of Oligonucleotides Via Phosphoramidite Derivatives. Tetrahedron. Mar. 5, 1993;49(10):1925-1963.
Beauchamp et al., Dynamics of myoblast transplantation reveal a discrete minority of precursors with stem cell-like properties as the myogenic source. J Cell Biol. Mar. 22, 1999;144(6):1113-22.
Becker et al., Cytological demonstration of the clonal nature of spleen colonies derived from transplanted mouse marrow cells. Nature. Feb. 2, 1963;197:452-4.
Beebe et al., Functional hydrogel structures for autonomous flow control inside microfluidic channels. Nature. Apr. 6, 2000;404(6778):588-90.
Bekiari et al., Study of poly(N,N-dimethylacrylamide)/CdS nanocomposite organic/inorganic gels. Langmuir. Sep. 14, 2004;20(19):7972-5.
Bell, Models for the specific adhesion of cells to cells. Science. May 12, 1978;200(4342):618-27.
Bencherif et al., End-group effects on the properties of PEG-co-PGA hydrogels. Acta Biomater. Jul. 2009;5(6):1872-83.
Bencherif et al., Influence of cross-linker chemistry on release kinetics of PEG-co-PGA hydrogels. J Biomed Mater Res A. Jul. 2009;90(1):142-53.
Bencherif et al., Influence of the degree of methacrylation on hyaluronic acid hydrogels properties. Biomaterials. Apr. 2008;29(12):1739-49.
Bencherif et al., Injectable preformed scaffolds with shape-memory properties. Proc Natl Acad Sci U S A. Nov. 27, 2012;109(48):19590-5.
Bencherif et al., Nanostructured hybrid hydrogels prepared by a combination of atom transfer radical polymerization and free radical polymerization. Biomaterials. Oct. 2009;30(29):5270-8.
Bencherif et al., Synthesis by AGET ATRP of degradable nanogel precursors for in situ formation of nanostructured hyaluronic acid hydrogel. Biomacromolecules. Sep. 14, 2009;10(9):2499-507.
Benton et al., Photocrosslinking of gelatin macromers to synthesize porous hydrogels that promote valvular interstitial cell function. Tissue Eng Part A. Nov. 2009;15(11):3221-30.

(56) References Cited

OTHER PUBLICATIONS

Berg et al., Il-10 is a central regulator of cyclooxygenase-2 expression and prostaglandin production. J Immunol. Feb. 15, 2001;166(4):2674-80.
Bergstraesser et al., Stimulation and inhibition of human mammary epithelial cell duct morphogenesis in vitro. Proc Assoc Am Physicians. Mar. 1996;108(2):140-54.
Bianco et al., The meaning, the sense and the significance: translating the science of mesenchymal stem cells into medicine. Nat Med. Jan. 2013; 19(1):35-42.
Bilodeau et al., Regular Pyramid Punch Problem. J Appl Mech. 1992;59(3):519-523.
Bischoff, Proliferation of muscle satellite cells on intact myofibers in culture. Dev Biol. May 1986;115(1):129-39.
Bjork et al., Tuning the shape of mesoporous silica particles by alterations in parameter space: from rods to platelets. Langmuir. Nov. 5, 2013;29(44):13551-61.
Blanas et al., Induction of autoimmune diabetes by oral administration of autoantigen. Science. Dec. 6, 1996;274(5293):1707-9.
Blumenthal et al., Polyurethane scaffolds seeded with genetically engineered skeletal myoblasts: a promising tool to regenerate myocardial function. Artif Organs. Feb. 2010;34(2):E46-54.
Boateng et al., Wound healing dressings and drug delivery systems: a review. J Pharm Sci. Aug. 2008;97(8):2892-923.
Boerckel et al., Mechanical regulation of vascular growth and tissue regeneration in vivo. Proc Natl Acad Sci U S A. Sep. 13, 2011;108(37):E674-80.
Bohl et al., Role of synthetic extracellular matrix in development of engineered dental pulp. J Biomater Sci Polym Ed. 1998;9(7):749-64.
Bojarova et al., Sugared biomaterial binding lectins: achievements and perspectives. Biomater Sci. Jul. 19, 2016;4(8):1142-60.
Bonauer et al., MicroRNA-92a controls angiogenesis and functional recovery of ischemic tissues in mice. Science. Jun. 26, 2009;324(5935):1710-3.
Boontheekul et al., Controlling alginate gel degradation utilizing partial oxidation and bimodal molecular weight distribution. Biomaterials. May 2005;26(15):2455-65.
Boontheekul et al., Regulating myoblast phenotype through controlled gel stiffness and degradation. Tissue Eng. Jul. 2007;13(7):1431-42.
Borselli et al., Functional muscle regeneration with combined delivery of angiogenesis and myogenesis factors. Proc Natl Acad Sci U S A. Feb. 23, 2010;107(8):3287-92.
Bouhadir et al., Degradation of partially oxidized alginate and its potential application for tissue engineering. Biotechnol Prog. Sep.-Oct. 2001;17(5):945-50.
Bouhadir et al., Synthesis of Cross-Linked Poly(aldehyde guluronate) Hydrogels. Polymer. Jun. 1999;40(12):3575-3584.
Bowne et al., Injection of DNA encoding granulocyte-macrophage colony-stimulating factor recruits dendritic cells for immune adjuvant effects. Cytokines Cell Mol Ther. Dec. 1999;5(4):217-25.
Brignone et al., A phase I pharmacokinetic and biological correlative study of IMP321, a novel MHC class II agonist, in patients with advanced renal cell carcinoma. Clin Cancer Res. Oct. 1, 2009;15(19):6225-31.
Brinkman et al., Photo-cross-linking of type I collagen gels in the presence of smooth muscle cells: mechanical properties, cell viability, and function. Biomacromolecules. Jul.-Aug. 2003;4(4):890-5.
Brinkmann et al., Neutrophil extracellular traps kill bacteria. Science. Mar. 5, 2004;303(5663):1532-5.
Bristol-Myers Squibb, Investigational Anti-PD-1 Immunotherapy BMS-936558 Showed Clinical Activity in Phase 1 Trial of Patients with Previously-Treated non-Small-Cell Lung Cancer, Metastatic Melanoma adn Renal Cell Cancer. Financial Times. 3 pages, Jun. 2, 2012.
Brouwers et al., Can the growth factors PTHrP, Ihh and VEGF, together regulate the development of a long bone? J Biomech. 2006;39(15):2774-82.

Broxmeyer, Insights into the biology of cord blood stem/progenitor cells. Cell Prolif. Apr. 2011;44 Suppl 1:55-9.
Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;5(11):6278-86.
Bryant et al., Photo-patterning of porous hydrogels for tissue engineering. Biomaterials. Jul. 2007;28(19):2978-86.
Bucki et al., Combined antibacterial and anti-inflammatory activity of a cationic disubstituted dexamethasone-spermine conjugate. Antimicrob Agents Chemother. Jun. 2010;54(6):2525-33.
Buckwalter et al., Form of Antigen Dictates Immunity: Irradiated Cell vs. Whole Cell Lysate Vaccination. J Immunol. Apr. 1, 2007;178(1 Suppl):S77.
Bullard et al., Fetal wound healing: current biology. World J Surg. Jan. 2003;27(1):54-61.
Buonaguro et al., Translating tumor antigens into cancer vaccines. Clin Vaccine Immunol. Jan. 2011;18(1):23-34.
Burdick et al., Controlled degradation and mechanical behavior of photopolymerized hyaluronic acid networks. Biomacromolecules. Jan.-Feb. 2005;6(1):386-91.
Burdick et al., Photoencapsulation of osteoblasts in injectable RGD-modified PEG hydrogels for bone tissue engineering. Biomaterials. Nov. 2002;23(22):4315-23.
Burdick et al., Stimulation of neurite outgrowth by neurotrophins delivered from degradable hydrogels. Biomaterials. Jan. 2006;27(3):452-9.
Burger et al., Effect of VEGF and its receptor antagonist SU-5416, an inhibitor of angiogenesis, on processing of the beta-amyloid precursor protein in primary neuronal cells derived from brain tissue of Tg2576 mice. Int J Dev Neurosci. Nov. 2010;28(7):597-604.
Bégué et al., Vaccination against human papillomavirus. Implementation and efficacy against cervical cancer control. Bull Acad Natl Med. Dec. 2007;191(9):1805-16.
Callahan et al., At the bedside: CTLA-4- and PD-1-blocking antibodies in cancer immunotherapy. J Leukoc Biol. Jul. 2013;94(1):41-53.
Calvert, Electroactive Polymer Gels. Electroactive Polymer (EAP) Acutators as Artificial Muscle: Reality, Potential, and Challenges. Bar-Cohen, (Ed.), Spie Press, Bellingham, WA. 151-170. (2004).
Calvert, Gel Sensors and Actuators. MRS Bullet. 2008;33(3):207-212.
Cameron et al., The influence of substrate creep on mesenchymal stem cell behaviour and phenotype. Biomaterials. Sep. 2011;32(26):5979-93.
Cao et al., Promoting angiogenesis via manipulation of VEGF responsiveness with notch signaling. Biomaterials. Sep. 2009;30(25):4085-93.
care.diabetesjournals.org, Standards of Medical Care in Diabetes. Diabetes Care. Jan. 2013;36(Suppl 1):S1-S2.
Carlson et al., Notch signaling pathway and tissue engineering. Front Biosci. Sep. 1, 2007;12:5143-56.
Carmeliet et al., Angiogenesis in cancer and other diseases. Nature. Sep. 14, 2000;407(6801):249-57.
Carmeliet, Mechanisms of angiogenesis and arteriogenesis. Nat Med. Apr. 2000;6(4):389-95.
Caulfield et al., Regulation of major histocompatibility complex class II antigens on human alveolar macrophages by granulocyte-macrophage colony-stimulating factor in the presence of glucocorticoids. Immunology. Sep. 1999;98(1):104-10.
Ceriello et al., Clinical review 2: The "metabolic memory": is more than just tight glucose control necessary to prevent diabetic complications? J Clin Endocrinol Metab. Feb. 2009;94(2):410-5.
Ceriello et al., The emerging challenge in diabetes: the "metabolic memory". Vascul Pharmacol. Nov.-Dec. 2012;57(5-6):133-8.
Champion et al., Shape induced inhibition of phagocytosis of polymer particles. Pharm Res. Jan. 2009;26(1):244-9.
Chan et al., Antifibrotic effects of suramin in injured skeletal muscle after laceration. J Appl Physiol. Sep. 2003;95(2):771-80.
Chan et al., Helix induction in antimicrobial peptides by alginate in biofilms. J Biol Chem. Sep. 10, 2004;279(37):38749-54.
Chan et al., Traction dynamics of filopodia on compliant substrates. Science. Dec. 12, 2008;322(5908):1687-91.

(56) References Cited

OTHER PUBLICATIONS

Chang, Mouse models for studies of retinal degeneration and diseases. Methods Mol Biol. 2013;935:27-39.
Chapman, Endosomal proteases in antigen presentation. Curr Opin Immunol. Feb. 2006;18(1):78-84.
Chen et al., Adipogenic differentiation of adipose tissue-derived human mesenchymal stem cells: effect of gastric bypass surgery. Surg Endosc. Dec. 2012;26(12):3449-56.
Chen et al., Functional Human Vascular Network Generated in Photocrosslinkable Gelatin Methacrylate Hydrogels. Adv Funct Mater. May 23, 2012;22(10):2027-2039.
Chen et al., Integrated approach to designing growth factor delivery systems. FASEB J. Dec. 2007;21(14):3896-903.
Chen et al., Polymeric growth factor delivery strategies for tissue engineering. Pharm Res. Aug. 2003;20(8):1103-12.
Chen et al., Programmed cell death of dendritic cells in immune regulation. Immunol Rev. Jul. 2010;236:11-27.
Chen et al., Skeletal muscle stem cells. Reprod Biol Endocrinol. Nov. 13, 2003;1:101. 7 pages.
Chen et al., Spatio-temporal VEGF and PDGF delivery patterns blood vessel formation and maturation. Pharm Res. Feb. 2007;24(2):258-64.
Chiang et al., Whole tumor antigen vaccines. Semin Immunol. Jun. 2010;22(3):132-43.
Choi et al., In vitro mineralization by preosteoblasts in poly(DL-lactide-co-glycolide) inverse opal scaffolds reinforced with hydroxyapatite nanoparticles. Langmuir. Jul. 20, 2010;26(14):12126-31.
Choi et al., Three-dimensional scaffolds for tissue engineering: the importance of uniformity in pore size and structure. Langmuir. Dec. 21, 2010;26(24):19001-6.
Choi, Replacement Organs, Hot Off the Press. New Scientist. 2003;177(2379):16.
Chou et al., Characterization of Photocross Linked Alginate Hydrogels for Nucleus Pulposus Cell Encapsulation. J Biomed Mater Res A. 2009;91A(1):187-194.
Chromiak et al., Bioreactor perfusion system for the long-term maintenance of tissue-engineered skeletal muscle organoids. In Vitro Cell Dev Biol Anim. Oct. 1998;34(9):694-703.
Clark et al., Myosin II and mechanotransduction: a balancing act. Trends Cell Biol. Apr. 2007;17(4):178-86.
Clauss et al., Interstitial transport of rabbit and sheep antibodies in normal and neoplastic tissues. Cancer Res. Jun. 15, 1990;50(12):3487-92.
ClinicalTrials.gov, NCT00729664, Multiple Ascending Dose (MDX1105-01) (Anti-PDL1). 4 pages, Sep. 3, 2015.
ClinicalTrials.gov, NCT00730639, A Phase 1 Study of Nivolumab (BMS-936558) in Subjects with Advanced or Recurrent Malignancies (MDX1 106-03). 5 pages, Mar. 24, 2016.
ClinicalTrials.gov, NCT01352884, Study to Assess the Safety, and Pharmacokinetics of AMP-224 in Patients with Advanced Cancer. 3 pages, Sep. 2, 2016.
ClinicalTrials.gov, NCT01391143, Safety Study of MGA271 in Refractory Cancer. 4 pages, Sep. 28, 2016.
Cohen et al., Controlled delivery systems for proteins based on poly(lactic/glycolic acid) microspheres. Pharm Res. Jun. 1991;8(6):713-20.
Comisar et al., Engineering RGD nanopatterned hydrogels to control preosteoblast behavior: a combined computational and experimental approach. Biomaterials. Oct. 2007;28(30):4409-17.
Conboy et al., The regulation of Notch signaling controls satellite cell activation and cell fate determination in postnatal myogenesis. Dev Cell. Sep. 2002;3(3):397-409.
Conconi et al., In vitro and in vivo evaluation of acellular diaphragmatic matrices seeded with muscle precursors cells and coated with VEGF silica gels to repair muscle defect of the diaphragm. J Biomed Mater Res A. May 2009;89(2):304-16.
Conn et al., Purification of a glycoprotein vascular endothelial cell mitogen from a rat glioma-derived cell line. Proc Natl Acad Sci U S A. Feb. 1990;87(4):1323-7.
Cook et al., A sialomucopeptide liberated by trypsin from the human erythrocyte. Nature. Dec. 17, 1960;188:1011-2.
Cooper et al., Extended amplification in vitro and replicative senescence: key factors implicated in the success of human myoblast transplantation. Hum Gene Ther. Aug. 10, 2003;14(12):1169-79.
Cooper, Metabolic memory: implications for diabetic vascular complications. Pediatr Diabetes. Aug. 2009;10(5):343-6.
Corcione et al., CCL19 and CXCL12 trigger in vitro chemotaxis of human mantle cell lymphoma B cells. Clin Cancer Res. Feb. 1, 2004;10(3):964-71.
Cornelison et al., Single-cell analysis of regulatory gene expression in quiescent and activated mouse skeletal muscle satellite cells. Dev Biol. Nov. 15, 1997;191(2):270-83.
Cornelison et al., Syndecan-3 and syndecan-4 specifically mark skeletal muscle satellite cells and are implicated in satellite cell maintenance and muscle regeneration. Dev Biol. Nov. 1, 2001;239(1):79-94.
Coulson et al., Flow of Fluids through Granular Beds and Packed Columns. Chemical Engineering, vol. 2. Third Edition. Pergamon Press. Chapter 4, pp. 125-171, (1978).
Coutinho et al., The anti-inflammatory and immunosuppressive effects of glucocorticoids, recent developments and mechanistic insights. Mol Cell Endocrinol. Mar. 15, 2011;335(1):2-13.
Crameri et al., Improved green fluorescent protein by molecular evolution using DNA shuffling. Nat Biotechnol. Mar. 1996;14(3):315-9.
Cuda et al., In vitro actin filament sliding velocities produced by mixtures of different types of myosin. Biophys J. Apr. 1997;72(4):1767-79.
Cukierman et al., Taking cell-matrix adhesions to the third dimension. Science. Nov. 23, 2001;294(5547):1708-12.
Cullen et al., Investigation of vascular endothelial growth factor effects on pulmonary endothelial monolayer permeability and neutrophil transmigration. Gen Pharmacol. Sep. 2000;35(3):149-57.
Curiel et al., Tumor immunotherapy: inching toward the finish line. J Clin Invest. Feb. 2002;109(3):311-2.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80.
D'Amico et al., The early progenitors of mouse dendritic cells and plasmacytoid predendritic cells are within the bone marrow hemopoietic precursors expressing Flt3. J Exp Med. Jul. 21, 2003;198(2):293-303.
Dainiak et al., Gelatin-fibrinogen cryogel dermal matrices for wound repair: preparation, optimisation and in vitro study. Biomaterials. Jan. 2010;31(1):67-76.
Dar et al., Optimization of cardiac cell seeding and distribution in 3D porous alginate scaffolds. Biotechnol Bioeng. Nov. 5, 2002;80(3):305-12.
Daro et al., Polyethylene glycol-modified GM-CSF expands CD11b(high)CD11c(high) but not CD11b(low)CD11c(high) murine dendritic cells in vivo: a comparative analysis with Flt3 ligand. J Immunol. Jul. 1, 2000;165(1):49-58.
David et al., The in vitro Desensitization of Sensitive Cells by Trypsin. J Exp Med. Dec. 1, 1964;120:1189-200.
Davies et al., Antibody-antigen complexes. Annu Rev Biochem. 1990;59:439-73.
De Jong et al., Regulation of Notch signaling genes during BMP2-induced differentiation of osteoblast precursor cells. Biochem Biophys Res Commun. Jul. 16, 2004;320(1):100-7.
De Temmerman et al., Particulate vaccines: on the quest for optimal delivery and immune response. Drug Discov Today. Jul. 2011;16(13-14):569-82.
Dembo et al., Stresses at the cell-to-substrate interface during locomotion of fibroblasts. Biophys J. Apr. 1999;76(4):2307-16.
Den Haan et al., CD8(+) but not CD8(-) dendritic cells cross-prime cytotoxic T cells in vivo. J Exp Med. Dec. 18, 2000;192(12):1685-96.
Dennis et al., Excitability and contractility of skeletal muscle engineered from primary cultures and cell lines. Am J Physiol Cell Physiol. Feb. 2001;280(2):C288-95.

(56) References Cited

OTHER PUBLICATIONS

Dennis et al., Excitability and isometric contractile properties of mammalian skeletal muscle constructs engineered in vitro. In Vitro Cell Dev Biol Anim. May 2000;36(5):327-35.
Deshmane et al., Monocyte chemoattractant protein-1 (MCP-1): an overview. J Interferon Cytokine Res. Jun. 2009;29(6):313-26.
Dexter et al., Conditions controlling the proliferation of haemopoietic stem cells in vitro. J Cell Physiol. Jun. 1977;91(3):335-44.
Di Nicola et al., Human bone marrow stromal cells suppress T-lymphocyte proliferation induced by cellular or nonspecific mitogenic stimuli. Blood. May 15, 2002;99(10):3838-43.
Diduch et al., Two cell lines from bone marrow that differ in terms of collagen synthesis, osteogenic characteristics, and matrix mineralization. J Bone Joint Surg Am. Jan. 1993;75(1):92-105.
Dieu et al., Selective recruitment of immature and mature dendritic cells by distinct chemokines expressed in different anatomic sites. J Exp Med. Jul. 20, 1998;188(2):373-86.
Diridollou et al., Skin ageing: changes of physical properties of human skin in vivo. Int J Cosmet Sci. Dec. 2001;23(6):353-62.
Discher et al., Tissue cells feel and respond to the stiffness of their substrate. Science. Nov. 18, 2005;310(5751):1139-43.
Disis et al., Granulocyte-macrophage colony-stimulating factor: an effective adjuvant for protein and peptide-based vaccines. Blood. Jul. 1, 1996;88(1):202-10.
Doan et al., Antigens and Receptors. Lippincott's Illustrated Reviews: Immunology. Wolters Kluwer/Lippincott Williams & Wilsons, Philadelphia. Chapter 12, pp. 11-23, (2008).
Doan et al., Subcellular localization of a sporulation membrane protein is achieved through a network of interactions along and across the septum. Mol Microbiol. Mar. 2005;55(6):1767-81.
Donati et al., New hypothesis on the role of alternating sequences in calcium-alginate gels Biomacromolecules. Mar.-Apr. 2005;6(2):1031-40.
Dong et al., Antitumor effect of secreted Flt3-ligand can act at distant tumor sites in a murine model of head and neck cancer. Cancer Gene Ther. Feb. 2003;10(2):96-104.
Dor et al., Making vascular networks in the adult: branching morphogenesis without a roadmap. Trends Cell Biol. Mar. 2003;13(3):131-6.
Douay et al., Ex vivo production of human red blood cells from hematopoietic stem cells: what is the future in transfusion? Transfus Med Rev. Apr. 2007;21(2):91-100.
Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.
Dranoff, Cytokines in cancer pathogenesis and cancer therapy. Nat Rev Cancer. Jan. 2004;4(1):11-22.
Dranoff, GM-CSF-based cancer vaccines. Immunol Rev. Oct. 2002;188:147-54.
Dudley et al. Adoptive cell transfer therapy following nonmyeloablative but lymphodepleting chemotherapy for the treatment of patients with refractory metastatic melanoma. J Clin Oncol. Apr. 1, 2005;23(10):2346-57.
Dufort et al., Balancing forces: architectural control of mechanotransduction. Nat Rev Mol Cell Biol. May 2011;12(5):308-19.
Dupont et al., Role of YAP/TAZ in mechanotransduction. Nature. Jun. 8, 2011;474(7350):179-83.
Duraiswamy et al., Dual blockade of PD-1 and CTLA-4 combined with tumor vaccine effectively restores T-cell rejection function in tumors—response. Cancer Res. Jan. 15, 2014;74(2):633-4.
Duraiswamy et al., Dual blockade of PD-1 and CTLA-4 combined with tumor vaccine effectively restores T-cell rejection function in tumors. Cancer Res. Jun. 15, 2013;73(12):3591-603.
Edwards et al., Evaluation of biomechanical properties of human skin. Clin Dermatol. Jul.-Aug. 1995:13(4):375-80.
Egholm et al., Peptide Nucleic Acids (PNA). Oligonucleotide Analogues with an Achiral Peptide Backbone. J Am Chem Soc. 1992;114(5):1895-1897.
Egholm et al., PNA hybridizes to complementary oligonucleotides obeying the Watson-Crick hydrogen-bonding rules. Nature. Oct. 7, 1993;365(6446):566-8.
Ehrbar et al., Endothelial cell proliferation and progenitor maturation by fibrin-bound VEGF variants with differential susceptibilities to local cellular activity. J Control Release. Jan. 3, 2005;101(1-3):93-109.
Eiselt et al., Porous carriers for biomedical applications based on alginate hydrogels. Biomaterials. Oct. 2000;21(19):1921-7.
El-Backly et al., Regeneration of dentine/pulp-like tissue using a dental pulp stem cell/poly(lactic-co-glycolic) acid scaffold construct in New Zealand white rabbits. Aust Endod J. Aug. 2008;34(2):52-67.
El-Behi et al., The encephalitogenicity of T(H)17 cells is dependent on IL-1- and IL-23-induced production of the cytokine GM-CSF. Nat Immunol. Jun. 2011;12(6):568-75.
Eldar et al., Elucidating mechanisms underlying robustness of morphogen gradients. Curr Opin Genet Dev. Aug. 2004;14(4):435-9.
Eldar et al., Robustness of the BMP morphogen gradient in *Drosophila* embryonic patterning. Nature. Sep. 19, 2002;419(6904):304-8.
Eldar et al., Self-enhanced ligand degradation underlies robustness of morphogen gradients. Dev Cell. Oct. 2003;5(4):635-46.
Eming et al., Inflammation in wound repair: molecular and cellular mechanisms. J Invest Dermatol. Mar. 2007;127(3):514-25.
Engler et al., Matrix elasticity directs stem cell lineage specification. Cell. Aug. 25, 2006;126(4):677-89.
Engler et al., Microtissue elasticity: measurements by atomic force microscopy and its influence on cell differentiation. Methods Cell Biol. 2007;83:521-45.
Engler et al., Substrate compliance versus ligand density in cell on gel responses. Biophys J. Jan. 2004;86(1 Pt 1):617-28.
Ennett et al., Temporally regulated delivery of VEGF in vitro and in vivo. J Biomed Mater Res A. Oct. 2006;79(1):176-84.
Exposito et al., The fibrillar collagen family. Int J Mol Sci. Jan. 28, 2010;11(2):407-26.
Faissner et al., Boundaries and inhibitory molecules in developing neural tissues. Glia. Apr. 1995;13(4):233-54.
Falanga, Wound healing and its impairment in the diabetic foot. Lancet. Nov. 12, 2005;366(9498):1736-43.
Falsey et al., Peptide and small molecule microarray for high throughput cell adhesion and functional assays. Bioconjug Chem. May-Jun. 2001;12(3):346-53.
Farrar et al., T helper subset development: roles of instruction, selection, and transcription. J Clin Invest. Feb. 2002;109(4):431-5.
Fauquemberque et al., HLA-A*0201-restricted CEA-derived peptide CAP1 is not a suitable target for T-cell-based immunotherapy. J Immunother. May 2010;33(4):402-13.
Ferrara et al., Angiogenesis as a therapeutic target. Nature. Dec. 15, 2005;438(7070):967-74.
Ferrara et al., Discovery and development of bevacizumab, an anti-VEGF antibody for treating cancer. Nat Rev Drug Discov. May 2004;3(5):391-400.
Fischbach et al., Polymeric Systems for Bioinspired Delivery of Angiogenic Molecules. Adv Polym Sci. 2006;203:191-221.
Fischer et al., A brilliant monomeric red fluorescent protein to visualize cytoskeleton dynamics in Dictyostelium. FEBS Lett. Nov. 5, 2004;577(1-2):227-32.
Fischer et al., Visualizing cytoskeleton dynamics in mammalian cells using a humanized variant of monomeric red fluorescent protein. FEBS Lett. May 1, 2006;580(10):2495-502.
Fisher et al., The study of protein mechanics with the atomic force microscope. Trends Biochem Sci. Oct. 1999;24(10):379-84.
Folkman, Angiogenesis. Annu Rev Med. 2006;57:1-18.
Fonseca et al., Capitalizing on the immunogenicity of dying tumor cells. Clin Cancer Res. Mar. 15, 2008;14(6):1603-8.
Fontaine et al., Surgical treatment of peripheral circulation disorders. Helv Chir Acta. Dec. 1954;21(5-6):499-533.
Ford et al., Specificity, magnitude, and kinetics of MOG-specific CD8+ T cell responses during experimental autoimmune encephalomyelitis. Eur J Immunol. Jan. 2005;35(1):76-85.
Fox, Management of worsening multiple sclerosis with mitoxantrone: a review. Clin Ther. Apr. 2006;28(4):461-74.

(56) References Cited

OTHER PUBLICATIONS

Fransen et al., Local immunomodulation for cancer therapy: Providing treatment where needed. Oncoimmunology. Nov. 1, 2013;2(11):e26493.
Friedenstein et al., Fibroblast precursors in normal and irradiated mouse hematopoietic organs. Exp Hematol. Sep. 1976;4(5):267-74.
Friedrich et al., Promoter traps in embryonic stem cells: a genetic screen to identify and mutate developmental genes in mice. Genes Dev. Sep. 1991;5(9):1513-23.
Fukushima et al., The use of an antifibrosis agent to improve muscle recovery after laceration. Am J Sports Med. Jul.-Aug. 2001;29(4):394-402.
Furqan et al., STAT inhibitors for cancer therapy. J Hematol Oncol. Dec. 5, 2013;6:90. 11 pages.
Gamvrellis et al., Vaccines that facilitate antigen entry into dendritic cells. Immunol Cell Biol. Oct. 2004;82(5):506-16.
Ganguly et al., The role of dendritic cells in autoimmunity. Nat Rev Immunol. Aug. 2013;13(8):566-77.
Gardel et al., Traction stress in focal adhesions correlates biphasically with actin retrograde flow speed. J Cell Biol. Dec. 15, 2008;183(6):999-1005.
Gasic et al., Removal and regeneration of the cell coating in tumour cells. Nature. Oct. 13, 1962;196:170.
Gauthier et al., Temporary increase in plasma membrane tension coordinates the activation of exocytosis and contraction during cell spreading. Proc Natl Acad Sci U S A. Aug. 30, 2011;108(35):14467-72.
Geerligs et al., Linear viscoelastic behavior of subcutaneous adipose tissue. Biorheology. 2008;45(6):677-88.
GenBank Accession No. 000082.2, May 10, 2014.
GenBank Accession No. 000091.4, May 10, 2014.
GenBank Accession No. 000230.2, Dec. 17, 2012.
GenBank Accession No. 000514.3, Aug. 19, 2012.
GenBank Accession No. 000572.2, May 18, 2014.
GenBank Accession No. 000601.4, Nov. 25, 2012.
GenBank Accession No. 000614.3, Sep. 9, 2012.
GenBank Accession No. 000629.3, May 4, 2014.
GenBank Accession No. 000638.3, May 4, 2014.
GenBank Accession No. 000660.4, Dec. 9, 2012.
GenBank Accession No. 000749.2, May 4, 2014.
GenBank Accession No. 000758.3, May 4, 2014.
GenBank Accession No. 000800.3, Mar. 4, 2012.
GenBank Accession No. 000876.3, Apr. 13, 2014.
GenBank Accession No. 000885.4, Apr. 13, 2014.
GenBank Accession No. 000954.1, Jun. 13, 2014.
GenBank Accession No. 000963.3, Jun. 13, 2014.
GenBank Accession No. 001001522.1, May 18, 2014.
GenBank Accession No. 001096124.1, Dec. 16, 2012.
GenBank Accession No. 001102654.1, Dec. 16, 2012.
GenBank Accession No. 001111283.1, Dec. 9, 2012.
GenBank Accession No. 001171630.1, Dec. 9, 2012.
GenBank Accession No. 001202.3, Nov. 18, 2012.
GenBank Accession No. 001836.2, May 3, 2014.
GenBank Accession No. 001845.4, May 3, 2014.
GenBank Accession No. 001892.1, May 18, 2014.
GenBank Accession No. 001901.2, May 18, 2014.
GenBank Accession No. 002010.2, Dec. 9, 2012.
GenBank Accession No. 002421.3, May 11, 2014.
GenBank Accession No. 002506.2, Dec. 9, 2012.
GenBank Accession No. 002632.4, May 4, 2011.
GenBank Accession No. 002973.1, May 3, 2014.
GenBank Accession No. 002982.3, May 3, 2014.
GenBank Accession No. 003236.2, Aug. 21, 2011.
GenBank Accession No. 003239.2, Feb. 18, 2014.
GenBank Accession No. 003254.2, Jan. 5, 2013.
GenBank Accession No. 003255.2, Jan. 6, 2013.
GenBank Accession No. 003259.2, Nov. 25, 2012.
GenBank Accession No. 003263.3, Jan. 5, 2013.
GenBank Accession No. 003264.3, Jan. 6, 2013.
GenBank Accession No. 003268.5, Nov. 25, 2012.
GenBank Accession No. 003368.1, May 5, 2014.
GenBank Accession No. 003377.4, May 5, 2014.
GenBank Accession No. 003383.2, May 5, 2014.
GenBank Accession No. 003392.4, May 5, 2014.
GenBank Accession No. 004460.1, May 25, 2014.
GenBank Accession No. 004469.4, May 25, 2014.
GenBank Accession No. 005420.1, May 11, 2014.
GenBank Accession No. 005429.3, Mar. 31, 2014.
GenBank Accession No. 006059.2, Oct. 28, 2012.
GenBank Accession No. 006068.4, Oct. 28, 2012.
GenBank Accession No. 015719.3, Feb. 26, 2014.
GenBank Accession No. 016562.3, Jan. 6, 2013.
GenBank Accession No. 030956.3, Oct. 28, 2012.
GenBank Accession No. 033023.4, Nov. 18, 2012.
GenBank Accession No. 056534.2, Feb. 26, 2014.
GenBank Accession No. 057646.1, Jan. 6, 2013.
GenBank Accession No. 112218.2, Oct. 28, 2012.
GenBank Accession No. 138554.4, Dec. 29, 2012.
GenBank Accession No. 138636.4, Dec. 23, 2012.
GenBank Accession No. 170731.4, Dec. 9, 2012.
GenBank Accession No. 205819.3, Dec. 6, 2012.
GenBank Accession No. 205820.1, Jan. 5, 2013.
GenBank Accession No. 205823.2, Jan. 6, 2013.
GenBank Accession No. 570912.2, Nov. 18, 2012.
GenBank Accession No. 612564.1, Dec. 29, 2012.
GenBank Accession No. 619542.1, Dec. 23, 2012.
GenBank Accession No. 991388.2, Dec. 6, 2012.
GenBank Accession No. 991389.1, Jan. 5, 2013.
GenBank Accession No. 991392.1, Jan. 6, 2013.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AAI44040, Mar. 18, 2009.
GenBank Accession No. ABC86910, Jan. 3, 2011.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_001025081.1, Jan. 19, 2019.
GenBank Accession No. NP_001020252.1, Jan. 19, 2019.

(56) References Cited

OTHER PUBLICATIONS

GenBank Accession No. P49771.1, Jan. 9, 2013.

GenBank Accession No. U76381.2, Jul. 12, 1999.

Genes et al., Effect of substrate mechanics on chondrocyte adhesion to modified alginate surfaces. Arch Biochem Biophys. Feb. 15, 2004;422(2):161-7.

Gerhardt et al., VEGF guides angiogenic sprouting utilizing endothelial tip cell filopodia. J Cell Biol. Jun. 23, 2003;161(6):1163-77.

Getts et al., Current landscape for T-cell targeting in autoimmunity and transplantation. Immunotherapy. Jul. 2011;3(7):853-70.

Gilboa, DC-based cancer vaccines. J Clin Invest. May 2007;117(5):1195-203.

Glasbey et al., Image Analysis and Three-Dimensional Modelling of Pores in Soil Aggregates. Eur J Soil Sci. Sep. 1991;42(3):479-486.

Gnjatic et al., Toll-like receptor agonists: are they good adjuvants? Cancer J. Jul.-Aug. 2010;16(4):382-91.

Godbey et al. Tracking the intracellular path of poly(ethylenimine)/DNA complexes for gene delivery. Proc Natl Acad Sci U S A. Apr. 27, 1999;96(9):5177-81.

Godbey et al., Size matters: molecular weight affects the efficiency of poly(ethylenimine) as a gene delivery vehicle. J Biomed Mater Res. Jun. 5, 1999;45(3):268-75.

Goddard et al., Polymer surface modification for the attachment of bioactive compounds. Progress in Polymer Science. Jul. 2007;32(7):698-725.

Gomez-Cambronero, Rapamycin inhibits GM-CSF-induced neutrophil migration. FEBS Lett. Aug. 28, 2003;550(1-3):94-100.

Gospodarowicz et al., Effect of fibroblast growth factor on the division and fusion of bovine myoblasts. J Cell Biol. Aug. 1976;70(2 pt 1):395-405.

Graessley, Entangled Linear, Branched and Network Polymer Systems—Molecular Theories. Adv Poly Sci. 1982;47:67-117.

Griffith et al., Tissue engineering—current challenges and expanding opportunities. Science. Feb. 8, 2002;295(5557):1009-14.

Grimmer et al., Tracheal reconstruction using tissue-engineered cartilage. Arch Otolaryngol Head Neck Surg. Oct. 2004;130(10):1191-6.

Gros et al., A common somitic origin for embryonic muscle progenitors and satellite cells. Nature. Jun. 16, 2005;435(7044):954-8.

Guillaume et al., Two abundant proteasome subtypes that uniquely process some antigens presented by HLA class I molecules. Proc Natl Acad Sci U S A. Oct. 26, 2010;107(43):18599-604.

Gullberg et al., Extracellular matrix and its receptors during development. Int J Dev Biol. Oct. 1995;39(5):845-54.

Guo et al., Droplet microfluidics for high-throughput biological assays. Lab Chip. Jun. 21, 2012;12(12):2146-55.

Gupta et al., Magnetically controlled targeted micro-carrier systems. Life Sci. 1989;44(3):175-86.

Gurkan et al., The mechanical environment of bone marrow: a review. Ann Biomed Eng. Dec. 2008;36(12):1978-91.

Gussoni et al., Dystrophin expression in the mdx mouse restored by stem cell transplantation. Nature. Sep. 23, 1999;401(6751):390-4.

Gutsmiedl et al., Copper-free "click" modification of DNA via nitrile oxide-norbornene 1,3-dipolar cycloaddition. Org Lett. Jun. 4, 2009;11(11):2405-8.

Haase et al., CD40 is necessary for activation of naïve T cells by a dendritic cell line in vivo but not in vitro. Scand J Immunol. Mar. 2004;59(3):237-45.

Halim et al., Biologic and synthetic skin substitutes: An overview. Indian J Plast Surg. Sep. 2010;43(Suppl):S23-8.

Hamby et al., Small molecule inhibitors of tumor-promoted angiogenesis, including protein tyrosine kinase inhibitors. Pharmacol Ther. May-Jun. 1999;82(2-3):169-93.

Hamdy et al., Targeting dendritic cells with nano-particulate PLGA cancer vaccine formulations. Adv Drug Deliv Rev. Sep. 10, 2011;63(10-11):943-55.

Hamilton et al., GM-CSF Biology. Growth Factors. Dec. 2004;22(4):225-31.

Hamilton, GM-CSF in inflammation and autoimmunity. Trends Immunol. Aug. 2002;23(8):403-8.

Hanada, Efficacy of rehabilitative therapy in regional musculoskeletal conditions. Best Pract Res Clin Rheumatol. Feb. 2003;17(1):151-66.

Hansell et al., Additive-free clicking for polymer functionalization and coupling by tetrazine-norbornene chemistry. J Am Chem Soc. Sep. 7, 2011;133(35):13828-31.

Hansen et al., Comparison of clinical grade type 1 polarized and standard matured dendritic cells for cancer immunotherapy. Vaccine. Jan. 11, 2013;31(4):639-46.

Hansen et al., Integrin binding and cell spreading on extracellular matrix act at different points in the cell cycle to promote hepatocyte growth. Mol Biol Cell. Sep. 1994;5(9):967-75.

Harris et al., Open pore biodegradable matrices formed with gas foaming. J Biomed Mater Res. Dec. 5, 1998;42(3):396-402.

Harris, Classification, Diagnostic Criteria, and Screening for Diabetes. Diabetes in America. NIH Publication No. 95-1468. Chapter 2. (1995):15-36.

Harrison, What is the status of reaction-diffusion theory thirty-four years after turing? J Theor Biol. Apr. 21, 1987;125(4):369-84.

Hartgerink et al., Peptide-amphiphile nanofibers: a versatile scaffold for the preparation of self-assembling materials. Proc Natl Acad Sci U S A. Apr. 16, 2002;99(8):5133-8.

Hartmann et al., CpG DNA: a potent signal for growth, activation, and maturation of human dendritic cells. Proc Natl Acad Sci U S A. Aug. 3, 1999;96(16):9305-10.

Hashimoto et al., Development of alginate wound dressings linked with hybrid peptides derived from laminin and elastin. Biomaterials. Mar.-Apr. 2004;25(7-8):1407-14.

Hawke et al., Myogenic satellite cells: physiology to molecular biology. J Appl Physiol (1985). Aug. 2001;91(2):534-51.

Heath, Cells for tissue engineering. Trends Biotechnol. Jan. 2000;18(1):17-9.

Helm et al., Synergy between interstitial flow and VEGF directs capillary morphogenesis in vitro through a gradient amplification mechanism. Proc Natl Acad Sci U S A. Nov. 1, 2005;102(44):15779-84.

Henry et al., VIVA Investigators. The VIVA trial: Vascular endothelial growth factor in Ischemia for Vascular Angiogenesis. Circulation. Mar. 18, 2003;107(10):1359-65.

Hermanson, Bioconjugate Techniques. Academic Press, New York. pp. 152-186, (1996).

Heslop et al., Transplanted primary neonatal myoblasts can give rise to functional satellite cells as identified using the Myf5nlacZl+ mouse. Gene Ther. May 2001;8(10):778-83.

Hildner et al., Batf3 deficiency reveals a critical role for CD8alpha+ dendritic cells in cytotoxic T cell immunity. Science. Nov. 14, 2008;322(5904):1097-100.

Hill et al., Designing scaffolds to enhance transplanted myoblast survival and migration. Tissue Eng. May 2006;12(5):1295-304.

Hill et al., Muscle satellite (stem) cell activation during local tissue injury and repair. J Anat. Jul. 2003;203(1):89-99.

Hill, Macroporous Scaffold Architecture, Peptide, HGF/FGF and Myoblast Incorporation Enhance Myogenesis. IADR/AADR/CADR 83rd General Session. Mar. 9-12, 2005. Poster #2829.

Hirano et al., Peptide and Protein Presenting Materials for Tissue Engineering. Adv Mat. Jan. 16, 2004;16(1):17-25.

Hodge-Dufour et al., Inhibition of interferon gamma induced interleukin 12 production: a potential mechanism for the anti-inflammatory activities of tumor necrosis factor. Proc Natl Acad Sci U S A. Nov. 10, 1998;95(23):13806-11.

Hodi et al., Immunologic and clinical effects of antibody blockade of cytotoxic T lymphocyte-associated antigen 4 in previously vaccinated cancer patients. Proc Natl Acad Sci U S A. Feb. 26, 2008;105(8):3005-10.

Hodi et al., Improved survival with ipilimumab in patients with metastatic melanoma. N Engl J Med. Aug. 19, 2010;363(8):711-23.

Holland et al., Dual growth factor delivery from degradable oligo(poly(ethylene glycol) fumarate) hydrogel scaffolds for cartilage tissue engineering. Journal of Controlled Release. 2005;101:111-125.

(56) References Cited

OTHER PUBLICATIONS

Holland et al., Transforming growth factor-beta 1 release from oligo(poly(ethylene glycol)fumarate) hydrogels in conditions that model the cartilage wound healing environment. J Control Release. Jan. 8, 2004;94(1):101-14.
Horsley et al., IL-4 acts as a myoblast recruitment factor during mammalian muscle growth. Cell. May 16, 2003;113(4):483-94.
Howard et al., Polymer micelles with hydrazone-ester dual linkers for tunable release of dexamethasone. Pharm Res. Oct. 2011;28(10):2435-46.
Hsiong et al., Differentiation stage alters matrix control of stem cells. J Biomed Mater Res A. Apr. 2008;85A(1):145-56.
Hu et al., Tolerogenic dendritic cells and their potential applications. Immunology. Mar. 2011;132(3):307-14.
Huang et al., Fabrication and in vitro Testing of Polymeric Delivery Systems for Condensed DNA. J Biomed Mater Res. 2003;67:1384-1392.
Huang et al., Long-Term In Vivo Gene Expression via Delivery of PEI-DNA Condensates From Porous Polymer Scaffolds. Hum Gene Ther. 2005;16(5):609-617.
Hubbell et al., Materials Engineering for Immunomodulation. Nature. 2009;462:449-460.
Hubbell, Biomaterials in tissue engineering. Biotechnology (N Y). Jun. 1995;13(6):565-76.
Huebsch et al., Harnessing traction-mediated manipulation of the cell/matrix interface to control stem-cell fate. Nat Mater. Jun. 2010;9(6):518-26.
Humphries et al., Integrin ligands at a glance. J Cell Sci. Oct. 1, 2006;119(Pt 19):3901-3.
Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Hutson et al., Synthesis and characterization of tunable poly(ethylene glycol): gelatin methacrylate composite hydrogels. Tissue Eng Part A. Jul. 2011;17(13-14):1713-23.
Hwang et al., Fabrication of three-dimensional porous cell-laden hydrogel for tissue engineering. Biofabrication. Sep. 2010;2(3):035003. 12 pages.
Ichida et al., A small-molecule inhibitor of tgf-Beta signaling replaces sox2 in reprogramming by inducing nanog. Cell Stem Cell. Nov. 6, 2009;5(5):491-503.
Iellem et al., Unique chemotactic response profile and specific expression of chemokine receptors CCR4 and CCR8 by CD4(+)CD25(+) regulatory T cells. J Exp Med. Sep. 17, 2001;194(6):847-53.
Ihnat et al., Hypothesis: the 'metabolic memory', the new challenge of diabetes. Diabet Med. Jun. 2007;24(6):582-6.
Il et al., A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmacol. Apr. 2006;69(4):1288-95.
Irintchev et al., Formation of Skeletal Muscle After Subcutaneous Implantation of Cultured Myoblasts. Bio/Technology. p. 366, Abstract 153.06, Jun. 1995.
Irvine et al., Engineering synthetic vaccines using cues from natural immunity. Nat Mater. Nov. 2013;12(11):978-90.
Isern et al., Self-renewing human bone marrow mesenspheres promote hematopoietic stem cell expansion. Cell Rep. May 30, 2013;3(5):1714-24.
Ishihara et al., Roles of bradykinin in vascular permeability and angiogenesis in solid tumor. Int Immunopharmacol. Mar. 2002;2(4):499-509.
Iwamoto et al., Preparation of an Ionic Polymer Gel Microactuator and Measurement of its Periodic Motions. Nippon Kagaku Kaishi. 1997;9:609-614.
Jager et al., Effector and regulatory T-cell subsets in autoimmunity and tissue inflammation. Scand J Immunol. Sep. 2010;72(3):173-84.
Jain, Molecular Regeneration of Vessel Maturation. Nat Med. Jun. 1, 2003;9:685-693.
Jain, The manufacturing techniques of various drug loaded biodegradable poly(lactide-co-glycolide) (PLGA) devices. Biomaterials. Dec. 2000;21(23):2475-90.
Jankovic et al., In the absence of IL-12, CD4(+) T cell responses to intracellular pathogens fail to default to a Th2 pattern and are host protective in an IL-10(-/-) setting. Immunity. Mar. 2002;16(3):429-39.
Janmey et al., From tissue mechanics to transcription factors. Differentiation. Oct. 2013;86(3):112-20.
Jego et al., Plasmacytoid dendritic cells induce plasma cell differentiation through type I interferon and interleukin 6. Immunity. Aug. 2003;19(2):225-34.
Jewett et al., Rapid Cu-free click chemistry with readily synthesized biarylazacyclooctynones. J Am Chem Soc. Mar. 24, 2010;132(11):3688-90.
Jiang et al. Two-piconewton slip bond between fibronectin and the cytoskeleton depends on talin. Nature. Jul. 17, 2003;424(6946):334-7.
Jiang et al., Click hydrogels, microgels and nanogels: emerging platforms for drug delivery and tissue engineering. Biomaterials. Jun. 2014;35(18):4969-85.
Jiang et al., Self-organization of periodic patterns by dissociated feather mesenchymal cells and the regulation of size, No. and spacing of primordia. Development. Nov. 1999;126(22):4997-5009.
Jinushi et al., Enhancing the clinical activity of granulocyte-macrophage colony-stimulating factor-secreting tumor cell vaccines. Immunol Rev. Apr. 2008;222:287-98.
Jinushi et al., MFG-E8-mediated uptake of apoptotic cells by APCs links the pro- and antiinflammatory activities of GM-CSF. J Clin Invest. Jul. 2007;117(7):1902-13.
Johnson et al., Activation of skeletal muscle satellite cells and the role of fibroblast growth factor receptors. Exp Cell Res. Aug. 1995;219(2):449-53.
Jokinen et al., Integrin-mediated cell adhesion to type I collagen fibrils. J Biol Chem. Jul. 23, 2004;279(30):31956-63.
Jones et al., Preparation of 6 alpha- and 6 beta-carboxymethyl steroid conjugates and their use in radioimmunoassay for progesterone. Steroids. Mar. 1974;23(3):323-36.
Jorgensen et al., Treatment of an immortalized APC cell line with both cytokines and LPS ensures effective T-cell activation in vitro. Scand J Immunol. Nov. 2002;56(5):492-503.
Jugdutt et al., Aging and defective healing, adverse remodeling, and blunted post-conditioning in the reperfused wounded heart. J Am Coll Cardiol. Apr. 8, 2008;51(14):1399-403.
Juntanon et al., Electrically controlled release of sulfosalicylic acid from crosslinked poly(vinyl alcohol) hydrogel. Int J Pharm. May 22, 2008;356(1-2):1-11.
Kang et al., Effect of Porous Structure on the Degradation of Freeze-Dried Gelatin Hydrogels J Bioact Compat Poly. Jul. 1, 1999;14(4):331-343.
Kanzler et al., Therapeutic targeting of innate immunity with Toll-like receptor agonists and antagonists. Nat Med. May 2007;13(5):552-9.
Kared et al., Treatment with granulocyte colony-stimulating factor prevents diabetes in NOD mice by recruiting plasmacytoid dendritic cells and functional CD4(+)CD25(+) regulatory T-cells. Diabetes. Jan. 2005;54(1):78-84.
Katayama et al., Integrated analysis of the genome and the transcriptome by FANTOM. Brief Bioinform. Sep. 2004;5(3):249-58.
Kathuria et al., Synthesis and characterization of elastic and macroporous chitosan-gelatin cryogels for tissue engineering. Acta Biomater. Jan. 2009;5(1):406-18.
Kawai et al., Innate immune recognition of viral infection. Nat Immunol. Feb. 2006;7(2):131-7.
Kawashima et al., Pulmonary delivery of insulin with nebulized DL-lactide/glycolide copolymer (PLGA) nanospheres to prolong hypoglycemic effect. J Control Release. Nov. 1, 1999;62(1-2):279-87.
Kearney et al., Macroscale delivery systems for molecular and cellular payloads. Nat Mater. Nov. 2013;12(11):1004-17.

(56) References Cited

OTHER PUBLICATIONS

Kennedy et al., Rapid and extensive collapse from electrically responsive macroporous hydrogels. Adv Healthc Mater. Apr. 2014;3(4):500-7.
Khetan et al., Degradation-mediated cellular traction directs stem cell fate in covalently crosslinked three-dimensional hydrogels. Nat Mater. May 2013;12(5):458-65.
Khomyakova et al., DNA or RNA oligonucleotide 2'-hydrazides for chemoselective click-type ligation with carbonyl compounds. Nucleosides Nucleotides Nucleic Acids. Jul.-Aug. 2011;30(7-8):577-84.
Khownium et al., Novel endotoxin-sequestering compounds with terephthalaldehyde-bis-guanylhydrazone scaffolds. Bioorg Med Chem Lett. Mar. 1, 2006;16(5):1305-8.
Kim et al., An overview of cartilage tissue engineering. Yonsei Med J. Dec. 2000;41(6):766-73.
Kim et al., Multifunctional capsule-in-capsules for immunoprotection and trimodal imaging. Angew Chem Int Ed Engl. Mar. 1, 2011;50(10):2317-21.
Kim et al., Synthesis and characterization of dexamethasone-conjugated linear polyethylenimine as a gene carrier. Journal of Cellular Biochemistry. Jun. 1, 2010;110(3):743-751.
Kim et al., The effect of VEGF on the myogenic differentiation of adipose tissue derived stem cells within thermosensitive hydrogel matrices. Biomaterials. Feb. 2010;31(6):1213-8.
Kinoshita et al., Successive injections in mdx mice of myoblasts grown with bFGF. Neuromuscul Disord. May 1996;6(3):187-93.
Kisak et al. The vesosome—a multicompartment drug delivery vehicle. Curr Med Chem. Jan. 2004;11(2):199-219.
Klebanoff et al., CD8+ T-cell memory in tumor immunology and immunotherapy. Immunol Rev. Jun. 2006;211:214-24.
Klein et al., Cell-Cycle Control by Physiological Matrix Elasticity and In Vivo Tissue Stiffening. Curr Biol. Sep. 29, 2009;19:1511-1518.
Klinman, Immunotherapeutic uses of CpG oligodeoxynucleotides. Nat Rev Immunol. Apr. 2004;4(4):249-58.
Knight et al., Synthesis and evaluation of an 18F-labelled norbornene derivative for copper-free click chemistry reactions. Org Biomol Chem. Jun. 21, 2013;11(23):3817-25.
Koehler et al., A Diels-Alder modulated approach to control and sustain the release of dexamethasone and induce osteogenic differentiation of human mesenchymal stem cells. Biomaterials. May 2013;34(16):4150-4158.
Kohane, Microparticles and nanoparticles for drug delivery. Biotechnol Bioeng. Feb. 1, 2007;96(2):203-9.
Kondo et al., A reaction-diffusion wave on the skin of the marine angelfish *Pomacanthus*. Nature. Aug. 31, 1995;376(6543):765-8.
Kong et al., Controlling Degradation of Hydrogels via the Size of Cross-Linked Junctions. Adv Mater. Nov. 30, 2004;16(21):1917-1921.
Kong et al., Controlling rigidity and degradation of alginate hydrogels via molecular weight distribution. Biomacromolecules. Sep.-Oct. 2004;5(5):1720-7.
Kong et al., Decoupling the Dependence of Rheological/Mechanical Properties of Hydrogels from Solids Concentration. Polymer. 2002;43(23):6239-6246.
Kong et al., Design of biodegradable hydrogel for the local and sustained delivery of angiogenic plasmid DNA. Pharm Res. May 2008;25(5):1230-8.
Kong et al., Designing alginate hydrogels to maintain viability of immobilized cells. Biomaterials. Oct. 2003;24(22):4023-9.
Kong et al., FRET measurements of cell-traction forces and nano-scale clustering of adhesion ligands varied by substrate stiffness. Proc Natl Acad Sci U S A. Mar. 22, 2005;102(12):4300-5.
Kong et al., Non-viral gene delivery regulated by stiffness of cell adhesion substrates. Nat Mater. Jun. 2005;4(6):460-4.
Koo et al., Bioorthogonal copper-free click chemistry in vivo for tumor-targeted delivery of nanoparticles. Angew Chem Int Ed Engl. Nov. 19, 2012;51(47):11836-40.
Kratky et al., Direct activation of antigen-presenting cells is required for CD8+ T-cell priming and tumor vaccination. Proc Natl Acad Sci U S A. Oct. 18, 2011;108(42):17414-9.
Kratz, Albumin as a drug carrier: design of prodrugs, drug conjugates and nanoparticles. J Control Release. Dec. 18, 2008;132(3):171-83.
Krieg, Development of TLR9 agonists for cancer therapy. J Clin Invest. May 2007;117(5):1184-94.
Krishnamachari et al., PLGA Microparticles that Co-deliver Antigen and Toll Like Receptor Ligand Adjuvants for Applications in Cancer Immunotherapy. AAPS Annual Meeting and Exposition. Nov. 9, 2009. 1 page.
Kruisbeek et al., Proliferative assays for T cell function. Curr Protoc Immunol. May 2004;Chapter 3:Unit 3.12. 20 pages.
Kumamoto et al., Induction of tumor-specific protective immunity by in situ Langerhans cell vaccine. Nat Biotechnol. Jan. 2002;20(1):64-9.
Kumar et al., Toll-like receptors and innate immunity. Biochem Biophys Res Commun. Oct. 30, 2009;388(4):621-5.
Kurts et al., CD8 T cell ignorance or tolerance to islet antigens depends on antigen dose. Proc Natl Acad Sci U S A. Oct. 26, 1999;96(22):12703-7.
Kuwahara et al., Cell delivery using an injectable and adhesive transglutaminase-gelatin gel. Tissue Eng Part C Methods. Aug. 2010;16(4):609-18.
Kwon et al., Electrically erodible polymer gel for controlled release of drugs. Nature. Nov. 28, 1991;354(6351):291-3.
Kwon et al., In vivo targeting of dendritic cells for activation of cellular immunity using vaccine carriers based on pH-responsive microparticles. Proc Natl Acad Sci U S A. Dec. 20, 2005;102(51):18264-8.
Kyi et al., Checkpoint blocking antibodies in cancer immunotherapy. FEBS Lett. Jan. 21, 2014;588(2):368-76.
Langenkamp et al., Kinetics of dendritic cell activation: impact on priming of TH1, TH2 and nonpolarized T cells. Nat Immunol. Oct. 2000;1(4):311-6.
Langer et al., Tissue engineering. Science. May 14, 1993;260(5110):920-6.
Lanzavecchia et al., Regulation of T cell immunity by dendritic cells. Cell. Aug. 10, 2001;106(3):263-6.
Lao et al., Magnetic and hydrogel composite materials for hyperthermia applications. J Mater Sci Mater Med. Oct. 2004;15(10):1061-4.
Latorre et al., Applications of magnetic nanoparticles in medicine: magnetic fluid hyperthermia. P R Health Sci J. Sep. 2009;28(3):227-38.
Latz et al., TLR9 signals after translocating from the ER to CpG DNA in the lysosome. Nat Immunol. Feb. 2004;5(2):190-8.
Lauterbach et al., Mouse CD8alpha+ DCs and human BDCA3+ DCs are major producers of IFN-lambda in response to poly IC. J Exp Med. Nov. 22, 2010;207(12):2703-17.
Leach et al., Coating of VEGF-releasing scaffolds with bioactive glass for angiogenesis and bone regeneration. Biomaterials. Jun. 2006;27(17):3249-55.
Lee et al., Controlling Mechanical and Swelling Properties of Alginate Hydrogels Independently by Cross-Linker Type and Cross-Linking Density. Macromolecules. Apr. 2000;33(11):4291-4294.
Lee et al., Engineering liver tissue spheroids with inverted colloidal crystal scaffolds. Biomaterials. Sep. 2009;30(27):4687-94.
Lee et al., Hydrogel Formation via Vell Crosslinking. Advanced Materials. Nov. 2003;15(21):1828-1832.
Lee et al., Hydrogels for tissue engineering. Chem Rev. Jul. 2001;101(7):1869-79.
Lee et al., Intravenous hMSCs improve myocardial infarction in mice because cells embolized in lung are activated to secrete the anti-inflammatory protein TSG-6. Cell Stem Cell. Jul. 2, 2009;5(1):54-63.
Lefaucheur et al., The cellular events of injured muscle regeneration depend on the nature of the injury. Neuromuscul Disord. Nov. 1995;5(6):501-9.
Lele et al., Investigating complexity of protein-protein interactions in focal adhesions. Biochem Biophys Res Commun. May 9, 2008;369(3):929-34.

(56) References Cited

OTHER PUBLICATIONS

Lensch et al., Scientific and clinical opportunities for modeling blood disorders with embryonic stem cells. Blood. Apr. 1, 2006;107(7):2605-12.
Leor et al., Cells, scaffolds, and molecules for myocardial tissue engineering. Pharmacol Ther. Feb. 2005;105(2):151-63.
Leshem et al., Hepatocyte growth factor (HGF) inhibits skeletal muscle cell differentiation: a role for the bHLH protein twist and the cdk inhibitor p27. J Cell Physiol. Jul. 2000;184(1):101-9.
Letsinger et al., Phosphoramidate analogs of oligonucleotides. J Org Chem. Nov. 1970;35(11):3800-3.
Levental et al., Soft biological materials and their impact on cell function. Soft Matter. 2007;3:299-306.
Li et al., Effect of growth factors and extracellular matrix materials on the proliferation and differentiation of microencapsulated myoblasts. J Biomater Sci Polym Ed. 2003;14(6):533-49.
Li et al., Effects of Three-Dimensional Scaffolds on Cell Organization and Tissue Development. Biotechnology and Bioprocess Engineering. Oct. 2001;6(5):311-325.
Li et al., pH sensitive Laponite/alginate hybrid hydrogels: swelling behaviour and release mechanism. Soft Matter. 2011;7:6231-6238.
Li et al., Purified hybrid cells from dendritic cell and tumor cell fusions are superior activators of antitumor immunity. Cancer Immunol Immunother. Nov. 2001;50(9):456-62.
Li et al., Recent advances of biomaterials in biotherapy. Regen Biomater. Jun. 2016;3(2):99-105.
Li, TNF-alpha is a mitogen in skeletal muscle. Am J Physiol Cell Physiol. Aug. 2003;285(2):C370-6.
Liederer et al., Enzymes involved in the bioconversion of ester-based prodrugs. J Pharm Sci. Jun. 2006;95(6):1177-95.
Lin et al., Transdermal regulation of vascular network bioengineering using a photopolymerizable methacrylated gelatin hydrogel. Biomaterials. Sep. 2013;34(28):6785-96.
Lipton et al., Developmental fate of skeletal muscle satellite cells. Science. Sep. 21, 1979;205(4412):1292-4.
Liu et al., Heterobifunctional poly(ethylene glycol)-tethered bone morphogenetic protein-2-stimulated bone marrow mesenchymal stromal cell differentiation and osteogenesis. Tissue Eng. May 2007;13(5):1113-24.
Liu et al., Immunostimulatory CpG oligodeoxynucleotides enhance the immune response to vaccine strategies involving granulocyte-macrophage colony-stimulating factor. Blood. Nov. 15, 1998;92(10):3730-6.
Liu et al., Nanostructured materials designed for cell binding and transduction. Biomacromolecules. 2001 Summer;2(2):362-8.
Liu et al., On the viscoelastic character of liver tissue: experiments and modelling of the linear behaviour. Biorheology. 2000;37(3):191-201.
Liu et al., Preparation of uniform calcium alginate gel beads by membrane emulsification coupled with internal gelation. Journal of Applied Polymer Science. Nov. 22, 2002;87(5):848-852.
Liu et al., Selective inhibition of IDO1 effectively regulates mediators of antitumor immunity. Blood. Apr. 29, 2010;115(17):3520-30.
Liu et al., Syntheses of click PEG-dexamethasone conjugates for the treatment of rheumatoid arthritis. Biomacromolecules. Oct. 11, 2010;11(10):2621-8.
Liu, Dendritic cell subsets and lineages, and their functions in innate and adaptive immunity. Cell. Aug. 10, 2001;106(3):259-62.
Lo et al., Cell movement is guided by the rigidity of the substrate. Biophys J. Jul. 2000;79(1):144-52.
Lodish et al., Collagen: The Fibrous Proteins of the Matrix. Molecular Cell Biology. W.H. Freeman, New York. 2000;Section 22.3:979-985.
Lopez et al., Magnetic Applications of Polymer Gels. Macromol Symp. 2001;166(1):173-178.
Lu et al., Muscle-derived stem cells seeded into acellular scaffolds develop calcium-dependent contractile activity that is modulated by nicotinic receptors. Urology. Jun. 2003;61(6):1285-91.

Lubeck, The costs of musculoskeletal disease: health needs assessment and health economics. Best Pract Res Clin Rheumatol. Jun. 2003;17(3):529-39.
Ludewig et al., Immunotherapy with dendritic cells directed against tumor antigens shared with normal host cells results in severe autoimmune disease. J Exp Med. Mar. 6, 2000;191(5):795-804.
Lumelsky et al., Differentiation of embryonic stem cells to insulin-secreting structures similar to pancreatic islets. Science. May 18, 2001;292(5520):1389-94.
Lutolf et al., Repair of bone defects using synthetic mimetics of collagenous extracellular matrices. Nat Biotechnol. May 2003;21(5):513-8.
Lutterotti et al., Antigen-specific tolerance by autologous myelin peptide-coupled cells: a phase 1 trial in multiple sclerosis. Sci Transl Med. Jun. 5, 2013;5(188):188ra75.
Mach et al., Differences in dendritic cells stimulated in vivo by tumors engineered to secrete granulocyte-macrophage colony-stimulating factor or Flt3-ligand. Cancer Res. Jun. 15, 2000;60(12):3239-46.
Magram et al., IL-12-deficient mice are defective but not devoid of type 1 cytokine responses. Ann N Y Acad Sci. Oct. 31, 1996;795:60-70.
Maini, Spatial and spatio-temporal patterns in a cell-haptotaxis model. J Math Biol. 1989;27(5):507-22.
Majeti et al., Identification of a hierarchy of multipotent hematopoietic progenitors in human cord blood. Cell Stem Cell. Dec. 13, 2007;1(6):635-45.
Maldonado et al., How tolerogenic dendritic cells induce regulatory T cells. Adv Immunol. 2010;108:111-65.
Maley et al., Extracellular matrix, growth factors,genetics: their influence on cell proliferation and myotube formation in primary cultures of adult mouse skeletal muscle. Exp Cell Res. Jul. 1995;219(1):169-79.
Malhotra et al., Use of an oncolytic virus secreting GM-CSF as combined oncolytic and immunotherapy for treatment of colorectal and hepatic adenocarcinomas. Surgery. Apr. 2007;141(4):520-9.
Malmqvist, Biospecific interaction analysis using biosensor technology. Nature. Jan. 14, 1993;361(6408):186-7.
Mammoto et al., Mechanical control of tissue and organ development. Development. May 2010; 137(9):1407-20.
Manavski et al., Vascular niche controls organ regeneration. Circ Res. Mar. 28, 2014;114(7):1077-9.
Mansoor et al., Engineering T cells for cancer therapy. Br J Cancer. Nov. 14, 2005;93(10):1085-91.
Martinsen et al., Alginate as immobilization material: I. Correlation between chemical and physical properties of alginate gel beads. Biotechnol Bioeng. Jan. 5, 1989;33(1):79-89.
Marui et al., Simultaneous application of basic fibroblast growth factor and hepatocyte growth factor to enhance the blood vessels formation. J Vasc Surg. Jan. 2005;41(1):82-90.
Masedunskas et al., Role for the actomyosin complex in regulated exocytosis revealed by intravital microscopy. Proc Natl Acad Sci U S A. Aug. 16, 2011;108(33):13552-7.
Massia et al., An RGD spacing of 440 nm is sufficient for integrin alpha V beta 3-mediated fibroblast spreading and 140 nm for focal contact and stress fiber formation. J Cell Biol. Sep. 1991;114(5):1089-100.
Matthew et al., Subperiosteal behaviour of alginate and cellulose wound dressing materials. Biomaterials. Mar. 1995;16(4):275-8.
McColl, Chemokines and dendritic cells: a crucial alliance. Immunol Cell Biol. Oct. 2002;80(5):489-96.
McConnell et al., Vaccination with outer membrane complexes elicits rapid protective immunity to multidrug-resistant Acinetobacter baumannii. Infect Immun. Jan. 2011;79(1):518-26.
McDonald et al., Early fracture callus displays smooth muscle-like viscoelastic properties ex vivo: implications for fracture healing. J Orthop Res. Nov. 2009;27(11):1508-13.
McKinney-Freeman et al., Muscle-derived hematopoietic stem cells are hematopoietic in origin. Proc Natl Acad Sci U S A. Feb. 5, 2002;99(3):1341-6.
McKinnon et al., Biophysically defined and cytocompatible covalently adaptable networks as viscoelastic 3D cell culture systems. Adv Mater. Feb. 12, 2014;26(6):865-72.

(56) References Cited

OTHER PUBLICATIONS

McPherron et al., Regulation of skeletal muscle mass in mice by a new TGF-beta superfamily member. Nature. May 1, 1997;387(6628):83-90.
McQualter et al., Granulocyte macrophage colony-stimulating factor: a new putative therapeutic target in multiple sclerosis. J Exp Med. Oct. 1, 2001;194(7):873-82.
McWhorter et al., Modulation of macrophage phenotype by cell shape. Proc Natl Acad Sci USA. Oct. 22, 2013;110(43):17253-8.
Mehta et al., Engineering New Approaches to Cancer Vaccines. Cancer Immunol Res. Aug. 2015;3(8):836-43.
Meier et al., Peptide Nucleic Acids(PNAs)-Unusual Properties of Noionic Oligonucleotide Analogues. Angewandte Chemie, Int'l Edition. Aug. 1992;31(8):1008-1010.
Melero-Martin et al., Engineering robust and functional vascular networks in vivo with human adult and cord blood-derived progenitor cells. Circ Res. Jul. 18, 2008;103(2):194-202. Includes supplementary materials.
Melief et al., Immunotherapy of established (pre)malignant disease by synthetic long peptide vaccines. Nat Rev Cancer. May 2008;8(5):351-60.
Mellman et al., Dendritic cells: specialized and regulated antigen processing machines. Cell. Aug. 10, 2001;106(3):255-8.
Menetry et al., Suturing Versus Immobilization of a Muscle Laceration: A Morphological and Functional Study in a Mouse Model. Am J Sports Med. 1999;27(2):222-229.
Meraz et al., Mesoporous Silicon Particles for the Presentation of Tumor Antigens and Adjuvant for Anti-Cancer Immunity. Cancer Res. 2011;71(S24):159s-160s, Abstract #P1-01-12.
Merck, Merck Announces Presentation of Interim Data from Phase 1B Study of MK-3475, Investigational anti-PD-1 Immunotherapy, in Previously-Treated Patients with Non-Small Cell Lung Cancer (NSCLC) at 15th World Conference on Lung Cancer. Merck Newsroom Home. 3 pages, Oct. 29, 2013.
Merkel et al., Using mechanobiological mimicry of red blood cells to extend circulation times of hydrogel microparticles. Proc Natl Acad Sci U S A. Jan. 11, 2011;108(2):586-91.
Merriam-Webster, Transient. Merriam-Webster Dictionary. Web. Jul. 18, 2014. www.merriam-webster.com/dictionary/transient. 3 pages.
Metters et al., Fundamental studies of biodegradable hydrogels as cartilage replacement materials. Biomed Sci Instrum. 1999;35:33-8.
Meyer et al., Clinical investigations of Toll-like receptor agonists. Expert Opin Investig Drugs. Jul. 2008;17(7):1051-65.
Meylan et al., Intracellular pattern recognition receptors in the host response. Nature. Jul. 6, 2006;442(7098):39-44.
MGI, Mouse Facts. Retrieved online at: http://www.informatics.jax.org/mgihome/other/mouse_facts1.shtml. 2 pages. Jul. 31, 2018.
Miljkovic et al., Chondrogenesis, bone morphogenetic protein-4 and mesenchymal stem cells. Osteoarthritis Cartilage. Oct. 2008;16(10):1121-30.
Miller et al., Hepatocyte growth factor affects satellite cell activation and differentiation in regenerating skeletal muscle. Am J Physiol Cell Physiol. Jan. 2000;278(1):C174-81.
Miller et al., Lipopolysaccharide sequestrants: structural correlates of activity and toxicity in novel acylhomospermines. J Med Chem. Apr. 7, 2005;48(7):2589-99.
Miller et al., Melanoma. N Engl J Med. Jul. 6, 2006;355(1):51-65.
Miralles et al., Actin dynamics control SRF activity by regulation of its coactivator MAL. Cell. May 2, 2003;113(3):329-42.
Mitchell et al., The exogenous administration of basic fibroblast growth factor to regenerating skeletal muscle in mice does not enhance the process of regeneration. Growth Factors. 1996;13(1-2):37-55.
Miyata et al., Biomolecule-sensitive hydrogels. Adv Drug Deliv Rev. Jan. 17, 2002;54(1):79-98.
Mohan et al., Novel Porous, Polysaccharide Scaffolds for Tissue Engineering Applications. Trends Biomater Artif Organs. 2005;18(2):219-224.
Moioli et al., Matrices and scaffolds for drug delivery in dental, oral and craniofacial tissue engineering. Adv Drug Deliv Rev. May 30, 2007;59(4-5):308-24.
Molinari et al., Modification of surface membrane antigens by trypsin. Proc Soc Exp Biol Med. Apr. 1975;148(4):991-4.
Molloy et al., Movement and force produced by a single myosin head. Nature. Nov. 9, 1995;378(6553):209-12.
Mooney et al., Cytoskeletal filament assembly and the control of cell spreading and function by extracellular matrix. J Cell Sci. Jun. 1995;108 (Pt 6):2311-20.
Mooney et al., Switching from differentiation to growth in hepatocytes: control by extracellular matrix. J Cell Physiol. Jun. 1992;151(3):497-505.
Moser et al., Dendritic cell regulation of TH1-TH2 development. Nat Immunol. Sep. 2000;1(3):199-205.
Mulder et al., Wound Management: Past, Present, and Future. Clinicians' Pocket Guide to Chronic Wound Repair. Springhouse Corporation, Springhouse, Pennsylvania. 1998:85-90.
Muralidharan-Chari et al., ARF6-regulated shedding of tumor cell-derived plasma membrane microvesicles. Curr Biol. Dec. 1, 2009;19(22):1875-85.
Murdan, Electro-responsive drug delivery from hydrogels. J Control Release. Sep. 19, 2003;92(1-2):1-17.
Nagai et al., A variant of yellow fluorescent protein with fast and efficient maturation for cell-biological applications. Nat Biotechnol. Jan. 2002;20(1):87-90.
Naik et al., Development of plasmacytoid and conventional dendritic cell subtypes from single precursor cells derived in vitro and in vivo. Nat Immunol. Nov. 2007;8(11):1217-26.
Nair et al., Polymers as biomaterials for tissue engineering and controlled drug delivery. Adv Biochem Eng Biotechnol. 2006;102:47-90.
NCBI Accession No. 000749.2, Apr. 1, 2012.
NCBI Accession No. 000758, Apr. 1, 2012.
NCBI Accession No. 001020537, Jan. 30, 2011.
NCBI Accession No. 001020538, Jan. 30, 2011.
NCBI Accession No. 001020539, Jan. 30, 2011.
NCBI Accession No. 001020540, Jan. 30, 2011.
NCBI Accession No. 001028928, Jan. 30, 2011.
NCBI Accession No. 001193, May 3, 2014.
NCBI Accession No. 001552.2, Mar. 16, 2014.
NCBI Accession No. 001561.5, Mar. 16, 2014.
NCBI Accession No. 003237.2, May 25, 2014.
NCBI Accession No. 003265, Dec. 30, 2012.
NCBI Accession No. 003318.1, May 4, 2014.
NCBI Accession No. 003327.3, May 4, 2014.
NCBI Accession No. 003367, Jan. 30, 2011.
NCBI Accession No. 004119, Apr. 14, 2013.
NCBI Accession No. 004448.3, Apr. 23, 2014.
NCBI Accession No. 005009.2, Apr. 27, 2014.
NCBI Accession No. 005018.2, Apr. 27, 2014.
NCBI Accession No. 006274.2, Mar. 31, 2013.
NCBI Accession No. 017442, Apr. 14, 2012.
NCBI Accession No. 059138, Apr. 14, 2012.
NCBI Accession No. 181780.3, Jan. 27, 2014.
NCBI Accession No. 861445.3, Jan. 27, 2014.
Nehls et al., A novel, microcarrier-based in vitro assay for rapid and reliable quantification of three-dimensional cell migration and angiogenesis. Microvasc Res. Nov. 1995;50(3):311-22.
Nestle et al., Vaccination of melanoma patients with peptide- or tumorlysate-pulsed dendritic cells. Nature Medicine. Mar. 1, 1998;4(3):328-32.
Neves et al., Imaging cell surface glycosylation in vivo using "double click" chemistry. Bioconjug Chem. Jun. 19, 2013;24(6):934-41.
Niamlang et al., Electrically controlled release of salicylic acid from poly(p-phenylene vinylene)/polyacrylamide hydrogels. Int J Pharm. Apr. 17, 2009;371(1-2):126-33.
Nichol et al., Cell-laden microengineered gelatin methacrylate hydrogels. Biomaterials. Jul. 2010;31(21):5536-44.
Nicodemus et al., Cell encapsulation in biodegradable hydrogels for tissue engineering applications. Tissue Eng Part B Rev. Jun. 2008;14(2):149-65.

(56) References Cited

OTHER PUBLICATIONS

Niessen et al., The alpha 6 beta 4 integrin is a receptor for both laminin and kalinin. Exp Cell Res. Apr. 1994;211(2):360-7.
NIH—National Cancer Institute, AMP-224, anti-PD-1 fusion protein AMP-224. Retrieved online at: https://www.cancer/gov/publications/dictionaries/cancer-drug/def/anti-pd-1-fusion-protein-amp-224. 1 page, (2019).
Ning et al., Protein modification by strain-promoted alkyne-nitrone cycloaddition. Angew Chem Int Ed Engl. Apr. 12, 2010;49(17):3065-8.
Nogueira De Francischi et al., Inhibition by rapamycin of leukocyte migration and bronchial hyperreactivity induced by injection of Sephadex beads to guinea-pigs. Br J Pharmacol. Dec. 1993;110(4):1381-6.
Noguera-Troise et al., Blockade of Dll4 inhibits tumour growth by promoting non-productive angiogenesis. Nature. Dec. 21, 2006;444(7122):1032-7.
Nuttelman et al., Dexamethasone-functionalized gels induce osteogenic differentiation of encapsulated hMSCs. J Biomed Mater Res A. Jan. 2006;76(1):183-95.
Ní Annaidh et al., Characterization of the anisotropic mechanical properties of excised human skin. J Mech Behav Biomed Mater. Jan. 2012;5(1):139-48.
O'Garra et al., Are dendritic cells afraid of commitment? Nat Immunol. Dec. 2004;5(12):1206-8.
O'Shea et al., Type 1 IFNs and regulation of TH1 responses: enigmas both resolved and emerge. Nat Immunol. Jul. 2000;1(1):17-9.
Ohashi et al., Surgical excision combined with autologous whole tumor cell vaccination is an effective therapy for murine neuroblastoma. J Pediatr Surg. Aug. 2006;41(8):1361-8.
Ohlstein et al., The stem cell niche: theme and variations. Curr Opin Cell Biol. Dec. 2004;16(6):693-9.
Oldenburg et al., TLR13 recognizes bacterial 23S rRNA devoid of erythromycin resistance-forming modification. Science. Aug. 31, 2012;337(6098):1111-5.
Oldenhove et al., Decrease of Foxp3+ Treg cell number and acquisition of effector cell phenotype during lethal infection. Immunity. Nov. 20, 2009;31(5):772-86.
Oneto et al., Implantable biomaterial based on click chemistry for targeting small molecules. Acta Biomaterialia. 2014;10:5099-5105.
Orner et al., Arrays for the combinatorial exploration of cell adhesion. J Am Chem Soc. Sep. 8, 2004;126(35):10808-9.
Osunkoya et al., Synthesis and fate of immunological surface receptors on cultured Burkitt lymphoma cells. Int J Cancer. Mar. 15, 1969;4(2):159-65.
Ota et al., Percutaneous subxiphoid access to the epicardium using a miniature crawling robotic device. Innovations (Phila). 2006 Fall;1(5):227-31.
Overwijk et al., Tumor regression and autoimmunity after reversal of a functionally tolerant state of self-reactive CD8+ T cells. J Exp Med. Aug. 18, 2003;198(4):569-80.
Ozawa et al., Microenvironmental VEGF concentration, not total dose, determines a threshold between normal and aberrant angiogenesis. J Clin Invest. Feb. 2004;113(4):516-27.
Padilla et al., Insufficient TLR activation contributes to the slow development of CD8+ T cell responses in Trypanosoma cruzi infection. J Immunol. Jul. 15, 2009;183(2):1245-52.
Page-McCaw et al., Matrix metalloproteinases and the regulation of tissue remodelling. Nat Rev Mol Cell Biol. Mar. 2007;8(3):221-33.
Pailler-Mattei et al., In vivo measurements of the elastic mechanical properties of human skin by indentation tests. Med Eng Phys. Jun. 2008;30(5):599-606.
Pajonk et al., From sol-gel to aerogels and cryogels. J Non Cryst Solids. May 1990;121(1-3):66-67.
Palacio et al., Interleukin 10 and tumor necrosis factor alpha gene expression in respiratory and peripheral muscles. Relation to sarcolemmal damage. Arch Bronconeumol. Jul. 2002;38(7):311-6.
Paradee et al., Effects of crosslinking ratio, model drugs, and electric field strength on electrically controlled release for alginate-based hydrogel. J Mater Sci Mater Med. Apr. 2012;23(4):999-1010.
Pardoll, The blockade of immune checkpoints in cancer immunotherapy. Nat Rev Cancer. Mar. 22, 2012;12(4):252-64.
Parekh et al., Modulus-driven differentiation of marrow stromal cells in 3D scaffolds that is independent of myosin-based cytoskeletal tension. Biomaterials. Mar. 2011;32(9):2256-64.
Parekkadan et al., Mesenchymal stem cell-derived molecules reverse fulminant hepatic failure. PLoS One. Sep. 26, 2007;2(9):e941.
Park et al., Photopolymerized hyaluronic acid-based hydrogels and interpenetrating networks. Biomaterials. Mar. 2003;24(6):893-900.
Parker et al., Effect of mitoxantrone on outcome of children with first relapse of acute lymphoblastic leukaemia (All R3): an open-label randomised trial. Lancet. Dec. 11, 2010;376(9757):2009-17.
Partridge et al., Conversion of mdx myofibres from dystrophin-negative to -positive by injection of normal myoblasts. Nature. Jan. 12, 1989;337(6203):176-9.
Patterson et al., Differential binding of chemokines to macrophages and neutrophils in the human inflamed synovium. Arthritis Res. 2002;4(3):209-14.
Pawlaczyk et al., Age-dependent biomechanical properties of the skin. Postepy Dermatol Alergol. Oct. 2013;30(5):302-6.
Pedersen et al., Induction of regulatory dendritic cells by dexamethasone and 1alpha, 25-Dihydroxyvitamin D(3). Immunol Lett. Jan. 30, 2004;91(1):63-9.
Pek et al., The effect of matrix stiffness on mesenchymal stem cell differentiation in a 3D thixotropic gel. Biomaterials. Jan. 2010;31(3):385-91.
Pelinkovic et al., Tissue engineering and gene therapy of the musculoskeletal system with muscle cells. Z Orthop Ihre Grenzgeb. Sep.-Oct. 2000;138(5):402-6.
Pena et al., Effects of TGF-beta and TGF-beta neutralizing antibodies on fibroblast-induced collagen gel contraction: implications for proliferative vitreoretinopathy. Invest Ophthalmol Vis Sci. May 1994;35(6):2804-8.
Peters et al., Engineering vascular networks in porous polymer matrices. J Biomed Mater Res. Jun. 15, 2002;60(4):668-78.
Peyton et al., The use of poly(ethylene glycol) hydrogels to investigate the impact of ECM chemistry and mechanics on smooth muscle cells. Biomaterials. Oct. 2006;27(28):4881-93.
Phillippi, Patterning of Multiple Cell Lineages from a Single Stem Cell Population. Annual Meeting of the American Society for Cell Biology. Dec. 10, 2006.
Pinho et al., PDGFRa and CD51 mark human nestin+ sphere-forming mesenchymal stem cells capable of hematopoietic progenitor cell expansion. J Exp Med. Jul. 1, 2013;210(7):1351-67.
Platten et al., Cancer Immunotherapy by Targeting IDO1/TDO and Their Downstream Effectors. Front Immunol. Jan. 12, 2015;5:673. 7 pages.
Pluen et al., Role of tumor-host interactions in interstitial diffusion of macromolecules: cranial vs. subcutaneous tumors. Proc Natl Acad Sci U S A. Apr. 10, 2001;98(8):4628-33.
Pooyan et al., Conjugates bearing multiple formyl-methionyl peptides display enhanced binding to but not activation of phagocytic cells. Bioconjug Chem. Mar.-Apr. 2002;13(2):216-23.
Pope et al., Organ-specific regulation of the CD8 T cell response to Listeria monocytogenes infection. J Immunol. Mar. 1, 2001;166(5):3402-9.
Porter et al., Separation of Natural Populations of Coliform Bacteria from Freshwater and Sewage by Magnetic-Bead Cell Sorting. J Microbiol Meth. 1998;33(3):221-226.
Pouzet et al., Factors affecting functional outcome after autologous skeletal myoblast transplantation. Ann Thorac Surg. Mar. 2001;71(3):844-50; discussion 850-1.
PRnewswire, GlaxoSmithKline and Amplimmune Form Global Strategic Collaboration. Alliance to Focus on AMP-224 for Cancer and Other Diseases. 3 pages, Aug. 4, 2010.
Pulendran et al., Flt3-ligand and granulocyte colony-stimulating factor mobilize distinct human dendritic cell subsets in vivo. J Immunol. Jul. 1, 2000;165(1):566-72.

(56) References Cited

OTHER PUBLICATIONS

Qi et al., Patterned differentiation of individual embryoid bodies in spatially organized 3D hybrid microgels. Adv Mater. Dec. 7, 2010;22(46):5276-81.
Qin et al., Soft lithography for micro- and nanoscale patterning. Nat Protoc. Mar. 2010;5(3):491-502.
Qiu et al., Environment-sensitive hydrogels for drug delivery. Adv Drug Deliv Rev. Dec. 31, 2001;53(3):321-39.
Qu et al., Development of approaches to improve cell survival in myoblast transfer therapy. J Cell Biol. Sep. 7, 1998;142(5):1257-67.
Qu-Petersen et al., Identification of a novel population of muscle stem cells in mice: potential for muscle regeneration. J Cell Biol. May 27, 2002;157(5):851-64.
Quezada et al., CTLA4 blockade and GM-CSF combination immunotherapy alters the intratumor balance of effector and regulatory T cells. J Clin Invest. Jul. 2006;116(7):1935-45.
Quintana et al., Autoantibody patterns in diabetes-prone NOD mice and in standard C57BL/6 mice. J Autoimmun. Nov. 2001; 17(3):191-7.
Raeber et al., Molecularly engineered PEG hydrogels: a novel model system for proteolytically mediated cell migration. Biophys J. Aug. 2005;89(2):1374-88.
Rajagopalan et al., Regional angiogenesis with vascular endothelial growth factor in peripheral arterial disease: a phase II randomized, double-blind, controlled study of adenoviral delivery of vascular endothelial growth factor 121 in patients with disabling intermittent claudication. Circulation. Oct. 21, 2003;108(16):1933-8.
Ramón-azcon et al., Gelatin methacrylate as a promising hydrogel for 3D microscale organization and proliferation of dielectrophoretically patterned cells. Lab on a Chip. Aug. 21, 2012;12(16):2959-69.
Randolph et al., Migration of dendritic cell subsets and their precursors. Annu Rev Immunol. 2008;26:293-316.
Ranganath et al., Harnessing the mesenchymal stem cell secretome for the treatment of cardiovascular disease. Cell Stem Cell. Mar. 2, 2012;10(3):244-58.
Raposo et al., Extracellular vesicles: exosomes, microvesicles, and friends. J Cell Biol. Feb. 18, 2013;200(4):373-83.
Rappolee et al., Macrophage-derived growth factors. Curr Top Microbiol Immunol. 1992;181:87-140.
Rapraeger, Syndecan-regulated receptor signaling. J Cell Biol. May 29, 2000;149(5):995-8.
Rautio et al., Prodrugs: design and clinical applications. Nat Rev Drug Discov. Mar. 2008;7(3):255-70.
Reddy et al., Exploiting lymphatic transport and complement activation in nanoparticle vaccines. Nat Biotechnol. Oct. 2007;25(10):1159-64.
Reimann et al., Satellite Cells in Normal and Regenerated Soleus Muscles of mdx and Control Mice. Eur J Neurosci. 1998;10:366, Abstract No. 153.07.
Reis E Sousa., Activation of dendritic cells: translating innate into adaptive immunity. Curr Opin Immunol. Feb. 2004;16(1):21-5.
Research Results of National Institute of Advanced Industrial Science and Technology, retrieved online at: http://www.aist.go.jp/aist_j/press_release/pr2006/pr20060719.html. 4 pages, (2006).
Rhoads et al., Satellite cell-mediated angiogenesis in vitro coincides with a functional hypoxia-inducible factor pathway. Am J Physiol Cell Physiol. Jun. 2009;296(6):C1321-8.
Ribas et al., Phase III randomized clinical trial comparing tremelimumab with standard-of-care chemotherapy in patients with advanced melanoma. J Clin Oncol. Feb. 10, 2013;31(5):616-22.
Richards Grayson et al., Multi-pulse drug delivery from a resorbable polymeric microchip device. Nat Mater. Nov. 2003;2(11):767-72.
Richardson et al., Polymeric system for dual growth factor delivery. Nat Biotechnol. Nov. 2001;19(11):1029-34.
Riddle et al., Role of poly(lactide-co-glycolide) particle size on gas-foamed scaffolds. J Biomater Sci Polym Ed. 2004;15(12):1561-70.
Ridgway et al., Inhibition of Dll4 signalling inhibits tumour growth by deregulating angiogenesis. Nature. Dec. 21, 2006;444(7122):1083-7.
Rinderknecht et al., The amino acid sequence of human insulin-like growth factor I and its structural homology with proinsulin. J Biol Chem. Apr. 25, 1978;253(8):2769-76.
Rizzo et al., An improved cyan fluorescent protein variant useful for FRET. Nat Biotechnol. Apr. 2004;22(4):445-9.
Roccaro et al., BM mesenchymal stromal cell-derived exosomes facilitate multiple myeloma progression. J Clin Invest. Apr. 2013;123(4):1542-55.
Rodriguez et al., Minimal "Self" peptides that inhibit phagocytic clearance and enhance delivery of nanoparticles. Science. Feb. 22, 2013;339(6122):971-5.
Rosenberg et al., Cancer immunotherapy: moving beyond current vaccines. Nat Med. Sep. 2004;10(9):909-15.
Rosenberg et al., Impact of cytokine administration on the generation of antitumor reactivity in patients with metastatic melanoma receiving a peptide vaccine. J Immunol. Aug. 1, 1999;163(3):1690-5.
Rossin et al., Diels-Alder reaction for tumor pretargeting: in vivo chemistry can boost tumor radiation dose compared with directly labeled antibody. J Nucl Med. Nov. 2013;54(11):1989-95.
Rossin et al., In vivo chemistry for pretargeted tumor imaging in live mice. Angew Chem Int Ed Engl. Apr. 26, 2010;49(19):3375-8.
Roth et al., SC68896, a novel small molecule proteasome inhibitor, exerts antiglioma activity in vitro and in vivo. Clin Cancer Res. Nov. 1, 2009;15(21):6609-18.
Rowlands et al., Directing osteogenic and myogenic differentiation of MSCs: interplay of stiffness and adhesive ligand presentation. Am J Physiol Cell Physiol. Oct. 2008;295(4):C1037-44.
Rowley et al., Alginate hydrogels as synthetic extracellular matrix materials. Biomaterials. Jan. 1999;20(1):45-53.
Rowley et al., Alginate type and RGD density control myoblast phenotype. J Biomed Mater Res. May 2002;60(2):217-23.
Rowley et al., Biomaterials to Spatially Regulate Cell Fate. Adv Mater. Jun. 2002;14(12):886-889.
Rubin et al., Dissociation of heparan sulfate and receptor binding domains of hepatocyte growth factor reveals that heparan sulfate-c-met interaction facilitates signaling. J Biol Chem. Aug. 31, 2001;276(35):32977-83.
Ryten et al., ATP regulates the differentiation of mammalian skeletal muscle by activation of a P2X5 receptor on satellite cells. J Cell Biol. Jul. 22, 2002;158(2):345-55.
Ryu et al., The construction of three-dimensional micro-fluidic scaffolds of biodegradable polymers by solvent vapor based bonding of micro-molded layers. Biomaterials. Feb. 2007;28(6):1174-84.
Sacchetti et al., Self-renewing osteoprogenitors in bone marrow sinusoids can organize a hematopoietic microenvironment. Cell. Oct. 19, 2007;131(2):324-36.
Sakai et al., An injectable, in situ enzymatically gellable, gelatin derivative for drug delivery and tissue engineering. Biomaterials. Jul. 2009;30(20):3371-7.
Salem et al., Defining the antigen-specific T-cell response to vaccination and poly(I:C)/TLR3 signaling: evidence of enhanced primary and memory CD8 T-cell responses and antitumor immunity. J Immunother. May-Jun. 2005;28(3):220-8.
Salvador et al., Combination of immune stimulating adjuvants with poly(lactide-co-glycolide) microspheres enhances the immune response of vaccines. Vaccine. Jan. 11, 2012;30(3):589-96.
Salvay et al., Inductive tissue engineering with protein and DNA-releasing scaffolds. Mol Biosyst. Jan. 2006;2(1):36-48.
Sano et al., Swift development of protective effector functions in naive CD8(+) T cells against malaria liver stages. J Exp Med. Jul. 16, 2001;194(2):173-9.
Sansonetti, The innate signaling of dangers and the dangers of innate signaling. Nat Immunol. Dec. 2006;7(12):1237-42.
Santini et al., A controlled-release microchip. Nature. Jan. 28, 1999;397(6717):335-8.
Sarkar et al., Condensation of oligonucleotides assembled into nicked and gapped duplexes: potential structures for oligonucleotide delivery. Nucleic Acids Res. Jan. 7, 2005;33(1):143-51.
Sato, Human dendritic cells. Biotherapy. Nov. 2004;18(6):467-77.

(56) References Cited

OTHER PUBLICATIONS

Saxena et al., Skeletal muscle tissue engineering using isolated myoblasts on synthetic biodegradable polymers: preliminary studies. Tissue Eng. Dec. 1999;5(6):525-32.
Saxon et al., Cell surface engineering by a modified Staudinger reaction. Science. Mar. 17, 2000;287(5460):2007-10.
Schaefer et al., Innate immunity in the human female reproductive tract: antiviral response of uterine epithelial cells to the TLR3 agonist poly(I:C). J Immunol. Jan. 15, 2005;174(2):992-1002.
Scheel et al., Toll-like receptor-dependent activation of several human blood cell types by protamine-condensed mRNA. Eur J Immunol. May 2005;35(5):1557-66.
Schijns et al., Mice lacking IL-12 develop polarized Th1 cells during viral infection. J Immunol. Apr. 15, 1998;160(8):3958-64.
Schnorrer et al., The dominant role of CD8+ dendritic cells in cross-presentation is not dictated by antigen capture. Proc Natl Acad Sci U S A. Jul. 11, 2006;103(28):10729-34.
Schofield, The relationship between the spleen colony-forming cell and the haemopoietic stem cell. Blood Cells. 1978;4(1-2):7-25.
Schuler et al., The use of dendritic cells in cancer immunotherapy. Curr Opin Immunol. Apr. 2003;15(2):138-47.
Schwartz, Integrins and extracellular matrix in mechanotransduction. Cold Spring Harb Perspect Biol. Dec. 2010;2(12):a005066.
Seale et al., Pax7 is required for the specification of myogenic satellite cells. Cell. Sep. 15, 2000;102(6):777-86.
Sensi et al., Unique tumor antigens: evidence for immune control of genome integrity and immunogenic targets for T cell-mediated patient-specific immunotherapy. Clin Cancer Res. Sep. 1, 2006;12(17):5023-32.
Serafini et al., High-dose granulocyte-macrophage colony-stimulating factor-producing vaccines impair the immune response through the recruitment of myeloid suppressor cells. Cancer Res. Sep. 1, 2004;64(17):6337-43.
Shakweh et al., Design and characterisation of poly(lactide-co-glycolide) small particulate systems for the delivery of immunostimulant CpG oligonucleotide. J Nanosci Nanotechnol. Sep.-Oct. 2006;6(9-10):2811-20.
Shaner et al., Improved monomeric red, orange and yellow fluorescent proteins derived from *Discosoma* sp. red fluorescent protein. Nat Biotechnol. Dec. 2004;22(12):1567-72.
Shansky et al., A simplified method for tissue engineering skeletal muscle organoids in vitro. In Vitro Cell Dev Biol Anim. Oct. 1997;33(9):659-61.
Shapiro et al., Sizing it up: cellular MRI using micron-sized iron oxide particles. Magn Reson Med. Feb. 2005;53(2):329-38.
Sheehan et al., Skeletal muscle satellite cell proliferation in response to members of the fibroblast growth factor family and hepatocyte growth factor. J Cell Physiol. Dec. 1999;181(3):499-506.
Sheppard et al., Polyethyleneimine is a potent systemic adjuvant for glycoprotein antigens. Int Immunol. Oct. 2014;26(10):531-8.
Sheridan et al., Bioabsorbable polymer scaffolds for tissue engineering capable of sustained growth factor delivery. J Control Release. Feb. 14, 2000;64(1-3):91-102.
Shi et al., A novel Toll-like receptor that recognizes vesicular stomatitis virus. J Biol Chem. Feb. 11, 2011;286(6):4517-24.
Shi et al., Granulocyte-macrophage colony-stimulating factor (GM-CSF) and T-cell responses: what we do and don't know. Cell Res. Feb. 2006;16(2):126-33.
Shin et al., Contractile forces sustain and polarize hematopoiesis from stem and progenitor cells. Cell Stem Cell. Jan. 2, 2014;14(1):81-93.
Shin et al., Lamins regulate cell trafficking and lineage maturation of adult human hematopoietic cells. Proc Natl Acad Sci U S A. Nov. 19, 2013;110(47):18892-7.
Shin et al., Myosin-II inhibition and soft 2D matrix maximize multinucleation and cellular projections typical of platelet-producing megakaryocytes. Proc Natl Acad Sci U S A. Jul. 12, 2011;108(28):11458-63.
Shoichet et al., Stability of hydrogels used in cell encapsulation: An in vitro comparison of alginate and agarose. Biotechnol Bioeng. May 20, 1996;50(4):374-81.
Shortman et al., Steady-state and inflammatory dendritic-cell development. Nat Rev Immunol. Jan. 2007;7(1):19-30.
Sick et al., WNT and DKK determine hair follicle spacing through a reaction-diffusion mechanism. Science. Dec. 1, 2006;314(5804):1447-50.
Siegwart et al., Synthesis, characterization, and in vitro cell culture viability of degradable poly(N-isopropylacrylamide-co-5,6-benzo-2-methylene-1,3-dioxepane)-based polymers and crosslinked gels. J Biomed Mater Res A. Nov. 2008;87(2):345-58.
Silva et al., Effects of VEGF temporal and spatial presentation on angiogenesis. Biomaterials. Feb. 2010;31(6):1235-41.
Silva et al., Material-based deployment enhances efficacy of endothelial progenitor cells. Proc Natl Acad Sci U S A. Sep. 23, 2008;105(38):14347-52.
Silva et al., Spatiotemporal control of vascular endothelial growth factor delivery from injectable hydrogels enhances angiogenesis. J Thromb Haemost. Mar. 2007;5(3):590-8.
Simmons et al., GM-CSF as a systemic adjuvant in a phase II prostate cancer vaccine trial. Prostate. Jun. 1, 1999;39(4):291-7.
Simpson et al., Fc-dependent depletion of tumor-infiltrating regulatory T cells co-defines the efficacy of anti-CTLA-4 therapy against melanoma. J Exp Med. Aug. 26, 2013;210(9):1695-710.
Singer et al., Cutaneous wound healing. N Engl J Med. Sep. 2, 1999;341(10):738-46.
Skokos et al., CD8-DCs induce IL-12-independent Th1 differentiation through Delta 4 Notch-like ligand in response to bacterial LPS. J Exp Med. Jul. 9, 2007;204(7):1525-31.
Skuk et al., Efficacy of myoblast transplantation in nonhuman primates following simple intramuscular cell injections: toward defining strategies applicable to humans. Exp Neurol. May 2002;175(1):112-26.
Skuk et al., Myoblast transplantation: the current status of a potential therapeutic tool for myopathies. J Muscle Res Cell Motil. 2003;24(4-6):285-300.
Sletten et al., A bioorthogonal quadricyclane ligation. J Am Chem Soc. Nov. 9, 2011;133(44):17570-3.
Sletten et al., A hydrophilic azacyclooctyne for Cu-free click chemistry. Org Lett. Jul. 17, 2008;10(14):3097-9.
Smidsrød et al., Alginate as immobilization matrix for cells. Trends Biotechnol. Mar. 1990;8(3):71-8.
Sohier et al., Critical factors in the design of growth factor releasing scaffolds for cartilage tissue engineering. Expert Opin Drug Deliv. May 2008;5(5):543-66.
Solon et al., Fibroblast adaptation and stiffness matching to soft elastic substrates. Biophys J. Dec. 15, 2007;93(12):4453-61.
Sonawane et al., Chloride accumulation and swelling in endosomes enhances DNA transfer by polyamine-DNA polyplexes. J Biol Chem. Nov. 7, 2003;278(45):44826-31.
Stachowiak et al., Inverse opal hydrogel-collagen composite scaffolds as a supportive microenvironment for immune cell migration. J Biomed Mater Res A. Jun. 1, 2008;85(3):815-28.
Steinman et al., Taking dendritic cells into medicine. Nature. Sep. 27, 2007;449(7161):419-26.
Stockmann et al., Exploring isonitrile-based click chemistry for ligation with biomolecules. Organic & Biomolecular Chemistry. 2011;9:7300-7302.
Storrie et al., Sustained delivery of plasmid DNA from polymeric scaffolds for tissue engineering. Adv Drug Deliv Rev. Jul. 7, 2006;58(4):500-14.
Straub et al., Animal models for muscular dystrophy show different patterns of sarcolemmal disruption. J Cell Biol. Oct. 20, 1997;139(2):375-85.
Sun et al., Biomimetic interpenetrating polymer network hydrogels based on methacrylated alginate and collagen for 3D pre-osteoblast spreading and osteogenic differentiation. Soft Matter. Jan. 12, 2012;8:2398-2404.
Sun et al., Highly stretchable and tough hydrogels. Nature. Sep. 6, 2012;489(7414):133-6.

(56) References Cited

OTHER PUBLICATIONS

Sun et al., Sustained vascular endothelial growth factor delivery enhances angiogenesis and perfusion in ischemic hind limb. Pharm Res. Jul. 2005;22(7):1110-6.
Suri et al., Photopatterned collagen-hyaluronic acid interpenetrating polymer network hydrogels. Acta Biomater. Sep. 2009;5(7):2385-97.
Suzuki et al., A novel small-molecule inhibitor of transforming growth factor beta type I receptor kinase (SM16) inhibits murine mesothelioma tumor growth in vivo and prevents tumor recurrence after surgical resection. Cancer Res. Mar. 1, 2007;67(5):2351-9.
Swift et al., Nuclear lamin-A scales with tissue stiffness and enhances matrix-directed differentiation. Science. Aug. 30, 2013;341(6149):1240104. 17 pages.
Syed et al., Stem cell therapy market. Nat Rev Drug Discov. Mar. 2013;12(3):185-6.
Tabata et al., Enhanced Vascularization and Tissue Granulation by Basic Fibroblast Growth Factor Impregnated in Gelatin Hydrogels. Journal of Controlled Release. Sep. 1994;31(2):189-199.
Takahashi et al., Induction of pluripotent stem cells from adult human fibroblasts by defined factors. Cell. Nov. 30, 2007;131(5):861-72.
Takeshita et al., Therapeutic angiogenesis. A single intraarterial bolus of vascular endothelial growth factor augments revascularization in a rabbit ischemic hind limb model. J Clin Invest. Feb. 1994;93(2):662-70.
Tamura et al., Immunotherapy of tumors with autologous tumor-derived heat shock protein preparations. Science. Oct. 3, 1997;278(5335):117-20.
Tanaka et al., Collapse of gels in an electric field. Science. Oct. 29, 1982;218(4571):467-9.
Tang et al., Combining radiation and immunotherapy: a new systemic therapy for solid tumors? Cancer Immunol Res. Sep. 2014;2(9):831-8.
Tannous, Gaussia luciferase reporter assay for monitoring biological processes in culture and in vivo. Nat Protoc. 2009;4(4):582-91.
Tatsumi et al., HGF/SF is present in normal adult skeletal muscle and is capable of activating satellite cells. Dev Biol. Feb. 1, 1998;194(1):114-28.
Ten Dijke et al., Growth Factors for Wound Healing. Nat Biotechnol. 1989;7:793-798.
Thelin et al., In Vivo Enrichment of Diabetogenic T Cells. Diabetes. Aug. 2017;66(8):2220-2229.
Thomas et al., Intravenous infusion of bone marrow in patients receiving radiation and chemotherapy. N Engl J Med. Sep. 12, 1957;257(11):491-6.
Thornton et al., Shape retaining injectable hydrogels for minimally invasive bulking. J Urol. Aug. 2004;172(2):763-8.
Thurner et al., Vaccination with mage-3A1 peptide-pulsed mature, monocyte-derived dendritic cells expands specific cytotoxic T cells and induces regression of some metastases in advanced stage IV melanoma. J Exp Med. Dec. 6, 1999;190(11):1669-78.
Thurston et al., The Delta paradox: DLL4 blockade leads to more tumour vessels but less tumour growth. Nat Rev Cancer. May 2007;7(5):327-31.
Tidball, Inflammatory cell response to acute muscle injury. Med Sci Sports Exerc. Jul. 1995;27(7):1022-32.
Tomer et al., Electrically Controlled Release of Macromolecules from Cross-Linked Hyaluronic Acid Hydrogels. Journal of Controlled Release. Mar. 1995:33(3):405-413.
Tong et al., Engineering interpenetrating network hydrogels as biomimetic cell niche with independently tunable biochemical and mechanical properties. Biomaterials. Feb. 2014;35(6):1807-15.
Tourniaire et al., Polymer microarrays for cellular adhesion. Chem Commun (Camb). May 28, 2006;(20):2118-20.
Trappmann et al., Extracellular-matrix tethering regulates stem-cell fate. Nat Mater. May 27, 2012;11(7):642-9.
Trappmann et al., How cells sense extracellular matrix stiffness: a material's perspective. Curr Opin Biotechnol. Oct. 2013;24(5):948-53.
Tripathi et al., Elastic and macroporous agarose-gelatin cryogels with isotropic and anisotropic porosity for tissue engineering. J Biomed Mater Res A. Sep. 1, 2009;90(3):680-94.
Tsien, The green fluorescent protein. Annu Rev Biochem. 1998;67:509-44.
Turing, Discussion: Turing's Theory of Morphogenesis—Its Influence on Modelling Biological Pattern and Form. Bull Math Biol. 1990;52(1-2):119-159.
Turing, The Chemical Basis of Morphogenesis. Philosophical Transactions of the Royal Society of London. Series B. 1952;237(641):37-72.
Uchida et al., Immunization by particle bombardment of antigen-loaded poly-(DL-lactide-co-glycolide) microspheres in mice. Vaccine. Mar. 15, 2006;24(12):2120-30.
Udono, Cancer immunotherapy with blocking of immune checkpoint. Journal of Okayama Medical Association. Apr. 2013;125:13-18.
Ugarte et al., Notch signaling enhances osteogenic differentiation while inhibiting adipogenesis in primary human bone marrow stromal cells. Exp Hematol. Jul. 2009;37(7):867-875.
Uhlenbruck, Action of proteolytic enzymes on the human erythrocyte surface. Nature. Apr. 8, 1961;190:181.
Ulrich et al., Probing cellular mechanobiology in three-dimensional culture with collagen-agarose matrices. Biomaterials. Mar. 2010;31(7):1875-84.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q61885.1, Feb. 13, 2019.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Urbanek et al., Stem cell niches in the adult mouse heart. Proc Natl Acad Sci U S A. Jun. 13, 2006;103(24):9226-31.
Van Berkel et al., Metal-free triazole formation as a tool for bioconjugation. Chembiochem. Sep. 3, 2007;8(13):1504-8.
Van Der Bruggen et al., Peptide Database: T cell-defined tumor antigens. Cancer Immunity. Retrieved online at: http://www.cancerimmunity.org/peptide/ 59 pages. (2013).
Van Duin et al., Triggering TLR signaling in vaccination. Trends Immunol. Jan. 2006;27(1):49-55.
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.
Van Elsas et al., Elucidating the autoimmune and antitumor effector mechanisms of a treatment based on cytotoxic T lymphocyte antigen-4 blockade in combination with a B16 melanoma vaccine: comparison of prophylaxis and therapy. J Exp Med. Aug. 20, 2001;194(4):481-9.
Vandenburgh et al., Tissue-engineered skeletal muscle organoids for reversible gene therapy. Hum Gene Ther. Nov. 10, 1996;7(17):2195-200.

(56) References Cited

OTHER PUBLICATIONS

Venturoni et al., Investigations into the polymorphism of rat tail tendon fibrils using atomic force microscopy. Biochem Biophys Res Commun. Apr. 4, 2003;303(2):508-13.
Vieira et al., Polysaccharide-based hydrogels: preparation, characterization, and drug interaction behaviour. Biomacromolecules. Apr. 2008;9(4):1195-9.
Vieira et al., The bulk of endogenously produced IgG2a is eliminated from the serum of adult C57BL/6 mice with a half-life of 6-8 days. Eur J Immunol. Jul. 1986;16(7):871-4.
Vieira et al., The half-lives of serum immunoglobulins in adult mice. Eur J Immunol. Feb. 1988;18(2):313-6.
Villadangos et al., Intrinsic and cooperative antigen-presenting functions of dendritic-cell subsets in vivo. Nat Rev Immunol. Jul. 2007;7(7):543-55.
Villadangos, Presentation of antigens by MHC class II molecules: getting the most out of them. Mol Immunol. Sep. 2001;38(5):329-46.
Vincent et al., Stem cell differentiation: Post-degradation forces kick in. Nat Mater. May 2013; 12(5):384-6.
Vogel et al., Local force and geometry sensing regulate cell functions. Nat Rev Mol Cell Biol. Apr. 2006;7(4):265-75.
Von Dassow et al., The segment polarity network is a robust developmental module. Nature. Jul. 13, 2000;406(6792):188-92.
Von Mehren et al., The influence of granulocyte macrophage colony-stimulating factor and prior chemotherapy on the immunological response to a vaccine (ALVAC-CEA B7.1) in patients with metastatic carcinoma. Clin Cancer Res. May 2001;7(5):1181-91.
W.H.O., World Health Organization, Global Burden of Musculoskeletal Disease Revealed in new WHO Report. Bull World Health Organ. 2003;81(11):853-854.
W.H.O., World Health Organization, The World Health Report 2004: Changing History. The World Health Report. 2004:1-169.
Wakim et al., Dendritic cell-induced memory T cell activation in nonlymphoid tissues. Science. Jan. 11, 2008;319(5860):198-202.
Waldron-Lynch et al., Advances in Type 1 diabetes therapeutics: immunomodulation and beta-cell salvage. Endocrinol Metab Clin North Am. Jun. 2009;38(2):303-17.
Wan et al., Peritoneal macrophage uptake, pharmacokinetics and biodistribution of macrophage-targeted PEG-fMLF (N-formyl-methionyl-leucyl-phenylalanine) nanocarriers for improving HIV drug delivery. Pharm Res. Nov. 2007;24(11):2110-9.
Wang et al., Biological activity of bevacizumab, a humanized anti-VEGF antibody in vitro. Angiogenesis. 2004;7(4):335-45.
Wang et al., Evolution of new nonantibody proteins via iterative somatic hypermutation. Proc Natl Acad Sci U S A. Nov. 30, 2004;101(48):16745-9.
Wang et al., Mechanotransduction at a distance: mechanically coupling the extracellular matrix with the nucleus. Nat Rev Mol Cell Biol. Jan. 2009;10(1):75-82.
Wang et al., Photothermal effects of supramolecularly assembled gold nanoparticles for the targeted treatment of cancer cells. Angew Chem Int Ed Engl. May 17, 2010;49(22):3777-81.
Wang-Gillam et al., A phase I study of IMP321 and gemcitabine as the front-line therapy in patients with advanced pancreatic adenocarcinoma. Invest New Drugs. Jun. 2013;31(3):707-13.
Warner et al., Cyclooxygenases: new forms, new inhibitors, and lessons from the clinic. FASEB J. May 2004;18(7):790-804.
Webber et al., Controlled release of dexamethasone from peptide nanofiber gels to modulate inflammatory response. Biomaterials. Oct. 2012;33(28):6823-32.
Weeks et al., The effects of chemokine, adhesion and extracellular matrix molecules on binding of mesenchymal stromal cells to poly(I-lactic acid). Cytotherapy. Oct. 2012;14(9):1080-8.
Wegmann et al., Polyethyleneimine is a potent mucosal adjuvant for viral glycoprotein antigens. Nat Biotechnol. Sep. 2012;30(9):883-8.
Wei et al., Global mapping of H3K4me3 and H3K27me3 reveals specificity and plasticity in lineage fate determination of differentiating CD4+ T cells. Immunity. Jan. 16, 2009;30(1):155-67.
Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.
Weiner, Induction and mechanism of action of transforming growth factor-beta-secreting Th3 regulatory cells. Immunol Rev. Aug. 2001;182:207-14.
Weisenberger et al., Comprehensive DNA Methylation Analysis on the Illumina® Infinium® Assay Platform. Illumina, Inc., 4 pages, Mar. 25, 2008.
Weiss et al., The demonstration of rupture of cell surfaces by an immunological technique. Exp Cell Res. Apr. 1963;30:331-8.
Wen et al., Mechanically Robust Gelatin-Alginate IPN Hydrogels by a Combination of Enzymatic and Ionic Crosslinking Approaches. Macromol Mater Eng. Apr. 2014;299(4):504-513.
Wernig et al., Function of skeletal muscle tissue formed after myoblast transplantation into irradiated mouse muscles. J Physiol. Jan. 15, 2000;522 Pt 2:333-45.
White et al., Leukemia inhibitory factor enhances regeneration in skeletal muscles after myoblast transplantation. Muscle Nerve. May 2001;24(5):695-7.
Wieland et al., Engineering molecular circuits using synthetic biology in mammalian cells. Annu Rev Chem Biomol Eng. 2012;3:209-34.
Wipff et al., Myofibroblast contraction activates latent TGF-beta1 from the extracellular matrix. J Cell Biol. Dec. 17, 2007;179(6):1311-23.
Wong et al., Focal adhesion kinase links mechanical force to skin fibrosis via inflammatory signaling. Nat Med. Dec. 11, 2011;18(1):148-52.
Wong et al., Mechanical force prolongs acute inflammation via T-cell-dependent pathways during scar formation. FASEB J. Dec. 2011;25(12):4498-510.
Wong et al., Pushing back: wound mechanotransduction in repair and regeneration. J Invest Dermatol. Nov. 2011;131(11):2186-96.
Wozniak et al., Mechanotransduction in development: a growing role for contractility. Nat Rev Mol Cell Biol. Jan. 2009;10(1):34-43.
Wright et al., Muscle-based gene therapy and tissue engineering for the musculoskeletal system. Drug Discov Today. Jul. 1, 2001;6(14):728-733.
Wu et al., Intraperitoneal administration of poly(I:C) with polyethylenimine leads to significant antitumor immunity against murine ovarian tumors. Cancer Immunol Immunother. Aug. 2011;60(8):1085-96.
Xie et al., Preparation and Application of Surface-Coated Superparamagnetic Nanobeads in the Isolation of Genomic DNA. J Magn Magnetic Mater. Jun. 2004;277(1-2):16-23.
Xiong et al., Transcription Factor STAT3 as a Novel Molecular Target for Cancer Prevention. Cancers (Basel). Apr. 16, 2014;6(2):926-57.
Yamazaki et al., CD8+ CD205+ splenic dendritic cells are specialized to induce Foxp3+ regulatory T cells. J Immunol. Nov. 15, 2008;181(10):6923-33.
Yancopoulos et al., Vascular-specific growth factors and blood vessel formation. Nature. Sep. 14, 2000;407(6801):242-8.
Yang et al., The effect of incorporating RGD adhesive peptide in polyethylene glycol diacrylate hydrogel on osteogenesis of bone marrow stromal cells. Biomaterials. Oct. 2005;26(30):5991-8.
Yeung et al., Effects of substrate stiffness on cell morphology, cytoskeletal structure, and adhesion. Cell Motil Cytoskeleton. Jan. 2005;60(1):24-34.
Yoo et al., Bio-inspired, bioengineered and biomimetic drug delivery carriers. Nat Rev Drug Discov. Jul. 1, 2011;10(7):521-35.
Yoon, Hidden Markov Models and their Applications in Biological Sequence Analysis. Curr Genomics. Sep. 2009;10(6):402-15.
Young et al., Gelatin as a delivery vehicle for the controlled release of bioactive molecules. J Control Release. Dec. 5, 2005;109(1-3):256-74.
Yu et al., Induced pluripotent stem cell lines derived from human somatic cells. Science. Dec. 21, 2007;318(5858):1917-20.
Yuen et al., Mimicking nature by codelivery of stimulant and inhibitor to create temporally stable and spatially restricted angiogenic zones. Proc Natl Acad Sci U S A. Oct. 19, 2010;107(42):17933-8.

(56) References Cited

OTHER PUBLICATIONS

Yuk et al., Electric current-sensitive drug delivery systems using sodium alginate/polyacrylic acid composites. Pharm Res. Jul. 1992;9(7):955-7.
Zammit et al., Kinetics of myoblast proliferation show that resident satellite cells are competent to fully regenerate skeletal muscle fibers. Exp Cell Res. Nov. 15, 2002;281(1):39-49.
Zammit et al., Muscle satellite cells adopt divergent fates: a mechanism for self-renewal? J Cell Biol. Aug. 2, 2004;166(3):347-57.
Zeltinger et al., Effect of pore size and void fraction on cellular adhesion, proliferation, and matrix deposition. Tissue Eng. Oct. 2001;7(5):557-72.
Zemel et al., Optimal matrix rigidity for stress fiber polarization in stem cells. Nat Phys. Jun. 1, 2010;6(6):468-473.
Zhang et al., A comparative study of the antigen-specific immune response induced by co-delivery of CpG ODN and antigen using fusion molecules or biodegradable microparticles. J Pharm Sci. Dec. 2007;96(12):3283-92.
Zhang et al., A tension-induced mechanotransduction pathway promotes epithelial morphogenesis. Nature. Mar. 3, 2011;471(7336):99-103.
Zhang et al., Generation of a syngeneic mouse model to study the effects of vascular endothelial growth factor in ovarian carcinoma. Am J Pathol. Dec. 2002;161(6):2295-309.
Zhang et al., Talin depletion reveals independence of initial cell spreading from integrin activation and traction. Nat Cell Biol. Sep. 2008;10(9):1062-8.
Zhao et al., A cell-permeable Stat3 SH2 domain mimetic inhibits Stat3 activation and induces antitumor cell effects in vitro. J Biol Chem. Nov. 12, 2010;285(46):35855-65.
Zhao et al., Active scaffolds for on-demand drug and cell delivery. Proc Natl Acad Sci U S A. Jan. 4, 2011;108(1):67-72.
Zhao et al., Directed cell migration via chemoattractants released from degradable microspheres. Biomaterials. Aug. 2005;26(24):5048-63.
Zhao et al., Stress-relaxation behavior in gels with ionic and covalent crosslinks. J Appl Phys. Mar. 15, 2010;107(6):63509.
Zhou et al., Instability of the transcription factor Foxp3 leads to the generation of pathogenic memory T cells in vivo. Nat Immunol. Sep. 2009;10(9):1000-7.
Zhou et al., Microstructure and Mechanical Properties of Poly(L-lactide) Scaffolds Fabricated by Gelatin Particle Leaching Method. J Appl Polymer Sci. Nov. 5, 2005;98(3):1373-1379.
Zhou et al., Peptide-labeled quantum dots for imaging GPCRs in whole cells and as single molecules. Bioconjug Chem. Mar.-Apr. 2007;18(2):323-32.
Zizzari et al., The Macrophage Galactose-Type C-Type Lectin (MGL) Modulates Regulatory T Cell Functions. PLoS One. Jul. 6, 2015;10(7):e0132617. 12 pages.
Japanese Office Action for Application No. 2016-565339, dated Jan. 8, 2019. 9 pages.
Anderson et al., Crosslinking CD3 with CD2 using sepharose-immobilized antibodies enhances T lymphocyte proliferation. Cell Immunol. Sep. 1988;115(2):246-56.
Andersson et al., HSP70 promoter-driven activation of gene expression for immunotherapy using gold nanorods and near infrared light. Vaccines (Basel). Mar. 25, 2014;2(2):216-27.
Baroja et al., The anti-T cell monoclonal antibody 9.3 (anti-CD28) provides a helper signal and bypasses the need for accessory cells in T cell activation with immobilized anti-CD3 and mitogens. Cell Immunol. Apr. 15, 1989;120(1):205-17.
Bhardwaj et al., TLR Agonists: Are They Good Adjuvants? Cancer J. 2010;16(4):382-391.
Bierer et al., T cell receptors: adhesion and signaling. Adv Cancer Res. 1991;56:49-76.
Brodie et al., In vivo migration and function of transferred HIV-1-specific cytotoxic T cells. Nat Med. Jan. 1999;5(1):34-41.
Casanova et al., Human Mannose-binding Lectin in Immunity: Friend, Foe, or Both ?. J Exp Med. 2004;199(10):1295-1299.
Chao et al., Morphological control on SBA-15 mesoporous silicas via a slow self-assembling rate. J Mater Sci. 2009;44:6453-62.
Che et al., Synthesis and characterization of chiral mesoporous silica. Nature. May 20, 2004;429(6989):281-4.
Chen et al., Enhanced humoral and cell-mediated immune responses generated by cationic polymer-coated PLA microspheres with adsorbed HBsAg. Mol Pharm. Jun. 2, 2014;11(6):1772-84.
Chen et al., Morphological control of mesoporous silica SBA-15 synthesized at low temperature without additives. J Porous Mater. 2011;18:211-6.
Chen et al., Quantitative proteomic profiling of pancreatic cancer juice. Proteomics. Jul. 2006;6(13):3871-9.
Cheung et al., Engineered Materials for Cancer Immunotherapy. Nano Today. Aug. 1, 2015;10(4):511-531.
Cheung et al., Scaffolds that mimic antigen-presenting cells enable ex vivo expansion of primary T cells. Nat Biotechnol. Feb. 2018;36(2):160-169.
Choi et al., Facile synthesis of high quality mesoporous SBA-15 with enhanced control of the porous network connectivity and wall thickness. Chem Commun (Camb). Jun. 21, 2003;(12):1340-1.
Cooper, A Genetic Pathogen Capture Technology for Sepsis Diagnosis. Submitted to the Department of Chemical Engineering in Partial Fulfillment of the Requirements for the Degree of Doctor of Philosophy in Medical and Engineering Physics at the Massachusetts Institute of Technology. 130 pages, May 1, 2013.
Damle et al., Stimulation via the CD3 and CD28 molecules induces responsiveness to IL-4 in CD4+CD29+CD45R-memory T lymphocytes. J Immunol. Sep. 15, 1989;143(6):1761-7.
Del Chiaro et al., Early detection and prevention of pancreatic cancer: is it really possible today? World J Gastroenterol. Sep. 14, 2014;20(34):12118-31.
Dengler et al., Mesoporous silica-supported lipid bilayers (protocells) for DNA cargo delivery to the spinal cord. J Control Release. Jun. 10, 2013;168(2):209-24.
Drury et al., Hydrogels for tissue engineering: scaffold design variables and applications. Biomaterials. Nov. 2003;24(24):4337-51.
Dudley et al., CD8+ enriched "young" tumor infiltrating lymphocytes can mediate regression of metastatic melanoma. Clin Cancer Res. Dec. 15, 2010;16(24):6122-31.
Egea et al., Role of secreted glyceraldehyde-3-phosphate dehydrogenase in the infection mechanism of enterohemorrhagic and enteropathogenic *Escherichia coli*: interaction of the extracellular enzyme with human plasminogen and fibrinogen. Int J Biochem Cell Biol. 2007;39(6):1190-203.
Eggermont et al., Towards efficient cancer immunotherapy: advances in developing artificial antigen-presenting cells. Trends Biotechnol. Sep. 2014;32(9):456-65.
Ennett, Temporal Delivery of Multiple Growth Factors from Polymer Scaffolds to Enhance Neovascularization. A dissertation submitted in partial fulfillment of the requirements for the degree of Doctor of Philosophy (Biomedical Engineering) in the University of Michigan. 186 pages, (2004).
Fadel et al., A carbon nanotube-polymer composite for T-cell therapy. Nat Nanotechnol. Aug. 2014;9(8):639-47.
Fadel et al., Enhanced cellular activation with single walled carbon nanotube bundles presenting antibody stimuli. Nano Lett. Jul. 2008;8(7):2070-6.
Fesnak et al., Engineered T cells: the promise and challenges of cancer immunotherapy. Nat Rev Cancer. Aug. 23, 2016;16(9):566-81.
Gao et al., Immune cell recruitment and cell-based system for cancer therapy. Pharm Res. Apr. 2008;25(4):752-68.
Garlie et al., T cells coactivated with immobilized anti-CD3 and anti-CD28 as potential immunotherapy for cancer. J Immunother. Jul. 1999;22(4):336-45.
Gimmi et al., B-cell surface antigen B7 provides a costimulatory signal that induces T cells to proliferate and secrete interleukin 2. Proc Natl Acad Sci U S A. Aug. 1, 1991;88(15):6575-9.
Grabowska et al., Systemic in vivo delivery of siRNA to tumours using combination of polyethyleneimine and transferrin-polyethyleneimine conjugates. Biomater Sci. Nov. 2015;3(11):1439-48.

(56) References Cited

OTHER PUBLICATIONS

Han et al., Synthesis of rod-like mesoporous silica using mixed surfactants of cetyltrimethylammonium bromide and cetyltrimethylammonium chloride as templates. Materials Letters. 2003;57:4520-4.
Harding et al., CD28-mediated signalling co-stimulates murine T cells and prevents induction of anergy in T-cell clones. Nature. Apr. 16, 1992;356(6370):607-9.
Hasan et al., Artificial Antigen Presenting Cells: An Off the Shelf Approach for Generation of Desirable T-Cell Populations for Broad Application of Adoptive Immunotherapy. Advancements in Genetic Engineering. 2015;4(3):1-10.
Haso et al., Anti-CD22-chimeric antigen receptors targeting B-cell precursor acute lymphoblastic leukemia. Blood. Feb. 14, 2013;121(7):1165-74.
Hollyman et al., Manufacturing validation of biologically functional T cells targeted to CD19 antigen for autologous adoptive cell therapy. J Immunother. Feb.-Mar. 2009;32(2):169-80.
Huppa et al., T-cell-antigen recognition and the immunological synapse. Nat Rev Immunol. Dec. 2003;3(12):973-83.
Jiang, Application of polymers in nucleic acid delivery. Thesis in partial fulfillment of the requirements for the Doctor of Philosophy degree in Pharmacy in the Graduate College of The University of Iowa. 138 pages, Dec. 2011.
Johansson, Controlling the Pore Size and Morphology of Mesoporous Silica. Linkoping Studies in Science and Technology Licentiate Thesis No. 1451, 53 pages, (2010).
John et al., Passive and active mechanisms trap activated CD8+ T cells in the liver. J Immunol. May 1, 2004;172(9):5222-9.
June et al., Adoptive cellular therapy: a race to the finish line. Sci Transl Med. Mar. 25, 2015;7(280):280ps7.
June et al., The B7 and CD28 receptor families. Immunol Today. Jul. 1994;15(7):321-31.
Kosuge et al., Morphological Control of Rod- and Fiberlike SBA-15 Type Mesoporous Silica Using Water-Soluble Sodium Silicate. Chem Mater. 2004;16:899-905.
Kupferschmidt et al., Mesoporous silica particles potentiate antigen-specific T-cell responses. Nanomedicine (Lond). 2014;9(12):1835-46.
Lacy et al., Cytokine release from innate immune cells: association with diverse membrane trafficking pathways. Blood. 2011;118(1):9-18.
Lauw et al., Proinflammatory effects of IL-10 during human endotoxemia. J Immunol. Sep. 1, 2000;165(5):2783-9.
Lee et al., The immunological synapse balances T cell receptor signaling and degradation. Science. Nov. 14, 2003;302(5648):1218-22.
Levine et al., Effects of CD28 costimulation on long-term proliferation of CD4+ T cells in the absence of exogenous feeder cells. J Immunol. Dec. 15, 1997;159(12):5921-30.
Li et al., Mesoporous silica nanoparticles in biomedical applications. Chem Soc Rev. Apr. 7, 2012;41(7):2590-605.
Li et al., The effect of surface modification of mesoporous silica micro-rod scaffold on immune cell activation and infiltration. Biomaterials. Mar. 2016;83:249-56.
Liao et al., Synthesis of mesoporous silica nanoparticle-encapsulated alginate microparticles for sustained release and targeting therapy. J Biomed Mater Res B Appl Biomater. Feb. 2014;102(2):293-302.
Lindstein et al., Regulation of lymphokine messenger RNA stability by a surface-mediated T cell activation pathway. Science. Apr. 21, 1989;244(4902):339-43.
Linsley et al., The role of the CD28 receptor during T cell responses to antigen. Annu Rev Immunol. 1993;11:191-212.
Liu et al., Porous nanoparticle supported lipid bilayers (protocells) as delivery vehicles. J Am Chem Soc. Feb. 4, 2009;131(4):1354-5.
Mahony et al., Mesoporous silica nanoparticles act as a self-adjuvant for ovalbumin model antigen in mice. Small. Sep. 23, 2013;9(18):3138-46.

Mandal et al., Polymer-based synthetic dendritic cells for tailoring robust and multifunctional T cell responses. ACS Chem Biol. Feb. 20, 2015;10(2):485-92.
Mangsbo et al., Enhanced tumor eradication by combining CTLA-4 or PD-1 blockade with CpG therapy. J Immunother. Apr. 2010;33(3):225-35.
Maus et al., Ex vivo expansion of polyclonal and antigen-specific cytotoxic T lymphocytes by artificial APCs expressing ligands for the T-cell receptor, CD28 and 4-1BB. Nat Biotechnol. Feb. 2002;20(2):143-8.
McKay et al., Click chemistry in complex mixtures: bioorthogonal bioconjugation. Chem Biol. Sep. 18, 2014;21(9):1075-101.
Melief et al., T-cell immunotherapy of tumors by adoptive transfer of cytotoxic T lymphocytes and by vaccination with minimal essential epitopes. Immunol Rev. Jun. 1995;145:167-77.
Meng et al., Use of a lipid-coated mesoporous silica nanoparticle platform for synergistic gemcitabine and paclitaxel delivery to human pancreatic cancer in mice. ACS Nano. 2015;9(4):3540-57.
Meyer et al., Biodegradable nanoellipsoidal artificial antigen presenting cells for antigen specific T-cell activation. Small. Apr. 2015;11(13):1519-25.
Millar et al., Prediction of local recurrence, distant metastases, and death after breast-conserving therapy in early-stage invasive breast cancer using a five-biomarker panel. J Clin Oncol. Oct. 1, 2009;27(28):4701-8.
Milone et al., Powered and controlled T-cell production. Nat Biomed Eng. Mar. 2018;2(3):148-150.
Mu et al., Identification and characterization of a mannose-binding lectin from Nile tilapia (*Oreochromis niloticus*). Fish Shellfish Immunol. 2017;67:244-253.
NCBI, MeSH. Nivolumab. Retrieved online at: https://www.ncbi.nlm.nih/gov/mesh/?term=nivolumab. 3 pages, (2010).
Perica et al., Enrichment and Expansion with Nanoscale Artificial Antigen Presenting Cells for Adoptive Immunotherapy. ACS Nano. Jul. 28, 2015;9(7):6861-71.
Qiao et al., Synthesis and Bio-adsorptive Properties of Large-Pore Periodic Mesoporous Organosilica Rods. Chem Mater. 2005;17:6172-6.
Qin et al., CD22-Targeted Chimeric Antigen Receptor (CAR) T Cells Containing The 4-1BB Costimulatory Domain Demonstrate Enhanced Persistence and Superior Efficacy Against B-Cell Precursor Acute Lymphoblastic Leukemia (ALL) Compared To Those Containing CD28. Blood. 2013;122:1431.
Riddell et al., Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington. Human Gene Therapy. Jun. 1992;3(3):319-338.
Riddell et al., Principles for adoptive T cell therapy of human viral diseases. Annu Rev Immunol. 1995;13:545-86.
Riddell et al., Restoration of viral immunity in immunodeficient humans by the adoptive transfer of T cell clones. Science. Jul. 10, 1992;257(5067):238-41.
Riddell et al., The use of anti-CD3 and anti-CD28 monoclonal antibodies to clone and expand human antigen-specific T cells. J Immunol Methods. Apr. 17, 1990;128(2):189-201.
Rosenberg et al., Adoptive cell transfer as personalized immunotherapy for human cancer. Science. Apr. 3, 2015;348(6230):62-8.
Rosenberg et al., Durable complete responses in heavily pretreated patients with metastatic melanoma using T-cell transfer immunotherapy. Clin Cancer Res. Jul. 1, 2011;17(13):4550-7.
Rubbi et al., Evidence of surface antigen detachment during incubation of cells with immunomagnetic beads. J Immunol Methods. Dec. 3, 1993;166(2):233-41.
Schwartz, A cell culture model for T lymphocyte clonal anergy. Science. Jun. 15, 1990;248(4961):1349-56.
Shibuya et al., Anti-CD3/anti-CD28 bead stimulation overcomes CD3 unresponsiveness in patients with head and neck squamous cell carcinoma. Arch Otolaryngol Head Neck Surg. Apr. 2000;126(4):473-9.
Singh et al., Hydrogels and scaffolds for immunomodulation. Adv Mater. Oct. 2014;26(38):6530-41.

(56) References Cited

OTHER PUBLICATIONS

Springer et al., The lymphocyte function-associated LFA-1, CD2, and LFA-3 molecules: cell adhesion receptors of the immune system. Annu Rev Immunol. 1987;5:223-52.
Stanley et al., Transjugular intrahepatic portosystemic shunt as a treatment for protein-losing enteropathy caused by portal hypertension. Gastroenterology. Dec. 1996;111(6):1679-82.
Steenblock et al., A comprehensive platform for ex vivo T-cell expansion based on biodegradable polymeric artificial antigen-presenting cells. Mol Ther. Apr. 2008;16(4):765-72.
Steenblock et al., An artificial antigen-presenting cell with paracrine delivery of IL-2 impacts the magnitude and direction of the T cell response. J Biol Chem. Oct. 7, 2011;286(40):34883-92.
Stephan et al., Biopolymer implants enhance the efficacy of adoptive T-cell therapy. Nat Biotechnol. Jan. 2015;33(1):97-101.
Sunshine et al., Nanoengineering approaches to the design of artificial antigen-presenting cells. Nanomedicine. 2013;8(7):1173-89.
Sunshine et al., Particle shape dependence of CD8+ T cell activation by artificial antigen presenting cells. Biomaterials. Jan. 2014;35(1):269-277.
Takamura et al., Regulatory role of lymphoid chemokine CCL19 and CCL21 in the control of allergic rhinitis. J Immunol. 2007;179(9):5897-5906.
Thielemann et al., Pore structure and surface area of silica SBA-15: influence of washing and scale-up. Beilstein J Nanotechnol. 2011;2:110-8.
Turtle et al., Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes. Blood. 2015;126:184.
Turtle et al., CD19 CAR-T cells of defined CD4+:CD8+ composition in adult B cell ALL patients. J Clin Invest. Jun. 1, 2016;126(6):2123-38.
Veldhoen et al., TGFbeta1, a "Jack of all trades": the link with pro-inflammatory IL-17-producing T cells. Trends Immunol. Aug. 2006;27(8):358-61.
Wang et al., Mouse CD229 Ligation Co-stimulates T Cell Activation. The Journal of Immunology. May 2012; 188(suppl 1):176.7.
Yee et al., Melanocyte destruction after antigen-specific immunotherapy of melanoma: direct evidence of t cell-mediated vitiligo. J Exp Med. Dec. 4, 2000;192(11):1637-44.
Yu, Designed synthesis of mono-dispersed silica-based nanostructures and their applications in drug/gene delivery. A thesis submitted for the degree of Doctor of Philosophy at The University of Queensland in 2014, 196 pages.
Zappasodi et al., The effect of artificial antigen-presenting cells with preclustered anti-CD28/-CD3/-LFA-1 monoclonal antibodies on the induction of ex vivo expansion of functional human antitumor T cells. Haematologica. Oct. 2008;93(10):1523-34.
Jain et al., Macroporous interpenetrating cryogel network of poly(acrylonitrile) and gelatin for biomedical applications. J Mater Sci Mater Med. Dec. 2009;20 Suppl 1:S173-9.
Kim et al., Galectin-3 binding protein promotes cell motility in colon cancer by stimulating the shedding of protein tyrosine phosphatase kappa by proprotein convertase 5. Biochem Biophys Res Commun. Jan. 7, 2011;404(1):96-102.
Lee et al., Effect of dual treatment with SDF-1 and BMP-2 on ectopic and orthotopic bone formation. PLoS One. Mar. 17, 2015;10(3):e0120051, 15 pages.
Wegman et al., Combination of bone morphogenetic protein-2 plasmid DNA with chemokine CXCL 12 creates an additive effect on bone formation onset and volume. Eur Cell Mater. Jul. 27, 2015;30:1-11.
Yu et al., Specific bone cells produce DLL4 to generate thymus-seeding progenitors from bone marrow. J Exp Med. May 4, 2015;212(5):759-74.
U.S. Appl. No. 15/434,781, filed Feb. 16, 2017, 2017-0246281, Published.

U.S. Appl. No. 16/121,988, filed Sep. 5, 2018, Pending.
U.S. Appl. No. 15/564,905, filed Oct. 6, 2017, 2018-0164298, Published.
U.S. Appl. No. 16/170,313, filed Oct. 25, 2018, Pending.
U.S. Appl. No. 15/617,837, filed Jun. 8, 2017, 2018-0243231, Published.
U.S. Appl. No. 15/935,392, filed Mar. 26, 2018, 2018-0344821, Published.
U.S. Appl. No. 15/303,985, filed Oct. 13, 2016, 2017-0042995, Published.
U.S. Appl. No. 12/867,426, filed Jan. 13, 2012, 2012-0100182, Allowed.
U.S. Appl. No. 15/345,131, filed Nov. 7, 2016, 2017-0182138, Allowed.
U.S. Appl. No. 15/818,509, filed Nov. 20, 2017, 2018-0289789, Published.
U.S. Appl. No. 15/563,878, filed Oct. 2, 2017, 2018-0117171, Published.
U.S. Appl. No. 17/015,177, filed Sep. 9, 2020, Pending.
U.S. Appl. No. 16/170,313, filed Oct. 25, 2018, 2019-0125849, Published.
U.S. Appl. No. 17/083,720, filed Oct. 29, 2020, Pending.
Beduer et al., A compressible scaffold for minimally invasive delivery of large intact neuronal networks. Adv Healthc Mater. Jan. 28, 2015;4(2):301-12.
Dolgin, Cancer vaccines: Material breach. Nature. Dec. 19, 2013;504(7480):S16-7.
Drake et al., Koch Institute Symposium on Cancer Immunology and Immunotherapy. Cancer Immunology Researcy. 2013;1(4):217-22.
Emens et al., The interplay of immunotherapy and chemotherapy: harnessing potential synergies. Cancer Immunol Res. May 2015;3(5):436-43.
Furdui et al., Immunomagnetic T cell capture from blood for PCR analysis using microfluidic systems. Lab Chip. Dec. 2004;4(6):614-8.
Kim et al., Injectable, spontaneously assembling, inorganic scaffolds modulate immune cells in vivo and increase vaccine efficacy. Nat Biotechnol. Jan. 2015;33(1):64-72.
Kohrt et al., Donor immunization with WT1 peptide augments antileukemic activity after MHC-matched bone marrow transplantation. Blood. Nov. 10, 2011;118(19):5319-29.
Lee et al., Chemical tumor-targeting of nanoparticles based on metabolic glycoengineering and click chemistry. ACS Nano. Mar. 25, 2014;8(3):2048-63.
Lipson et al., Ipilimumab: an anti-CTLA-4 antibody for metastatic melanoma. Clin Cancer Res. Nov. 15, 2011;17(22):6958-62.
Manzari-Tavakoli et al., The Cross-Talks Among Bone Morphogenetic Protein (BMP) Signaling and Other Prominent Pathways Involved in Neural Differentiation. Front Mol Neurosci. Mar. 15, 2022;15:827275, 15 pages.
MeSH, Nivolumab. Retrieved online at: https://www.ncbi.nlm.nih.gov/mesh/?term=nivolumab. 2 pages, (2010).
Shah et al., An injectable bone marrow-like scaffold enhances T cell immunity after hematopoietic stem cell transplantation. Nat Biotechnol. Mar. 2019;37(3):293-302, with correction Nat Biotechnol. Nov. 2021;39:1466.
Shukla, Controlled Generation of Progenitor T-cells from Hematopoietic Stem Cells and Pluripotent Stem Cells. A thesis submitted in conformity with the requirements for the degree of Doctorate of Philosophy, Institute of Biomaterials and Biomedical Engineering, University of Toronto. 214 pages, (2017).
Sobral et al., Antigen-free cancer vaccine to treat poorly immunogenic tumors. Cancer Immunol Res. 2019;7(2 Suppl): Abstract B045.
Super et al., Biomaterial vaccines capturing pathogen-associated molecular patterns protect against bacterial Infections and septic shock. Nat Biomed Eng. Jan. 2022;6(1):8-18.
Titan et al., Growth Factor Delivery to a Bovine Defect Using Leukocyte-Rich Platelet-Rich Concentrates on a Hyaluronic Acid Scaffold. Arthroscopy: The Journal of Arthroscopic and Related Surgery. Pre-publication edition, 33 pages, Dec. 2019.

(56) References Cited

OTHER PUBLICATIONS

Van De Walle et al., Jagged2 acts as a Delta-like Notch ligand during early hematopoietic cell fate decisions. Blood. Apr. 28, 2011;117(17):4449-59.
Van Tendeloo et al., Induction of complete and molecular remissions in acute myeloid leukemia by Wilms' tumor 1 antigen-targeted dendritic cell vaccination. Proc Natl Acad Sci U S A. Aug. 3, 2010;107(31):13824-9.
Wang et al., Bone Morphogenetic Protein (BMP) signaling in development and human diseases. Genes Dis. Sep. 2014;1(1):87-105.
Wikipedia, Matrigel. Retrieved online at: https://en.wikipedia.org/wiki/Matrigel. 4 pages, Oct. 10, 2018.
Wolchok et al., Nivolumab plus ipilimumab in advanced melanoma. N Engl J Med. Jul. 11, 2013;369(2):122-33.
U.S. Appl. No. 17/015,177, filed Sep. 9, 2020, 2021-0170007, Published.
U.S. Appl. No. 16/316,778, filed Jan. 10, 2019, 2019-0292517, Published.
U.S. Appl. No. 16/033,025, filed Jul. 11, 2018, 2019-0076373, Published.
U.S. Appl. No. 17/693,017, filed Mar. 11, 2022, Pending.
U.S. Appl. No. 16/877,274, filed May 18, 2020, 2020-0276290, Published.
U.S. Appl. No. 15/135,294, filed Apr. 21, 2016, 2016-0220668, Abandoned.
U.S. Appl. No. 15/546,852, filed Jul. 27, 2017, 2018-0021253, Published.
U.S. Appl. No. 16/075,937, filed Aug. 6, 2018, 2019-0060525, Abandoned.
U.S. Appl. No. 16/708,218, filed Dec. 9, 2019, 2020-0206333, Published.
U.S. Appl. No. 17/869,611, filed Jul. 20, 2022, Pending.
U.S. Appl. No. 15/434,781, filed Feb. 16, 2017, U.S. Pat. No. 10,813,988, Issued.
U.S. Appl. No. 17/015,177, filed Sep. 9, 2020, U.S. Pat. No. 11,638,748, Issued.
U.S. Appl. No. 18/186,588, filed Mar. 20, 2023, Pending.
U.S. Appl. No. 13/386,950, filed Jan. 25, 2012, U.S. Pat. No. 8,728,456, Issued.
U.S. Appl. No. 14/185,494, filed Feb. 20, 2014, U.S. Pat. No. 9,381,235, Issued.
U.S. Appl. No. 15/147,442, filed May 5, 2016, U.S. Pat. No. 10,080,789, Issued.
U.S. Appl. No. 16/121,988, filed Sep. 5, 2018, 2019-0183992, Abandoned.
U.S. Appl. No. 15/564,905, filed Oct. 6, 2017, U.S. Pat. No. 11,150,242, Issued.
U.S. Appl. No. 17/501,821, filed Oct. 14, 2021, 2022-0107308, Published.
U.S. Appl. No. 16/316,778, filed Jan. 10, 2019, U.S. Pat. No. 11,555,177, Issued.
U.S. Appl. No. 18/072,449, filed Nov. 30, 2022, 2023-0340404, Published.
U.S. Appl. No. 11/638,796, filed Dec. 13, 2006, U.S. Pat. No. 8,067,237, Issued.
U.S. Appl. No. 13/305,088, filed Nov. 28, 2011, U.S. Pat. No. 8,932,583, Issued.
U.S. Appl. No. 14/223,759, filed Mar. 24, 2014, U.S. Pat. No. 9,132,210, Issued.
U.S. Appl. No. 14/750,423, filed Jun. 25, 2015, U.S. Pat. No. 9,446,107, Issued.
U.S. Appl. No. 15/085,858, filed Mar. 30, 2016, 2016-0271298, Abandoned.
U.S. Appl. No. 15/135,207, filed Apr. 21, 2016, U.S. Pat. No. 10,149,897, Issued.
U.S. Appl. No. 15/135,213, filed Apr. 21, 2016, U.S. Pat. No. 10,137,184, Issued.
U.S. Appl. No. 16/170,313, filed Oct. 25, 2018, U.S. Pat. No. 11,096,997, Issued.
U.S. Appl. No. 17/381,031, filed Jul. 20, 2021, Abandoned.
U.S. Appl. No. 13/877,572, filed Nov. 19, 2013, U.S. Pat. No. 11,202,759, Issued.
U.S. Appl. No. 17/522,297, filed Nov. 9, 2021, 2022-0192986, Published.
U.S. Appl. No. 14/112,096, filed Dec. 27, 2013, U.S. Pat. No. 10,045,947, Issued.
U.S. Appl. No. 14/166,689, filed Jan. 28, 2014, U.S. Pat. No. 9,675,561, Issued.
U.S. Appl. No. 15/617,837, filed Jun. 8, 2017, 2018-0243231, Abandoned.
U.S. Appl. No. 16/033,025, filed Jul. 11, 2018, 2019-0076373, Abandoned.
U.S. Appl. No. 17/083,720, filed Oct. 29, 2020, 2021-0205233, Published.
U.S. Appl. No. 18/095,488, filed Jan. 10, 2023, 2023-0404936, Published.
U.S. Appl. No. 14/394,552, filed Oct. 15, 2014, U.S. Pat. No. 9,937,249, Issued.
U.S. Appl. No. 15/935,392, filed Mar. 26, 2018, U.S. Pat. No. 11,278,604, Issued.
U.S. Appl. No. 17/693,017, filed Mar. 11, 2022, 2023-0000961, Published.
U.S. Appl. No. 15/303,985, filed Oct. 13, 2016, U.S. Pat. No. 10,682,400, Issued.
U.S. Appl. No. 16/877,274, filed May 18, 2020, 2020-0276290, Allowed.
U.S. Appl. No. 12/867,426, filed Jan. 13, 2012, U.S. Pat. No. 10,328,133, Issued.
U.S. Appl. No. 15/135,255, filed Apr. 21, 2016, U.S. Pat. No. 10,258,677, Issued.
U.S. Appl. No. 15/135,290, filed Apr. 21, 2016, 2016-0228543, Abandoned.
U.S. Appl. No. 15/135,294, filed Apr. 21, 2016, 2016-022066, Abandoned.
U.S. Appl. No. 13/510,356, filed May 17, 2012, Abandoned.
U.S. Appl. No. 14/123,615, filed Mar. 17, 2014, U.S. Pat. No. 9,486,512, Issued.
U.S. Appl. No. 15/345,131, filed Nov. 7, 2016, U.S. Pat. No. 10,406,216, Issued.
U.S. Appl. No. 13/741,271, filed Jan. 14, 2013, U.S. Pat. No. 9,370,558, Issued.
U.S. Appl. No. 15/135,216, filed Apr. 21, 2016, U.S. Pat. No. 9,821,045, Issued.
U.S. Appl. No. 15/818,509, filed Nov. 20, 2017, U.S. Pat. No. 10,568,949, Issued.
U.S. Appl. No. 15/563,878, filed Oct. 2, 2017, 2018-0117171, Abandoned.
U.S. Appl. No. 15/546,852, filed Jul. 27, 2017, U.S. Pat. No. 11,786,457, Issued.
U.S. Appl. No. 17/206,050, filed Mar. 18, 2021, 2021-0284776, Published.
U.S. Appl. No. 16/075,937, filed Aug. 6, 2018, U.S. Pat. No. 11,752,238, Issued.
U.S. Appl. No. 18/224,444, filed Jul. 20, 2023, Pending.
U.S. Appl. No. 16/708,218, filed Dec. 9, 2019, 2020-0206333, Abandoned.
U.S. Appl. No. 17/414,037, filed Jun. 15, 2021, 2022-0047778, Published.
U.S. Appl. No. 17/701,270, filed Mar. 22, 2022, 2022-0339274, Published.
U.S. Appl. No. 17/869,611, filed Jul. 20, 2022, 2023-0085214, Published.
Butler et al., Long-lived antitumor CD8+ lymphocytes for adoptive therapy generated using an artificial antigen-presenting cell. Clin Cancer Res. Mar. 15, 2007;13(6):1857-67.
Lozinsky et al., Polymeric cryogels as promising materials of biotechnological interest. Trends Biotechnol. Oct. 2003;21(10):445-51.
Mailander et al., Complete remission in a patient with recurrent acute myeloid leukemia induced by vaccination with WT1 peptide in the absence of hematological or renal toxicity. Leukemia. Jan. 2004;18(1):165-6.

(56) References Cited

OTHER PUBLICATIONS

Wang et al., Biomaterial-based scaffold for in situ chemo-immunotherapy to treat poorly immunogenic tumors. Nat Commun. Nov. 10, 2020;11(1):5696, 41 pages with supplementary materials.

Xue et al., Efficient cancer cell capturing SiNWAs prepared via surface-initiated SET-LRP and click chemistry. Polymer Chemistry. 2015;6:3708-15. Pre-publication edition.

* cited by examiner

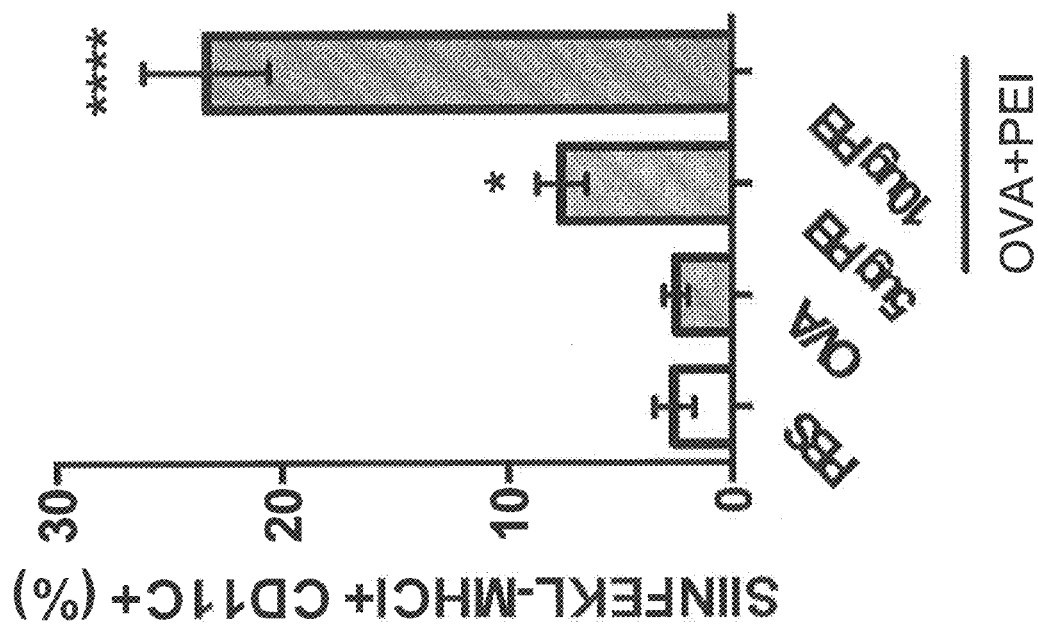

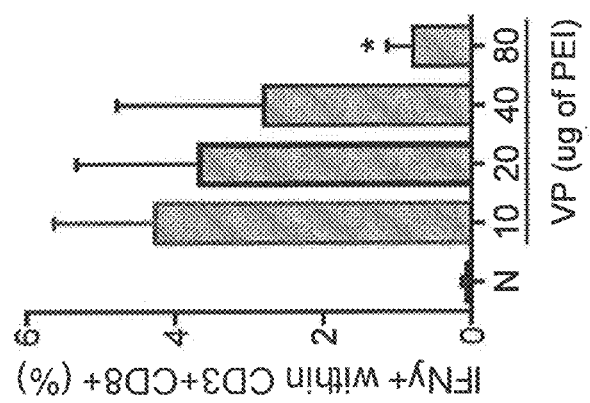
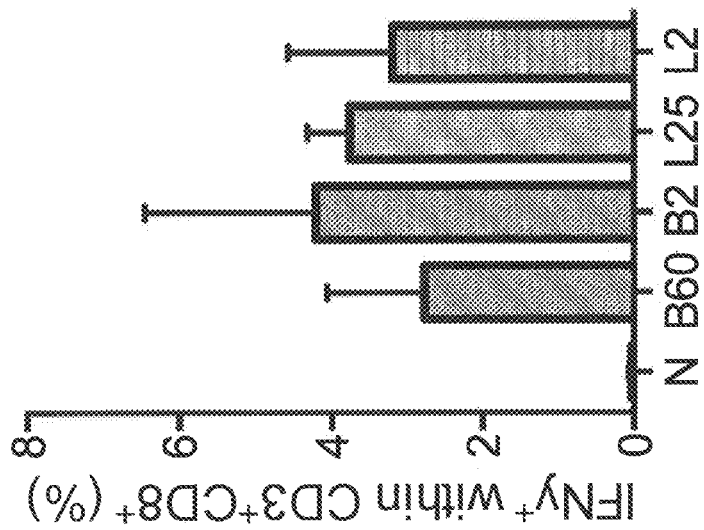
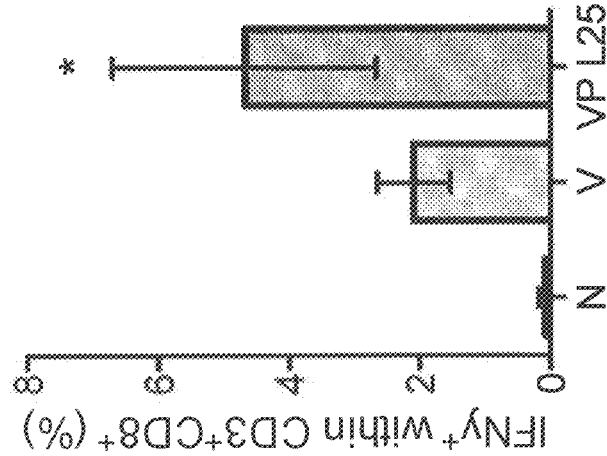
FIG. 3F
FIG. 3E
FIG. 3D

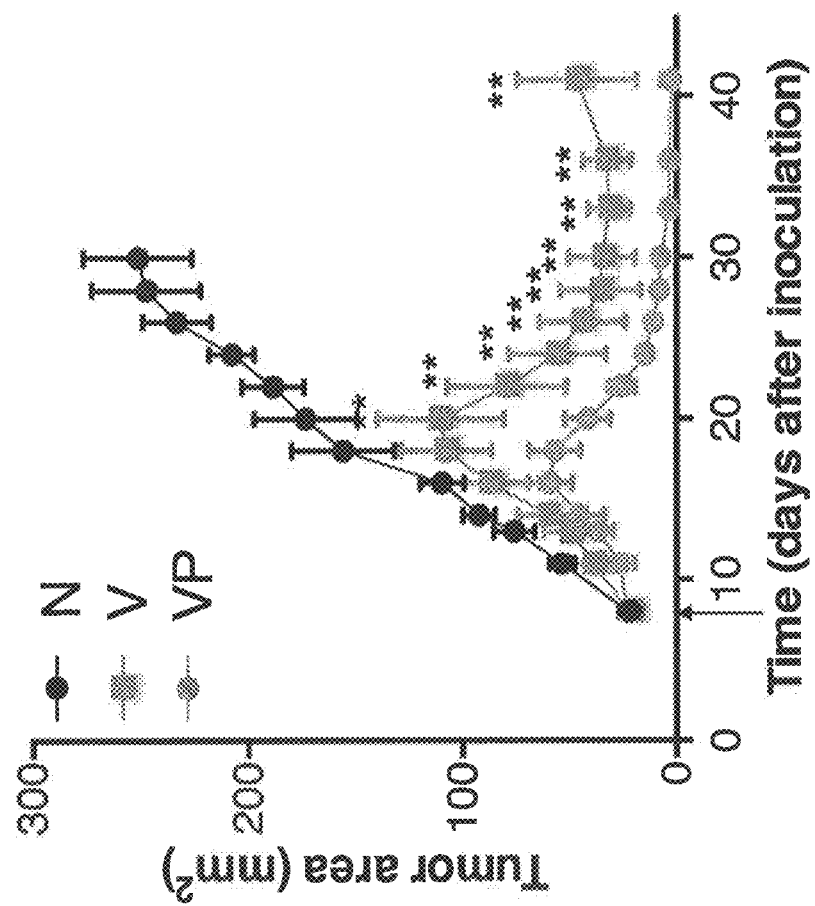

FIG. 5H
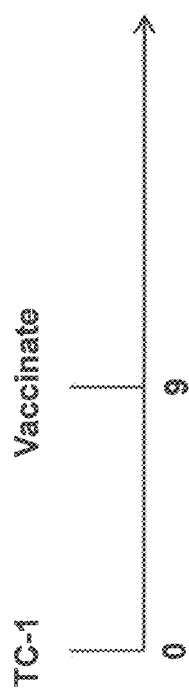
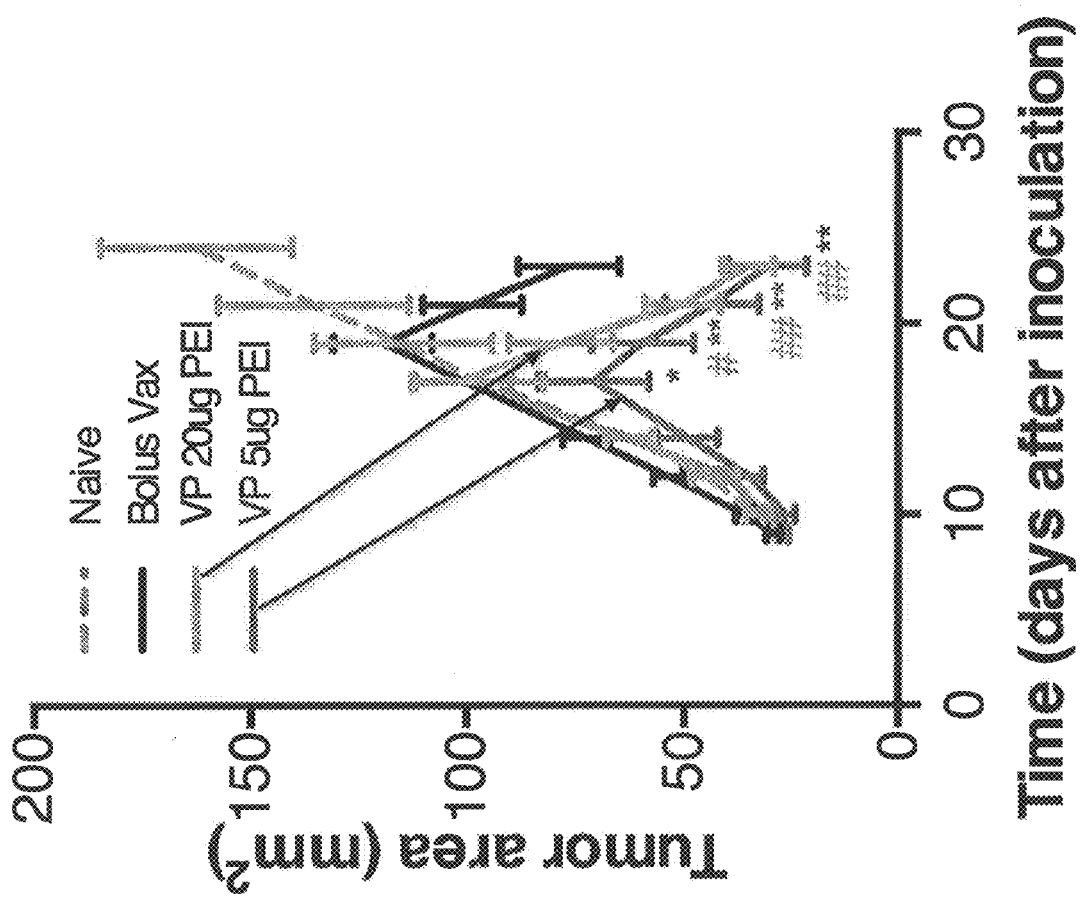

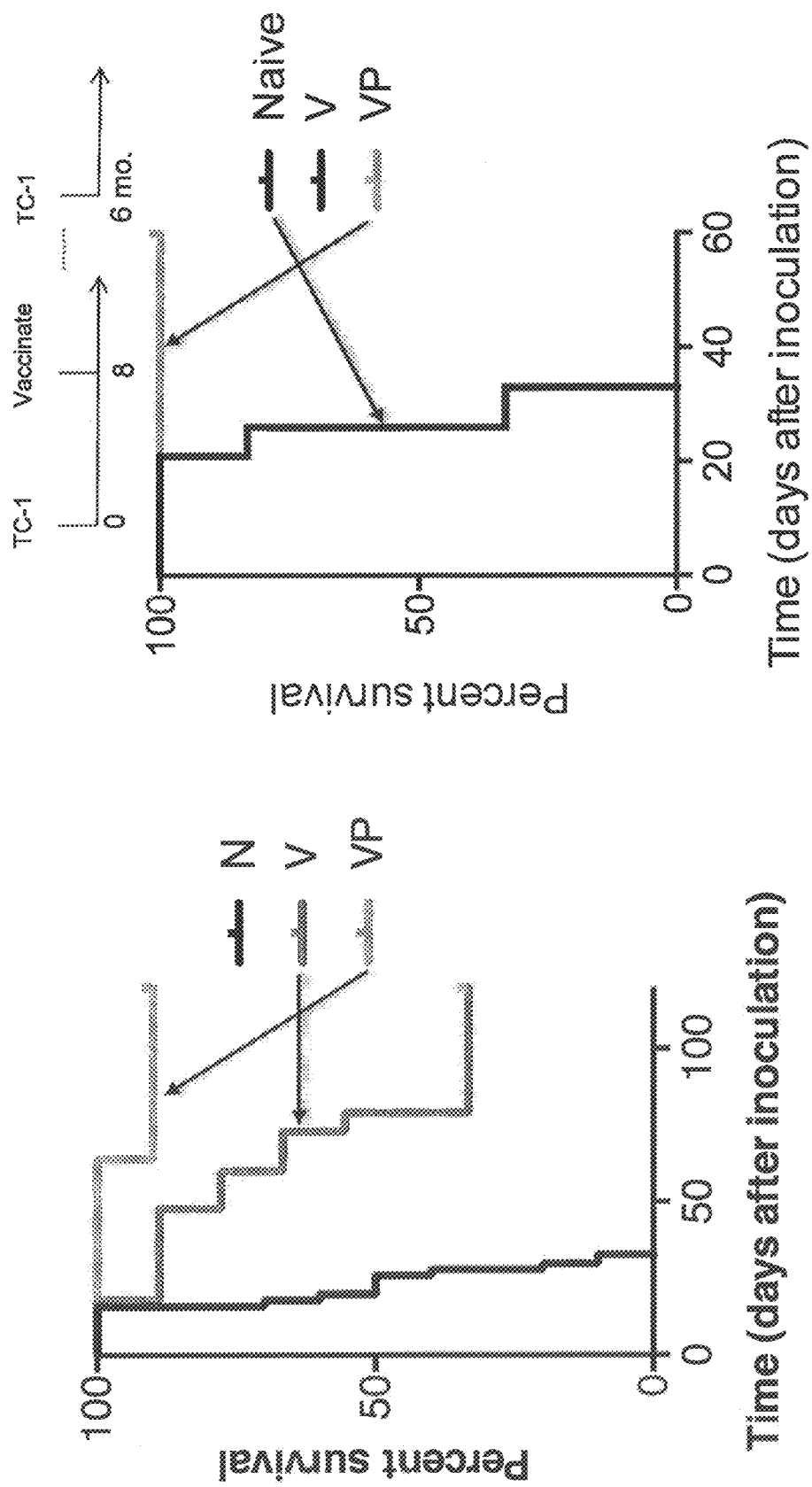

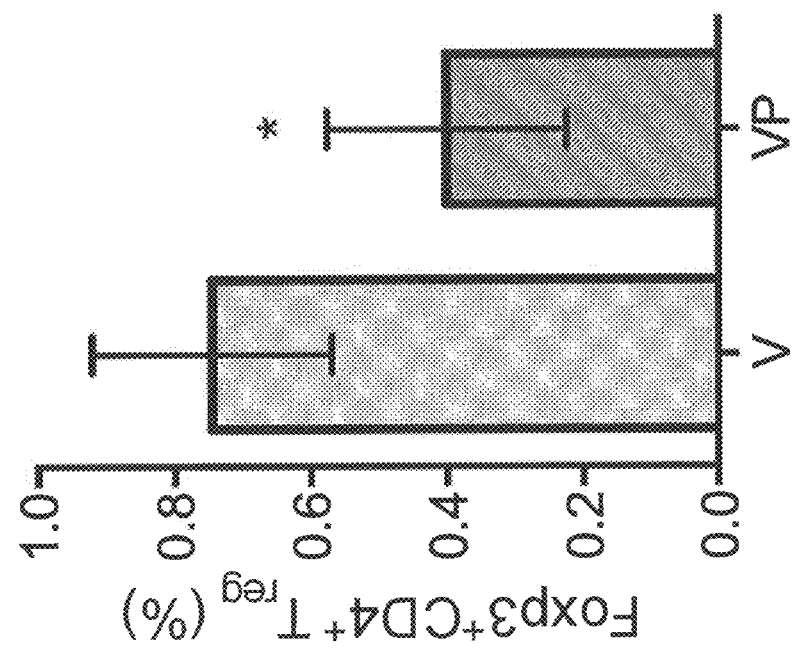

Macroporous scaffold formed after injection

MPS vaccine = MPS rods loaded with GM-CSF, CpG and antigen source

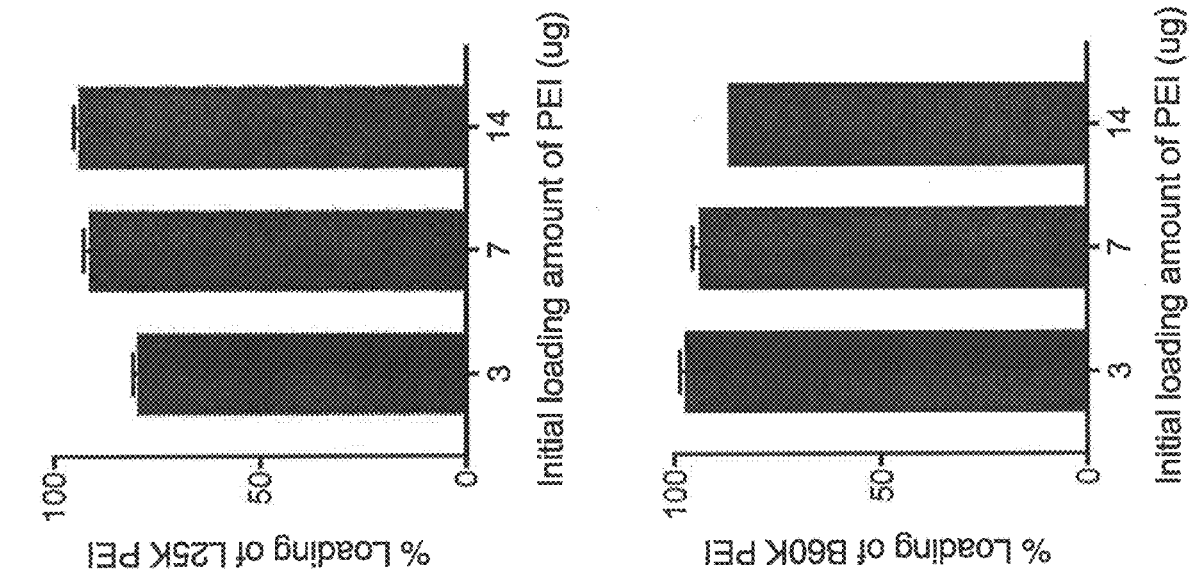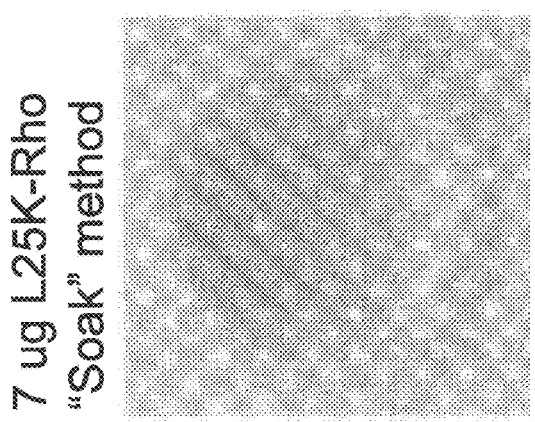
FIG. 15

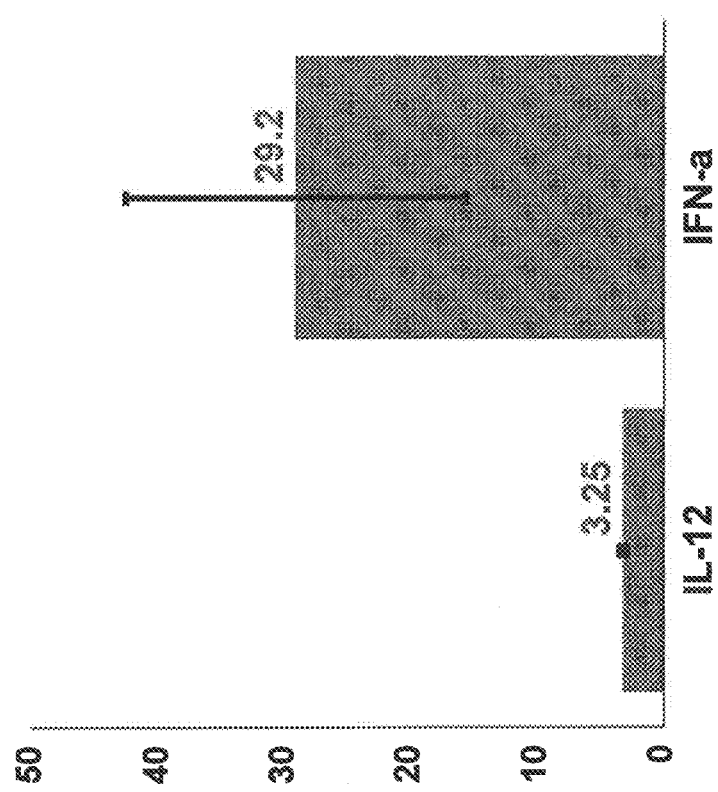
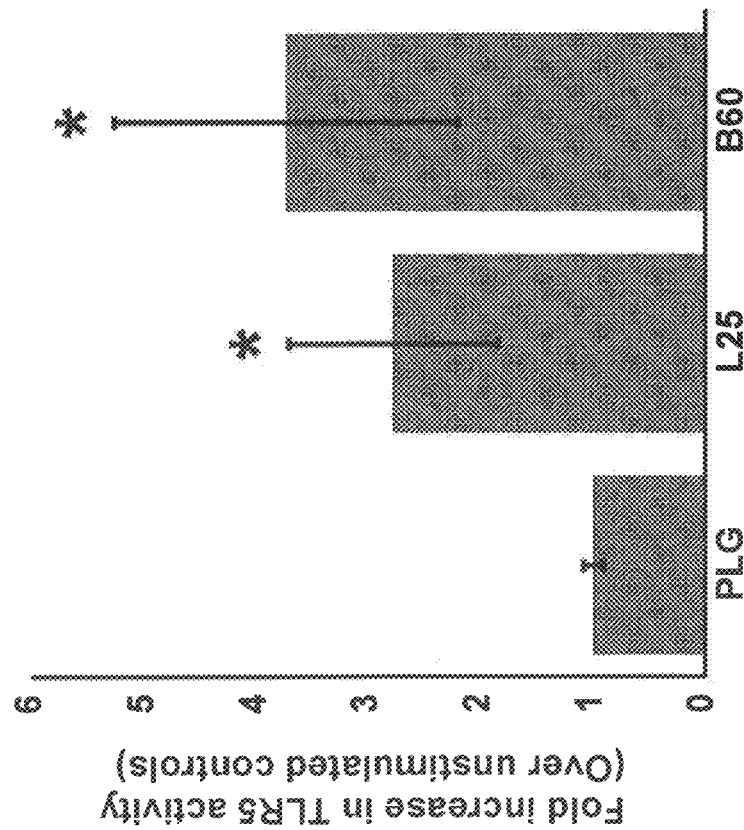
FIG. 19A
FIG. 19B

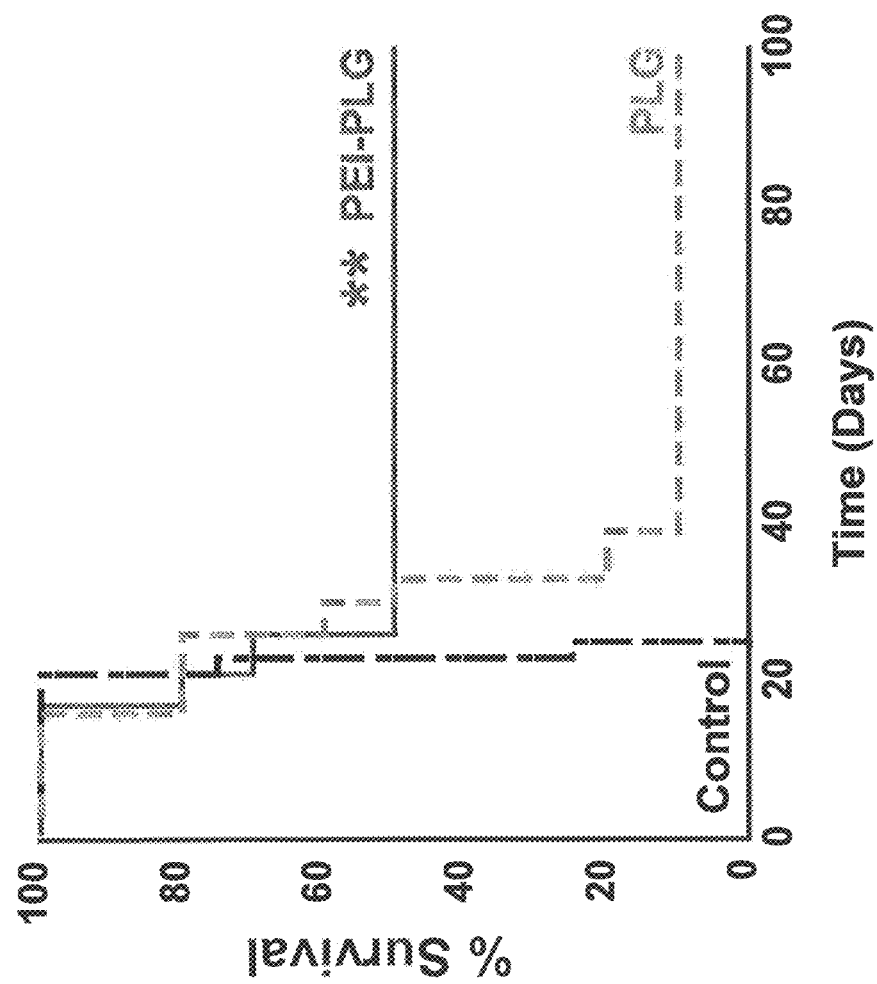

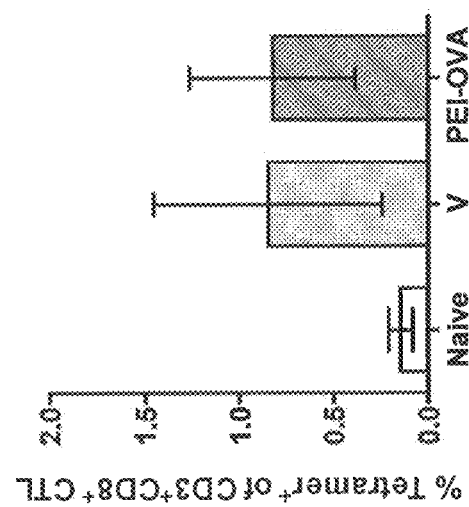
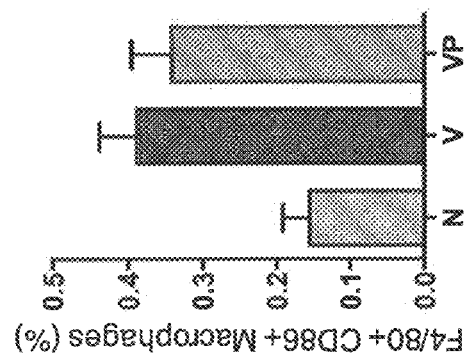
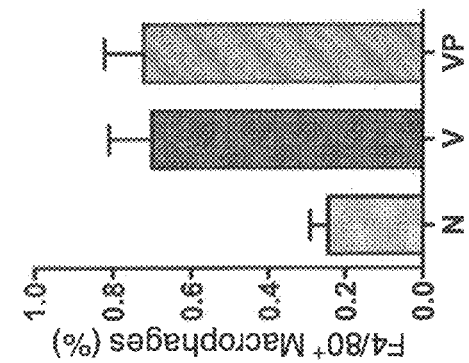

FIG. 32B
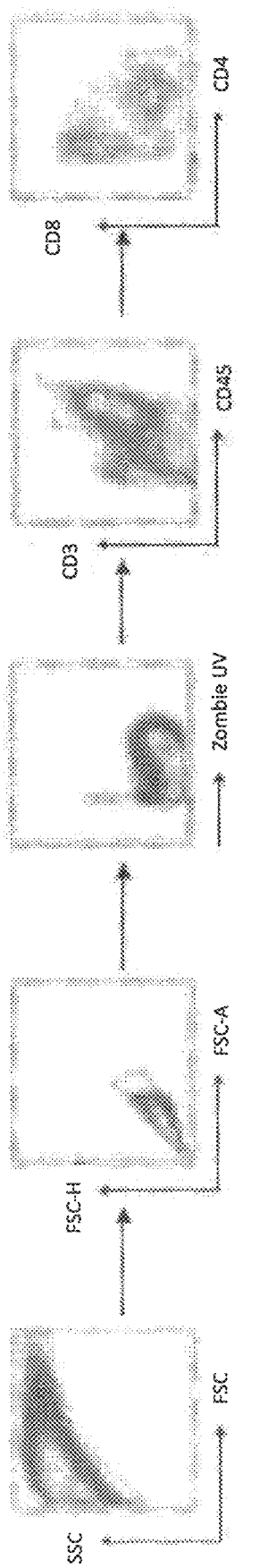
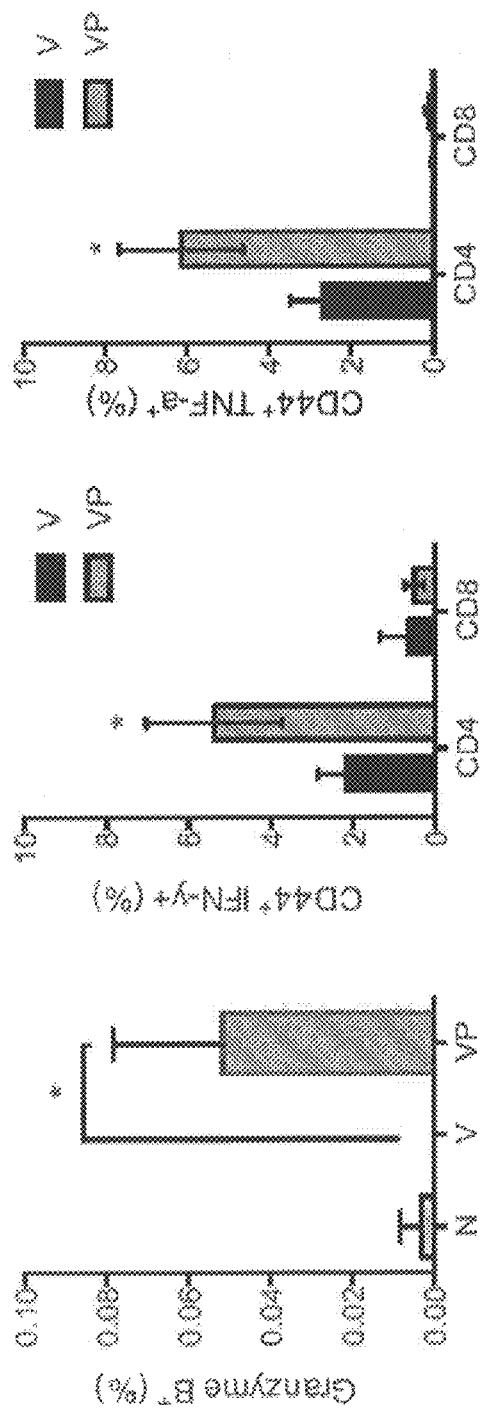

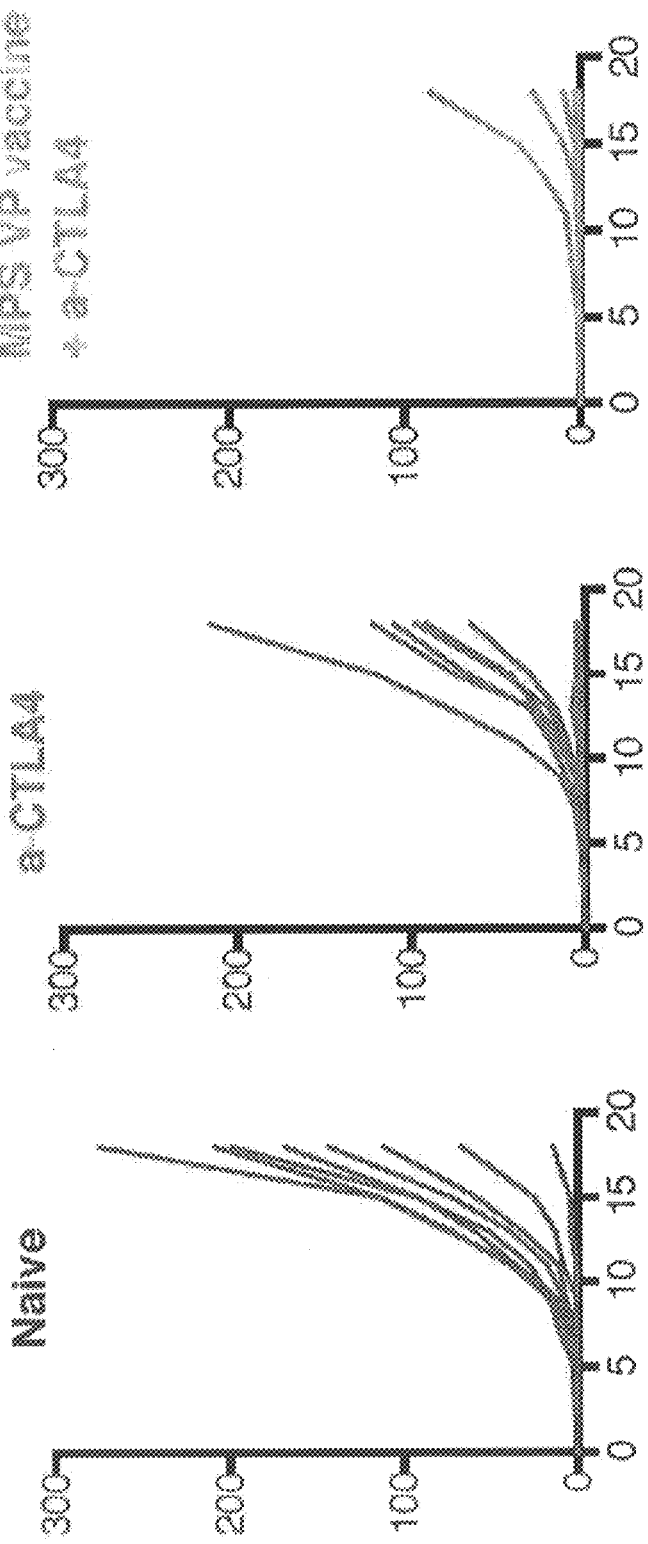
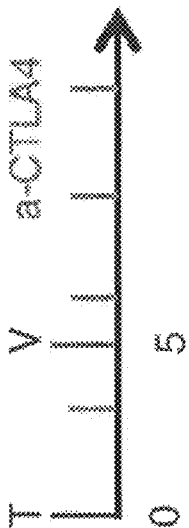
FIG. 33C

FIG. 34A

| Antigen | Antigen category | Epitope | In vivo response |
|---|---|---|---|
| Oral tumor lysate | Mixture | Mixture | Oral tumor model |
| MiCA | Protein | CD4, B cell | MiCA tumor model |
| MiCB | Protein | CD4, B cell | MiCB tumor model |
| E7 | Peptide | CD4, CD8 | TC-1 tumor model |
| B16-M27 | Peptide | CD4 | Melanoma tumor model |
| B16-M30 | Peptide | CD8 | Melanoma tumor model |
| B16-M27 | Peptide | CD4 | Melanoma tumor model |
| B16-M30 | Peptide | CD4 | Melanoma tumor model |
| Trp2 | Peptide | CD4, CD8 | Melanoma tumor model |
| Her2 | Peptide | CD4, B cell | Antibody reactivity |

SEQUENCE LISTING

```
<160> NUMBER OF SEQ ID NOS: 293

<210> SEQ ID NO 1
<211> LENGTH: 6
<212> TYPE: PRT
<213> ORGANISM: Artificial Sequence
<220> FEATURE:
<223> OTHER INFORMATION: TGF-Beta inhibitor
<220> FEATURE:
<221> NAME/KEY: Y is phosphotyrosine
<222> LOCATION: (2)..(2)

<400> SEQUENCE: 1

Pro Tyr Leu Lys Thr Lys
```

```
1               5

<210> SEQ ID NO 2
<211> LENGTH: 6
<212> TYPE: PRT
<213> ORGANISM: Artificial Sequence
<220> FEATURE:
<223> OTHER INFORMATION: TGF-Beta Inhibitor
<220> FEATURE:
<221> NAME/KEY: Y is phosphotyrosine
<222> LOCATION: (1)..(1)

<400> SEQUENCE: 2

Tyr Leu Pro Gln Thr Val
1               5

<210> SEQ ID NO 3
<211> LENGTH: 143
<212> TYPE: PRT
<213> ORGANISM: Homo sapiens

<400> SEQUENCE: 3

Trp Leu Gln Ser Leu Leu Leu Gly Thr Val Ala Cys Ser Ile Ser
1               5                   10                  15

Ala Pro Ala Arg Ser Pro Ser Pro Ser Thr Gln Pro Trp Glu His Val
            20                  25                  30

Asn Ala Ile Gln Glu Ala Arg Arg Leu Leu Asn Leu Ser Arg Asp Thr
        35                  40                  45

Ala Ala Glu Met Asn Glu Thr Val Glu Val Ile Ser Glu Met Phe Asp
    50                  55                  60

Leu Gln Glu Pro Thr Cys Leu Gln Thr Arg Leu Glu Leu Tyr Lys Gln
65                  70                  75                  80

Gly Leu Arg Gly Ser Leu Thr Lys Leu Lys Gly Pro Leu Thr Met Met
                85                  90                  95

Ala Ser His Tyr Lys Gln His Cys Pro Pro Thr Pro Glu Thr Ser Cys
            100                 105                 110

Ala Thr Gln Ile Ile Thr Phe Glu Ser Phe Lys Glu Asn Leu Lys Asp
        115                 120                 125

Phe Leu Leu Val Ile Pro Phe Asp Cys Trp Glu Pro Val Gln Glu
    130                 135                 140

<210> SEQ ID NO 4
<211> LENGTH: 235
<212> TYPE: PRT
<213> ORGANISM: Homo sapiens

<400> SEQUENCE: 4

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95
```

-continued

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
                180                 185                 190

Pro Val Gly Leu Leu Leu Ala Ala Ala Trp Cys Leu His Trp Gln
            195                 200                 205

Arg Thr Arg Arg Arg Thr Pro Arg Pro Gly Glu Gln Val Pro Pro Val
    210                 215                 220

Pro Ser Pro Gln Asp Leu Leu Val Glu His
225                 230                 235

<210> SEQ ID NO 5
<211> LENGTH: 95
<212> TYPE: PRT
<213> ORGANISM: Homo sapiens

<400> SEQUENCE: 5

Met Cys Cys Thr Lys Ser Leu Leu Leu Ala Ala Leu Met Ser Val Leu
1               5                   10                  15

Leu Leu His Leu Cys Gly Glu Ser Glu Ala Ser Asn Phe Asp Cys Cys
            20                  25                  30

Leu Gly Tyr Thr Asp Arg Ile Leu His Pro Lys Phe Ile Val Gly Phe
        35                  40                  45

Thr Arg Gln Leu Ala Asn Glu Gly Cys Asp Ile Asn Ala Ile Ile Phe
    50                  55                  60

His Thr Lys Lys Lys Leu Ser Val Cys Ala Asn Pro Lys Gln Thr Trp
65                  70                  75                  80

Val Lys Tyr Ile Val Arg Leu Leu Ser Lys Lys Val Lys Asn Met
                85                  90                  95

<210> SEQ ID NO 6
<211> LENGTH: 135
<212> TYPE: PRT
<213> ORGANISM: Homo sapiens

<400> SEQUENCE: 6

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

```
Ser Asn Gly Asn Val Thr Glu Ser Gly Cys Lys Glu Cys Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
    130                 135

<210> SEQ ID NO 7
<211> LENGTH: 114
<212> TYPE: PRT
<213> ORGANISM: Homo sapiens

<400> SEQUENCE: 7

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser Asp Lys Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
            85                  90                  95

Thr Lys Pro Thr Gly Thr Gln Gln Ser Thr Asn Thr Ala Val Thr Leu
            100                 105                 110

Thr Gly

<210> SEQ ID NO 8
<211> LENGTH: 107
<212> TYPE: PRT
<213> ORGANISM: Homo sapiens

<400> SEQUENCE: 8

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
        35                  40                  45

Leu Gln Gly Ile His Pro Lys Asn Ile Gln Ser Val Asn Val Lys Ser
    50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
            85                  90                  95

Ile Glu Lys Met Leu Asn Ser Asp Lys Ser Asn
            100                 105

<210> SEQ ID NO 9
<211> LENGTH: 189
<212> TYPE: PRT
<213> ORGANISM: Homo sapiens

<400> SEQUENCE: 9

Met Ala Ser Pro Phe Ala Leu Leu Met Val Leu Val Val Leu Ser Cys
1               5                   10                  15
```

Lys Ser Ser Cys Ser Leu Gly Cys Asp Leu Pro Glu Thr His Ser Leu
            20                  25                  30

Asp Asn Arg Arg Thr Leu Met Leu Ala Gln Met Ser Arg Ile Ser
            35                  40                  45

Pro Ser Ser Cys Leu Met Asp Arg His Asp Phe Gly Phe Pro Gln Glu
 50                  55                  60

Glu Phe Asp Gly Asn Gln Phe Gln Lys Ala Pro Ala Ile Ser Val Leu
 65                  70                  75                  80

His Glu Leu Ile Gln Gln Ile Phe Asn Leu Phe Thr Thr Lys Asp Ser
                85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Glu Glu Arg
            115                 120                 125

Val Gly Glu Thr Pro Leu Met Asn Ala Asp Ser Ile Leu Ala Val Lys
130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Leu Ser Thr Asn Leu Gln Glu Arg Leu Arg Arg Lys Glu
            180                 185

<210> SEQ ID NO 10
<211> LENGTH: 187
<212> TYPE: PRT
<213> ORGANISM: Homo sapiens

<400> SEQUENCE: 10

Met Thr Asn Lys Cys Leu Leu Gln Ile Ala Leu Leu Leu Cys Phe Ser
 1               5                  10                  15

Thr Thr Ala Leu Ser Met Ser Tyr Asn Leu Leu Gly Phe Leu Gln Arg
            20                  25                  30

Ser Ser Asn Cys Gln Cys Gln Lys Leu Leu Trp Gln Leu Asn Gly Arg
            35                  40                  45

Leu Glu Tyr Cys Leu Lys Asp Arg Arg Asn Phe Asp Ile Pro Glu Glu
 50                  55                  60

Ile Lys Gln Leu Gln Gln Phe Gln Lys Glu Asp Ala Ala Val Thr Ile
 65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Arg Asn His Leu Lys Thr Val Leu Glu Glu Lys Leu Glu
            115                 120                 125

Lys Glu Asp Phe Thr Arg Gly Lys Arg Met Ser Ser Leu His Leu Lys
            130                 135                 140

Arg Tyr Tyr Gly Arg Ile Leu His Tyr Leu Lys Ala Lys Glu Asp Ser
145                 150                 155                 160

His Cys Ala Trp Thr Ile Val Arg Val Glu Ile Leu Arg Asn Phe Tyr
                165                 170                 175

Val Ile Asn Arg Leu Thr Gly Tyr Leu Arg Asn
            180                 185

```
<210> SEQ ID NO 11
<211> LENGTH: 306
<212> TYPE: PRT
<213> ORGANISM: Homo sapiens

<400> SEQUENCE: 11

Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
290                 295                 300

Cys Ser
305

<210> SEQ ID NO 12
<211> LENGTH: 197
<212> TYPE: PRT
<213> ORGANISM: Homo sapiens

<400> SEQUENCE: 12

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
```

```
                    20                  25                  30
Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
            115                 120                 125

Arg Gln Ile Phe Leu Asp Gln Asn Met Leu Ala Val Ile Asp Glu Leu
            130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195
```

<210> SEQ ID NO 13
<211> LENGTH: 1448
<212> TYPE: DNA
<213> ORGANISM: Homo sapiens

<400> SEQUENCE: 13

```
gtgaccgagc ggcgcggacg gccgcctgcc ccctctgcca cctggggcgg tgcgggcccg      60
gagcccggag cccgggtagc gcgtagagcc ggcgcgatgc acgtgcgctc actgcgagct     120
gcggcgccgc acagcttcgt ggcgctctgg gcacccctgt tcctgctgcg ctccgccctg     180
gccgacttca gcctggacaa cgaggtgcac tcgagcttca tccaccggcg cctccgcagc     240
caggagcggc gggagatgca gcgcgagatc ctctccattt tgggcttgcc ccaccgcccg     300
cgcccgcacc tccagggcaa gcacaactcg cacccatgt tcatgctgga cctgtacaac     360
gccatggcgg tggaggaggg cggcgggccc ggcggccagg gcttctccta cccctacaag     420
gccgtcttca gtacccaggg ccccccctct gccagcctgc aagatagcca tttcctcacc     480
gacgccgaca tggtcatgag cttcgtcaac ctcgtggaac atgacaagga attcttccac     540
ccacgctacc accatcgaga gttccggttt gatctttcca agatcccaga agggaagct     600
gtcacggcag ccgaattccg gatctacaag gactacatcc gggaacgctt cgacaatgag     660
acgttccgga tcagcgttta tcaggtgctc caggagcact gggcaggga tcggatctc     720
ttcctgctcg acagccgtac cctctgggcc tcggaggagg gctggctggt gtttgacatc     780
acagccacca gcaaccactg ggtggtcaat ccgcggcaca acctgggcct gcagctctcg     840
gtggagacgc tggatgggca gagcatcaac cccaagttgg cgggcctgat tgggcggcac     900
gggccccaga acaagcagcc cttcatggtg gctttcttca aggccacgga ggtccacttc     960
cgcagcatcc ggtccacggg gagcaaacag cgcagccaga accgctccaa gacgcccaag    1020
aaccaggaag ccctgcggat ggccaacgtg cagagaaca gcagcagcga ccagaggcag    1080
```

| | |
|---|---|
| gcctgtaaga agcacgagct gtatgtcagc ttccgagacc tgggctggca ggactggatc | 1140 |
| atcgcgcctg aaggctacgc cgcctactac tgtgaggggg agtgtgcctt ccctctgaac | 1200 |
| tcctacatga acgccaccaa ccacgccatc gtgcagacgc tggtccactt catcaacccg | 1260 |
| gaaacggtgc ccaagccctg ctgtgcgccc acgcagctca atgccatctc cgtcctctac | 1320 |
| ttcgatgaca gctccaacgt catcctgaag aaatacagaa acatggtggt ccgggcctgt | 1380 |
| ggctgccact agctcctccg agaattcaga ccctttgggg ccaagttttt ctggatcctc | 1440 |
| cattgctc | 1448 |

<210> SEQ ID NO 14
<211> LENGTH: 4978
<212> TYPE: DNA
<213> ORGANISM: Homo sapiens

<400> SEQUENCE: 14

| | |
|---|---|
| ggtttccgga gctgcggcgg cgcagactgg gaggggagc cggggttcc gacgtcgcag | 60 |
| ccgagggaac aagccccaac cggatcctgg acaggcaccc cggcttggcg ctgtctctcc | 120 |
| ccctcggctc ggagaggccc ttcggcctga gggagcctcg ccgcccgtcc ccggcacacg | 180 |
| cgcagccccg gcctctcggc ctctgccgga gaaacagttg gaccccctga ttttagcagg | 240 |
| atggcccaat ggaatcagct acagcagctt gacacacggt acctggagca gctccatcag | 300 |
| ctctacagtg cacgcttccc aatggagctg cggcagtttc tggccccttg gattgagagt | 360 |
| caagattggg catatgcggc cagcaaagaa tcacatgcca ctttggtgtt tcataatctc | 420 |
| ctgggagaga ttgaccagca gtatagccgc ttcctgcaag agtcgaatgt tctctatcag | 480 |
| cacaatctac gaagaatcaa gcagtttctt cagagcaggt atcttgagaa gccaatggag | 540 |
| attgcccgga ttgtggcccg gtgcctgtgg gaagaatcac gccttctaca gactgcagcc | 600 |
| actgcggccc agcaagggg ccaggccaac cacccacag cagccgtggt gacggagaag | 660 |
| cagcagatgc tggagcagca ccttcaggat gtccggaaga gagtgcagga tctagaacag | 720 |
| aaaatgaaag tggtagagaa tctccaggat gactttgatt caactataa aaccctcaag | 780 |
| agtcaaggag acatgcaaga tctgaatgga acaaccagt cagtgaccag gcagaagatg | 840 |
| cagcagctgg aacagatgct cactgcgctg gaccagatgc ggagaagcat cgtgagtgag | 900 |
| ctggcggggc ttttgtcagc gatggagtac gtgcagaaaa ctctcacgga cgaggagctg | 960 |
| gctgactgga agaggcggca acagattgcc tgcattggag gcccgcccaa catctgccta | 1020 |
| gatcggctag aaaactggat aacgtcatta gcagaatctc aacttcagac cgtcaacaa | 1080 |
| attaagaaac tggaggagtt gcagcaaaaa gtttcctaca aggggaccc cattgtacag | 1140 |
| caccggccga tgctgaagga gagaatcgtg gagctgttta gaaacttaat gaaaagtgcc | 1200 |
| tttgtggtgg agcggcagcc ctgcatgccc atgcatcctg accggcccct cgtcatcaag | 1260 |
| accggcgtcc agttcactac taaagtcagg ttgctggtca aattccctga gttgaattat | 1320 |
| cagcttaaaa ttaaagtgtg cattgacaaa gactctgggg acgttgcagc tctcagagga | 1380 |
| tcccggaaat ttaacattct gggcacaaac acaaagtga tgaacatgga agaatccaac | 1440 |
| aacggcagcc tctctgcaga attcaaacac ttgaccctga gggagcagag atgtgggaat | 1500 |
| ggggccgag ccaattgtga tgcttccctg attgtgactg aggagctgca cctgatcacc | 1560 |
| tttgagaccg aggtgtatca ccaaggcctc aagattgacc tagagaccca ctccttgcca | 1620 |
| gttgtggtga tctccaacat ctgtcagatg ccaaatgcct gggcgtccat cctgtggtac | 1680 |
| aacatgctga ccaacaatcc caagaatgta aactttttta ccaagccccc aattggaacc | 1740 |

```
tgggatcaag tggccgaggt cctgagctgg cagttctcct ccaccaccaa gcgaggactg    1800
agcatcgagc agctgactac actggcagag aaactcttgg gacctggtgt gaattattca    1860
gggtgtcaga tcacatgggc taaattttgc aaagaaaaca tggctggcaa gggcttctcc    1920
ttctgggtct ggctggacaa tatcattgac cttgtgaaaa agtacatcct gccccttcgg   1980
aacgaagggt acatcatggg ctttatcagt aaggagcggg agcgggccat cttgagcact    2040
aagcctccag gcaccttcct gctaagattc agtgaaagca gcaaagaagg aggcgtcact    2100
ttcacttggg tggagaagga catcagcggt aagacccaga tccagtccgt ggaaccatac    2160
acaaagcagc agctgaacaa catgtcattt gctgaaatca tcatgggcta taagatcatg    2220
gatgctacca atatcctggt gtctccactg gtctatctct atcctgacat tcccaaggag    2280
gaggcattcg gaaagtattg tcggccagag agccaggagc atcctgaagc tgacccaggt    2340
agcgctgccc catacctgaa gaccaagttt atctgtgtga caccaacgac ctgcagcaat    2400
accattgacc tgccgatgtc cccccgcact ttagattcat tgatgcagtt tggaaataat    2460
ggtgaaggtg ctgaaccctc agcaggaggg cagtttgagt ccctcaccta tgacatggag    2520
ttgacctcgg agtgcgctac ctcccccatg tgaggagctg agaacggaag ctgcagaaag    2580
atacgactga ggcgcctacc tgcattctgc cacccctcac acagccaaac cccagatcat    2640
ctgaaactac taactttgtg gttccagatt ttttttaatc tcctacttct gctatctttg    2700
agcaatctgg gcacttttaa aaatagagaa atgagtgaat gtgggtgatc tgcttttatc    2760
taaatgcaaa taaggatgtg ttctctgaga cccatgatca ggggatgtgg cggggggtgg    2820
ctagagggag aaaaaggaaa tgtcttgtgt tgttttgttc ccctgccctc ctttctcagc    2880 agcttttgt tattgttgtt gttgttctta gacaagtgcc tcctggtgcc tgcggcatcc    2940
ttctgcctgt ttctgtaagc aaatgccaca ggccaccat agctacatac tcctggcatt    3000
gcacttttta accttgctga catccaaata gaagataga ctatctaagc cctaggtttc    3060
tttttaaatt aagaaataat aacaattaaa gggcaaaaa cactgtatca gcatagcctt    3120
tctgtattta agaaacttaa gcagccgggc atggtggctc acgcctgtaa tcccagcact    3180
ttgggaggcc gaggcggatc ataaggtcag gagatcaaga ccatcctggc taacacggtg    3240
aaaccccgtc tctactaaaa gtacaaaaaa ttagctgggt gtggtggtgg gcgcctgtag    3300
tcccagctac tcgggaggct gaggcaggag aatcgcttga acctgagagg cggaggttgc    3360
agtgagccaa aattgcacca ctgcacactg cactccatcc tgggcgacag tctgagactc    3420
tgtctcaaaa aaaaaaaaa aaaaagaaa cttcagttaa cagcctcctt ggtgctttaa    3480
gcattcagct ccttcaggc tggtaattta tataatccct gaaacgggct tcaggtcaaa    3540
cccttaagac atctgaagct gcaacctggc ctttggtgtt gaaataggaa ggtttaagga    3600
gaatctaagc attttagact ttttttata aatagactta ttttccttg taatgtattg    3660 gcctttagt gagtaaggct gggcagaggg tgcttacaac cttgactccc tttctccctg    3720
gacttgatct gctgtttcag aggctaggtt gtttctgtgg gtgccttatc agggctggga    3780
tacttctgat tctggcttcc ttcctgcccc accctcccga ccccagtccc cctgatcctg    3840
ctagaggcat gtctccttgc gtgtctaaag gtccctcatc ctgtttgttt taggaatcct    3900
ggtctcagga cctcatggaa gaagaggggg agagagttac aggttggaca tgatgcacac    3960
tatgggcccc cagcgacgtg tctggttgag ctcaggggaat atggttctta gccagtttct    4020
tggtgatatc cagtggcact tgtaatggcg tcttcattca gttcatgcag ggcaaaggct    4080
```

| | |
|---|---|
| tactgataaa cttgagtctg ccctcgtatg agggtgtata cctggcctcc ctctgaggct | 4140 |
| ggtgactcct ccctgctggg gccccacagg tgaggcagaa cagctagagg gcctccccgc | 4200 |
| ctgcccgcct tggctggcta gctcgcctct cctgtgcgta tgggaacacc tagcacgtgc | 4260 |
| tggatgggct gcctctgact cagaggcatg gccggatttg gcaactcaaa accaccttgc | 4320 |
| ctcagctgat cagagtttct gtggaattct gtttgttaaa tcaaattagc tggtctctga | 4380 |
| attaagggggg agacgacctt ctctaagatg aacagggttc gccccagtcc tcctgcctgg | 4440 |
| agacagttga tgtgtcatgc agagctctta cttctccagc aacactcttc agtacataat | 4500 |
| aagcttaact gataaacaga atatttagaa aggtgagact tgggcttacc attgggttta | 4560 |
| aatcataggg acctagggcg agggttcagg gcttctctgg agcagatatt gtcaagttca | 4620 |
| tggccttagg tagcatgtat ctggtcttaa ctctgattgt agcaaaagtt ctgagaggag | 4680 |
| ctgagccctg ttgtggccca ttaaagaaca gggtcctcag gccctgcccg cttcctgtcc | 4740 |
| actgccccct ccccatcccc agcccagccg agggaatccc gtgggttgct tacctaccta | 4800 |
| taaggtggtt tataagctgc tgtcctggcc actgcattca aattccaatg tgtacttcat | 4860 |
| agtgtaaaaa tttatattat tgtgaggttt tttgtctttt ttttttttt tttttttgg | 4920 |
| tatattgctg tatctacttt aacttccaga ataaacgtt ataggaac cgtaaaaa | 4978 |

<210> SEQ ID NO 15
<211> LENGTH: 1944
<212> TYPE: DNA
<213> ORGANISM: Homo sapiens

<400> SEQUENCE: 15

| | |
|---|---|
| aatttctcac tgcccctgtg ataaactgtg gtcactggct gtggcagcaa ctattataag | 60 |
| atgctctgaa aactcttcag acactgaggg gcaccagagg agcagactac aagaatggca | 120 |
| cacgctatgg aaaactcctg gacaatcagt aaagagtacc atattgatga agaagtgggc | 180 |
| tttgctctgc caaatccaca ggaaaatcta cctgattttt ataatgactg gatgttcatt | 240 |
| gctaaacatc tgcctgatct catagagtct ggccagcttc gagaaagagt tgagaagtta | 300 |
| aacatgctca gcattgatca tctcacagac cacaagtcac agcgccttgc acgtctagtt | 360 |
| ctgggatgca tcaccatggc atatgtgtgg ggcaaaggtc atggagatgt ccgtaaggtc | 420 |
| ttgccaagaa atattgctgt tccttactgc caactctcca gaaaactgga actgcctcct | 480 |
| attttggttt atgcagactg tgtcttggca aactggaaga aaaaggatcc taataagccc | 540 |
| ctgacttatg agaacatgga cgttttgttc tcatttcgtg atggagactg cagtaaagga | 600 |
| ttcttcctgg tctctctatt ggtggaaata gcagctgctt ctgcaatcaa agtaattcct | 660 |
| actgtattca aggcaatgca aatgcaagaa cgggacactt tgctaaaggc gctgttggaa | 720 |
| atagcttctt gcttggagaa agcccttcaa gtgtttcacc aaatccacga tcatgtgaac | 780 |
| ccaaaagcat ttttcagtgt tcttcgcata tatttgtctg gctggaaagg caaccccag | 840 |
| ctatcagacg gtctggtgta tgaagggttc tgggaagacc caaaggagtt gcagggggc | 900 |
| agtgcaggcc aaagcagcgt ctttcagtgc tttgacgtcc tgctgggcat ccagcagact | 960 |
| gctggtggag acatgctgc tcagttcctc caggacatga agatatat gccaccagct | 1020 |
| cacaggaact tcctgtgctc attagagtca atccctcag tccgtgagtt tgtcctttca | 1080 |
| aaaggtgatg ctggcctgcg ggaagcttat gacgcctgtg tgaagctct ggtctccctg | 1140 |
| aggagctacc atctgcaaat cgtgactaag tacatcctga ttcctgcaag ccagcagcca | 1200 |
| aaggagaata agacctctga agacccttca aaactggaag ccaaaggaac tggaggcact | 1260 |

| | |
|---|---:|
| gatttaatga atttcctgaa gactgtaaga agtacaactg agaaatccct tttgaaggaa | 1320 |
| ggttaatgta acccaacaag agcacatttt atcatagcag agacatctgt atgcattcct | 1380 |
| gtcattaccc attgtaacag agccacaaac taatactatg caatgtttta ccaataatgc | 1440 |
| aatacaaaag acctcaaaat acctgtgcat ttcttgtagg aaaacaacaa aaggtaatta | 1500 |
| tgtgtaatta tactagaagt tttgtaatct gtatcttatc attggaataa aatgacattc | 1560 |
| aataaataaa aatgcataag atatattctg tcggctgggc gcggtggctc acgcctgtaa | 1620 |
| tcccagcact ttgggaggcc gaggcgggcg gatcacaagg tcaggagatc gagaccatct | 1680 |
| tggctaacac ggtgaaaccc cgtctctact aaaaatacaa aaaattagcc gggcgcggtg | 1740 |
| gcgggcacct gtagtcccag ctactcggga ggctgaggca ggagaatggc gtgaacctgg | 1800 |
| gaggcggagc ttgcagtgag ccaagattgt gccactgcaa tccggcctgg gctaaagagc | 1860 |
| gggactccgt ctcaaaaaaa aaaaaaaaaa gatatattct gtcataataa ataaaaatgc | 1920 |
| ataagatata aaaaaaaaaa aaaa | 1944 |

<210> SEQ ID NO 16
<211> LENGTH: 2115
<212> TYPE: DNA
<213> ORGANISM: Homo sapiens

<400> SEQUENCE: 16

| | |
|---|---:|
| agtttccctt ccgctcacct ccgcctgagc agtggagaag gcggcactct ggtgggctg | 60 |
| ctccaggcat gcagatccca caggcgccct ggccagtcgt ctgggcggtg ctacaactgg | 120 |
| gctggcggcc aggatggttc ttagactccc cagacaggcc ctggaacccc ccaccttct | 180 |
| ccccagccct gctcgtggtg accgaagggg acaacgccac cttcacctgc agcttctcca | 240 |
| acacatcgga gagcttcgtg ctaaactggt accgcatgag ccccagcaac cagacggaca | 300 |
| agctggccgc cttccccgag gaccgcagcc agcccggcca ggactgccgc ttccgtgtca | 360 |
| cacaactgcc caacgggcgt gacttccaca tgagcgtggt cagggcccgg cgcaatgaca | 420 |
| gcggcaccta cctctgtggg gccatctccc tggcccccaa ggcgcagatc aaagagagcc | 480 |
| tgcgggcaga gctcagggtg acagagagaa gggcagaagt gccacagcc caccccagcc | 540 |
| cctcacccag gccagccggc cagttccaaa ccctggtggt tggtgtcgtg ggcggcctgc | 600 |
| tgggcagcct ggtgctgcta gtctgggtcc tggccgtcat ctgctcccgg gccgcacgag | 660 |
| ggacaatagg agccaggcgc accggccagc ccctgaagga ggaccctca gccgtgcctg | 720 |
| tgttctctgt ggactatggg gagctggatt tccagtggcg agagaagacc ccggagcccc | 780 |
| ccgtgccctg tgtccctgag cagacggagt atgccaccat tgtctttcct agcggaatgg | 840 |
| gcacctcatc ccccgcccgc aggggctcag ctgacggccc tcggagtgcc cagccactga | 900 |
| ggcctgagga tggacactgc tcttggcccc tctgaccggc ttccttggcc accagtgttc | 960 |
| tgcagaccct ccaccatgag cccggtcag cgcatttcct caggagaagc aggcagggtg | 1020 |
| caggccattg caggccgtcc aggggctgag ctgcctgggg gcgaccgggg ctccagcctg | 1080 |
| cacctgcacc aggcacagcc ccaccacagg actcatgtct caatgccac agtgagccca | 1140 |
| ggcagcaggt gtcaccgtcc cctacaggga gggccagatg cagtcactgc ttcaggtcct | 1200 |
| gccagcacag agctgcctgc gtccagctcc ctgaatctct gctgctgctg ctgctgctgc | 1260 |
| tgctgctgcc tgcggcccgg ggctgaaggc gccgtggccc tgcctgacgc cccggagcct | 1320 |
| cctgcctgaa cttgggggct ggttggagat ggccttggag cagccaaggt gcccctggca | 1380 |

```
gtggcatccc gaaacgccct ggacgcaggg cccaagactg ggcacaggag tgggaggtac    1440
atggggctgg ggactcccca ggagttatct gctccctgca ggcctagaga agtttcaggg    1500
aaggtcagaa gagctcctgg ctgtggtggg cagggcagga aacccctcca cctttacaca    1560
tgcccaggca gcacctcagg ccctttgtgg ggcaggaag ctgaggcagt aagcgggcag    1620
gcagagctgg aggcctttca ggcccagcca gcactctggc ctcctgccgc cgcattccac    1680
cccagcccct cacaccactc gggagaggga catcctacgg tcccaaggtc aggagggcag    1740
ggctggggtt gactcaggcc cctcccagct gtggccacct gggtgttggg agggcagaag    1800
tgcaggcacc tagggccccc catgtgccca ccctgggagc tctccttgga acccattcct    1860
gaaattattt aaaggggttg gccgggctcc caccagggcc tgggtgggaa ggtacaggcg    1920
ttcccccggg gcctagtacc cccgccgtgg cctatccact cctcacatcc acacactgca    1980
cccccactcc tggggcaggg ccaccagcat ccaggcggcc agcaggcacc tgagtggctg    2040
ggacaaggga tccccctttcc ctgtggttct attatattat aattataatt aaatatgaga    2100
gcatgctaag gaaaa                                                     2115

<210> SEQ ID NO 17
<211> LENGTH: 3691
<212> TYPE: DNA
<213> ORGANISM: Homo sapiens

<400> SEQUENCE: 17
ggcgcaacgc tgagcagctg gcgcgtcccg cgcggcccca gttctgcgca gcttcccgag      60
gctccgcacc agccgcgctt ctgtccgcct gcagggcatt ccagaaagat gaggatattt     120 gctgtctta tattcatgac ctactggcat ttgctgaacg catttactgt cacggttccc      180
aaggacctat atgtggtaga gtatggtagc aatatgacaa ttgaatgcaa attcccagta     240
gaaaaacaat tagacctggc tgcactaatt gtctattggg aaatggagga taagaacatt     300
attcaatttg tgcatggaga ggaagacctg aaggttcagc atagtagcta cagacagagg     360
gcccggctgt tgaaggacca gctctccctg ggaaatgctg cacttcagat cacagatgtg     420
aaattgcagg atgcagggt gtaccgctgc atgatcagct atggtggtgc cgactacaag     480
cgaattactg tgaaagtcaa tgccccatac aacaaaatca ccaaagaat tttggttgtg     540 gatccagtca cctctgaaca tgaactgaca tgtcaggctg agggctaccc caaggccgaa     600
gtcatctgga caagcagtga ccatcaagtc ctgagtggta agaccaccac caccaattcc     660
aagagagagg agaagctttt caatgtgacc agcacactga gaatcaacac aacaactaat     720
gagattttct actgcacttt taggagatta gatcctgagg aaaaccatac agctgaattg     780
gtcatcccag aactacctct ggcacatcct ccaaatgaaa ggactcactt ggtaattctg     840
ggagccatct tattatgcct tggtgtagca ctgacattca tcttccgttt aagaaaaggg     900
agaatgatgg atgtgaaaaa atgtggcatc caagatacaa actcaaagaa gcaaagtgat     960
acacatttgg aggagcgta atccagcatt ggaacttctg atcttcaagc agggattctc    1020
aacctgtggt ttagggttc atcggggctg agcgtgacaa gaggaaggaa tgggcccgtg    1080
ggatgcaggc aatgtgggac ttaaaaggcc caagcactga aatggaacc tggcgaaagc    1140 agaggaggag aatgaagaaa gatggagtca acagggagc ctggagggag accttgatac    1200
tttcaaatgc ctgaggggct catcgacgcc tgtgacaggg agaaaggata cttctgaaca    1260
aggagcctcc aagcaaatca tccattgctc atcctaggaa gacgggttga gaatccctaa    1320
tttgagggtc agttcctgca gaagtgccct ttgcctccac tcaatgcctc aatttgtttt    1380
```

```
ctgcatgact gagagtctca gtgttggaac gggacagtat ttatgtatga gttttttccta   1440
tttattttga gtctgtgagg tcttcttgtc atgtgagtgt ggttgtgaat gatttctttt   1500
gaagatatat tgtagtagat gttacaattt tgtcgccaaa ctaaacttgc tgcttaatga   1560
tttgctcaca tctagtaaaa catggagtat ttgtaaggtg cttggtctcc tctataacta   1620
caagtataca ttggaagcat aaagatcaaa ccgttggttg cataggatgt cacctttatt   1680
taacccatta atactctggt tgacctaatc ttattctcag acctcaagtg tctgtgcagt   1740
atctgttcca tttaaatatc agctttacaa ttatgtggta gcctacacac ataatctcat   1800
ttcatcgctg taaccaccct gttgtgataa ccactattat tttacccatc gtacagctga   1860
ggaagcaaac agattaagta acttgcccaa accagtaaat agcagacctc agactgccac   1920
ccactgtcct tttataatac aatttacagc tatattttac tttaagcaat tcttttattc   1980
aaaaaccatt tattaagtgc ccttgcaata tcaatcgctg tgccaggcat tgaatctaca   2040
gatgtgagca agacaaagta cctgtcctca aggagctcat agtataatga ggagattaac   2100
aagaaaatgt attattacaa tttagtccag tgtcatagca taaggatgat gcgaggggaa   2160
aacccgagca gtgttgccaa gaggaggaaa taggccaatg tggtctggga cggttggata   2220
tacttaaaca tcttaataat cagagtaatt ttcatttaca aagagaggtc ggtacttaaa   2280
ataaccctga aaataacac tggaattcct tttctagcat tatatttatt cctgatttgc   2340
ctttgccata taatctaatg cttgtttata tagtgtctgg tattgtttaa cagttctgtc   2400
ttttctattt aaatgccact aaattttaaa ttcataccctt tccatgattc aaaattcaaa   2460
agatcccatg ggagatggtt ggaaaatctc cacttcatcc tccaagccat tcaagtttcc   2520
tttccagaag caactgctac tgcctttcat tcatatgttc ttctaaagat agtctacatt   2580
tggaaatgta tgttaaaagc acgtattttt aaaattttt tcctaaatag taacacattg   2640
tatgtctgct gtgtactttg ctattttat ttattttagt gtttcttata tagcagatgg   2700
aatgaatttg aagttcccag ggctgaggat ccatgccttc tttgtttcta agttatcttt   2760
cccatagctt ttcattatct ttcatatgat ccagtatatg ttaaatatgt cctacatata   2820
catttagaca accaccattt gttaagtatt tgctctagga cagagtttgg atttgtttat   2880
gtttgctcaa aaggagaccc atgggctctc cagggtgcac tgagtcaatc tagtcctaaa   2940
aagcaatctt attattaact ctgtatgaca gaatcatgtc tggaactttt gttttctgct   3000
ttctgtcaag tataaacttc actttgatgc tgtacttgca aaatcacatt ttctttctgg   3060
aaattccggc agtgtacctt gactgctagc taccctgtgc cagaaaagcc tcattcgttg   3120
tgcttgaacc cttgaatgcc accagctgtc atcactacac agccctccta agaggcttcc   3180
tggaggtttc gagattcaga tgccctggga gatcccagag tttcctttcc ctcttggcca   3240
tattctggtg tcaatgacaa ggagtacctt ggctttgcca catgtcaagg ctgaagaaac   3300
agtgtctcca acagagctcc ttgtgttatc tgtttgtaca tgtgcatttg tacagtaatt   3360
ggtgtgacag tgttctttgt gtgaattaca ggcaagaatt gtggctgagc aaggcacata   3420
gtctactcag tctattccta agtcctaact cctccttgtg gtgttggatt tgtaaggcac   3480
tttatcccctt ttgtctcatg tttcatcgta aatggcatag gcagagatga tacctaattc   3540
tgcatttgat tgtcactttt tgtacctgca ttaatttaat aaaatattct tatttatttt   3600
gttacttggt acaccagcat gtccatttc ttgtttattt tgtgtttaat aaaatgttca   3660
gtttaacatc ccagtgggaga aagttaaaaa a                                 3691
```

<210> SEQ ID NO 18
<211> LENGTH: 1923
<212> TYPE: DNA
<213> ORGANISM: Homo sapiens

<400> SEQUENCE: 18

| | | | | | |
|---|---|---|---|---|---|
| cttctgtgtg | tgcacatgtg | taatacatat | ctgggatcaa | agctatctat | ataaagtcct | 60 |
| tgattctgtg | tgggttcaaa | cacatttcaa | agcttcagga | tcctgaaagg | ttttgctcta | 120 |
| cttcctgaag | acctgaacac | cgctcccata | aagccatggc | ttgccttgga | tttcagcggc | 180 |
| acaaggctca | gctgaacctg | gctaccagga | cctggccctg | cactctcctg | ttttttcttc | 240 |
| tcttcatccc | tgtcttctgc | aaagcaatgc | acgtggccca | gcctgctgtg | gtactggcca | 300 |
| gcagccgagg | catcgccagc | tttgtgtgtg | agtatgcatc | tccaggcaaa | gccactgagg | 360 |
| tccgggtgac | agtgcttcgg | caggctgaca | gccaggtgac | tgaagtctgt | gcggcaacct | 420 |
| acatgatggg | gaatgagttg | accttcctag | atgattccat | ctgcacgggc | acctccagtg | 480 |
| gaaatcaagt | gaacctcact | atccaaggac | tgagggccat | ggacacggga | ctctacatct | 540 |
| gcaaggtgga | gctcatgtac | ccaccgccat | actacctggg | cataggcaac | ggaacccaga | 600 |
| tttatgtaat | tgctaaagaa | aagaagccct | cttacaacag | gggtctatgt | gaaaatgccc | 660 |
| ccaacagagc | cagaatgtga | aaagcaattt | cagccttatt | ttattcccat | caattgagaa | 720 |
| accattatga | agaagagagt | ccatatttca | atttccaaga | gctgaggcaa | ttctaacttt | 780 |
| tttgctatcc | agctattttt | atttgtttgt | gcatttgggg | ggaattcatc | tctctttaat | 840 |
| ataaagttgg | atgcggaacc | caaattacgt | gtactacaat | ttaaagcaaa | ggagtagaaa | 900 |
| gacagagctg | ggatgtttct | gtcacatcag | ctccactttc | agtgaaagca | tcacttggga | 960 |
| ttaatatggg | gatgcagcat | tatgatgtgg | gtcaaggaat | taagttaggg | aatggcacag | 1020 |
| cccaaagaag | gaaaaggcag | ggagcgaggg | agaagactat | attgtacaca | ccttatattt | 1080 |
| acgtatgaga | cgtttatagc | cgaaatgatc | ttttcaagtt | aaattttatg | ccttttattt | 1140 |
| cttaaacaaa | tgtatgatta | catcaaggct | tcaaaaatac | tcacatggct | atgttttagc | 1200 |
| cagtgatgct | aaaggttgta | ttgcatatat | acatatatat | atatatatat | atatatatat | 1260 |
| atatatatat | atatatatat | atatatattt | taatttgata | gtattgtgca | tagagccacg | 1320 |
| tatgtttttg | tgtatttgtt | aatggtttga | atataaacac | tatatggcag | tgtctttcca | 1380 |
| ccttgggtcc | cagggaagtt | ttgtggagga | gctcaggaca | ctaatacacc | aggtagaaca | 1440 |
| caaggtcatt | tgctaactag | cttggaaact | ggatgaggtc | atagcagtgc | ttgattgcgt | 1500 |
| ggaattgtgc | tgagttggtg | ttgacatgtg | ctttggggct | tttacaccag | ttcctttcaa | 1560 |
| tggtttgcaa | ggaagccaca | gctggtggta | tctgagttga | cttgacagaa | cactgtcttg | 1620 |
| aagacaatgg | cttactccag | gagacccaca | ggtatgacct | tctaggaagc | tccagttcga | 1680 |
| tgggcccaat | tcttcaaaac | atgtggttaa | tgccatggac | agaagaaggc | agcaggtggc | 1740 |
| agaatggggt | gcatgaaggt | ttctgaaaat | taacactgct | tgtgttttta | actcaatatt | 1800 |
| ttccatgaaa | atgcaacaac | atgtataata | tttttaatta | aataaaaatc | tgtggtggtc | 1860 |
| gttttaaaaa | aaaaaaaaaa | aaaaaaaaaa | aaaaaaaaaa | aaaaaaaaaa | aaaaaaaaaa | 1920 |
| aaa | | | | | | 1923 |

<210> SEQ ID NO 19
<211> LENGTH: 1872
<212> TYPE: DNA
<213> ORGANISM: Homo sapiens

<400> SEQUENCE: 19

```
tcaggctgcc tgatctgccc agcttttccag ctttcctctg gattccggcc tctggtcatc    60
cctccccacc ctctctccaa ggccctctcc tggtctccct tcttctagaa cccttcctc    120
cacctccctc tctgcagaac ttctccttta ccccccaccc cccaccactg cccccttttcc   180
ttttctgacc tccttttgga gggctcagcg ctgcccagac cataggagag atgtgggagg    240
ctcagttcct gggcttgctg tttctgcagc cgctttgggt ggctccagtg aagcctctcc    300
agccagggggc tgaggtcccg gtggtgtggg cccaggaggg ggctcctgcc cagctcccct    360
gcagccccac aatcccctc caggatctca gccttctgcg aagagcaggg gtcacttggc    420
agcatcagcc agacagtggc ccgcccgctg ccgcccccgg ccatcccctg gccccggcc    480
ctcacccggc ggcgccctcc tcctgggggc ccaggcccg ccgctacacg gtgctgagcg    540
tgggtcccgg aggcctgcgc agcgggaggc tgccctgca gccccgcgtc cagctggatg    600
agcgcggccg gcagcgcggg gacttctcgc tatggctgcg cccagcccgg cgcgcggacg    660
ccggcgagta ccgcgccgcg gtgcacctca gggaccgcgc cctctcctgc cgcctccgtc    720
tgcgcctggg ccaggcctcg atgactgcca gccccccagg atctctcaga gcctccgact    780
gggtcatttt gaactgctcc ttcagccgcc ctgaccgccc agcctctgtg cattggttcc    840
ggaaccgggg ccagggccga gtccctgtcc gggagtcccc ccatcaccac ttagcggaaa    900
gcttcctctt cctgccccaa gtcagcccca tggactctgg gccctggggc tgcatcctca    960
cctacagaga tggcttcaac gtctccatca tgtataacct cactgttctg ggtctggagc   1020
ccccaactcc cttgacagtg tacgctggag caggttccag ggtggggctg ccctgccgcc   1080
tgcctgctgg tgtggggacc cggtctttcc tcactgccaa gtggactcct cctggggag   1140
gccctgacct cctggtgact ggagacaatg gcgactttac ccttcgacta gaggatgtga   1200
gccaggccca ggctgggacc tacacctgcc atatccatct gcaggaacag cagctcaatg   1260
ccactgtcac attggcaatc atcacagtga ctcccaaatc ctttgggtca cctggatccc   1320
tggggaagct gctttgtgag gtgactccag tatctggaca agaacgcttt gtgtggagct   1380
ctctggacac cccatcccag aggagtttct caggaccttg gctggaggca caggaggccc   1440
agctcctttc ccagccttgg caatgccagc tgtaccaggg ggagaggctt cttggagcag   1500
cagtgtactt cacagagctg tctagcccag gtgcccaacg ctctgggaga gcccaggtg    1560
ccctcccagc aggccacctc ctgctgtttc tcacccttgg tgtcctttct ctgctccttt    1620
tggtgactga agcctttggc tttcaccttt ggagaagaca gtggcgacca agacgatttt    1680
ctgccttaga gcaagggatt caccctccgc aggctcagag caagatagag gagctggagc    1740
aagaaccgga gccggagccg gagccggaac cggagcccga gcccgagccc gagccggagc    1800
agctctgacc tggagctgag gcagccagca gatctcagca gcccagtcca aataaacgtc    1860
ctgtctagca gc                                                         1872
```

<210> SEQ ID NO 20
<211> LENGTH: 1116
<212> TYPE: DNA
<213> ORGANISM: Homo sapiens

<400> SEQUENCE: 20

```
ggagagttaa aactgtgcct aacagaggtg tcctctgact tttcttctgc aagctccatg    60
ttttcacatc ttcccttga ctgtgtcctg ctgctgctgc tgctactact tacaaggtcc   120
```

-continued

```
tcagaagtgg aatacagagc ggaggtcggt cagaatgcct atctgccctg cttctacacc    180
ccagccgccc cagggaacct cgtgcccgtc tgctggggca aaggagcctg tcctgtgttt    240
gaatgtggca acgtggtgct caggactgat gaaagggatg tgaattattg gacatccaga    300
tactggctaa atggggattt ccgcaaagga gatgtgtccc tgaccataga gaatgtgact    360
ctagcagaca gtgggatcta ctgctgccgg atccaaatcc caggcataat gaatgatgaa    420
aaatttaacc tgaagttggt catcaaacca gccaaggtca cccctgcacc gactctgcag    480
agagacttca ctgcagcctt tccaaggatg cttaccacca ggggacatgg cccagcagag    540
acacagacac tggggagcct ccctgatata aatctaacac aaatatccac attggccaat    600
gagttacggg actctagatt ggccaatgac ttacgggact ctggagcaac catcagaata    660
ggcatctaca tcggagcagg gatctgtgct gggctggctc tggctcttat cttcggcgct    720
ttaattttca aatggtattc tcatagcaaa gagaagatac agaatttaag cctcatctct    780
ttggccaacc tccctccctc aggattggca aatgcagtag cagagggaat tcgctcagaa    840
gaaaacatct ataccattga agagaacgta tatgaagtgg aggagcccaa tgagtattat    900
tgctatgtca gcagcaggca gcaaccctca caacctttgg gttgtcgctt gcaatgcca    960 tagatccaac caccttattt ttgagcttgg tgttttgtct ttttcagaaa ctatgagctg   1020
tgtcacctga ctggttttgg aggttctgtc cactgctatg gagcagagtt ttcccatttt   1080
cagaagataa tgactcacat gggaattgaa ctggga                             1116
```

<210> SEQ ID NO 21
<211> LENGTH: 20
<212> TYPE: DNA
<213> ORGANISM: Artificial Sequence
<220> FEATURE:
<223> OTHER INFORMATION: ODN 1585

<400> SEQUENCE: 21

```
ggggtcaacg ttgagggggg                                                 20
```

<210> SEQ ID NO 22
<211> LENGTH: 20
<212> TYPE: DNA
<213> ORGANISM: Artificial Sequence
<220> FEATURE:
<223> OTHER INFORMATION: ODN 1668.

<400> SEQUENCE: 22

```
tccatgacgt tcctgatgct                                                 20
```

<210> SEQ ID NO 23
<211> LENGTH: 20
<212> TYPE: DNA
<213> ORGANISM: Artificial Sequence
<220> FEATURE:
<223> OTHER INFORMATION: ODN 1826

<400> SEQUENCE: 23

```
tccatgacgt tcctgacgtt                                                 20
```

<210> SEQ ID NO 24
<211> LENGTH: 24
<212> TYPE: DNA
<213> ORGANISM: Artificial Sequence
<220> FEATURE:
<223> OTHER INFORMATION: ODN 2006

<400> SEQUENCE: 24

-continued tcgtcgtttt gtcgttttgt cgtt                                          24

<210> SEQ ID NO 25
<211> LENGTH: 29
<212> TYPE: DNA
<213> ORGANISM: Artificial Sequence
<220> FEATURE:
<223> OTHER INFORMATION: ODN 2006-G5

<400> SEQUENCE: 25
tcgtcgtttt gtcgttttgt cgttggggg                                     29

<210> SEQ ID NO 26
<211> LENGTH: 20
<212> TYPE: DNA
<213> ORGANISM: Artificial Sequence
<220> FEATURE:
<223> OTHER INFORMATION: ODN 2216

<400> SEQUENCE: 26 ggggggacgat cgtcgggggg                                              20

<210> SEQ ID NO 27
<211> LENGTH: 21
<212> TYPE: DNA
<213> ORGANISM: Artificial Sequence
<220> FEATURE:
<223> OTHER INFORMATION: ODN 2336

<400> SEQUENCE: 27
ggggacgacg tcgtggggggg g                                            21

<210> SEQ ID NO 28
<211> LENGTH: 22
<212> TYPE: DNA
<213> ORGANISM: Artificial Sequence
<220> FEATURE:
<223> OTHER INFORMATION: ODN 2395

<400> SEQUENCE: 28
tcgtcgtttt cggcgcgcgc cg                                            22

<210> SEQ ID NO 29
<211> LENGTH: 25
<212> TYPE: DNA
<213> ORGANISM: Artificial Sequence
<220> FEATURE:
<223> OTHER INFORMATION: ODN M362

<400> SEQUENCE: 29
tcgtcgtcgt tcgaacgacg ttgat                                         25

<210> SEQ ID NO 30
<211> LENGTH: 128
<212> TYPE: PRT
<213> ORGANISM: Homo sapiens

<400> SEQUENCE: 30

Met Ala Pro Ala Arg Ser Pro Ser Pro Ser Thr Gln Pro Trp Glu His
1               5                   10                  15

Val Asn Ala Ile Gln Glu Ala Arg Arg Leu Leu Asn Leu Ser Arg Asp
            20                  25                  30

Thr Ala Ala Glu Met Asn Glu Thr Val Glu Val Ile Ser Glu Met Phe
        35                  40                  45

Asp Leu Gln Glu Pro Thr Cys Leu Gln Thr Arg Leu Glu Leu Tyr Lys
            50                  55                  60

Gln Gly Leu Arg Gly Ser Leu Thr Lys Leu Lys Gly Pro Leu Thr Met
 65                  70                  75                  80

Met Ala Ser His Tyr Lys Gln His Cys Pro Pro Thr Pro Glu Thr Ser
                 85                  90                  95

Cys Ala Thr Gln Ile Ile Thr Phe Glu Ser Phe Lys Glu Asn Leu Lys
                100                 105                 110

Asp Phe Leu Leu Val Ile Pro Phe Asp Cys Trp Glu Pro Val Gln Glu
            115                 120                 125

<210> SEQ ID NO 31
<211> LENGTH: 125
<212> TYPE: PRT
<213> ORGANISM: Mus musculus

<400> SEQUENCE: 31

Met Ala Pro Thr Arg Ser Pro Ile Thr Val Thr Arg Pro Trp Lys His
 1               5                  10                  15

Val Glu Ala Ile Lys Glu Ala Leu Asn Leu Leu Asp Asp Met Pro Val
                20                  25                  30

Thr Leu Asn Glu Glu Val Glu Val Val Ser Asn Glu Phe Ser Phe Lys
            35                  40                  45

Lys Leu Thr Cys Val Gln Thr Arg Leu Lys Ile Phe Glu Gln Gly Leu
        50                  55                  60

Arg Gly Asn Phe Thr Lys Leu Lys Gly Ala Leu Asn Met Thr Ala Ser
 65                  70                  75                  80

Tyr Tyr Gln Thr Tyr Cys Pro Pro Thr Pro Glu Thr Asp Cys Glu Thr
                 85                  90                  95

Gln Val Thr Thr Tyr Ala Asp Phe Ile Asp Ser Leu Lys Thr Phe Leu
                100                 105                 110

Thr Asp Ile Pro Phe Glu Cys Lys Lys Pro Val Gln Lys
            115                 120                 125

<210> SEQ ID NO 32
<211> LENGTH: 781
<212> TYPE: DNA
<213> ORGANISM: Homo sapiens

<400> SEQUENCE: 32
acacagagag aaaggctaaa gttctctgga ggatgtggct gcagagcctg ctgctcttgg      60
gcactgtggc ctgcagcatc tctgcacccg cccgctcgcc cagccccagc acgcagccct     120
gggagcatgt gaatgccatc caggaggccc ggcgtctcct gaacctgagt agagacactg     180
ctgctgagat gaatgaaaca gtagaagtca tctcagaaat gtttgacctc aggagccgaa     240
cctgcctaca gacccgcctg gagctgtaca gcagggcct gcggggcagc ctcaccaagc      300
tcaagggccc cttgaccatg atggccagcc actacaagca gcactgccct ccaaccccgg     360
aaacttcctg tgcaacccag attatcacct ttgaaagttt caagagaaac ctgaaggact     420
ttctgcttgt catccccttt gactgctggg agccagtcca ggagtgagac cggccagatg     480
aggctggcca agccggggag ctgctctctc atgaaacaag agctagaaac tcaggatggt     540
catcttggag ggaccaaggg gtgggccaca gccatggtgg gagtggcctg gacctgccct     600
gggccacact gaccctgata caggcatggc agaagaatgg gaatatttta tactgacaga     660
aatcagtaat atttatatat ttatattttt aaaatattta tttatttatt tatttaagtt     720

```
catattccat atttattcaa gatgttttac cgtaataatt attattaaaa atatgcttct    780
a                                                                   781
```

<210> SEQ ID NO 33
<211> LENGTH: 144
<212> TYPE: PRT
<213> ORGANISM: Homo sapiens

<400> SEQUENCE: 33

Met Trp Leu Gln Ser Leu Leu Leu Gly Thr Val Ala Cys Ser Ile
1               5                   10                  15

Ser Ala Pro Ala Arg Ser Pro Ser Thr Gln Pro Trp Glu His
            20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
    50                  55                      60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 34
<211> LENGTH: 10
<212> TYPE: DNA
<213> ORGANISM: Artificial Sequence
<220> FEATURE:
<223> OTHER INFORMATION: TLR13 Agonist Sequence

<400> SEQUENCE: 34
cggaaagacc                                                          10

<210> SEQ ID NO 35
<211> LENGTH: 255
<212> TYPE: PRT
<213> ORGANISM: Homo sapiens

<400> SEQUENCE: 35

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu

```
                    100                 105                 110
Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 36
<211> LENGTH: 277
<212> TYPE: PRT
<213> ORGANISM: Homo sapiens

<400> SEQUENCE: 36

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220
```

```
Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
            245                 250                 255

Gly Ser Phe Arg Thr Pro Ile Gln Glu Glu Gln Ala Asp Ala His Ser
        260                 265                 270

Thr Leu Ala Lys Ile
        275

<210> SEQ ID NO 37
<211> LENGTH: 277
<212> TYPE: PRT
<213> ORGANISM: Homo sapiens

<400> SEQUENCE: 37

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 38
<211> LENGTH: 19
<212> TYPE: PRT
<213> ORGANISM: Artificial Sequence
```

```
<220> FEATURE:
<223> OTHER INFORMATION: epitope derived from measles

<400> SEQUENCE: 38

Lys Leu Leu Ser Leu Ile Lys Gly Val Ile Val His Arg Leu Glu Gly
1               5                   10                  15

Val Glu Gly

<210> SEQ ID NO 39
<211> LENGTH: 36
<212> TYPE: PRT
<213> ORGANISM: Artificial Sequence
<220> FEATURE:
<223> OTHER INFORMATION: MVP-Her2

<400> SEQUENCE: 39

Lys Leu Leu Ser Leu Ile Lys Gly Val Ile Val His Arg Leu Glu Gly
1               5                   10                  15

Val Glu Gly Pro Ser Leu Ile Trp Lys Phe Pro Asp Glu Glu Gly Ala
            20                  25                  30

Cys Gln Pro Leu
        35

<210> SEQ ID NO 40
<211> LENGTH: 14
<212> TYPE: PRT
<213> ORGANISM: Artificial Sequence
<220> FEATURE:
<223> OTHER INFORMATION: Her2/neu

<400> SEQUENCE: 40

Ile Trp Lys Phe Pro Asp Glu Glu Gly Ala Cys Gln Pro Leu
1               5                   10

<210> SEQ ID NO 41
<211> LENGTH: 11
<212> TYPE: PRT
<213> ORGANISM: Artificial Sequence
<220> FEATURE:
<223> OTHER INFORMATION: trastuzumab binding domain of Her2

<400> SEQUENCE: 41

Lys Phe Pro Asp Glu Glu Gly Ala Cys Gln Pro
1               5                   10

<210> SEQ ID NO 42
<211> LENGTH: 35
<212> TYPE: PRT
<213> ORGANISM: Artificial Sequence
<220> FEATURE:
<223> OTHER INFORMATION: E7 oncoprotein

<400> SEQUENCE: 42

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 43
<211> LENGTH: 9
<212> TYPE: PRT
<213> ORGANISM: Artificial Sequence
```

```
<220> FEATURE:
<223> OTHER INFORMATION: E7 oncoprotein

<400> SEQUENCE: 43

Arg Ala His Tyr Asn Ile Val Thr Phe
1               5

<210> SEQ ID NO 44
<211> LENGTH: 27
<212> TYPE: PRT
<213> ORGANISM: Artificial Sequence
<220> FEATURE:
<223> OTHER INFORMATION: B16-M27 neoantigen

<400> SEQUENCE: 44

Arg Glu Gly Val Glu Leu Cys Pro Gly Asn Lys Tyr Glu Met Arg Arg
1               5                   10                  15

His Gly Thr Thr His Ser Leu Val Ile His Asp
            20                  25

<210> SEQ ID NO 45
<211> LENGTH: 27
<212> TYPE: PRT
<213> ORGANISM: Artificial Sequence
<220> FEATURE:
<223> OTHER INFORMATION: B16-M30 neoantigen

<400> SEQUENCE: 45

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu
            20                  25

<210> SEQ ID NO 46
<211> LENGTH: 27
<212> TYPE: PRT
<213> ORGANISM: Artificial Sequence
<220> FEATURE:
<223> OTHER INFORMATION: B16-M47 neoantigen

<400> SEQUENCE: 46

Gly Arg Gly His Leu Leu Gly Arg Leu Ala Ala Ile Val Gly Lys Gln
1               5                   10                  15

Val Leu Leu Gly Arg Lys Val Val Val Val Arg
            20                  25

<210> SEQ ID NO 47
<211> LENGTH: 27
<212> TYPE: PRT
<213> ORGANISM: Artificial Sequence
<220> FEATURE:
<223> OTHER INFORMATION: Trp2 neoantigen

<400> SEQUENCE: 47

Ser His Cys His Trp Asn Asp Leu Ala Val Ile Pro Ala Gly Val Val
1               5                   10                  15

His Asn Trp Asp Phe Glu Pro Arg Lys Val Ser
            20                  25

<210> SEQ ID NO 48
<211> LENGTH: 28
<212> TYPE: PRT
<213> ORGANISM: Artificial Sequence
<220> FEATURE:
<223> OTHER INFORMATION: Trp2 neoantigen
```

```
<400> SEQUENCE: 48

Ser Val Tyr Asp Phe Phe Val Trp Leu Lys Phe Phe His Arg Thr Cys
1               5                   10                  15

Lys Cys Thr Gly Asn Phe Ala Gly Gly Asp Asp Asp
            20                  25

<210> SEQ ID NO 49
<211> LENGTH: 15
<212> TYPE: PRT
<213> ORGANISM: Artificial Sequence
<220> FEATURE:
<223> OTHER INFORMATION: neoantigen

<400> SEQUENCE: 49

Ser Val Gly Asp Phe Ser Gln Glu Phe Ser Pro Ile Gln Glu Ala
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: neoantigen

<400> SEQUENCE: 50

Asp Phe Ser Gln Glu Phe Ser Pro Ile Gln Glu Ala Gln Gln Asp
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: neoantigen

<400> SEQUENCE: 51

Leu Pro Gly Lys Ile His Leu Phe Glu Ala Glu Phe Thr Gln Val
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: neoantigen

<400> SEQUENCE: 52

Ile His Leu Phe Glu Ala Glu Phe Thr Gln Val Ala Lys Lys Glu
1               5                   10                  15

<210> SEQ ID NO 53
<211> LENGTH: 17
<212> TYPE: PRT
<213> ORGANISM: Artificial Sequence
<220> FEATURE:
<223> OTHER INFORMATION: neoantigen

<400> SEQUENCE: 53

His Asp Leu Gly Arg Leu His Ser Cys Val Met Ala Ser Leu Arg Ala
1               5                   10                  15

Gln

<210> SEQ ID NO 54
<211> LENGTH: 15
```

```
<212> TYPE: PRT
<213> ORGANISM: Artificial Sequence
<220> FEATURE:
<223> OTHER INFORMATION: neoantigen

<400> SEQUENCE: 54

Arg Thr Gln Leu Leu Trp Thr Pro Ala Ala Pro Thr Ala Met Ala
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: neoantigen

<400> SEQUENCE: 55

Asp Arg Ala Ser Phe Leu Leu Thr Asp Tyr Ala Leu Ser Pro Asp
1               5                   10                  15

<210> SEQ ID NO 56
<211> LENGTH: 25
<212> TYPE: PRT
<213> ORGANISM: Artificial Sequence
<220> FEATURE:
<223> OTHER INFORMATION: neoantien

<400> SEQUENCE: 56

Asp Arg Ser Val Leu Ala Lys Lys Leu Lys Phe Val Thr Leu Val Phe
1               5                   10                  15

Arg His Gly Asp Arg Ser Pro Ile Asp
            20                  25

<210> SEQ ID NO 57
<211> LENGTH: 22
<212> TYPE: PRT
<213> ORGANISM: Artificial Sequence
<220> FEATURE:
<223> OTHER INFORMATION: neoantigen

<400> SEQUENCE: 57

Asn Asn Ser Lys Lys Lys Trp Phe Leu Phe Gln Asp Ser Lys Lys Ile
1               5                   10                  15

Gln Val Glu Gln Pro Gln
            20

<210> SEQ ID NO 58
<211> LENGTH: 24
<212> TYPE: PRT
<213> ORGANISM: Artificial Sequence
<220> FEATURE:
<223> OTHER INFORMATION: neoantigen

<400> SEQUENCE: 58

Ser Pro Ile Lys Leu Val Gln Lys Val Ala Ser Lys Ile Pro Phe Pro
1               5                   10                  15

Asp Arg Ile Thr Glu Glu Ser Val
            20

<210> SEQ ID NO 59
<211> LENGTH: 23
<212> TYPE: PRT
<213> ORGANISM: Artificial Sequence
<220> FEATURE:
<223> OTHER INFORMATION: neoantigen
```

```
<400> SEQUENCE: 59

Thr Lys Arg Gln Val Ile Leu Leu His Thr Glu Leu Glu Arg Phe Leu
1               5                   10                  15

Glu Tyr Leu Pro Leu Arg Phe
            20

<210> SEQ ID NO 60
<211> LENGTH: 22
<212> TYPE: PRT
<213> ORGANISM: Artificial Sequence
<220> FEATURE:
<223> OTHER INFORMATION: neoantigen

<400> SEQUENCE: 60

Ser His Thr Gln Thr Thr Leu Phe His Thr Phe Tyr Glu Leu Leu Ile
1               5                   10                  15

Gln Lys Asn Lys His Lys
            20

<210> SEQ ID NO 61
<211> LENGTH: 20
<212> TYPE: PRT
<213> ORGANISM: Artificial Sequence
<220> FEATURE:
<223> OTHER INFORMATION: neoantigen

<400> SEQUENCE: 61

Arg Leu Val Leu Gly Lys Phe Gly Asp Leu Thr Asn Asn Phe Ser Ser
1               5                   10                  15

Pro His Ala Arg
            20

<210> SEQ ID NO 62
<211> LENGTH: 20
<212> TYPE: PRT
<213> ORGANISM: Artificial Sequence
<220> FEATURE:
<223> OTHER INFORMATION: neoantigen

<400> SEQUENCE: 62

Leu Ser Pro Arg Glu Glu Phe Leu Arg Leu Cys Lys Lys Ile Met Met
1               5                   10                  15

Arg Ser Ile Gln
            20

<210> SEQ ID NO 63
<211> LENGTH: 25
<212> TYPE: PRT
<213> ORGANISM: Artificial Sequence
<220> FEATURE:
<223> OTHER INFORMATION: neoantigen

<400> SEQUENCE: 63

Pro Ser Thr Ala Asn Tyr Asn Ser Phe Ser Ser Ala Pro Met Pro Gln
1               5                   10                  15

Ile Pro Val Ala Ser Val Thr Pro Thr
            20                  25

<210> SEQ ID NO 64
<211> LENGTH: 20
<212> TYPE: PRT
<213> ORGANISM: Artificial Sequence
<220> FEATURE:
<223> OTHER INFORMATION: neoantigen.
```

<400> SEQUENCE: 64

Leu Cys Pro Arg Glu Glu Phe Leu Arg Leu Cys Lys Lys Ile Met Met
1               5                   10                  15

Arg Ser Ile Gln
            20

<210> SEQ ID NO 65
<211> LENGTH: 22
<212> TYPE: PRT
<213> ORGANISM: Artificial Sequence
<220> FEATURE:
<223> OTHER INFORMATION: neoantigen

<400> SEQUENCE: 65

Ser His Asn Glu Leu Ala Asp Ser Gly Ile Pro Glu Asn Ser Phe Asn
1               5                   10                  15

Val Ser Ser Leu Val Glu
            20

<210> SEQ ID NO 66
<211> LENGTH: 26
<212> TYPE: PRT
<213> ORGANISM: Artificial Sequence
<220> FEATURE:
<223> OTHER INFORMATION: neoantigen

<400> SEQUENCE: 66

Ser Gly Ser Pro Pro Leu Arg Val Ser Val Gly Asp Phe Ser Gln Glu
1               5                   10                  15

Phe Ser Pro Ile Gln Glu Ala Gln Gln Asp
            20                  25

<210> SEQ ID NO 67
<211> LENGTH: 27
<212> TYPE: PRT
<213> ORGANISM: Artificial Sequence
<220> FEATURE:
<223> OTHER INFORMATION: neoantigen

<400> SEQUENCE: 67

Arg Pro Ala Gly Arg Thr Gln Leu Leu Trp Thr Pro Ala Ala Pro Thr
1               5                   10                  15

Ala Met Ala Glu Val Gly Pro Gly His Thr Pro
            20                  25

<210> SEQ ID NO 68
<211> LENGTH: 21
<212> TYPE: PRT
<213> ORGANISM: Artificial Sequence
<220> FEATURE:
<223> OTHER INFORMATION: neoantigen

<400> SEQUENCE: 68

Arg Gly Gln Ile Lys Leu Ala Asp Phe Arg Leu Ala Arg Leu Tyr Ser
1               5                   10                  15

Ser Glu Glu Ser Arg
            20

<210> SEQ ID NO 69
<211> LENGTH: 30
<212> TYPE: PRT
<213> ORGANISM: Artificial Sequence
<220> FEATURE:

<223> OTHER INFORMATION: neoantigen

<400> SEQUENCE: 69

Asp Glu Gln Gly Arg Glu Ala Glu Leu Ala Arg Ser Gly Pro Ser Ala
1               5                   10                  15

Ala Gly Pro Val Arg Leu Lys Pro Gly Leu Val Pro Gly Leu
            20                  25                  30

<210> SEQ ID NO 70
<211> LENGTH: 16
<212> TYPE: PRT
<213> ORGANISM: Artificial Sequence
<220> FEATURE:
<223> OTHER INFORMATION: neoantigen

<400> SEQUENCE: 70

Ala Ala Val Arg Pro Glu Gln Arg Pro Ala Ala Arg Gly Ser Arg Val
1               5                   10                  15

<210> SEQ ID NO 71
<211> LENGTH: 24
<212> TYPE: PRT
<213> ORGANISM: Artificial Sequence
<220> FEATURE:
<223> OTHER INFORMATION: neoantigen

<400> SEQUENCE: 71

Pro Glu Thr Gly Glu Ile Gln Val Lys Thr Phe Leu Asp Arg Glu Gln
1               5                   10                  15

Arg Glu Ser Tyr Glu Leu Lys Val
            20

<210> SEQ ID NO 72
<211> LENGTH: 23
<212> TYPE: PRT
<213> ORGANISM: Artificial Sequence
<220> FEATURE:
<223> OTHER INFORMATION: neoantigen

<400> SEQUENCE: 72

Glu Val Val Gly Gly Tyr Thr Trp Pro Ser Gly Asn Ile Tyr Gln Gly
1               5                   10                  15

Tyr Trp Ala Gln Gly Lys Arg
            20

<210> SEQ ID NO 73
<211> LENGTH: 15
<212> TYPE: PRT
<213> ORGANISM: Artificial Sequence
<220> FEATURE:
<223> OTHER INFORMATION: neoantigen

<400> SEQUENCE: 73

Thr Ile Lys Asn Ser Asp Lys Asn Val Val Leu Glu His Phe Gly
1               5                   10                  15

<210> SEQ ID NO 74
<211> LENGTH: 29
<212> TYPE: PRT
<213> ORGANISM: Artificial Sequence
<220> FEATURE:
<223> OTHER INFORMATION: neoantigen

<400> SEQUENCE: 74

Thr Arg Asn Ser Phe Ala Leu Val Pro Ser Leu Gln Arg Leu Met Leu

```
                       1               5                  10                  15
Arg Lys Val Ala Leu Lys Asn Val Asp Ser Ser Pro Ser
            20                  25

<210> SEQ ID NO 75
<211> LENGTH: 22
<212> TYPE: PRT
<213> ORGANISM: Artificial Sequence
<220> FEATURE:
<223> OTHER INFORMATION: neoantigen

<400> SEQUENCE: 75

Ser Ser His Tyr Lys Phe Ser Lys Pro Ala Leu Gln Ser Gln Ser Ile
1               5                   10                  15

Ser Leu Val Gln Gln Ser
            20

<210> SEQ ID NO 76
<211> LENGTH: 24
<212> TYPE: PRT
<213> ORGANISM: Artificial Sequence
<220> FEATURE:
<223> OTHER INFORMATION: neoantigen

<400> SEQUENCE: 76

Thr Glu Thr Val Asn His His Tyr Leu Leu Phe Gln Asn Thr Asp Leu
1               5                   10                  15

Gly Ser Phe His Asp Leu Leu Arg
            20

<210> SEQ ID NO 77
<211> LENGTH: 23
<212> TYPE: PRT
<213> ORGANISM: Artificial Sequence
<220> FEATURE:
<223> OTHER INFORMATION: neoantigen

<400> SEQUENCE: 77

Asp Arg Ala Ser Phe Leu Leu Thr Asp Tyr Ala Leu Ser Pro Asp Gly
1               5                   10                  15

Ser Ile Arg Lys Ala Thr Gly
            20

<210> SEQ ID NO 78
<211> LENGTH: 27
<212> TYPE: PRT
<213> ORGANISM: Artificial Sequence
<220> FEATURE:
<223> OTHER INFORMATION: neoantigen

<400> SEQUENCE: 78

Glu Arg Phe Trp Arg Asn Ile Leu Leu Leu Ser Leu His Lys Gly Ser
1               5                   10                  15

Leu Tyr Pro Arg Ile Pro Gly Leu Gly Lys Glu
            20                  25

<210> SEQ ID NO 79
<211> LENGTH: 24
<212> TYPE: PRT
<213> ORGANISM: Artificial Sequence
<220> FEATURE:
<223> OTHER INFORMATION: neoantigen

<400> SEQUENCE: 79
```

Arg Gly Arg Leu Pro Ala Gly Ala Val Arg Thr Leu Leu Ser Gln Val
1               5                   10                  15

Asn Lys Val Trp Asp Gln Ser Ser
            20

<210> SEQ ID NO 80
<211> LENGTH: 25
<212> TYPE: PRT
<213> ORGANISM: Artificial Sequence
<220> FEATURE:
<223> OTHER INFORMATION: neoantigen

<400> SEQUENCE: 80

Gly His Glu His Gln Pro Asp Met Gln Lys Ser Leu Leu Arg Ala Ala
1               5                   10                  15

Phe Phe Gly Lys Cys Phe Leu Asp Arg
            20                  25

<210> SEQ ID NO 81
<211> LENGTH: 29
<212> TYPE: PRT
<213> ORGANISM: Artificial Sequence
<220> FEATURE:
<223> OTHER INFORMATION: neoantigen

<400> SEQUENCE: 81

Glu Leu Gln Tyr Arg Gly Arg Glu Leu Arg Phe Asn Leu Ile Ala Asn
1               5                   10                  15

Gln His Leu Leu Ala Pro Gly Phe Val Ser Glu Thr Arg
            20                  25

<210> SEQ ID NO 82
<211> LENGTH: 23
<212> TYPE: PRT
<213> ORGANISM: Artificial Sequence
<220> FEATURE:
<223> OTHER INFORMATION: neoantigen

<400> SEQUENCE: 82

Glu Asp Leu Asp Ala Asn Leu Arg Lys Leu Asn Phe Arg Leu Phe Val
1               5                   10                  15

Ile Arg Gly Gln Pro Ala Asp
            20

<210> SEQ ID NO 83
<211> LENGTH: 26
<212> TYPE: PRT
<213> ORGANISM: Artificial Sequence
<220> FEATURE:
<223> OTHER INFORMATION: neoantigen

<400> SEQUENCE: 83

Gly His Gln Lys Leu Pro Gly Lys Ile His Leu Phe Glu Ala Glu Phe
1               5                   10                  15

Thr Gln Val Ala Lys Lys Glu Pro Asp Gly
            20                  25

<210> SEQ ID NO 84
<211> LENGTH: 23
<212> TYPE: PRT
<213> ORGANISM: Artificial Sequence
<220> FEATURE:
<223> OTHER INFORMATION: neoantigen

<400> SEQUENCE: 84

```
Thr Thr Pro Ser Gly Ser Ala Glu Tyr Met Ala Ser Glu Val Val Glu
1               5                   10                  15

Val Phe Thr Asp Gln Ala Thr
            20

<210> SEQ ID NO 85
<211> LENGTH: 27
<212> TYPE: PRT
<213> ORGANISM: Artificial Sequence
<220> FEATURE:
<223> OTHER INFORMATION: neoantigen

<400> SEQUENCE: 85

Ser Val Leu Arg Glu Asp Leu Gly Gln Leu Glu Tyr Lys Tyr Gln Tyr
1               5                   10                  15

Ala Tyr Phe Arg Met Gly Ile Lys His Pro Asp
            20                  25

<210> SEQ ID NO 86
<211> LENGTH: 23
<212> TYPE: PRT
<213> ORGANISM: Artificial Sequence
<220> FEATURE:
<223> OTHER INFORMATION: neoantigen

<400> SEQUENCE: 86

Pro Glu Asn Asp Asp Leu Phe Met Met Pro Arg Ile Val Asp Val Thr
1               5                   10                  15

Ser Leu Ala Thr Glu Gly Gly
            20

<210> SEQ ID NO 87
<211> LENGTH: 26
<212> TYPE: PRT
<213> ORGANISM: Artificial Sequence
<220> FEATURE:
<223> OTHER INFORMATION: neoantigen

<400> SEQUENCE: 87

Thr Leu Asp Asp Ile Lys Glu Trp Leu Glu Asp Glu Gly Gln Val Leu
1               5                   10                  15

Asn Ile Gln Met Arg Arg Thr Leu His Lys
            20                  25

<210> SEQ ID NO 88
<211> LENGTH: 25
<212> TYPE: PRT
<213> ORGANISM: Artificial Sequence
<220> FEATURE:
<223> OTHER INFORMATION: neoantigen

<400> SEQUENCE: 88

Gly Arg Met Ser Pro Ser Gln Phe Ala Arg Val Pro Gly Tyr Val Gly
1               5                   10                  15

Ser Pro Leu Ala Ala Met Asn Pro Lys
            20                  25

<210> SEQ ID NO 89
<211> LENGTH: 25
<212> TYPE: PRT
<213> ORGANISM: Artificial Sequence
<220> FEATURE:
<223> OTHER INFORMATION: neoantigen
```

<400> SEQUENCE: 89

Lys Ala His Val Glu Gly Asp Gly Val Val Glu Glu Ile Ile Arg Tyr
1               5                   10                  15

His Pro Phe Leu Tyr Asp Arg Glu Thr
            20                  25

<210> SEQ ID NO 90
<211> LENGTH: 19
<212> TYPE: PRT
<213> ORGANISM: Artificial Sequence
<220> FEATURE:
<223> OTHER INFORMATION: neoantigen

<400> SEQUENCE: 90

Asp Gly Val Ser Glu Glu Phe Trp Leu Val Asp Leu Leu Pro Ser Thr
1               5                   10                  15

His Tyr Thr

<210> SEQ ID NO 91
<211> LENGTH: 24
<212> TYPE: PRT
<213> ORGANISM: Artificial Sequence
<220> FEATURE:
<223> OTHER INFORMATION: neoantigen

<400> SEQUENCE: 91

Asp Ser Tyr His Leu Tyr Ala Tyr His Glu Glu Leu Ser Ala Thr Val
1               5                   10                  15

Pro Ser Gln Trp Lys Lys Ile Gly
            20

<210> SEQ ID NO 92
<211> LENGTH: 28
<212> TYPE: PRT
<213> ORGANISM: Artificial Sequence
<220> FEATURE:
<223> OTHER INFORMATION: neoantigen

<400> SEQUENCE: 92

Gly Asp Gln Tyr Lys Ala Thr Asp Phe Val Ala Asp Trp Ala Gly Thr
1               5                   10                  15

Phe Lys Met Val Phe Thr Pro Lys Asp Gly Ser Gly
            20                  25

<210> SEQ ID NO 93
<211> LENGTH: 25
<212> TYPE: PRT
<213> ORGANISM: Artificial Sequence
<220> FEATURE:
<223> OTHER INFORMATION: neoantigen

<400> SEQUENCE: 93

Glu Tyr Trp Lys Val Leu Asp Gly Glu Leu Glu Val Ala Pro Glu Tyr
1               5                   10                  15

Pro Gln Ser Thr Ala Arg Asp Trp Leu
            20                  25

<210> SEQ ID NO 94
<211> LENGTH: 25
<212> TYPE: PRT
<213> ORGANISM: Artificial Sequence
<220> FEATURE:
<223> OTHER INFORMATION: neoantigen

```
<400> SEQUENCE: 94

Thr Thr Thr Ser Val Lys Lys Glu Glu Leu Val Leu Ser Glu Glu Asp
1               5                   10                  15

Phe Gln Gly Ile Thr Pro Gly Ala Gln
            20                  25

<210> SEQ ID NO 95
<211> LENGTH: 23
<212> TYPE: PRT
<213> ORGANISM: Artificial Sequence
<220> FEATURE:
<223> OTHER INFORMATION: neoantigen

<400> SEQUENCE: 95

Ser Leu Thr Glu Glu Ser Gly Gly Ala Val Ala Phe Phe Pro Gly Asn
1               5                   10                  15

Leu Ser Thr Ser Ser Ser Ala
            20

<210> SEQ ID NO 96
<211> LENGTH: 24
<212> TYPE: PRT
<213> ORGANISM: Artificial Sequence
<220> FEATURE:
<223> OTHER INFORMATION: neoantigen

<400> SEQUENCE: 96

Lys Leu Arg Thr Ile Pro Leu Ser Asp Asn Thr Ile Phe Arg Arg Ile
1               5                   10                  15

Cys Thr Ile Ala Lys His Leu Glu
            20

<210> SEQ ID NO 97
<211> LENGTH: 25
<212> TYPE: PRT
<213> ORGANISM: Artificial Sequence
<220> FEATURE:
<223> OTHER INFORMATION: neoantigen

<400> SEQUENCE: 97

Ser His His Thr His Ser Tyr Gln Arg Tyr Ser His Pro Leu Phe Leu
1               5                   10                  15

Pro Gly His Arg Leu Asp Pro Pro Ile
            20                  25

<210> SEQ ID NO 98
<211> LENGTH: 26
<212> TYPE: PRT
<213> ORGANISM: Artificial Sequence
<220> FEATURE:
<223> OTHER INFORMATION: neoantigen

<400> SEQUENCE: 98

Asp Val Thr Gly Pro His Leu Tyr Ser Ile Tyr Leu His Gly Ser Thr
1               5                   10                  15

Asp Lys Leu Pro Tyr Val Thr Met Gly Ser
            20                  25

<210> SEQ ID NO 99
<211> LENGTH: 25
<212> TYPE: PRT
<213> ORGANISM: Artificial Sequence
<220> FEATURE:
<223> OTHER INFORMATION: neoantigen
```

<400> SEQUENCE: 99

Ala Arg Leu Gln Ser Lys Glu Tyr Pro Val Ile Phe Lys Ser Ile Met
1               5                   10                  15

Arg Gln Arg Leu Ile Ser Pro Gln Leu
            20                  25

<210> SEQ ID NO 100
<211> LENGTH: 24
<212> TYPE: PRT
<213> ORGANISM: Artificial Sequence
<220> FEATURE:
<223> OTHER INFORMATION: neoantigen

<400> SEQUENCE: 100

Leu His Thr His Tyr Asp Tyr Val Ser Ala Leu His Pro Val Ser Thr
1               5                   10                  15

Pro Ser Lys Glu Tyr Thr Ser Ala
            20

<210> SEQ ID NO 101
<211> LENGTH: 19
<212> TYPE: PRT
<213> ORGANISM: Artificial Sequence
<220> FEATURE:
<223> OTHER INFORMATION: neoantigen

<400> SEQUENCE: 101

Ser Asp Ala Phe Ser Gly Leu Thr Ala Leu Pro Gln Ser Ile Leu Leu
1               5                   10                  15

Phe Gly Pro

<210> SEQ ID NO 102
<211> LENGTH: 22
<212> TYPE: PRT
<213> ORGANISM: Artificial Sequence
<220> FEATURE:
<223> OTHER INFORMATION: neoantigen

<400> SEQUENCE: 102

Ser His Gln Ile His Ser Tyr Gln Leu Tyr Thr His Pro Leu Leu His
1               5                   10                  15

Pro Trp Asp His Arg Asp
            20

<210> SEQ ID NO 103
<211> LENGTH: 23
<212> TYPE: PRT
<213> ORGANISM: Artificial Sequence
<220> FEATURE:
<223> OTHER INFORMATION: neoantigen

<400> SEQUENCE: 103

Ser Thr Gln His Ala Asp Leu Thr Ile Ile Asp Asn Ile Lys Glu Met
1               5                   10                  15

Asn Phe Leu Arg Arg Tyr Lys
            20

<210> SEQ ID NO 104
<211> LENGTH: 26
<212> TYPE: PRT
<213> ORGANISM: Artificial Sequence
<220> FEATURE:
<223> OTHER INFORMATION: neoantigen

```
<400> SEQUENCE: 104

Ala Ser Ala Thr Glu Pro Ala Asn Asp Ser Leu Phe Ser Pro Gly Ala
1               5                   10                  15

Ala Asn Leu Phe Ser Thr Tyr Leu Ala Arg
            20                  25

<210> SEQ ID NO 105
<211> LENGTH: 27
<212> TYPE: PRT
<213> ORGANISM: Artificial Sequence
<220> FEATURE:
<223> OTHER INFORMATION: neoantigen

<400> SEQUENCE: 105

Ala Ala Ser Ala Ala Ala Phe Pro Ser Gln Arg Thr Ser Trp Glu Phe
1               5                   10                  15

Leu Gln Ser Leu Val Ser Ile Lys Gln Glu Lys
            20                  25

<210> SEQ ID NO 106
<211> LENGTH: 26
<212> TYPE: PRT
<213> ORGANISM: Artificial Sequence
<220> FEATURE:
<223> OTHER INFORMATION: neoantigen

<400> SEQUENCE: 106

Gly Ser Val Leu Gln Phe Met Pro Phe Thr Thr Val Ser Glu Leu Met
1               5                   10                  15

Lys Val Ser Ala Met Ser Ser Pro Lys Val
            20                  25

<210> SEQ ID NO 107
<211> LENGTH: 20
<212> TYPE: PRT
<213> ORGANISM: Artificial Sequence
<220> FEATURE:
<223> OTHER INFORMATION: neoantigen

<400> SEQUENCE: 107

Asp Lys Gly His Gln Phe His Val His Pro Leu Leu His Ser Gly Asp
1               5                   10                  15

Asp Leu Asp Pro
            20

<210> SEQ ID NO 108
<211> LENGTH: 26
<212> TYPE: PRT
<213> ORGANISM: Artificial Sequence
<220> FEATURE:
<223> OTHER INFORMATION: neoantigen

<400> SEQUENCE: 108

Asn Gln Val Leu Ala Ser Arg Tyr Gly Ile Arg Gly Phe Ser Thr Ile
1               5                   10                  15

Lys Ile Phe Gln Lys Gly Glu Ser Pro Val
            20                  25

<210> SEQ ID NO 109
<211> LENGTH: 19
<212> TYPE: PRT
<213> ORGANISM: Artificial Sequence
<220> FEATURE:
```

```
<223> OTHER INFORMATION: neoantigen

<400> SEQUENCE: 109

Met Ala Gly Pro Lys Gly Phe Gln Tyr Arg Ala Leu Tyr Pro Phe Arg
1               5                   10                  15

Arg Glu Arg

<210> SEQ ID NO 110
<211> LENGTH: 22
<212> TYPE: PRT
<213> ORGANISM: Artificial Sequence
<220> FEATURE:
<223> OTHER INFORMATION: neoantigen

<400> SEQUENCE: 110

Val Thr Leu Asn Asp Met Lys Ala Arg Gln Lys Ala Leu Val Arg Glu
1               5                   10                  15

Arg Glu Arg Gln Leu Ala
            20

<210> SEQ ID NO 111
<211> LENGTH: 24
<212> TYPE: PRT
<213> ORGANISM: Artificial Sequence
<220> FEATURE:
<223> OTHER INFORMATION: neoantigen

<400> SEQUENCE: 111

Ser Arg Leu Gln Thr Arg Lys Asn Lys Lys Leu Ala Leu Ser Ser Thr
1               5                   10                  15

Pro Ser Asn Ile Ala Pro Ser Asp
            20

<210> SEQ ID NO 112
<211> LENGTH: 18
<212> TYPE: PRT
<213> ORGANISM: Artificial Sequence
<220> FEATURE:
<223> OTHER INFORMATION: neoantigen

<400> SEQUENCE: 112

Leu Asn Thr Gly Leu Phe Arg Ile Lys Phe Lys Glu Pro Leu Glu Asn
1               5                   10                  15

Leu Ile

<210> SEQ ID NO 113
<211> LENGTH: 24
<212> TYPE: PRT
<213> ORGANISM: Artificial Sequence
<220> FEATURE:
<223> OTHER INFORMATION: neoantigen

<400> SEQUENCE: 113

Ser Leu Arg Asn Asn Met Phe Glu Ile Ser Asp Arg Phe Ile Gly Ile
1               5                   10                  15

Tyr Lys Thr Tyr Asn Ile Thr Lys
            20

<210> SEQ ID NO 114
<211> LENGTH: 22
<212> TYPE: PRT
<213> ORGANISM: Artificial Sequence
<220> FEATURE:
<223> OTHER INFORMATION: neoantigen
```

<400> SEQUENCE: 114

Trp Cys Thr Glu Met Lys Arg Val Phe Gly Phe Pro Val His Tyr Thr
1               5                   10                  15

Asp Val Ser Asn Met Ser
            20

<210> SEQ ID NO 115
<211> LENGTH: 23
<212> TYPE: PRT
<213> ORGANISM: Artificial Sequence
<220> FEATURE:
<223> OTHER INFORMATION: neoantigen

<400> SEQUENCE: 115

Val Lys Gln Leu Glu Arg Gly Glu Ala Ser Val Val Asp Phe Lys Lys
1               5                   10                  15

Asn Leu Glu Tyr Ala Ala Thr
            20

<210> SEQ ID NO 116
<211> LENGTH: 28
<212> TYPE: PRT
<213> ORGANISM: Artificial Sequence
<220> FEATURE:
<223> OTHER INFORMATION: neoantigen

<400> SEQUENCE: 116

Ser Thr Glu Val Glu Pro Lys Glu Ser Pro His Leu Ala Arg His Arg
1               5                   10                  15

His Leu Met Lys Thr Leu Val Lys Ser Leu Ser Thr
            20                  25

<210> SEQ ID NO 117
<211> LENGTH: 16
<212> TYPE: PRT
<213> ORGANISM: Artificial Sequence
<220> FEATURE:
<223> OTHER INFORMATION: neoantigen

<400> SEQUENCE: 117

Leu Met Ser Asn Leu Ala Phe Ala Asp Phe Cys Met Arg Met Tyr Leu
1               5                   10                  15

<210> SEQ ID NO 118
<211> LENGTH: 24
<212> TYPE: PRT
<213> ORGANISM: Artificial Sequence
<220> FEATURE:
<223> OTHER INFORMATION: neoantigen

<400> SEQUENCE: 118

Thr Lys Leu Lys Ser Lys Ala Pro His Trp Thr Asn Cys Ile Leu His
1               5                   10                  15

Glu Tyr Lys Asn Leu Ser Thr Ser
            20

<210> SEQ ID NO 119
<211> LENGTH: 21
<212> TYPE: PRT
<213> ORGANISM: Artificial Sequence
<220> FEATURE:
<223> OTHER INFORMATION: neoantigen

<400> SEQUENCE: 119

```
Pro Ala Ala Gly Asp Phe Ile Arg Phe Arg Phe Phe Gln Leu Leu Arg
1               5                   10                  15

Leu Glu Arg Phe Phe
            20
```

<210> SEQ ID NO 120
<211> LENGTH: 22
<212> TYPE: PRT
<213> ORGANISM: Artificial Sequence
<220> FEATURE:
<223> OTHER INFORMATION: neoantigen

<400> SEQUENCE: 120

```
Tyr Leu Ser His Thr Leu Gly Ala Ala Ser Ser Phe Met Arg Pro Thr
1               5                   10                  15

Val Pro Pro Pro Gln Phe
            20
```

<210> SEQ ID NO 121
<211> LENGTH: 21
<212> TYPE: PRT
<213> ORGANISM: Artificial Sequence
<220> FEATURE:
<223> OTHER INFORMATION: neoantigen

<400> SEQUENCE: 121

```
Ala Leu Leu Gln Asn Val Glu Leu Arg Arg Asn Val Leu Val Ser Pro
1               5                   10                  15

Thr Pro Leu Ala Asn
            20
```

<210> SEQ ID NO 122
<211> LENGTH: 23
<212> TYPE: PRT
<213> ORGANISM: Artificial Sequence
<220> FEATURE:
<223> OTHER INFORMATION: neoantigen

<400> SEQUENCE: 122

```
Phe Ala Lys Gly Phe Arg Glu Ser Asp Leu Asn Ser Trp Pro Val Ala
1               5                   10                  15

Pro Arg Pro Leu Leu Ser Val
            20
```

<210> SEQ ID NO 123
<211> LENGTH: 30
<212> TYPE: PRT
<213> ORGANISM: Artificial Sequence
<220> FEATURE:
<223> OTHER INFORMATION: neoantigen

<400> SEQUENCE: 123

```
Gly Leu Thr Arg Ile Ser Ile Gln Arg Ala Gln Pro Leu Pro Pro Cys
1               5                   10                  15

Leu Pro Ser Phe Arg Pro Pro Thr Ala Leu Gln Gly Leu Ser
            20                  25                  30
```

<210> SEQ ID NO 124
<211> LENGTH: 24
<212> TYPE: PRT
<213> ORGANISM: Artificial Sequence
<220> FEATURE:
<223> OTHER INFORMATION: neoantigen -continued

<400> SEQUENCE: 124

Thr Gly Lys Pro Glu Met Asp Phe Val Arg Leu Ala Gln Leu Phe Ala
1               5                   10                  15

Arg Ala Arg Pro Met Gly Leu Phe
            20

<210> SEQ ID NO 125
<211> LENGTH: 21
<212> TYPE: PRT
<213> ORGANISM: Artificial Sequence
<220> FEATURE:
<223> OTHER INFORMATION: neoantigen

<400> SEQUENCE: 125

Asp Gly Ala Trp Pro Val Leu Leu Asp Lys Phe Val Glu Trp Tyr Lys
1               5                   10                  15

Asp Lys Gln Met Ser
            20

<210> SEQ ID NO 126
<211> LENGTH: 25
<212> TYPE: PRT
<213> ORGANISM: Artificial Sequence
<220> FEATURE:
<223> OTHER INFORMATION: neoantigen

<400> SEQUENCE: 126

Asp Arg Ser Val Leu Ala Lys Lys Leu Lys Phe Val Thr Leu Val Phe
1               5                   10                  15

Arg His Gly Asp Arg Ser Pro Ile Asp
            20                  25

<210> SEQ ID NO 127
<211> LENGTH: 25
<212> TYPE: PRT
<213> ORGANISM: Artificial Sequence
<220> FEATURE:
<223> OTHER INFORMATION: neoantigen

<400> SEQUENCE: 127

Asp Arg Ser Val Leu Ala Lys Lys Leu Lys Phe Val Thr Leu Val Phe
1               5                   10                  15

Arg His Gly Asp Arg Ser Pro Ile Asp
            20                  25

<210> SEQ ID NO 128
<211> LENGTH: 23
<212> TYPE: PRT
<213> ORGANISM: Artificial Sequence
<220> FEATURE:
<223> OTHER INFORMATION: neoantigen

<400> SEQUENCE: 128

Thr Lys Arg Gln Val Ile Leu Leu His Thr Glu Leu Glu Arg Phe Leu
1               5                   10                  15

Glu Tyr Leu Pro Leu Arg Phe
            20

<210> SEQ ID NO 129
<211> LENGTH: 20
<212> TYPE: PRT
<213> ORGANISM: Artificial Sequence
<220> FEATURE:
<223> OTHER INFORMATION: neoantigen

<400> SEQUENCE: 129

Leu Gly Glu Thr Met Gly Gln Val Thr Glu Lys Leu Gln Pro Thr Tyr
1               5                   10                  15

Met Glu Glu Thr
            20

<210> SEQ ID NO 130
<211> LENGTH: 17
<212> TYPE: PRT
<213> ORGANISM: Artificial Sequence
<220> FEATURE:
<223> OTHER INFORMATION: neoantigen

<400> SEQUENCE: 130

Thr Phe Pro Lys Lys Ile Gln Met Leu Ala Arg Asp Phe Leu Asp Glu
1               5                   10                  15

Tyr

<210> SEQ ID NO 131
<211> LENGTH: 27
<212> TYPE: PRT
<213> ORGANISM: Artificial Sequence
<220> FEATURE:
<223> OTHER INFORMATION: neoantigen

<400> SEQUENCE: 131

Glu Arg Phe Trp Arg Asn Ile Leu Leu Leu Ser Leu His Lys Gly Ser
1               5                   10                  15

Leu Tyr Pro Arg Ile Pro Gly Leu Gly Lys Glu
            20                  25

<210> SEQ ID NO 132
<211> LENGTH: 24
<212> TYPE: PRT
<213> ORGANISM: Artificial Sequence
<220> FEATURE:
<223> OTHER INFORMATION: neoantigen

<400> SEQUENCE: 132

Arg Gly Arg Leu Pro Ala Gly Ala Val Arg Thr Leu Leu Ser Gln Val
1               5                   10                  15

Asn Lys Val Trp Asp Gln Ser Ser
            20

<210> SEQ ID NO 133
<211> LENGTH: 25
<212> TYPE: PRT
<213> ORGANISM: Artificial Sequence
<220> FEATURE:
<223> OTHER INFORMATION: neoantigen

<400> SEQUENCE: 133

Gly His Glu His Gln Pro Asp Met Gln Lys Ser Leu Leu Arg Ala Ala
1               5                   10                  15

Phe Phe Gly Lys Cys Phe Leu Asp Arg
            20                  25

<210> SEQ ID NO 134
<211> LENGTH: 25
<212> TYPE: PRT
<213> ORGANISM: Artificial Sequence
<220> FEATURE:
<223> OTHER INFORMATION: neoantigen

<400> SEQUENCE: 134

Lys Met Gln Arg Arg Asn Asp Asp Lys Ser Ile Leu Met His Gly Leu
1               5                   10                  15

Val Ser Leu Arg Glu Ser Ser Arg Gly
            20                  25

<210> SEQ ID NO 135
<211> LENGTH: 22
<212> TYPE: PRT
<213> ORGANISM: Artificial Sequence
<220> FEATURE:
<223> OTHER INFORMATION: neoantigen

<400> SEQUENCE: 135

Ser Thr Leu Pro Val Ile Ser Asp Ser Thr Thr Lys Arg Arg Trp Ser
1               5                   10                  15

Ala Leu Val Ile Gly Leu
            20

<210> SEQ ID NO 136
<211> LENGTH: 24
<212> TYPE: PRT
<213> ORGANISM: Artificial Sequence
<220> FEATURE:
<223> OTHER INFORMATION: neoantigen

<400> SEQUENCE: 136

Lys Leu Arg Thr Ile Pro Leu Ser Asp Asn Thr Ile Phe Arg Arg Ile
1               5                   10                  15

Cys Thr Ile Ala Lys His Leu Glu
            20

<210> SEQ ID NO 137
<211> LENGTH: 19
<212> TYPE: PRT
<213> ORGANISM: Artificial Sequence
<220> FEATURE:
<223> OTHER INFORMATION: neoantigen

<400> SEQUENCE: 137

Pro Ala Ser Ala Lys Ser Arg Arg Glu Phe Asp Lys Ile Glu Leu Ala
1               5                   10                  15

Tyr Arg Arg

<210> SEQ ID NO 138
<211> LENGTH: 25
<212> TYPE: PRT
<213> ORGANISM: Artificial Sequence
<220> FEATURE:
<223> OTHER INFORMATION: neoantigen

<400> SEQUENCE: 138

Ala Arg Leu Gln Ser Lys Glu Tyr Pro Val Ile Phe Lys Ser Ile Met
1               5                   10                  15

Arg Gln Arg Leu Ile Ser Pro Gln Leu
            20                  25

<210> SEQ ID NO 139
<211> LENGTH: 23
<212> TYPE: PRT
<213> ORGANISM: Artificial Sequence
<220> FEATURE:
<223> OTHER INFORMATION: neoantigen

<400> SEQUENCE: 139

Phe Pro Val Val Gln Ser Thr Glu Asp Val Phe Pro Gln Gly Leu Pro
1               5                   10                  15

Asn Glu Tyr Ala Phe Val Thr
            20

<210> SEQ ID NO 140
<211> LENGTH: 23
<212> TYPE: PRT
<213> ORGANISM: Artificial Sequence
<220> FEATURE:
<223> OTHER INFORMATION: neoantigen

<400> SEQUENCE: 140

Phe Pro Val Val Gln Ser Thr Glu Asp Val Phe Pro Gln Gly Leu Pro
1               5                   10                  15

Asn Glu Tyr Ala Phe Val Thr
            20

<210> SEQ ID NO 141
<211> LENGTH: 23
<212> TYPE: PRT
<213> ORGANISM: Artificial Sequence
<220> FEATURE:
<223> OTHER INFORMATION: neoantigen

<400> SEQUENCE: 141

Phe Pro Val Val Gln Ser Thr Glu Asp Val Phe Pro Gln Gly Leu Pro
1               5                   10                  15

Asn Glu Tyr Ala Phe Val Thr
            20

<210> SEQ ID NO 142
<211> LENGTH: 22
<212> TYPE: PRT
<213> ORGANISM: Artificial Sequence
<220> FEATURE:
<223> OTHER INFORMATION: neoantigen

<400> SEQUENCE: 142

Val Thr Leu Asn Asp Met Lys Ala Arg Gln Lys Ala Leu Val Arg Glu
1               5                   10                  15

Arg Glu Arg Gln Leu Ala
            20

<210> SEQ ID NO 143
<211> LENGTH: 18
<212> TYPE: PRT
<213> ORGANISM: Artificial Sequence
<220> FEATURE:
<223> OTHER INFORMATION: neoantigen

<400> SEQUENCE: 143

Leu Asn Thr Gly Leu Phe Arg Ile Lys Phe Lys Glu Pro Leu Glu Asn
1               5                   10                  15

Leu Ile

<210> SEQ ID NO 144
<211> LENGTH: 27
<212> TYPE: PRT
<213> ORGANISM: Artificial Sequence
<220> FEATURE:
<223> OTHER INFORMATION: neoantigen

<400> SEQUENCE: 144

Lys Val Val Gln His Ala Leu Asp Lys Ala Arg Thr Gly Lys Thr Cys
1               5                   10                  15

Leu Val Val Thr His Arg Leu Ser Ala Ile Gln
            20                  25

<210> SEQ ID NO 145
<211> LENGTH: 27
<212> TYPE: PRT
<213> ORGANISM: Artificial Sequence
<220> FEATURE:
<223> OTHER INFORMATION: neoantigen

<400> SEQUENCE: 145

Asn Gln Glu Ala Phe Lys His Leu Tyr Phe Glu Lys Phe Ser Gly Tyr
1               5                   10                  15

Tyr Asp Thr Met Asp Ala Gly Tyr Met Asp Glu
            20                  25

<210> SEQ ID NO 146
<211> LENGTH: 27
<212> TYPE: PRT
<213> ORGANISM: Artificial Sequence
<220> FEATURE:
<223> OTHER INFORMATION: neoantigen

<400> SEQUENCE: 146

Pro Ser Phe Leu Gly Met Glu Ser Cys Gly Ile His Glu Ile Thr Phe
1               5                   10                  15

Asn Ser Ile Met Lys Cys Asp Val Asp Ile Arg
            20                  25

<210> SEQ ID NO 147
<211> LENGTH: 27
<212> TYPE: PRT
<213> ORGANISM: Artificial Sequence
<220> FEATURE:
<223> OTHER INFORMATION: neoantigen

<400> SEQUENCE: 147

Tyr Pro Lys Gly Ala Gly Glu Met Leu Glu Asp Gln Gln Ala Ala Arg
1               5                   10                  15

Met Glu Lys Leu Ala Gly Leu Val Glu Glu Leu
            20                  25

<210> SEQ ID NO 148
<211> LENGTH: 24
<212> TYPE: PRT
<213> ORGANISM: Artificial Sequence
<220> FEATURE:
<223> OTHER INFORMATION: neoantigen

<400> SEQUENCE: 148

Lys Glu Glu Leu Gln Lys Ser Leu Asn Ile Leu Thr Ala Leu Gln Lys
1               5                   10                  15

Lys Gly Ala Glu Lys Glu Glu Leu
            20

<210> SEQ ID NO 149
<211> LENGTH: 27
<212> TYPE: PRT
<213> ORGANISM: Artificial Sequence
<220> FEATURE:

```
<223> OTHER INFORMATION: neoantigen

<400> SEQUENCE: 149

Val Thr Cys Val Pro Asn Gly Thr Trp Arg Asn Tyr Lys Val Glu Val
1               5                   10                  15

Arg Phe Glu Pro Arg His Arg Pro Thr Arg Phe
            20                  25

<210> SEQ ID NO 150
<211> LENGTH: 27
<212> TYPE: PRT
<213> ORGANISM: Artificial Sequence
<220> FEATURE:
<223> OTHER INFORMATION: neoantigen

<400> SEQUENCE: 150

Val Phe Asp Thr Ala Phe Ser Arg His Phe Ser Leu Leu Lys Ser Gln
1               5                   10                  15

Arg Glu Phe Val Arg Arg Phe Arg Gly Gln Ala
            20                  25

<210> SEQ ID NO 151
<211> LENGTH: 27
<212> TYPE: PRT
<213> ORGANISM: Artificial Sequence
<220> FEATURE:
<223> OTHER INFORMATION: neoantigen

<400> SEQUENCE: 151

Pro Gln Thr Leu Gly Lys Lys Gly Ser Lys Asn Asn Ile Phe Val Tyr
1               5                   10                  15

Met Thr Leu Asn Gln Lys Lys Ser Asp Ser Ser
            20                  25

<210> SEQ ID NO 152
<211> LENGTH: 27
<212> TYPE: PRT
<213> ORGANISM: Artificial Sequence
<220> FEATURE:
<223> OTHER INFORMATION: neoantigen

<400> SEQUENCE: 152

Cys Glu Asp Cys Arg Thr Arg Gly Gln Phe Asn Ala Phe Pro Tyr His
1               5                   10                  15

Phe Arg Gly Arg Arg Ser Leu Glu Phe Ser Tyr
            20                  25

<210> SEQ ID NO 153
<211> LENGTH: 27
<212> TYPE: PRT
<213> ORGANISM: Artificial Sequence
<220> FEATURE:
<223> OTHER INFORMATION: neoantigen

<400> SEQUENCE: 153

Ser Pro Glu Leu Ser Ala Ala Glu Ser Ala Val Val Leu Asn Leu Leu
1               5                   10                  15

Met Ser Leu Pro Glu Glu Leu Pro Leu Leu Pro
            20                  25

<210> SEQ ID NO 154
<211> LENGTH: 27
<212> TYPE: PRT
<213> ORGANISM: Artificial Sequence
```

```
<220> FEATURE:
<223> OTHER INFORMATION: neoantigen

<400> SEQUENCE: 154

Val Phe Ala Arg Val Ala Pro Lys Gln Lys Glu Phe Val Phe Thr Ser
1               5                   10                  15

Leu Lys Glu Leu Gly Tyr Val Thr Leu Met Cys
            20                  25

<210> SEQ ID NO 155
<211> LENGTH: 27
<212> TYPE: PRT
<213> ORGANISM: Artificial Sequence
<220> FEATURE:
<223> OTHER INFORMATION: neoantigen

<400> SEQUENCE: 155

Ser Ala Asp Ala Arg Leu Met Val Phe Asp Lys Thr Glu Arg Thr Trp
1               5                   10                  15

Arg Leu Leu Cys Ser Ser Arg Ser Asn Ala Arg
            20                  25

<210> SEQ ID NO 156
<211> LENGTH: 27
<212> TYPE: PRT
<213> ORGANISM: Artificial Sequence
<220> FEATURE:
<223> OTHER INFORMATION: neoantigen

<400> SEQUENCE: 156

Met Gly Pro Leu Leu Val Ala Thr Phe Trp Pro Glu Leu Ser Glu Lys
1               5                   10                  15

Ile Asp Ala Val Tyr Glu Ala Pro Gln Glu Glu
            20                  25

<210> SEQ ID NO 157
<211> LENGTH: 27
<212> TYPE: PRT
<213> ORGANISM: Artificial Sequence
<220> FEATURE:
<223> OTHER INFORMATION: neoantigen

<400> SEQUENCE: 157

Cys Gly Pro Cys Ser Glu Lys Arg Phe Leu Leu Pro Ser Arg Ser Ser
1               5                   10                  15

Lys Pro Val Arg Ile Cys Asp Phe Cys Tyr Asp
            20                  25

<210> SEQ ID NO 158
<211> LENGTH: 27
<212> TYPE: PRT
<213> ORGANISM: Artificial Sequence
<220> FEATURE:
<223> OTHER INFORMATION: neoantigen

<400> SEQUENCE: 158

Leu Thr Val Thr Leu Arg Ser Pro Thr Trp Met Arg Met Asn Gln Gly
1               5                   10                  15

Val Cys Cys Asn Leu Glu Tyr His Ser Ser Gly
            20                  25

<210> SEQ ID NO 159
<211> LENGTH: 27
<212> TYPE: PRT
```

```
<213> ORGANISM: Artificial Sequence
<220> FEATURE:
<223> OTHER INFORMATION: neoantigen

<400> SEQUENCE: 159

Leu His Ser Asn Val Leu Ala Arg Ile Asp Ala Ala Ala Leu Thr Gly
1               5                   10                  15
Leu Ala Leu Leu Glu Gln Leu Asp Leu Ser Asp
            20                  25

<210> SEQ ID NO 160
<211> LENGTH: 27
<212> TYPE: PRT
<213> ORGANISM: Artificial Sequence
<220> FEATURE:
<223> OTHER INFORMATION: neoantigen

<400> SEQUENCE: 160

Leu Thr Ala Val Arg Pro Glu Gly Ser Glu Pro Pro Gly Leu Pro Thr
1               5                   10                  15
Ser Gly Pro Arg Arg Pro Gly Cys Ser Arg
            20                  25

<210> SEQ ID NO 161
<211> LENGTH: 25
<212> TYPE: PRT
<213> ORGANISM: Artificial Sequence
<220> FEATURE:
<223> OTHER INFORMATION: neoantigen

<400> SEQUENCE: 161

Ala Leu Pro Ser Leu Thr Cys Ser Leu Thr Pro Leu Gly Val Ala Leu
1               5                   10                  15
Val Leu Trp Thr Val Leu Gly Pro Cys
            20                  25

<210> SEQ ID NO 162
<211> LENGTH: 27
<212> TYPE: PRT
<213> ORGANISM: Artificial Sequence
<220> FEATURE:
<223> OTHER INFORMATION: neoantigen

<400> SEQUENCE: 162

Gly Gly Gly Thr Gly Asp Ser Glu Gly Ser Gly Ala Leu Arg Ser Leu
1               5                   10                  15
Thr Cys Ser Leu Thr Pro Leu Gly Leu Ala Leu
            20                  25

<210> SEQ ID NO 163
<211> LENGTH: 27
<212> TYPE: PRT
<213> ORGANISM: Artificial Sequence
<220> FEATURE:
<223> OTHER INFORMATION: neoantigen

<400> SEQUENCE: 163

Asp Val Glu Glu Arg Val Gln Lys Ser Phe Pro His Pro Val Asp Lys
1               5                   10                  15
Trp Ala Ile Ala Asp Ala Gln Ser Ala Ile Glu
            20                  25

<210> SEQ ID NO 164
<211> LENGTH: 27
```

```
<212> TYPE: PRT
<213> ORGANISM: Artificial Sequence
<220> FEATURE:
<223> OTHER INFORMATION: neoantigen

<400> SEQUENCE: 164

Ser Pro Gly Asp Leu Asp Val Phe Val Arg Phe Asp Phe Leu Tyr Pro
1               5                   10                  15

Asn Val Glu Glu Ala Gln Lys Asp Lys Thr Ser
            20                  25

<210> SEQ ID NO 165
<211> LENGTH: 27
<212> TYPE: PRT
<213> ORGANISM: Artificial Sequence
<220> FEATURE:
<223> OTHER INFORMATION: neoantigen

<400> SEQUENCE: 165

Asp Phe Ile Ala Gly Phe Cys Gly Glu Thr Glu Glu Asp Tyr Val Gln
1               5                   10                  15

Thr Val Ser Leu Leu Arg Glu Val Gln Tyr Asn
            20                  25

<210> SEQ ID NO 166
<211> LENGTH: 27
<212> TYPE: PRT
<213> ORGANISM: Artificial Sequence
<220> FEATURE:
<223> OTHER INFORMATION: neoantigen

<400> SEQUENCE: 166

Arg Ser Gln Met Thr Thr Ser Phe Thr Asp Pro Ala Ile Phe Met Asp
1               5                   10                  15

Leu Leu Arg Ala Val Leu Gln Pro Ser Ile Asn
            20                  25

<210> SEQ ID NO 167
<211> LENGTH: 27
<212> TYPE: PRT
<213> ORGANISM: Artificial Sequence
<220> FEATURE:
<223> OTHER INFORMATION: neoantigen

<400> SEQUENCE: 167

Thr Ala Ala Gly Ile His Pro Gln Ile Ser Ser Ile Phe Ile Leu Gly
1               5                   10                  15

Ser Leu Val Tyr Phe Ser Gln Glu Ala Ser Arg
            20                  25

<210> SEQ ID NO 168
<211> LENGTH: 27
<212> TYPE: PRT
<213> ORGANISM: Artificial Sequence
<220> FEATURE:
<223> OTHER INFORMATION: neoantigen

<400> SEQUENCE: 168

Arg Lys Asp Leu Leu Lys Ala Asn Val Lys Ile Phe Lys Phe Gln Gly
1               5                   10                  15

Ala Ala Leu Asp Lys Tyr Ala Lys Lys Ser Val
            20                  25

<210> SEQ ID NO 169
```

```
<211> LENGTH: 27
<212> TYPE: PRT
<213> ORGANISM: Artificial Sequence
<220> FEATURE:
<223> OTHER INFORMATION: neoantigen

<400> SEQUENCE: 169

His Val Leu Ser Gly Leu Ser Lys Asp Lys Glu Lys Arg Lys Glu Asn
1               5                   10                  15

Val Arg Asn Ser Phe Trp Ile Tyr Asp Ile Val
            20                  25

<210> SEQ ID NO 170
<211> LENGTH: 27
<212> TYPE: PRT
<213> ORGANISM: Artificial Sequence
<220> FEATURE:
<223> OTHER INFORMATION: neoantigen

<400> SEQUENCE: 170

Lys Thr Glu Trp Lys Ser Asn Val Tyr Leu Ala Arg Ser Trp Ile Gln
1               5                   10                  15

Gly Leu Gly Leu Tyr Ala Ala Arg Asp Ile Glu
            20                  25

<210> SEQ ID NO 171
<211> LENGTH: 27
<212> TYPE: PRT
<213> ORGANISM: Artificial Sequence
<220> FEATURE:
<223> OTHER INFORMATION: neoantigen

<400> SEQUENCE: 171

Pro Pro Thr Pro Leu Leu Asn Thr Thr Ser Ser Leu Ser Glu Tyr Pro
1               5                   10                  15

Leu Gly Arg Ala Asp Phe Asp His Tyr Thr Gly
            20                  25

<210> SEQ ID NO 172
<211> LENGTH: 27
<212> TYPE: PRT
<213> ORGANISM: Artificial Sequence
<220> FEATURE:
<223> OTHER INFORMATION: neoantigen

<400> SEQUENCE: 172

Leu Phe Leu Ala Leu Leu Ala Gly Ala His Ala Glu Phe Ser Gly Cys
1               5                   10                  15

Lys Ile Arg Val Thr Ser Lys Ala Leu Glu Leu
            20                  25

<210> SEQ ID NO 173
<211> LENGTH: 27
<212> TYPE: PRT
<213> ORGANISM: Artificial Sequence
<220> FEATURE:
<223> OTHER INFORMATION: neoantigen

<400> SEQUENCE: 173

Phe Thr Arg Ala Phe Asp Gln Ile Arg Met Ala Ala Ile Phe Glu Ser
1               5                   10                  15

Asn Ile Asn Leu Cys Gly Ser His Cys Gly Val
            20                  25
```

```
<210> SEQ ID NO 174
<211> LENGTH: 27
<212> TYPE: PRT
<213> ORGANISM: Artificial Sequence
<220> FEATURE:
<223> OTHER INFORMATION: neoantigen

<400> SEQUENCE: 174

Gly Lys Ser Tyr Gln Leu Leu Val Val Glu Asn Thr Val Lys Val Ala
1               5                   10                  15

Gln Phe Ile Asn Asn Asn Pro Glu Phe Leu Gln
            20                  25

<210> SEQ ID NO 175
<211> LENGTH: 27
<212> TYPE: PRT
<213> ORGANISM: Artificial Sequence
<220> FEATURE:
<223> OTHER INFORMATION: neoantigen

<400> SEQUENCE: 175

Ser Arg Trp Asp Asp Ser Gln Arg Phe Leu Ser Asp His Leu Tyr Leu
1               5                   10                  15

Val Cys Glu Glu Thr Ala Lys Tyr Leu Ile Leu
            20                  25

<210> SEQ ID NO 176
<211> LENGTH: 27
<212> TYPE: PRT
<213> ORGANISM: Artificial Sequence
<220> FEATURE:
<223> OTHER INFORMATION: neoantigen.

<400> SEQUENCE: 176

Ile Thr Lys His Leu Tyr Glu Asp Pro Arg Gln His Ser Ser Gly Val
1               5                   10                  15

Leu Thr Asp Leu Arg Ser Ala Leu Val Asn Asn
            20                  25

<210> SEQ ID NO 177
<211> LENGTH: 27
<212> TYPE: PRT
<213> ORGANISM: Artificial Sequence
<220> FEATURE:
<223> OTHER INFORMATION: neoantigen

<400> SEQUENCE: 177

Asp Val Glu Glu Arg His His Ala Tyr Leu Lys Pro Phe Cys Val Leu
1               5                   10                  15

Ile Ser Leu Leu Asp Lys Pro Glu Ile Gly Pro
            20                  25

<210> SEQ ID NO 178
<211> LENGTH: 27
<212> TYPE: PRT
<213> ORGANISM: Artificial Sequence
<220> FEATURE:
<223> OTHER INFORMATION: neoantigen

<400> SEQUENCE: 178

Ala Thr Gly Gln Ser Ala Phe Ala Gln Val Ile Ala Asp Cys His Lys
1               5                   10                  15

Ile Leu Phe Asp Arg Asn Ser Ala Ile Lys Ser
            20                  25
```

<210> SEQ ID NO 179
<211> LENGTH: 27
<212> TYPE: PRT
<213> ORGANISM: Artificial Sequence
<220> FEATURE:
<223> OTHER INFORMATION: neoantigen

<400> SEQUENCE: 179

```
Val Thr Val Leu Phe Ala Gly Gln His Ile Ala Lys Ser Leu Phe Glu
1               5                  10                  15

Val Tyr Val Asp Lys Ser Gln Gly Asp Ala Ser
            20                  25
```

<210> SEQ ID NO 180
<211> LENGTH: 27
<212> TYPE: PRT
<213> ORGANISM: Artificial Sequence
<220> FEATURE:
<223> OTHER INFORMATION: neoantigen

<400> SEQUENCE: 180

```
Val Asn Ala Val Phe Glu Trp His Ile Thr Lys Gly Gly Ile Ile Gly
1               5                  10                  15

Ala Lys Trp Thr Ile Asp Leu Lys Ser Gly Ser
            20                  25
```

<210> SEQ ID NO 181
<211> LENGTH: 27
<212> TYPE: PRT
<213> ORGANISM: Artificial Sequence
<220> FEATURE:
<223> OTHER INFORMATION: neoantigen

<400> SEQUENCE: 181

```
Ser Ser Ser Thr Thr Asn Asn Asp Pro Tyr Ala Lys Pro Ser Asp Thr
1               5                  10                  15

Pro Arg Pro Val Met Thr Asp Gln Phe Pro Lys
            20                  25
```

<210> SEQ ID NO 182
<211> LENGTH: 26
<212> TYPE: PRT
<213> ORGANISM: Artificial Sequence
<220> FEATURE:
<223> OTHER INFORMATION: neoantigen

<400> SEQUENCE: 182

```
Met Thr Glu Tyr Lys Leu Val Val Val Gly Ala Gly Asp Val Gly Lys
1               5                  10                  15

Ser Ala Leu Thr Ile Gln Leu Ile Gln Asn
            20                  25
```

<210> SEQ ID NO 183
<211> LENGTH: 27
<212> TYPE: PRT
<213> ORGANISM: Artificial Sequence
<220> FEATURE:
<223> OTHER INFORMATION: neoantigen

<400> SEQUENCE: 183

```
Val Lys Leu Leu Ile Gly Asn Arg Asp Ser Leu Asp Asn Leu Tyr Tyr
1               5                  10                  15

Asp Trp Tyr Ile Leu Val Thr Asn Lys Cys His
            20                  25
```

<210> SEQ ID NO 184
<211> LENGTH: 27
<212> TYPE: PRT
<213> ORGANISM: Artificial Sequence
<220> FEATURE:
<223> OTHER INFORMATION: neoantigen.

<400> SEQUENCE: 184

Met Ala Ile Ser Phe Leu Thr Thr Leu Ala Lys Val Tyr Ser Ser Ser
1               5                   10                  15

Leu Ser Lys Ile Ser Gly Ser Ile Leu Asn Glu
            20                  25

<210> SEQ ID NO 185
<211> LENGTH: 27
<212> TYPE: PRT
<213> ORGANISM: Artificial Sequence
<220> FEATURE:
<223> OTHER INFORMATION: neoantigen

<400> SEQUENCE: 185

Val Leu Ser His Val Ser Gly Leu Gly Trp Leu Ala Ser Asn Leu Pro
1               5                   10                  15

Ser Phe Leu Arg Val Pro Lys Trp Ile Ile Ala
            20                  25

<210> SEQ ID NO 186
<211> LENGTH: 27
<212> TYPE: PRT
<213> ORGANISM: Artificial Sequence
<220> FEATURE:
<223> OTHER INFORMATION: neoantigen

<400> SEQUENCE: 186

Ile Ala Glu Leu Glu Asn Lys Asn Arg Glu Ile Leu Gln Lys Ile Gln
1               5                   10                  15

Arg Leu Arg Leu Glu His Glu Gln Ala Ser Gln
            20                  25

<210> SEQ ID NO 187
<211> LENGTH: 27
<212> TYPE: PRT
<213> ORGANISM: Artificial Sequence
<220> FEATURE:
<223> OTHER INFORMATION: neoantigen

<400> SEQUENCE: 187

Pro Lys Gly Met Pro Lys Asp Leu Asn Val Gly Gln Gln Ser Leu Ser
1               5                   10                  15

Asn Ser Gly Ile Ser Glu Val Glu Gly Leu Ser
            20                  25

<210> SEQ ID NO 188
<211> LENGTH: 27
<212> TYPE: PRT
<213> ORGANISM: Artificial Sequence
<220> FEATURE:
<223> OTHER INFORMATION: neoantigen

<400> SEQUENCE: 188

Leu Ala Val Gly His Leu Tyr Arg Leu Ser Phe Leu Lys Lys Asp Ser
1               5                   10                  15

Gln Ser Cys Arg Val Ala Ala Leu Glu Ala Ser 20                  25

<210> SEQ ID NO 189
<211> LENGTH: 27
<212> TYPE: PRT
<213> ORGANISM: Artificial Sequence
<220> FEATURE:
<223> OTHER INFORMATION: neoantigen

<400> SEQUENCE: 189

Pro Leu Pro Pro His Pro His Pro His Pro His Ser Val Val Leu Pro
1               5                   10                  15

Pro Ala His Leu Pro Val Gln Gln Gln Pro
            20                  25

<210> SEQ ID NO 190
<211> LENGTH: 20
<212> TYPE: PRT
<213> ORGANISM: Artificial Sequence
<220> FEATURE:
<223> OTHER INFORMATION: neoantigen

<400> SEQUENCE: 190

Met Pro Pro Leu Pro Ile Phe Ser Leu Pro Trp Ser Val His Thr Trp
1               5                   10                  15

Thr Gln Gly Pro
            20

<210> SEQ ID NO 191
<211> LENGTH: 27
<212> TYPE: PRT
<213> ORGANISM: Artificial Sequence
<220> FEATURE:
<223> OTHER INFORMATION: neoantigen

<400> SEQUENCE: 191

Ala Lys Thr Val Lys His Gly Ala Gly Ala Glu Ile Ser Ile Val Asn
1               5                   10                  15

Pro Glu Gln Tyr Ser Lys Arg Phe Leu Asp Phe
            20                  25

<210> SEQ ID NO 192
<211> LENGTH: 27
<212> TYPE: PRT
<213> ORGANISM: Artificial Sequence
<220> FEATURE:
<223> OTHER INFORMATION: neoantigen

<400> SEQUENCE: 192

Pro Ser Arg Ala Gly Arg Pro His His Asp Gln Arg Ser Leu Ser Pro
1               5                   10                  15

His Leu Gly Arg Ser Lys Ser Pro Ser His
            20                  25

<210> SEQ ID NO 193
<211> LENGTH: 27
<212> TYPE: PRT
<213> ORGANISM: Artificial Sequence
<220> FEATURE:
<223> OTHER INFORMATION: neoantigen

<400> SEQUENCE: 193

Pro Pro Pro Pro Pro Gln Asn Asn Lys Pro Pro Val Pro Phe Thr Pro
1               5                   10                  15

Arg Pro Ser Ala Ser Ser Gln Ala Pro Pro
            20                  25

<210> SEQ ID NO 194
<211> LENGTH: 27
<212> TYPE: PRT
<213> ORGANISM: Artificial Sequence
<220> FEATURE:
<223> OTHER INFORMATION: neoantigen

<400> SEQUENCE: 194

Val Val Tyr Ser Ile Leu Gln Gly Gln Pro Tyr Phe Ser Leu Asp Pro
1               5                   10                  15

Lys Thr Gly Val Ile Arg Thr Ala Leu His Asn
            20                  25

<210> SEQ ID NO 195
<211> LENGTH: 27
<212> TYPE: PRT
<213> ORGANISM: Artificial Sequence
<220> FEATURE:
<223> OTHER INFORMATION: neoantigen

<400> SEQUENCE: 195

Glu Ile Gly Trp Leu Lys Pro Val Ile Gly Ser Gln Tyr Leu Leu Glu
1               5                   10                  15

Lys Val Ala Glu Ala His Glu Asn Ile Ile His
            20                  25

<210> SEQ ID NO 196
<211> LENGTH: 27
<212> TYPE: PRT
<213> ORGANISM: Artificial Sequence
<220> FEATURE:
<223> OTHER INFORMATION: neoantigen

<400> SEQUENCE: 196

Val Val Cys Tyr Gln Ser Asn Arg Asp Glu Leu Arg Arg Cys Ile Ile
1               5                   10                  15

Gln Trp Leu Glu Ala Glu Ile Ile Pro Asp Gly
            20                  25

<210> SEQ ID NO 197
<211> LENGTH: 27
<212> TYPE: PRT
<213> ORGANISM: Artificial Sequence
<220> FEATURE:
<223> OTHER INFORMATION: neoantigen

<400> SEQUENCE: 197

Ala Val Val Asp Thr Leu Glu Ser Glu Tyr Leu Lys Ile Ser Gly Asp
1               5                   10                  15

Gln Val Val Ser Val Val Phe Ile Lys Glu Leu
            20                  25

<210> SEQ ID NO 198
<211> LENGTH: 25
<212> TYPE: PRT
<213> ORGANISM: Artificial Sequence
<220> FEATURE:
<223> OTHER INFORMATION: neoantigen

<400> SEQUENCE: 198

Lys Glu Ala Lys Arg Ser Asn Ser Asn Lys Thr Met Asp Leu Ser Cys
1               5                   10                  15

```
Leu Lys Trp Thr Pro Pro Lys Gly Thr
            20              25

<210> SEQ ID NO 199
<211> LENGTH: 27
<212> TYPE: PRT
<213> ORGANISM: Artificial Sequence
<220> FEATURE:
<223> OTHER INFORMATION: neoantigen

<400> SEQUENCE: 199

Arg Asp Trp Ala Phe Val Pro Ala Pro Cys Ala Thr Ser Ser Tyr Thr
1               5                   10                  15

Gly Phe Ala Asn Lys His Gly Ser Lys Pro Ser
            20              25

<210> SEQ ID NO 200
<211> LENGTH: 27
<212> TYPE: PRT
<213> ORGANISM: Artificial Sequence
<220> FEATURE:
<223> OTHER INFORMATION: neoantigen

<400> SEQUENCE: 200

Leu Ser Lys Val Thr Lys Val Lys Thr Asp Arg Pro Leu Leu Glu Asn
1               5                   10                  15

Pro Tyr His Ser Arg Pro Arg Pro Asp Pro Ser
            20              25

<210> SEQ ID NO 201
<211> LENGTH: 23
<212> TYPE: PRT
<213> ORGANISM: Artificial Sequence
<220> FEATURE:
<223> OTHER INFORMATION: neoantigen

<400> SEQUENCE: 201

Met Ala Ala Val Ser Val Tyr Ala Pro Leu Val Gly Gly Phe Ser Phe
1               5                   10                  15

Asp Asn Cys Arg Arg Asn Ala
            20

<210> SEQ ID NO 202
<211> LENGTH: 27
<212> TYPE: PRT
<213> ORGANISM: Artificial Sequence
<220> FEATURE:
<223> OTHER INFORMATION: neoantigen

<400> SEQUENCE: 202

Asp Thr Pro Pro Phe Tyr Ser Asn Ser Thr Asn Ser Phe Gln Asn Thr
1               5                   10                  15

Val Glu Gly Tyr Ser Asp Pro Thr Gly Lys Tyr
            20              25

<210> SEQ ID NO 203
<211> LENGTH: 27
<212> TYPE: PRT
<213> ORGANISM: Artificial Sequence
<220> FEATURE:
<223> OTHER INFORMATION: neoantigen

<400> SEQUENCE: 203

Lys Ser Arg Pro Gly Ser Val Val Pro Thr Thr Leu Phe Lys Gly Ile
```

```
                 1               5                  10                  15
Lys Thr Val Asn Pro Thr Phe Arg Gly Tyr Ser
             20                  25
```

<210> SEQ ID NO 204
<211> LENGTH: 27
<212> TYPE: PRT
<213> ORGANISM: Artificial Sequence
<220> FEATURE:
<223> OTHER INFORMATION: neoantigen

<400> SEQUENCE: 204

```
Ile Gly Leu Ile Phe Val Val Asp Ser Asn Asp Arg Glu Gln Val Asn
1               5                  10                  15

Glu Ala Arg Glu Glu Leu Met Arg Met Leu Ala
             20                  25
```

<210> SEQ ID NO 205
<211> LENGTH: 27
<212> TYPE: PRT
<213> ORGANISM: Artificial Sequence
<220> FEATURE:
<223> OTHER INFORMATION: neoantigen

<400> SEQUENCE: 205

```
Gln Gly Leu Ile Phe Val Val Asp Ser Asn Asp Arg Glu Gln Val Asn
1               5                  10                  15

Glu Ala Arg Glu Glu Leu Met Arg Met Leu Ala
             20                  25
```

<210> SEQ ID NO 206
<211> LENGTH: 27
<212> TYPE: PRT
<213> ORGANISM: Artificial Sequence
<220> FEATURE:
<223> OTHER INFORMATION: neoantigen

<400> SEQUENCE: 206

```
Ser Arg Lys Lys Arg Gly Cys Ser Ser Ser Lys Tyr Ala Ser Tyr
1               5                  10                  15

Tyr His Val Met Pro Lys Gln Asn Ser Thr Leu
             20                  25
```

<210> SEQ ID NO 207
<211> LENGTH: 27
<212> TYPE: PRT
<213> ORGANISM: Artificial Sequence
<220> FEATURE:
<223> OTHER INFORMATION: neoantigen

<400> SEQUENCE: 207

```
Ala Met Ala Ala Thr Cys Ile Ser Asp Thr Leu Gly Ile Phe Leu Ser
1               5                  10                  15

Gly Leu Leu Ala Leu Pro Leu His Asp Phe Leu
             20                  25
```

<210> SEQ ID NO 208
<211> LENGTH: 27
<212> TYPE: PRT
<213> ORGANISM: Artificial Sequence
<220> FEATURE:
<223> OTHER INFORMATION: neoantigen

<400> SEQUENCE: 208

Lys Leu Ile Val Gln Ile Lys Gly Ser Val Glu Asp Ile Ser Val Met
1               5                   10                  15

Leu Val Gly Asn Lys Cys Asp Glu Thr Gln Arg
            20                  25

<210> SEQ ID NO 209
<211> LENGTH: 27
<212> TYPE: PRT
<213> ORGANISM: Artificial Sequence
<220> FEATURE:
<223> OTHER INFORMATION: neoantigen

<400> SEQUENCE: 209

Gly His Gln Glu Asn Ala Lys Asn Glu Glu Ile Leu Asn Phe Leu Lys
1               5                   10                  15

Tyr Val Arg Pro Gly Gly Gly Phe Glu Pro Asn
            20                  25

<210> SEQ ID NO 210
<211> LENGTH: 14
<212> TYPE: PRT
<213> ORGANISM: Artificial Sequence
<220> FEATURE:
<223> OTHER INFORMATION: neoantigen

<400> SEQUENCE: 210

Ser Ile Leu Asp Leu Phe Leu Gly Arg Trp Phe Arg Ser Trp
1               5                   10

<210> SEQ ID NO 211
<211> LENGTH: 27
<212> TYPE: PRT
<213> ORGANISM: Artificial Sequence
<220> FEATURE:
<223> OTHER INFORMATION: neoantigen

<400> SEQUENCE: 211

Arg Ala Gln Cys His Gly His Gly Arg Cys Val Arg Arg His Pro Ser
1               5                   10                  15

Ala Ser Thr Phe Leu His Leu Ser Thr Asn Ser
            20                  25

<210> SEQ ID NO 212
<211> LENGTH: 27
<212> TYPE: PRT
<213> ORGANISM: Artificial Sequence
<220> FEATURE:
<223> OTHER INFORMATION: neoantigen

<400> SEQUENCE: 212

Thr Ser Leu Glu Leu Pro Met Ala Met Arg Phe Arg His Phe Lys Lys
1               5                   10                  15

Thr Ser Lys Glu Ala Val Gly Val Tyr Arg Ser
            20                  25

<210> SEQ ID NO 213
<211> LENGTH: 27
<212> TYPE: PRT
<213> ORGANISM: Artificial Sequence
<220> FEATURE:
<223> OTHER INFORMATION: neoantigen

<400> SEQUENCE: 213

Cys Gly Lys Asp Phe Ser Gln Arg Ala His Leu Thr Ile Tyr Gln Arg
1               5                   10                  15

Thr His Thr Gly Glu Lys Pro Tyr Lys Cys Leu
            20                  25

<210> SEQ ID NO 214
<211> LENGTH: 27
<212> TYPE: PRT
<213> ORGANISM: Artificial Sequence
<220> FEATURE:
<223> OTHER INFORMATION: neoantigen

<400> SEQUENCE: 214

Lys Glu Thr Thr Glu Ala Ala Cys Arg Tyr Gly Ala Phe Arg Leu Pro
1               5                   10                  15

Ile Thr Val Ala His Val Asp Gly Gln Thr His
            20                  25

<210> SEQ ID NO 215
<211> LENGTH: 27
<212> TYPE: PRT
<213> ORGANISM: Artificial Sequence
<220> FEATURE:
<223> OTHER INFORMATION: neoantigen

<400> SEQUENCE: 215

Glu Leu Val Thr Glu Gly Val Ala Glu Ser Leu Phe Leu Leu Arg Thr
1               5                   10                  15

Asp Tyr Ser Phe His Lys Phe His Tyr Leu Thr
            20                  25

<210> SEQ ID NO 216
<211> LENGTH: 27
<212> TYPE: PRT
<213> ORGANISM: Artificial Sequence
<220> FEATURE:
<223> OTHER INFORMATION: neoantigen

<400> SEQUENCE: 216

Ala Val Arg Gln Ala Glu Lys Tyr Tyr Ile Leu Arg Pro Asp Val Ile
1               5                   10                  15

Glu Thr Tyr Trp Tyr Leu Trp Arg Phe Thr His
            20                  25

<210> SEQ ID NO 217
<211> LENGTH: 17
<212> TYPE: PRT
<213> ORGANISM: Artificial Sequence
<220> FEATURE:
<223> OTHER INFORMATION: neoantigen

<400> SEQUENCE: 217

Ser Val Leu His Leu Val Leu Ala Leu Arg Gly Gly Gly Ser Leu Arg
1               5                   10                  15

Gln

<210> SEQ ID NO 218
<211> LENGTH: 27
<212> TYPE: PRT
<213> ORGANISM: Artificial Sequence
<220> FEATURE:
<223> OTHER INFORMATION: neoantigen

<400> SEQUENCE: 218

Gln Ala Val Phe Ser Thr Ser Ser Arg Phe Trp Ser Ser Ser Pro Leu
1               5                   10                  15

Leu Gly Gln Gln Pro Gly Pro Ser Gln Asp Ile
            20                  25

<210> SEQ ID NO 219
<211> LENGTH: 27
<212> TYPE: PRT
<213> ORGANISM: Artificial Sequence
<220> FEATURE:
<223> OTHER INFORMATION: neoantigen

<400> SEQUENCE: 219

Pro Gln Trp Gln Lys Asp Glu Leu Arg Glu Thr Leu Lys Phe Leu Lys
1               5                   10                  15

Lys Val Met Asp Asp Leu Asp Arg Ala Ser Lys
            20                  25

<210> SEQ ID NO 220
<211> LENGTH: 27
<212> TYPE: PRT
<213> ORGANISM: Artificial Sequence
<220> FEATURE:
<223> OTHER INFORMATION: neoantigen

<400> SEQUENCE: 220

Val Ile Lys Asp Gly Cys Ile Val Glu Arg Gly Arg His Lys Ala Leu
1               5                   10                  15

Leu Ser Arg Gly Gly Val Tyr Ala Asp Met Trp
            20                  25

<210> SEQ ID NO 221
<211> LENGTH: 27
<212> TYPE: PRT
<213> ORGANISM: Artificial Sequence
<220> FEATURE:
<223> OTHER INFORMATION: neoantigen

<400> SEQUENCE: 221

Arg Ala Glu Ser Asp Val Glu Arg Lys Glu Trp Met Gln Val Leu Gln
1               5                   10                  15

Gln Ala Met Ala Glu Gln Arg Ala Arg Ala Arg
            20                  25

<210> SEQ ID NO 222
<211> LENGTH: 27
<212> TYPE: PRT
<213> ORGANISM: Artificial Sequence
<220> FEATURE:
<223> OTHER INFORMATION: neoantigen

<400> SEQUENCE: 222

Arg Ser Leu Arg Lys Ile Asn Ser Ala Pro Pro Thr Glu Ile Lys Ser
1               5                   10                  15

Leu Arg Ile Ala Ser Arg Ser Thr Arg His Ser
            20                  25

<210> SEQ ID NO 223
<211> LENGTH: 27
<212> TYPE: PRT
<213> ORGANISM: Artificial Sequence
<220> FEATURE:
<223> OTHER INFORMATION: neoantigen

<400> SEQUENCE: 223

Ser Asn Lys Tyr Asp Pro Pro Leu Glu Asp Gly Ala Met Leu Ser Ala

Arg Leu Arg Lys Leu Glu Val Glu Ala Asn Asn
            20                  25

<210> SEQ ID NO 224
<211> LENGTH: 27
<212> TYPE: PRT
<213> ORGANISM: Artificial Sequence
<220> FEATURE:
<223> OTHER INFORMATION: neoantigen

<400> SEQUENCE: 224

Ser Asp Arg Cys Lys Asp Phe Ser Leu Cys Tyr Trp Asn Leu Tyr Trp
1               5                   10                  15

Met Leu Pro Ser Asp Val Cys Gly Met Asn Cys
            20                  25

<210> SEQ ID NO 225
<211> LENGTH: 27
<212> TYPE: PRT
<213> ORGANISM: Artificial Sequence
<220> FEATURE:
<223> OTHER INFORMATION: neoantigen

<400> SEQUENCE: 225

Gly Val Lys Leu Val Val Glu Thr Pro Glu Glu Thr Leu Leu Thr Tyr
1               5                   10                  15

Gln Gly Ala Ser Val Ile Leu Pro Cys Arg Tyr
            20                  25

<210> SEQ ID NO 226
<211> LENGTH: 27
<212> TYPE: PRT
<213> ORGANISM: Artificial Sequence
<220> FEATURE:
<223> OTHER INFORMATION: neoantigen

<400> SEQUENCE: 226

Gly Met Ser Thr Ala Met Gly Arg Ser Pro Ser Pro Lys Ile Ser Leu
1               5                   10                  15

Ser Ala Pro Pro Asn Ser Ser Ser Thr Glu Asn
            20                  25

<210> SEQ ID NO 227
<211> LENGTH: 27
<212> TYPE: PRT
<213> ORGANISM: Artificial Sequence
<220> FEATURE:
<223> OTHER INFORMATION: neoantigen

<400> SEQUENCE: 227

Gly Gly Pro Pro Ser Pro Pro Pro Gly Ile Pro Gly Gln Ser Leu Pro
1               5                   10                  15

Ser Pro Thr Arg Leu His Leu Gly Gly Gly Arg
            20                  25

<210> SEQ ID NO 228
<211> LENGTH: 27
<212> TYPE: PRT
<213> ORGANISM: Artificial Sequence
<220> FEATURE:
<223> OTHER INFORMATION: neoantigen

<400> SEQUENCE: 228

Gln Val Gly Arg Met Glu Arg Glu Leu Asn His Glu Lys Val Arg Cys
1               5                   10                  15

Asp Gln Leu Gln Ala Glu Gln Lys Gly Leu Thr
            20                  25

<210> SEQ ID NO 229
<211> LENGTH: 27
<212> TYPE: PRT
<213> ORGANISM: Artificial Sequence
<220> FEATURE:
<223> OTHER INFORMATION: neoantigen

<400> SEQUENCE: 229

Glu Asp Ala Glu Leu Ala Glu Ala Ala Glu Asn Ser Leu Phe Ser Tyr
1               5                   10                  15

Asn Ser Glu Val Asp Glu Ile Pro Asp Glu Leu
            20                  25

<210> SEQ ID NO 230
<211> LENGTH: 27
<212> TYPE: PRT
<213> ORGANISM: Artificial Sequence
<220> FEATURE:
<223> OTHER INFORMATION: neoantigen

<400> SEQUENCE: 230

Glu Ile Gly Val Gly Ala Tyr Gly Thr Val Tyr Lys Ala Leu Asp Pro
1               5                   10                  15

His Ser Gly His Phe Val Ala Leu Lys Ser Val
            20                  25

<210> SEQ ID NO 231
<211> LENGTH: 27
<212> TYPE: PRT
<213> ORGANISM: Artificial Sequence
<220> FEATURE:
<223> OTHER INFORMATION: neoantigen

<400> SEQUENCE: 231

Ile Gln Val Gly Ser Leu Leu Gly Ala Val Ala Met Phe Ser Pro Thr
1               5                   10                  15

Ser Ile Tyr His Val Phe His Ser Arg Lys Asp
            20                  25

<210> SEQ ID NO 232
<211> LENGTH: 27
<212> TYPE: PRT
<213> ORGANISM: Artificial Sequence
<220> FEATURE:
<223> OTHER INFORMATION: neoantigen

<400> SEQUENCE: 232

Gly Tyr Leu Leu Lys Leu Ser Ala Met Gly Trp Gly Phe Ser Ile Phe
1               5                   10                  15

Leu Val Thr Leu Val Ala Leu Val Asp Val Asp
            20                  25

<210> SEQ ID NO 233
<211> LENGTH: 27
<212> TYPE: PRT
<213> ORGANISM: Artificial Sequence
<220> FEATURE:
<223> OTHER INFORMATION: neoantigen

<400> SEQUENCE: 233

Ile Asp Asn Leu Ser Ala Ser Asn His Ser Val Ala Glu Val Leu Leu
1               5                   10                  15

Leu Phe Leu Glu Ser Leu Pro Glu Pro Val Ile
            20                  25

<210> SEQ ID NO 234
<211> LENGTH: 27
<212> TYPE: PRT
<213> ORGANISM: Artificial Sequence
<220> FEATURE:
<223> OTHER INFORMATION: neoantigen

<400> SEQUENCE: 234

Ala Val Leu Asp Leu Gln Leu Arg Ser Ala Pro Ala Ala Phe Glu Arg
1               5                   10                  15

Pro Leu Trp Asp Thr Ser Leu Arg Ala Pro Ser
            20                  25

<210> SEQ ID NO 235
<211> LENGTH: 27
<212> TYPE: PRT
<213> ORGANISM: Artificial Sequence
<220> FEATURE:
<223> OTHER INFORMATION: neoantigen

<400> SEQUENCE: 235

Phe Leu Arg Lys Thr Glu Cys His Cys Gln Ile Val Asn Phe Gly Ala
1               5                   10                  15

Gly Met Asp Thr Thr Phe Trp Arg Leu Lys Asp
            20                  25

<210> SEQ ID NO 236
<211> LENGTH: 27
<212> TYPE: PRT
<213> ORGANISM: Artificial Sequence
<220> FEATURE:
<223> OTHER INFORMATION: neoantigen

<400> SEQUENCE: 236

Tyr Ala Gly Tyr Ser Phe Glu Lys Leu Phe Pro Asp Val Phe Phe Pro
1               5                   10                  15

Ala Asp Ser Glu His Asn Lys Leu Lys Ala Ser
            20                  25

<210> SEQ ID NO 237
<211> LENGTH: 27
<212> TYPE: PRT
<213> ORGANISM: Artificial Sequence
<220> FEATURE:
<223> OTHER INFORMATION: neoantigen

<400> SEQUENCE: 237

Arg Pro Gly Phe Val Phe Ala Pro Cys Pro His Glu Leu Ser Cys Pro
1               5                   10                  15

Gln Leu Thr Asn Leu Ala Cys Ser Phe Ser Gln
            20                  25

<210> SEQ ID NO 238
<211> LENGTH: 27
<212> TYPE: PRT
<213> ORGANISM: Artificial Sequence
<220> FEATURE:
<223> OTHER INFORMATION: neoantigen

```
<400> SEQUENCE: 238

Lys Lys Phe Ile Arg Arg Asp Phe Leu Leu Asp Glu Ala Ile Gly Leu
1               5                   10                  15

Leu Pro Asp Asp Lys Leu Thr Leu Phe Cys Glu
            20                  25

<210> SEQ ID NO 239
<211> LENGTH: 27
<212> TYPE: PRT
<213> ORGANISM: Artificial Sequence
<220> FEATURE:
<223> OTHER INFORMATION: neoantigen

<400> SEQUENCE: 239

Glu Leu Arg Lys Glu Tyr Gly Met Thr Tyr Asn Asp Phe Leu Met Val
1               5                   10                  15

Leu Thr Asp Val Asp Leu Arg Val Lys Gln Tyr
            20                  25

<210> SEQ ID NO 240
<211> LENGTH: 21
<212> TYPE: PRT
<213> ORGANISM: Artificial Sequence
<220> FEATURE:
<223> OTHER INFORMATION: neoantigen

<400> SEQUENCE: 240

Lys Phe Gly Gln Gly Leu Glu Asp Gln Leu Ala Gln Thr Lys Ser Leu
1               5                   10                  15

Ser Leu Asp Asp Cys
            20

<210> SEQ ID NO 241
<211> LENGTH: 27
<212> TYPE: PRT
<213> ORGANISM: Artificial Sequence
<220> FEATURE:
<223> OTHER INFORMATION: neoantigen

<400> SEQUENCE: 241

His Leu Leu Leu Val Tyr Thr Gly Lys Thr Arg Leu Ala Trp Asn Leu
1               5                   10                  15

Leu Gln Asp Val Leu Arg Ser Trp Tyr Ala Arg
            20                  25

<210> SEQ ID NO 242
<211> LENGTH: 27
<212> TYPE: PRT
<213> ORGANISM: Artificial Sequence
<220> FEATURE:
<223> OTHER INFORMATION: neoantigen

<400> SEQUENCE: 242

Pro Val Pro Gly Val Pro Phe Arg Asn Val Asn Asp Phe Pro Thr
1               5                   10                  15

Ser Val Glu Leu Glu Asp Trp Val Asp Ala Gln
            20                  25

<210> SEQ ID NO 243
<211> LENGTH: 27
<212> TYPE: PRT
<213> ORGANISM: Artificial Sequence
<220> FEATURE:
<223> OTHER INFORMATION: neoantigen
```

<400> SEQUENCE: 243

Ser Thr Lys Val Glu Ser Leu Val Ala Leu Leu Asn Asn Phe Ser Glu
1               5                   10                  15

Met Lys Leu Val Gln Met Lys Trp His Glu Ala
            20                  25

<210> SEQ ID NO 244
<211> LENGTH: 27
<212> TYPE: PRT
<213> ORGANISM: Artificial Sequence
<220> FEATURE:
<223> OTHER INFORMATION: neoantigen

<400> SEQUENCE: 244

Leu Phe Gly Gln Leu Ala Ala Phe Ala Gly Arg Lys Trp Ile Lys Phe
1               5                   10                  15

Phe Thr Ser Gln Val Lys Gln Thr Arg Asp Ser
            20                  25

<210> SEQ ID NO 245
<211> LENGTH: 27
<212> TYPE: PRT
<213> ORGANISM: Artificial Sequence
<220> FEATURE:
<223> OTHER INFORMATION: neoantigen

<400> SEQUENCE: 245

Val Pro Leu Glu Arg Gly Ala Pro Asn Lys Glu Glu Thr Ser Ala Thr
1               5                   10                  15

Glu Ser Pro Asp Thr Gly Leu Tyr Tyr His Arg
            20                  25

<210> SEQ ID NO 246
<211> LENGTH: 27
<212> TYPE: PRT
<213> ORGANISM: Artificial Sequence
<220> FEATURE:
<223> OTHER INFORMATION: neoantigen

<400> SEQUENCE: 246

Tyr Cys Met His His Ser Leu Val Glu Phe His Leu Lys Lys Leu Arg
1               5                   10                  15

Asn Lys Asp Thr Asn Ile Glu Val Thr Phe Leu
            20                  25

<210> SEQ ID NO 247
<211> LENGTH: 27
<212> TYPE: PRT
<213> ORGANISM: Artificial Sequence
<220> FEATURE:
<223> OTHER INFORMATION: neoantigen

<400> SEQUENCE: 247

Gln Ile Lys Ile Ser Thr Arg Lys Gln Lys Ser Val Lys Val Ile Ser
1               5                   10                  15

Ser Tyr Thr Pro Lys Asp Cys Thr Ser Arg Asn
            20                  25

<210> SEQ ID NO 248
<211> LENGTH: 27
<212> TYPE: PRT
<213> ORGANISM: Artificial Sequence
<220> FEATURE:

```
<223> OTHER INFORMATION: neoantigen

<400> SEQUENCE: 248

Ile Leu Thr Val Leu Gln Cys Ala Thr Val Ile Gly Phe Phe Tyr Trp
1               5                   10                  15

Ala Ser Glu Leu Ile Leu Ala Gln Gln Gln Gln
            20                  25

<210> SEQ ID NO 249
<211> LENGTH: 27
<212> TYPE: PRT
<213> ORGANISM: Artificial Sequence
<220> FEATURE:
<223> OTHER INFORMATION: neoantigen

<400> SEQUENCE: 249

Val Arg Leu Phe Leu Asp Ser Lys His Pro Gly His Tyr Val Val Tyr
1               5                   10                  15

Asn Leu Ser Pro Arg Thr Tyr Arg Pro Ser Arg
            20                  25

<210> SEQ ID NO 250
<211> LENGTH: 27
<212> TYPE: PRT
<213> ORGANISM: Artificial Sequence
<220> FEATURE:
<223> OTHER INFORMATION: neoantigen

<400> SEQUENCE: 250

Ser His Thr Lys Gly Ile Trp Met Trp Cys Val Pro His Phe Lys Lys
1               5                   10                  15

Pro Gly His Ile Leu Val Leu Leu Asp Thr Glu
            20                  25

<210> SEQ ID NO 251
<211> LENGTH: 27
<212> TYPE: PRT
<213> ORGANISM: Artificial Sequence
<220> FEATURE:
<223> OTHER INFORMATION: neoantigen

<400> SEQUENCE: 251

Ser Thr Leu Ile Ser Val Pro Asp Arg Asp Pro Ala Ser Phe Leu Arg
1               5                   10                  15

Met Ala Asn Ser Ala Leu Ile Ser Val Gly Cys
            20                  25

<210> SEQ ID NO 252
<211> LENGTH: 27
<212> TYPE: PRT
<213> ORGANISM: Artificial Sequence
<220> FEATURE:
<223> OTHER INFORMATION: neoantigen

<400> SEQUENCE: 252

Phe Ala Glu Ser Ala Asp Ala Ala Leu Gln Gly Asp Pro Val Leu Gln
1               5                   10                  15

Asp Ala Gly Asp Ser Ser Arg Lys Glu Tyr Phe
            20                  25

<210> SEQ ID NO 253
<211> LENGTH: 27
<212> TYPE: PRT
<213> ORGANISM: Artificial Sequence
```

<220> FEATURE:
<223> OTHER INFORMATION: neoantigen

<400> SEQUENCE: 253

Ala Asn Leu Glu Ile Met Thr Lys Arg Ser Asn Tyr Thr Ser Ile Thr
1               5                   10                  15

Asn Asp Lys Phe Thr Pro Pro Val Val Asn Val
            20                  25

<210> SEQ ID NO 254
<211> LENGTH: 27
<212> TYPE: PRT
<213> ORGANISM: Artificial Sequence
<220> FEATURE:
<223> OTHER INFORMATION: neoantigen

<400> SEQUENCE: 254

Glu Gln Thr Leu Val Leu Gln Ile Val Ala Gly Ile Leu Tyr Leu Gly
1               5                   10                  15

Asn Ile Ser Phe Lys Glu Val Gly Asn Tyr Ala
            20                  25

<210> SEQ ID NO 255
<211> LENGTH: 27
<212> TYPE: PRT
<213> ORGANISM: Artificial Sequence
<220> FEATURE:
<223> OTHER INFORMATION: neoantigen

<400> SEQUENCE: 255

Lys Tyr Thr Ala Gln Glu Ser Arg Glu Met Phe Pro Arg Leu Phe Ile
1               5                   10                  15

Arg Leu Leu Arg Ser Lys Val Ser Arg Phe Leu
            20                  25

<210> SEQ ID NO 256
<211> LENGTH: 27
<212> TYPE: PRT
<213> ORGANISM: Artificial Sequence
<220> FEATURE:
<223> OTHER INFORMATION: neoantigen

<400> SEQUENCE: 256

Arg Asp Glu Glu Val Ser Ser Ala Asp Ile Ser Ser Ser Phe Glu Val
1               5                   10                  15

Ile Ser Gln His Leu Val Ser Tyr Arg Asn Ile
            20                  25

<210> SEQ ID NO 257
<211> LENGTH: 27
<212> TYPE: PRT
<213> ORGANISM: Artificial Sequence
<220> FEATURE:
<223> OTHER INFORMATION: neoantigen

<400> SEQUENCE: 257

Ser Gln Asn Thr Asp Met Val Gln Lys Ser Val Ser Lys Ile Leu Pro
1               5                   10                  15

Ser Thr Trp Ser Asp Pro Ser Val Asn Ile Ser
            20                  25

<210> SEQ ID NO 258
<211> LENGTH: 27
<212> TYPE: PRT

<213> ORGANISM: Artificial Sequence
<220> FEATURE:
<223> OTHER INFORMATION: neoantigen

<400> SEQUENCE: 258

Asp Glu Ile Pro Leu Tyr Leu Lys Gly Gly Val Ala Asp Val Leu Leu
1               5                   10                  15

Tyr Arg Ala Thr Met Ile Leu Thr Val Gly Gly
            20                  25

<210> SEQ ID NO 259
<211> LENGTH: 27
<212> TYPE: PRT
<213> ORGANISM: Artificial Sequence
<220> FEATURE:
<223> OTHER INFORMATION: neoantigen

<400> SEQUENCE: 259

Ile Ile Ala Arg Thr Asp Leu Lys Lys Asn Arg Asp Tyr Arg Leu Ala
1               5                   10                  15

Ser Lys Asp Ala Lys Lys Gln Leu Leu Cys Gly
            20                  25

<210> SEQ ID NO 260
<211> LENGTH: 27
<212> TYPE: PRT
<213> ORGANISM: Artificial Sequence
<220> FEATURE:
<223> OTHER INFORMATION: neoantigen

<400> SEQUENCE: 260

Leu Phe Arg His Leu Leu Ser Ser Asp Gln Met Met Asp Tyr Ile Leu
1               5                   10                  15

Ala Asp Glu Ala Phe Phe Ser Val Asn Ser Ser
            20                  25

<210> SEQ ID NO 261
<211> LENGTH: 27
<212> TYPE: PRT
<213> ORGANISM: Artificial Sequence
<220> FEATURE:
<223> OTHER INFORMATION: neoantigen

<400> SEQUENCE: 261

Trp Glu Ser Val Lys Leu Leu Phe Val Lys Thr Glu Lys Leu Ala Ala
1               5                   10                  15

Leu Pro Ile Phe Ser Ser Phe Val Ser Asn Trp
            20                  25

<210> SEQ ID NO 262
<211> LENGTH: 27
<212> TYPE: PRT
<213> ORGANISM: Artificial Sequence
<220> FEATURE:
<223> OTHER INFORMATION: neoantigen

<400> SEQUENCE: 262

Val Leu Ser Glu Glu Arg Ala Ala Leu Leu Glu Leu Trp Lys Leu Arg
1               5                   10                  15

Arg Gln Gln Tyr Glu Gln Cys Met Asp Leu Gln
            20                  25

<210> SEQ ID NO 263
<211> LENGTH: 27

```
<212> TYPE: PRT
<213> ORGANISM: Artificial Sequence
<220> FEATURE:
<223> OTHER INFORMATION: neoantigen

<400> SEQUENCE: 263

Glu Lys Arg Gln Ala Lys Tyr Ser Glu Asn Lys Leu Lys Leu Ile Lys
1               5                   10                  15

Ala Arg Asn Glu Tyr Leu Leu Thr Leu Glu Ala
            20                  25

<210> SEQ ID NO 264
<211> LENGTH: 27
<212> TYPE: PRT
<213> ORGANISM: Artificial Sequence
<220> FEATURE:
<223> OTHER INFORMATION: neoantigen

<400> SEQUENCE: 264

Lys Ser His Arg Leu Pro Arg Leu Pro Lys Arg His Ser Tyr Asp Asp
1               5                   10                  15

Met Leu Leu Leu Ala Gln Leu Ser Leu Pro Ser
            20                  25

<210> SEQ ID NO 265
<211> LENGTH: 20
<212> TYPE: PRT
<213> ORGANISM: Artificial Sequence
<220> FEATURE:
<223> OTHER INFORMATION: neoantigen

<400> SEQUENCE: 265

Met Ser Glu Phe Arg Ile Tyr His Asp Val Asn Glu Leu Leu Ser Leu
1               5                   10                  15

Leu Arg Val His
            20

<210> SEQ ID NO 266
<211> LENGTH: 27
<212> TYPE: PRT
<213> ORGANISM: Artificial Sequence
<220> FEATURE:
<223> OTHER INFORMATION: neoantigen

<400> SEQUENCE: 266

Thr Arg Leu Ser Lys Val Phe Ser Ala Met Leu Ala Ile Tyr Ser Asn
1               5                   10                  15

Lys Pro Ala Leu Trp Ile Met Ala Ala Lys Trp
            20                  25

<210> SEQ ID NO 267
<211> LENGTH: 2867
<212> TYPE: DNA
<213> ORGANISM: Homo sapiens

<400> SEQUENCE: 267
acagactgcc aaatggaaca gacaagcagg ttgtcttgtg ttaaagaaaa tgagatataa      60
gtcagttact cccggaggca atgctgctgt tcagctcttc tgttttttgtg gccagggtct    120 tcatgaacac taatagggggt accaggcccct cttcctcgtt agaagaaatc aggataacaa    180
aggcatattg ggcaccccta caaaaggaat ctgtatctgt atcaagatga tctgaagaac     240
agcttctacc tttaggaatg tctagtgttc caaaatgact agcatcttcc attttgccat     300
```

```
tatcttcatg ttaatacttc agatcagaat acaattatct gaagaaagtg aattttagt      360 tgataggtca aaaaacggtc tcatccacgt tcctaaagac ctatcccaga aaacaacaat      420
cttaaatata tcgcaaaatt atatatctga gctttggact tctgacatct tatcactgtc      480
aaaactgagg attttgataa tttctcataa tagaatccag tatcttgata tcagtgtttt      540
caaattcaac caggaattgg aatacttgga tttgtcccac aacaagttgg tgaagatttc      600
ttgccaccct actgtgaacc tcaagcactt ggacctgtca tttaatgcat ttgatgccct      660
gcctatatgc aaagagtttg gcaatatgtc tcaactaaaa tttctggggt tgagcaccac      720
acacttagaa aaatctagtg tgctgccaat tgctcatttg aatatcagca aggtcttgct      780
ggtcttagga gagacttatg gggaaaaaga agaccctgag ggccttcaag actttaacac      840
tgagagtctg cacattgtgt tccccacaaa caaagaattc catttttattt tggatgtgtc      900 agtcaagact gtagcaaatc tggaactatc taatatcaaa tgtgtgctag aagataacaa      960
atgttcttac ttcctaagta ttctggcgaa acttcaaaca aatccaaagt tatcaaatct     1020
taccttaaac aacattgaaa caacttggaa ttctttcatt aggatcctcc agctggtttg     1080
gcatacaact gtatggtatt tctcaatttc aaacgtgaag ctacagggtc agctggactt     1140
cagagatttt gattattctg gcacttcctt gaaggccttg tctatacacc aagttgtcag     1200
cgatgtgttc ggttttccgc aaagttatat ctatgaaatc ttttcgaata tgaacatcaa     1260
aaatttcaca gtgtctggta cacgcatggt ccacatgctt tgcccatcca aaattagccc     1320
gttcctgcat ttggattttt ccataatctc cttaacagac acggttttg aaaattgtgg      1380 gcaccttact gagttggaga cacttatttt acaaatgaat caattaaaag aactttcaaa     1440
aatagctgaa atgactacac agatgaagtc tctgcaacaa ttggatatta gccagaattc     1500
tgtaagctat gatgaaaaga aaggagactg ttcttggact aaaagtttat taagtttaaa     1560
tatgtcttca aatatactta ctgacactat tttcagatgt ttacctccca ggatcaaggt     1620
acttgatctt cacagcaata aaataaagag cattcctaaa caagtcgtaa aactggaagc     1680
tttgcaagaa ctcaatgttg cttttcaattc tttaactgac cttcctggat gtggcagctt     1740
tagcagcctt tctgtattga tcattgatca caattcagtt tcccacccat cggctgattt     1800
cttccagagc tgccagaaga tgaggtcaat aaaagcaggg gacaatccat tccaatgtac     1860
ctgtgagcta ggagaatttg tcaaaaatat agaccaagta tcaagtgaag tgttagaggg     1920
ctggcctgat tcttataagt gtgactaccc ggaaagttat agaggaaccc tactaaagga     1980 cttttcacatg tctgaattat cctgcaacat aactctgctg atcgtcacca tcgttgccac     2040
catgctggtg ttggctgtga ctgtgacctc cctctgcagc tacttggatc tgccctggta     2100
tctcaggatg gtgtgccagt ggacccagac ccggcgcagg gccaggaaca tacccttaga     2160
agaactccaa agaaatctcc agtttcatgc atttattca tatagtgggc acgattcttt      2220
ctgggtgaag aatgaattat tgccaaacct agagaaagaa ggtatgcaga tttgccttca     2280
tgagagaaac tttgttcctg gcaagagcat tgtggaaaat atcatcacct gcattgagaa     2340
gagttacaag tccatctttg ttttgtctcc caacttgtc cagagtgaat ggtgccatta      2400
tgaactctac tttgcccatc acaatctctt tcatgaagga tctaatagct taatcctgat     2460
cttgctggaa cccattccgc agtactccat tcctagcagt tatcacaagc tcaaaagtct     2520
catggccagg aggacttatt tggaatggcc caaggaaaag agcaaacgtg gcctttttg      2580 ggctaactta agggcagcca ttaatattaa gctgacagag caagcaaaga aatagattac     2640
acatcaagtg aaaaatattc ctcctgttga tattgctgct tttggaagtt ccaacaatga     2700
```

```
cttatttg catcagcata gatgtaaaca caattgtgag tgtatgatgt aggtaaaaat    2760
atataccttc gggtcgcagt tcaccattta tatgtggtat taaaaattaa tgaaatgata    2820
taactttgat ttaaacagtt ctgacacata aaaaaaaaaa aaaaaaa                 2867
```

<210> SEQ ID NO 268
<211> LENGTH: 786
<212> TYPE: PRT
<213> ORGANISM: Homo sapiens

<400> SEQUENCE: 268

```
Met Thr Ser Ile Phe His Phe Ala Ile Ile Phe Met Leu Ile Leu Gln
1               5                   10                  15

Ile Arg Ile Gln Leu Ser Glu Glu Ser Glu Phe Leu Val Asp Arg Ser
            20                  25                  30

Lys Asn Gly Leu Ile His Val Pro Lys Asp Leu Ser Gln Lys Thr Thr
        35                  40                  45

Ile Leu Asn Ile Ser Gln Asn Tyr Ile Ser Glu Leu Trp Thr Ser Asp
    50                  55                  60

Ile Leu Ser Leu Ser Lys Leu Arg Ile Leu Ile Ser His Asn Arg
65                  70                  75                  80

Ile Gln Tyr Leu Asp Ile Ser Val Phe Lys Phe Asn Gln Glu Leu Glu
                85                  90                  95

Tyr Leu Asp Leu Ser His Asn Lys Leu Val Lys Ile Ser Cys His Pro
            100                 105                 110

Thr Val Asn Leu Lys His Leu Asp Leu Ser Phe Asn Ala Phe Asp Ala
        115                 120                 125

Leu Pro Ile Cys Lys Glu Phe Gly Asn Met Ser Gln Leu Lys Phe Leu
    130                 135                 140

Gly Leu Ser Thr Thr His Leu Glu Lys Ser Ser Val Leu Pro Ile Ala
145                 150                 155                 160

His Leu Asn Ile Ser Lys Val Leu Leu Val Leu Gly Glu Thr Tyr Gly
                165                 170                 175

Glu Lys Glu Asp Pro Glu Gly Leu Gln Asp Phe Asn Thr Glu Ser Leu
            180                 185                 190

His Ile Val Phe Pro Thr Asn Lys Glu Phe His Phe Ile Leu Asp Val
        195                 200                 205

Ser Val Lys Thr Val Ala Asn Leu Glu Leu Ser Asn Ile Lys Cys Val
    210                 215                 220

Leu Glu Asp Asn Lys Cys Ser Tyr Phe Leu Ser Ile Leu Ala Lys Leu
225                 230                 235                 240

Gln Thr Asn Pro Lys Leu Ser Asn Leu Thr Leu Asn Asn Ile Glu Thr
                245                 250                 255

Thr Trp Asn Ser Phe Ile Arg Ile Leu Gln Leu Val Trp His Thr Thr
            260                 265                 270

Val Trp Tyr Phe Ser Ile Ser Asn Val Lys Leu Gln Gly Gln Leu Asp
        275                 280                 285

Phe Arg Asp Phe Asp Tyr Ser Gly Thr Ser Leu Lys Ala Leu Ser Ile
    290                 295                 300

His Gln Val Val Ser Asp Val Phe Gly Phe Pro Gln Ser Tyr Ile Tyr
305                 310                 315                 320

Glu Ile Phe Ser Asn Met Asn Ile Lys Asn Phe Thr Val Ser Gly Thr
                325                 330                 335

Arg Met Val His Met Leu Cys Pro Ser Lys Ile Ser Pro Phe Leu His
```

```
                340             345             350
Leu Asp Phe Ser Asn Leu Leu Thr Asp Thr Val Phe Glu Asn Cys
            355             360             365
Gly His Leu Thr Glu Leu Glu Thr Leu Ile Leu Gln Met Asn Gln Leu
            370             375             380
Lys Glu Leu Ser Lys Ile Ala Glu Met Thr Thr Gln Met Lys Ser Leu
385             390             395             400
Gln Gln Leu Asp Ile Ser Gln Asn Ser Val Ser Tyr Asp Glu Lys Lys
            405             410             415
Gly Asp Cys Ser Trp Thr Lys Ser Leu Leu Ser Leu Asn Met Ser Ser
            420             425             430
Asn Ile Leu Thr Asp Thr Ile Phe Arg Cys Leu Pro Pro Arg Ile Lys
            435             440             445
Val Leu Asp Leu His Ser Asn Lys Ile Lys Ser Ile Pro Lys Gln Val
450             455             460
Val Lys Leu Glu Ala Leu Gln Glu Leu Asn Val Ala Phe Asn Ser Leu
465             470             475             480
Thr Asp Leu Pro Gly Cys Gly Ser Phe Ser Ser Leu Ser Val Leu Ile
            485             490             495
Ile Asp His Asn Ser Val Ser His Pro Ser Ala Asp Phe Phe Gln Ser
            500             505             510
Cys Gln Lys Met Arg Ser Ile Lys Ala Gly Asp Asn Pro Phe Gln Cys
            515             520             525
Thr Cys Glu Leu Gly Glu Phe Val Lys Asn Ile Asp Gln Val Ser Ser
            530             535             540
Glu Val Leu Glu Gly Trp Pro Asp Ser Tyr Lys Cys Asp Tyr Pro Glu
545             550             555             560
Ser Tyr Arg Gly Thr Leu Leu Lys Asp Phe His Met Ser Glu Leu Ser
            565             570             575
Cys Asn Ile Thr Leu Leu Ile Val Thr Ile Val Ala Thr Met Leu Val
            580             585             590
Leu Ala Val Thr Val Thr Ser Leu Cys Ser Tyr Leu Asp Leu Pro Trp
            595             600             605
Tyr Leu Arg Met Val Cys Gln Trp Thr Gln Thr Arg Arg Arg Ala Arg
            610             615             620
Asn Ile Pro Leu Glu Glu Leu Gln Arg Asn Leu Gln Phe His Ala Phe
625             630             635             640
Ile Ser Tyr Ser Gly His Asp Ser Phe Trp Val Lys Asn Glu Leu Leu
            645             650             655
Pro Asn Leu Glu Lys Glu Gly Met Gln Ile Cys Leu His Glu Arg Asn
            660             665             670
Phe Val Pro Gly Lys Ser Ile Val Glu Asn Ile Ile Thr Cys Ile Glu
            675             680             685
Lys Ser Tyr Lys Ser Ile Phe Val Leu Ser Pro Asn Phe Val Gln Ser
            690             695             700
Glu Trp Cys His Tyr Glu Leu Tyr Phe Ala His His Asn Leu Phe His
705             710             715             720
Glu Gly Ser Asn Ser Leu Ile Leu Ile Leu Leu Glu Pro Ile Pro Gln
            725             730             735
Tyr Ser Ile Pro Ser Ser Tyr His Lys Leu Lys Ser Leu Met Ala Arg
            740             745             750
Arg Thr Tyr Leu Glu Trp Pro Lys Glu Lys Ser Lys Arg Gly Leu Phe
            755             760             765
```

Trp Ala Asn Leu Arg Ala Ala Ile Asn Ile Lys Leu Thr Glu Gln Ala
    770                 775                 780
Lys Lys
785

<210> SEQ ID NO 269
<211> LENGTH: 3417
<212> TYPE: DNA
<213> ORGANISM: Homo sapiens

<400> SEQUENCE: 269

| | | | | | |
|---|---|---|---|---|---|
| cggaggcagc | gagaaagcgc | agccaggcgg | ctgctcggcg | ttctctcagg | tgactgctcg | 60 |
| gagttctccc | agtgtttggt | gttgcaagca | ggatccaaag | gagacctata | gtgactccca | 120 |
| ggagctctta | gtgaccaagt | gaaggtacct | gtggggctca | ttgtgcccat | tgctcttttca | 180 |
| ctgctttcaa | ctggtagttg | tgggttgaag | cactggacaa | tgccacatac | tttgtggatg | 240 |
| gtgtgggtct | tggggtcat | catcagcctc | tccaaggaag | aatcctccaa | tcaggcttct | 300 |
| ctgtcttgtg | accgcaatgg | tatctgcaag | ggcagctcag | gatctttaaa | ctccattccc | 360 |
| tcagggctca | cagaagctgt | aaaaagcctt | gacctgtcca | acaacaggat | cacctacatt | 420 |
| agcaacagtg | acctacagag | gtgtgtgaac | ctccaggctc | tggtgctgac | atccaatgga | 480 |
| attaacacaa | tagaggaaga | ttcttttttct | tccctgggca | gtcttgaaca | tttagactta | 540 |
| tcctataatt | acttatctaa | tttatcgtct | tcctggttca | agccccttttc | ttctttaaca | 600 |
| ttcttaaact | tactgggaaa | tccttacaaa | accctagggg | aaacatctct | tttttctcat | 660 |
| ctcacaaaat | tgcaaatcct | gagagtggga | aatatggaca | ccttcactaa | gattcaaaga | 720 |
| aaagattttg | ctggacttac | cttccttgag | gaacttgaga | ttgatgcttc | agatctacag | 780 |
| agctatgagc | caaaaagttt | gaagtcaatt | cagaatgtaa | gtcatctgat | ccttcatatg | 840 |
| aagcagcata | ttttactgct | ggagattttt | gtagatgtta | caagttccgt | ggaatgtttg | 900 |
| gaactgcgag | atactgattt | ggacacttttc | cattttttcag | aactatccac | tggtgaaaca | 960 |
| aattcattga | ttaaaaagtt | tacatttaga | aatgtgaaaa | tcaccgatga | aagtttgttt | 1020 |
| caggttatga | aacttttgaa | tcagatttct | ggattgttag | aattagagtt | tgatgactgt | 1080 |
| acccttaatg | gagttggtaa | ttttagagca | tctgataatg | acagagttat | agatccaggt | 1140 |
| aaagtggaaa | cgttaacaat | ccggaggctg | catattccaa | ggttttactt | atttttatgat | 1200 |
| ctgagcactt | tatattcact | tacagaaaga | gttaaaagaa | tcacagtaga | aaacagtaaa | 1260 |
| gtttttctgg | ttccttgttt | actttcacaa | catttaaaat | cattagaata | cttggatctc | 1320 |
| agtgaaaatt | tgatggttga | agaatacttg | aaaaattcag | cctgtgagga | tgcctggccc | 1380 |
| tctctacaaa | ctttaatttt | aaggcaaaat | catttggcat | cattgaaaaa | aaccggagag | 1440 |
| actttgctca | ctctgaaaaa | cttgactaac | attgatatca | gtaagaatag | ttttcattct | 1500 |
| atgcctgaaa | cttgtcagtg | gccagaaaag | atgaaatatt | tgaacttatc | cagcacacga | 1560 |
| atacacagtg | taacaggctg | cattcccaag | acactggaaa | ttttagatgt | tagcaacaac | 1620 |
| aatctcaatt | tattttcttt | gaatttgccg | caactcaaag | aactttatat | ttccagaaat | 1680 |
| aagttgatga | ctctaccaga | tgcctccctc | ttacccatgt | tactagtatt | gaaaatcagt | 1740 |
| aggaatgcaa | taactacgtt | ttctaaggag | caacttgact | catttcacac | actgaagact | 1800 |
| ttggaagctg | gtggcaataa | cttcatttgc | tcctgtgaat | tcctctcctt | cactcaggag | 1860 |
| cagcaagcac | tggccaaagt | cttgattgat | tggccagcaa | attacctgtg | tgactctcca | 1920 |

| | | | |
|---|---|---|---|
| tcccatgtgc gtggccagca ggttcaggat gtccgcctct cggtgtcgga atgtcacagg | | | 1980 |
| acagcactgg tgtctggcat gtgctgtgct ctgttcctgc tgatcctgct cacggggggtc | | | 2040 |
| ctgtgccacc gtttccatgg cctgtggtat atgaaaatga tgtgggcctg gctccaggcc | | | 2100 |
| aaaaggaagc ccaggaaagc tcccagcagg aacatctgct atgatgcatt tgtttcttac | | | 2160 |
| agtgagcggg atgcctactg ggtggagaac cttatggtcc aggagctgga gaacttcaat | | | 2220 |
| ccccccttca agttgtgtct tcataagcgg gacttcattc ctggcaagtg gatcattgac | | | 2280 |
| aatatcattg actccattga aaagagccac aaaactgtct ttgtgctttc tgaaaacttt | | | 2340 |
| gtgaagagtg agtggtgcaa gtatgaactg gacttctccc atttccgtct ttttgatgag | | | 2400 |
| aacaatgatg ctgccattct cattcttctg gagcccattg agaaaaaagc cattccccag | | | 2460 |
| cgcttctgca agctgcggaa gataatgaac accaagacct acctggagtg gcccatggac | | | 2520 |
| gaggctcagc gggaaggatt tgggtaaat ctgagagctg cgataaagtc ctaggttccc | | | 2580 |
| atatttaaga ccagtctttg tctagttggg atctttatgt cactagttat agttaagttc | | | 2640 |
| attcagacat aattatataa aaactacgtg gatgtaccgt catttgagga cttgcttact | | | 2700 |
| aaaactacaa aacttcaaat tttgtctggg gtgctgtttt ataaacatat gccagattta | | | 2760 |
| aaaattggtt tttggttttt cttttttcta tgagataacc atgatcataa gtctattact | | | 2820 |
| gatatctgaa tatagtccct tggtatccaa gggaattggt tgcaggatcc tcgtggatat | | | 2880 |
| caaaattcat agatgatcaa gtcccttata agagtggcat agtatttgca tataacctgt | | | 2940 |
| gtacattctc ctgtatactt taaatcatct ctagattact tatgataccc aatacaatgt | | | 3000 |
| aaatactatg taaatagttg tactgtcttt ttatttatat tattattgtt attttttatt | | | 3060 |
| ttcaaaattt ttaaaacata cttttgatcc acagttggtt gacttcatgg atgcagaacc | | | 3120 |
| catggatata gagggccaac tgtaatctgt agcaactggc ttagttcatt aggaaacagc | | | 3180 |
| acaaatgaac ttaagattct caatgactgt gtcattcttt cttcctgcta agagactcct | | | 3240 |
| ctgtggccac aaaaggcatt ctctgtccta cctagctgtc acttctctgt gcagctgatc | | | 3300 |
| tcaagagcaa caaggcaaag tatttgggc actccccaaa acttgttgct attcctagaa | | | 3360 |
| aaaagtgctg tgtatttcct attaaacttt acaggatgag aaaaaaaaaa aaaaaaa | | | 3417 |

<210> SEQ ID NO 270
<211> LENGTH: 784
<212> TYPE: PRT
<213> ORGANISM: Homo sapiens

<400> SEQUENCE: 270

Met Pro His Thr Leu Trp Met Val Trp Val Leu Gly Val Ile Ile Ser
1               5                   10                  15

Leu Ser Lys Glu Glu Ser Ser Asn Gln Ala Ser Leu Ser Cys Asp Arg
            20                  25                  30

Asn Gly Ile Cys Lys Gly Ser Ser Gly Ser Leu Asn Ser Ile Pro Ser
        35                  40                  45

Gly Leu Thr Glu Ala Val Lys Ser Leu Asp Leu Ser Asn Asn Arg Ile
    50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

```
Ser Asn Leu Ser Ser Ser Trp Phe Lys Pro Leu Ser Ser Leu Thr Phe
            115                 120                 125

Leu Asn Leu Leu Gly Asn Pro Tyr Lys Thr Leu Gly Glu Thr Ser Leu
        130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
        275                 280                 285

Leu Asn Gly Val Gly Asn Phe Arg Ala Ser Asp Asn Asp Arg Val Ile
    290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
        355                 360                 365

Glu Asn Leu Met Val Glu Glu Tyr Leu Lys Asn Ser Ala Cys Glu Asp
    370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
            420                 425                 430

Gln Trp Pro Glu Lys Met Lys Tyr Leu Asn Leu Ser Ser Thr Arg Ile
        435                 440                 445

His Ser Val Thr Gly Cys Ile Pro Lys Thr Leu Glu Ile Leu Asp Val
    450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
```

```
                    530                 535                 540
Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Thr Ala Leu Val Ser
                580                 585                 590

Gly Met Cys Cys Ala Leu Phe Leu Leu Ile Leu Leu Thr Gly Val Leu
                595                 600                 605

Cys His Arg Phe His Gly Leu Trp Tyr Met Lys Met Met Trp Ala Trp
                610                 615                 620

Leu Gln Ala Lys Arg Lys Pro Arg Lys Ala Pro Ser Arg Asn Ile Cys
625                 630                 635                 640

Tyr Asp Ala Phe Val Ser Tyr Ser Glu Arg Asp Ala Tyr Trp Val Glu
                645                 650                 655

Asn Leu Met Val Gln Glu Leu Glu Asn Phe Asn Pro Pro Phe Lys Leu
                660                 665                 670

Cys Leu His Lys Arg Asp Phe Ile Pro Gly Lys Trp Ile Ile Asp Asn
                675                 680                 685

Ile Ile Asp Ser Ile Glu Lys Ser His Lys Thr Val Phe Val Leu Ser
                690                 695                 700

Glu Asn Phe Val Lys Ser Glu Trp Cys Lys Tyr Glu Leu Asp Phe Ser
705                 710                 715                 720

His Phe Arg Leu Phe Asp Glu Asn Asn Asp Ala Ala Ile Leu Ile Leu
                725                 730                 735

Leu Glu Pro Ile Glu Lys Lys Ala Ile Pro Gln Arg Phe Cys Lys Leu
                740                 745                 750

Arg Lys Ile Met Asn Thr Lys Thr Tyr Leu Glu Trp Pro Met Asp Glu
                755                 760                 765

Ala Gln Arg Glu Gly Phe Trp Val Asn Leu Arg Ala Ala Ile Lys Ser
                770                 775                 780

<210> SEQ ID NO 271
<211> LENGTH: 3057
<212> TYPE: DNA
<213> ORGANISM: Homo sapiens

<400> SEQUENCE: 271
cactttcgag agtgccgtct atttgccaca cacttccctg atgaaatgtc tggatttgga      60
ctaaagaaaa aaggaaaggc tagcagtcat ccaacagaat catgagacag actttgcctt     120
gtatctactt ttgggggggc cttttgccct ttgggatgct gtgtgcatcc tccaccacca     180
agtgcactgt tagccatgaa gttgctgact gcagccacct gaagttgact caggtacccg     240
atgatctacc cacaaacata acagtgttga accttaccca taatcaactc agaagattac     300
cagccgccaa cttcacaagg tatagccagc taactagctt ggatgtagga tttaacacca     360
tctcaaaact ggagccagaa ttgtgccaga aacttcccat gttaaaagtt ttgaacctcc     420
agcacaatga gctatctcaa ctttctgata aaaccttttgc cttctgcacg aatttgactg     480
aactccatct catgtccaac tcaatccaga aaattaaaaa taatcccttt gtcaagcaga     540
agaatttaat cacattagat ctgtctcata atggcttgtc atctacaaaa ttaggaactc     600
aggttcagct ggaaaatctc caagagcttc tattatcaaa caataaaatt caagcgctaa     660
aaagtgaaga actggatatc tttgccaatt catctttaaa aaaattagag ttgtcatcga     720
```

```
atcaaattaa agagttttct ccagggtgtt tcacgcaat tggaagatta tttggcctct      780
ttctgaacaa tgtccagctg ggtcccagcc ttacagagaa gctatgtttg gaattagcaa      840
acacaagcat tcggaatctg tctctgagta acagccagct gtccaccacc agcaatacaa      900
cttcttggg actaaagtgg acaaatctca ctatgctcga tctttcctac aacaacttaa       960
atgtggttgg taacgattcc tttgcttggc ttccacaact agaatatttc ttcctagagt     1020
ataataatat acagcatttg ttttctcact ctttgcacgg gcttttcaat gtgaggtacc     1080
tgaatttgaa acggtctttt actaaacaaa gtatttccct tgcctcactc cccaagattg     1140
atgattttc tttcagtgg ctaaaatgtt tggagcacct taacatggaa gataatgata      1200
ttccaggcat aaaaagcaat atgttcacag gattgataaa cctgaaatac ttaagtctat     1260
ccaactcctt tacaagtttg cgaactttga caaatgaaac atttgtatca cttgctcatt     1320
ctcccttaca catactcaac ctaaccaaga ataaaatctc aaaaatagag agtgatgctt     1380
tctcttggtt gggccaccta gaagtacttg acctgggcct taatgaaatt gggcaagaac     1440
tcacaggcca ggaatggaga ggtctagaaa atatttcga atctatctt tcctacaaca       1500
agtacctgca gctgactagg aactcctttg ccttggtccc aagccttcaa cgactgatgc     1560
tccgaagggt ggcccttaaa aatgtggata gctctccttc accattccag cctcttcgta     1620
acttgaccat tctggatcta agcaacaaca acatagccaa cataaatgat gacatgttgg     1680
agggtcttga gaaactagaa attctcgatt tgcagcataa caacttagca cggctctgga     1740
aacacgcaaa ccctggtggt cccatttatt tcctaaaggg tctgtctcac ctccacatcc     1800
ttaacttgga gtccaacggc tttgacgaga tcccagttga ggtcttcaag gatttatttg     1860
aactaaagat catcgattta ggattgaata atttaaacac acttccagca tctgtcttta     1920
ataatcaggt gtctctaaag tcattgaacc ttcagaagaa tctcataaca tccgttgaga     1980
agaaggtttt cgggccagct ttcaggaacc tgactgagtt agatatgcgc tttaatccct     2040
ttgattgcac gtgtgaaagt attgcctggt ttgttaattg gattaacgag acccatacca     2100
acatccctga gctgtcaagc cactaccttt gcaacactcc acctcactat catgggttcc     2160
cagtgagact ttttgataca tcatcttgca aagacagtgc ccccttttgaa ctctttttca     2220
tgatcaatac cagtatcctg ttgattttta tctttattgt acttctcatc cactttgagg     2280
gctggaggat atcttttat tggaatgttt cagtacatcg agttcttggt ttcaaagaaa      2340
tagacagaca gacagaacag tttgaatatg cagcatatat aattcatgcc tataaagata     2400
aggattgggt ctgggaacat ttctcttcaa tggaaaagga agaccaatct ctcaaatttt     2460
gtctggaaga aagggacttt gaggcgggtg ttttttgaact agaagcaatt gttaacagca     2520
tcaaaagaag cagaaaaatt attttttgtta taacacacca tctattaaaa gacccattat     2580
gcaaaagatt caaggtacat catgcagttc aacaagctat tgaacaaaat ctggattcca     2640
ttatattggt tttccttgag gagattccag attataaact gaaccatgca ctctgtttgc     2700
gaagaggaat gtttaaatct cactgcatct tgaactggcc agttcagaaa gaacggatag     2760
gtgcctttcg tcataaattg caagtagcac ttggatccaa aaactctgta cattaaattt     2820
atttaaatat tcaattagca aaggagaaac tttctcaatt taaaaagttc tatggcaaat     2880
ttaagttttc cataaaggtg ttataattg tttattcata ttttgtaaatg attatattct      2940
atcacaatta catctcttct aggaaaatgt gtctccttat ttcaggccta tttttgacaa     3000
ttgacttaat tttacccaaa ataaaacata taagcacgta aaaaaaaaaa aaaaaaa        3057
```

<210> SEQ ID NO 272
<211> LENGTH: 904
<212> TYPE: PRT
<213> ORGANISM: Homo sapiens

<400> SEQUENCE: 272

Met Arg Gln Thr Leu Pro Cys Ile Tyr Phe Trp Gly Gly Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
                35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285

Val Gly Asn Asp Ser Phe Ala Trp Leu Pro Gln Leu Glu Tyr Phe Phe
    290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
        355                 360                 365

Gly Ile Lys Ser Asn Met Phe Thr Gly Leu Ile Asn Leu Lys Tyr Leu
    370                 375                 380

```
Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
            435                 440                 445

Gly Gln Glu Trp Arg Gly Leu Glu Asn Ile Phe Glu Ile Tyr Leu Ser
    450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
                485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
            515                 520                 525

Leu Glu Lys Leu Glu Ile Leu Asp Leu Gln His Asn Asn Leu Ala Arg
    530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
            595                 600                 605

Gln Val Ser Leu Lys Ser Leu Asn Leu Gln Lys Asn Leu Ile Thr Ser
    610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
            660                 665                 670

Ser His Tyr Leu Cys Asn Thr Pro Pro His Tyr His Gly Phe Pro Val
            675                 680                 685

Arg Leu Phe Asp Thr Ser Cys Lys Asp Ser Ala Pro Phe Glu Leu
    690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
            755                 760                 765

Trp Val Trp Glu His Phe Ser Ser Met Glu Lys Glu Asp Gln Ser Leu
    770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
```

|   |   |   | 805 |   |   |   | 810 |   |   |   | 815 |   |
|---|---|---|---|---|---|---|---|---|---|---|---|---|
| Ile | Thr | His | His | Leu | Leu | Lys | Asp | Pro | Leu | Cys | Lys | Arg | Phe | Lys | Val |
|   |   |   | 820 |   |   |   | 825 |   |   |   | 830 |   |

His His Ala Val Gln Gln Ala Ile Glu Gln Asn Leu Asp Ser Ile Ile
    835       840       845

Leu Val Phe Leu Glu Glu Ile Pro Asp Tyr Lys Leu Asn His Ala Leu
 850       855       860

Cys Leu Arg Arg Gly Met Phe Lys Ser His Cys Ile Leu Asn Trp Pro
865       870       875       880

Val Gln Lys Glu Arg Ile Gly Ala Phe Arg His Lys Leu Gln Val Ala
      885       890       895

Leu Gly Ser Lys Asn Ser Val His
    900

<210> SEQ ID NO 273
<211> LENGTH: 5661
<212> TYPE: DNA
<213> ORGANISM: Homo sapiens

<400> SEQUENCE: 273

```
tagcttcctc ttgctgtttc tttagccact ggtctgcagg cgttttcttc ttctaacttc      60
ctctcctgtg acaaaagaga taactattag agaaacaaaa gtccagaatg ctaaggttgc     120
cgctttcact tcctctcacc ctttagccca gaactgcttt gaatacacca attgctgtgg     180
ggcggctcga ggaagagaag acaccagtgc ctcagaaact gctcggtcag acggtgatag     240
cgagccacgc attcacaggg ccactgctgc tcacagaagc agtgaggatg atgccaggat     300
gatgtctgcc tcgcgcctgg ctgggactct gatcccagcc atggccttcc tctcctgcgt     360
gagaccagaa agctgggagc cctgcgtgga ggtggttcct aatattactt atcaatgcat     420
ggagctgaat ttctacaaaa tccccgacaa cctcccttc tcaaccaaga acctggacct     480
gagctttaat cccctgaggc atttaggcag ctatagcttc ttcagtttcc cagaactgca     540
ggtgctggat ttatccaggt gtgaaatcca gacaattgaa gatggggcat atcagagcct     600
aagccacctc tctaccttaa tattgacagg aaacccatc cagagtttag ccctgggagc     660
ctttctgga ctatcaagtt tacagaagct ggtggctgtg agacaaatc tagcatctct     720
agagaacttc cccattggac atctcaaaac tttgaaagaa cttaatgtgg ctcacaatct     780
tatccaatct ttcaaattac ctgagtattt ttctaatctg accatctag agcacttgga     840
cctttccagc aacaagattc aaagtattta ttgcacagac ttgcgggttc tacatcaaat     900
gccctactc aatctctctt tagacctgtc cctgaaccct atgaacttta ccaaccagg     960
tgcatttaaa gaaattaggc ttcataagct gactttaaga ataaattttg atagtttaaa    1020
tgtaatgaaa acttgtattc aaggtctggc tggtttagaa gtccatcgtt tggttctggg    1080
agaatttaga aatgaaggaa acttggaaaa gtttgacaaa tctgctctag agggcctgtg    1140
caatttgacc attgaagaat tccgattagc atacttagac tactacctcg atgatattat    1200
tgacttattt aattgtttga caaatgtttc ttcattttcc ctggtgagtg tgactattga    1260
aagggtaaaa gacttttctt ataatttcgg atggcaacat ttagaattag ttaactgtaa    1320
atttggacag tttcccacat tgaaactcaa atctctcaaa aggcttactt tcacttccaa    1380
caaggtggg aatgctttt cagaagttga tctaccaagc cttgagtttc tagatctcag    1440
tagaaatggc ttgagtttca aaggttgctg ttctcaaagt gatttgggga caaccagcct    1500
aaagtattta gatctgagct tcaatggtgt tattaccatg agttcaaact tcttgggctt    1560
```

| | |
|---|---|
| agaacaacta gaacatctgg atttccagca ttccaatttg aaacaaatga gtgagttttc | 1620 |
| agtattccta tcactcagaa acctcattta ccttgacatt tctcatactc acaccagagt | 1680 |
| tgctttcaat ggcatcttca atggcttgtc cagtctcgaa gtcttgaaaa tggctggcaa | 1740 |
| ttctttccag gaaaacttcc ttccagatat cttcacagag ctgagaaact tgaccttcct | 1800 |
| ggacctctct cagtgtcaac tggagcagtt gtctccaaca gcatttaact cactctccag | 1860 |
| tcttcaggta ctaaatatga gccacaacaa cttcttttca ttggatacgt ttccttataa | 1920 |
| gtgtctgaac tccctccagg ttcttgatta cagtctcaat cacataatga cttccaaaaa | 1980 |
| acaggaacta cagcattttc caagtagtct agctttctta aatcttactc agaatgactt | 2040 |
| tgcttgtact tgtgaacacc agagtttcct gcaatggatc aaggaccaga ggcagctctt | 2100 |
| ggtggaagtt gaacgaatgg aatgtgcaac accttcagat aagcagggca tgcctgtgct | 2160 |
| gagtttgaat atcacctgtc agatgaataa gaccatcatt ggtgtgtcgg tcctcagtgt | 2220 |
| gcttgtagta tctgttgtag cagttctggt ctataagttc tattttcacc tgatgcttct | 2280 |
| tgctggctgc ataaagtatg gtagaggtga aaacatctat gatgcctttg ttatctactc | 2340 |
| aagccaggat gaggactggg taaggaatga gctagtaaag aatttagaag aaggggtgcc | 2400 |
| tccatttcag ctctgccttc actacagaga ctttattccc ggtgtggcca ttgctgccaa | 2460 |
| catcatccat gaaggtttcc ataaaagccg aaaggtgatt gttgtggtgt cccagcactt | 2520 |
| catccagagc cgctggtgta tctttgaata tgagattgct cagacctggc agtttctgag | 2580 |
| cagtcgtgct ggtatcatct tcattgtcct gcagaaggtg gagaagaccc tgctcaggca | 2640 |
| gcaggtggag ctgtaccgcc ttctcagcag gaacacttac ctggagtggg aggacagtgt | 2700 |
| cctggggcgg cacatcttct ggagacgact cagaaaagcc ctgctggatg gtaaatcatg | 2760 |
| gaatccagaa ggaacagtgg gtacaggatg caattggcag gaagcaacat ctatctgaag | 2820 |
| aggaaaaata aaaccctcct gaggcatttc ttgcccagct gggtccaaca cttgttcagt | 2880 |
| taataagtat taaatgctgc cacatgtcag gccttatgct aagggtgagt aattccatgg | 2940 |
| tgcactagat atgcagggct gctaatctca aggagcttcc agtgcagagg gaataaaatgc | 3000 |
| tagactaaaa tacagagtct tccaggtggg catttcaacc aactcagtca aggaacccat | 3060 |
| gacaagaaa gtcatttcaa ctcttacctc atcaagttga ataaagacag agaaaacaga | 3120 |
| aagagacatt gttctttttcc tgagtctttt gaatggaaat tgtattatgt tatagccatc | 3180 |
| ataaaaccat tttggtagtt ttgactgaac tgggtgttca cttttttcctt tttgattgaa | 3240 |
| tacaatttaa attctacttg atgactgcag tcgtcaaggg gctcctgatg caagatgccc | 3300 |
| cttccatttt aagtctgtct ccttacagag gttaaagtct agtggctaat tcctaaggaa | 3360 |
| acctgattaa cacatgctca caaccatcct ggtcattctc gagcatgttc tatttttaa | 3420 |
| ctaatcaccc ctgatatatt tttattttta tatatccagt tttcattttt ttacgtcttg | 3480 |
| cctataagct aatatcataa ataaggttgt ttaagacgtg cttcaaatat ccatattaac | 3540 |
| cactattttt caaggaagta tggaaaagta cactctgtca ctttgtcact cgatgtcatt | 3600 |
| ccaaagttat tgcctactaa gtaatgactg tcatgaaagc agcattgaaa taatttgttt | 3660 |
| aaaggggca ctcttttaaa cgggaagaaa atttccgctt cctggtctta tcatggacaa | 3720 |
| tttgggctag aggcaggaag gaagtgggat gacctcagga ggtcaccttt tcttgattcc | 3780 |
| agaaacatat gggctgataa acccggggtg acctcatgaa atgagttgca gcagaagttt | 3840 |
| attttttca gaacaagtga tgtttgatgg acctctgaat ctctttaggg agacacagat | 3900 |

```
ggctgggatc cctcccctgt acccttctca ctgccaggag aactacgtgt gaaggtattc    3960
aaggcaggga gtatacattg ctgtttcctg ttgggcaatg ctccttgacc acattttggg    4020
aagagtggat gttatcattg agaaaacaat gtgtctggaa ttaatgggt tcttataaag     4080
aaggttccca gaaagaatg ttcatccagc ctcctcagaa acagaacatt caagaaaagg     4140
acaatcagga tgtcatcagg gaaatgaaaa taaaaaccac aatgagatat caccttatac    4200
caggtagaat ggctactata aaaaaatgaa gtgtcatcaa ggatatagag aaattggaac    4260
ccttcttcac tgctggaggg aatggaaaat ggtgtagccg ttatgaaaaa cagtacggag    4320
gtttctcaaa aattaaaaat agaactgcta tatgatccag caatctcact tctgtatata    4380
tacccaaaat aattgaaatc agaatttcaa gaaatatttt acactcccat gttcattgtg    4440
gcactcttca caatcactgt ttccaaagtt atggaaacaa cccaaatttc cattgaaaaa    4500
taaatggaca agaaaatgt gcatatacgt acaatgggat attattcagc ctaaaaaaag    4560
ggggaatcct gttatttatg acaacatgaa taaacccgga ggccattatg ctatgtaaaa    4620
tgagcaagta acagaaagac aaatactgcc tgatttcatt tatatgaggt tctaaaatag    4680
tcaaactcat agaagcagag aatagaacag tggttcctag ggaaaaggag gaagggagaa    4740
atgaggaaat agggagttgt ctaattggta taaaattata gtatgcaaga tgaattagct    4800
ctaaagatca gctgtatagc agagttcgta taatgaacaa tactgtatta tgcacttaac    4860
attttgttaa gagggtacct ctcatgttaa gtgttcttac catatacata tacacaagga    4920
agcttttgga ggtgatggat atatttatta ccttgattgt ggtgatggtt tgacaggtat    4980
gtgactatgt ctaaactcat caaattgtat acattaaata tatgcagttt tataatatca    5040
attatgtctg aatgaagcta taaaaagaa aagacaacaa aattcagttg tcaaaactgg     5100
aaatatgacc acagtcagaa gtgtttgtta ctgagtgttt cagagtgtgt ttggtttgag    5160
caggtctagg gtgattgaac atccctgggt gtgttccat gtctcatgta ctagtgaaag     5220
tagatgtgtg catttgtgca catatcccta tgtatcccta tcagggctgt gtgtatttga    5280
aagtgtgtgt gtccgcatga tcatatctgt atagaagaga gtgtgattat atttcttgaa    5340
gaatacatcc atttgaaatg gatgtctatg gctgtttgag atgagttctc tactcttgtg    5400
cttgtacagt agtctcccct tatcccttat gcttggtgga tacgttctta gaccccaagt    5460
ggatctctga daccgcagat ggtaccaaac ctcatatatg caatatttt tcctatacat     5520
aaatacctaa gataaagttc atcttctgaa ttaggcacag taagagatta acaataacta    5580
acaataaaat tgaatagtta taataatata ttgtaataaa agttatgtga atgtgatctc    5640
tttctttctc tctctcaaaa t                                              5661
```

<210> SEQ ID NO 274
<211> LENGTH: 839
<212> TYPE: PRT
<213> ORGANISM: Homo sapiens

<400> SEQUENCE: 274

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
            20                  25                  30

Val Pro Asn Ile Thr Tyr Gln Cys Met Glu Leu Asn Phe Tyr Lys Ile
        35                  40                  45

Pro Asp Asn Leu Pro Phe Ser Thr Lys Asn Leu Asp Leu Ser Phe Asn
    50                  55                  60

-continued

```
Pro Leu Arg His Leu Gly Ser Tyr Ser Phe Ser Phe Pro Glu Leu
 65                  70                  75                  80

Gln Val Leu Asp Leu Ser Arg Cys Glu Ile Gln Thr Ile Glu Asp Gly
                 85                  90                  95

Ala Tyr Gln Ser Leu Ser His Leu Ser Thr Leu Ile Leu Thr Gly Asn
                100                 105                 110

Pro Ile Gln Ser Leu Ala Leu Gly Ala Phe Ser Gly Leu Ser Ser Leu
                115                 120                 125

Gln Lys Leu Val Ala Val Glu Thr Asn Leu Ala Ser Leu Glu Asn Phe
    130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                    165                 170                 175

Leu Glu His Leu Asp Leu Ser Ser Asn Lys Ile Gln Ser Ile Tyr Cys
                180                 185                 190

Thr Asp Leu Arg Val Leu His Gln Met Pro Leu Leu Asn Leu Ser Leu
                195                 200                 205

Asp Leu Ser Leu Asn Pro Met Asn Phe Ile Gln Pro Gly Ala Phe Lys
    210                 215                 220

Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                    245                 250                 255

Arg Leu Val Leu Gly Glu Phe Arg Asn Glu Gly Asn Leu Glu Lys Phe
                260                 265                 270

Asp Lys Ser Ala Leu Glu Gly Leu Cys Asn Leu Thr Ile Glu Glu Phe
    275                 280                 285

Arg Leu Ala Tyr Leu Asp Tyr Tyr Leu Asp Asp Ile Ile Asp Leu Phe
    290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

Leu Val Asn Cys Lys Phe Gly Gln Phe Pro Thr Leu Lys Leu Lys Ser
                340                 345                 350

Leu Lys Arg Leu Thr Phe Thr Ser Asn Lys Gly Gly Asn Ala Phe Ser
                355                 360                 365

Glu Val Asp Leu Pro Ser Leu Glu Phe Leu Asp Leu Ser Arg Asn Gly
    370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
                420                 425                 430

Asn Leu Lys Gln Met Ser Glu Phe Ser Val Phe Leu Ser Leu Arg Asn
                435                 440                 445

Leu Ile Tyr Leu Asp Ile Ser His Thr His Thr Arg Val Ala Phe Asn
                450                 455                 460

Gly Ile Phe Asn Gly Leu Ser Ser Leu Glu Val Leu Lys Met Ala Gly
465                 470                 475                 480
```

```
Asn Ser Phe Gln Glu Asn Phe Leu Pro Asp Ile Phe Thr Glu Leu Arg
            485                 490                 495

Asn Leu Thr Phe Leu Asp Leu Ser Gln Cys Gln Leu Glu Gln Leu Ser
        500                 505                 510

Pro Thr Ala Phe Asn Ser Leu Ser Ser Leu Gln Val Leu Asn Met Ser
    515                 520                 525

His Asn Asn Phe Phe Ser Leu Asp Thr Phe Pro Tyr Lys Cys Leu Asn
530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
        595                 600                 605

Cys Ala Thr Pro Ser Asp Lys Gln Gly Met Pro Val Leu Ser Leu Asn
    610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
    690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
    770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
            820                 825                 830

Trp Gln Glu Ala Thr Ser Ile
        835

<210> SEQ ID NO 275
<211> LENGTH: 4277
<212> TYPE: DNA
<213> ORGANISM: Homo sapiens

<400> SEQUENCE: 275
ggttttcagg agcccgagcg agggcgccgc ttttgcgtcc gggaggagcc aaccgtggcg      60
```

-continued

| | | | | |
|---|---|---|---|---|
| caggcggcgc | ggggaggcgt | cccagagtct | cactctgccg | cccaggctgg actgcagtga | 120 |
| cacaatctcg | gctgactgca | accactgcct | ccagggttca | agcgattctc ttgcctcagc | 180 |
| ctcccaagta | gctgggatta | cagattgatg | ttcatgttcc | tgacactact acaagattca | 240 |
| tactcctgat | gctactgaca | acgtggcttc | tccacagtca | ccaaaccagg gatgctatac | 300 |
| tggacttccc | tactctcatc | tgctccagcc | ccctgacctt | atagttgccc agctttcctg | 360 |
| gcaattgact | tgcccatca | atacacagga | tttagcatcc | agggaagatg tcggagcctc | 420 |
| agatgttaat | tttctaattg | agaatgttgg | cgctgtccga | acctggagac aggaaaacaa | 480 |
| aaagtccttt | ctcctgattc | accaaaaaat | aaaatactga | ctaccatcac tgtgatgaga | 540 |
| ttcctatagt | ctcaggaact | gaagtcttta | aacaaccagg | accctctgc ccctagaata | 600 |
| agaacatact | agaagtccct | tctgctagga | caacgaggat | catgggagac acctggacc | 660 |
| ttctcctagg | agtggtgctc | atggccggtc | ctgtgtttgg | aattccttcc tgctcctttg | 720 |
| atggccgaat | agccttttat | cgtttctgca | acctcaccca | ggtccccag gtcctcaaca | 780 |
| ccactgagag | gctcctgctg | agcttcaact | atatcaggac | agtcactgct tcatccttcc | 840 |
| cctttctgga | acagctgcag | ctgctggagc | tcgggagcca | gtataccccc ttgactattg | 900 |
| acaaggaggc | cttcagaaac | ctgcccaacc | ttagaatctt | ggacctggga agtagtaaga | 960 |
| tatacttctt | gcatccagat | gcttttcagg | gactgttcca | tctgtttgaa cttagactgt | 1020 |
| atttctgtgg | tctctctgat | gctgtattga | agatggttta | tttcagaaat ttaaaggctt | 1080 |
| taactcgctt | ggatctatcc | aaaaatcaga | ttcgtagcct | ttaccttcat ccttcatttg | 1140 |
| ggaagttgaa | ttccttaaag | tccatagatt | tttcctccaa | ccaaatattc cttgtatgtg | 1200 |
| aacatgagct | cgagccccta | caagggaaaa | cgctctcctt | ttttagcctc gcagctaata | 1260 |
| gcttgtatag | cagagtctca | gtggactggg | gaaaatgtat | gaacccattc agaaacatgg | 1320 |
| tgctggagat | actagatgtt | tctggaaatg | gctggacagt | ggacatcaca ggaaacttta | 1380 |
| gcaatgccat | cagcaaaagc | caggccttct | ctttgattct | tgcccaccac atcatgggtg | 1440 |
| ccgggtttgg | cttccataac | atcaaagatc | ctgaccagaa | cacatttgct ggcctggcca | 1500 |
| gaagttcagt | gagacacctg | gatctttcac | atgggtttgt | cttctccctg aactcacgag | 1560 |
| tctttgagac | actcaaggat | ttgaaggttc | tgaaccttgc | ctacaacaag ataaataaga | 1620 |
| ttgcagatga | agcattttac | ggacttgaca | acctccaagt | tctcaatttg tcatataacc | 1680 |
| ttctggggga | actttacagt | tcgaatttct | atggactacc | taaggtagcc tacattgatt | 1740 |
| tgcaaaagaa | tcacattgca | ataattcaag | accaaacatt | caaattcctg gaaaaattac | 1800 |
| agaccttgga | tctccgagac | aatgctctta | caaccattca | ttttattcca agcatacccg | 1860 |
| atatcttctt | gagtggcaat | aaactagtga | cttttgccaaa | gatcaacctt acagcgaacc | 1920 |
| tcatccactt | atcagaaaac | aggctagaaa | atctagatat | tctctacttt ctcctacggg | 1980 |
| tacctcatct | ccagattctc | atttttaaatc | aaaatcgctt | ctcctcctgt agtggagatc | 2040 |
| aaaccccttc | agagaatccc | agcttagaac | agcttttcct | tggagaaaat atgttgcaac | 2100 |
| ttgcctggga | aactgagctc | tgttgggatg | tttttgaggg | actttctcat cttcaagttc | 2160 |
| tgtatttgaa | tcataactat | cttaattccc | ttccaccagg | agtatttagc catctgactg | 2220 |
| cattaagggg | actaagcctc | aactccaaca | ggctgacagt | tctttctcac aatgatttac | 2280 |
| ctgctaattt | agagatcctg | gacatatcca | ggaaccagct | cctagctcct aatcctgatg | 2340 |
| tatttgtatc | acttagtgtc | ttggatataa | ctcataacaa | gttcatttgt gaatgtgaac | 2400 |
| ttagcacttt | tatcaattgg | cttaatcaca | ccaatgtcac tatagctggg cctcctgcag | 2460 |

```
acatatattg tgtgtaccct gactcgttct ctggggtttc cctcttctct ctttccacgg    2520
aaggttgtga tgaagaggaa gtcttaaagt ccctaaagtt ctcccttttc attgtatgca    2580
ctgtcactct gactctgttc ctcatgacca tcctcacagt cacaaagttc cggggcttct    2640
gttttatctg ttataagaca gcccagagac tggtgttcaa ggaccatccc cagggcacag    2700
aacctgatat gtacaaatat gatgcctatt tgtgcttcag cagcaaagac ttcacatggg    2760
tgcagaatgc tttgctcaaa cacctggaca ctcaatacag tgaccaaaac agattcaacc    2820
tgtgctttga agaaagagac tttgtcccag gagaaaaccg cattgccaat atccaggatg    2880
ccatctggaa cagtagaaag atcgtttgtc ttgtgagcag acacttcctt agagatggct    2940
ggtgccttga agccttcagt tatgcccagg gcaggtgctt atctgacctt aacagtgctc    3000
tcatcatggg ggtggttggg tccttgtccc agtaccagtt gatgaaacat caatccatca    3060
gaggctttgt acagaaacag cagtatttga ggtggcctga ggatctccag gatgttggct    3120
ggtttcttca taaactctct caacagatac taaagaaaga aaagaaaag aagaaagaca    3180 ataacattcc gttgcaaact gtagcaacca tctcctaatc aaaggagcaa tttccaactt    3240
atctcaagcc acaaataact cttcactttg tatttgcacc aagttatcat tttggggtcc    3300
tctctggagg ttttttttt cttttgcta ctatgaaaac aacataaatc tctcaatttt    3360
cgtatcaaca ccatgttctg tctcactaac ctccaaatgg aaaataatag atctagaaaa    3420
ttgcaactgc ccttagaggt ttccagtctc cattgatttt ctttcagatc caataatacc    3480
gttctgtcct gctgtgttga ttatggaatg tatcctaatc atgggaaggg cacccttggga    3540 gaagttgcag atggctgacg tgctttctct agcattcagc taaaaatgg gatggtccat    3600 gattctgcgt tctctgtgtt ctgcaaaaca acattaagta gaaaacaaac agaagcagag    3660
gcacatttcc ttcttttgcc acagaaacaa tgccactgtt gagtgcaagt cacactttgt    3720
ctcatagata agaggtggcc ccaaagaagc tgggatgaat gagtcactac ctgtcttgtg    3780
actgtactgc acttcatgtt cttaccttcg gcttctccag gtctcgccct agtgagccaa    3840
gaactttctc tcacatgctg cctttatttta agcctggcct tcaagacctt ccatgattta    3900
tcaccaacct acctttcag ctttgtttcc tagcacacct cattgatcag ctgctcaggc    3960
tgttgcatga agaacatgga ctttgcacac agatcctggg ttgagttctg agtcagctgt    4020
gtattagcca tgtaaccttg gccttggtat gcccttgctg gacctacatt ttctcacgta    4080
acagcatcta tgtcatagaa ttcctgtgaa aattaaattg ccaaggatg tcagggcttc    4140 tcagatcttt tccttcgttg ccctaatgac cacaagagaa cacatacact gaaggcctcc    4200
tggggggcag ttgcaatttc actgaagttg tatttttta tcttaaatga aatctatgtg    4260 tatttcaaa aaaaaaa                                                    4277
```

<210> SEQ ID NO 276
<211> LENGTH: 858
<212> TYPE: PRT
<213> ORGANISM: Homo sapiens

<400> SEQUENCE: 276

```
Met Gly Asp His Leu Asp Leu Leu Gly Val Val Leu Met Ala Gly
1               5                   10                  15

Pro Val Phe Gly Ile Pro Ser Cys Ser Phe Asp Gly Arg Ile Ala Phe
            20                  25                  30

Tyr Arg Phe Cys Asn Leu Thr Gln Val Pro Gln Val Leu Asn Thr Thr
        35                  40                  45
```

```
Glu Arg Leu Leu Leu Ser Phe Asn Tyr Ile Arg Thr Val Ala Ser
    50                  55                  60

Ser Phe Pro Phe Leu Glu Gln Leu Gln Leu Leu Glu Leu Gly Ser Gln
65              70                  75                  80

Tyr Thr Pro Leu Thr Ile Asp Lys Glu Ala Phe Arg Asn Leu Pro Asn
                85                  90                  95

Leu Arg Ile Leu Asp Leu Gly Ser Ser Lys Ile Tyr Phe Leu His Pro
            100                 105                 110

Asp Ala Phe Gln Gly Leu Phe His Leu Phe Glu Leu Arg Leu Tyr Phe
            115                 120                 125

Cys Gly Leu Ser Asp Ala Val Leu Lys Asp Gly Tyr Phe Arg Asn Leu
    130                 135                 140

Lys Ala Leu Thr Arg Leu Asp Leu Ser Lys Asn Gln Ile Arg Ser Leu
145             150                 155                 160

Tyr Leu His Pro Ser Phe Gly Lys Leu Asn Ser Leu Lys Ser Ile Asp
                165                 170                 175

Phe Ser Ser Asn Gln Ile Phe Leu Val Cys Glu His Glu Leu Glu Pro
            180                 185                 190

Leu Gln Gly Lys Thr Leu Ser Phe Phe Ser Leu Ala Ala Asn Ser Leu
    195                 200                 205

Tyr Ser Arg Val Ser Val Asp Trp Gly Lys Cys Met Asn Pro Phe Arg
210                 215                 220

Asn Met Val Leu Glu Ile Leu Asp Val Ser Gly Asn Gly Trp Thr Val
225             230                 235                 240

Asp Ile Thr Gly Asn Phe Ser Asn Ala Ile Ser Lys Ser Gln Ala Phe
                245                 250                 255

Ser Leu Ile Leu Ala His His Ile Met Gly Ala Gly Phe Gly Phe His
            260                 265                 270

Asn Ile Lys Asp Pro Asp Gln Asn Thr Phe Ala Gly Leu Ala Arg Ser
            275                 280                 285

Ser Val Arg His Leu Asp Leu Ser His Gly Phe Val Phe Ser Leu Asn
    290                 295                 300

Ser Arg Val Phe Glu Thr Leu Lys Asp Leu Lys Val Leu Asn Leu Ala
305                 310                 315                 320

Tyr Asn Lys Ile Asn Lys Ile Ala Asp Glu Ala Phe Tyr Gly Leu Asp
                325                 330                 335

Asn Leu Gln Val Leu Asn Leu Ser Tyr Asn Leu Leu Gly Glu Leu Tyr
            340                 345                 350

Ser Ser Asn Phe Tyr Gly Leu Pro Lys Val Ala Tyr Ile Asp Leu Gln
    355                 360                 365

Lys Asn His Ile Ala Ile Gln Asp Gln Thr Phe Lys Phe Leu Glu
370                 375                 380

Lys Leu Gln Thr Leu Asp Leu Arg Asp Asn Ala Leu Thr Thr Ile His
385                 390                 395                 400

Phe Ile Pro Ser Ile Pro Asp Ile Phe Leu Ser Gly Asn Lys Leu Val
                405                 410                 415

Thr Leu Pro Lys Ile Asn Leu Thr Ala Asn Leu Ile His Leu Ser Glu
            420                 425                 430

Asn Arg Leu Glu Asn Leu Asp Ile Leu Tyr Phe Leu Leu Arg Val Pro
        435                 440                 445

His Leu Gln Ile Leu Ile Leu Asn Gln Asn Arg Phe Ser Ser Cys Ser
    450                 455                 460
```

```
Gly Asp Gln Thr Pro Ser Glu Asn Pro Ser Leu Glu Gln Leu Phe Leu
465                 470                 475                 480

Gly Glu Asn Met Leu Gln Leu Ala Trp Glu Thr Glu Leu Cys Trp Asp
            485                 490                 495

Val Phe Glu Gly Leu Ser His Leu Gln Val Leu Tyr Leu Asn His Asn
        500                 505                 510

Tyr Leu Asn Ser Leu Pro Pro Gly Val Phe Ser His Leu Thr Ala Leu
    515                 520                 525

Arg Gly Leu Ser Leu Asn Ser Asn Arg Leu Thr Val Leu Ser His Asn
530                 535                 540

Asp Leu Pro Ala Asn Leu Glu Ile Leu Asp Ile Ser Arg Asn Gln Leu
545                 550                 555                 560

Leu Ala Pro Asn Pro Asp Val Phe Val Ser Leu Ser Val Leu Asp Ile
                565                 570                 575

Thr His Asn Lys Phe Ile Cys Glu Cys Glu Leu Ser Thr Phe Ile Asn
            580                 585                 590

Trp Leu Asn His Thr Asn Val Thr Ile Ala Gly Pro Pro Ala Asp Ile
        595                 600                 605

Tyr Cys Val Tyr Pro Asp Ser Phe Ser Gly Val Ser Leu Phe Ser Leu
    610                 615                 620

Ser Thr Glu Gly Cys Asp Glu Glu Val Leu Lys Ser Leu Lys Phe
625                 630                 635                 640

Ser Leu Phe Ile Val Cys Thr Val Thr Leu Thr Phe Leu Met Thr
                645                 650                 655

Ile Leu Thr Val Thr Lys Phe Arg Gly Phe Cys Phe Ile Cys Tyr Lys
            660                 665                 670

Thr Ala Gln Arg Leu Val Phe Lys Asp His Pro Gln Gly Thr Glu Pro
        675                 680                 685

Asp Met Tyr Lys Tyr Asp Ala Tyr Leu Cys Phe Ser Ser Lys Asp Phe
    690                 695                 700

Thr Trp Val Gln Asn Ala Leu Leu Lys His Leu Asp Thr Gln Tyr Ser
705                 710                 715                 720

Asp Gln Asn Arg Phe Asn Leu Cys Phe Glu Glu Arg Asp Phe Val Pro
                725                 730                 735

Gly Glu Asn Arg Ile Ala Asn Ile Gln Asp Ala Ile Trp Asn Ser Arg
            740                 745                 750

Lys Ile Val Cys Leu Val Ser Arg His Phe Leu Arg Asp Gly Trp Cys
        755                 760                 765

Leu Glu Ala Phe Ser Tyr Ala Gln Gly Arg Cys Leu Ser Asp Leu Asn
    770                 775                 780

Ser Ala Leu Ile Met Val Val Val Gly Ser Leu Ser Gln Tyr Gln Leu
785                 790                 795                 800

Met Lys His Gln Ser Ile Arg Gly Phe Val Gln Lys Gln Tyr Leu
                805                 810                 815

Arg Trp Pro Glu Asp Leu Gln Asp Val Gly Trp Phe Leu His Lys Leu
            820                 825                 830

Ser Gln Gln Ile Leu Lys Lys Glu Lys Glu Lys Lys Asp Asn Asn
        835                 840                 845

Ile Pro Leu Gln Thr Val Ala Thr Ile Ser
    850                 855

<210> SEQ ID NO 277
<211> LENGTH: 5891
<212> TYPE: DNA
```

<213> ORGANISM: Homo sapiens

<400> SEQUENCE: 277

```
aattgtattt ccgttcattt acaagttatt ttctcttctt ctgaaaaaga gatcttgaat     60
ttggactcat atcaagatgc tctgaagaag aacaacccct taggatagcc actgcaacat    120
catgaccaaa gacaaagaac ctattgttaa aagcttccat tttgtttgcc ttatgatcat    180
aatagttgga accagaatcc agttctccga cggaaatgaa tttgcagtag acaagtcaaa    240
aagaggtctt attcatgttc caaaagacct accgctgaaa accaaagtct tagatatgtc    300
tcagaactac atcgctgagc ttcaggtctc tgacatgagc tttctatcag agttgacagt    360
tttgagactt tcccataaca gaatccagct acttgattta agtgttttca gttcaaccca    420
ggatttagaa tatttggatt tatctcataa tcagttgcaa aagatatcct gccatcctat    480
tgtgagtttc aggcatttag atctctcatt caatgatttc aaggccctgc ccatctgtaa    540
ggaatttggc aacttatcac aactgaattt cttgggattg agtgctatga agctgcaaaa    600
attagatttg ctgccaattg ctcacttgca tctaagttat atccttctgg atttaagaaa    660
ttattatata aagaaaatg agacagaaag tctacaaatt ctgaatgcaa aaacccttca    720
ccttgttttt cacccaacta gtttattcgc tatccaagtg aacatatcag ttaatacttt    780
agggtgctta caactgacta atattaaatt gaatgatgac aactgtcaag ttttcattaa    840
atttttatca gaactcacca gaggttcaac cttactgaat tttaccctca accacataga    900
aacgacttgg aaatgcctgg tcagagtctt tcaatttctt tggcccaaac ctgtggaata    960
tctcaatatt tacaatttaa caataattga aagcattcgt gaagaagatt ttacttattc   1020
taaaacgaca ttgaaagcat tgacaataga acatatcacg aaccaagttt ttctgttttc   1080
acagacagct ttgtacaccg tgtttttctga gatgaacatt atgatgttaa ccatttcaga   1140
tacaccttt atacacatgc tgtgtcctca tgcaccaagc acattcaagt ttttgaactt   1200
tacccagaac gttttcacag atagtatttt tgaaaaatgt tccacgttag ttaaattgga   1260
gacacttatc ttacaaaaga atggattaaa agacctttc aaagtaggtc tcatgacgaa   1320
ggatatgcct tctttggaaa tactggatgt tagctggaat tctttggaat ctggtagaca   1380
taaagaaaac tgcacttggg ttgagagtat agtggtgtta aatttgtctt caaatatgct   1440
tactgactct gttttcagat gtttacctcc caggatcaag gtacttgatc ttcacagcaa   1500
taaaataaag agcgttccta acaagtcgt aaaactggaa gctttgcaag aactcaatgt   1560
tgctttcaat tctttaactg accttcctgg atgtggcagc tttagcagcc tttctgtatt   1620
gatcattgat cacaattcag tttcccaccc atcggctgat ttcttccaga gctgccagaa   1680
gatgaggtca ataaaagcag gggacaatcc attccaatgt acctgtgagc taagagaatt   1740
tgtcaaaaat atagaccaag tatcaagtga agtgttagag ggctggcctg attcttataa   1800
gtgtgactac ccagaaaagtt atagaggaag cccactaaag gactttcaca tgtctgaatt   1860
atcctgcaac ataactctgc tgatcgtcac catcggtgcc accatgctgg tgttggctgt   1920
gactgtgacc tccctctgca tctacttgga tctgcctgg tatctcagga tggtgtgcca   1980
gtggacccag actcggcgca gggccaggaa catacccta gaagaactcc aaagaaacct   2040
ccagtttcat gcttttattt catatagtga acatgattct gcctgggtga aaagtgaatt   2100
ggtaccttac ctagaaaaag aagatataca gatttgtctt catgagagaa actttgtccc   2160
tggcaagagc attgtggaaa atatcatcaa ctgcattgag aagagttaca gtccatcctt   2220
tgttttgtct cccaactttg tccagagtga gtggtgccat tacgaactct attttgccca   2280
```

```
tcacaatctc tttcatgaag gatctaataa cttaatcctc atcttactgg aacccattcc    2340
acagaacagc attcccaaca agtaccacaa gctgaaggct ctcatgacgc agcggactta    2400
tttgcagtgg cccaaggaga aaagcaaacg tgggctcttt tgggctaaca ttagagccgc    2460
ttttaatatg aaattaacac tagtcactga aaacaatgat gtgaaatctt aaaaaaattt    2520
aggaaattca acttaagaaa ccattattta cttggatgat ggtgaatagt acagtcgtaa    2580
gtaactgtct ggaggtgcct ccattatcct catgccttca ggaaagactt aacaaaaaca    2640
atgtttcatc tggggaactg agctaggcgg tgaggttagc ctgccagtta gagacagccc    2700
agtctcttct ggtttaatca ttatgtttca aattgaaaca gtctcttttg agtaaatgct    2760 cagttttca gctcctctcc actctgcttt cccaaatgga ttctgttgtg agcaagagtt    2820
tatatggctt catggcagca agggaacagt caacttcagc atcatatgca ccagtcctcg    2880
gagtgccctg tgaatcatat tggtctttgg gtcagtgtca tcattctctt caagtctggg    2940 gcttgggaa aaaattagat cagctacggc atataaaaaa gtcttttgtt tcacatatgt    3000
gtaatagctt atttaatttt ttatcctgct acacaaatat gtaattaacc aatgaggact    3060
catgacttga tagtgtatgt atgtaaaggg atatatggac ttaatcataa gctgttgagg    3120
tgaaagacgt ggatccacct gctttccaag aaaactcggc caaatttatt tgcagctgga    3180
tattgaatgg gacttttctg gttgtcttag aattctggct aaaggctcaa agctgacgaa    3240
agacagtaac tgcaccaaca tgatactaga cacagccagt ctggacttat caaaagagca    3300
gaaagagacc aatgactccc agtccgtatt atccatctct agaagactag agtcaaaagc    3360
gtgattaaag agtcattaag cggaggttct aggccatagg gagattgctt tgaatttctt    3420
gcagacaagt gtgagggact cagcatggta gaaggtagcc tggcatccca ctccaagact    3480
gaaagcttgc agagtaacag gagcacacag gttcagtgca gcagatgtgg tgtggcttga    3540
gaattcttgg aagagcttga tgagtgtttg ctggagtccg agggtgggca ctgggaacac    3600
agagactggt aaatagtgtt tggcaaatac aagtgcttga tgaatatttg ttgaatgaat    3660
agatgagttc ttcccccctg gggaattcag gaggtgaaag gttggcttga gcacccaaaa    3720
tggcaggatg agagaagaga agcactgata gcaacctgcc ctcccattat tgacatggta    3780
aaaggatgtg aatttcttca catggctttg actatggaag agtagctggg cttgcattgt    3840
catgacggga tatcagccaa cagggtagcc tgttgtgcaa agaaactata gcagtaagag    3900
gacacggggt taggcagaag aggggtttgg ggtggaggtt gctgcaagag gtcagccaga    3960
taatgtggcc ctgcatcatg gaactgtgca atgtggggta cactcaaggc cctccaataa    4020
ctcacagatg tgccctatga aaaagccagc atttggactc tgccatagca gctggcagga    4080
tcatgctggc ctgtctgcct tattcaatag ttaactacag gaagatctgc tcctctttgt    4140 gtaatacccct cttcccttgc aatggcatag ggacatctag aatatagaga agacagagac    4200
aatggaggaa gagtaaagaa actgactata tgccttcgtc atttcactgc aaggaaggcc    4260
aagcagattt ttgaatgagg tgtgagattg ctgttaaatt ggactggcct ggacatttta    4320
atcccttaaa tagaggtgca atgactaaag tgagatttgt cactaaaatt tatggtatct    4380
gcccaagatt caggagtgat gatgggagga gatccaacag aactttgttg taaggcaatg    4440
gttagagaaa aatgaagccc tcgctttctg gacttagttc attcaataaa ccagtttcgg    4500
ccaggcacgt tggctcacat ctataatccc agtactgtgg gaggctgagg caggtggatc    4560
acttgaggtc aggagttcga gaccagcctg gccaacatgg tgaaaccctg tctgtactaa    4620
```

-continued

```
aaatacaaaa attagccggg tgtggtggtg tgcacctgta gtcccagcta ctcgggaggc    4680
tgaggcagga aaatcacttg aacctgggag acagaggctg tagtgagctg agacagcgct    4740
actgtactcc ccgctgggca acagagtgag actccatctc aaaaaagtta aagaaaaaa     4800
aatctggttt cataatagct gtaacgaaat aagccttaat gatattttat tagcatcatc    4860
ttctgtctgc attagccctt ccttgctctt caggagaaca catttgttt tcctccctag     4920
gctctatccc aaacggcaca ttcttccaca acccctgttg aacagatttt ttaaactgtt    4980
gcctaatcta aaacaataa aaacaacaaa caaccacagt aacaacaacg acaaaaaaa      5040
ctgccacaga ttctaaataa tcagatcttt ttaaatggta tcaatgtttc ccacaaaata    5100
ttgttgacat tgaaaatata gaattttagc attaattttg ttaaacctac atcccctcgg    5160
cagaggggcc tccctgcatc ccagtggaaa gtaggttcct cacagtcctc tccgtcacat    5220
tcttcccatt tcttttcttc acagaacaca tcactgtcta aaattatctt gtttgcttag    5280
ttgcttactc atcttcttct tctctcctct gaagtctaag ctccaggaaa aagggagact    5340
tctccacctg ttccctgcct ctccccagtg ccgagggac actgtgcacc ccattgtaga     5400
tgcgcagtaa aaactcgtgg gatgagcaaa tgactctgaa acggtcccat gcgggaaatg    5460
tccatgaagt cctggatttt atctaaaaag cccaggcagg ggggggcggg ggcggcgggg    5520
ctacagttcc acgctgagct gcctcctggc cgctcgtccc cgccgcagtg cctgggcggc    5580
ccgggcgccc gaccttggcc gtggacacct tcgcggtggg tgctgctcct ccccatctgc    5640
cactggaaga tgctggggcg acccggctcc aggtttagca ggacactgag aaaagggaat    5700
ggctgccttt cggaggctgg gtgagcccct tctctgtgcct cacctgcccg ccccacagcg    5760
gccctgcacc tcgtcccacg gggcccattg ccccggtagg atgcgcgctt ttgttttgag    5820
ggtcaggcat cttccctgcc gtcgtttctg ggaggttgaa aaattgatcc agaaagacct    5880
aaaacaaaaa a                                                         5891
```

<210> SEQ ID NO 278
<211> LENGTH: 796
<212> TYPE: PRT
<213> ORGANISM: Homo sapiens

<400> SEQUENCE: 278

```
Met Thr Lys Asp Lys Glu Pro Ile Val Lys Ser Phe His Phe Cys
1               5                   10                  15

Leu Met Ile Ile Ile Val Gly Thr Arg Ile Gln Phe Ser Asp Gly Asn
            20                  25                  30

Glu Phe Ala Val Asp Lys Ser Lys Arg Gly Leu Ile His Val Pro Lys
        35                  40                  45

Asp Leu Pro Leu Lys Thr Lys Val Leu Asp Met Ser Gln Asn Tyr Ile
    50                  55                  60

Ala Glu Leu Gln Val Ser Asp Met Ser Phe Leu Ser Glu Leu Thr Val
65                  70                  75                  80

Leu Arg Leu Ser His Asn Arg Ile Gln Leu Leu Asp Leu Ser Val Phe
                85                  90                  95

Lys Phe Asn Gln Asp Leu Glu Tyr Leu Asp Leu Ser His Asn Gln Leu
            100                 105                 110

Gln Lys Ile Ser Cys His Pro Ile Val Ser Phe Arg His Leu Asp Leu
        115                 120                 125

Ser Phe Asn Asp Phe Lys Ala Leu Pro Ile Cys Lys Glu Phe Gly Asn
    130                 135                 140
```

```
Leu Ser Gln Leu Asn Phe Leu Gly Leu Ser Ala Met Lys Leu Gln Lys
145                 150                 155                 160

Leu Asp Leu Leu Pro Ile Ala His Leu His Leu Ser Tyr Ile Leu Leu
            165                 170                 175

Asp Leu Arg Asn Tyr Tyr Ile Lys Glu Asn Glu Thr Glu Ser Leu Gln
        180                 185                 190

Ile Leu Asn Ala Lys Thr Leu His Leu Val Phe His Pro Thr Ser Leu
    195                 200                 205

Phe Ala Ile Gln Val Asn Ile Ser Val Asn Thr Leu Gly Cys Leu Gln
    210                 215                 220

Leu Thr Asn Ile Lys Leu Asn Asp Asp Asn Cys Gln Val Phe Ile Lys
225                 230                 235                 240

Phe Leu Ser Glu Leu Thr Arg Gly Ser Thr Leu Leu Asn Phe Thr Leu
            245                 250                 255

Asn His Ile Glu Thr Thr Trp Lys Cys Leu Val Arg Val Phe Gln Phe
            260                 265                 270

Leu Trp Pro Lys Pro Val Glu Tyr Leu Asn Ile Tyr Asn Leu Thr Ile
        275                 280                 285

Ile Glu Ser Ile Arg Glu Glu Asp Phe Thr Tyr Ser Lys Thr Thr Leu
    290                 295                 300

Lys Ala Leu Thr Ile Glu His Ile Thr Asn Gln Val Phe Leu Phe Ser
305                 310                 315                 320

Gln Thr Ala Leu Tyr Thr Val Phe Ser Glu Met Asn Ile Met Met Leu
            325                 330                 335

Thr Ile Ser Asp Thr Pro Phe Ile His Met Leu Cys Pro His Ala Pro
            340                 345                 350

Ser Thr Phe Lys Phe Leu Asn Phe Thr Gln Asn Val Phe Thr Asp Ser
        355                 360                 365

Ile Phe Glu Lys Cys Ser Thr Leu Val Lys Leu Glu Thr Leu Ile Leu
370                 375                 380

Gln Lys Asn Gly Leu Lys Asp Leu Phe Lys Val Gly Leu Met Thr Lys
385                 390                 395                 400

Asp Met Pro Ser Leu Glu Ile Leu Asp Val Ser Trp Asn Ser Leu Glu
            405                 410                 415

Ser Gly Arg His Lys Glu Asn Cys Thr Trp Val Glu Ser Ile Val Val
        420                 425                 430

Leu Asn Leu Ser Ser Asn Met Leu Thr Asp Ser Val Phe Arg Cys Leu
        435                 440                 445

Pro Pro Arg Ile Lys Val Leu Asp Leu His Ser Asn Lys Ile Lys Ser
450                 455                 460

Val Pro Lys Gln Val Val Lys Leu Glu Ala Leu Gln Glu Leu Asn Val
465                 470                 475                 480

Ala Phe Asn Ser Leu Thr Asp Leu Pro Gly Cys Gly Ser Phe Ser Ser
            485                 490                 495

Leu Ser Val Leu Ile Ile Asp His Asn Ser Val Ser His Pro Ser Ala
        500                 505                 510

Asp Phe Phe Gln Ser Cys Gln Lys Met Arg Ser Ile Lys Ala Gly Asp
        515                 520                 525

Asn Pro Phe Gln Cys Thr Cys Glu Leu Arg Glu Phe Val Lys Asn Ile
        530                 535                 540

Asp Gln Val Ser Ser Glu Val Leu Glu Gly Trp Pro Asp Ser Tyr Lys
545                 550                 555                 560

Cys Asp Tyr Pro Glu Ser Tyr Arg Gly Ser Pro Leu Lys Asp Phe His
```

```
                        565                 570                 575
Met Ser Glu Leu Ser Cys Asn Ile Thr Leu Leu Ile Val Thr Ile Gly
                    580                 585                 590

Ala Thr Met Leu Val Leu Ala Val Thr Val Thr Ser Leu Cys Ile Tyr
                595                 600                 605

Leu Asp Leu Pro Trp Tyr Leu Arg Met Val Cys Gln Trp Thr Gln Thr
            610                 615                 620

Arg Arg Arg Ala Arg Asn Ile Pro Leu Glu Glu Leu Gln Arg Asn Leu
625                 630                 635                 640

Gln Phe His Ala Phe Ile Ser Tyr Ser Glu His Asp Ser Ala Trp Val
                645                 650                 655

Lys Ser Glu Leu Val Pro Tyr Leu Glu Lys Glu Asp Ile Gln Ile Cys
                660                 665                 670

Leu His Glu Arg Asn Phe Val Pro Gly Lys Ser Ile Val Glu Asn Ile
            675                 680                 685

Ile Asn Cys Ile Glu Lys Ser Tyr Lys Ser Ile Phe Val Leu Ser Pro
690                 695                 700

Asn Phe Val Gln Ser Glu Trp Cys His Tyr Glu Leu Tyr Phe Ala His
705                 710                 715                 720

His Asn Leu Phe His Glu Gly Ser Asn Asn Leu Ile Leu Ile Leu Leu
                725                 730                 735

Glu Pro Ile Pro Gln Asn Ser Ile Pro Asn Lys Tyr His Lys Leu Lys
            740                 745                 750

Ala Leu Met Thr Gln Arg Thr Tyr Leu Gln Trp Pro Lys Glu Lys Ser
                755                 760                 765

Lys Arg Gly Leu Phe Trp Ala Asn Ile Arg Ala Ala Phe Asn Met Lys
770                 775                 780

Leu Thr Leu Val Thr Glu Asn Asn Asp Val Lys Ser
785                 790                 795

<210> SEQ ID NO 279
<211> LENGTH: 4992
<212> TYPE: DNA
<213> ORGANISM: Homo sapiens

<400> SEQUENCE: 279
gaagactcca gatataggat cactccatgc catcaagaaa gttgatgcta ttgggcccat    60
ctcaagctga tcttggcacc tctcatgctc tgctctcttc aaccagacct ctacattcca   120
ttttggaaga agactaaaaa tggtgtttcc aatgtggaca ctgaagagac aaattcttat   180 ccttttttaac ataatcctaa tttccaaact ccttgggggct agatggtttc ctaaaactct   240
gccctgtgat gtcactctgg atgttccaaa gaaccatgtg atcgtggact gcacagacaa   300
gcatttgaca gaaattcctg gaggtattcc cacgaacacc acgaacctca ccctcaccat   360
taaccacata ccagacatct ccccagcgtc ctttcacaga ctggaccatc tggtagagat   420
cgatttcaga tgcaactgtg tacctattcc actggggtca aaaaacaaca tgtgcatcaa   480
gaggctgcag attaaaccca gaagctttag tggactcact tatttaaaat cccttttacct   540 ggatggaaac cagctactag agataccgca gggcctcccg cctagcttac agcttctcag   600
ccttgaggcc aacaacatct tttccatcag aaaagagaat ctaacagaac tggccaacat   660
agaaatactc tacctgggcc aaaactgtta ttatcgaaat ccttgttatg tttcatattc   720
aatagagaaa gatgccttcc taaacttgac aaagttaaaa gtgctctccc tgaaagataa   780
caatgtcaca gccgtcccta ctgttttgcc atctacttta acagaactat atctctacaa   840
```

-continued

```
caacatgatt gcaaaaatcc aagaagatga ttttaataac ctcaaccaat tacaaattct    900
tgacctaagt ggaaattgcc ctcgttgtta taatgcccca tttccttgtg cgccgtgtaa    960
aaataattct cccctacaga tccctgtaaa tgcttttgat gcgctgacag aattaaaagt   1020
tttacgtcta cacagtaact ctcttcagca tgtgccccca agatggttta agaacatcaa   1080
caaactccag gaactggatc tgtcccaaaa cttcttggcc aaagaaattg gggatgctaa   1140
atttctgcat tttctcccca gcctcatcca attggatctg tctttcaatt ttgaacttca   1200
ggtctatcgt gcatctatga atctatcaca agcattttct tcactgaaaa gcctgaaaat   1260
tctgcggatc agaggatatg tctttaaaga gttgaaaagc tttaacctct cgccattaca   1320
taatcttcaa aatcttgaag ttcttgatct tggcactaac tttataaaaa ttgctaacct   1380
cagcatgttt aaacaattta aaagactgaa agtcatagat ctttcagtga ataaaatatc   1440
accttcagga gattcaagtg aagttggctt ctgctcaaat gccagaactt ctgtagaaag   1500
ttatgaaccc caggtcctgg aacaattaca ttatttcaga tatgataagt atgcaaggag   1560
ttgcagattc aaaaacaaag aggcttcttt catgtctgtt aatgaaagct gctacaagta   1620
tgggcagacc ttggatctaa gtaaaaatag tatatttttt gtcaagtcct ctgattttca   1680
gcatctttct ttcctcaaat gcctgaatct gtcaggaaat ctcattagcc aaactcttaa   1740
tggcagtgaa ttccaacctt tagcagagct gagatatttg gacttctcca acaaccggct   1800
tgatttactc cattcaacag catttgaaga gcttcacaaa ctggaagttc tggatataag   1860
cagtaatagc cattattttc aatcagaagg aattactcat atgctaaact ttaccaagaa   1920
cctaaaggtt ctgcagaaac tgatgatgaa cgacaatgac atctcttcct ccaccagcag   1980
gaccatggag agtgagtctc ttagaactct ggaattcaga ggaaatcact tagatgtttt   2040
atggagagaa ggtgataaca gatacttaca attattcaag aatctgctaa aattagagga   2100
attagacatc tctaaaaatt ccctaagttt cttgccttct ggagttttg atggtatgcc   2160
tccaaatcta aagaatctct ctttggccaa aaatgggctc aaatctttca gttggaagaa   2220
actccagtgt ctaaagaacc tggaaacttt ggacctcagc cacaaccaac tgaccactgt   2280
ccctgagaga ttatccaact gttccagaag cctcaagaat ctgattctta agaataatca   2340
aatcaggagt ctgacgaagt attttctaca agatgccttc cagttgcgat atctggatct   2400
cagctcaaat aaaatccaga tgatccaaaa gaccagcttc ccagaaaatg tcctcaacaa   2460
tctgaagatg ttgctttttgc atcataatcg gtttctgtgc acctgtgatg ctgtgtggtt   2520
tgtctggtgg gttaaccata cggaggtgac tattccttac ctggccacag atgtgacttg   2580
tgtggggcca ggagcacaca agggccaaag tgtgatctcc ctggatctgt acacctgtga   2640
gttagatctg actaacctga ttctgttctc actttccata tctgtatctc tctttctcat   2700
ggtgatgatg acagcaagtc acctctattt ctgggatgtg tggtatattt accatttctg   2760
taaggccaag ataaaggggt atcagcgtct aatatcacca gactgttgct atgatgcttt   2820
tattgtgtat gacactaaag acccagctgt gaccgagtgg gttttggctg agctggtggc   2880
caaactggaa gacccaagag agaaacattt taatttatgt ctcgaggaaa gggactggtt   2940
accagggcag ccagttctgg aaaaccttc ccagagcata cagcttagca aaagacagt   3000
gtttgtgatg acagacaagt atgcaaagac tgaaaatttt aagatagcat tttacttgtc   3060
ccatcagagg ctcatggatg aaaaagttga tgtgattatc ttgatatttc ttgagaagcc   3120
cttttcagaag tccaagttcc tccagctccg gaaaaggctc tgtgggagtt ctgtccttga   3180
```

```
gtggccaaca aacccgcaag ctcacccata cttctggcag tgtctaaaga acgccctggc   3240
cacagacaat catgtggcct atagtcaggt gttcaaggaa acggtctagc ccttcttgc    3300 aaaacacaac tgcctagttt accaaggaga ggcctggctg tttaaattgt tttcatatat   3360
atcacaccaa aagcgtgttt tgaaattctt caagaaatga gattgcccat atttcagggg   3420
agccaccaac gtctgtcaca ggagttggaa agatggggtt tatataatgc atcaagtctt   3480
ctttcttatc tctctgtgtc tctatttgca cttgagtctc tcacctcagc tcctgtaaaa   3540
gagtggcaag taaaaaacat ggggctctga ttctcctgta attgtgataa ttaaatatac   3600
acacaatcat gacattgaga agaactgcat ttctacccct aaaaagtact ggtatataca   3660
gaaatagggt taaaaaaaac tcaagctctc tctatatgag accaaaatgt actagagtta   3720
gtttagtgaa ataaaaaacc agtcagctgg ccgggcatgg tggctcatgc ttgtaatccc   3780
agcactttgg gaggccgagg caggtggatc acgaggtcag gagtttgaga ccagtctggc   3840
caacatggtg aaaccccgtc tgtactaaaa atacaaaaat tagctgggcg tggtggtggg   3900
tgcctgtaat cccagctact gggaggctg aggcaggaga tcgcttgaa cccgggaggt     3960 ggaggtggca gtgagccgag atcacgccac tgcaatgcag cccgggcaac agagctagac   4020
tgtctcaaaa gaacaaaaaa aaaaaaacac aaaaaaactc agtcagcttc ttaaccaatt   4080
gcttccgtgt catccagggc cccattctgt gcagattgag tgtgggcacc acacaggtgg   4140
ttgctgcttc agtgcttcct gctcttttc cttgggcctg cttctgggtt ccataggaa     4200 acagtaagaa agaaagacac atccttacca taaatgcata tggtccacct acaaatagaa   4260
aaatatttaa atgatctgcc tttatacaaa gtgatattct ctacctttga taatttacct   4320
gcttaaatgt ttttatctgc actgcaaagt actgtatcca agtaaaaatt tcctcatcca   4380
atatctttca aactgttttg ttaactaatg ccatatattt gtaagtatct gcacacttga   4440
tacagcaacg ttagatggtt ttgatggtaa accctaaagg aggactccaa gagtgtgtat   4500
ttatttatag ttttatcaga gatgacaatt atttgaatgc caattatatg gattcctttc   4560
attttttgct ggaggatggg agaagaaacc aaagtttata gaccttcaca ttgagaaagc   4620
ttcagttttg aacttcagct atcagattca aaaacaacag aaagaaccaa gacattctta   4680
agatgcctgt actttcagct gggtataaat tcatgagttc aaagattgaa acctgaccaa   4740
tttgctttat ttcatggaag aagtgatcta caaaggtgtt tgtgccattt ggaaaacagc   4800
gtgcatgtgt tcaagcctta gattggcgat gtcgtatttt cctcacgtgt ggcaatgcca   4860
aaggctttac tttacctgtg agtacacact atatgaatta tttccaacgt acatttaatc   4920
aataagggtc acaaattccc aaatcaatct ctggaataaa tagagaggta attaaattgc   4980
tggagccaac ta                                                       4992
```

<210> SEQ ID NO 280
<211> LENGTH: 1049
<212> TYPE: PRT
<213> ORGANISM: Homo sapiens

<400> SEQUENCE: 280

Met Val Phe Pro Met Trp Thr Leu Lys Arg Gln Ile Leu Ile Leu Phe
1               5                   10                  15

Asn Ile Ile Leu Ile Ser Lys Leu Leu Gly Ala Arg Trp Phe Pro Lys
            20                  25                  30

Thr Leu Pro Cys Asp Val Thr Leu Asp Val Pro Lys Asn His Val Ile
        35                  40                  45

```
Val Asp Cys Thr Asp Lys His Leu Thr Glu Ile Pro Gly Gly Ile Pro
 50                  55                  60

Thr Asn Thr Thr Asn Leu Thr Leu Thr Ile Asn His Ile Pro Asp Ile
 65                  70                  75                  80

Ser Pro Ala Ser Phe His Arg Leu Asp His Leu Val Glu Ile Asp Phe
                 85                  90                  95

Arg Cys Asn Cys Val Pro Ile Pro Leu Gly Ser Lys Asn Asn Met Cys
                100                 105                 110

Ile Lys Arg Leu Gln Ile Lys Pro Arg Ser Phe Ser Gly Leu Thr Tyr
                115                 120                 125

Leu Lys Ser Leu Tyr Leu Asp Gly Asn Gln Leu Leu Glu Ile Pro Gln
130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser
                180                 185                 190

Tyr Ser Ile Glu Lys Asp Ala Phe Leu Asn Leu Thr Lys Leu Lys Val
        195                 200                 205

Leu Ser Leu Lys Asp Asn Asn Val Thr Ala Val Pro Thr Val Leu Pro
210                 215                 220

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Ala Pro
                260                 265                 270

Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
        290                 295                 300

Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
                325                 330                 335

His Phe Leu Pro Ser Leu Ile Gln Leu Asp Leu Ser Phe Asn Phe Glu
                340                 345                 350

Leu Gln Val Tyr Arg Ala Ser Met Asn Leu Ser Gln Ala Phe Ser Ser
        355                 360                 365

Leu Lys Ser Leu Lys Ile Leu Arg Ile Arg Gly Tyr Val Phe Lys Glu
370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
                420                 425                 430

Ile Ser Pro Ser Gly Asp Ser Ser Glu Val Gly Phe Cys Ser Asn Ala
                435                 440                 445

Arg Thr Ser Val Glu Ser Tyr Glu Pro Gln Val Leu Glu Gln Leu His
450                 455                 460

Tyr Phe Arg Tyr Asp Lys Tyr Ala Arg Ser Cys Arg Phe Lys Asn Lys
```

-continued

```
            465                 470                 475                 480
        Glu Ala Ser Phe Met Ser Val Asn Glu Ser Cys Tyr Lys Tyr Gly Gln
                        485                 490                 495
        Thr Leu Asp Leu Ser Lys Asn Ser Ile Phe Phe Val Lys Ser Ser Asp
                        500                 505                 510
        Phe Gln His Leu Ser Phe Leu Lys Cys Leu Asn Leu Ser Gly Asn Leu
                        515                 520                 525
        Ile Ser Gln Thr Leu Asn Gly Ser Glu Phe Gln Pro Leu Ala Glu Leu
                        530                 535                 540
        Arg Tyr Leu Asp Phe Ser Asn Asn Arg Leu Asp Leu Leu His Ser Thr
        545                 550                 555                 560
        Ala Phe Glu Glu Leu His Lys Leu Glu Val Leu Asp Ile Ser Ser Asn
                        565                 570                 575
        Ser His Tyr Phe Gln Ser Glu Gly Ile Thr His Met Leu Asn Phe Thr
                        580                 585                 590
        Lys Asn Leu Lys Val Leu Gln Lys Leu Met Met Asn Asp Asn Asp Ile
                        595                 600                 605
        Ser Ser Ser Thr Ser Arg Thr Met Glu Ser Glu Ser Leu Arg Thr Leu
                        610                 615                 620
        Glu Phe Arg Gly Asn His Leu Asp Val Leu Trp Arg Glu Gly Asp Asn
        625                 630                 635                 640
        Arg Tyr Leu Gln Leu Phe Lys Asn Leu Leu Lys Leu Glu Glu Leu Asp
                        645                 650                 655
        Ile Ser Lys Asn Ser Leu Ser Phe Leu Pro Ser Gly Val Phe Asp Gly
                        660                 665                 670
        Met Pro Pro Asn Leu Lys Asn Leu Ser Leu Ala Lys Asn Gly Leu Lys
                        675                 680                 685
        Ser Phe Ser Trp Lys Lys Leu Gln Cys Leu Lys Asn Leu Glu Thr Leu
                        690                 695                 700
        Asp Leu Ser His Asn Gln Leu Thr Thr Val Pro Glu Arg Leu Ser Asn
        705                 710                 715                 720
        Cys Ser Arg Ser Leu Lys Asn Leu Ile Leu Lys Asn Asn Gln Ile Arg
                        725                 730                 735
        Ser Leu Thr Lys Tyr Phe Leu Gln Asp Ala Phe Gln Leu Arg Tyr Leu
                        740                 745                 750
        Asp Leu Ser Ser Asn Lys Ile Gln Met Ile Gln Lys Thr Ser Phe Pro
                        755                 760                 765
        Glu Asn Val Leu Asn Asn Leu Lys Met Leu Leu Leu His His Asn Arg
                        770                 775                 780
        Phe Leu Cys Thr Cys Asp Ala Val Trp Phe Val Trp Trp Val Asn His
        785                 790                 795                 800
        Thr Glu Val Thr Ile Pro Tyr Leu Ala Thr Asp Val Thr Cys Val Gly
                        805                 810                 815
        Pro Gly Ala His Lys Gly Gln Ser Val Ile Ser Leu Asp Leu Tyr Thr
                        820                 825                 830
        Cys Glu Leu Asp Leu Thr Asn Leu Ile Leu Phe Ser Leu Ser Ile Ser
                        835                 840                 845
        Val Ser Leu Phe Leu Met Val Met Met Thr Ala Ser His Leu Tyr Phe
                        850                 855                 860
        Trp Asp Val Trp Tyr Ile Tyr His Phe Cys Lys Ala Lys Ile Lys Gly
        865                 870                 875                 880
        Tyr Gln Arg Leu Ile Ser Pro Asp Cys Cys Tyr Asp Ala Phe Ile Val
                        885                 890                 895
```

```
Tyr Asp Thr Lys Asp Pro Ala Thr Glu Trp Val Leu Ala Glu Leu
                900             905                 910

Val Ala Lys Leu Glu Asp Pro Arg Glu Lys His Phe Asn Leu Cys Leu
    915                 920                 925

Glu Glu Arg Asp Trp Leu Pro Gly Gln Pro Val Leu Glu Asn Leu Ser
930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
            965                 970                 975

Arg Leu Met Asp Glu Lys Val Asp Val Ile Ile Leu Ile Phe Leu Glu
            980                 985                 990

Lys Pro Phe Gln Lys Ser Lys Phe  Leu Gln Leu Arg Lys  Arg Leu Cys
            995                 1000                1005

Gly Ser  Ser Val Leu Glu Trp  Pro Thr Asn Pro Gln  Ala His Pro
    1010                1015                1020

Tyr Phe  Trp Gln Cys Leu Lys  Asn Ala Leu Ala Thr  Asp Asn His
    1025                1030                1035

Val Ala  Tyr Ser Gln Val Phe  Lys Glu Thr Val
    1040                1045

<210> SEQ ID NO 281
<211> LENGTH: 4216
<212> TYPE: DNA
<213> ORGANISM: Homo sapiens

<400> SEQUENCE: 281
agtttctctt ctcggccacc tcctgcatag agggtaccat tctgcgctgc tgcaagttac      60
ggaatgaaaa attagaacaa cagaaacatg gaaaacatgt tccttcagtc gtcaatgctg     120
acctgcattt tcctgctaat atctggttcc tgtgagttat cgcgccgaaga aaattttttct    180 agaagctatc cttgtgatga gaaaaagcaa aatgactcag ttattgcaga gtgcagcaat     240
cgtcgactac aggaagttcc ccaaacggtg ggcaaatatg tgacagaact agacctgtct     300
gataatttca tcacacacat aacgaatgaa tcatttcaag ggctgcaaaa tctcactaaa     360
ataaatctaa accacaaccc caatgtacag caccagaacg gaaatcccgg tatacaatca     420
aatggcttga atatcacaga cggggcattc ctcaacctaa aaaacctaag ggagttactg     480
cttgaagaca accagttacc ccaaatacccc tctggtttgc cagagtcttt gacagaactt     540
agtctaattc aaaacaatat atacaacata actaaagagg gcatttcaag acttataaac     600
ttgaaaaatc tctatttggc ctggaactgc tattttaaca agtttgcga gaaaactaac     660 atagaagatg gagtatttga aacgctgaca aatttggagt tgctatcact atcttttcaat   720 tctctttcac acgtgccacc caaactgcca agctccctac gcaaactttt tctgagcaac    780
acccagatca aatacattag tgaagaagat tcaagggat tgataaattt aacattacta    840
gatttaagcg ggaactgtcc gaggtgcttc aatgccccat ttccatgcgt gccttgtgat    900
ggtggtgctt caattaatat agatcgtttt gcttttcaaa acttgacccca acttcgatac   960 ctaaacctct ctagcacttc cctcaggaag attaatgctg cctggtttaa aaatatgcct  1020
catctgaagg tgctggatct tgaattcaac tatttagtgg gagaaatagc ctctggggca  1080 ttttaacga tgctgccccg cttagaaata cttgacttgt cttttaacta tataaaggg   1140 agttatccac agcatattaa tatttccaga aacttctcta aacttttgtc tctacgggca  1200
```

```
ttgcatttaa gaggttatgt gttccaggaa ctcagagaag atgatttcca gcccctgatg    1260
cagcttccaa actatcgac tatcaacttg ggtattaatt ttattaagca aatcgatttc    1320 aaactttcc aaaatttctc caatctggaa attatttact tgtcagaaaa cagaatatca    1380
ccgttggtaa aagatacccg gcagagttat gcaaatagtt cctcttttca acgtcatatc    1440
cggaaacgac gctcaacaga ttttgagttt gacccacatt cgaactttta tcatttcacc    1500
cgtcctttaa taaagccaca atgtgctgct tatggaaaag ccttagattt aagcctcaac    1560
agtattttct tcattgggcc aaaccaattt gaaaatcttc ctgacattgc ctgtttaaat    1620
ctgtctgcaa atagcaatgc tcaagtgtta agtggaactg aattttcagc cattcctcat    1680
gtcaaatatt tggatttgac aaacaataga ctagactttg ataatgctag tgctcttact    1740
gaattgtccg acttggaagt tctagatctc agctataatt cacactattt cagaatagca    1800
ggcgtaacac atcatctaga atttattcaa aatttcacaa atctaaaagt tttaaacttg    1860
agccacaaca acatttatac tttaacagat aagtataacc tggaaagcaa gtccctggta    1920
gaattagttt tcagtggcaa tcgccttgac attttgtgga atgatgatga caacaggtat    1980
atctccattt tcaaaggtct caagaatctg acacgtctgg atttatccct taataggctg    2040
aagcacatcc caaatgaagc attccttaat ttgccagcga gtctcactga actacatata    2100
aatgataata tgttaaagtt ttttaactgg acattactcc agcagtttcc tcgtctcgag    2160
ttgcttgact tacgtggaaa caaactactc tttttaactg atagcctatc tgactttaca    2220
tcttcccttc ggacactgct gctgagtcat aacaggattt cccacctacc ctctggcttt    2280 cttttctgaag tcagtagtct gaagcacctc gatttaagtt ccaatctgct aaaaacaatc    2340
aacaaatccg cacttgaaac taagaccacc accaaattat ctatgttgga actacacgga    2400
aacccctttg aatgcacctg tgacattgga gatttccgaa gatggatgga tgaacatctg    2460
aatgtcaaaa ttcccagact ggtagatgtc atttgtgcca gtcctgggga tcaaagaggg    2520
aagagtattg tgagtctgga gctaacaact tgtgtttcag atgtcactgc agtgatatta    2580 ttttcttca cgttctttat caccaccatg gttatgttgg ctgccctggc tcaccatttg    2640
ttttactggg atgtttggtt tatatataat gtgtgtttag ctaaggtaaa aggctacagg    2700
tctctttcca catcccaaac tttctatgat gcttacattt cttatgacac caaagatgcc    2760
tctgttactg actgggtgat aaatgagctg cgctaccacc ttgaagagag ccagacaaa    2820 aacgttctcc tttgtctaga ggagagggat tgggatccgg gattggccat catcgacaac    2880
ctcatgcaga gcatcaacca aagcaagaaa acagtatttg ttttaaccaa aaaatatgca    2940
aaaagctgga acttaaaac agcttttac ttggctttgc agaggctaat ggatgagaac    3000
atggatgtga ttatatttat cctgctggag ccagtgttac agcattctca gtatttgagg    3060
ctacggcagc ggatctgtaa gagctccatc ctccagtggc ctgacaaccc gaaggcagaa    3120
ggcttgtttt ggcaaactct gagaaatgtg gtcttgactg aaaatgattc acggtataac    3180
aatatgtatg tcgattccat taagcaatac taactgacgt taagtcatga tttcgcgcca    3240
taataaagat gcaaggaat gacatttctg tattagttat ctattgctat gtaacaaatt    3300
atcccaaaac ttagtggttt aaaacaacac atttgctggc ccacagtttt tgagggtcag    3360
gagtccaggc ccagcataac tgggtcctct gctcagggtg tctcagaggc tgcaatgtag    3420
gtgttcacca gagacatagg catcactggg gtcacactca tgtggttgtt ttctggattc    3480
aattcctcct gggctattgg ccaaaggcta tactcatgta agccatgcga gcctctccca    3540
caaggcagct tgcttcatca gagctagcaa aaaagagagg ttgctagcaa gatgaagtca    3600
```

-continued

```
caatcttttg taatcgaatc aaaaaagtga tatctcatca ctttggccat attctatttg    3660
ttagaagtaa accacaggtc ccaccagctc catgggagtg accacctcag tccagggaaa    3720
acagctgaag accaagatgg tgagctctga ttgcttcagt tggtcatcaa ctattttccc    3780
ttgactgctg tcctgggatg gcctgctatc ttgatgatag attgtgaata tcaggaggca    3840
gggatcactg tggaccatct tagcagttga cctaacacat cttcttttca atatctaaga    3900
acttttgcca ctgtgactaa tggtcctaat attaagctgt tgtttatatt tatcatatat    3960
ctatggctac atggttatat tatgctgtgg ttgcgttcgg ttttatttac agttgctttt    4020
acaaatattt gctgtaacat ttgacttcta aggtttagat gccatttaag aactgagatg    4080
gatagctttt aaagcatctt ttacttctta ccattttta aaagtatgca gctaaattcg     4140
aagcttttgg tctatattgt taattgccat tgctgtaaat cttaaaatga atgaataaaa    4200
atgtttcatt ttacaa                                                    4216
```

<210> SEQ ID NO 282
<211> LENGTH: 1041
<212> TYPE: PRT
<213> ORGANISM: Homo sapiens

<400> SEQUENCE: 282

```
Met Glu Asn Met Phe Leu Gln Ser Ser Met Leu Thr Cys Ile Phe Leu
1               5                   10                  15

Leu Ile Ser Gly Ser Cys Glu Leu Cys Ala Glu Glu Asn Phe Ser Arg
            20                  25                  30

Ser Tyr Pro Cys Asp Glu Lys Lys Gln Asn Asp Ser Val Ile Ala Glu
        35                  40                  45

Cys Ser Asn Arg Arg Leu Gln Glu Val Pro Gln Thr Val Gly Lys Tyr
    50                  55                  60

Val Thr Glu Leu Asp Leu Ser Asp Asn Phe Ile Thr His Ile Thr Asn
65                  70                  75                  80

Glu Ser Phe Gln Gly Leu Gln Asn Leu Thr Lys Ile Asn Leu Asn His
                85                  90                  95

Asn Pro Asn Val Gln His Gln Asn Gly Asn Pro Gly Ile Gln Ser Asn
            100                 105                 110

Gly Leu Asn Ile Thr Asp Gly Ala Phe Leu Asn Leu Lys Asn Leu Arg
        115                 120                 125

Glu Leu Leu Leu Glu Asp Asn Gln Leu Pro Gln Ile Pro Ser Gly Leu
    130                 135                 140

Pro Glu Ser Leu Thr Glu Leu Ser Leu Ile Gln Asn Asn Ile Tyr Asn
145                 150                 155                 160

Ile Thr Lys Glu Gly Ile Ser Arg Leu Ile Asn Leu Lys Asn Leu Tyr
                165                 170                 175

Leu Ala Trp Asn Cys Tyr Phe Asn Lys Val Cys Glu Lys Thr Asn Ile
            180                 185                 190

Glu Asp Gly Val Phe Glu Thr Leu Thr Asn Leu Glu Leu Leu Ser Leu
        195                 200                 205

Ser Phe Asn Ser Leu Ser His Val Pro Pro Lys Leu Pro Ser Ser Leu
    210                 215                 220

Arg Lys Leu Phe Leu Ser Asn Thr Gln Ile Lys Tyr Ile Ser Glu Glu
225                 230                 235                 240

Asp Phe Lys Gly Leu Ile Asn Leu Thr Leu Leu Asp Leu Ser Gly Asn
                245                 250                 255
```

-continued

Cys Pro Arg Cys Phe Asn Ala Pro Phe Pro Cys Val Pro Cys Asp Gly
                260                 265                 270

Gly Ala Ser Ile Asn Ile Asp Arg Phe Ala Phe Gln Asn Leu Thr Gln
            275                 280                 285

Leu Arg Tyr Leu Asn Leu Ser Ser Thr Ser Leu Arg Lys Ile Asn Ala
        290                 295                 300

Ala Trp Phe Lys Asn Met Pro His Leu Lys Val Leu Asp Leu Glu Phe
305                 310                 315                 320

Asn Tyr Leu Val Gly Glu Ile Ala Ser Gly Ala Phe Leu Thr Met Leu
                325                 330                 335

Pro Arg Leu Glu Ile Leu Asp Leu Ser Phe Asn Tyr Ile Lys Gly Ser
            340                 345                 350

Tyr Pro Gln His Ile Asn Ile Ser Arg Asn Phe Ser Lys Leu Leu Ser
        355                 360                 365

Leu Arg Ala Leu His Leu Arg Gly Tyr Val Phe Gln Glu Leu Arg Glu
    370                 375                 380

Asp Asp Phe Gln Pro Leu Met Gln Leu Pro Asn Leu Ser Thr Ile Asn
385                 390                 395                 400

Leu Gly Ile Asn Phe Ile Lys Gln Ile Asp Phe Lys Leu Phe Gln Asn
                405                 410                 415

Phe Ser Asn Leu Glu Ile Ile Tyr Leu Ser Glu Asn Arg Ile Ser Pro
            420                 425                 430

Leu Val Lys Asp Thr Arg Gln Ser Tyr Ala Asn Ser Ser Phe Gln
        435                 440                 445

Arg His Ile Arg Lys Arg Ser Thr Asp Phe Glu Phe Asp Pro His
    450                 455                 460

Ser Asn Phe Tyr His Phe Thr Arg Pro Leu Ile Lys Pro Gln Cys Ala
465                 470                 475                 480

Ala Tyr Gly Lys Ala Leu Asp Leu Ser Leu Asn Ser Ile Phe Phe Ile
                485                 490                 495

Gly Pro Asn Gln Phe Glu Asn Leu Pro Asp Ile Ala Cys Leu Asn Leu
            500                 505                 510

Ser Ala Asn Ser Asn Ala Gln Val Leu Ser Gly Thr Glu Phe Ser Ala
        515                 520                 525

Ile Pro His Val Lys Tyr Leu Asp Leu Thr Asn Asn Arg Leu Asp Phe
    530                 535                 540

Asp Asn Ala Ser Ala Leu Thr Glu Leu Ser Asp Leu Glu Val Leu Asp
545                 550                 555                 560

Leu Ser Tyr Asn Ser His Tyr Phe Arg Ile Ala Gly Val Thr His His
                565                 570                 575

Leu Glu Phe Ile Gln Asn Phe Thr Asn Leu Lys Val Leu Asn Leu Ser
            580                 585                 590

His Asn Asn Ile Tyr Thr Leu Thr Asp Lys Tyr Asn Leu Glu Ser Lys
        595                 600                 605

Ser Leu Val Glu Leu Val Phe Ser Gly Asn Arg Leu Asp Ile Leu Trp
    610                 615                 620

Asn Asp Asp Asp Asn Arg Tyr Ile Ser Ile Phe Lys Gly Leu Lys Asn
625                 630                 635                 640

Leu Thr Arg Leu Asp Leu Ser Leu Asn Arg Leu Lys His Ile Pro Asn
                645                 650                 655

Glu Ala Phe Leu Asn Leu Pro Ala Ser Leu Thr Glu Leu His Ile Asn
            660                 665                 670

Asp Asn Met Leu Lys Phe Phe Asn Trp Thr Leu Leu Gln Gln Phe Pro

```
                675                 680                 685
Arg Leu Glu Leu Leu Asp Leu Arg Gly Asn Lys Leu Leu Phe Leu Thr
690                 695                 700

Asp Ser Leu Ser Asp Phe Thr Ser Ser Leu Arg Thr Leu Leu Leu Ser
705                 710                 715                 720

His Asn Arg Ile Ser His Leu Pro Ser Gly Phe Leu Ser Glu Val Ser
                725                 730                 735

Ser Leu Lys His Leu Asp Leu Ser Ser Asn Leu Leu Lys Thr Ile Asn
            740                 745                 750

Lys Ser Ala Leu Glu Thr Lys Thr Thr Thr Lys Leu Ser Met Leu Glu
        755                 760                 765

Leu His Gly Asn Pro Phe Glu Cys Thr Cys Asp Ile Gly Asp Phe Arg
770                 775                 780

Arg Trp Met Asp Glu His Leu Asn Val Lys Ile Pro Arg Leu Val Asp
785                 790                 795                 800

Val Ile Cys Ala Ser Pro Gly Asp Gln Arg Gly Lys Ser Ile Val Ser
                805                 810                 815

Leu Glu Leu Thr Thr Cys Val Ser Asp Val Thr Ala Val Ile Leu Phe
            820                 825                 830

Phe Phe Thr Phe Phe Ile Thr Thr Met Val Met Leu Ala Ala Leu Ala
        835                 840                 845

His His Leu Phe Tyr Trp Asp Val Trp Phe Ile Tyr Asn Val Cys Leu
850                 855                 860

Ala Lys Val Lys Gly Tyr Arg Ser Leu Ser Thr Ser Gln Thr Phe Tyr
865                 870                 875                 880

Asp Ala Tyr Ile Ser Tyr Asp Thr Lys Asp Ala Ser Val Thr Asp Trp
                885                 890                 895

Val Ile Asn Glu Leu Arg Tyr His Leu Glu Glu Ser Arg Asp Lys Asn
            900                 905                 910

Val Leu Leu Cys Leu Glu Glu Arg Asp Trp Asp Pro Gly Leu Ala Ile
        915                 920                 925

Ile Asp Asn Leu Met Gln Ser Ile Asn Gln Ser Lys Lys Thr Val Phe
930                 935                 940

Val Leu Thr Lys Lys Tyr Ala Lys Ser Trp Asn Phe Lys Thr Ala Phe
945                 950                 955                 960

Tyr Leu Ala Leu Gln Arg Leu Met Asp Glu Asn Met Asp Val Ile Ile
                965                 970                 975

Phe Ile Leu Leu Glu Pro Val Leu Gln His Ser Gln Tyr Leu Arg Leu
            980                 985                 990

Arg Gln Arg Ile Cys Lys Ser Ser Ile Leu Gln Trp Pro Asp Asn Pro
        995                 1000                1005

Lys Ala Glu Gly Leu Phe Trp Gln Thr Leu Arg Asn Val Val Leu
        1010                1015                1020

Thr Glu Asn Asp Ser Arg Tyr Asn Asn Met Tyr Val Asp Ser Ile
        1025                1030                1035

Lys Gln Tyr
        1040

<210> SEQ ID NO 283
<211> LENGTH: 3922
<212> TYPE: DNA
<213> ORGANISM: Homo sapiens

<400> SEQUENCE: 283
```

| | |
|---|---|
| ggaggtcttg tttccggaag atgttgcaag gctgtggtga aggcaggtgc agcctagcct | 60 |
| cctgctcaag ctacaccctg gccctccacg catgaggccc tgcagaactc tggagatggt | 120 |
| gcctacaagg gcagaaaagg acaagtcggc agccgctgtc ctgagggcac cagctgtggt | 180 |
| gcaggagcca agacctgagg gtggaagtgt cctcttagaa tggggagtgc ccagcaaggt | 240 |
| gtacccgcta ctggtgctat ccagaattcc catctctccc tgctctctgc ctgagctctg | 300 |
| ggccttagct cctccctggg cttggtagag acaggtgtg aggccctcat gggatgtagg | 360 |
| ctgtctgaga ggggagtgga agaggaagg ggtgaaggag ctgtctgcca tttgactatg | 420 |
| caaatggcct ttgactcatg ggaccctgtc ctcctcactg ggggcagggt ggagtggagg | 480 |
| gggagctact aggctggtat aaaaatctta cttcctctat tctctgagcc gctgctgccc | 540 |
| ctgtgggaag ggacctcgag tgtgaagcat ccttccctgt agctgctgtc cagtctgccc | 600 |
| gccagaccct ctggagaagc ccctgccccc cagcatgggt ttctgccgca gcgccctgca | 660 |
| cccgctgtct ctcctggtgc aggccatcat gctggccatg accctggccc tgggtacctt | 720 |
| gcctgccttc ctaccctgtg agctccagcc ccacggcctg gtgaactgca actggctgtt | 780 |
| cctgaagtct gtgccccact tctccatggc agcaccccgt ggcaatgtca ccagcctttc | 840 |
| cttgtcctcc aaccgcatcc accacctcca tgattctgac tttgcccacc tgcccagcct | 900 |
| gcggcatctc aacctcaagt ggaactgccc gccggttggc ctcagcccca tgcacttccc | 960 |
| ctgccacatg accatcgagc ccagcacctt cttggctgtg cccacccctgg aagagctaaa | 1020 |
| cctgagctac aacaacatca tgactgtgcc tgcgctgccc aaatccctca tatccctgtc | 1080 |
| cctcagccat accaacatcc tgatgctaga ctctgccagc ctcgccggcc tgcatgccct | 1140 |
| gcgcttccta ttcatggacg gcaactgtta ttacaagaac cctgcaggc aggcactgga | 1200 |
| ggtggcccccg ggtgccctcc ttggcctggg caacctcacc cacctgtcac tcaagtacaa | 1260 |
| caacctcact gtggtgcccc gcaacctgcc ttccagcctg gagtatctgc tgttgtccta | 1320 |
| caaccgcatc gtcaaactgg cgcctgagga cctggccaat ctgaccgccc tgcgtgtgct | 1380 |
| cgatgtgggc ggaaattgcc gccgctgcga ccacgctccc aaccctgca tggagtgccc | 1440 |
| tcgtcacttc ccccagctac atcccgatac cttcagccac ctgagccgtc ttgaaggcct | 1500 |
| ggtgttgaag acagttctc tctcctggct gaatgccagt tggttccgtg ggctgggaaa | 1560 |
| cctccgagtg ctggacctga gtgagaactt cctctacaaa tgcatcacta aaaccaaggc | 1620 |
| cttccagggc ctaacacagc tgcgcaagct taacctgtcc ttcaattacc aaaagagggt | 1680 |
| gtcctttgcc cacctgtctc tggcccctcc cttcgggagc ctggtcgccc tgaaggagct | 1740 |
| ggacatgcac ggcatcttct tccgctcact cgatgagacc acgctccggc cactggcccg | 1800 |
| cctgcccatg ctccagactc tgcgtctgca gatgaacttc atcaaccagg cccagctcgg | 1860 |
| catcttcagg gccttccctg cctgcgcta cgtggacctg tcggacaacc gcatcagcgg | 1920 |
| agcttcggag ctgacagcca ccatggggga ggcagatgga ggggagaagg tctggctgca | 1980 |
| gcctggggac cttgctccgg ccccagtgga cactcccagc tctgaagact tcaggcccaa | 2040 |
| ctgcagcacc ctcaacttca cccttggatct gtcacggaac aacctggtga ccgtgcagcc | 2100 |
| ggagatgttt gccagctct cgcacctgca gtgcctgcgc ctgagccaca actgcatctc | 2160 |
| gcaggcagtc aatggctccc agttcctgcc gctgaccggt ctgcaggtgc tagacctgtc | 2220 |
| ccacaataag ctggacctct accacgagca ctcattcacg gagctaccgc gactggaggc | 2280 |
| cctggacctc agctacaaca gccagccctt tggcatgcag ggcgtgggcc acaacttcag | 2340 |
| cttcgtggct cacctgcgca ccctgcgcca cctcagcctg gcccacaaca acatccacag | 2400 |

-continued

```
ccaagtgtcc cagcagctct gcagtacgtc gctgcgggcc ctggacttca gcggcaatgc   2460
actgggccat atgtgggccg agggagacct ctatctgcac ttcttccaag gcctgagcgg   2520
tttgatctgg ctggacttgt cccagaaccg cctgcacacc ctcctgcccc aaaccctgcg   2580
caacctcccc aagagcctac aggtgctgcg tctccgtgac aattacctgg ccttctttaa   2640
gtggtggagc ctccacttcc tgcccaaact ggaagtcctc gacctggcag aaaccagct    2700 gaaggccctg accaatggca gcctgcctgc tggcacccgg ctccggaggc tggatgtcag   2760
ctgcaacagc atcagcttcg tggcccccgg cttcttttcc aaggccaagg agctgcgaga   2820
gctcaaccct agcgccaacg ccctcaagac agtggaccac tcctggtttg gcccctggc    2880 gagtgccctg caaatactag atgtaagcgc caaccctctg cactgcgcct gtggggcggc   2940
ctttatggac ttcctgctgg aggtgcaggc tgccgtgccc ggtctgccca gccgggtgaa   3000
gtgtggcagt ccgggccagc tccagggcct cagcatcttt gcacaggacc tgcgcctctg   3060
cctggatgag gccctctcct gggactgttt cgccctctcg ctgctggctg tggctctggg   3120
cctgggtgtg cccatgctgc atcacctctg tggctgggac ctctggtact gcttccacct   3180
gtgcctggcc tggcttccct ggcgggggcg gcaaagtggg cgagatgagg atgccctgcc   3240
ctacgatgcc ttcgtggtct tcgacaaaac gcagagcgca gtggcagact gggtgtacaa   3300
cgagcttcgg gggcagctgg aggagtgccg tgggcgctgg gcactccgcc tgtgcctgga   3360
ggaacgcgac tggctgcctg caaaaccct ctttgagaac ctgtgggcct cggtctatgg    3420
cagccgcaag acgctgtttg tgctggccca cacggaccgg gtcagtggtc tcttgcgcgc   3480
cagcttcctg ctggcccagc agcgcctgct ggaggaccgc aaggacgtcg tggtgctggt   3540
gatcctgagc cctgacggcc gccgctcccg ctacgtgcgg ctgcgccagc gcctctgccg   3600
ccagagtgtc ctcctctggc cccaccagcc cagtggtcag cgcagcttct gggcccagct   3660
gggcatggcc ctgaccaggg acaaccacca cttctataac cggaacttct gccagggacc   3720
cacggccgaa tagccgtgag ccggaatcct gcacggtgcc acctccacac tcacctcacc   3780
tctgcctgcc tggtctgacc ctcccctgct cgcctccctc accccacacc tgacacagag   3840
caggcactca ataaatgcta ccgaaggcta aaaaaaaaa aaaaaaaaa aaaaaaaaa      3900 aaaaaaaaaa aaaaaaaaaa aa                                           3922
```

<210> SEQ ID NO 284
<211> LENGTH: 1032
<212> TYPE: PRT
<213> ORGANISM: Homo sapiens

<400> SEQUENCE: 284

Met Gly Phe Cys Arg Ser Ala Leu His Pro Leu Ser Leu Val Gln
1               5                   10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
    50                  55                  60

Val Thr Ser Leu Ser Leu Ser Ser Asn Arg Ile His His Leu His Asp
65                  70                  75                  80

Ser Asp Phe Ala His Leu Pro Ser Leu Arg His Leu Asn Leu Lys Trp
                85                  90                  95

-continued

| | | | | | | | | | | | |
|---|---|---|---|---|---|---|---|---|---|---|---|
|Asn|Cys|Pro|Pro 100|Val|Gly|Leu|Ser|Pro 105|Met|His|Phe|Pro|Cys 110|His|Met|

Asn Cys Pro Pro Val Gly Leu Ser Pro Met His Phe Pro Cys His Met
              100                 105               110

Thr Ile Glu Pro Ser Thr Phe Leu Ala Val Pro Thr Leu Glu Glu Leu
            115                 120             125

Asn Leu Ser Tyr Asn Asn Ile Met Thr Val Pro Ala Leu Pro Lys Ser
        130                 135             140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
            180                 185                 190

Gly Ala Leu Leu Gly Leu Gly Asn Leu Thr His Leu Ser Leu Lys Tyr
            195                 200                 205

Asn Asn Leu Thr Val Val Pro Arg Asn Leu Pro Ser Ser Leu Glu Tyr
        210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
            260                 265                 270

Pro Gln Leu His Pro Asp Thr Phe Ser His Leu Ser Arg Leu Glu Gly
            275                 280                 285

Leu Val Leu Lys Asp Ser Ser Leu Ser Trp Leu Asn Ala Ser Trp Phe
            290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
            325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
            355                 360                 365

Leu Asp Met His Gly Ile Phe Phe Arg Ser Leu Asp Glu Thr Thr Leu
            370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
            405                 410                 415

Leu Arg Tyr Val Asp Leu Ser Asp Asn Arg Ile Ser Gly Ala Ser Glu
            420                 425                 430

Leu Thr Ala Thr Met Gly Glu Ala Asp Gly Gly Glu Lys Val Trp Leu
            435                 440                 445

Gln Pro Gly Asp Leu Ala Pro Ala Pro Val Asp Thr Pro Ser Ser Glu
            450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
            485                 490                 495

His Leu Gln Cys Leu Arg Leu Ser His Asn Cys Ile Ser Gln Ala Val
            500                 505                 510

Asn Gly Ser Gln Phe Leu Pro Leu Thr Gly Leu Gln Val Leu Asp Leu

-continued

```
            515                 520                 525
Ser His Asn Lys Leu Asp Leu Tyr His Glu His Ser Phe Thr Glu Leu
530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser
                580                 585                 590

Gln Gln Leu Cys Ser Thr Ser Leu Arg Ala Leu Asp Phe Ser Gly Asn
            595                 600                 605

Ala Leu Gly His Met Trp Ala Glu Gly Asp Leu Tyr Leu His Phe Phe
610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
                660                 665                 670

Leu His Phe Leu Pro Lys Leu Glu Val Leu Asp Leu Ala Gly Asn Gln
            675                 680                 685

Leu Lys Ala Leu Thr Asn Gly Ser Leu Pro Ala Gly Thr Arg Leu Arg
690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                725                 730                 735

Leu Lys Thr Val Asp His Ser Trp Phe Gly Pro Leu Ala Ser Ala Leu
                740                 745                 750

Gln Ile Leu Asp Val Ser Ala Asn Pro Leu His Cys Ala Cys Gly Ala
            755                 760                 765

Ala Phe Met Asp Phe Leu Leu Glu Val Gln Ala Val Pro Gly Leu
770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815

Asp Cys Phe Ala Leu Ser Leu Leu Ala Val Ala Leu Gly Leu Gly Val
                820                 825                 830

Pro Met Leu His His Leu Cys Gly Trp Asp Leu Trp Tyr Cys Phe His
            835                 840                 845

Leu Cys Leu Ala Trp Leu Pro Trp Arg Gly Arg Gln Ser Gly Arg Asp
850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
                900                 905                 910

Trp Leu Pro Gly Lys Thr Leu Phe Glu Asn Leu Trp Ala Ser Val Tyr
            915                 920                 925

Gly Ser Arg Lys Thr Leu Phe Val Leu Ala His Thr Asp Arg Val Ser
930                 935                 940
```

```
Gly Leu Leu Arg Ala Ser Phe Leu Leu Ala Gln Gln Arg Leu Leu Glu
945                 950                 955                 960

Asp Arg Lys Asp Val Val Leu Val Ile Leu Ser Pro Asp Gly Arg
            965                 970                 975

Arg Ser Arg Tyr Val Arg Leu Arg Gln Arg Leu Cys Arg Gln Ser Val
            980                 985                 990

Leu Leu Trp Pro His Gln Pro Ser Gly Gln Arg Ser Phe Trp Ala Gln
            995                 1000                1005

Leu Gly Met Ala Leu Thr Arg Asp Asn His His Phe Tyr Asn Arg
    1010                1015                1020

Asn Phe Cys Gln Gly Pro Thr Ala Glu
    1025                1030

<210> SEQ ID NO 285
<211> LENGTH: 3990
<212> TYPE: DNA
<213> ORGANISM: Homo sapiens

<400> SEQUENCE: 285
agccaattct gaccgtgtca acgaatcatc cacgcacctg cagctctgct gagagagtgc    60
aagccgtggg aattcagcag ctgaatatca agacctttga attcaacaag aagttaagac   120
atttatagtt gtctaacaac agactgaaga ttgtggcttg gtattcactg gcaggtttca   180
gacatttaga tctttctttt aatgactaac accatgccta tctgtggaga agctggcaac   240
atgtcacacc tggaaattgt ttttcaacat taatactatt atttggcagt aatccagatt   300
gcttttgcca ccaacctgaa gacatataga ggcagaagga caggaataat tctatttgtt   360
tcctgttttg aaacttccat ctgtaaggct atcaaaagga gatgtgagag agggtattga   420
gtctggcctg acaatgcagt tcttaaacca aggtccatt atgcttctcc tctctgagaa    480
tcctgactta cctcaacaac ggagacatgg cacagtagcc agcttggaga cttctcagcc   540
aatgctctga gatcaagtcg aagacccaat atacagggtt ttgagctcat cttcatcatt   600
catatgagga aataagtggt aaaatccttg gaaatacaat gagactcatc agaaacattt   660
acatattttg tagtattgtt atgacagcag agggtgatgc tccagagctg ccagaagaaa   720
gggaactgat gaccaactgc tccaacatgt ctctaagaaa ggttcccgca gacttgaccc   780
cagccacaac gacactggat ttatcctata acctcctttt tcaactccag agttcagatt   840
ttcattctgt ctccaaactg agagttttga ttctatgcca taacagaatt caacagctgg   900
atctcaaaac ctttgaattc aacaaggagt taagatattt agatttgtct aataacagac   960
tgaagagtgt aacttggtat ttactggcag gtctcaggta tttagatctt tcttttaatg  1020
actttgacac catgcctatc tgtgaggaag ctggcaacat gtcacacctg gaaatcctag  1080
gtttgagtgg ggcaaaaata caaaaatcag atttccagaa aattgctcat ctgcatctaa  1140
atactgtctt cttaggattc agaactcttc ctcattatga agaaggtagc ctgcccatct  1200
taaacacaac aaaaactgca cattgtttta caatggacac aaatttctgg ttctttttgc  1260
gtgatggaat caagacttca aaaatattag aaatgacaaa tatagatggc aaaagccaat  1320
ttgtaagtta tgaaatgcaa cgaaatctta gtttagaaaa tgctaagaca tcggttctat  1380
tgcttaataa agttgattta ctctgggacg acctttttcct tatcttacaa tttgtttggc  1440
atacatcagt ggaacacttt cagatccgaa atgtgacttt tggtggtaag gcttatcttg  1500
accacaattc atttgactac tcaaatactg taatgagaac tataaaattg gagcatgtac  1560
```

```
atttcagagt gttttacatt caacaggata aaatctattt gcttttgacc aaaatggaca    1620
tagaaaacct gacaatatca aatgcacaaa tgccacacat gcttttcccg aattatccta    1680
cgaaattcca atatttaaat tttgccaata atatcttaac agacgagttg tttaaaagaa    1740
ctatccaact gcctcacttg aaaactctca ttttgaatgg caataaactg agacacttt     1800
ctttagtaag ttgctttgct aacaacacac ccttggaaca cttggatctg agtcaaaatc    1860
tattacaaca taaaaatgat gaaaattgct catggccaga aactgtggtc aatatgaatc    1920
tgtcatacaa taaattgtct gattctgtct tcaggtgctt gcccaaaagt attcaaatac    1980
ttgacctaaa aataaccaa atccaaactg tacctaaaga gactattcat ctgatggcct     2040
tacgagaact aaatattgca tttaattttc taactgatct ccctggatgc agtcatttca    2100
gtagactttc agttctgaac attgaaatga acttcattct cagcccatct ctggattttg    2160
ttcagagctg ccaggaagtt aaaactctaa atgcgggaag aaatccattc cggtgtacct    2220
gtgaattaaa aaatttcatt cagcttgaaa catattcaga ggtcatgatg gttggatggt    2280
cagattcata cacctgtgaa tacccttttaa acctaagggg aactaggtta aaagacgttc    2340
atctccacga attatcttgc aacacagctc tgttgattgt caccattgtg gttattatgc    2400
tagttctggg gttggctgtg gccttctgct gtctccactt tgatctgccc tggtatctca    2460
ggatgctagg tcaatgcaca caaacatggc acagggttag gaaaacaacc caagaacaac    2520
tcaagagaaa tgtccgattc cacgcattta tttcatacag tgaacatgat tctctgtggg    2580
tgaagaatga attgatcccc aatctagaga aggaagatgg ttctatcttg atttgccttt    2640
atgaaagcta ctttgaccct ggcaaaagca ttagtgaaaa tattgtaagc ttcattgaga    2700
aaagctataa gtccatcttt gttttgtctc ccaactttgt ccagaatgag tggtgccatt    2760
atgaattcta ctttgcccac cacaatctct tccatgaaaa ttctgatcat ataattctta    2820
tcttactgga acccattcca ttctattgca ttcccaccag gtatcataaa ctgaaagctc    2880
tcctggaaaa aaaagcatac ttggaatggc ccaaggatag gcgtaaatgt gggcttttct    2940
gggcaaacct tcgagctgct attaatgtta atgtattagc caccagagaa atgtatgaac    3000
tgcagacatt cacagagtta aatgaagagt ctcgaggttc tacaatctct ctgatgagaa    3060
cagattgtct ataaaatccc acagtccttg ggaagttggg gaccacatac actgttggga    3120
tgtacattga tacaaccttt atgatggcaa tttgacaata tttattaaaa taaaaaatgg    3180
ttattccctt catatcagtt tctagaagga tttctaagaa tgtatcctat agaaacacct    3240
tcacaagttt ataagggctt atggaaaaag gtgttcatcc caggattgtt tataatcatg    3300
aaaaatgtgg ccaggtgcag tggctcactc ttgtaatccc agcactatgg gaggccaagg    3360
tgggtgaccc acgaggtcaa gagatggaga ccatcctggc caacatgtg aaaccctgtc     3420
tctactaaaa atacaaaaat tagctgggcg tgatggtgca cgcctgtagt cccagctact    3480
tgggaggctg aggcaggaga atcgcttgaa cccgggaggt ggcagttgca gtgagctgag    3540
atcgagccac tgcactccag cctggtgaca gagcgagact ccatctcaaa aaaagaaaa    3600
aaaaaaaga aaaaatgga aacatcctc atggccacaa ataaggtct aattcaataa       3660
attatagtac attaatgtaa tataatatta catgccacta aaaagaataa ggtagctgta    3720
tatttcctgg tatggaaaaa acatattaat atgttataaa ctattaggtt ggtgcaaaac    3780
taattgtggt ttttgccatt gaatggcat tgaaataaaa gtgtaaagaa atctatacca     3840
gatgtagtaa cagtggtttg ggtctgggag gttggattac agggagcatt tgatttctat    3900
gttgtgtatt tctataatgt ttgaattgtt tagaatgaat ctgtatttct tttataagta    3960
```

-continued gaaaaaaaat aaagatagtt tttacagcct                    3990

<210> SEQ ID NO 286
<211> LENGTH: 811
<212> TYPE: PRT
<213> ORGANISM: Homo sapiens

<400> SEQUENCE: 286

Met Arg Leu Ile Arg Asn Ile Tyr Ile Phe Cys Ser Ile Val Met Thr
1               5                   10                  15

Ala Glu Gly Asp Ala Pro Glu Leu Pro Glu Glu Arg Glu Leu Met Thr
            20                  25                  30

Asn Cys Ser Asn Met Ser Leu Arg Lys Val Pro Ala Asp Leu Thr Pro
        35                  40                  45

Ala Thr Thr Thr Leu Asp Leu Ser Tyr Asn Leu Leu Phe Gln Leu Gln
    50                  55                  60

Ser Ser Asp Phe His Ser Val Ser Lys Leu Arg Val Leu Ile Leu Cys
65                  70                  75                  80

His Asn Arg Ile Gln Gln Leu Asp Leu Lys Thr Phe Glu Phe Asn Lys
                85                  90                  95

Glu Leu Arg Tyr Leu Asp Leu Ser Asn Asn Arg Leu Lys Ser Val Thr
            100                 105                 110

Trp Tyr Leu Leu Ala Gly Leu Arg Tyr Leu Asp Leu Ser Phe Asn Asp
        115                 120                 125

Phe Asp Thr Met Pro Ile Cys Glu Glu Ala Gly Asn Met Ser His Leu
    130                 135                 140

Glu Ile Leu Gly Leu Ser Gly Ala Lys Ile Gln Lys Ser Asp Phe Gln
145                 150                 155                 160

Lys Ile Ala His Leu His Leu Asn Thr Val Phe Leu Gly Phe Arg Thr
                165                 170                 175

Leu Pro His Tyr Glu Glu Gly Ser Leu Pro Ile Leu Asn Thr Thr Lys
            180                 185                 190

Leu His Ile Val Leu Pro Met Asp Thr Asn Phe Trp Val Leu Leu Arg
        195                 200                 205

Asp Gly Ile Lys Thr Ser Lys Ile Leu Glu Met Thr Asn Ile Asp Gly
    210                 215                 220

Lys Ser Gln Phe Val Ser Tyr Glu Met Gln Arg Asn Leu Ser Leu Glu
225                 230                 235                 240

Asn Ala Lys Thr Ser Val Leu Leu Asn Lys Val Asp Leu Leu Trp
                245                 250                 255

Asp Asp Leu Phe Leu Ile Leu Gln Phe Val Trp His Thr Ser Val Glu
            260                 265                 270

His Phe Gln Ile Arg Asn Val Thr Phe Gly Gly Lys Ala Tyr Leu Asp
        275                 280                 285

His Asn Ser Phe Asp Tyr Ser Asn Thr Val Met Arg Thr Ile Lys Leu
    290                 295                 300

Glu His Val His Phe Arg Val Phe Tyr Ile Gln Gln Asp Lys Ile Tyr
305                 310                 315                 320

Leu Leu Leu Thr Lys Met Asp Ile Glu Asn Leu Thr Ile Ser Asn Ala
                325                 330                 335

Gln Met Pro His Met Leu Phe Pro Asn Tyr Pro Thr Lys Phe Gln Tyr
            340                 345                 350

Leu Asn Phe Ala Asn Asn Ile Leu Thr Asp Glu Leu Phe Lys Arg Thr
        355                 360                 365

```
Ile Gln Leu Pro His Leu Lys Thr Leu Ile Leu Asn Gly Asn Lys Leu
    370                 375                 380

Glu Thr Leu Ser Leu Val Ser Cys Phe Ala Asn Asn Thr Pro Leu Glu
385                 390                 395                 400

His Leu Asp Leu Ser Gln Asn Leu Leu Gln His Lys Asn Asp Glu Asn
                405                 410                 415

Cys Ser Trp Pro Glu Thr Val Val Asn Met Asn Leu Ser Tyr Asn Lys
            420                 425                 430

Leu Ser Asp Ser Val Phe Arg Cys Leu Pro Lys Ser Ile Gln Ile Leu
        435                 440                 445

Asp Leu Asn Asn Asn Gln Ile Gln Thr Val Pro Lys Glu Thr Ile His
450                 455                 460

Leu Met Ala Leu Arg Glu Leu Asn Ile Ala Phe Asn Phe Leu Thr Asp
465                 470                 475                 480

Leu Pro Gly Cys Ser His Phe Ser Arg Leu Ser Val Leu Asn Ile Glu
                485                 490                 495

Met Asn Phe Ile Leu Ser Pro Ser Leu Asp Phe Val Gln Ser Cys Gln
            500                 505                 510

Glu Val Lys Thr Leu Asn Ala Gly Arg Asn Pro Phe Arg Cys Thr Cys
        515                 520                 525

Glu Leu Lys Asn Phe Ile Gln Leu Glu Thr Tyr Ser Glu Val Met Met
    530                 535                 540

Val Gly Trp Ser Asp Ser Tyr Thr Cys Glu Tyr Pro Leu Asn Leu Arg
545                 550                 555                 560

Gly Thr Arg Leu Lys Asp Val His Leu His Glu Leu Ser Cys Asn Thr
                565                 570                 575

Ala Leu Leu Ile Val Thr Ile Val Val Ile Met Leu Val Leu Gly Leu
            580                 585                 590

Ala Val Ala Phe Cys Cys Leu His Phe Asp Leu Pro Trp Tyr Leu Arg
        595                 600                 605

Met Leu Gly Gln Cys Thr Gln Thr Trp His Arg Val Arg Lys Thr Thr
    610                 615                 620

Gln Glu Gln Leu Lys Arg Asn Val Arg Phe His Ala Phe Ile Ser Tyr
625                 630                 635                 640

Ser Glu His Asp Ser Leu Trp Val Lys Asn Glu Leu Ile Pro Asn Leu
                645                 650                 655

Glu Lys Glu Asp Gly Ser Ile Leu Ile Cys Leu Tyr Glu Ser Tyr Phe
            660                 665                 670

Asp Pro Gly Lys Ser Ile Ser Glu Asn Ile Val Ser Phe Ile Glu Lys
        675                 680                 685

Ser Tyr Lys Ser Ile Phe Val Leu Ser Pro Asn Phe Val Gln Asn Glu
    690                 695                 700

Trp Cys His Tyr Glu Phe Tyr Phe Ala His His Asn Leu Phe His Glu
705                 710                 715                 720

Asn Ser Asp His Ile Ile Leu Ile Leu Leu Glu Pro Ile Pro Phe Tyr
                725                 730                 735

Cys Ile Pro Thr Arg Tyr His Lys Leu Lys Ala Leu Leu Glu Lys Lys
            740                 745                 750

Ala Tyr Leu Glu Trp Pro Lys Asp Arg Arg Lys Cys Gly Leu Phe Trp
        755                 760                 765

Ala Asn Leu Arg Ala Ala Ile Asn Val Asn Val Leu Ala Thr Arg Glu
    770                 775                 780
```

```
Met Tyr Glu Leu Gln Thr Phe Thr Glu Leu Asn Glu Glu Ser Arg Gly
785                 790                 795                 800

Ser Thr Ile Ser Leu Met Arg Thr Asp Cys Leu
                805                 810

<210> SEQ ID NO 287
<211> LENGTH: 3212
<212> TYPE: DNA
<213> ORGANISM: Mus musculus

<400> SEQUENCE: 287
agagcagcca ccattgtgga gggaagagga aggttttctt ctttaactac gggagatgaa    60
agaaaacacc tcctgagaac ctgaatctgt ctccaccacc ccatgctcaa agaatcgatg   120
ccaaggatgg aaagacatca gttctgctct gttctcctca ttctgatact attgactctg   180
gtgagcctta ccttgactgg ctgggcatgg accatccctg attgcatcat agcagacagt   240
ttgttatttc ctaacctttc ctactacatc ccattctgta cctcggcccc aggactgcac   300
cttttggcat cttgctctaa tgttaaaaac ttaaatcaga ccctaaaaag agtgcccaga   360
aatacagagg tactctgcct ccagggcatg gttcctactc tgccagctaa ggctttatt    420 cgcttccact ccctacagct tctaaggctg caattgcgta caaccagtgt cacatctagg   480 actttcaag gactggacca gctacaatac cttttttttg atcatcatgc tccctgttgc   540
ctaagtttgt tcctctctcc aaattgtttt gagtctctta gatcccttag tagtcttcc    600 tttcaaggat attgcctgac ttatagccaa agcatctact tgccaactag tcttaggcat   660
ctaactctga ggaatagctg tctaacaaag tttcaggacc ttcaaaggct cttcccagac   720
cttctgctga gtacctcctc tacacccaat atcaaaccag ggcacccctt tttagagacg   780
ctggatttat cttacaacct tcagctgaaa caggcaggtg tcagagactt gtatggcctc   840
acactccatt ccctaatatt ggatggtacc ccactaaaag cacttgatct cacagactca   900
ggactgctcc acttgcattt cctctccctt gtgggaacag gaatagaaaa agtgcctgca   960
agtttgactg ctactctga gcttcgtgca cttgaccttg gaaaaaccaa aatccaaaac  1020
atcttggaaa atggagaaat cccaggttat aaagccctgg aattccttag ccttcatgat  1080
aaccatctgc aaacacttcc taccaggttt ctacatactc taccccagct tcagaagctc  1140
aacctatcta tgaataagct tggcccaatc ttggagcttc agaaggact ctttagcaca   1200 aacttaaaag tgctagatct atcctataat caactctgtg atgtacccca tgggcttta   1260 tcccttttgt cacagctcca ggagctctgg ttgagtggca ataacatctc tagtttatcc  1320
aatgaaagcc tgcagggact gaggcagctg aggacactag acttaagttg gaatcaaatt  1380
aaagtactca aaccaggctg gctctctcat cttcctgctc tgactacctt gaaccttctg  1440
ggcacctact tagaatatat cttaggcata caacttcagg gtcccaagat gctaaggcat  1500
ttacaactgg gttcttatcc aatactggac atatatcctc cctggcccc aacactcctt   1560 agcttagaaa tacaagcaga atcatgtatt cagtttatga ttcacagtgg acagccattc  1620
ttattcttgg agaaccttac cttagagact tccattctat tactaaaacc agacaacatc  1680
acaattcatt ttccctccct gcgtcgcctc acttgcgtg gctacagctt catcttctca   1740
accagtcaac ttcagagatt cttcccacaa cagcttcctc ttctggagca cttctttatc  1800
tggtgtgaaa acagctatgc agtagacctc tatctatttg ggatgccag gctacgtgtg   1860 ctagagctgg ggtaccttaa ctttttctat gagtcaagta ctatgaagct agagatgcta  1920
ttgaaggagg tacctcagtt acaggtactg gcattgagcc acctgaatct caggaacctc  1980
```

-continued

```
tctgtgtcca gctttaagag cttgcaggac ctcaaactgc tgctcttcaa ctctgaaagg    2040
gcgctggaga tgaacagcaa cctccaggag tttattcctc agatgcctca gtacgtttac    2100
ttctctgatg tcacctttac ttgccagtgt gaagcttcct ggctggagtc ttgggctaca    2160
cgggccccaa acacatttgt ttatgggctg aaaaatcca tttgcatagc taatgcctca     2220
gactactcca aaactctact attctctttc cttgctacta attgtccaca cggtactgag    2280
ttttggggct ttctcaccag tttcattctg ctgcttctgt tgattatcct tcctctgatt    2340
agctgtccta atggtcctg gcttcatcac ctctggacac tctttcatac ttgttggtgg     2400
aaattatgtg gacatagact cagaggccaa ttcaactatg atgtctttat atcctattgt    2460
gaggaggatc aagcttgggt gctggaagaa ctggttccag ttctggagaa agcccctcct    2520
gaaggtgaag gcttgaggtt gtgcctgcct gccagggact ttgggattgg aaatgacagg    2580
atggaatcca tgattgccag catgggcaaa agcagagcca ccctctgtgt gctcacagga    2640
caggccttag caagtccctg gtgcaatcta gagttacgac tggccactta ccacttggta   2700
gccaggcctg ggaccactca tctcctgctg ttgtttctgg agcccttga taggcagagg    2760 ctccatagtt accatcgcct atcccgttgg ctccagaagg aggactattt tgatttgtcc    2820
caagggaaag tggagtggaa ctctttctgt gagcaactga agagacggct cagcaaagct    2880
ggacaagaaa gagattaagg actgcaggaa tgctgttgtg cagaagatcc tttcagcagc    2940
agagggaatg tgctctcatc actaaagcat gggctcacca aggggcaaa atgatatatt     3000 aaattccact gggagggaag tcttttaaaa cactgaaaaa tattaatcca ggaagggaaa    3060
aattcattca gaaaacaatt ctgttacctg ttagtgtgtt ccagcacgag atactgctca    3120
ccacacaaga catgcataca aagtggtttg tgcaatcctg tgtatgtttt tccaaagttt    3180
ttcaaaagta aatacattct gcctctaaaa aa                                  3212
```

<210> SEQ ID NO 288
<211> LENGTH: 931
<212> TYPE: PRT
<213> ORGANISM: Mus musculus

<400> SEQUENCE: 288

```
Met Leu Lys Glu Ser Met Pro Arg Met Glu Arg His Gln Phe Cys Ser
1               5                   10                  15

Val Leu Leu Ile Leu Ile Leu Thr Leu Val Ser Leu Thr Leu Thr
                20                  25                  30

Gly Trp Ala Trp Thr Ile Pro Asp Cys Ile Ile Ala Asp Ser Leu Leu
            35                  40                  45

Phe Pro Asn Leu Ser Tyr Tyr Ile Pro Phe Cys Thr Ser Ala Pro Gly
        50                  55                  60

Leu His Leu Leu Ala Ser Cys Ser Asn Val Lys Asn Leu Asn Gln Thr
65                  70                  75                  80

Leu Lys Arg Val Pro Arg Asn Thr Glu Val Leu Cys Leu Gln Gly Met
                85                  90                  95

Val Pro Thr Leu Pro Ala Lys Ala Phe Ile Arg Phe His Ser Leu Gln
                100                 105                 110

Leu Leu Arg Leu Gln Leu Arg Thr Thr Ser Val Thr Ser Arg Thr Phe
            115                 120                 125

Gln Gly Leu Asp Gln Leu Gln Tyr Leu Phe Phe Asp His His Ala Pro
        130                 135                 140

Cys Cys Leu Ser Leu Phe Leu Ser Pro Asn Cys Phe Glu Ser Leu Arg
```

```
            145                 150                 155                 160
Ser Leu Ser Ser Leu Ser Phe Gln Gly Tyr Cys Leu Thr Tyr Ser Gln
                165                 170                 175

Ser Ile Tyr Leu Pro Thr Ser Leu Arg His Leu Thr Leu Arg Asn Ser
                180                 185                 190

Cys Leu Thr Lys Phe Gln Asp Leu Gln Arg Leu Phe Pro Asp Leu Leu
                195                 200                 205

Leu Ser Thr Ser Ser Thr Pro Asn Ile Lys Pro Gly Ala Pro Phe Leu
    210                 215                 220

Glu Thr Leu Asp Leu Ser Tyr Asn Leu Gln Leu Lys Gln Ala Gly Val
225                 230                 235                 240

Arg Asp Leu Tyr Gly Leu Thr Leu His Ser Leu Ile Leu Asp Gly Thr
                245                 250                 255

Pro Leu Lys Ala Leu Asp Leu Thr Asp Ser Gly Leu Leu His Leu His
                260                 265                 270

Phe Leu Ser Leu Val Gly Thr Gly Ile Glu Lys Val Pro Ala Ser Leu
                275                 280                 285

Thr Gly Tyr Ser Glu Leu Arg Ala Leu Asp Leu Gly Lys Asn Gln Ile
                290                 295                 300

Gln Asn Ile Leu Glu Asn Gly Glu Ile Pro Gly Tyr Lys Ala Leu Glu
305                 310                 315                 320

Phe Leu Ser Leu His Asp Asn His Leu Gln Thr Leu Pro Thr Arg Phe
                325                 330                 335

Leu His Thr Leu Pro Gln Leu Gln Lys Leu Asn Leu Ser Met Asn Lys
                340                 345                 350

Leu Gly Pro Ile Leu Glu Leu Pro Glu Gly Leu Phe Ser Thr Asn Leu
                355                 360                 365

Lys Val Leu Asp Leu Ser Tyr Asn Gln Leu Cys Asp Val Pro His Gly
    370                 375                 380

Ala Leu Ser Leu Ser Gln Leu Gln Glu Leu Trp Leu Ser Gly Asn
385                 390                 395                 400

Asn Ile Ser Ser Leu Ser Asn Glu Ser Leu Gln Gly Leu Arg Gln Leu
                405                 410                 415

Arg Thr Leu Asp Leu Ser Trp Asn Gln Ile Lys Val Leu Lys Pro Gly
                420                 425                 430

Trp Leu Ser His Leu Pro Ala Leu Thr Thr Leu Asn Leu Leu Gly Thr
    435                 440                 445

Tyr Leu Glu Tyr Ile Leu Gly Ile Gln Leu Gly Pro Lys Met Leu
450                 455                 460

Arg His Leu Gln Leu Gly Ser Tyr Pro Ile Leu Asp Ile Tyr Pro Pro
465                 470                 475                 480

Trp Pro Pro Thr Leu Ser Leu Glu Ile Gln Ala Glu Ser Cys Ile
                485                 490                 495

Gln Phe Met Ile His Ser Gly Gln Pro Phe Leu Phe Leu Glu Asn Leu
                500                 505                 510

Thr Leu Glu Thr Ser Ile Leu Leu Lys Pro Asp Asn Ile Thr Ile
                515                 520                 525

His Phe Pro Ser Leu Arg Arg Leu Thr Leu Arg Gly Tyr Ser Phe Ile
                530                 535                 540

Phe Ser Thr Ser Gln Leu Gln Arg Phe Phe Pro Gln Gln Leu Pro Leu
545                 550                 555                 560

Leu Glu His Phe Phe Ile Trp Cys Glu Asn Ser Tyr Ala Val Asp Leu
                565                 570                 575
```

```
Tyr Leu Phe Gly Met Pro Arg Leu Arg Val Leu Glu Leu Gly Tyr Leu
            580                 585                 590

Asn Phe Phe Tyr Glu Ser Ser Thr Met Lys Leu Glu Met Leu Leu Lys
        595                 600                 605

Glu Val Pro Gln Leu Gln Val Leu Ala Leu Ser His Leu Asn Leu Arg
    610                 615                 620

Asn Leu Ser Val Ser Ser Phe Lys Ser Leu Gln Asp Leu Lys Leu Leu
625                 630                 635                 640

Leu Phe Asn Ser Glu Arg Ala Leu Glu Met Asn Ser Asn Leu Gln Glu
                645                 650                 655

Phe Ile Pro Gln Met Pro Gln Tyr Val Tyr Phe Ser Asp Val Thr Phe
            660                 665                 670

Thr Cys Gln Cys Glu Ala Ser Trp Leu Glu Ser Trp Ala Thr Arg Ala
        675                 680                 685

Pro Asn Thr Phe Val Tyr Gly Leu Glu Lys Ser Ile Cys Ile Ala Asn
    690                 695                 700

Ala Ser Asp Tyr Ser Lys Thr Leu Leu Phe Ser Phe Leu Ala Thr Asn
705                 710                 715                 720

Cys Pro His Gly Thr Glu Phe Trp Gly Phe Leu Thr Ser Phe Ile Leu
                725                 730                 735

Leu Leu Leu Leu Ile Ile Leu Pro Leu Ile Ser Cys Pro Lys Trp Ser
            740                 745                 750

Trp Leu His His Leu Trp Thr Leu Phe His Thr Cys Trp Lys Leu
        755                 760                 765

Cys Gly His Arg Leu Arg Gly Gln Phe Asn Tyr Asp Val Phe Ile Ser
770                 775                 780

Tyr Cys Glu Glu Asp Gln Ala Trp Val Leu Glu Glu Leu Val Pro Val
785                 790                 795                 800

Leu Glu Lys Ala Pro Pro Glu Gly Glu Gly Leu Arg Leu Cys Leu Pro
                805                 810                 815

Ala Arg Asp Phe Gly Ile Gly Asn Asp Arg Met Glu Ser Met Ile Ala
            820                 825                 830

Ser Met Gly Lys Ser Arg Ala Thr Leu Cys Val Leu Thr Gly Gln Ala
        835                 840                 845

Leu Ala Ser Pro Trp Cys Asn Leu Glu Leu Arg Leu Ala Thr Tyr His
    850                 855                 860

Leu Val Ala Arg Pro Gly Thr Thr His Leu Leu Leu Phe Leu Glu
865                 870                 875                 880

Pro Leu Asp Arg Gln Arg Leu His Ser Tyr His Arg Leu Ser Arg Trp
                885                 890                 895

Leu Gln Lys Glu Asp Tyr Phe Asp Leu Ser Gln Gly Lys Val Glu Trp
            900                 905                 910

Asn Ser Phe Cys Glu Gln Leu Lys Arg Arg Leu Ser Lys Ala Gly Gln
        915                 920                 925

Glu Arg Asp
    930
```

<210> SEQ ID NO 289
<211> LENGTH: 3174
<212> TYPE: DNA
<213> ORGANISM: Mus musculus

<400> SEQUENCE: 289
agtgctaagt atctccaagt cggcctcctc acttcccggc ttccacagtg gccctttgac   60

```
ggtgctcccg accttgcag gtactctgag gtggatgaga gtattggtaa cccggaggca      120
taggagtcta aagtcctctc agctctgatt cctctggtgt agagatgggc aggtactggc      180
tgctgccagg tctcctcctt tccctgcctc tggtaactgg gtggagcact tccaactgcc      240
tggtgaccga aggctcccga ctgccctgg tctcccgcta tttcacattc tgccgccatt      300
ccaagctatc ctttcttgct gcatgcctct ccgtgagcaa cctgacacag accttggaag      360
ttgtacctcg gactgtggag gggctctgcc tcggtggtac tgtgtctact ctgcttccag      420
atgctttctc tgcttttcct ggtctcaagg tcctggcact gagtctgcac cttacccaac      480
ttctgccagg agctctccgg ggtctgggac agttgcagag cctctctttt tttgactctc      540
ctcttaggag atctctcttt ctacctcctg atgccttcag tgacctgatt ccctccaga       600 gactccatat ctctggccct tgcctggata agaaggcagg catccgcctg cctcccggtc      660
tgcaatggct gggtgtcacg ctcagttgca ttcaggacgt gggagagctg gctggtatgt      720
tcccagatct ggtgcaaggt tcctcctcca gggtttcgtg gaccctgcag aagttggatc      780
tgtcatccaa ctggaagctg aagatggcta gtcctgggtc cctccagggt ctccaggtgg      840
agattctgga cctgacaaga acaccactgg atgccgtgtg gctgaaggc ctgggacttc       900 agaaactcga tgtcttgtat gcacagactg ccacggccga gctggctgct gaggctgttg      960
cccactttga gctgcagggc ttgattgtga agaaagcaa gataggatct atatctcagg      1020
aggctctggc ttcctgccac agcctgaaga ccttgggtct ttcaagcact ggcctaacca     1080
agcttccacc aggcttcctg actgccatgc ctaggcttca gcgactggag ctgtccggaa      1140
accaactgca gagcgccgtg ctgtgcatga atgagacggg agatgtgtca ggactcacga      1200
ctctggatct gtcaggcaac aggttgcgca tcctgcctcc agccgccttc tcctgcttac      1260
cccacttgcg agagctgctg cttcggtaca accagctgct ttccctggag ggataccat      1320 tccaggagct ccagcaacta gagaccttga agctggatgg aaaccccctg cttcacctgg      1380
gtaagaactg gttggcggct ctgcctgcat tgaccaccct tagcttgcta gatacccaaa      1440
tacggatgag cccagagcct ggcttctggg gagcaaagaa tctgcatacc ttgagcctga      1500
agcttcccgc tctccctgct ccggcagtat tgttcctgcc catgtatctg accagcttag      1560
agcttcatat agcctcaggc acgacggagc actggacgct gtccccagcg atctttcctt      1620
ccttggagac cttgactata agcggcgggg gactgaagct gaagctgggg tcccagaatg      1680
cttctggggt cttccctgct ctccagaagc tctccctgct taagaacagc ttggatgcct      1740
tctgctccca gggtacctcc aaccttttcc tctggcagct ccccaaactt cagtccttga      1800
gggtatgggg tgctggaaac agctccagac cctgccttat cactgggctg ccagcctac      1860 gggagctgaa gctggcgtcg cttcagtcca taacccagcc ccgttcggtg cagctggagg      1920
agctggtggg tgaccttcca cagctccagg ccttagtgct atccagcaca ggcctcaagt      1980
cactgtcggc tgctgctttc cagcgcctgc acagtctcca ggtcttagtg ctagaatacg      2040
agaaggactt gatgctgcag gacagtctga gggagtacag ccctcagatg ccccactata      2100
tatacattct ggagtcaaac ctggcctgcc actgtgccaa tgcgtggatg gagccatggg      2160
ttaagcggtc cactaaaacg tacatataca taagagacaa tcgcttatgt ccaggacaag      2220
acaggctctc tgctagggt tcccttccct cctttctctg ggaccactgc ccccagacgt       2280
tggagctgaa actcttttg gctagttctg ccttggtgtt catgctaatt gccttgcctc       2340
tcctccaaga agccaggaac tcttggatcc cctacctgca ggccttgttc agggtttggc      2400
```

```
tccagggtct gaggggtaag ggagacaagg ggaagaggtt ccttttttgat gtattcgtgt    2460 cccactgcag gcaagaccag ggctgggtga tagaggaact tctgcctgct ctggagggct    2520
tccttccagc tggcctgggc ctgcgcctct gtctccccga gcgtgacttt gagcctggta    2580
aggatgtagt tgataatgtg gtagatagca tgttgagcag ccgtaccaca ctctgcgtgt    2640
tgagtgggca ggccctgtgt aaccccgat gccgcctgga gctccgcttg ccacctctc     2700 tcctcctggc tgccccgtcc cctccagtgt tgctgctagt cttcttggaa cccatttctc    2760
ggcaccagct tccgggttac cacagactgg ctcggctgct tcgaagagga gactactgtc    2820
tgtggcccga ggaagaggag agaaagagtg ggttctggac ttggctgagg agcaggctag    2880
ggtagccata gccagcactg gtgtggggtg gtgcatgtga attttggggt ggggttgggg    2940
gaagggaagc aagcctgcct gtcaaggagt tggtgtgttt gtaggtgcag ggtcggggac    3000
agtgggtcta agaggctgaa gtcagccttt tgcagcgcag gaatccacgt gctgtgaaca    3060
caggttttgg ggggcctgga ggttgaatga ggaaaactga gagatggaag gtgtccgcgg    3120
ggtatgtgac attcccaaga tcttcaaatc ctcagtaaac ttgctaaatt catg          3174
```

<210> SEQ ID NO 290
<211> LENGTH: 906
<212> TYPE: PRT
<213> ORGANISM: Mus musculus

<400> SEQUENCE: 290

```
Met Gly Arg Tyr Trp Leu Leu Pro Gly Leu Leu Ser Leu Pro Leu
1               5                   10                  15

Val Thr Gly Trp Ser Thr Ser Asn Cys Leu Val Thr Glu Gly Ser Arg
            20                  25                  30

Leu Pro Leu Val Ser Arg Tyr Phe Thr Phe Cys Arg His Ser Lys Leu
        35                  40                  45

Ser Phe Leu Ala Ala Cys Leu Ser Val Ser Asn Leu Thr Gln Thr Leu
    50                  55                  60

Glu Val Val Pro Arg Thr Val Glu Gly Leu Cys Leu Gly Gly Thr Val
65                  70                  75                  80

Ser Thr Leu Leu Pro Asp Ala Phe Ser Ala Phe Pro Gly Leu Lys Val
                85                  90                  95

Leu Ala Leu Ser Leu His Leu Thr Gln Leu Leu Pro Gly Ala Leu Arg
            100                 105                 110

Gly Leu Gly Gln Leu Gln Ser Leu Ser Phe Phe Asp Ser Pro Leu Arg
        115                 120                 125

Arg Ser Leu Phe Leu Pro Pro Asp Ala Phe Ser Asp Leu Ile Ser Leu
    130                 135                 140

Gln Arg Leu His Ile Ser Gly Pro Cys Leu Asp Lys Lys Ala Gly Ile
145                 150                 155                 160

Arg Leu Pro Pro Gly Leu Gln Trp Leu Gly Val Thr Leu Ser Cys Ile
                165                 170                 175

Gln Asp Val Gly Glu Leu Ala Gly Met Phe Pro Asp Leu Val Gln Gly
            180                 185                 190

Ser Ser Ser Arg Val Ser Trp Thr Leu Gln Lys Leu Asp Leu Ser Ser
        195                 200                 205

Asn Trp Lys Leu Lys Met Ala Ser Pro Gly Ser Leu Gln Gly Leu Gln
    210                 215                 220

Val Glu Ile Leu Asp Leu Thr Arg Thr Pro Leu Asp Ala Val Trp Leu
225                 230                 235                 240
```

```
Lys Gly Leu Gly Leu Gln Lys Leu Asp Val Leu Tyr Ala Gln Thr Ala
                245                 250                 255

Thr Ala Glu Leu Ala Ala Glu Ala Val Ala His Phe Glu Leu Gln Gly
            260                 265                 270

Leu Ile Val Lys Glu Ser Lys Ile Gly Ser Ile Ser Gln Glu Ala Leu
        275                 280                 285

Ala Ser Cys His Ser Leu Lys Thr Leu Gly Leu Ser Ser Thr Gly Leu
    290                 295                 300

Thr Lys Leu Pro Pro Gly Phe Leu Thr Ala Met Pro Arg Leu Gln Arg
305                 310                 315                 320

Leu Glu Leu Ser Gly Asn Gln Leu Gln Ser Ala Val Leu Cys Met Asn
                325                 330                 335

Glu Thr Gly Asp Val Ser Gly Leu Thr Thr Leu Asp Leu Ser Gly Asn
            340                 345                 350

Arg Leu Arg Ile Leu Pro Pro Ala Ala Phe Ser Cys Leu Pro His Leu
        355                 360                 365

Arg Glu Leu Leu Leu Arg Tyr Asn Gln Leu Leu Ser Leu Glu Gly Tyr
    370                 375                 380

Leu Phe Gln Glu Leu Gln Gln Leu Glu Thr Leu Lys Leu Asp Gly Asn
385                 390                 395                 400

Pro Leu Leu His Leu Gly Lys Asn Trp Leu Ala Ala Leu Pro Ala Leu
                405                 410                 415

Thr Thr Leu Ser Leu Leu Asp Thr Gln Ile Arg Met Ser Pro Glu Pro
            420                 425                 430

Gly Phe Trp Gly Ala Lys Asn Leu His Thr Leu Ser Leu Lys Leu Pro
        435                 440                 445

Ala Leu Pro Ala Pro Ala Val Leu Phe Leu Pro Met Tyr Leu Thr Ser
    450                 455                 460

Leu Glu Leu His Ile Ala Ser Gly Thr Thr Glu His Trp Thr Leu Ser
465                 470                 475                 480

Pro Ala Ile Phe Pro Ser Leu Glu Thr Leu Thr Ile Ser Gly Gly Gly
                485                 490                 495

Leu Lys Leu Lys Leu Gly Ser Gln Asn Ala Ser Gly Val Phe Pro Ala
            500                 505                 510

Leu Gln Lys Leu Ser Leu Leu Lys Asn Ser Leu Asp Ala Phe Cys Ser
        515                 520                 525

Gln Gly Thr Ser Asn Leu Phe Leu Trp Gln Leu Pro Lys Leu Gln Ser
    530                 535                 540

Leu Arg Val Trp Gly Ala Gly Asn Ser Ser Arg Pro Cys Leu Ile Thr
545                 550                 555                 560

Gly Leu Pro Ser Leu Arg Glu Leu Lys Leu Ala Ser Leu Gln Ser Ile
                565                 570                 575

Thr Gln Pro Arg Ser Val Gln Leu Glu Glu Leu Val Gly Asp Leu Pro
            580                 585                 590

Gln Leu Gln Ala Leu Val Leu Ser Ser Thr Gly Leu Lys Ser Leu Ser
        595                 600                 605

Ala Ala Ala Phe Gln Arg Leu His Ser Leu Gln Val Leu Val Leu Glu
    610                 615                 620

Tyr Glu Lys Asp Leu Met Leu Gln Asp Ser Arg Glu Tyr Ser Pro
625                 630                 635                 640

Gln Met Pro His Tyr Ile Tyr Ile Leu Glu Ser Asn Leu Ala Cys His
                645                 650                 655

Cys Ala Asn Ala Trp Met Glu Pro Trp Val Lys Arg Ser Thr Lys Thr
```

```
                    660                 665                 670
Tyr Ile Tyr Ile Arg Asp Asn Arg Leu Cys Pro Gly Gln Asp Arg Leu
            675                 680                 685

Ser Ala Arg Gly Ser Leu Pro Ser Phe Leu Trp Asp His Cys Pro Gln
        690                 695                 700

Thr Leu Glu Leu Lys Leu Phe Leu Ala Ser Ser Ala Leu Val Phe Met
705                 710                 715                 720

Leu Ile Ala Leu Pro Leu Leu Gln Glu Ala Arg Asn Ser Trp Ile Pro
                725                 730                 735

Tyr Leu Gln Ala Leu Phe Arg Val Trp Leu Gln Gly Leu Arg Gly Lys
            740                 745                 750

Gly Asp Lys Gly Lys Arg Phe Leu Phe Asp Val Phe Ser His Cys
        755                 760                 765

Arg Gln Asp Gln Gly Trp Val Ile Glu Glu Leu Pro Ala Leu Glu
        770                 775                 780

Gly Phe Leu Pro Ala Gly Leu Gly Leu Arg Leu Cys Leu Pro Glu Arg
785                 790                 795                 800

Asp Phe Glu Pro Gly Lys Asp Val Val Asp Asn Val Val Asp Ser Met
                805                 810                 815

Leu Ser Ser Arg Thr Thr Leu Cys Val Leu Ser Gly Gln Ala Leu Cys
            820                 825                 830

Asn Pro Arg Cys Arg Leu Glu Leu Arg Leu Ala Thr Ser Leu Leu Leu
            835                 840                 845

Ala Ala Pro Ser Pro Val Leu Leu Val Phe Leu Glu Pro Ile
850                 855                 860

Ser Arg His Gln Leu Pro Gly Tyr His Arg Leu Ala Arg Leu Leu Arg
865                 870                 875                 880

Arg Gly Asp Tyr Cys Leu Trp Pro Glu Glu Glu Arg Lys Ser Gly
                885                 890                 895

Phe Trp Thr Trp Leu Arg Ser Arg Leu Gly
                900                 905

<210> SEQ ID NO 291
<211> LENGTH: 4014
<212> TYPE: DNA
<213> ORGANISM: Mus musculus

<400> SEQUENCE: 291
tttagcaaag atgaacaatt gtactatgtg ctaggagctt ctgagagaac ctttccttg      60 caagatacct gtggtatgtg tcttggggcc cagcaatgat tcctggttct ctgcttcctc    120
tgttgcatga tgtcgagaca ctgatacact gatgcttgaa ggatgaagca gagttcagaa    180
tgagtgggct ctacaggatc ctggtccagc tggaacaaag tccatatgtg aagaccgtgc    240
ctttgaacat gagaagggat ttttttttcc tggttgtaac ctggatgcct aagacagtca    300
agatgaatgg gagcagcttt gtgccatctc tacagctcct gctcatgtta gtaggatttt    360
ctctgccgcc tgtggcagag acatatgggt tcaacaagtg cacacagtat gaatttgata    420
ttcaccatgt gctctgcatt aggaagaaga tcaccaactt gacagaggcc attagtgaca    480
tacctagata tactactcac cttaacctca cacacaacga aattcaagtc ctccctccct    540
ggagttttac caatctgtct gctctggtgg acttgagact agagtggaac tcaatttgga    600
agatcgacga aggtgccttt aggggacttg aaaatttgac tctgctgaat ttagtggaaa    660
ataagattca aagtgtgaat aactcctttg agggcctgtc cagcctgaag accctgctcc    720
```

-continued

| | |
|---|---|
| tgagccataa tcagattacc catattcaca aagacgcctt cactcctcta atcaaattga | 780 |
| aatatttgag cctatctcga aacaacatta gcgattttc tggtattctt gaagcagtcc | 840 |
| agcatcttcc atgcctggag cgccttgatc taactaacaa cagcatcatg tacttggacc | 900 |
| acagccctag gtcactggtt tctctgaccc acctgagttt tgaggggaac aaactaaggg | 960 |
| agttaaactt ctctgctttg tcattaccta acttaaccaa tctaagtgct tcccggaatg | 1020 |
| gcaataaagt cattcagaat gtgtatctta aaactctgcc ccaacttaaa agcttgaatc | 1080 |
| tgagtggaac ggtgataaaa ttggaaaatc tttcggccaa acacctgcag aatctaagag | 1140 |
| ctatggatct cagtaattgg gagcttagac atggtcactt agatatgaaa actgtttgtc | 1200 |
| acctgctcgg aaacctaccc aagttagaga cactggtttt tcagaaaaat gtcaccaatg | 1260 |
| cagagggcat taagcagctg gcaaagtgca ccaggctctt gttccttgac ctgggtcaaa | 1320 |
| acagtgactt gatttatctc aatgacagcg agttcaatgc tctgcccagt ctccaaaaac | 1380 |
| tgaatttgaa caagtgccag ctctccttca tcaacaacag gacctggagt tccttgcaga | 1440 |
| acttgaccag cctagatctg agccacaaca agtttaaaag cttccagat tttgcatttt | 1500 |
| cccccttgaa gcacttggag tttctctctc tttcaagaaa ccccatcaca gaactcaata | 1560 |
| atctggcctt tagtgggcta tttgcactga aggagctcaa cttggctgca tgttggattg | 1620 |
| taacaattga caggtattcc tttactcagt ttccaaactt agaggtctta gatcttggag | 1680 |
| acaacaatat tcggactctc aaccacggaa ccttccgacc tctgaaaaaa ctccagtctt | 1740 |
| tgattctttc ccacaactgc ctaaaaatcc tggagccaaa ttcgttttct ggtctcacta | 1800 |
| acctacgttc ccttgacctg atgtacaaca gcttgtcata ttttcatgaa cccttttct | 1860 |
| cgggccttga aaagcttctg attttgaaac ttggttttaa taagatcaca tatgaaacta | 1920 |
| ctaggaccct tcagtatcct ccatttataa agctcaagtc tttgaaacag cttaacctag | 1980 |
| aaggacaaag acacgggatt caggttgttc cgagcaactt tttccaagga ttgggtagtt | 2040 |
| tgcaggagtt actcttagga aaaaatccct ctgtattcct ggaccaccac caattttgacc | 2100 |
| ctctgattaa cctcacaaag ttggatatct caggaacaaa agatggagat cgaagcctct | 2160 |
| atttaaatgc ttccttattc caaaacctca aaggctaaaa gatcctccgc cttgaaaata | 2220 |
| acaacttaga gtcactggtt cctgacatgt tctccagctt acagagcctc caggtcttt | 2280 |
| ctttaagatt caacaacttg aaggtcatta atcaaagtca tctgaagaat ctgaaatcac | 2340 |
| tgatgttttt tgatgtctat gggaacaaac ttcagtgcac ctgtgacaat tgtgggttca | 2400 |
| agaactggtc aatgaacaca gaggaggtcc acatcccctt cctccggagc tatccctgtc | 2460 |
| agcagccagg cagccagagt ttacttatag attttgatga tgccatgtgt aattttgact | 2520 |
| tgggaaaggt ctacttctta tgttccttca gtatggtcct cagcaccatg gtcttctctt | 2580 |
| ggttcagtac caagatgatt gcatctctgt ggtatggttt gtacatatgt agggcctggt | 2640 |
| acctcactaa atggcacaaa acggagaaga agttcttata tgatgcgttt gtctctttct | 2700 |
| cggccactga tgaggcatgg gtatacaaag agcttgttcc agcccctagaa caaggcagcc | 2760 |
| agaccacctt taaactctgt cttcaccaac gggattttga accaggcatt gatatcttcg | 2820 |
| agaacatcca gaatgctatt aacacaagca ggaaaaacctt gtgcgtagtc agtaaccact | 2880 |
| acctacacag tgaatggtgc cgacttgaag tccagctggc tagcatgaag atgttttatg | 2940 |
| agcacaagga tgtcattatc ttgatcttcc ttgaagagat tccgaactat aagctgtcca | 3000 |
| gctaccaccg actcaggaaa ctcataaaca aacagacgtt tatcacttgg ccggacagtg | 3060 |
| ttcaccagca gccacttttc tgggctcgca tcagaaatgc gttgggcaag gagactgtgg | 3120 |

```
agaaagaaaa tacacatcta attgttgttg agtgactcga gtcttaacaa tcccaaaccc   3180
ggctgcatga atgttgccca aaataaatgt aagctgtttg actaaatgaa ctctctctct   3240
ctctccagag acaaacatga ttgcttagat agtgttcatc agaagagtag ggaggactgc   3300
ttggaaaact ttcaggagca gggtcccact atgatgggat tggatatgca gaaggaattc   3360
ctattttatt aaggagagga cttagaacaa cagtcatctg aacactgagg aacaggaagg   3420
tcttcgcata tattcgatat ctttgctcat gttgtttctc caaatcagtt gtggtcatgg   3480
gagactgcac ttgtgtatcc aaattgcccc aagattgaaa cttttccatct tgaaaggaaa  3540 cttcctatga cagaggttta cagggagaga gaacaacagg atgttctaag gggagattga   3600
aatattccac cctgcatgga agcttgttaa gacaggaggt aaatgactca aaatagtttc   3660
atgaagtctc tgaaactgac cagggactag gcccctttcct tccccaagtg tatataaaac  3720
aatagagact gctgagacaa tcagacaagc ctagctgcct ggaagaagca gagagcagcc   3780
ttggtgcctg gaagaggctc agaccagctg agccaccagg aaaggacact ctccatcctg   3840
ttgagctgcc tgcagcctgt gcagtatgct ccaggttccc agcattttttg agctgtcacc  3900 catgctgggg tgggctttag tgatgcagct gtctttgaaa catttctgct cctgtgagta   3960
acccttcacc tatgttcttg taagtaaccc caataaaact cattggttca ccaa         4014
```

<210> SEQ ID NO 292
<211> LENGTH: 991
<212> TYPE: PRT
<213> ORGANISM: Mus musculus

<400> SEQUENCE: 292

```
Met Ser Gly Leu Tyr Arg Ile Leu Val Gln Leu Glu Gln Ser Pro Tyr
1               5                   10                  15

Val Lys Thr Val Pro Leu Asn Met Arg Arg Asp Phe Phe Phe Leu Val
            20                  25                  30

Val Thr Trp Met Pro Lys Thr Val Lys Met Asn Gly Ser Ser Phe Val
        35                  40                  45

Pro Ser Leu Gln Leu Leu Leu Met Leu Val Gly Phe Ser Leu Pro Pro
    50                  55                  60

Val Ala Glu Thr Tyr Gly Phe Asn Lys Cys Thr Gln Tyr Glu Phe Asp
65                  70                  75                  80

Ile His His Val Leu Cys Ile Arg Lys Lys Ile Thr Asn Leu Thr Glu
                85                  90                  95

Ala Ile Ser Asp Ile Pro Arg Tyr Thr Thr His Leu Asn Leu Thr His
            100                 105                 110

Asn Glu Ile Gln Val Leu Pro Pro Trp Ser Phe Thr Asn Leu Ser Ala
        115                 120                 125

Leu Val Asp Leu Arg Leu Glu Trp Asn Ser Ile Trp Lys Ile Asp Glu
    130                 135                 140

Gly Ala Phe Arg Gly Leu Glu Asn Leu Thr Leu Leu Asn Leu Val Glu
145                 150                 155                 160

Asn Lys Ile Gln Ser Val Asn Asn Ser Phe Glu Gly Leu Ser Ser Leu
                165                 170                 175

Lys Thr Leu Leu Leu Ser His Asn Gln Ile Thr His Ile His Lys Asp
            180                 185                 190

Ala Phe Thr Pro Leu Ile Lys Leu Lys Tyr Leu Ser Leu Ser Arg Asn
        195                 200                 205

Asn Ile Ser Asp Phe Ser Gly Ile Leu Glu Ala Val Gln His Leu Pro
```

```
            210                 215                 220
Cys Leu Glu Arg Leu Asp Leu Thr Asn Asn Ser Ile Met Tyr Leu Asp
225                 230                 235                 240

His Ser Pro Arg Ser Leu Val Ser Leu Thr His Leu Ser Phe Glu Gly
                245                 250                 255

Asn Lys Leu Arg Glu Leu Asn Phe Ser Ala Leu Ser Leu Pro Asn Leu
                260                 265                 270

Thr Asn Leu Ser Ala Ser Arg Asn Gly Asn Lys Val Ile Gln Asn Val
            275                 280                 285

Tyr Leu Lys Thr Leu Pro Gln Leu Lys Ser Leu Asn Leu Ser Gly Thr
        290                 295                 300

Val Ile Lys Leu Glu Asn Leu Ser Ala Lys His Leu Gln Asn Leu Arg
305                 310                 315                 320

Ala Met Asp Leu Ser Asn Trp Glu Leu Arg His Gly His Leu Asp Met
                325                 330                 335

Lys Thr Val Cys His Leu Leu Gly Asn Leu Pro Lys Leu Glu Thr Leu
                340                 345                 350

Val Phe Gln Lys Asn Val Thr Asn Ala Glu Gly Ile Lys Gln Leu Ala
            355                 360                 365

Lys Cys Thr Arg Leu Leu Phe Leu Asp Leu Gly Gln Asn Ser Asp Leu
        370                 375                 380

Ile Tyr Leu Asn Asp Ser Glu Phe Asn Ala Leu Pro Ser Leu Gln Lys
385                 390                 395                 400

Leu Asn Leu Asn Lys Cys Gln Leu Ser Phe Ile Asn Asn Arg Thr Trp
                405                 410                 415

Ser Ser Leu Gln Asn Leu Thr Ser Leu Asp Leu Ser His Asn Lys Phe
            420                 425                 430

Lys Ser Phe Pro Asp Phe Ala Phe Ser Pro Leu Lys His Leu Glu Phe
        435                 440                 445

Leu Ser Leu Ser Arg Asn Pro Ile Thr Glu Leu Asn Asn Leu Ala Phe
450                 455                 460

Ser Gly Leu Phe Ala Leu Lys Glu Leu Asn Leu Ala Ala Cys Trp Ile
465                 470                 475                 480

Val Thr Ile Asp Arg Tyr Ser Phe Thr Gln Phe Pro Asn Leu Glu Val
                485                 490                 495

Leu Asp Leu Gly Asp Asn Asn Ile Arg Thr Leu Asn His Gly Thr Phe
                500                 505                 510

Arg Pro Leu Lys Lys Leu Gln Ser Leu Ile Leu Ser His Asn Cys Leu
            515                 520                 525

Lys Ile Leu Glu Pro Asn Ser Phe Ser Gly Leu Thr Asn Leu Arg Ser
        530                 535                 540

Leu Asp Leu Met Tyr Asn Ser Leu Ser Tyr Phe His Glu His Leu Phe
545                 550                 555                 560

Ser Gly Leu Glu Lys Leu Leu Ile Leu Lys Leu Gly Phe Asn Lys Ile
                565                 570                 575

Thr Tyr Glu Thr Thr Arg Thr Leu Gln Tyr Pro Pro Phe Ile Lys Leu
                580                 585                 590

Lys Ser Leu Lys Gln Leu Asn Leu Glu Gly Gln Arg His Gly Ile Gln
            595                 600                 605

Val Val Pro Ser Asn Phe Phe Gln Gly Leu Gly Ser Leu Gln Glu Leu
        610                 615                 620

Leu Leu Gly Lys Asn Pro Ser Val Phe Leu Asp His Gln Phe Asp
625                 630                 635                 640
```

```
Pro Leu Ile Asn Leu Thr Lys Leu Asp Ile Ser Gly Thr Lys Asp Gly
            645                 650                 655

Asp Arg Ser Leu Tyr Leu Asn Ala Ser Leu Phe Gln Asn Leu Lys Arg
            660                 665                 670

Leu Lys Ile Leu Arg Leu Glu Asn Asn Asn Leu Glu Ser Leu Val Pro
            675                 680                 685

Asp Met Phe Ser Ser Leu Gln Ser Leu Gln Val Phe Ser Leu Arg Phe
            690                 695                 700

Asn Asn Leu Lys Val Ile Asn Gln Ser His Leu Lys Asn Leu Lys Ser
705                 710                 715                 720

Leu Met Phe Phe Asp Val Tyr Gly Asn Lys Leu Gln Cys Thr Cys Asp
            725                 730                 735

Asn Leu Trp Phe Lys Asn Trp Ser Met Asn Thr Glu Glu Val His Ile
            740                 745                 750

Pro Phe Leu Arg Ser Tyr Pro Cys Gln Gln Pro Gly Ser Gln Ser Leu
            755                 760                 765

Leu Ile Asp Phe Asp Asp Ala Met Cys Asn Phe Asp Leu Gly Lys Val
            770                 775                 780

Tyr Phe Leu Cys Ser Phe Ser Met Val Leu Ser Thr Met Val Phe Ser
785                 790                 795                 800

Trp Phe Ser Thr Lys Met Ile Ala Ser Leu Trp Tyr Gly Leu Tyr Ile
            805                 810                 815

Cys Arg Ala Trp Tyr Leu Thr Lys Trp His Lys Thr Glu Lys Lys Phe
            820                 825                 830

Leu Tyr Asp Ala Phe Val Ser Phe Ser Ala Thr Asp Glu Ala Trp Val
            835                 840                 845

Tyr Lys Glu Leu Val Pro Ala Leu Glu Gln Gly Ser Gln Thr Thr Phe
            850                 855                 860

Lys Leu Cys Leu His Gln Arg Asp Phe Glu Pro Gly Ile Asp Ile Phe
865                 870                 875                 880

Glu Asn Ile Gln Asn Ala Ile Asn Thr Ser Arg Lys Thr Leu Cys Val
            885                 890                 895

Val Ser Asn His Tyr Leu His Ser Glu Trp Cys Arg Leu Glu Val Gln
            900                 905                 910

Leu Ala Ser Met Lys Met Phe Tyr Glu His Lys Asp Val Ile Ile Leu
            915                 920                 925

Ile Phe Leu Glu Glu Ile Pro Asn Tyr Lys Leu Ser Ser Tyr His Arg
            930                 935                 940

Leu Arg Lys Leu Ile Asn Lys Gln Thr Phe Ile Thr Trp Pro Asp Ser
945                 950                 955                 960

Val His Gln Gln Pro Leu Phe Trp Ala Arg Ile Arg Asn Ala Leu Gly
            965                 970                 975

Lys Glu Thr Val Glu Lys Glu Asn Thr His Leu Ile Val Val Glu
            980                 985                 990
```

```
<210> SEQ ID NO 293
<211> LENGTH: 11
<212> TYPE: PRT
<213> ORGANISM: Artificial Sequence
<220> FEATURE:
<223> OTHER INFORMATION: TAT 47-57 peptide

<400> SEQUENCE: 293

Tyr Gly Arg Lys Lys Arg Arg Gln Arg Arg Arg
1               5                   10
```

…

BIOMATERIALS FOR MODULATING IMMUNE RESPONSES

RELATED APPLICATIONS

This application is a continuation of International Application No: PCT/US2017/045022, filed Aug. 2, 2017, which claims the benefit of priority under 35 U.S.C. § 119(e) to U.S. Provisional Application No. 62/473,699, filed Mar. 20, 2017, U.S. Provisional Application No. 62/460,652, filed Feb. 17, 2017, and U.S. Provisional Application No. 62/370,211, filed Aug. 2, 2016, the entire contents of each of which are incorporated herein by reference in their entireties.

GOVERNMENT SUPPORT

This invention was made with Government support under Grant No. R01EB015498 awarded by the National Institutes of Health. The Government has certain rights in the invention.

REFERENCE TO THE SEQUENCE LISTING

The content of the text file named "117823-16904_SEQ_LISTING.TXT", which was created on Jan. 30, 2019, is 299,940 bytes in size, is filed as part of this application, and is hereby incorporated herein in its entirety.

BACKGROUND

Dendritic cells (DCs) collect and process antigens for presentation to T cells. DCs are the most potent activators of the immune system among antigen presenting cells. Research focused on using dendritic cells for a therapeutic benefit has been slow because dendritic cells are rare and difficult to isolate.

BRIEF SUMMARY

The present subject matter provides devices, biomaterials, compositions, and methods for modulating an immune response.

In an aspect, provided herein is a device comprising a delivery vehicle comprising a scaffold composition and any combination of one or more compounds (e.g., one or more adjuvants and/or one or more antigens) disclosed herein. In embodiments, the device comprises PEI. In embodiments, the device does not comprise PEI. In embodiments, one or more adjuvants and/or one or more antigens is attached to (e.g., condensed with) PEI (e.g., covalently or non-covalently). Included herein are devices comprising a scaffold composition and any one of, or any combination of (e.g., in or on the scaffold composition), the following: (a) at least one antigen; (b) at least one immunostimulatory compound; (c) at least one compound that attracts an immune cell to or into the delivery vehicle; (d) at least one compound that induces immunogenic cell death of a tumor cell; (e) at least one compound that inhibits T-cell or dendritic cell suppression; and/or (f) at least one compound that inhibits an immune-inhibitory protein.

In an aspect, included herein is a method for increasing, enhancing, or promoting an immune response, comprising contacting one or more immune cells (such as dendritic cells or T-cells) with a device provided herein. Aspects of the present subject matter include a method for increasing, enhancing, or promoting an immune response (e.g., vaccination) in a subject, comprising administering a device provided herein to the subject. In embodiments, the immune response is to a cancer antigen (e.g., a neoantigen). In embodiments, the immune response is to a pathogen or parasite (e.g., a viral, bacterial, fungal, or protozoan pathogen or parasite).

In an aspect, a method of treating cancer in a subject is provided, the method comprising administering a device disclosed herein to the subject.

In an aspect, included herein is a method of increasing the immunogenicity of an antigen. In embodiments, the method comprises combining the antigen with PEI. In embodiments, the method comprises further combining the antigen with one or more or any combination of: (a) at least one immunostimulatory compound; (b) at least one compound that attracts an immune cell to or into the delivery vehicle; (c) at least one compound that induces immunogenic cell death of a tumor cell; (d) at least one compound that inhibits T-cell or dendritic cell suppression; and/or (e) at least one compound that inhibits an immune-inhibitory protein. In embodiments the combination is in a device that further comprises a scaffold composition. In embodiments, the combination is in or on the scaffold composition.

In an aspect, provided herein is a library of mesoporous silica rods comprising a plurality of mesoporous silica rods (e.g., different groups or types of mesoporous silica rods). In embodiments, the plurality of mesoporous silica rods comprises different mesoporous silica rods, wherein each mesoporous silica rod (e.g. each different group or type of mesoporous silica rods) comprises any one of the following: (a) at least one antigen; (b) at least one immunostimulatory compound; (c) at least one compound that attracts an immune cell to or into the delivery vehicle; (d) at least one compound that induces immunogenic cell death of a tumor cell; (e) at least one compound that inhibits T-cell or dendritic cell suppression; and/or (f) at least one compound that inhibits an immune-inhibitory protein. In embodiments, each mesoporous silica rod (e.g. each different group or type of mesoporous silica rods) comprises a different antigen than each other separate mesoporous silica rod (e.g. each other separate group or type of mesoporous silica rods). In embodiments, the library comprises one or more of any mesoporous silica rod disclosed herein.

In an aspect, included herein is a mixture of mesoporous silica rods comprising 2 or more mesoporous silica rods (e.g., different groups or types of mesoporous silica rods). In embodiments, the 2 or more mesoporous silica rods comprise different mesoporous silica rods, wherein each mesoporous silica rod (e.g. each different group or type of mesoporous silica rods) comprises any one of the following: (a) at least one antigen; (b) at least one immunostimulatory compound; (c) at least one compound that attracts an immune cell to or into the delivery vehicle; (d) at least one compound that induces immunogenic cell death of a tumor cell; (e) at least one compound that inhibits T-cell or dendritic cell suppression; and/or (f) at least one compound that inhibits an immune-inhibitory protein. In embodiments, each mesoporous silica rod (e.g. each different group or type of mesoporous silica rods) comprises a different antigen than each other separate mesoporous silica rod (e.g. each other separate group or type of mesoporous silica rods). In embodiments, the mixture comprises one or more of any mesoporous silica rod disclosed herein.

In an aspect, provided herein is a method of making a device (e.g., a vaccine device) comprising combining a scaffold composition (e.g., a polymeric composition, such as any polymeric composition disclosed herein) with PEI and/or any one of the following: (a) at least one antigen; (b) at least one immunostimulatory compound; (c) at least one compound that attracts an immune cell to or into the delivery vehicle; (d) at least one compound that induces immunogenic cell death of a tumor cell; (e) at least one compound that inhibits T-cell or dendritic cell suppression; and/or (f) at least one compound that inhibits an immune-inhibitory protein. In embodiments, the PEI is combined with any one of the following: (a) at least one antigen; (b) at least one immunostimulatory compound; (c) at least one compound that attracts an immune cell to or into the delivery vehicle; (d) at least one compound that induces immunogenic cell death of a tumor cell; (e) at least one compound that inhibits T-cell or dendritic cell suppression; and/or (f) at least one compound that inhibits an immune-inhibitory protein, before the PEI is combined with the scaffold composition. In embodiments, the scaffold composition is combined with PEI before it is combined with any one of the following: (a) at least one antigen; (b) at least one immunostimulatory compound; (c) at least one compound that attracts an immune cell to or into the delivery vehicle; (d) at least one compound that induces immunogenic cell death of a tumor cell; (e) at least one compound that inhibits T-cell or dendritic cell suppression; and/or (f) at least one compound that inhibits an immune-inhibitory protein.

The present subject matter includes a device, library, or mixture as provided herein for treating cancer, reducing tumor burden, eliciting an immune response to a tumor antigen, increasing the immunogenicity of an antigen, and/or treating an infection.

Aspects of the present subject matter relate to a device comprising (a) a delivery vehicle comprising a scaffold composition, and (b) (i) polyethylenimine (PEI); (ii) free PEI; (iii) PEI and an antigen; or (iv) PEI attached to an antigen. In various embodiments, the PEI may be present as, e.g., free PEI or PEI that is attached to another compound. As used herein, "free PEI" is PEI that is not attached to another compound, with the exception that free PEI may optionally have an electrostatic interaction with a structural component of a scaffold composition (e.g., a polymer or a mesoporous silica rod), e.g., cationic PEI associated with an anionic polymer of the device. PEI that is "attached" to another compound may be bound to the compound, e.g., via a covalent bond or an electrostatic interaction. For example, PEI may be attached to one or more antigens via a covalent bond or via an electrostatic interaction. In some embodiments, PEI electrostatically interacts with one or more antigens to form a nanoparticle. In certain embodiments, the nanoparticle is a cationic nanoparticle.

In an aspect, provided herein is a device comprising a delivery vehicle comprising a scaffold composition. In embodiments, the scaffold composition does not comprise an adjuvant (e.g., CpG or poly(I:C)), such as an adjuvant condensed by a substance, e.g., PEI. In embodiments, the device comprises, consists essentially of, or consists of a scaffold composition and PEI. In embodiments, the device does not comprise a TLR agonist. In embodiments, the device comprises an antigen but not a TLR agonist.

The present subject matter also includes a method of making a PEI-surface-modified device (e.g., a vaccine device) comprising coating a polymeric composition with PEI, and subsequently adsorbing an antigen (e.g., an antigen described herein) to the coated polymeric composition, thereby making a PEI-surface-modified device. In an aspect, included herein is a method of making a PEI-surface-modified MPS device (e.g., a vaccine device) comprising coating a plurality of MPS rods with PEI, and subsequently adsorbing an antigen (e.g., an antigen described herein) to the coated MPS rods, thereby making a PEI-surface-modified MPS device. Also included herein is a method of making a PEI-surface-modified PLG device (e.g., vaccine device) comprising coating a plurality of PLG spheres (e.g., microspheres) with PEI, and subsequently adsorbing an antigen (e.g., an antigen described herein) to the coated PLG spheres, thereby making a PEI-surface-modified PLG device. In embodiments, the method further comprises contacting the coated MPS rods or coated PLG spheres with: (a) an immunostimulatory compound; (b) a compound that attracts an immune cell to or into the delivery vehicle; (c) a compound that induces immunogenic cell death of a tumor cell; (d) a compound that inhibits T-cell or dendritic cell suppression; (e) a compound that inhibits an immune-inhibitory protein, or any combination thereof.

In embodiments where PEI is attached to a CpG oligodeoxynucleotide (CpG-ODN) or poly (I:C) via an electrostatic interaction in a cationic nanoparticle, a device or scaffold provided herein further comprises (i) free PEI, (ii) PEI that is attached to an antigen, or (iii) PEI that is attached to an immunostimulatory compound other than CpG-ODN or poly (I:C). In certain embodiments, the immunostimulatory compound is not a polynucleotide.

In some embodiments, PEI is attached to CpG-ODN, poly(I:C), or polyadenylic-polyuridylic acid (poly (A:U)), e.g., via an electrostatic interaction. In some embodiments, PEI is not attached to CpG-ODN, poly(I:C), or poly (A:U) via an electrostatic interaction. In various embodiments, a device, biomaterial, composition, or method does not comprise a nanoparticle (such as a cationic nanoparticle) comprising PEI and a polynucleotide. In certain embodiments, the device, biomaterial, composition, or methods does not comprise a nanoparticle (such as a cationic nanoparticle) comprising PEI and CpG-ODN, poly(I:C), or poly (A:U). In some embodiments where PEI is attached to CpG-ODN, poly (I:C), or poly (A:U) via an electrostatic interaction in a cationic nanoparticle, a device or scaffold provided herein further comprises (i) free PEI, (ii) PEI that is attached to an antigen, and/or (iii) PEI that is attached to an immunostimulatory compound other than CpG-ODN, poly (I:C), or poly (A:U). In certain embodiments, PEI is not attached to a polynucleotide via an electrostatic interaction. In various embodiments, PEI is not attached to a polynucleotide in a cationic nanoparticle. In some embodiments, a device, biomaterial, composition, or method provided herein does not include a polynucleotide. In some embodiments, a device, biomaterial, composition, or method provided herein does not include CpG-ODN, poly(I:C), or poly (A:U).

In certain embodiments PEI is attached to an antigen, e.g., a tumor antigen or a microbial antigen. In some implementations the antigen is a tumor peptide antigen. For example, a tumor antigen may comprise a tumor cell lysate, purified antigen, e.g., a protein or tumor antigen peptide (e.g., 5, 6, 7, 8, 9, 0, 15, 20, 50, 75, 100, 200 or more amino acids in length). In some examples, the antigen does not comprise a glycoprotein or a pathogen-derived antigen, e.g., a viral [such as human immunodeficiency virus (HIV) or influenza virus] antigen. In preferred embodiments, the tumor antigen/PEI combination elicits a cytotoxic T-cell response against the tumor/tumor antigen, thereby leading to or contributing to tumor regression. In various embodiments, PEI is attached to an antigen, such as a tumor antigen. For example, PEI may be attached to the antigen via an electrostatic interaction or may be covalently bound to the antigen. In some embodiments, a device or scaffold provided herein comprises an immunostimulatory complex comprising a cationic PEI polymer and a peptide antigen. Alternatively or in addition, the device or scaffold comprises an antigen and free PEI that is not attached to the antigen. In some embodiments, an antigen comprises a pathogen-associated antigen (e.g., a protein or a virulence factor, or an amino acid sequence or fragment thereof).

In various embodiments, the antigen comprises a neoantigen. In some embodiments, the neoantigen comprises a polypeptide comprising a stretch of about 10, 15, 20, 25, 30, 35, 40, 45, 50, 75, 100, 150, 200, 250, 10-250, 50-250, 100-250, or 50-150 amino acids (or at least about 10, 15, 20, 25, 30, 35, 40, 45, 50, 75, 100, 150, 200, or 250 amino acids) that is identical to a sequence of amino acids within a tumor antigen or oncoprotein [such as Her2, E7, tyrosinase-related protein 2 (Trp2), Myc, Ras, or vascular endothelial growth factor (VEGF)]. Non-limiting examples of neoantigens include polypeptides comprising amino acids in the sequence of the binding domain or a portion of the binding domain of a protein to which a therapeutic anti-cancer antibody such as trastuzumab binds. In various embodiments, an antigen comprises a fusion peptide that includes (i) a polypeptide comprising amino acids in a sequence found within an oncoprotein, combined (ii) with an epitope (e.g., a CD4 epitope) derived from a pathogen (e.g., a virus such as measles) or another highly immunogenic polypeptide. In a non-limiting example, the fusion peptide contains a CD4 epitope derived from measles linked to a polypeptide from an oncoprotein (such as Her2, E7, Trp2, Myc, Ras, or VEGF). In some embodiments, the epitope derived from a pathogen is derived from measles and comprises amino acids in the sequence: KLLSLIKGVIVHRLEGVEG (SEQ ID NO: 38). In certain embodiments, an antigen comprises a fusion peptide containing a CD4 epitope derived from measles linked to a short (e.g., about 10, 11, 12, 13, 14, 15, 16, 17, 18, 19, 20, 21, 22, 23, 24, 25, 30, 35, 40, 45, 50, 75, 100, 50-100, or 50-150 amino acids) linear domain within the trastuzumab binding domain on Her2. In some embodiments, the antigen comprises a linear domain within the trastuzumab binding domain on Her2 that comprises amino acids in the sequence KFPDEEGACQP. In certain embodiments, the antigen comprises (i) a polypeptide comprising amino acids in a sequence found within an oncoprotein, and (ii) an epitope (e.g., a CD4 epitope) derived from a pathogen (e.g., a virus such as measles) or another highly immunogenic polypeptide, wherein (i) and (ii) are connected by a linker. In some embodiments, the linker comprises about, e.g., 1, 2, 3, 4, 5, 6, 7, 8, 9, or 10 amino acids. In certain embodiments, the linker comprises amino acids in the sequence GPSL. In various embodiments, the neoantigen comprises a B16 neoantigen. In some embodiments, an antigen comprises any one of the following amino acid sequences: (i) the amino acid sequence of MVP-Her2: KLLSLIKGVIVHRLEGVEGPSLIWKFPDEEGACQPL (SEQ ID NO: 39) (in which KLLSLIKGVIVHRLEGVEG (SEQ ID NO: 38) is from measles, GPSL is a flexible linker, and IWKFPDEEGACQPL (SEQ ID NO: 40) is from Her2/neu); (ii) an amino acid sequence derived from the trastuzumab binding domain of Her2: KFPDEEGACQP (SEQ ID NO: 41); (iii) an amino acid sequence derived from the E7 oncoprotein: GQAEPDRAHYNIVTFCCKCD-STLRLCVQSTHVDIR (SEQ ID NO: 42); (iv) an amino acid sequence derived from the E7 oncoprotein: RAHYNIVTF (SEQ ID NO: 43); (v) an amino acid sequence from a B16-M27 neoantigen: REGVELCPGNKYEMRRHGTTHSLVIHD (SEQ ID NO: 44); an amino acid sequence from a B16-M30 neoantigen: PSKPSFQEFVDWENVSPELNSTDQPFL (SEQ ID NO: 45); an amino acid sequence from a B16-M47 neoantigen: GRGHLLGRLAAIVGKQVLLGRKVVVVR (SEQ ID NO: 46); an amino acid sequence from a M48 neoantigen: SHCHWNDLAVIPAGVVHNWDFEPRKVS (SEQ ID NO: 47); or an amino acid from a Trp2 neoantigen: SVYDFFVWLKFFHRTCKCTGNFAGGDDD (SEQ ID NO: 48). Additional non-limiting examples of neoantigens include SVGDFSQEFSPIQEA (SEQ ID NO: 49),
DFSQEFSPIQEAQQD (SEQ ID NO: 50),
LPGKIHLFEAEFTQV (SEQ ID NO: 51),
IHLFEAEFTQVAKKE (SEQ ID NO: 52),
HDLGRLHSCVMASLRAQ (SEQ ID NO: 53),
RTQLLWTPAAPTAMA (SEQ ID NO: 54),
DRASFLLTDYALSPD (SEQ ID NO: 55),
DRSVLAKKLKFVTLVFRHGDRSPID (SEQ ID NO: 56),
NNSKKKWFLFQDSKKIQVEQPQ (SEQ ID NO: 57),
SPIKLVQKVASKIPFPDRITEESV (SEQ ID NO: 58),
TKRQVILLHTELERFLEYLPLRF (SEQ ID NO: 59),
SHTQTTLFHTFYELLIQKNKHK (SEQ ID NO: 60),
RLVLGKFGDLTNNFSSPHAR (SEQ ID NO: 61),
LSPREEFLRLCKKIMMRSIQ (SEQ ID NO: 62),
PSTANYNSFSSAPMPQIPVASVTPT (SEQ ID NO: 63),
LCPREEFLRLCKKIMMRSIQ (SEQ ID NO: 64),
SHNELADSGIPENSFNVSSLVE (SEQ ID NO: 65),
SGSPPLRVSVGDFSQEFSPIQEAQQD (SEQ ID NO: 66),
RPAGRTQLLWTPAAPTAMAEVGPGHTP (SEQ ID NO: 67),
RGQIKLADFRLARLYSSEESR (SEQ ID NO: 68),
DEQGREAELARSGPSAAGPVRLKPGLVPGL (SEQ ID NO: 69),
AAVRPEQRPAARGSRV (SEQ ID NO: 70),
PETGEIQVKTFLDREQRESYELKV (SEQ ID NO: 71),
EVVGGYTWPSGNIYQGYWAQGKR (SEQ ID NO: 72),
TIKNSDKNVVLEHFG (SEQ ID NO: 73),
TRNSFALVPSLQRLMLRKVALKNVDSSPS (SEQ ID NO: 74),
SSHYKFSKPALQSQSISLVQQS (SEQ ID NO: 75),
TETVNHHYLLFQNTDLGSFHDLLR (SEQ ID NO: 76),
DRASFLLTDYALSPDGSIRKATG (SEQ ID NO: 77),
ERFWRNILLLSLHKGSLYPRIPGLGKE (SEQ ID NO: 78),
RGRLPAGAVRTLLSQVNKVWDQSS (SEQ ID NO: 79),
GHEHQPDMQKSLLRAAFFGKCFLDR (SEQ ID NO: 80),
ELQYRGRELRFNLIANQHLLAPGFVSETR (SEQ ID NO: 81),
EDLDANLRKLNFRLFVIRGQPAD (SEQ ID NO: 82),
GHQKLPGKIHLFEAEFTQVAKKEPDG (SEQ ID NO: 83),
TTPSGSAEYMASEVVEVFTDQAT (SEQ ID NO: 84),
SVLREDLGQLEYKYQYAYFRMGIKHPD (SEQ ID NO: 85),
PENDDLFMMPRIVDVTSLATEGG (SEQ ID NO: 86),
TLDDIKEWLEDEGQVLNIQMRRTLHK (SEQ ID NO: 87),
GRMSPSQFARVPGYVGSPLAAMNPK (SEQ ID NO: 88),
KAHVEGDGVVEEIIRYHPFLYDRET (SEQ ID NO: 89),
DGVSEEFWLVDLLPSTHYT (SEQ ID NO: 90),
DSYHLYAYHEELSATVPSQWKKIG (SEQ ID NO: 91),
GDQYKATDFVADWAGTFKMVFTPKDGSG (SEQ ID NO: 92), EYWKVLDGELEVAPEYPQSTARDWL (SEQ ID NO: 93),
TTTSVKKEELVLSEEDFQGITPGAQ (SEQ ID NO: 94),
SLTEESGGAVAFFPGNLSTSSSA (SEQ ID NO: 95),
KLRTIPLSDNTIFRRICTIAKHLE (SEQ ID NO: 96),
SHHTHSYQRYSHPLFLPGHRLDPPI (SEQ ID NO: 97),
DVTGPHLYSIYLHGSTDKLPYVTMGS (SEQ ID NO: 98),
ARLQSKEYPVIFKSIMRQRLISPQL (SEQ ID NO: 99),
LHTHYDYVSALHPVSTPSKEYTSA (SEQ ID NO: 100),
SDAFSGLTALPQSILLFGP (SEQ ID NO: 101),
SHQIHSYQLYTHPLLHPWDHRD (SEQ ID NO: 102),
STQHADLTIIDNIKEMNFLRRYK (SEQ ID NO: 103),
ASATEPANDSLFSPGAANLFSTYLAR (SEQ ID NO: 104),
AASAAAFPSQRTSWEFLQSLVSIKQEK (SEQ ID NO: 105),
GSVLQFMPFTTVSELMKVSAMSSPKV (SEQ ID NO: 106),
DKGHQFHVHPLLHSGDDLDP (SEQ ID NO: 107),
NQVLASRYGIRGFSTIKIFQKGESPV (SEQ ID NO: 108),
MAGPKGFQYRALYPFRRER (SEQ ID NO: 109),
VTLNDMKARQKALVRERERQLA (SEQ ID NO: 110),
SRLQTRKNKKLALSSTPSNIAPSD (SEQ ID NO: 111),
LNTGLFRIKFKEPLENLI (SEQ ID NO: 112),
SLRNNMFEISDRFIGIYKTYNITK (SEQ ID NO: 113),
WCTEMKRVFGFPVHYTDVSNMS (SEQ ID NO: 114),
VKQLERGEASVVDFKKNLEYAAT (SEQ ID NO: 115),
STEVEPKESPHLARHRHLMKTLVKSLST (SEQ ID NO: 116),
LMSNLAFADFCMRMYL (SEQ ID NO: 117),
TKLKSKAPHWTNCILHEYKNLSTS (SEQ ID NO: 118),
PAAGDFIRFRFFQLLRLERFF (SEQ ID NO: 119),
YLSHTLGAASSFMRPTVPPPQF (SEQ ID NO: 120),
ALLQNVELRRNVLVSPTPLAN (SEQ ID NO: 121),
FAKGFRESDLNSWPVAPRPLLS V (SEQ ID NO: 122),
GLTRISIQRAQPLPPCLPSFRPPTALQGLS (SEQ ID NO: 123),
TGKPEMDFVRLAQLFARARPMGLF (SEQ ID NO: 124),
DGAWPVLLDKFVEWYKDKQMS (SEQ ID NO: 125),
DRSVLAKKLKFVTLVFRHGDRSPID (SEQ ID NO: 126),
DRSVLAKKLKFVTLVFRHGDRSPID (SEQ ID NO: 127),
TKRQVILLHTELERFLEYLPLRF (SEQ ID NO: 128),
LGETMGQVTEKLQPTYMEET (SEQ ID NO: 129),
TFPKKIQMLARDFLDEY (SEQ ID NO: 130),
ERFWRNILLLSLHKGSLYPRIPGLGKE (SEQ ID NO: 131),
RGRLPAGAVRTLLSQVNKVWDQSS (SEQ ID NO: 132),
GHEHQPDMQKSLLRAAFFGKCFLDR (SEQ ID NO: 133),
KMQRRNDDKSILMHGLVSLRESSRG (SEQ ID NO: 134),
STLPVISDSTTKRRWSALVIGL (SEQ ID NO: 135),
KLRTIPLSDNTIFRRICTIAKHLE (SEQ ID NO: 136),
PASAKSRREFDKIELAYRR (SEQ ID NO: 137),
ARLQSKEYPVIFKSIMRQRLISPQL (SEQ ID NO: 138),
FPVVQSTEDVFPQGLPNEYAFVT (SEQ ID NO: 139),
FPVVQSTEDVFPQGLPNEYAFVT (SEQ ID NO: 140),
FPVVQSTEDVFPQGLPNEYAFVT (SEQ ID NO: 141),
VTLNDMKARQKALVRERERQLA (SEQ ID NO: 142),
LNTGLFRIKFKEPLENLI (SEQ ID NO: 143),
KVVQHALDKARTGKTCLVVTHRLSAIQ (SEQ ID NO: 144),
NQEAFKHLYFEKFSGYYDTMDAGYMDE (SEQ ID NO: 145),
PSFLGMESCGIHEITFNSIMKCDVDIR (SEQ ID NO: 146),
YPKGAGEMLEDQQAARMEKLAGLVEEL (SEQ ID NO: 147),
KEELQKSLNILTALQKKGAEKEEL (SEQ ID NO: 148),
VTCVPNGTWRNYKVEVRFEPRHRPTRF (SEQ ID NO: 149),
VFDTAFSRHFSLLKSQREFVRRFRGQA (SEQ ID NO: 150),
PQTLGKKGSKNNIFVYMTLNQKKSDSS (SEQ ID NO: 151),
CEDCRTRGQFNAFPYHFRGRRSLEFSY (SEQ ID NO: 152),
SPELSAAESAVVLNLLMSLPEELPLLP (SEQ ID NO: 153),
VFARVAPKQKEFVFTSLKELGYVTLMC (SEQ ID NO: 154),
SADARLMVFDKTERTWRLLCSSRSNAR (SEQ ID NO: 155),
MGPLLVATFWPELSEKIDAVYEAPQEE (SEQ ID NO: 156),
CGPCSEKRFLLPSRSSKPVRICDFCYD (SEQ ID NO: 157),
LTVTLRSPTWMRMNQGVCCNLEYHSSG (SEQ ID NO: 158),
LHSNVLARIDAAALTGLALLEQLDLSD (SEQ ID NO: 159),
LTAVRPEGSEPPGLPTSGPRRRPGCSR (SEQ ID NO: 160),
ALPSLTCSLTPLGVALVLWTVLGPC (SEQ ID NO: 161),
GGGTGDSEGSGALRSLTCSLTPLGLAL (SEQ ID NO: 162),
DVEERVQKSFPHPVDKWAIADAQSAIE (SEQ ID NO: 163),
SPGDLDVFVRFDFLYPNVEEAQKDKTS (SEQ ID NO: 164),
DFIAGFCGETEEDYVQTVSLLREVQYN (SEQ ID NO: 165),
RSQMTTSFTDPAIFMDLLRAVLQPSIN (SEQ ID NO: 166),
TAAGIHPQISSIFILGSLVYFSQEASR (SEQ ID NO: 167),
RKDLLKANVKIFKFQGAALDKYAKKSV (SEQ ID NO: 168),
HVLSGLSKDKEKRKENVRNSFWIYDIV (SEQ ID NO: 169),
KTEWKSNVYLARSWIQGLGLYAARDIE (SEQ ID NO: 170),
PPTPLLNTTSSLSEYPLGRADFDHYTG (SEQ ID NO: 171),
LFLALLAGAHAEFSGCKIRVTSKALEL (SEQ ID NO: 172),
FTRAFDQIRMAAIFESNINLCGSHCGV (SEQ ID NO: 173),
GKSYQLLVVENTVKVAQFINNNPEFLQ (SEQ ID NO: 174), SRWDDSQRFLSDHLYLVCEETAKYLIL (SEQ ID NO: 175),
ITKHLYEDPRQHSSGVLTDLRSALVNN (SEQ ID NO: 176),
DVEERHHAYLKPFCVLISLLDKPEIGP (SEQ ID NO: 177),
ATGQSAFAQVIADCHKILFDRNSAIKS (SEQ ID NO: 178),
VTVLFAGQHIAKSLFEVYVDKSQGDAS (SEQ ID NO: 179),
VNAVFEWHITKGGIIGAKWTIDLKSGS (SEQ ID NO: 180),
SSSTTNNDPYAKPSDTPRPVMTDQFPK (SEQ ID NO: 181),
MTEYKLVVVGAGDVGKSALTIQLIQN (SEQ ID NO: 182),
VKLLIGNRDSLDNLYYDWYILVTNKCH (SEQ ID NO: 183),
MAISFLTTLAKVYSSSLSKISGSILNE (SEQ ID NO: 184),
VLSHVSGLGWLASNLPSFLRVPKWIIA (SEQ ID NO: 185),
IAELENKNREILQKIQRLRLEHEQASQ (SEQ ID NO: 186),
PKGMPKDLNVGQQSLSNSGISEVEGLS (SEQ ID NO: 187),
LAVGHLYRLSFLKKDSQSCRVAALEAS (SEQ ID NO: 188),
PLPPHPHPHPHSVVLPPAHLPVQQQQP (SEQ ID NO: 189),
MPPLPIFSLPWSVHTWTQGP (SEQ ID NO: 190),
AKTVKHGAGAEISIVNPEQYSKRFLDF (SEQ ID NO: 191),
PSRAGRPHHDQRSLSPHLGRSKSPPSH (SEQ ID NO: 192),
PPPPPQNNKPPVPFTPRPSASSQAPPP (SEQ ID NO: 193),
VVYSILQGQPYFSLDPKTGVIRTALHN (SEQ ID NO: 194),
EIGWLKPVIGSQYLLEKVAEAHENIIH (SEQ ID NO: 195),
VVCYQSNRDELRRCIIQWLEAEIIPDG (SEQ ID NO: 196),
AVVDTLESEYLKISGDQVVSVVFIKEL (SEQ ID NO: 197),
KEAKRSNSNKTMDLSCLKWTPPKGT (SEQ ID NO: 198),
RDWAFVPAPCATSSYTGFANKHGSKPS (SEQ ID NO: 199),
LSKVTKVKTDRPLLENPYHSRPRPDPS (SEQ ID NO: 200),
MAAVSVYAPLVGGFSFDNCRRNA (SEQ ID NO: 201),
DTPPFYSNSTNSFQNTVEGYSDPTGKY (SEQ ID NO: 202),
KSRPGSVVPTTLFKGIKTVNPTFRGYS (SEQ ID NO: 203),
IGLIFVVDSNDREQVNEAREELMRMLA (SEQ ID NO: 204),
QGLIFVVDSNDREQVNEAREELMRMLA (SEQ ID NO: 205),
SRKKRGCSSSKYASSYYHVMPKQNSTL (SEQ ID NO: 206),
AMAATCISDTLGIFLSGLLALPLHDFL (SEQ ID NO: 207),
KLIVQIKGSVEDISVMLVGNKCDETQR (SEQ ID NO: 208),
GHQENAKNEEILNFLKYVRPGGGFEPN (SEQ ID NO: 209),
SILDLFLGRWFRSW (SEQ ID NO: 210),
RAQCHGHGRCVRRHPSASTFLHLSTNS (SEQ ID NO: 211),
TSLELPMAMRFRHFKKTSKEAVGVYRS (SEQ ID NO: 212),
CGKDFSQRAHLTIYQRTHTGEKPYKCL (SEQ ID NO: 213),
KETTEAACRYGAFRLPITVAHVDGQTH (SEQ ID NO: 214),
ELVTEGVAESLFLLRTDYSFHKFHYLT (SEQ ID NO: 215),
AVRQAEKYYILRPDVIETYWYLWRFTH (SEQ ID NO: 216),
SVLHLVLALRGGGSLRQ (SEQ ID NO: 217),
QAVFSTSSRFWSSSPLLGQQPGPSQDI (SEQ ID NO: 218),
PQWQKDELRETLKFLKKVMDDLDRASK (SEQ ID NO: 219),
VIKDGCIVERGRHKALLSRGGVYADMW (SEQ ID NO: 220),
RAESDVERKEWMQVLQQAMAEQRARAR (SEQ ID NO: 221),
RSLRKINSAPPTEIKSLRIASRSTRHS (SEQ ID NO: 222),
SNKYDPPLEDGAMLSARLRKLEVEANN (SEQ ID NO: 223),
SDRCKDFSLCYWNLYWMLPSDVCGMNC (SEQ ID NO: 224),
GVKLVVETPEETLLTYQGASVILPCRY (SEQ ID NO: 225),
GMSTAMGRSPSPKISLSAPPNSSSTEN (SEQ ID NO: 226),
GGPPSPPPGIPGQSLPSPTRLHLGGGR (SEQ ID NO: 227),
QVGRMERELNHEKVRCDQLQAEQKGLT (SEQ ID NO: 228),
EDAELAEAAENSLFSYNSEVDEIPDEL (SEQ ID NO: 229),
EIGVGAYGTVYKALDPHSGHFVALK5V (SEQ ID NO: 230),
IQVGSLLGAVAMFSPTSIYHVFHSRKD (SEQ ID NO: 231),
GYLLKLSAMGWGFSIFLVTLVALVDVD (SEQ ID NO: 232),
IDNLSASNHSVAEVLLLFLESLPEPVI (SEQ ID NO: 233),
AVLDLQLRSAPAAFERPLWDTSLRAPS (SEQ ID NO: 234),
FLRKTECHCQIVNFGAGMDTTFWRLKD (SEQ ID NO: 235),
YAGYSFEKLFPDVFFPADSEHNKLKAS (SEQ ID NO: 236),
RPGFVFAPCPHELSCPQLTNLACSFSQ (SEQ ID NO: 237),
KKFIRRDFLLDEAIGLLPDDKLTLFCE (SEQ ID NO: 238),
ELRKEYGMTYNDFLMVLTDVDLRVKQY (SEQ ID NO: 239),
KFGQGLEDQLAQTKSLSLDDC (SEQ ID NO: 240),
HLLLVYTGKTRLAWNLLQDVLRSWYAR (SEQ ID NO: 241),
PVPGVPFRNVDNDFPTSVELEDWVDAQ (SEQ ID NO: 242),
STKVESLVALLNNFSEMKLVQMKWHEA (SEQ ID NO: 243), LFGQLAAFAGRKWIKFFTSQVKQTRDS (SEQ ID NO: 244),
VPLERGAPNKEETSATESPDTGLYYHR (SEQ ID NO: 245),
YCMHHSLVEFHLKKLRNKDTNIEVTFL (SEQ ID NO: 246),
QIKISTRKQKSVKVISSYTPKDCTSRN (SEQ ID NO: 247),
ILTVLQCATVIGFFYWASELILAQQQQ (SEQ ID NO: 248),
VRLFLDSKHPGHYVVYNLSPRTYRPSR, (SEQ ID NO: 249)
SHTKGIWMWCVPHFKKPGHILVLLDTE (SEQ ID NO: 250),
STLISVPDRDPASFLRMANSALISVGC (SEQ ID NO: 251),
FAESADAALQGDPVLQDAGDSSRKEYF (SEQ ID NO: 252),
ANLEIMTKRSNYTSITNDKFTPPVVNV (SEQ ID NO: 253),
EQTLVLQIVAGILYLGNISFKEVGNYA (SEQ ID NO: 254),
KYTAQESREMFPRLFIRLLRSKVSRFL (SEQ ID NO: 255),
RDEEVSSADISSSFEVISQHLVSYRNI (SEQ ID NO: 256),
SQNTDMVQKSVSKILPSTWSDPSVNIS (SEQ ID NO: 257),
DEIPLYLKGGVADVLLYRATMILTVGG (SEQ ID NO: 258),
IIARTDLKKNRDYRLASKDAKKQLLCG (SEQ ID NO: 259),
LFRHLLSSDQMMDYILADEAFFSVNSS (SEQ ID NO: 260),
WESVKLLFVKTEKLAALPIFSSFVSNW (SEQ ID NO: 261),
VLSEERAALLELWKLRRQQYEQCMDLQ (SEQ ID NO: 262),
EKRQAKYSENKLKLIKARNEYLLTLEA (SEQ ID NO: 263),
KSHRLPRLPKRHSYDDMLLLAQLSLPS (SEQ ID NO: 264),
MSEFRIYHDVNELLSLLRVH (SEQ ID NO: 265), and
TRLSKVFSAMLAIYSNKPALWIMAAKW (SEQ ID NO: 266), or a fragment thereof.

In various embodiments, cancer neoantigens arise from mutations that lead to antigen expression on cancer cells that are not shared by other host cells in the body. Thus, in some embodiments, a cancer neoantigen is not encoded by the host genome (i.e., the genome of noncancerous cells in the subject). In certain embodiments, these neoantigens may or may not have been previously recognized by the immune system prior to immunotherapy techniques, such as vaccination, that seek to enhance their immunogenicity. In various embodiments, neoantigens are proteins or peptides (typically 8 or more amino acids) that contain mutant epitope sequences. In some embodiments, the mutant sequence arises from a single point mutation. In certain embodiments, the mutation is in an ATP-binding cassette, sub-family B (MDR/TAP), member 5 (ABCB5), acyl-CoA synthetase short-chain family member 3 (ACSS3), actin, gamma 1 (ACTG1), anaphase promoting complex subunit 16 (ANAPC16), endoplasmic reticulum protein 29 (ERP29), family with sequence similarity 101, member B (FAM101B), nuclear prelamin A recognition factor-like (NARFL), PWWP domain containing 2A (PWWP2A), peroxidasin homolog (Drosophila) (PXDN), small nuclear RNA activating complex, polypeptide 2, 45 kDa (SNAPC2), ATPase type 13A1, hepsin, matrix metallopeptidase 2 (gelatinase A, 72 kDa gelatinase, 72 kDa type IV collagenase), pleckstrin homology domain containing family F (with FYVE domain) member 2, protein tyrosine phosphatase receptor type f polypeptide (PTPRF) interacting protein (liprin), alpha 4 (PPFIA4), reticulon 4 receptor (RTN4R), son of sevenless homolog 1 (Drosophila) (SOS1), coiled-coil and C2 domain containing 1A (CC2D1A), CDK5 regulatory subunit associated protein 1 (CDK5RAP1), deoxynucleotidyltransferase, terminal, interacting protein 1 (DNTTIP1), insulin induced gene 1 (INSIG), malate dehydrogenase 1, NAD (soluble) (MDH1), muskelin 1, intracellular mediator containing kelch motifs (MKLN1), myeloid/lymphoid or mixed-lineage leukemia 3 (MLL3), pleckstrin homology-like domain family B member 2 (PHLDB2), phospholipid transfer protein (PLTP), transketolase (TKT), complement component 7 (C7), cell division cycle 37-like 1 (CDC37L1), dicer 1, ribonuclease type III (DICER1), dopey family member 2 (DOPEY2), dermatan sulfate epimerase (DSE), filamin A alpha (FLNA), hydroxysteroid (17-beta) dehydrogenase 4 (HSD17B4), neuroblastoma RAS viral (v-ras) oncogene homolog (NRAS), sterile alpha motif domain containing 9-like (SAMD9L), cullin-associated and neddylation-dissociated 1 (CAND1), dehydrogenase/reductase (SDR family) member 1 (DHRS1), dystrobrevin, beta (DTNB), family with sequence similarity 135, member B (FAM135B), MMS19 nucleotide excision repair homolog (S. cerevisiae) (MMS19), MAX binding protein (MNT), nuclear receptor subfamily 4, group A, member 1 (NR4A1), phosphatidylinositol-5-phosphate 4-kinase, type II, alpha (PIP4K2A), tau tubulin kinase 2 (TTBK2), WAS/WASL interacting protein family member 1 (WIPF1), Cadherin 18 Type 2 (CDH18), crystallin, zeta (quinone reductase) (CRYZ), follistatin-like 1 (FSTL1), heparan sulfate proteoglycan 2 (HSPG2), K (lysine) acetyltransferase 7 (KAT7), kinesin family member 26B (KIF26B), NADH dehydrogenase (ubiquinone) 1 alpha subcomplex 8 19 kDa (NDUFA8), proteasome (prosome, macropain) subunit beta type 7 (PSMB7), tyrosinase-related protein 1 (TYRP1), ubiquitin specific peptidase 33 (USP33), ADP-ribosylation factor 3 (ARF3), ATPase family, AAA domain containing 2 (ATAD2), ceroid-lipofuscinosis, neuronal 3 (CLN3), DIRAS family GTP-binding RAS-like 1 (DIRAS1), glutathione peroxidase 1 (GPX1), HCLS1 associated protein X-1 (HAX1), hyaluronoglucosaminidase 2 (HYAL2), myeloid/lymphoid or mixed-lineage leukemia 4 (MLL4), zinc finger protein 287 (ZNF287), glutathione S-transferase kappa 1 (GSTK1), major histocompatibility complex, class II, DP alpha 1 (HLADPA1), mannosidase, alpha, class 1A, member 2 (MAN1A2), neural precursor cell expressed, developmentally downregulated 8 (NEDD8), TEA domain family member 3 (TEAD3), alanyl-tRNA synthetase (AARS), ATP-binding cassette, sub-family B (MDR/TAP) member 6 (ABCB6), ArfGAP with RhoGAP domain ankyrin repeat and PH domain 1 (ARAP1), bromodomain adjacent to zinc finger domain 1A (BAZ1A), capping protein (actin filament) muscle Z-line beta (CAPZB), glucoside xylosyltransferase 1 (GXYLT1), hyaluronan and proteoglycan link protein 3 (HAPLN3), interferon, gamma-inducible protein 16 (IFI16), sema domain, immunoglobulin domain (Ig) transmembrane domain (TM) and short cytoplasmic domain (semaphorin) 4C (SEMA4C), Tax1 (human T-cell leukemia virus type I) binding protein 1 (TAX1BP1), coiled-coil domain containing 111 (CCDC111), cyclin-dependent kinase 4 (CDK4), G protein-coupled receptor 172A (GPR172A), G protein-coupled receptor 56 (GPR56), inositol polyphosphate-5- phosphatase, 75 kDa (INPP5B), KIAA0415 (KIAA0415), leucine carboxyl methyltransferase 1 (LCMT1), mitogen-activated protein kinase 8 (MAPK8), methyltransferase like 17 (METTL17), speckle-type POZ protein (SPOP), coiled-coil domain containing 80 (CCDC80), double zinc ribbon and ankyrin repeat domains 1 (DZANK1), fucokinase (FUK), melanoma antigen family C, 2 (MAGEC2), mediator complex subunit 24 (MED24), maestro (MRO), nucleobindin 1 (NUCB1), phospholipase A1 member A (PLA1A), senataxin (SETX), transmembrane protein 127 (TMEM127), cyclin G associated kinase (GAK), guanylate binding protein 1, interferon-inducible (GBP1), glycoprotein (transmembrane) nmb (GPNMB), glycophorin C (Gerbich blood group) (GYPC), major histocompatibility complex, class II, DR alpha (HLA-DRA), myosin IE (MYO1E), retinol saturase (all-trans-retinol 13,14-reductase) (RETSAT), RWD domain containing 3 (RWDD3), signal peptide CUB domain EGF-like 2 (SCUBE2), translocated promoter region (to activated MET oncogene) (TPR), clathrin interactor 1 (CLINT1), cytochrome c oxidase subunit VIIa polypeptide 2 (liver)(COX7A2), IMP (inosine 5'-monophosphate) dehydrogenase 2 (IMPDH2), protein kinase, DNA-activated, catalytic polypeptide (PRKDC), ribosomal L1 domain containing 1 (RSL1D1), spectrin, alpha, non-erythrocytic 1 (alpha-fodrin) (SPTAN1), SLIT-ROBO Rho GTPase activating protein 1 (SRGAP1), suppression of tumorigenicity 5 (ST5), tubulin, gamma complex associated protein 2 (TUBGCP2), UTP6, small subunit (SSU) processome component homolog (yeast) (UTP6), acid phosphatase prostate (ACPP), Dephospho-CoA Kinase Domain Containing (DCAKD), DEAD-Box Helicase 3, X-Linked (DDX3X), caspase 1 (CASP1), caspase 5 (CASPS), Proline Rich Coiled-Coil 2C (PRRC2C), lumican (LUM), RUN And SH3 Domain Containing 2 (RUSC2), Adrenomedullin 2 (ADM2), Cyclin Dependent Kinase 13 (CDK13), Protocadherin 1 (PCDH1), Junctophilin 1 (JPH1), Toll Like Receptor 3 (TLR3), Transmembrane Protein 260 (C14orf101), Citron Rho-Interacting Serine/Threonine Kinase (CIT), DEAH-Box Helicase 40 (DHX40), Family With Sequence Similarity 200 Member A (FAM200A), Glutamate Ionotropic Receptor NMDA Type Subunit 2B (GRIN2B), Collagen Type XXII Alpha 1 Chain (COL22A1), RALGAPB (Ral GTPase Activating Protein Non-Catalytic Beta Subunit), Family With Sequence Similarity 50 Member B (FAM50B), Family With Sequence Similarity 190, Member A (FAM190A), Protogenin (PRTG), NLR Family CARD Domain Containing 4 (NLRC4), Adenosine Deaminase, RNA Specific B1 (ADARB1), General Transcription Factor IIIC Subunit 2 (GTF3C2), Potassium Voltage-Gated Channel Subfamily C Member 3 (KCNC3), Vacuolar Protein Sorting Protein 16 (VPS16), Cryptochrome Circadian Clock 1 (CRY1), ADAM Metallopeptidase With Thrombospondin Type 1 Motif 7 (ADAMTS7), Rho GTPase Activating Protein 29 (ARHGAP29), MAP Kinase Interacting Serine/Threonine Kinase 1 (MKNK1), Mitochondrial Transcription Termination Factor 4 (MTERFD2), MAX Gene-Associated Protein (MGA), Sjogren Syndrome Antigen B (SSB), Structural Maintenance Of Chromosomes Flexible Hinge Domain Containing 1 (SMCHD1), Tenascin R (TNR), Activating Transcription Factor 7 Interacting Protein (ATF7IP), Isocitrate Dehydrogenase (NADP(+)) 2 Mitochondrial (IDH2), Matrix Metallopeptidase 17 (MMP17), RNF40 (Ring Finger Protein 40), T-Box 4 (TBX4), Mucin 5B Oligomeric Mucus/Gel-Forming (MUCSB), Fidgetin, Microtubule Severing Factor (FIGN), Zinc Finger FYVE-Type Containing 26 (ZFYVE26), Zinc Finger Protein 281 (ZNF281), Phosphoinositide-3-Kinase Regulatory Subunit 2 (PIK3R2), Protein Disulfide Isomerase Family A Member 6 (PDIA6), Structural Maintenance Of Chromosomes 4 (SMC4), Thyroid Stimulating Hormone Receptor (TSHR), Krev Interaction Trapped 1 (KRIT1), Mannosyl (Alpha-1,3-)-Glycoprotein Beta-1,4-N-Acetylglucosaminyltransferase Isozyme B (MGAT4B), SET Binding Protein 1 (SETBP1), Nuclear Receptor Coactivator 6 (NCOA6), Tensin 1 (TNS1), Defective In Cullin Neddylation 1 Domain Containing 4 (DCUN1D4), Her2, Trp2, Myc, Ras, vascular endothelial growth factor (VEGF), Eukaryotic Translation Elongation Factor 2 (EEF2), DEAD-Box Helicase 23 (DDX23), GNAS Complex Locus (GNAS), Transportin 3 (TNPO3), Tubulin Beta 3 Class III (Tubb3), ATPase Phospholipid Transporting 11A (ATP11A), Anti-Silencing Function 1B Histone Chaperone (ASF1B), Dystroglycan 1 (DAG1), Procollagen-Lysine,2-Oxoglutarate 5-Dioxygenase 1 (PLOD1), Obscurin Like 1 (OBSL1), Protein Phosphatase 1 Regulatory Subunit 7 (PPP1R7), Methylenetetrahydrofolate Dehydrogenase (NADP+Dependent) 1-Like (MTHFD1L), Kinesin Family Member 18B (KIF18B), PDZ Binding Kinase (PBK), Transmembrane 9 Superfamily Member 3 (TM9SF3), Cleavage And Polyadenylation Specific Factor 3 (CPSF3L), Makorin Ring Finger Protein 1 (MKRN1), ACTININ ALPHA 4 (ACTN4), Ribosomal Protein L13a (RPL13A), Differentially Expressed In FDCP 8 Homolog (DEF8), Semaphorin 3B (SEMA3B), Solute Carrier Family 20 Member 1 (SLC20A1), Glypican 1 (GPC1), Nephrocystin 3 (NPHP3), Transmembrane Protein 87A (TMEM87A), Solute Carrier Family 4 Member 3 (SLC4A3), Chemokine (C-X-C Motif) Receptor 7 (CXCR7), E2F Transcription Factor 8 (E2F8), Alanine-Glyoxylate Aminotransferase 2-Like 2 (AGXT2L2), Nucleosome Assembly Protein 1 Like 4 (NAP1L4), DEAH-Box Helicase 35 (DHX35), Amyotrophic Lateral Sclerosis 2 Chromosomal Region Candidate Gene 6 Protein (ALS2), DEP Domain Containing MTOR Interacting Protein (DEPTOR), Thymine DNA Glycosylase (TDG), Dickkopf WNT Signaling Pathway Inhibitor 2 (DKK2), RNA Polymerase II Associated Protein 2 (RPAP2), STEAP2 Metalloreductase (STEAP2), Ubiquitin Specific Peptidase 26 (USP26), Neurobeachin (NBEA), Aldehyde Dehydrogenase 18 Family Member A1 (ALDH18A1), Zinc Finger CCCH-Type Containing 14 (ZC3H14), Drosha Ribonuclease III (DROSHA), Gen Endonuclease Homolog 1 (GEN1), RNA Polymerase II Subunit A (POLR2A), Transmembrane And Tetratricopeptide Repeat Containing 2 (TMTC2), Zinc Finger RNA Binding Protein (ZFR), Centrosomal Protein 120 (CEP120), Mucosa Associated Lymphoid Tissue Lymphoma Translocation Gene 1 (MALT1), WD Repeat Domain 11 (WDR11), Kelch Repeat And BTB Domain Containing 2 (KBTBD2), ADAM Metallopeptidase With Thrombospondin Type 1 Motif 9 (ADAMTS9), Pregnancy-Zone Protein (PZP), G Protein-Coupled Receptor Class C Group 5 Member A (GPRC5A), Energy Homeostasis Associated (ENHO), Doublesex- And Mab-3-Related Transcription Factor 5 (DMRTA2), Ras Related GTP Binding D (RRAGD), Zinc Finger ZZ-Type Containing 3 (ZZZ3), ILK ASSOCIATED SERINE/THREONINE PHOSPHATASE (ILKAP), or Centromere Protein F (CENPF) gene that results in a mutant amino acid sequence (e.g., a substitution or insertion) in a protein that is encoded and expressed by the gene. Additional non-limiting examples of neoantigen sequences and genes from which neoantigens may arise, as well as exemplary methods for identifying neoantigen sequences are described in Kreiter et al. (2015) *Nature* 520(7549): 692-696, Ott et al. (2017) *Nature* 547:217-221, and Sahin et al. (2017) *Nature* 547: 222-226, the entire contents of each of which are incorporated herein by reference.

As used herein the term "antigen" is a substance that induces an immune response.

As used herein the term "neoantigen" is an antigen that has at least one alteration that makes it distinct from the corresponding wild-type, parental form of the antigen. For example, a neoantigen may occur via mutation in a tumor cell or post-translational modification specific to a tumor cell. In various embodiments, a neoantigen is a gene product. A neoantigen can include a polypeptide sequence or a nucleotide sequence. A mutation can include a frameshift or nonframeshift indel, point mutation, missense or nonsense substitution, splice site alteration, genomic rearrangement or gene fusion, or any genomic or expression alteration giving rise to a DNA or RNA (such as mRNA) molecule that is distinct from corresponding wild-type DNA or RNA. A mutation can also include a splice variant. Post-translational modifications specific to a tumor cell can include aberrant phosphorylation. Post-translational modifications specific to a tumor cell can also include a proteasome-generated spliced antigen. See Liepe et al., A large fraction of HLA class I ligands are proteasome-generated spliced peptides; Science. 2016 Oct. 21; 354(6310):354-358, the entire contents of which are incorporated herein by reference.

As used herein the term "tumor neoantigen" is a neoantigen present in a subject's tumor cell or tissue but not in the subject's corresponding normal cell or tissue.

Included herein are mesoporous silica (MPS) nanoparticles or microparticles. Non-limiting examples include MPS rods. In some embodiments, the MPS rods comprise surface modification (e.g., the MPS rods have been treated with a substance such as glycolic acid or lactic acid, have been conjugated to an amine, thiol, chloro, or phosphonate group, or a compound such as PEI has been added to the MPS rods). In various embodiments a surface modified MPS rod is an MPS rod to which free PEI has been added. A rod is a straight substantially cylindrical structure that is longer than it is wide.

In some embodiments, free PEI is added to a scaffold (such as MPS, e.g., MPS rods, or a polymer) separately from another compound such as an antigen (such as an antigen comprising a polypeptide associated with cancer or a pathogen) an immunostimulatory compound (such as a TLR agonist or a STING agonist), and/or an immune suppression inhibitor. In certain embodiments, free PEI is added to a scaffold before (e.g., at least about 1, 6, 12, 15, 30, 60, 120, or 1-120 seconds or minutes before or less than about 1, 6, 12, 15, 30, 60, 120, or 1-120 seconds or minutes before) another compound or compounds. In various embodiments, free PEI is added to a scaffold after another (e.g., at least about 1, 6, 12, 15, 30, 60, 120, or 1-120 seconds or minutes after or less than about 1, 6, 12, 15, 30, 60, 120, or 1-120 seconds or minutes after) compound or compounds. In certain embodiments the PEI is added to a scaffold concurrently with another compound or compounds.

PEI may comprise, e.g., branched or linear PEI. In some embodiments, a device or scaffold composition provided herein comprises both branched PEI and linear PEI. In various embodiments, the PEI comprises branched dendrimeric PEI. In certain embodiments, the PEI comprises at least about 2, 3, 4, 5, 6, 7, 8, 9, 10, 20, or 30 primary, secondary, and/or tertiary amino groups. In some embodiments, the PEI comprises a molecular weight of (a) at least about 1, 2, 3, 4, 5, 10, 15, 20, 25, 30, 35, 40, 45, 50, 55, 60, 65, 70, 75, 100, 125, 150, 175, or 200 kilodaltons (kDa); (b) less than about 200, 175, 150, 125, 100, 75, 70, 65, 60, 55, 50, 45, 35, 25, 20, 15, 10, 5, 4, 3, 2, or 1 kDa; or (c) about 1, 2, 3, 4, 5, 10, 15, 20, 25, 30, 35, 40, 45, 50, 55, 60, 1-10, 2-25, 25-60, 25-75, 50-100, or 100-200 kDa. For example, the PEI may comprises linear PEI having a molecular weight of about 25 kDa and/or branched PEI having a molecular weight of about 60 kDa.

In some embodiment, PEI comprises the structure:

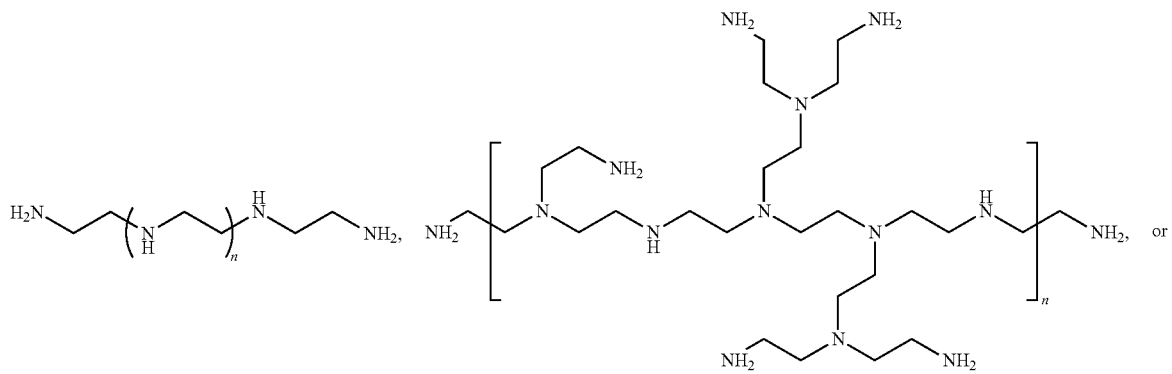

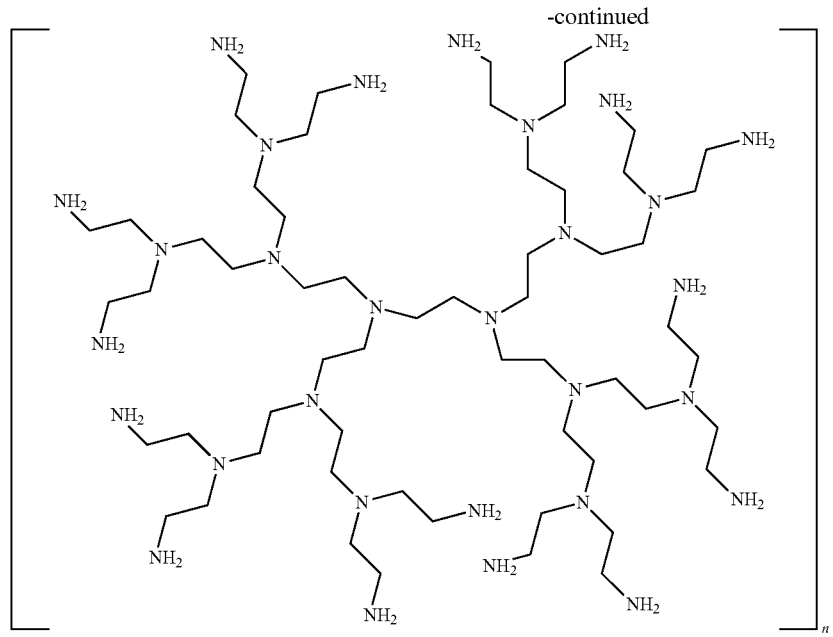

wherein n is at least about 1, 2, 3, 4, 5, 10, 15, or 20; (b) less than about 20, 15, 10, 5, 4, 3, 2, or 1 kDa; or (c) about 1, 2, 3, 4, 5, 10, 15, or 20.

In some embodiments, the PEI is present in an amount that is effective to increase antigen presentation, e.g. cross presentation. In certain embodiments, treating the subject increases humoral and/or T-cell mediated immunity to an antigen or a cell or virus comprising an antigen (such as a cancer cell or a pathogenic microbe). In various embodiments, the PEI is present in an amount that is effective to increase Major Histocompatibility Complex (MHC) Class I restricted antigen presentation to Cytotoxic T lymphocytes (CTLs). In certain embodiments, the PEI is present in an amount that is effective to increase MHC Class I CTL presentation of the antigen compared to a corresponding condition (e.g., administration) without the PEI, and the increase is about 5%, 10%, 15%, 20%, 25%, 30%, 35%, 40%, 45%, 50%, 75%, 100%, 150%, or 200%.

In certain embodiments, the PEI is present in an amount that is effective to increase the titer of one or more antibodies that are specific for the antigen. In embodiments, an antibody that is "specific" for an antigen has greater than 10-fold, preferably greater than 100-fold, and most preferably, greater than 1000-fold affinity for the target antigen as compared to another molecule. As the skilled artisan will appreciate the term specific is used to indicate that other biomolecules present in the sample do not significantly bind to the antibody that is specific for the target antigen. Preferably, the level of binding to a biomolecule other than the target antigen results in a binding affinity which is at most only 10% or less, only 5% or less only 2% or less or only 1% or less of the affinity to the target molecule, respectively. A preferred specific antibody will fulfill both the above minimum criteria for affinity as well as for specificity. For example, an antibody has a binding affinity in the low micromolar ($10^{-6}$), nanomolar ($10^{-7}$ to $10^{-9}$), with high affinity antibodies in the low nanomolar ($10^{-9}$) or picomolar ($10^{-12}$) range (or less) for its specific target antigen. In some embodiments, the antibody is an IgG1 or an IgG2 antibody. In various embodiments, the antibody is an IgG2a antibody.

In certain embodiments, the PEI is present in an amount that is effective to increase the titer of one or more antibodies that are specific for the antigen compared to a corresponding condition (e.g., administration) without the PEI, and the increase is about 5%, 10%, 15%, 20%, 25%, 30%, 35%, 40%, 45%, 50%, 75%, 100%, 150%, or 200%. In various embodiments, the PEI is present in an amount that is effective to increase B-cell activation. In certain embodiments, the PEI is present in an amount that is effective to increase B-cell activation compared to a corresponding condition (e.g., administration) without the PEI, and the increase is about 5%, 10%, 15%, 20%, 25%, 30%, 35%, 40%, 45%, 50%, 75%, 100%, 150%, or 200%.

In certain embodiments, the delivery vehicle comprises a dimension that is greater than about 5, 10, 15, 20, 25, 50, 100, 200, 300, 400, 500, 1000, or 10000 µm. In non-limiting examples, the delivery vehicle comprises a volume of at least about 0.1, 0.5, 1, 10, 20, 30, 40, 50, 60, 70, 80, 90, or 100 mm³.

In some embodiments, PEI is present in an amount that is effective to increase the production of granulocyte-colony stimulating factor (G-CSF), macrophage inflammatory protein-1a (MIP-1a), regulated on activation, normal T cell expressed and secreted (RANTES), keratinocyte chemoattractant (KC), interleukin-2 (IL-2), macrophage inflammatory protein-1b (MIP-1b), and/or interleukin 12 (IL-12) by immune cells in a subject compared to a corresponding device that does not comprise PEI. In certain embodiments, PEI is present in an amount that is effective to increase the level of active dendritic cells exiting a device by at least about 1, 2, 3, 4, 5, 6, 7, 8, 9, 10, 11, 12, 13, 14, 15, 16, 17, 18, 19, 20, 21, or 22 fold compared to a corresponding device that does not comprise PEI.

In various embodiments, the scaffold composition (i) comprises open interconnected macropores; or (ii) is a pore-forming scaffold composition. In some embodiments, the scaffold composition comprises a hydrogel or a cryogel. In certain embodiments, the scaffold composition comprises a cryogel that is characterized by shape memory following deformation by compression through a needle. For example, the cryogel may be characterized by shape memory following deformation by compression through a needle, such that the cryogel returns to its original undeformed three-dimensional shape less than 1, 2, 3, 4, or 5 seconds after compression through the needle.

In some embodiments, the scaffold composition is anionic or cationic.

In various embodiments, the scaffold composition comprises a polymer or a co-polymer of alginate, an alginate derivative, gelatin, collagen, agarose, fibrin, dextran, chitosan, carboxymethylcellulose, pullulan, polyethylene glycol (PEG), a PEG derivative, a peptide amphiphile, silk, fibronectin, chitin, hyaluronic acid, a laminin rich gel, a natural or synthetic polysaccharide, a polyamino acid, a polypeptide, a polyester, polylactic acid, polyglutamic acid, polyglycolic acid, poly(lactide-co-glycolide), poly(lactic-co-glycolic acid), polylysine, polyhydroxybutyrate, poly[(carboxy phenoxy)propane-sebacic acid], poly[pyromellitylimidoalanine-co-1,6-bis(p-carboxy phenoxy)hexane], polyphosphazene, a starch, xantham gum, gellan, emulsan, cellulose, albumin, polyhydroxyalkanoates, poly-epsilon-caprolactone, polycaprolactone, polydioxanone, polyglyconate, polyphosphazine, polyvinyl alcohol, polyalkylene oxide, polyethylene oxide, polyallylamine (PAM), poly(ortho ester I), poly(ortho ester) II, poly(ortho ester) III, poly (ortho ester) IV, polyacrylate, poly(4-aminomethylstyrene), poly(2-hydroxyethyl methacrylate), poly(methyl methacrylate), poly(ethylene terephthalate), poly(dimethylsiloxane), poly(N-isopropylacrylamide), polypropylene fumarate, polytetrafluoroethylene, polyethylene, polyurethane a modified styrene polymer, a pluronic polyol, polyoxamer, polyuronic acid, polyanhydride, polyacrylic acid, and/or polyvinylpyrrolidone. In certain embodiments, the polymer or copolymer is methacrylated. In some embodiments, the anionic scaffold composition comprises poly(lactide-co-glycolide), poly(lactic-co-glycolic acid), alginate, xantham gum, gellan, or emulsan.

Non-limiting examples of scaffold compositions include scaffold compositions comprising a copolymer of D,L-lactide and glycolide (PLG). In some embodiments, the PLG comprises a 85:15, 120 kDa copolymer of D,L-lactide and glycolide. In various embodiments, the PLG comprises a ratio of D,L-lactide to glycolide of about 50:50, 55:45, 60:40, 65:35, 70:30, 75:25, 80:20, 85:15, 90:10, or 95:5. In certain embodiments, the copolymer comprises a molecular weight of about 5 kDa, 6 kDa, 7 kDa, 8 kDa, 9 kDa, 10 kDa, 15 kDa, 20 kDa, 25 kDa, 30 kDa, 35 kDa, 40 kDa, 45 kDa, 50 kDa, 60 kDa, 70 kDa, 80 kDa, 90 kDa, 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 5-250 kDa, 7-240 kDa, 50-100 kDa, 50-150 kDa, 50-200 kDa, 100-150 kDa, 100-200 kDa, 150-250 kDa. In some embodiments, the PLG has a viscosity ranging from about 0.16-2.2 dl/g, 0.16-1.5 dl/g, 0.16-1 dl/g, 0.16-0.5 dl/g, or 1.5-2.2 dl/g, or about 0.16 dl/g, 0.18 dl/g, 0.2 dl/g, 0.3 dl/g, 0.4 dl/g, 0.5 dl/g, 0.6 dl/g, 0.7 dl/g, 0.8 dl/g, 0.9 dl/g, 1.0 dl/g, 1.1 dl/g, 1.2 dl/g, 1.3 dl/g, 1.4 dl/g, 1.5 dl/g, 1.6 dl/g, 1.7 dl/g, 1.8 dl/g, 1.9 dl/g, 2.0 dl/g, 2.1 dl/g, or 2.2 dl/g.

In some embodiments, the scaffold composition comprises open interconnected macropores. Alternatively or in addition, the scaffold composition comprises a pore-forming scaffold composition. In certain embodiments, the pore-forming scaffold composition may comprise a sacrificial porogen hydrogel and a bulk hydrogel, wherein the pore-forming scaffold composition lacks macropores. For example, the sacrificial porogen hydrogel may degrade at least 10% faster than the bulk hydrogel leaving macropores in its place following administration of said pore-forming scaffold into a subject. In some embodiments, the sacrificial porogen hydrogel is in the form of porogens that degrade to form said macropores. For example, the macropores may comprise pores having a diameter of, e.g., about 10-400 µm.

In certain embodiments, the scaffold composition comprises (i) a first zone comprising a chemoattractant of cancer cells and a cytotoxicity-inducing composition, and (ii) a second zone comprising an immune cell recruitment composition. In a non-limiting example, the second zone does not comprise a cytotoxicity-inducing composition.

In various embodiments, the scaffold composition comprises mesoporous silica rods. In some embodiments, the mesoporous silica rods comprise a length of about 100 nm, 150 nm, 200 nm, 250 nm, 300 nm, 350 nm, 400 nm, 450 nm, 500 nm, 600 nm, 700 nm, 800 nm, 900 nm, 100-250 nm, 250-500 nm, 500-750 nm, 750-1000 nm, 1 µm, 2 µm, 3 µm, 4 µm, 5 µm, 6 µm, 7 µm, 8 µm, 9 µm, 10 µm, 15 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 150 µm, 200 µm, 250 µm, 300 µm, 350 µm, 400 µm, 450 µm, 500 µm, 1-5 µm, 1-500 µm, 5-500 µm, 25-50 µm, 25-100 µm, 50-100 µm, 25-500 µm, or 50-500 µm. In certain embodiments, the mesoporous silica rods comprise of length from 100 nm, 150 nm, 200 nm, 250 nm, 300 nm, 350 nm, 400 nm, 450 nm, 500 nm, 600 nm, 700 nm, 800 nm, 900 nm, 100-250 nm, 250-500 nm, 500-750 nm, 750-1000 nm, 1 µm, 2 µm, 3 µm, 4 µm, 5 µm, 6 µm, 7 µm, 8 µm, 9 µm, 10 µm, 15 µm, 25 µm, 30 µm, 35 µm, 40 µm, 45 µm, or 50 µm to 55 µm, 60 µm, 65 µm, 70 µm, 75 µm, 80 µm, 85 µm, 90 µm, 95 µm, 100 µm, 150 µm, 200 µm, 250 µm, 300 µm, 350 µm, 400 µm, 450 µm, or 500 µm. In various embodiments, the mesoporous silica rods comprise a length of about or at least about any of 100 nm, 150 nm, 200 nm, 250 nm, 300 nm, 350 nm, 400 nm, 450 nm, 500 nm, 600 nm, 700 nm, 800 nm, 900 nm, 100-250 nm, 250-500 nm, 500-750 nm, 750-1000 nm, 1 µm, 2 µm, 3 µm, 4 µm, 5 µm, 6 µm, 7 µm, 8 µm, 9 µm, 10 µm, 15 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 150 µm, 200 µm, 250 µm, 1-500 µm, 5-500 µm, 25-50 µm, 25-100 µm, 50-100 µm, 25-500 µm, or 50-500 µm but less than 550 µm. In some embodiments, the mesoporous silica rods comprise a diameter of about or at least about any of 75 nm, 100 nm, 150 nm, 200 nm, 250 nm, 300 nm, 350 nm, 400 nm, 450 nm, 500 nm, 600 nm, 700 nm, 800 nm, 900 nm, 100-1000 nm, 100-500 nm, 100-250 nm, 250-500 nm, 500-750 nm, or 750-1000 nm, with the proviso that mesoporous silica rods comprise a length that is at least 10% greater than the diameter thereof. In certain embodiments, the mesoporous silica rods comprise a diameter from 75 nm, 100 nm, 150 nm, 200 nm, 250 nm, 300 nm, 350 nm, 400 nm, 450 nm, or 500 nm to 600 nm, 700 nm, 800 nm, 900 nm, or 1000 nm. In some embodiments, the mesoporous silica rods comprise a length that is at least about 10, 20, 25, 30, 35, 40, 45, 50, 55, 60, 65, 70, 75, 80, 85, 90, 95, 100, or 150% greater than the diameter of the mesoporous silica rods. In some embodiments, the mesoporous silica rods comprise a length that is at least about 2, 3, 4, 5, 6, 7, 8, 9, 10, 20, 30, 40, 50, 60, 70, 80, 90, 100, 150, 200, 250, 300, 400, or 500 times the diameter of the mesoporous silica rods. In certain embodiments, the mesoporous silica rods comprise pores having a diameter of about or at least about 1, 2, 3, 4, 5, 6, 7, 8, 9, 10, 15, 20, 25, 30, 35, 40, 45, or 50 nm, or about 1-10, 1-15, 1-5, 2-5, 2-10, 3-10, 4-10, 5-10, 5-15, or 10-25 nm. In certain embodiments, the mesoporous silica rods are 80 to 120 µm in length. For example, the mesoporous silica rods may comprise (a) pores having a diameter of between 2-50 nm, 3-50 nm, 5-50 nm, 5-25 nm, 5-10 nm; and/or (b) a length of about 5-25 μm, 80 to 120 μm. In some embodiments, the mesoporous silica rods may comprise a combination of rods with different lengths and/or rods with range of different sizes (e.g., within one of the ranges disclosed above or 1, 2, 3, 4, 5 or more of the ranges disclosed above). In some embodiments, rods with a length of about 100 nm, 150 nm, 200 nm, 250 nm, 300 nm, 350 nm, 400 nm, 450 nm, 500 nm, 600 nm, 700 nm, 800 nm, 900 nm, 100-250 nm, 250-500 nm, 500-750 nm, or 750-1000 nm are combined with rods having a length of about 5 μm, 6 μm, 7 μm, 8 μm, 9 μm, 10 μm, 15 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 150 μm, 200 μm, 250 μm, 300 μm, 350 μm, 400 μm, 450 μm, 500 μm, 5-500 μm, 25-50 μm, 25-100 μm, 50-100 μm, 25-500 μm, or 50-500 μm. In certain embodiments, the rods have a width of about 0.5 μm, 1.5 μm, 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 11 μm, 12 μm, 13 μm, 14 μm, 15 μm, 16 μm, 17 μm, 18 μm, 19 μm, 20 μm, 1-20 μm, 1-10 μm, 5-10 μm, 1-5 μm, 0.5-20 μm, 7.5-12.5 μm, or 5-15 μm. In some embodiments, one set of rods is small enough to be phagocytosed by immune cells such as dendritic cells or macrophages, and another set of rods is too big to be phagocytosed by the immune cells. In various embodiments, rods having different antigens or other compounds disclosed herein are mixed. Thus, provided herein are mixtures of 1, 2, 3, 4, 5, 6, 7, 8, 9, 10 or more classes of mesoporous silica rods, with each class of rods having a different antigen (e.g., antigenic peptide, such as a purified peptide). For example, a mixture may comprise a first class of rods comprising a first antigen, a second class of rods comprising a second antigen, a third class of rods comprising a third antigen, and so on. A mixture of rods may have the same or similar sizes or range of sizes, or may include one or more rods with a particular antigen or antigens (e.g., rods small enough to be phagocytosed) and another one or more rods with another antigen or antigens (e.g., rods too big to be phagocytosed). In certain embodiments, the rods that are too big to be phagocytosed form scaffolds upon administration (e.g., injection) into a subject. Injectable mesoporous silica rods randomly self-assemble to form a 3 dimensional (3D) scaffold in vivo. This system is designed such that it recruits and transiently houses immune cells (such as dendritic cells), present them with an antigen, and activate them (e.g., with an immune stimulatory compound such as PEI). After recruitment and temporary housing or presence of the cells in the structure, these immune cells migrate out of the device structure and homed to a lymph node. Thus, the composition is one in which cells traffic/circulate in and out of, their status of immune activation being altered/modulated as a result of the trafficking through the device. In various embodiments, the mesoporous silica rods are suspended in an aqueous solution, such as a buffer [e.g., phosphate buffered saline (PBS), Hank's balanced salt solution (HBSS), or another physiologically (e.g., pharmaceutically acceptable) buffer] for injection. In some embodiments, the mesoporous silica rods are injected in water. Mesoporous silica rods may be injected in a variety of concentrations. In some embodiments, the rods are injected at a concentration of about 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 30 mg/ml, 35 mg/ml, 40 mg/ml, 45 mg/ml, 50 mg/ml, 55 mg/ml, 60 mg/ml, 10-40 mg/ml, 20-35 mg/ml, 20-40 mg/ml, 25-35 mg/ml, 25-50 mg/ml, 25-45 mg/ml, 25-30 mg/ml, 30-50 mg/ml, 1-30 mg/ml, 1-40 mg/ml, 1-50 mg/ml, 1-60 mg/ml, 5-50 mg/ml, or 5-60 mg/ml.

One or more antigens may be selected based on an antigenic profile of a subject's cancer or of a pathogen. Included herein are libraries of mesoporous silica rods. In various embodiments, a library of mesoporous silica rods comprises a plurality of rods, each comprising a different antigen. Rods having a particular antigen may be separate from rods comprising another antigen, such that different rods may be selected, and optionally, combined. Aspects relate to detecting one or more antigens present on and/or in cancer cells or tumors of a subject, and then selecting one or more rods comprising antigens (or portions thereof) that are similar to the same as one or more antigens in/on cancer cells or tumors of the subject. Thus, a combination of mesoporous silica rods can be drawn from a library, such that the combination is selected in light of an antigenic profile of a subject. In various embodiments, the rods further comprise PEI. Similarly, antigen libraries are provided, from which antigens may be selected for inclusion in a hydrogel or cryogel such as a scaffold comprising PLG, alginate, and/or gelatin (or any other polymer known in the art and/or disclosed herein) based on the antigens that are present in/or a cancer cell or tumor from a subject. In some embodiments, the scaffolds further comprise PEI. In non-limiting examples, a library of rods or antigens comprises at least about 5, 6, 7, 8, 9, 10, 15, 20, 25, or 50 types of rods (e.g., separate groups of rods, each comprising a different antigen) or antigen. In some embodiments, the library is arranged as an array or is a collection of separate containers (e.g., tubes or vessels, each containing a different rod or antigen).

In some embodiments, the device is injectable. In various embodiments, the device further comprises (a) an immunostimulatory compound; (b) a compound that attracts an immune cell to or into the delivery vehicle; (c) a compound that induces immunogenic cell death of a tumor cell; (d) a compound that inhibits T-cell or dendritic cell suppression; (e) a compound that inhibits an immune-inhibitory protein, or any combination thereof.

In certain embodiments, the immunostimulatory compound comprises a toll-like receptor (TLR) agonist, a Stimulator of Interferon Gene (STING) agonist, and/or mesoporous silica. In some embodiments, immunostimulatory compound comprises a pathogen associated molecular pattern (PAMP). In some embodiments, the STING agonist comprises a cyclic dinucleotide. In certain embodiments, the TLR agonist comprises a TLR1, TLR2, TLR3, TLR4, TLR5, TLR6, TLR7, TLR8, TLR9, TLR10, TLR11, TLR12, or TLR13 agonist. In non-limiting examples, the device comprises TLR agonist such as a triacyl lipoprotein, a glycolipid, a lipopeptides, heparan sulfate, diacyl lipopeptides, bropirimine, lipoproteins, lipoteichoic acid, heat shock protein 70 (HSP70), zymosan, profilin, CpG oligonucleotide, double stranded ribonucleic acid (RNA), poly (I:C), poly (I:C), poly (A:U), monophosphoryl lipid A (MPLA), lipopolysaccharide (LPS), a heat shock protein, fibrinogen, heparin sulfate or a fragment thereof, hyaluronic acid or a fragment thereof, nickel, an opioid, α1-acid glycoprotein (AGP), RC-529, murine β-defensin 2, complete Freund's adjuvant (CFA), flagellin, a single-stranded RNA, a guanosine analogue, an imidazoqinoline, loxorbine, a fungal beta-glucan, imiquimod, CRX-527, or OM-174.

In various embodiments, the device comprises a compound that attracts an immune cell to or into the delivery vehicle, wherein the immune cell comprises a macrophage, T-cell, B-cell, natural killer (NK) cell, or dendritic cell. Non-limiting examples of compounds useful for attracting an immune cell to or into the delivery vehicle comprises granulocyte-macrophage colony stimulating factor (GM-CSF), an FMS-like tyrosine kinase 3 ligand (Flt3L), chemokine (C-C motif) ligand 19 (CCL-19), chemokine (C-C motif) ligand 20 (CCL20), chemokine (C-C motif) ligand 21 (CCL-21), a N-formyl peptide, fractalkine, monocyte chemotactic protein-1, and macrophage inflammatory protein-3 (MIP-3α).

In some embodiments, the compound that inhibits T-cell or dendritic cell suppression comprises a compound that inhibits an immune-inhibitory protein. In certain embodiments, the immune-inhibitory protein is cytotoxic T-lymphocyte-associated antigen 4 (CTLA4), programmed cell death protein 1 (PD1), programmed cell death protein 1 ligand (PDL1), lymphocyte activation gene 3 (LAGS), B7-H3, B7-H4, or T-cell membrane protein 3 (TIM3).

In various embodiments, the device further comprises an antigen. For example, in some embodiments, a device comprises both free PEI and an antigen. In some embodiments, the antigen comprises a tumor antigen or a non-tumor antigen. PEI may be added to a delivery vehicle before antigen, together with antigen (e.g., in an aqueous composition or mixture containing PEI and the antigen), or after an antigen. In some embodiments, PEI coats the outside of a delivery vehicle that contains an antigen. In certain embodiments, PEI is added to a delivery vehicle and then antigen is added to the delivery vehicle. In various embodiments, an antigen is added to a delivery vehicle and then PEI is added to the delivery vehicle. Some implementations relate to the combination of PEI with an antigen with which PEI does not electrostatically interact. In some embodiments, free PEI does not become attached (e.g., electrostatically attached) to an antigen within a delivery vehicle. In certain embodiments, free PEI becomes attached (e.g., electrostatically attached) to an antigen within a delivery vehicle. In various embodiments, PEI becomes attached (e.g., electrostatically attached) to an antigen and then is added to the delivery vehicle. Non-limiting examples of adding a compound (e.g., PEI or antigen) onto a delivery vehicle include incorporating the compound into the delivery vehicle during the production thereof (e.g., during or before polymerization or cryogelation of a hydrogel or cryogel), by adding (e.g., dropping) a composition comprising the compound onto the delivery vehicle, or by soaking the delivery vehicle in a composition comprising the compound.

In certain embodiments, the device lacks a tumor antigen prior to administration to a subject. In some embodiments, the device comprises an immunoconjugate, wherein the immunoconjugate comprises an immunostimulatory compound covalently linked to an antigen. In various embodiments, the antigen comprises a tumor antigen, such as a central nervous system (CNS) cancer antigen, CNS germ cell tumor antigen, lung cancer antigen, leukemia antigen, acute myeloid leukemia antigen, multiple myeloma antigen, renal cancer antigen, malignant glioma antigen, medulloblastoma antigen, breast cancer antigen, prostate cancer antigen, Kaposi's sarcoma antigen, ovarian cancer antigen, adenocarcinoma antigen, or melanoma antigen. In some embodiments, treating the subject comprises reducing metastasis in the subject.

In certain embodiments, the antigen comprises a non-tumor antigen such as a microbial antigen. For example, the microbial antigen may comprise a bacterial antigen, a viral antigen, a fungal antigen, an archaean antigen, or a protozoan antigen. In some embodiments, the microbial antigen is other than a viral antigen, e.g., other than an HIV or influenza antigen. In various embodiments, the antigen is other than a glycoprotein or fragment thereof.

Aspects of the present subject matter also provide a method of treating cancer in a subject, comprising administering a device or biomaterial disclosed herein to the subject.

In various embodiments, a flexible injectable biomaterial cryogel or hydrogel (such as a click hydrogel) is administered into a tumor or to an anatomical location in the proximity of a tumor, e.g., in direct contact with the tumor/ touching the tumor, within about 10, 9, 8, 7, 6, 5, 4, 3, 2, or 1 mm of a tumor, or into the tumor mass itself, to deliver immune modulating agents directly to the site of a growing tumor to facilitate cancer immunotherapy while bypassing systemic delivery (which can be associated with adverse side effects) and without loading a tumor antigen or tumor lysate into the delivery device prior to administration, e.g., injection, to a patient. Accordingly, a device/biomaterial (e.g., a cryogel or hydrogel) is administered in a peritumoral or intratumoral manner Peritumoral delivery substantially surrounds (50, 75, 85, 95, 99-100% of the perimeter of a tumor mass) the tumor with the device/biomaterial, either by direct physical contact or in close proximity to the tumor mass boundary. Intratumoral delivery is carried out by direct administration into a tumor mass through the boundary between tumor and normal tissue. For example, the biomaterial may be administered adjacent to but without compromising the integrity, e.g. piercing, of a tumor capsule, e.g., in the case of a solid tumor. Alternatively, the tumor capsule is compromised or pierced (intratumoral injection). In some embodiments, the tumor completely or partially envelopes a device or scaffold that is placed touching or proximal to the tumor. In such embodiments, the device or scaffold reshapes immune cell localization at or within the tumor. The present subject matter also relates to the administration of the biomaterial directly into the tumor (intratumoral), e.g., using a needle. Any tumor that can be diagnosed by taking a needle biopsy may be treated in this manner. For example, tumors to be treated include breast, brain, lung, prostate, liver, bone, thyroid, skin, cervical, oral, ovarian, endometrial, colon, bladder, and additional tumor types described below.

In various embodiments, the tumor is a solid tumor or a discrete tumor within defined, detectable boundaries. Accordingly, the present subject matter provides a method of reducing tumor-mediated immune evasion comprising administering to a tumor site (e.g., into a tumor (touching) or to a site adjacent to or in the proximity of a solid or discrete tumor mass) a biodegradable porous polymeric device comprising an inhibitor of T cell or dendritic cell suppression. For example, the inhibitor comprises a Transforming Growth Factor-Beta (TGF-β) pathway inhibitor, a Signal Transducer and Activator of Transcription 3 (STAT3) pathway inhibitor or an indoleamine-pyrrole 2,3-dioxygenase (IDO or INDO EC 1.13.11.52) inhibitor. In some examples, the inhibitor comprises at least one small molecule such as the TGF-β pathway inhibitor L12157299, GW788388, LY364947, R268712, RepSox, SB525334, and SD208; and/or the STAT3 pathway inhibitor BP-1-102, S3I-M2001, STA-21, S3I-201, Stattic, Galiellalactone, a polypeptide having the sequence PY*LKTK (where Y* represents phosphotyrosine; SEQ ID NO: 1), and a polypeptide having the sequence Y*LPQTV (where Y* represents phosphotyrosine; SEQ ID NO: 2); and/or the IDO inhibitor INCB24360, NLG919 (also known as GDC-0919), Norharmane, Rosmarinic Acid, 1-Methyltryptophan, and indoximod. In another example, the inhibitor comprises a blocker of an immune checkpoint protein such as programmed cell death 1 protein (PD-1), PD-1 ligand 1 (PD-L1), Cytotoxic T-lymphocyte-associated antigen 4 (CTLA-4), lymphocyte activation gene-3 (LAG-3), Cluster of Differentiation 276 (CD276; also known as B7-H3), and/or T-cell immunoglobulin domain and mucin domain 3 (TIM3) inhibitors. In some embodiments, the inhibitor of an immune checkpoint protein includes an anti-PD-1 antibody, an anti-PD-L1 antibody, and/or an anti-CTLA-4 antibody. In preferred embodiments, the device does not comprise a tumor antigen, e.g., a patient-derived tumor antigen or tumor cell lysate (or other tumor antigen), prior to administration to the tumor location of a subject.

In various embodiments, the biomaterial/device contains nanopores, micropores, macropores, or a combination thereof. The size of micropores and macropores permits cell migration or movement (e.g., immune cell, e.g., DC migration into and/or egress out of the delivery vehicle) through the micropores and macropores. For example, the composition comprises pores that are characterized by a diameter of 1-600 μm (e.g., 10-600 μm, 20-600 μm, 50-600 μm, 10-500 μm, 20-500 μm, 50-500 μm, or 10-300 μm).

In some situations, the device further comprises a chemotherapeutic agent that induces death, e.g., immunogenic cell death, of tumor cells Immunogenic cell death is a form of cell death that is recognized by the immune system and results in immune activation (as opposed to apoptosis as seen with most other chemotherapeutics). In this form of cell death, calreticulin is presented on the surface of dying cells allowing tumor antigen to be engulfed; high mobility group box 1 protein (HMGB1) is released which results in toll-like receptor-4 (TLR-4) stimulation on dendritic cells to cause their maturation; and release of ATP from the dying cells resulting in recruitment of antigen presenting cells into the tumor bed. Such chemotherapeutic agents include members of the anthracycline class of compounds, e.g., doxorubicin, daunorubicin, epirubicin, idarubicin, and vairubicin as well as mitoxantrone, an anthracycline analog. This class of compounds is preferred due to their ability to activate the immune system, in addition to directly killing cancer cells. The agents oxaliplatin and cyclophosphamide also lead to immunogenic cell death. Other non-limiting examples of compounds that induce immunogenic cell death include shikonin, the proteasome inhibitor bortezomib, 7A7 (an epidermal growth factor receptor-specific antibody), cardiac glycosides, and vorinostat (a histone deacetylase inhibitor). See, e.g., H Inoue and K Tani (2014) Cell Death and Differentiation 21, 39-49, the entire content of which is hereby incorporated herein by reference. In addition to chemotherapy drugs, the device is utilized in combination with radiation therapy, which also leads to immunogenic cell death, as well as other approaches that kill tumor cells while activating immune responses to the tumor.

Optionally, the device or scaffold further comprises a hyperthermia-inducing composition. Suitable hyperthermia-inducing compositions include a magnetic nanoparticle or a near infrared (NIR) absorbing nanoparticle. In some cases, the nanoparticle is magnetic, and the method further comprises contacting the magnetic nanoparticle with an alternative magnetic field (AMF) to induce local hyperthermia in situ, thereby altering or disrupting the cancer cell and producing a processed tumor antigen. In another example, the method further comprises contacting the NIR nanoparticle with NIR radiation to induce local hyperthermia in situ, thereby altering or disrupting the cancer cell and producing a processed tumor antigen. Hyperthermia is characterized by a local temperature of greater than 37 degrees Celsius (° C.). For example, the temperature of the device is temporarily heated to about 40, 45, 50, 60, 70, 75, 80, 85, 90, 95° C. or more. In some embodiments, the hyperthermia-inducing composition is on the surface of a device or scaffold of the invention, e.g., the device of scaffold is coated with the hyperthermia-inducing composition. In various embodiments, the hyperthermia-inducing composition is within or throughout a device or scaffold.

In some embodiments, the device or scaffold further comprises a radioactive isotope. Suitable radioactive isotopes include iodine-131, iodine-125, rhenium-185, phosphorous-33, phosphorous-32, palladium-100, palladium-101, palladium-201, palladium-103, palladium-105, palladium-106, palladium-108, palladium-109, palladium-110, palladium-111, palladium-112, caesium-137, iridium-192, cobalt-60, lutetium-177, yttrium-90, thallium-201, gallium-67, technetium-99m, strontium-90, or strontium-89. In some embodiments, the radioactive isotope is on the surface of a device or scaffold of the invention, e.g., the device of scaffold is coated with the radioactive isotope. In various embodiments, the radioactive isotope composition is within or throughout a device or scaffold.

In various embodiments, the device further comprises a RNA (e.g., mRNA or a viral genome or a portion thereof) or DNA molecule (e.g., a plasmid or a viral genome or a portion thereof) that encodes polypeptide. In embodiments, the polypeptide is an antigenic polypeptide. In some embodiments, the peptide comprises an amino acid sequence that is not present in any polypeptide that is encoded by the genome of the subject. In some embodiments, the peptide comprises an amino acid sequence that is not present in any polypeptide that is encoded by the genome of a normal cell in the subject. In certain embodiments, the polypeptide is present on the surface of cancerous cells. In embodiments, the polypeptide comprises an amino acid sequence of a polypeptide that is produced by a microbial pathogen or parasite (e.g., a viral, fungal, bacterial, or protozoan pathogen or parasite). In some embodiments, the peptides may be presented on autoreactive immune cells, including, for example, T cells, B-cells or antigen presenting cells. In certain embodiments, the peptide may be present within a therapeutic compound.

In some examples, the tumor comprises a discrete tumor with defined boundaries. In various embodiments, the tumor is a solid tumor or localized tumor mass. For example, the biomaterial-containing device is placed directly onto the tumor mass, into the tumor mass, or adjacent to the tumor mass (i.e., physically in contact with or in close proximity to) the tumor mass itself rather than at a site remote (e.g., more than 10 mm from) from the tumor mass, e.g., placed under the skin at a site remote from the tumor. Using the system described above, there is no need for patient-derived material, e.g., a patient-derived or biopsied tumor lysate or processed antigen, as a component of the device that serves as a tumor antigen, because dying tumor cells themselves provide any antigen required for generation of an adaptive immune cell response. In some embodiments, the scaffold or device does not comprise a tumor antigen prior to being administered to the subject.

Aspects of the present subject matter relate to the treatment of solid tumors. For example, the tumor is of a cancer that is other than a cancer of blood cells, such as leukemia. In certain embodiments, the cancer is metastatic. In various embodiments, the tumor is a skin cancer, such as melanoma. Implementations of the present subject matter relate to the treatment of cancer for which tumors may be biopsied (while avoiding the need for a biopsy to, e.g., produce a tumor antigen such as tumor cell lysate). In some embodiments, the tumor is a sarcoma or carcinoma tumor. Non-limiting tumors which may be targeted in embodiments of the present subject matter include breast cancer, testicular cancer, prostate cancer, ovarian cancer, pancreatic cancer, lung cancer, thyroid cancer, liver cancer (e.g., non-small cell lung cancer), colon, esophagus cancer, stomach cancer, cervical cancer, oral cancer, cancer associated with a virus such as Human Papillomavirus (HPV), brain cancer, renal cancer, retinoblastoma, acute myeloid leukemia, osteosarcoma, osteosarcoma, chondroblastoma, chondrosarcoma, Ewing sarcoma, Wilms tumor, malignant rhabdoid, hepatoblastoma, hepatocellular carcinoma, neuroblastoma, medulloblastoma, glioblastoma, adrenocortical carcinoma, nasopharyngeal carcinoma, rhabdomyosarcoma, desmoid, fibrosarcoma, or liposarcoma tumor. In some embodiments relating to the injection of a biomaterial device or scaffold, the needle may be guided visually and/or with the assistance of an imaging device such as an X-ray (e.g., using a computerized tomography (CT) scan), ultrasound, endoscope, or laparoscope device.

The methods and biomaterial devices of the present subject matter are useful for treating any vertebrate subject who suffers from a tumor. In various embodiments, the subject is an amphibian, reptile, equine, mammal, rodent, canine, feline, avian, porcine, or primate subject. For example, human medical and veterinarian implementations of the present subject matter are provided. In certain embodiments, the subject is a dog, a cat (such as a domesticated cat or a cat such as a lion, a tiger, a leopard, or a cheetah), a guinea pig, a pig, a horse, a donkey, a mule, a mouse, a rat, a human, a monkey, a chimpanzee, a gorilla, an orangutan, a bear (such as a panda bear), or a camel. The present subject also provides animals other than humans comprising a biomaterial device disclosed herein.

Also within the present subject matter is a biomaterial device comprising active components described herein. In some embodiments, the biomaterial device contains PEI. In certain embodiments, the biomaterial further comprises one or more of (i) an immunostimulatory compound (ii) a compound that causes immunological cell death of a tumor cell; (iii) a compound that inhibits T cell or dendritic cell suppression; (iv) a compound that inhibits an immune-inhibitory protein and (v) a cytokine (e.g., a chemoattractant of immune cells, such as dendritic cells).

In some embodiments, the immunostimulatory compound is a TLR agonist or a STING ligand. In some embodiments, the compound that causes immunological cell death is doxorubicin, mitoxantrone, oxaliplatin, or paclitaxel. In some embodiments, the compound that inhibits T cell or dendritic cell suppression is a TGF-β inhibitor, a STAT3 inhibitor, an IDO inhibitor, an anti-PD-1 antibody, or an anti-CTLA-4 antibody. In some embodiments, a device or scaffold comprises a cytokine such as GM-CSF, Flt3L, XCL1, IL-2, or IL-12. In various embodiments, a device or scaffold of the present subject matter comprises an mRNA or expression vector that encodes a protein such as an immunostimulatory compound or a cytokine. The mRNA or expression vector may be combined in the device or scaffold with the polypeptide it encodes, or without the polypeptide it encodes. In some embodiments, a device or scaffold comprises an mRNA molecule or an expression vector that encodes a cytokine described herein, such as a cytokine that attracts a dendritic cell into the device or scaffold. In certain embodiments, the mRNA or expression vector is condensed to facilitate delivery to cells of the subject. In various embodiments, the mRNA or expression vector may be present in a device or scaffold with a transfection agent. For example, the mRNA or expression vector may be condensed with polyethylimine (PEI), poly-L-lysine (PLL), or a polyamidoamine (PAMAM) dendrimer. See, e.g., Huang et al. (2005) Human Gene Therapy 16:609-617. Additional non-limiting examples of transfection agents include liposomes (e.g., lipofectamine). In some embodiments, the device comprises an inhibitor of T cell or dendritic cell suppression. In some embodiments, the device comprises an immunostimulatory compound. In some embodiments, said inhibitor comprises a transforming growth factor-beta (TGF-β) pathway inhibitor, or a signal transducer and activator of transcription 3 (STAT3) pathway inhibitor. In some embodiments, said inhibitor comprises a small molecule, an aptamer, a protein, an RNAi molecule, an antibody, or an antibody fragment. In some embodiments, the small molecule is an organic compound having a molecular weight less than 1000 Daltons. In some embodiments, said TGF-β pathway inhibitor comprises LY2157299 GW788388, LY364947, R268712, RepSox, SB525334, or SD208 and said STAT3 pathway inhibitor comprises BP-1-102, S3I-M2001, STA-21, S3I-201, Stattic, Galiellalactone, a polypeptide having the sequence PY*LKTK (SEQ ID NO: 1) (where Y* represents phosphotyrosine), and a polypeptide having the sequence Y*LPQTV (SEQ ID NO: 2) (where Y* represents phosphotyrosine). In some embodiments, said inhibitor comprises an inhibitor of an immune checkpoint. In some embodiments, the inhibitor of an immune checkpoint is a PD-1 pathway inhibitor, a LAG-3 pathway inhibitor, an IDO pathway inhibitor, a B7-H3 pathway inhibitor, or a TIM3 pathway inhibitor. In some embodiments, said inhibitor is a small molecule, an aptamer, a protein, an RNAi molecule, an antibody, or an antibody fragment. In some embodiments, the small molecule is an organic compound having a molecular weight less than 1000 Daltons. In some embodiments, the inhibitor is an antibody. In some embodiments, said antibody comprises an anti-PD-1 antibody, an anti-PD-L1 antibody, or an anti-CTLA-4 antibody. In some embodiments, the anti-PD-1 antibody is nivolumab, pembrolizumab, or pidilizumab. In some embodiments, the anti-PD-L1 antibody is BMS-936559 or MPDL3280A. In some embodiments, the anti-CTLA-4 antibody is ipilimumab. In some embodiments, the antibody is a Fv, Fab, Fab', Fab'-SH, F (ab')2, diabody, a linear antibodies or a scFv. In some embodiments, the antibody is a polyclonal antibody, a monoclonal antibody, a chimeric antibody, a humanized antibody, or a human antibody. In some embodiments, said inhibitor is an IDO inhibitor. In some embodiments, said IDO inhibitor is an IDO1 inhibitor. In some embodiments, said inhibitor is a small molecule, an aptamer, a protein, a RNAi molecule, an antibody, or an antibody fragment. In some embodiments, the small molecule is an organic compound having a molecular weight less than 1000 Daltons. In some embodiments, the small molecule is INCB24360 or NLG919. In some embodiments, said device further comprises an immunogenic cell death-inducing chemotherapeutic agent. In some embodiments, said chemotherapeutic agent comprises a member of the anthracycline class of compounds. In some embodiments, said chemotherapeutic agent comprises doxorubicin. In some embodiments, said tumor comprises a solid tumor or localized tumor mass. In some embodiments, said device does not comprise a purified tumor antigen or tumor cell lysate prior to administration to said tumor site. In some embodiments, said device comprises a hydrogel. In some embodiments, said device comprises a cryogel. In some embodiments, said cryogel comprises pores. In some embodiments, said device comprises a methacrylated gelatin cryogel, a methacrylated alginate cryogel, or a click alginate cryogel. In some embodiments, said device comprises an alginate hydrogel. In some embodiments, the alginate hydrogel is an alginate cryogel. In some embodiments, said alginate hydrogel comprises a click alginate. In some embodiments, the device is administered via injection. In some embodiments, the device is injected into the tumor. In some embodiments, the device is injected to a site in the subject within about 0.1-10 mm from the tumor. In some embodiments, the device further comprises a cytokine or a mRNA or expression vector encoding a cytokine. In some embodiments, the cytokine is granulocyte macrophage colony-stimulating factor (GM-CSF), FMS-like tyrosine kinase 3 ligand (Flt3L), Chemokine (C-C Motif) Ligand 20 (CCL20), Interleukin 15 (IL-15), Chemokine (C Motif) Ligand 1 (XCL1), Chemokine (C-X-C Motif) Ligand 10 (CXCL10), Interferon Alpha 1 (IFN-alpha), Interferon Beta (IFN-beta), or Interleukin 12 (IL-12). In some embodiments, the device further comprises an immunostimulatory compound. In some embodiments, the immunostimulatory compound is a TLR agonist, a STING ligand, or an immunostimulatory antibody. In some embodiments, the device has a volume of about 50, 60, 70, 80, 90, 100, 200, 300, 400, 500, or 50-500 µl or less than about 50, 60, 70, 80, 90, 100, 200, 300, 400, 500, or 50-500 µl. In some embodiments, said device further comprises laponite.

Aspects of the present subject matter provide a method of treating a subject afflicted with a tumor, comprising administering to a tumor site a biodegradable porous polymeric device disclosed herein. In some embodiments, the device comprises an inhibitor of T cell or dendritic cell suppression. In some embodiments, the device comprises an immunostimulatory compound. In some embodiments, treating the subject comprises (a) reducing the volume of the tumor; (b) reducing the growth of the tumor; (c) reducing metastasis of the tumor; (d) increasing the survival of the subject; (e) increasing the progression free survival of the subject; (f) increasing a T cell response to an antigen within the tumor; and/or (g) vaccinating the subject to an antigen within the tumor. In some embodiments, treating the subject comprises reducing the volume of the tumor at least about 5, 10, 15, 20, 25, 30, 35, 40, 45, 50, 55, 60, 65, 70, 75, 80, 85, 90, 95, 96, 97, 98, 99, or 100%. In some embodiments, treating the subject comprises reducing the volume of the tumor at least about 5, 10, 15, 20, 25, 30, 35, 40, 45, 50, 55, 60, 65, 70, 75, 80, 85, 90, 95, 96, 97, 98, 99, or 100% within about 1, 2, 3, 4, 5, 6, 7, 8, 9, 10, 14, 21, 28, 35, 41, 48, 180, 365 or 1-365 days or within about 1-12 months. In some embodiments, (a) one such biodegradable porous polymeric device is administered to the subject; or (b) two such biodegradable porous polymeric devices are administered to the subject. In some embodiments, said device comprises an alginate hydrogel. In some embodiments, said alginate hydrogel comprises a click alginate. In some embodiments, the device is administered via injection. In some embodiments, the device is injected into the tumor. In some embodiments, the device is injected to a site in the subject within about 0-10 mm from the tumor. In some embodiments, the device further comprises a cytokine. In some embodiments, the cytokine is granulocyte macrophage colony-stimulating factor (GM-CSF), FMS-like tyrosine kinase 3 ligand (Flt3L), Chemokine (C-C Motif) Ligand 20 (CCL20), Interleukin 15 (IL-15), Chemokine (C Motif) Ligand 1 (XCL1), Chemokine (C-X-C Motif) Ligand 10 (CXCL10), Interferon Alpha 1 (IFN-alpha), Interferon Beta (IFN-beta), or Interleukin 12 (IL-12). In some embodiments, the device further comprises an immunostimulatory compound. In some embodiments, the immunostimulatory compound is CpG, polyinosine-polycytidylic acid (poly (I:C)) PEI-poly (I:C), polyadenylic-polyuridylic acid (poly (A:U)), PEI-poly (A:U), double stranded ribonucleic acid (RNA), monophosphoryl lipid A (MPLA), or Imiquimod. In some embodiments, the device has a volume of about 50, 60, 70, 80, 90, 100, 200, 300, 400, 500, or 50-500 µl or less than about 50, 60, 70, 80, 90, 100, 200, 300, 400, 500, or 50-500 µl. In some embodiments, said subject has been identified as comprising a solid tumor.

Aspects of the present subject matter provide non-human mammal or a syringe comprising a device of the present subject matter. In some embodiments, the syringe is preloaded and packaged with a device. In some embodiments, the tumor is contacted with radiation. In some embodiments, a chemotherapeutic agent is administered systemically to the subject.

Also included herein are devices, biomaterials, methods, and compositions for increasing the immunogenicity of a compound, such as an antigen comprising a polypeptide. Increasing the immunogenicity of the compound may include increasing the production of one or more antibodies that are specific for the compound in a cell type or animal (e.g., a mammal). In some embodiments, the antibody is human or humanized before or after it is determined to be specific for the compound. In various embodiments, increasing the immunogenicity of the compound comprises combining the compound with PEI. In some embodiments, the compound and PEI are present in a device comprising a delivery vehicle such as a scaffold. In certain embodiments, the compound is electrostatically attached to the PEI.

Non-limiting descriptions of biomaterials and compositions for eliciting specific immune responses (e.g., to tumors and/or pathogens) are provided in U.S. Pat. No. 9,132,210, issued Sep. 15, 2015; U.S. Patent Application Publication No. 2012-0100182, published Apr. 26, 2012; U.S. Pat. No. 9,370,558, issued Jun. 21, 2016; PCT International Patent Application Publication No. WO 2015/168379, published May 11, 2015; and PCT International Patent Application No. PCT/US2016/025717, filed Apr. 1, 2016, the entire contents of each of which are incorporated herein by reference.

Non-limiting features relating to injectable pore-forming biomaterials for eliciting specific immune responses are described in U.S. Patent Application Publication No. 2014-0079752, published Mar. 20, 2014, the entire content of which is incorporated herein by reference.

Non-limiting descriptions of injectable cryogel biomaterials for eliciting specific immune responses (e.g., to tumors and/or pathogens) are described in U.S. Patent Application Publication No. 2014-0112990, published Apr. 24, 2014; and U.S. Patent Application Publication No. 2014-0227327, published Aug. 14, 2014, the entire contents of each of which are incorporated herein by reference.

Non-limiting aspects of in situ antigen-generating anti-cancer biomaterials are described in U.S. Patent Application Publication No. 2014-0193488, published Jul. 10, 2014, the entire content of which is incorporated herein by reference.

Exemplary descriptions of mesoporous silica compositions for modulating immune responses are provided in Kim et al., (2015) *Nature Biotechnology* 33, 64-72; U.S. Patent Application Publication No. 2015-0072009, published Mar. 12, 2015; and Björk et al. (2013) *Langmuir,* 29 (44): 13551-13561, the entire contents of each of which are incorporated herein by reference. In various embodiments, mesoporous silica nanoparticles are synthesized by reacting tetraethyl orthosilicate with a template made of micellar rods. The result is a collection of nano-sized spheres or rods that are filled with a regular arrangement of pores. The template can then be removed by washing with a solvent adjusted to the proper pH. In another non-limiting technique, the mesoporous particle is synthesized using a simple sol-gel method or a spray drying method. In some embodiments, tetraethyl orthosilicate is used with an additional polymer monomer (as a template). Other non-limiting methods include those described in U.S. Patent Publication 20120264599 and 20120256336, hereby incorporated by reference. In a non-limiting example, rods are produced in a process comprising dissolving a surfactant in an acidic solution then heating, adding a silicate (such as tetraethyl orthosilicate) and heating, and collecting rod particles. For example, rods may be produced in a process comprising: dissolving Pluronic P-123 (Sigma-Aldrich) surfactant in 1.6M HCl at room temperature, and heating to 40° C.; adding 42 mmol of tetraethyl orthosilicate (TEOS) (Sigma-Aldrich) and heating for 20 hours at 40° C. under stirring (600 rpm); heating to 100° C. for 24 hours; collecting the rod particles by filtration and air drying at room temperature; and extracting the particles in ethanol/HCl (5 parts HCl to 500 parts EtOH) overnight at 80° C. In some embodiments, the MPS composition may be stored and shipped for use before or after adding compounds (such as recruitment, activation, antigen, and immune suppression inhibitor compounds). For example, one or more compounds such as antigens may be processed and added to MPS particles shortly before administration to the patient.

Non-limiting features relating to biomaterials for reducing, reversing, and/or overcoming tumor immunosuppressive mechanisms are described in PCT/US2016/015825, filed Jan. 29, 2016, the entire content of which is incorporated herein by reference.

The invention encompasses the use of a device, library, or mixture as described herein for treating cancer in a subject, for reducing tumor burden in a subject, for treating an infection in a subject, and/or for eliciting an immune response to a tumor antigen or tumor neoantigen in a subject as well as for stimulating an immune response ex vivo or in vitro. Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIGS. 1A-I are graphs showing that PEI can be absorbed into mesoporous silica rods (MSRs) in vitro and that PEI activates murine BMDCs and human DCs in vitro. (A) Flow cytometry analysis of major histocompatibility complex class II (MHC-II) and Cluster of Differentiation 86 (CD86) expression on BMDCs after 18 hours of stimulation with various concentrations of PEI. (B) and (C) Enzyme-Linked Immunosorbent Assay (ELISA) analysis of TNF-α and IL-6 concentration in bone marrow-derived dendritic cell (BMDC) supernatant after 18 hours of stimulation with various concentration of PEI. (D) Loading efficiency of PEI onto the MSRs. (E) Flow cytometry analysis of MHC-II and CD86 expression on BMDCs after 18 hours of stimulation with various concentrations of PEI-MSR. (F) ELISA analysis of Tumor necrosis factor alpha (TNF-α) concentration in BMDC supernatant after 18 hours of stimulation with various concentration of PEI-MSR. PBS=Phosphate Buffered Saline; MPS=Mesoporous Silica; L25=Linear PEI having a molecular weight of 25 kDa. (G) Various concentrations of PEI were added to a TLR5 reporter cell (Invivogen, HEK Blue TLR-5) and activity was monitored using human embryonic kidney (HEK)-Blue detection (Invivogen). (H) ELISA analysis of TNF-α concentration in murine BMDC supernatant after stimulation with MSR-PEI. (I) Flow cytometry analysis of SIINFEKL presenting murine BMDCs after stimulation with OVA and OVA+PEI. B60=Branched PEI having a molecular weight of 60 kDa. OVA=Ovalbumin MSR may be used interchangeably with MPS (mesoporous silica) throughout the figures herein.

FIG. 2I is a series of images of MRS. (A) Schematics of the MSR vaccine (V) and MSR-PEI vaccine (VP). (B) Total cell number at the vaccine site explanted on day 3 post immunization. Numbers of CD11c+CD86+ activated DCs (C), CD11c+CCR7+LN homing DCs (D) and ovalbumin (OVA) model antigen peptide, SIINFEKL, presenting DC (E) recruited to the vaccine site on day 3 post immunization. (F) Total number of cells in the draining lymph node (dLN) on day 3 and 5 after immunization. Numbers of CD11c+CD86+ or CD11c+MHC-II+ activated DCs (G), and antigen presenting DC (H) in the dLN on day 3 and day 5 post immunization. (I) Fluorescence microscopy images of MSRs loaded with Rhodamine-PEI and AF488-OVA. V=MPS vaccine in the formulation: 5 mg MPS+1 µg GM-CSF, 100 µg CpG, 100 µg antigen (OVA protein); VP=MPS vaccine formulation with PEI: 5 mg MPS+10 µg PEI, 1 µg GM-CSF, 100 µg CpG, 100 µg antigen (OVA protein). 100 µg of OVA protein was used for these experiments. The antigen was adsorbed to PEI-MPS. In short, PEI was adsorbed onto MPS for 15 min at 37° C. to make PEI-MPS. Then, 100 µg of the antigen was adsorbed onto PEI-MPS.

FIGS. 3A-F are a timeline and graphs showing that PEI in a MSR vaccine enhances CD8$^+$ cytotoxic T-cell response. (A) Schematics for immunization and analysis and percentage of tetramer$^+$ T-cells in peripheral blood on day 7. (B) Percentage of IFN-γ$^+$ T-cells after stimulating with SIINFEKL in peripheral blood on day 7. (C) Ratio of CD8+ effector T cells ($T_{eff}$) and Foxp3+CD4+ regulatory T cells ($T_{reg}$) at the vaccine site on day 11. (D) percentage of tetramer$^+$ T cells in peripheral blood on day 7. (E) Percentage of IFN-γ$^+$ T-cells after stimulating with SIINFEKL in peripheral blood on day 7 after immunizing with MSR-PEI vaccine containing various types of PEI. (F) Percentage of IFN-γ+ T cells after stimulating with SIINFEKL in peripheral blood on day 7 after immunizing with MSR-PEI vaccine containing various doses of B60 PEI. L2=Linear PEI having a molecular weight of 2 kDa; B2=Branched PEI having a molecular weight of 2 kDa; N=naïve animals; V=MPS vaccine in the formulation: 5 mg MPS+1 µg GM-CSF, 100 µg CpG, 100 µg antigen (OVA protein); VP=MPS vaccine formulation with PEI: 5 mg MPS+10 µg PEI, 1 µg GM-CSF, 100 µg CpG, 100 µg antigen (OVA protein). 100 µg of OVA protein was used for these experiments. The antigen was adsorbed to PEI-MPS. In short, PEI was adsorbed onto MPS for 15 min at 37° C. to make PEI-MPS. Then, 100 µg of the antigen was adsorbed onto PEI-MPS.

FIGS. 5A-K are graphs and a timeline showing that MSR-PEI vaccine enhances immunogenicity and therapeutic efficacy of peptide vaccines. (A) Percentage of tetramer+ T-cells and (B) IFNγ+ T-cells in peripheral blood on day 7. (C) Schematics of therapeutic TC-1 subcutaneous tumor studies. (D) ELISA analysis of serum TNF-α and (E) IFN-γ level 24 hours post immunization. (F) Percentage of Foxp3+ CD4+ circulating regulatory T-cells 7 days post immunization. (G) Tumor growth in C57BL/6 mice inoculated with $3\times10^5$ TC-1. Mice were vaccinated with the MSR vaccine (V) and MSR-PEI vaccine (VP). (H) Tumor growth in C57BL/6 mice inoculated with $3\times10^5$ TC-1. Mice were treated with the MSR-PEI vaccine at 5 µg PEI or 20 µg PEI, or a bolus vaccine (bolus). (I) Survival of mice inoculated with $3\times10^5$ TC-1 cells treated with the MSR vaccine (V) and MSR-PEI vaccine (VP). (J) Survival of mice rechallenged with $3\times10^5$ cells 6 months after the first inoculation. (K) Circulating regulatory T cell after vaccination with the MSR vaccine or the MSR-PEI vaccine. N=naïve animals; V=MPS vaccine in the formulation: 5 mg MPS+1 µg GM-CSF, 100 µg CpG, 50 µg E7 peptide; VP=MPS vaccine formulation with PEI: 5 mg MPS+10 (or specific dose if indicated otherwise) µg PEI, 1 µg GM-CSF, 100 µg CpG, 50 µg E7 peptide. The amino acid sequence for the E7 peptide was GQAEPDRAHYNIVTFCCKCDSTLRLCVQSTHVDIR (SEQ ID NO: 42). 50 µg of E7 peptide was used. The peptide was adsorbed onto PEI-MPS.

Mesoporous silica is characterized by a large surface area. Synthetic amorphous silica is known to have good biocompatibility, supporting its development as a versatile platform for clinical applications. High-aspect ratio MSRs injected with a needle spontaneously assemble in vivo to form macroporous structures which provide a 3D cellular microenvironment for host immune cells. Recruitment of dendritic cells and their subsequent homing to lymph nodes can be modulated by sustained release of signaling molecules from the scaffold.

Figure 11A:
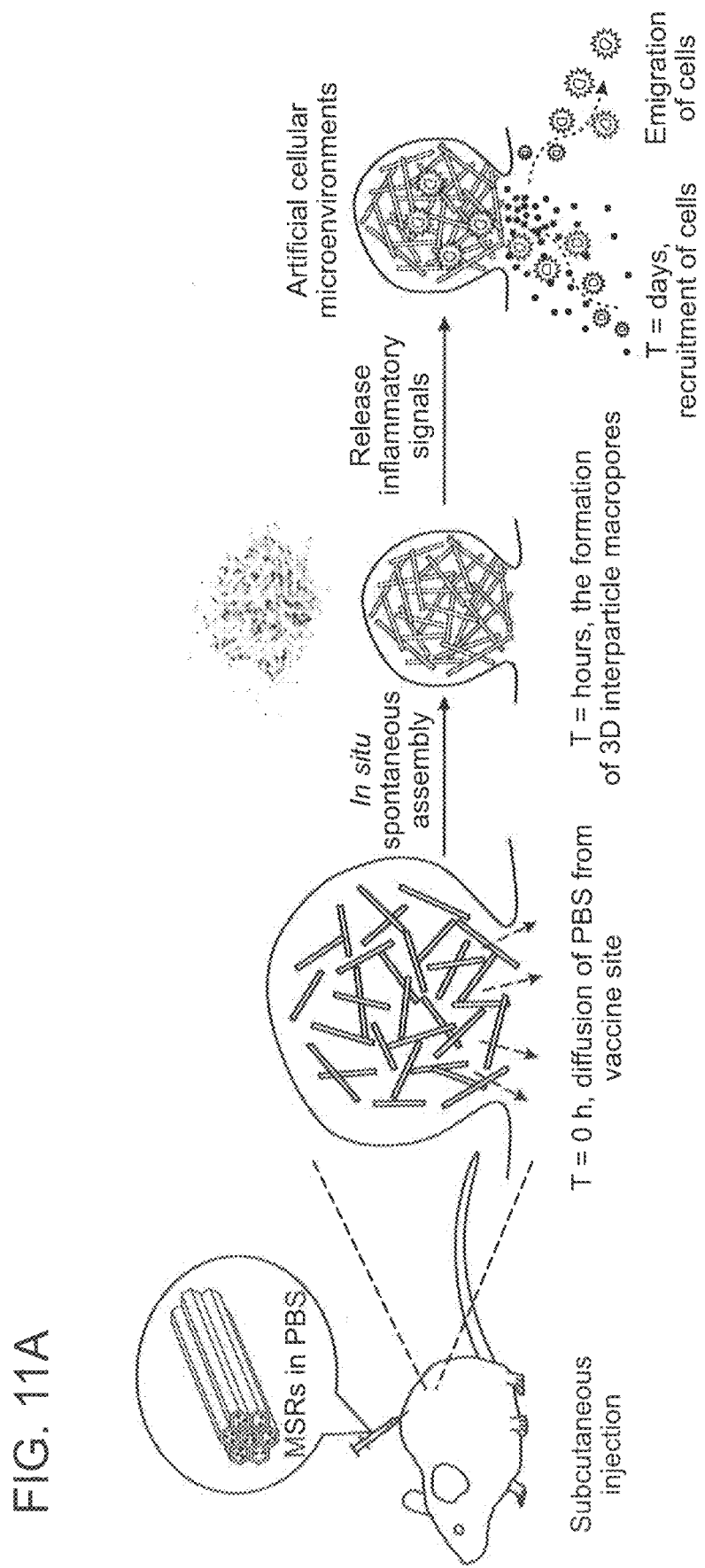
FIG. 11A is a cartoon showing the use of MSRs as a vaccine platform.
Figure 11B:
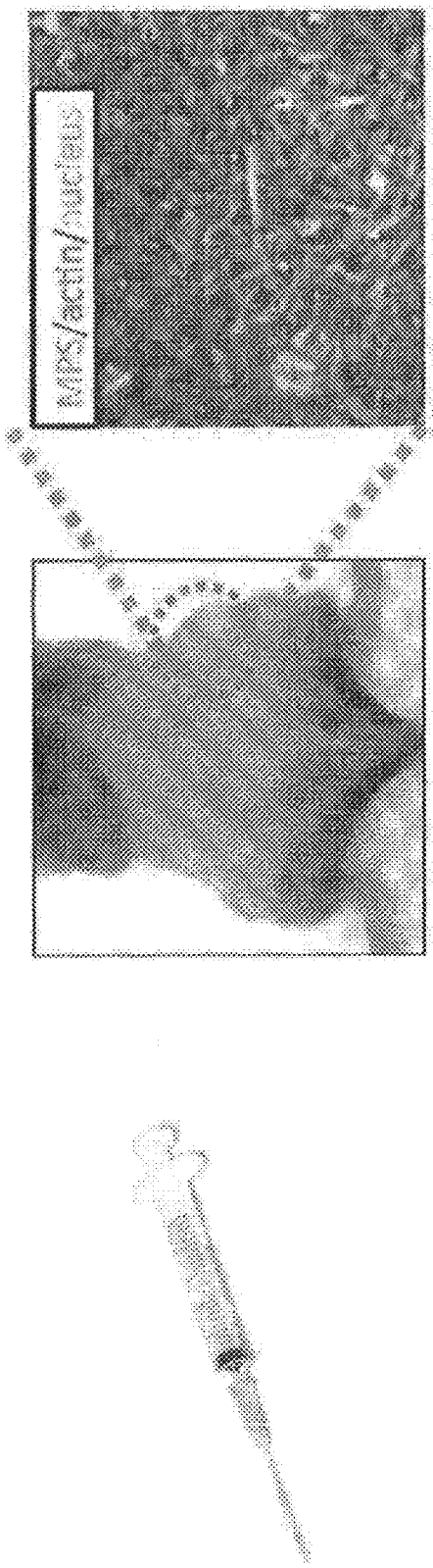
FIG. 11B is a set of images showing macroporous scaffold formation after injection of MSRs.
Figure 11C:
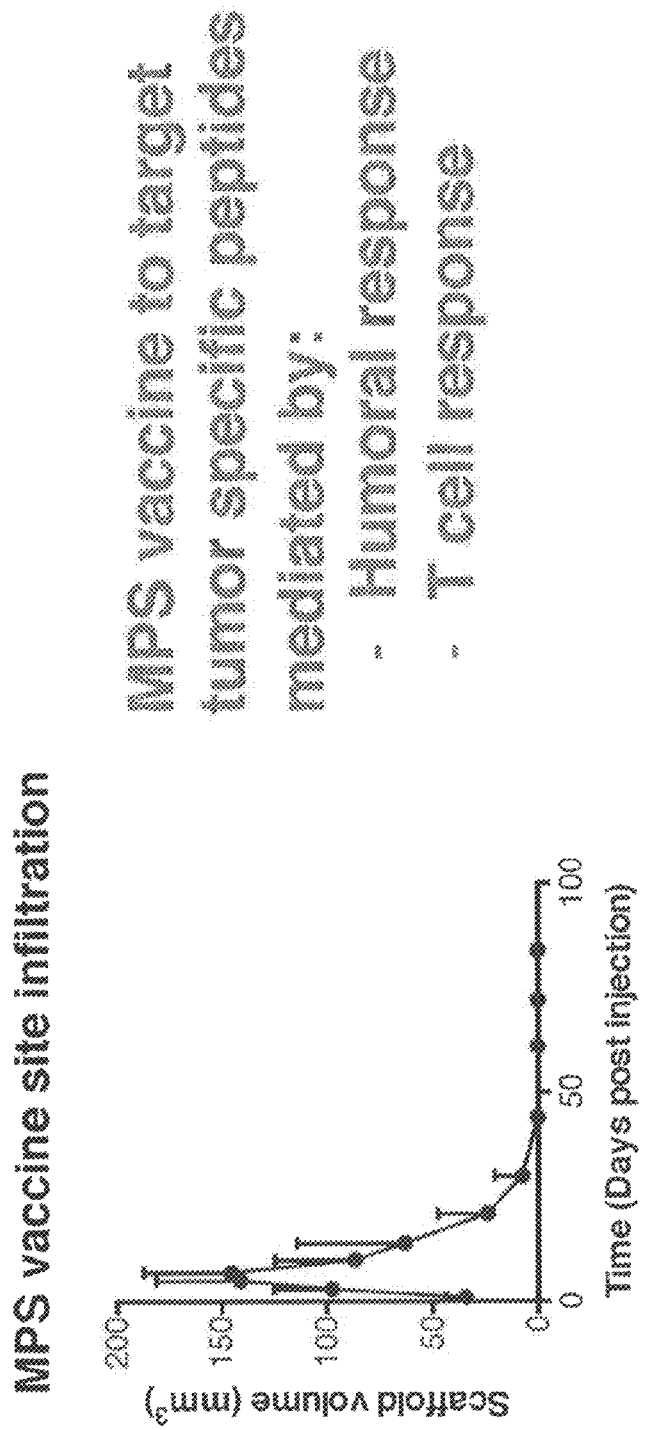
FIG. 11C is a graph showing MPS vaccine site infiltration.

MSRs are injectable, which overcomes limitations regarding the scaffolds that must be surgically implanted. MSRs can assemble into 3D microenvironments for dendritic cells directly in the body. In some embodiments, long rod-like microparticles that are a couple of orders of magnitude larger than the size of one immune cell are used. In certain embodiments, these microparticles are injected into tissues such as the skin, and because of their size, they do not diffuse away from the injection site. In various embodiments, due to a high aspect ratio, the rods stack on top of each other, forming pores in between the particles that allow for cell infiltration. In some embodiments, mesoporous silica is used to make the micro-rods. In certain embodiments, the vaccine is injected through a standard 23 gauge (G) needle. As shown in FIGS. 11A and B, after injecting such rods into animals under the skin, a scaffold formed readily, and millions of immune cells were able to infiltrate into the scaffold. In non-limiting examples, GM-CSF and CpG may be incorporated to recruit and activate host DCs to formulate the MPS vaccine. In various embodiments, the vaccine is degradable and is generally cleared from the injection site within about 2 months. In some embodiments, such a MPS vaccine system is used to generate anti-tumor immunity through both humoral and T cell driven pathways.

Figure 12:
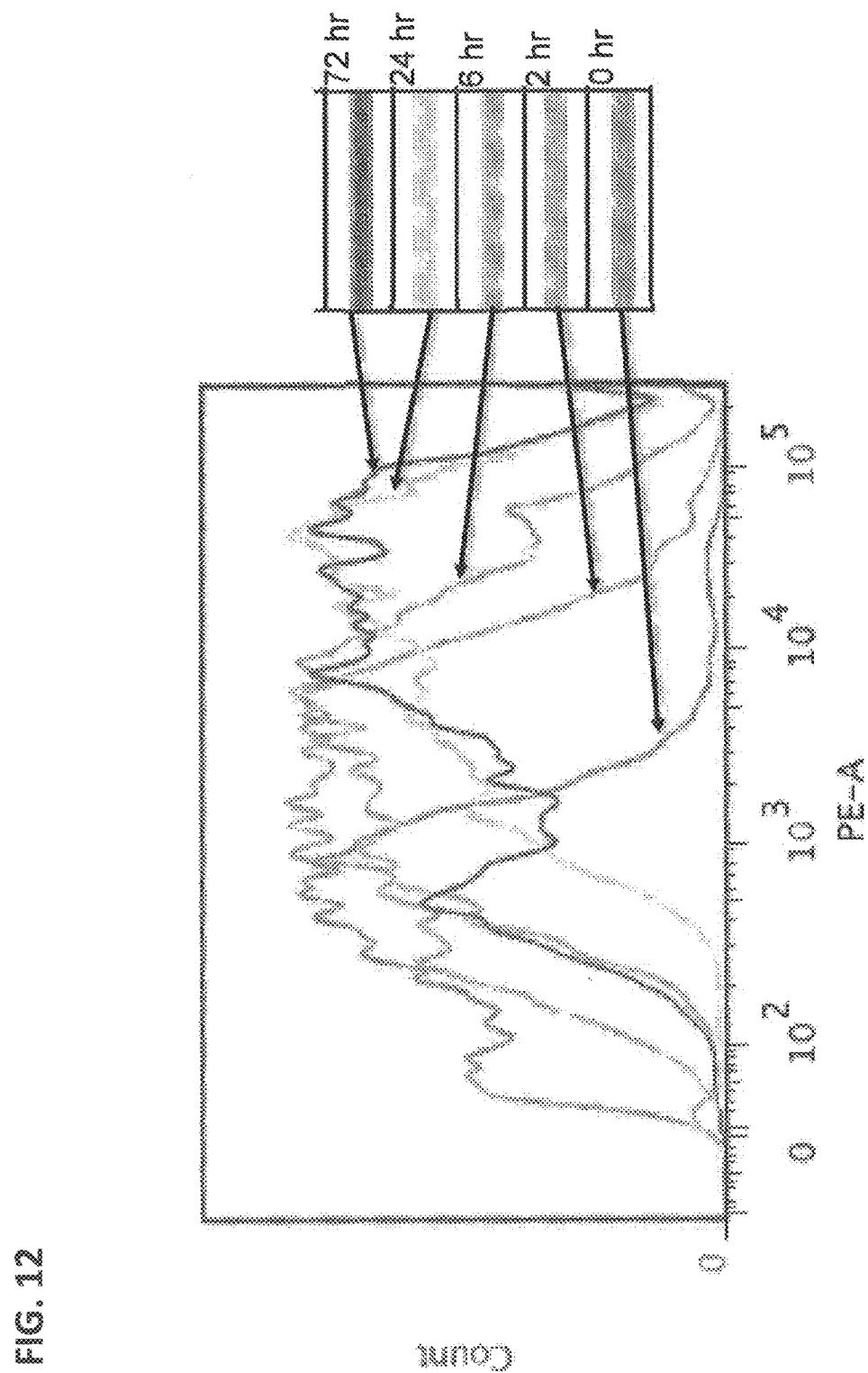

FIG. 12 is a graph showing that PEI is fully uptaken by BMDCs after 24 hours. Bone marrow derived DCs (BMDCs) were stimulated with rhodamine labeled PEI for 0, 2, 6, 24 or 72 hours and the uptake was quantified using flow cytometry.

Figure 13:
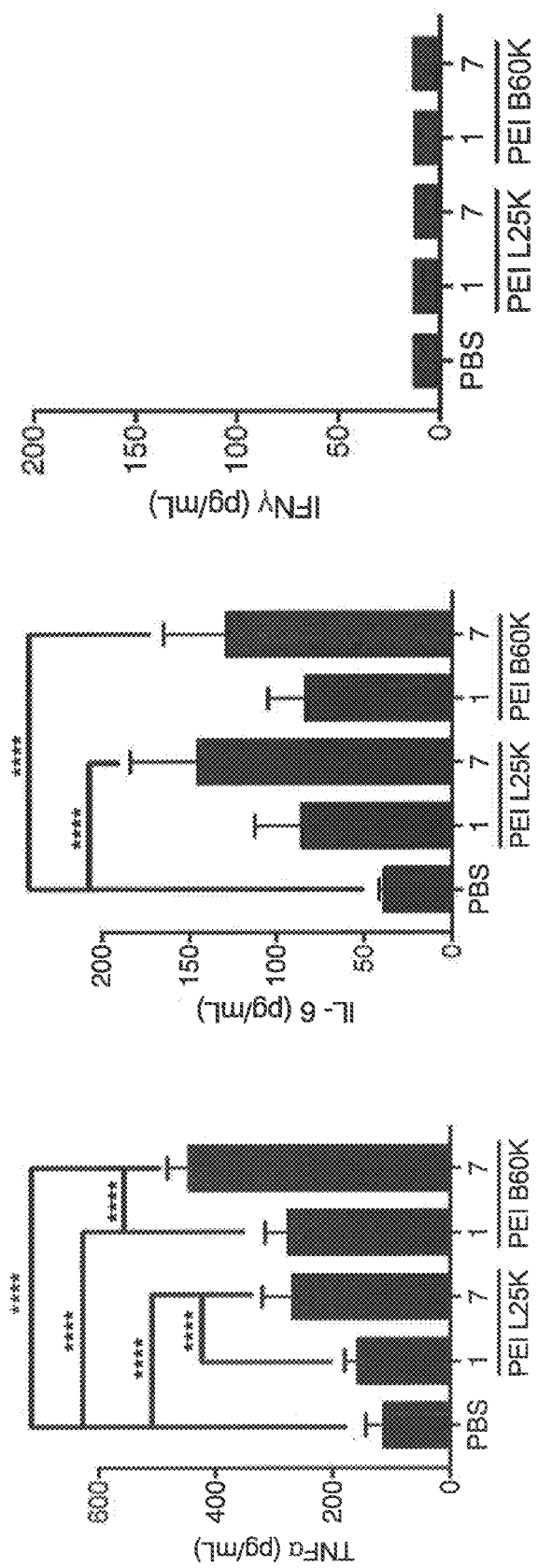

FIG. 13 is a series of graphs showing that BMDCs treated with increasing doses of free PEI show an increased pro-inflammatory profile. ELISA analysis of TNF-α, IL-6 and IFN-γ concentration in BMDC supernatant after 18 hours of stimulation with various concentration of PEI.

Figure 14:
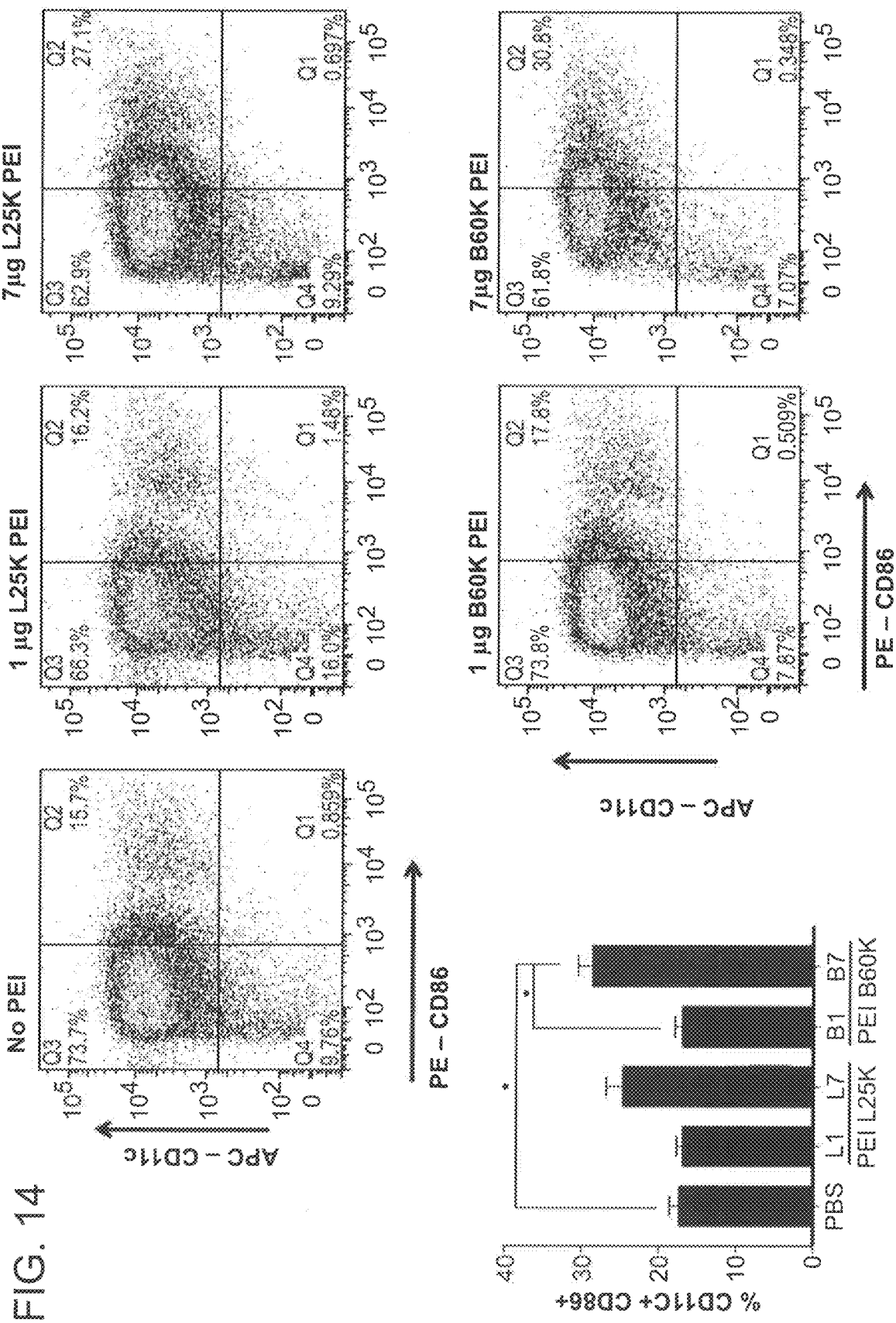

FIG. 14 is a graph and a set of fluorescence-activated cell sorting (FACS) charts showing that BMDCs treated with increasing doses of free PEI show increased activation and maturation. Flow cytometry analysis of CD11c and CD86 expression on BMDCs after 18 hours of stimulation with various concentrations of PEI is shown. The data show a clear linear upward trend for L25K groups, and for first two doses of B60K. L1=Linear PEI 25 KD 1 µg; L7=Linear PEI 25 kD 7 µg; B1=Branched PEI 60 kD 1 µg; B7=Branched PEI 60 kD 7 µg.

FIG. 15 is a series of images and graphs relating to non-limiting optimization of PEI loading into cryogels. Direct seeding and soaking methods were used. Two methods of loading PEI into alginate tough cryogel were investigated. PEI was diluted in a small volume and added directly into the cryogel (seed method). Alternatively, alginate cryogel was first partially collapsed and then rehydrated in small volume of PEI (soak method).

"Soaking" method: Extract free solution from cryogel to partially collapse pores, then drop that into PEI containing solution to take advantage of expansion of pores to incorporate PEI via electrostatic interactions. Non-limiting example of a "soaking" method: (i) Make 30 µL PEI solutions containing desired mass of PEI (one Eppendorf tube per gel); (ii) Remove ~25 µL of water around gel; (iii) Drop gel into respective 30 µL PEI solution; (iv) incubate at 37° C. for 30 minutes; (iv) Collect gels, wash in 100 µL distilled (dH$_2$O), place in Petri dish; (v) Store 100 µL wash and gel residue in original Eppendorf tube to quantify amount of PEI lost. Quantification of unlabeled PEI loading efficiency in cryogels was performed using LavaPep™ peptide quantification kit (Gel Company, San Francisco, CA, USA). In a non-limiting example of a "seeding" method, a small volume (e.g. 1-30 µl) of PEI solution was directly added to the gel.

Figure 16B:
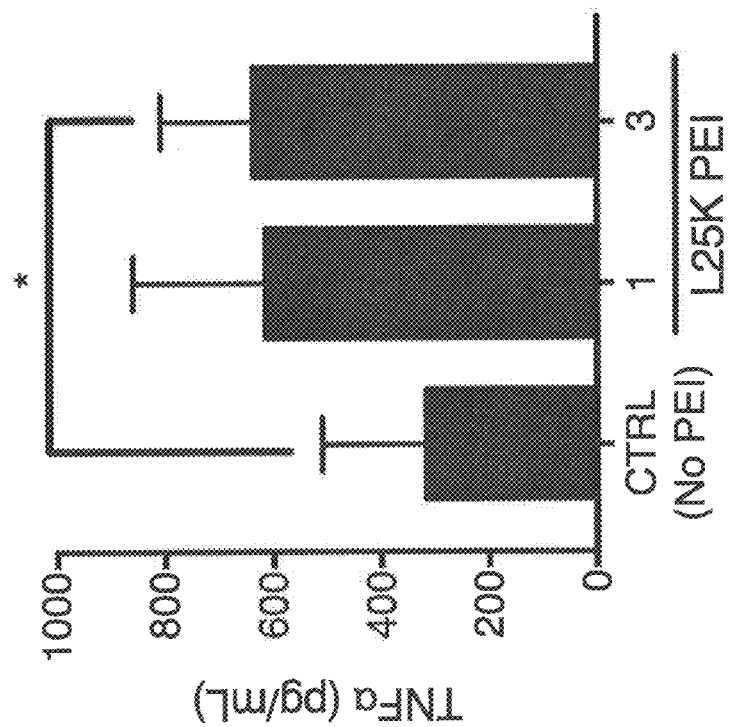
Figure 16A:
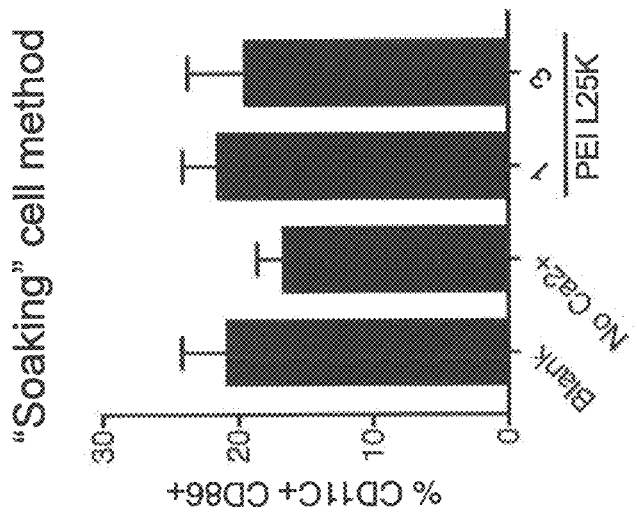

FIGS. 16A and B are graphs showing that BMDCs encapsulated in cryogels loaded with PEI increased pro-inflammatory profile. In blank cryogel, there is also activation, possibly coming from excess calcium, which forms calcium phosphate micro-particles (either due to interaction with PBS or media) that could trigger an immune response. (A) BMDCs were cultured in Alginate cryogel-PEI for 18 hours and the surface expression of CD11c and CD86 was analyzed using flow cytometry. (B) BMDCs were cultured in Alginate cryogel-PEI for 18 hours and the supernatant was measured for TNF-α production.

Figure 17:
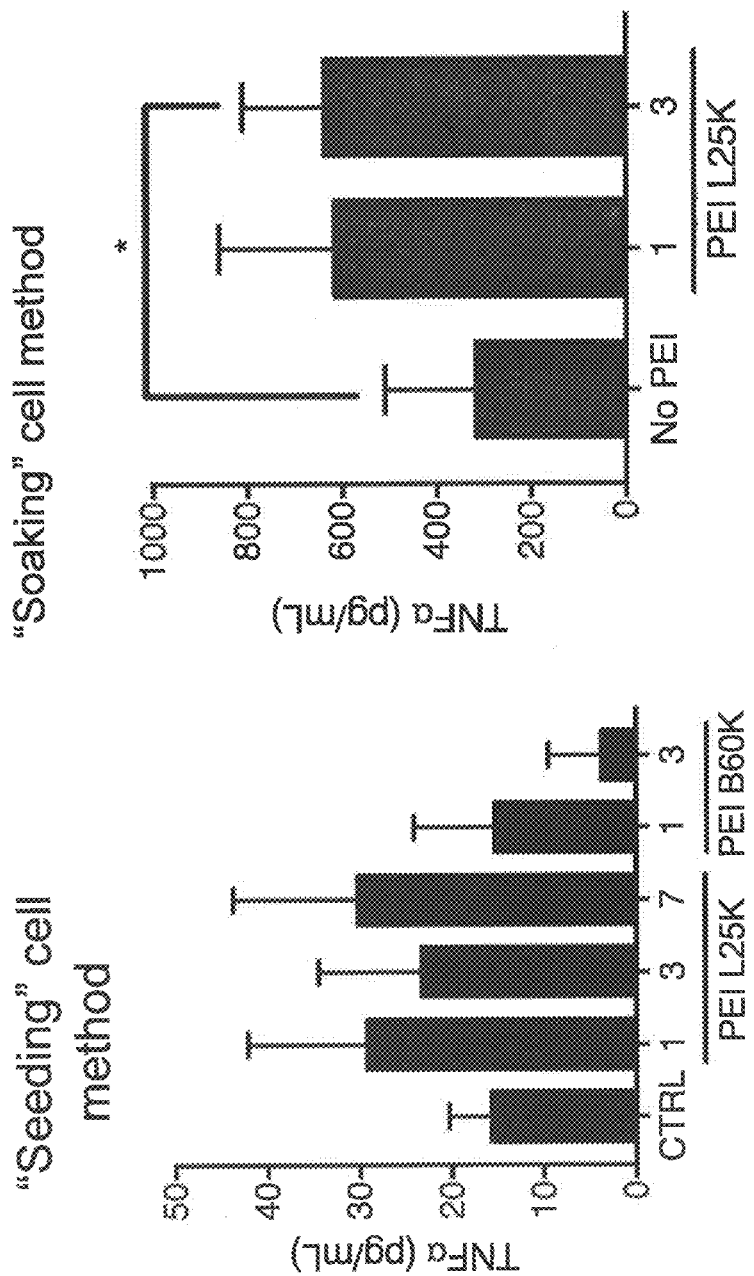

FIG. 17 is a set of graphs showing that BMDCs encapsulated in cryogels loaded with PEI may show an increased pro-inflammatory profile. Right Panel: BMDCs were cultured in alginate cryogel-PEI (synthesized using the "seeding" or "soaking" method as indicated) for 18 hours and supernatant was collected and analyzed for TNF-α using ELISA.

Figure 18B:
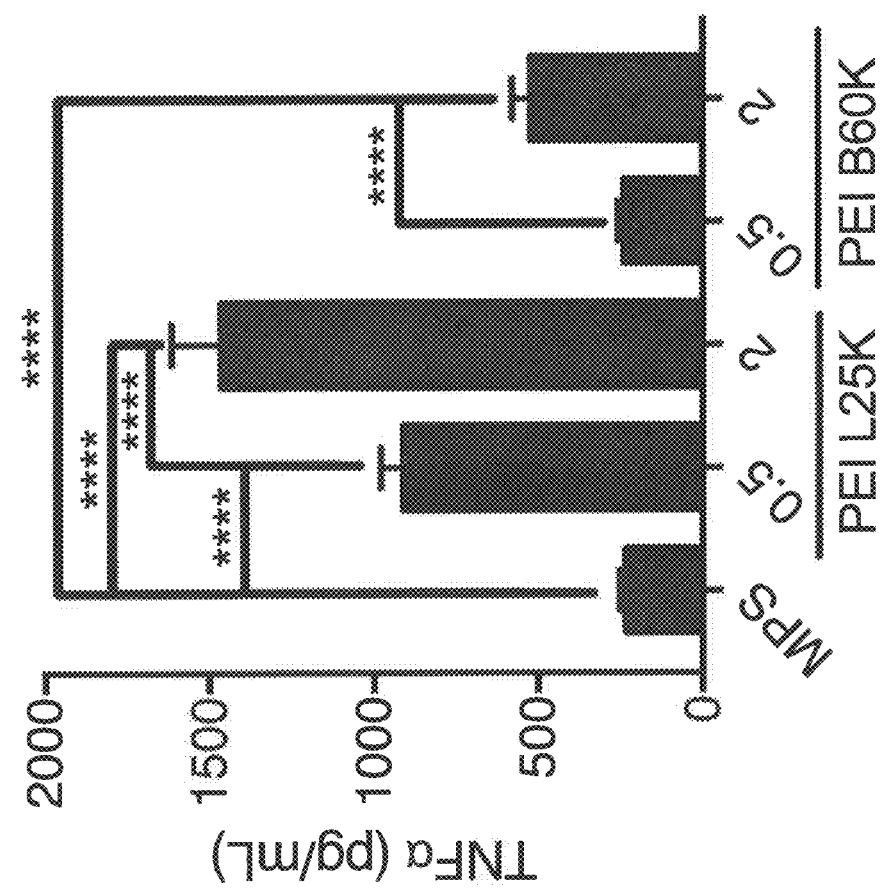
Figure 18A:
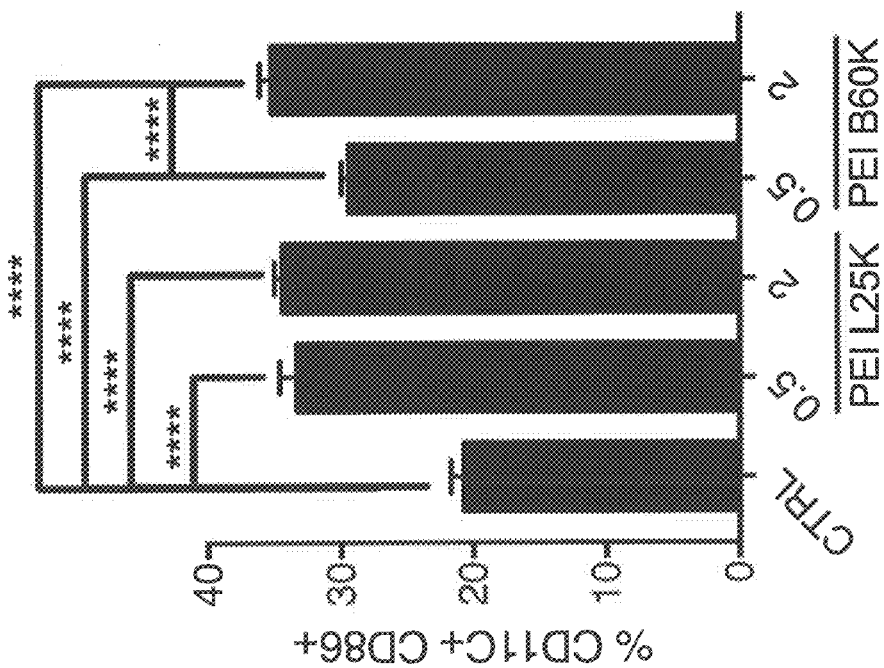

FIGS. 18A and B are graphs showing that BMDCs encapsulated in MPS loaded with PEI show increased activation, maturation and pro-inflammatory profile. (A) Flow cytometry analysis of CD11c and CD86 expression on BMDCs after 18 hours of stimulation with various concentrations of PEI-MSR. (B) ELISA analysis of TNF-α concentration in BMDC supernatant after 18 hours of stimulation with various concentrations of PEI-MSR.

FIGS. 19A and B are graphs showing in vitro stimulation by PEI incorporated into PLG scaffolds. (A) HEK293 cells co-transfected with hTLR5 gene and harboring an NF-κB-dependent secreted embryonic alkaline phosphatase reporter plasmid were seeded on PLG scaffolds (PLG) or scaffolds containing either linear (L25) or branched PEI (B60). (B) IL-12 and IFN-α cytokine production by BMDCs seeded onto branched-PEI scaffolds normalized to PLG controls.

Figure 20B:
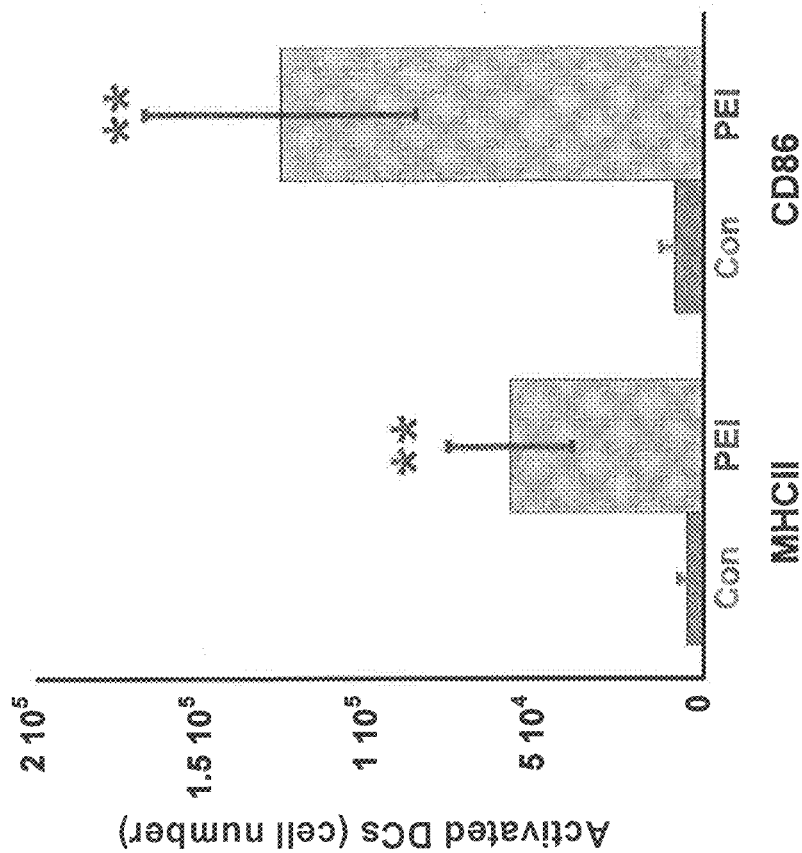
Figure 20A:
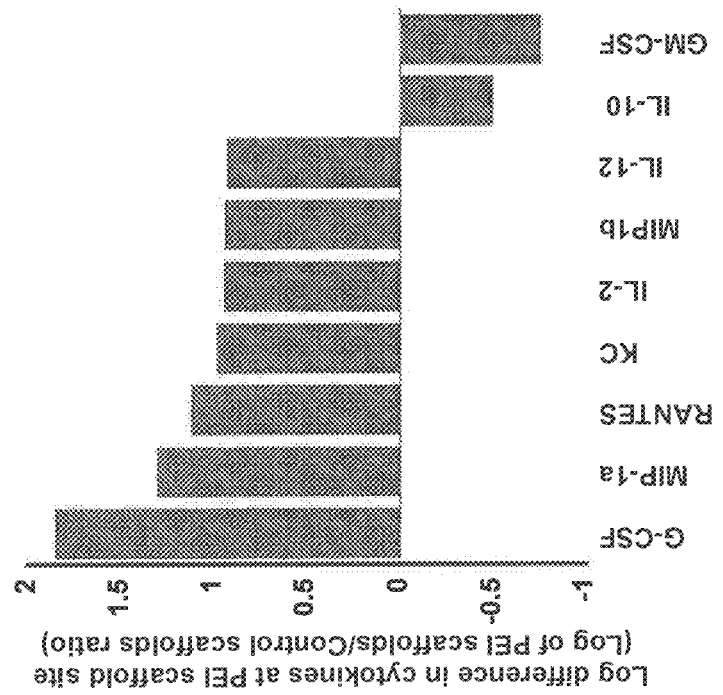

FIGS. 20A-C are graphs showing in vivo cytokine and activated DC induction and prophylactic vaccination with PEI-loaded PLG vaccines. (A) Log difference in cytokine concentration at PEI vaccine site relative to control vaccines. (n=5) (B) The number of MHCII+ and CD86+ at day 7 after implantation of PLG vaccines (con) and PEI-PLG vaccines (PEI). (N=5) (C) Mice were vaccinated with PLG vaccines 14 days prior to B16-F10 melanoma tumor challenge (105 cells). A comparison of survival in untreated mice (Control) and mice treated with PLG vaccines loaded with GM-CSF in combination with either B16 Lysate (PLG) or Lysate combined with PEI (PEI-PLG). n=10. **P<0.01 versus all other experimental conditions.

Figure 21B:
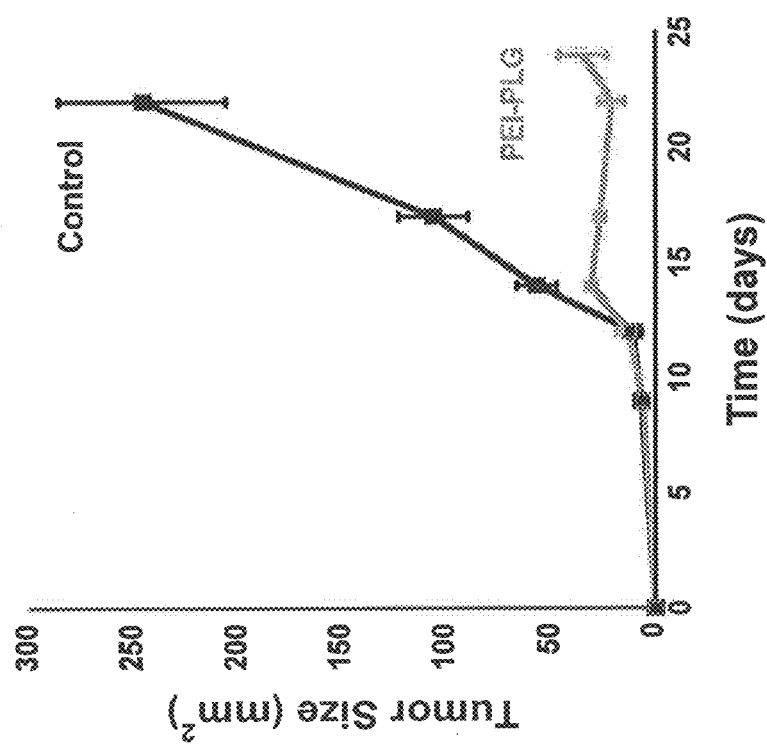
Figure 21A:
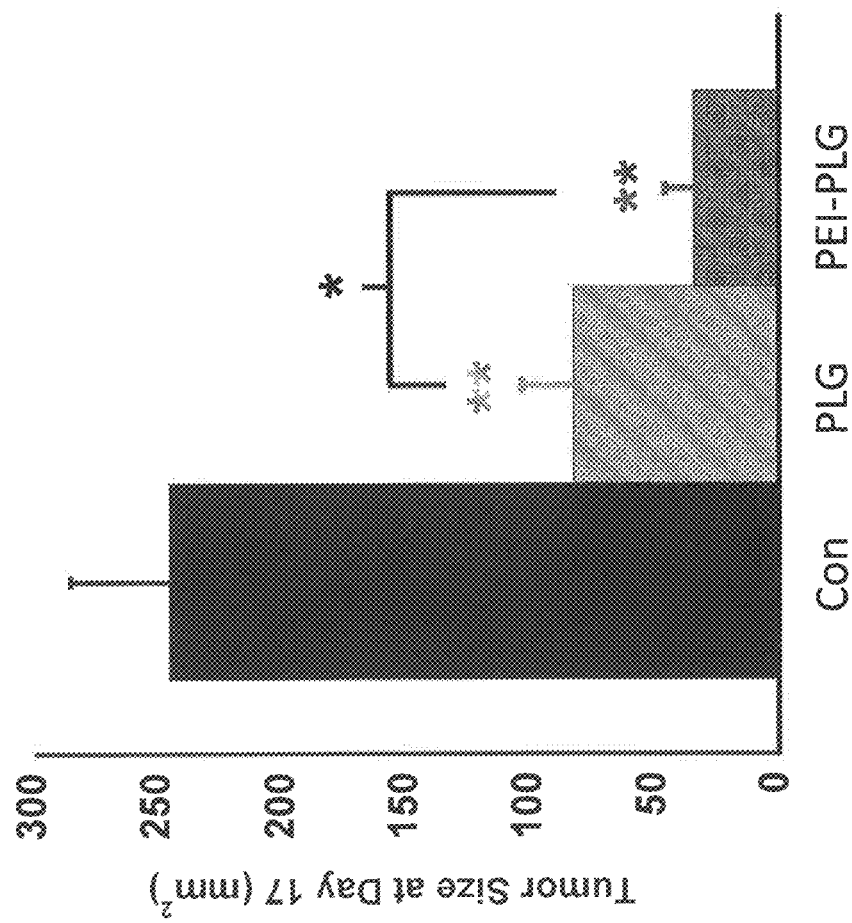
Figure 21C:
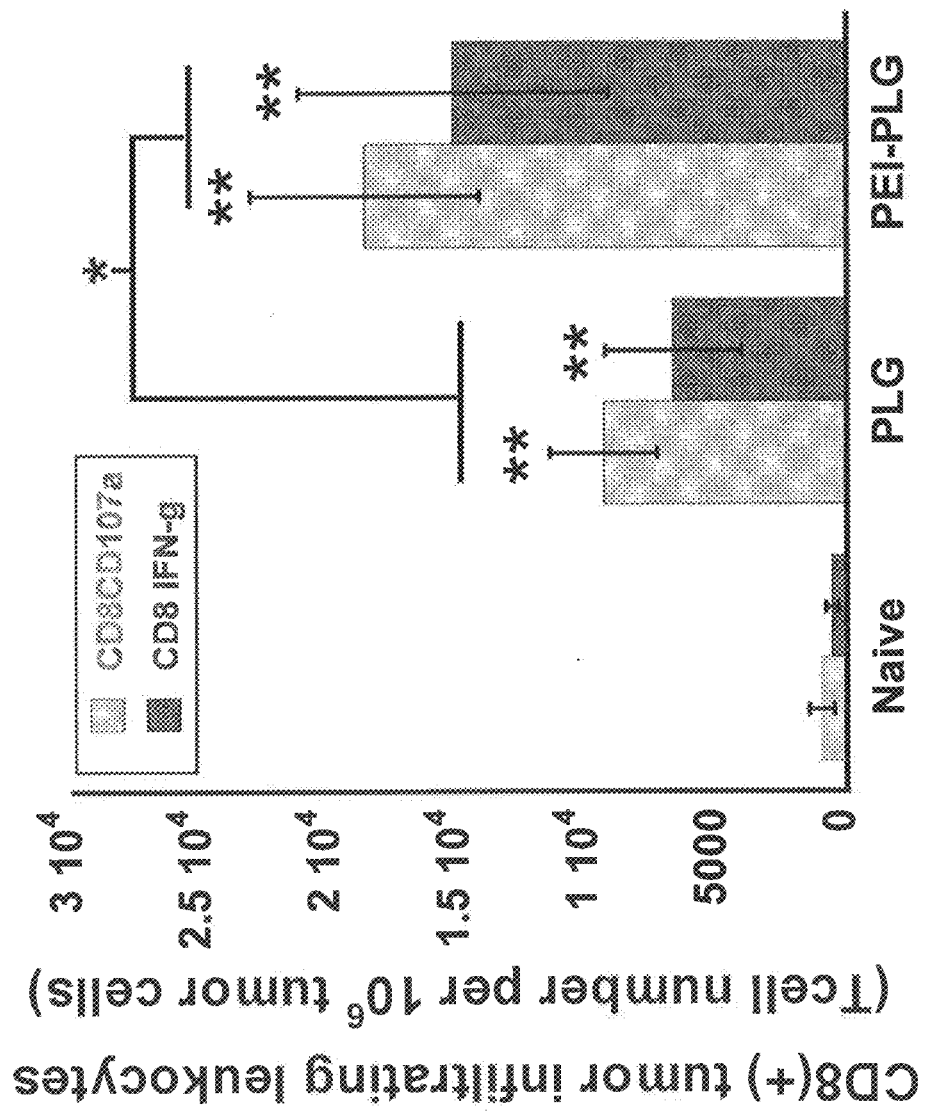

FIGS. 21A-C are graphs showing therapeutic vaccination with PLG scaffolds containing PEI conjugated lysate. The conjugation (attachment) occurs by electrostatic interactions. (A) A comparison of the day 17 tumor size and (B) tumor growth kinetics in mice bearing established B16-F10 tumors (inoculated with 5×10$^5$ B16-F10 cells and allowed to develop for 9 days) that were untreated (Con) or treated with PLG vaccines loaded with GM-CSF in combination with tumor lysate (PLG) or with lysate combined with PEI prior to incorporation. (C) Single cell suspensions were prepared from B16 tumors at Day 17 and stained for activated, cytotoxic T cell markers, IFNγ and CD107a. The numbers of CD3+CD8+, tumor-infiltrating T cells positive for either IFNγ or CD107a in untreated mice (naïve) or mice vaccinated with PLG vaccines (PLG) or PEI-PLG vaccines (PEI-PLG). * P<0.05 ** P<0.01 compared to controls, unless otherwise noted.

Figure 22B:
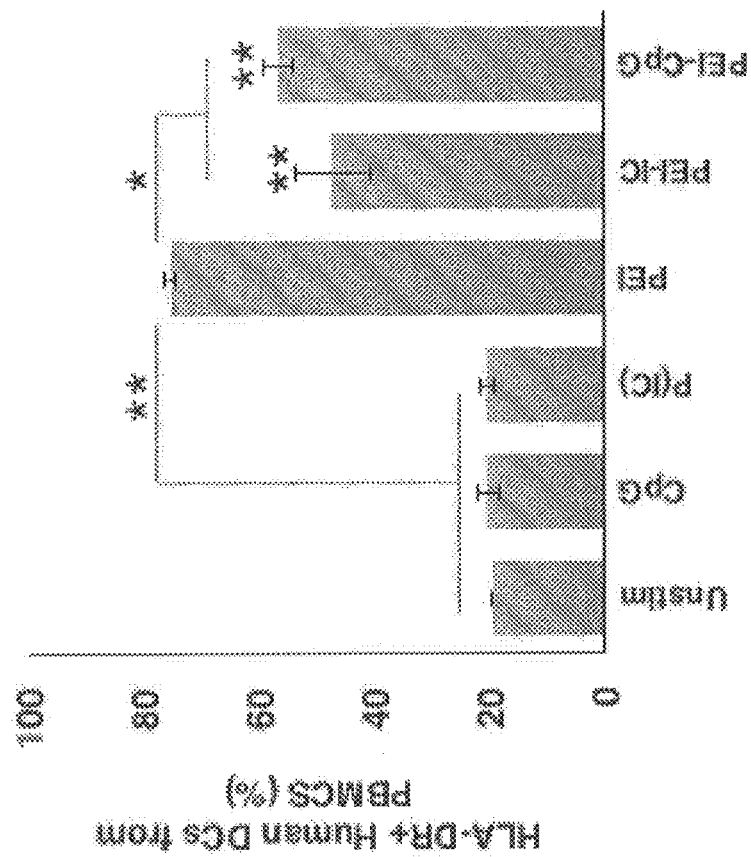
Figure 22A:
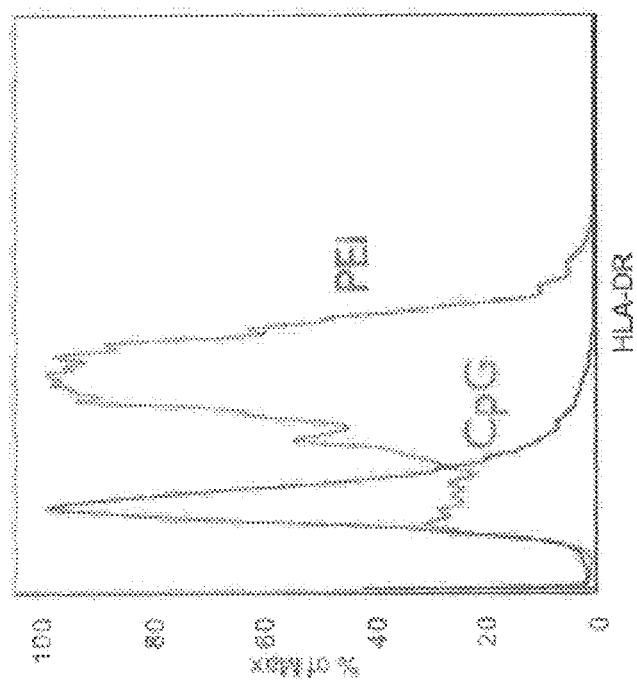
Figure 22C:
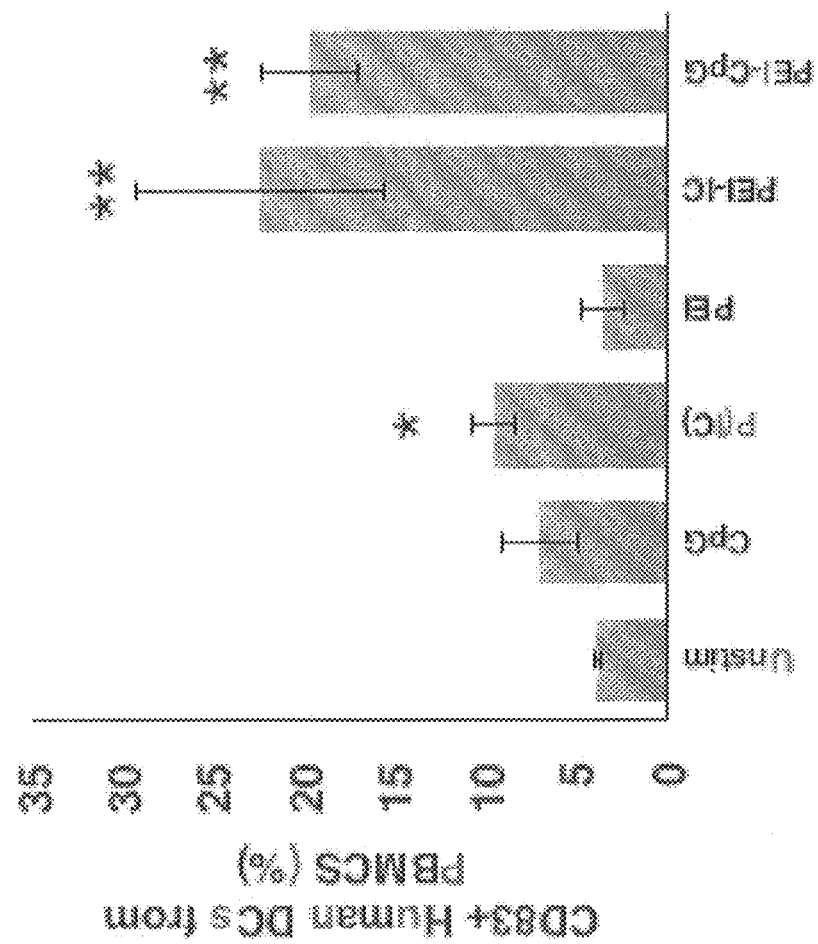

FIGS. 22A-C are graphs showing HLA and CD83 expression by human dendritic cells seeded onto PLG scaffolds. (A) Representative FACS histogram of HLA-DR expression on in vitro human dendritic cells seeded onto PLG scaffolds loaded with CpG or PEI. (B) HLA-DR and (C) CD83 expression on in vitro DCs seeded onto blank PLG scaffolds (Unstim) or scaffolds loaded with CpG-ODN (CpG), polyI:C (P(IC)), PEI alone or PEI in combination with p(IC) [PEI-p(IC)] or CpG (PEI-CpG). *P<0.05**P<0.01 compared to controls, unless otherwise noted.

Figure 23A:
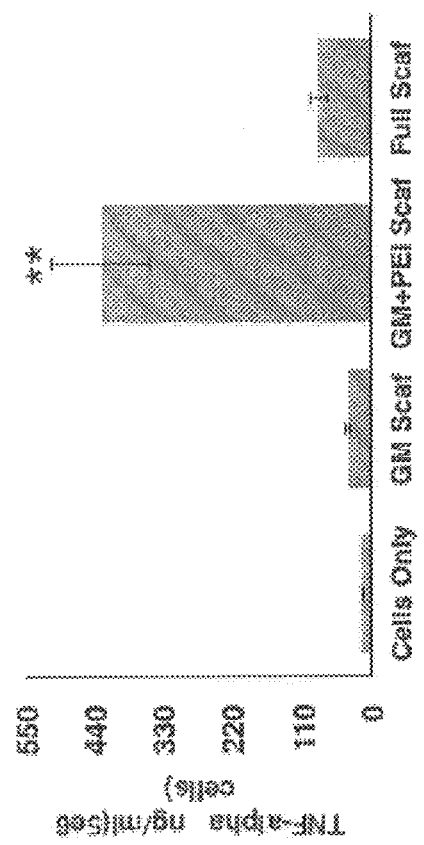
Figure 23B:
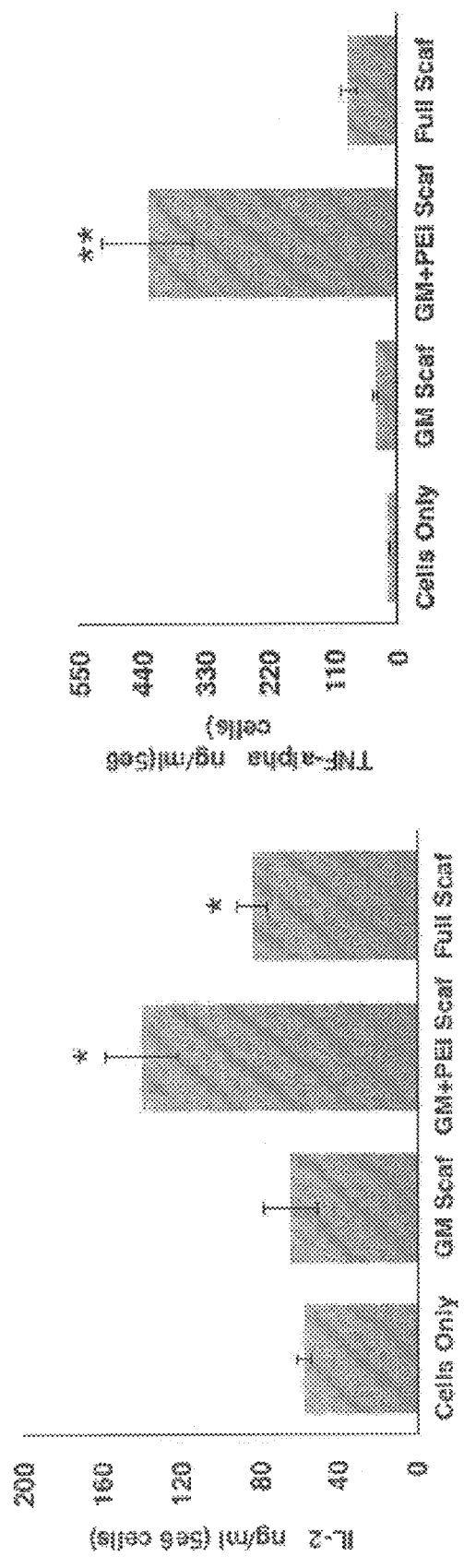
Figure 23C:
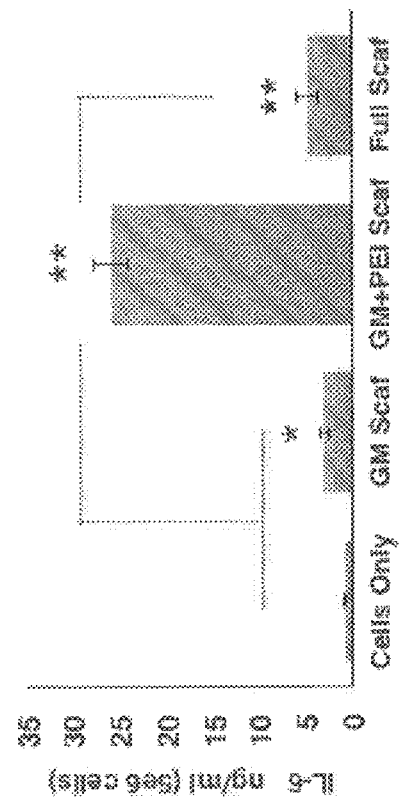

FIGS. 23A-C are graphs showing cytokine production by human dendritic cells seeded onto PLG scaffolds. (A) IL-2 (B) TNF-alpha and (C) IL-6 production by in vitro human DCs alone (cells only) or DCs seeded onto hGM-CSF loaded PLG scaffolds (GM Scat), or scaffolds loaded with hGM-CSF in combination with PEI (GM+PEI Scat) or CpG-ODN (Full scaf). *P<0.05**P<0.01 compared to controls, unless otherwise noted.

Figure 24A:
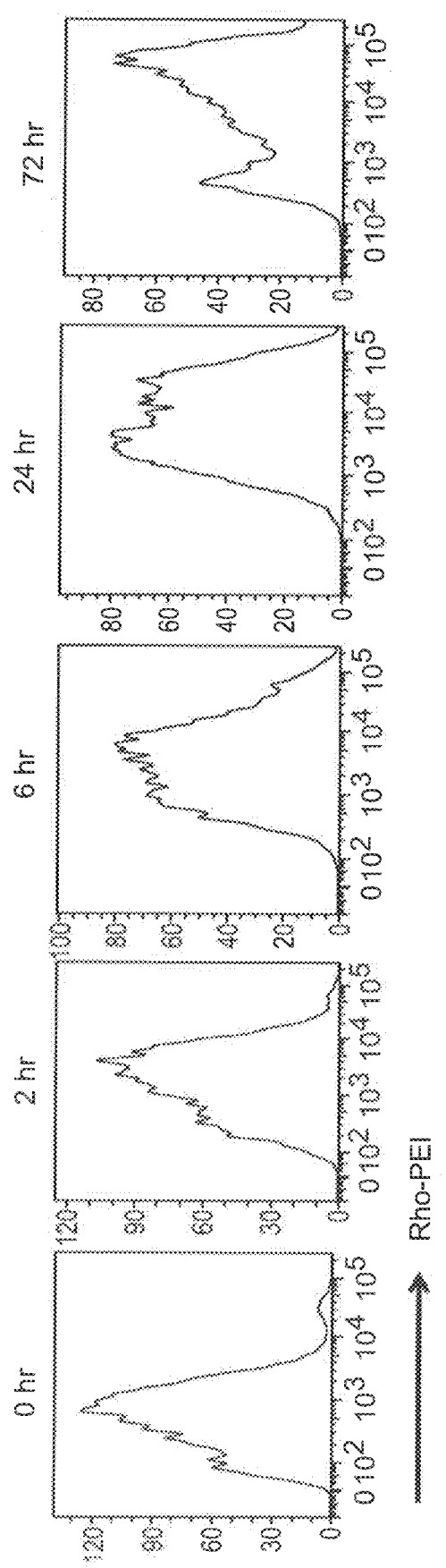
Figure 24B:
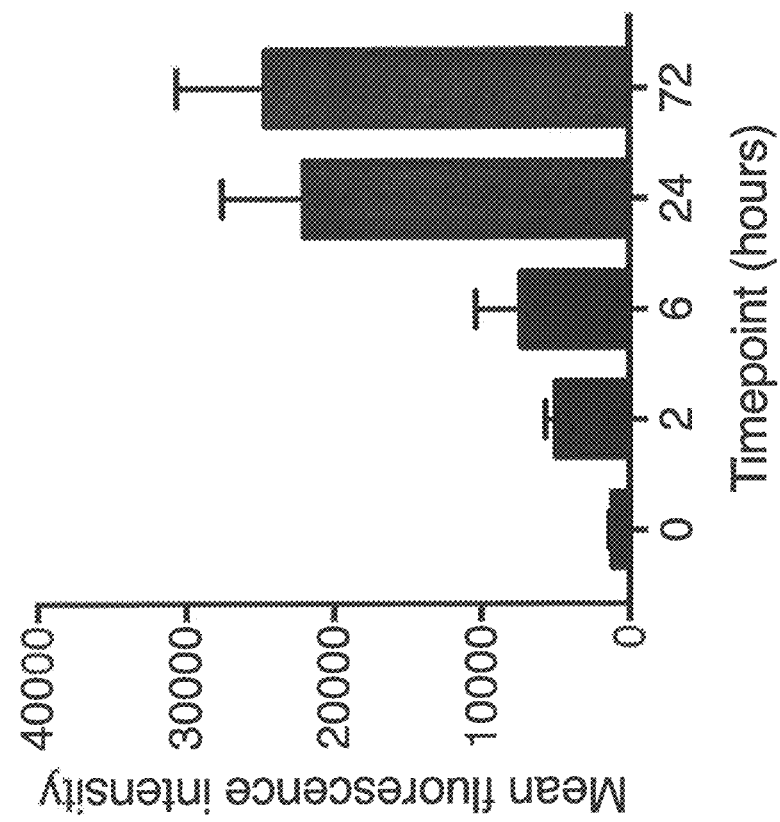
Figure 26B:
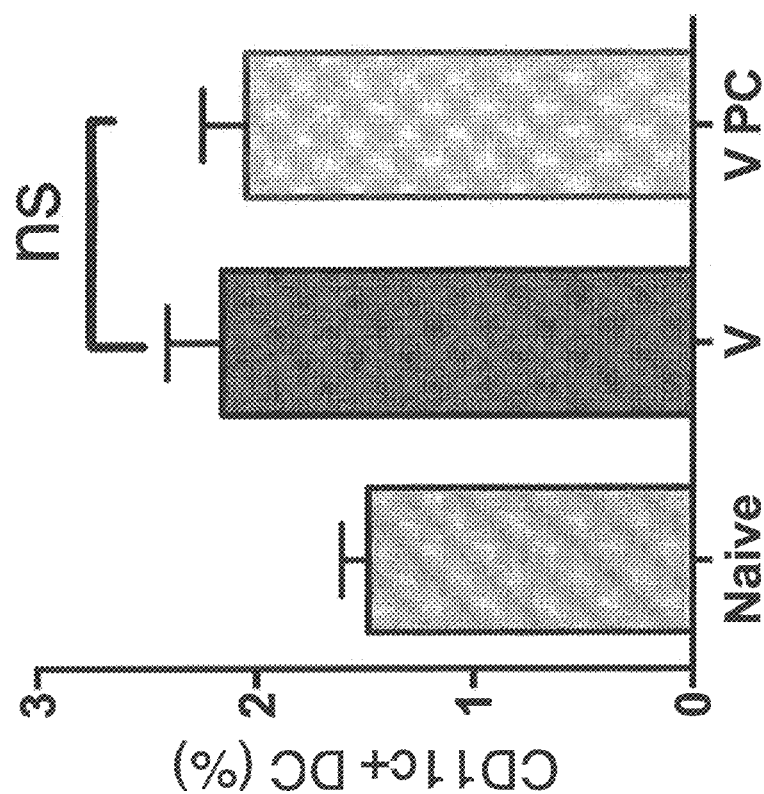
Figure 26A:
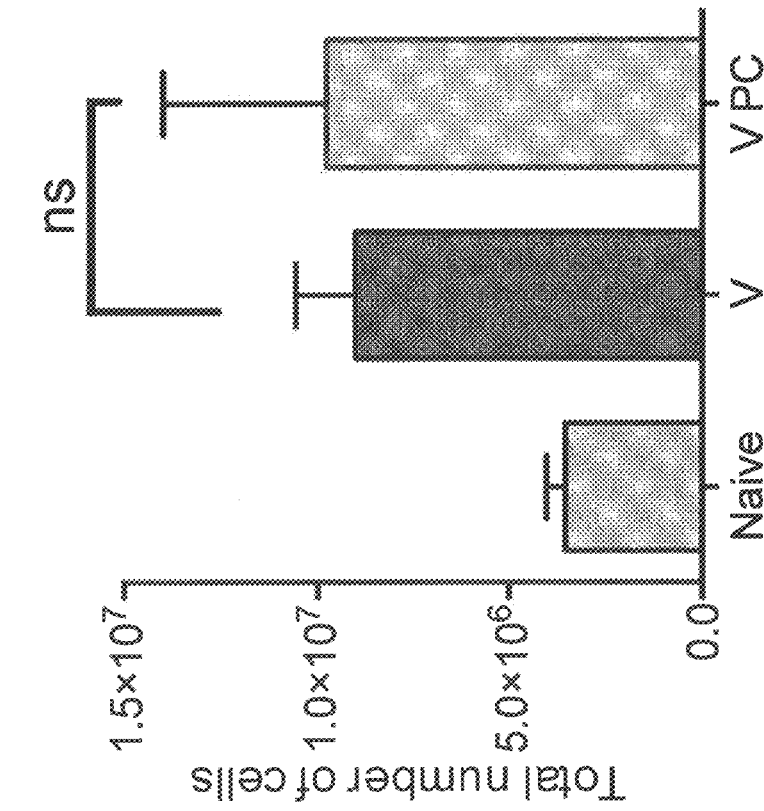
Figure 26D:
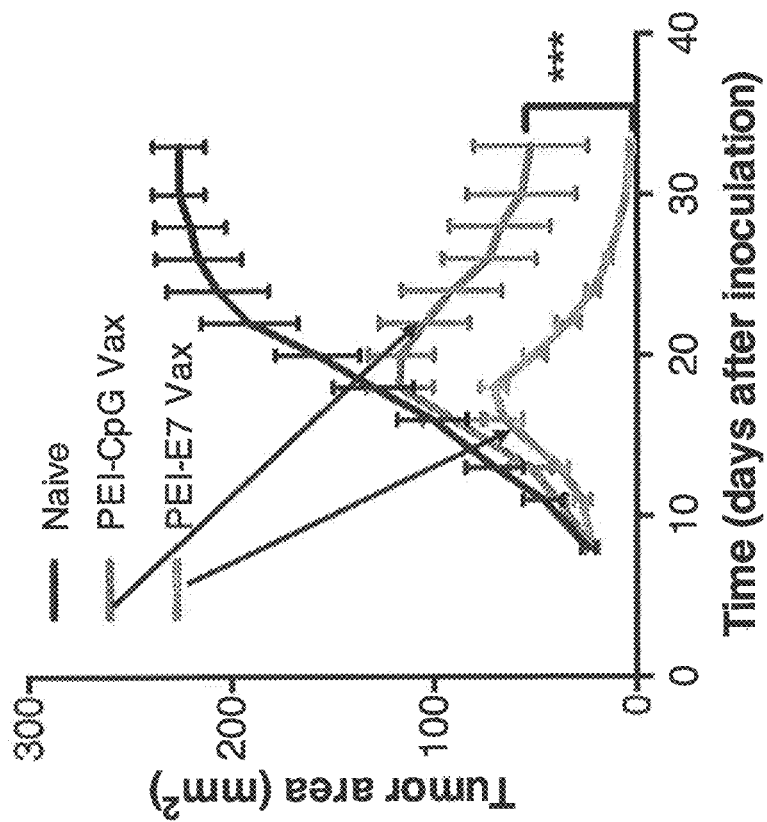
Figure 26C:
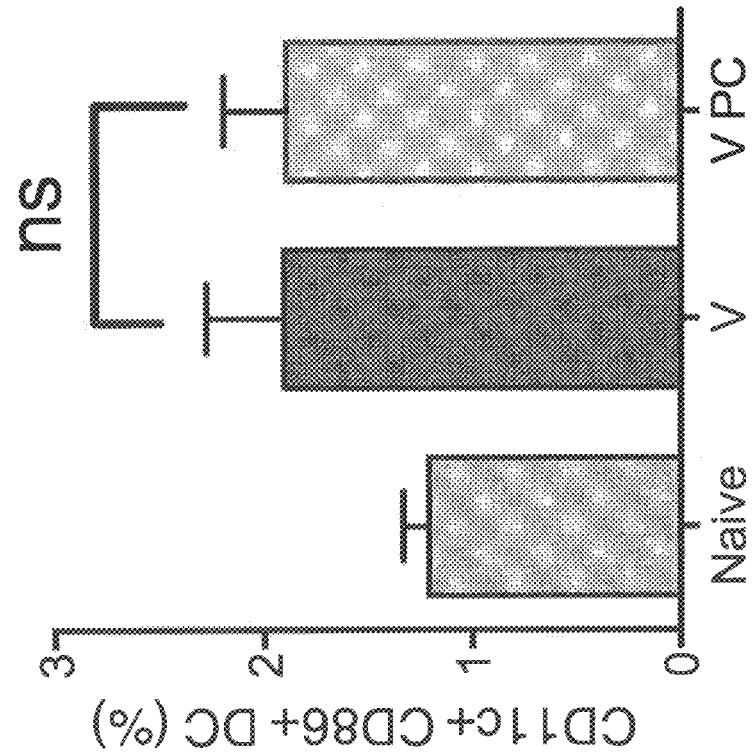

FIGS. 24A and B are graphs showing uptake kinetics of rhodamine labeled PEI by dendritic cells. (A) Flow cytometry graphs showing the uptake kinetics of rhodamine labeled PEI by dendritic cells from 0 h to 72 h. (B) Quantitative compilation of the data in (A).

FIGS. 25A-C are graphs showing immune activation. Percentage of (A) macrophages and (B) activated macrophages in the vaccine draining lymph node after immunization with the MSR vaccine (V) or the MSR-PEI vaccine (VP). (C) Circulating SIINFEKL specific CD8 T cells after immunization with the MSR vaccine (V) or vaccine containing only GM-CSF, PEI and the antigen OVA (PEI-OVA).

FIGS. 26A-D are graphs showing characterization of an MSR-PEI vaccine. (A) Total cell number, (B) percentage of CD11c DCs, and (C) percentage of activated DCs in the vaccine draining lymph node after immunization with the MSR vaccine (V) and MSR-PEI vaccine in which PEI is incorporated with CpG (V PC). (D) Tumor growth kinetics after inoculating with $3\times10^5$ TC-1 cells and treated with the MSR vaccine (V) and MSR-PEI vaccine in which PEI is incorporated with CpG (V PC).

Figure 27A:
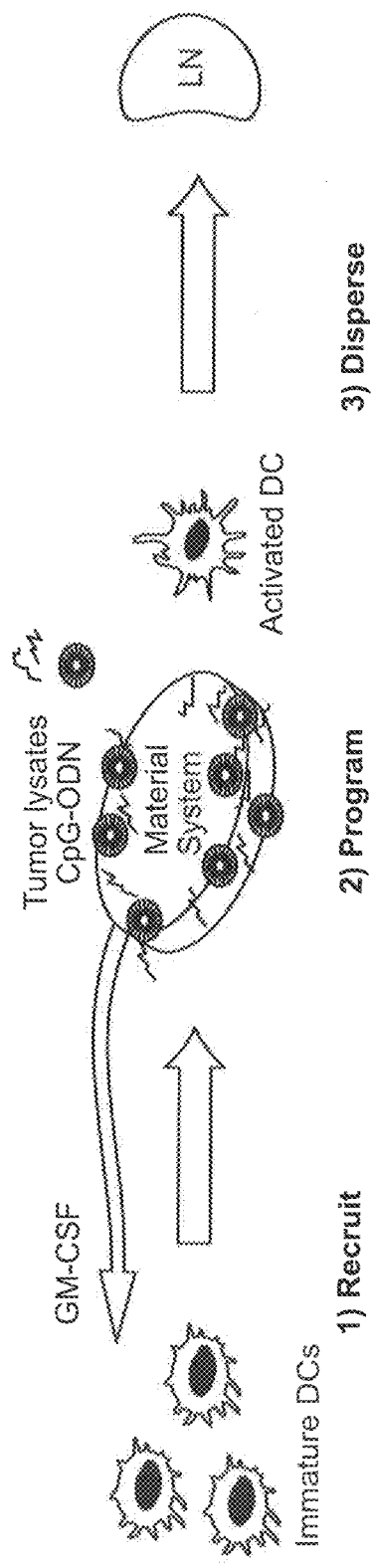
Figure 27B:
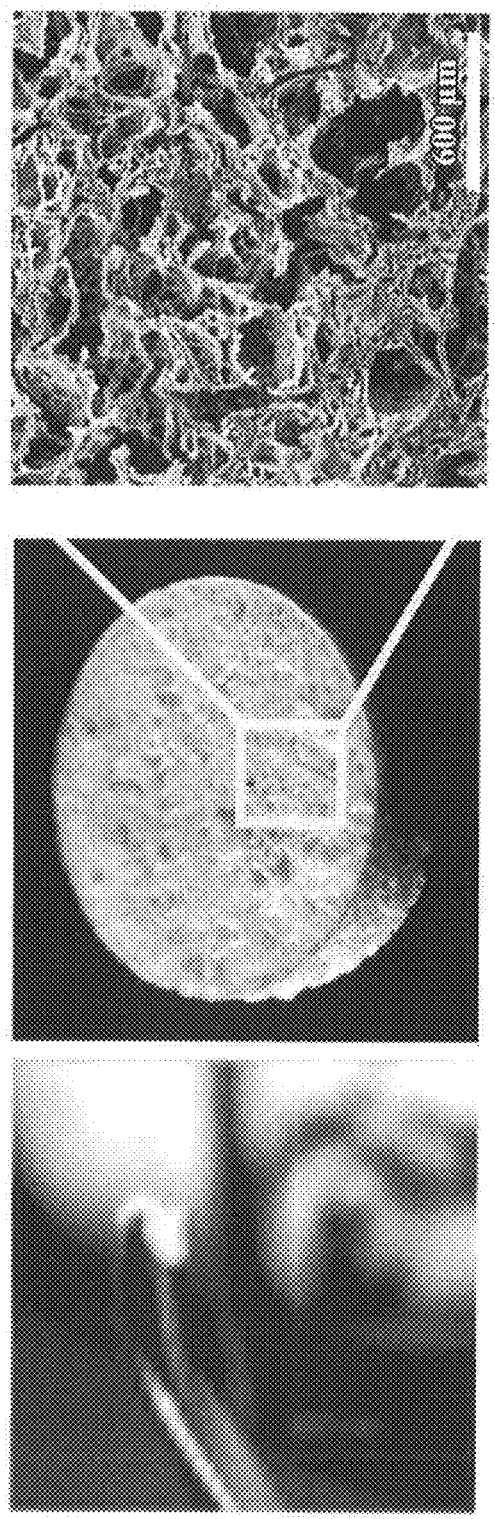

FIG. 27A is cartoon and FIG. 27B is a set of images relating to exemplary engineered polymer scaffolds that enhance cancer vaccines. Provided herein are strategies using biomaterials to modulate the function of immune cells in vivo. Without being bound by any scientific theory, FIG. 27A shows an exemplary process of recruitment, programming and dispersal of immune cells using engineered polymer (such as PLG) scaffolds to enhance cancer vaccination. FIG. 27B shows an exemplary biomaterial vaccine, which is a pill sized piece of plastic that contains interconnected pores and releases factors that support dendritic cell function. This engineered biomaterial can be surgically implanted under the skin of a tumor-bearing host as a vaccine to generate anti-tumor immunity against distant tumors. When it was tested in therapeutic a B16-F10 melanoma model, a biomaterial vaccine cured a large fraction of mice from established tumors. In some embodiments, a scaffold provided herein may be surgically implanted or injected. In certain embodiments, tumor lysate or specific purified tumor antigens are incorporated into or onto a scaffold.

Figure 28A:
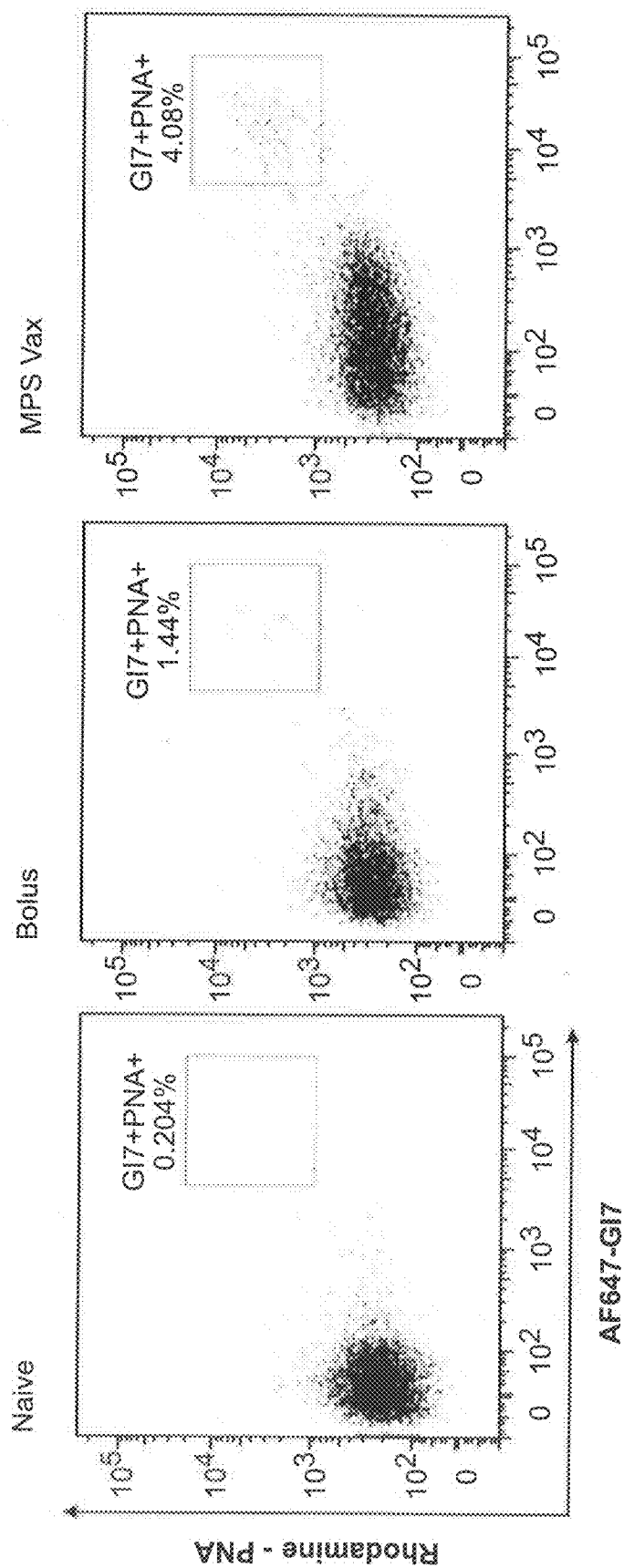
Figure 28B:
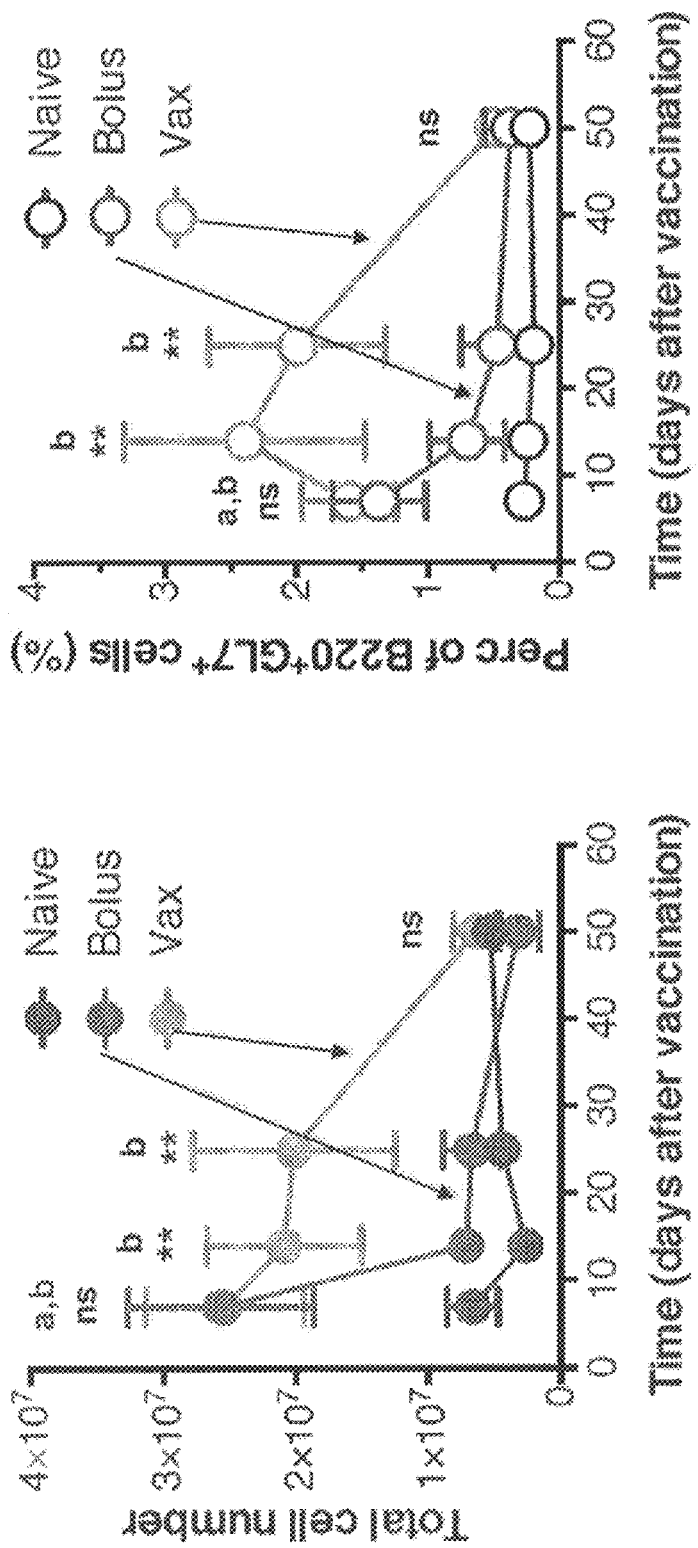
Figure 28C:
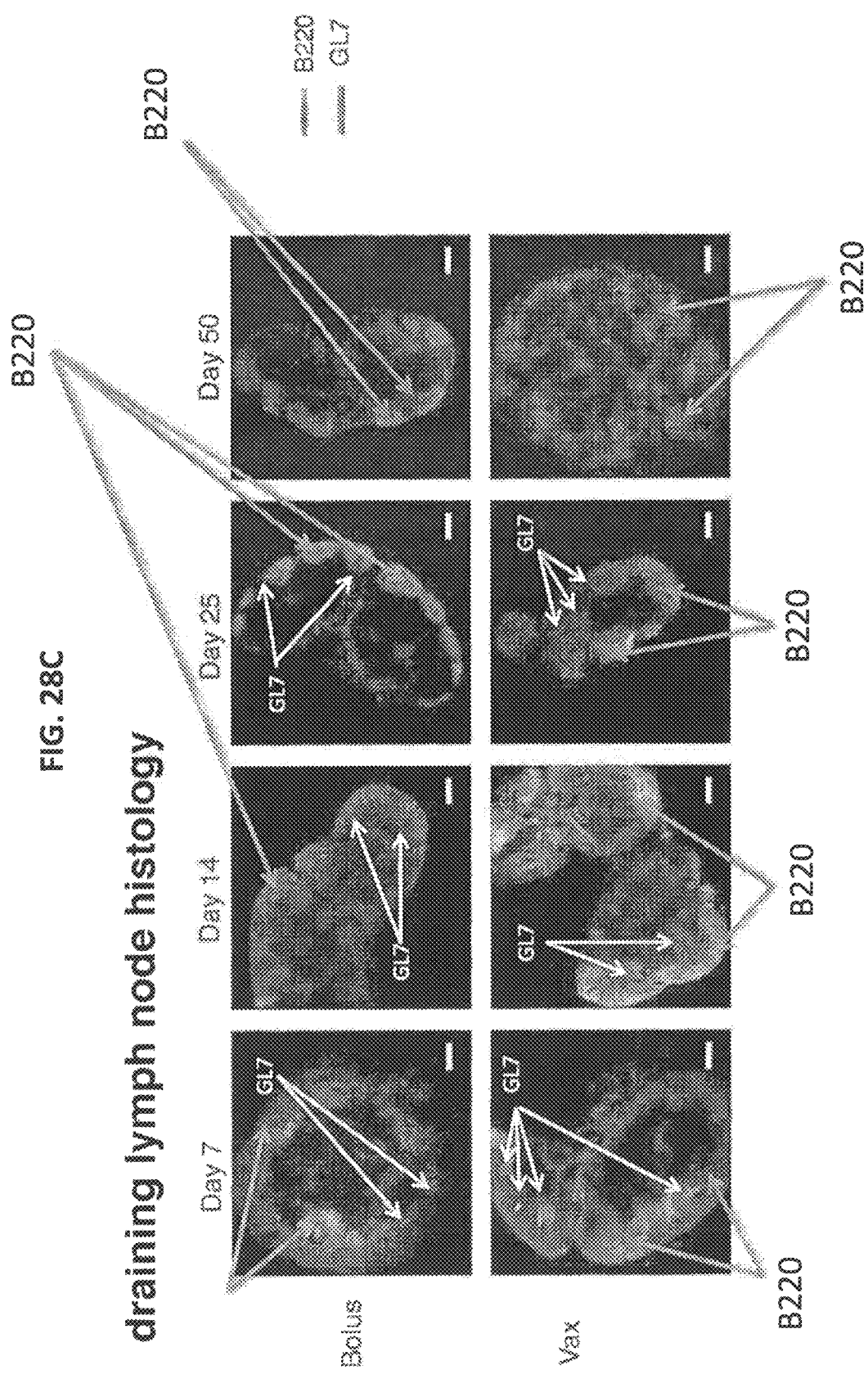

FIGS. 28A and B are graphs, and FIG. 28C is a set of images, showing that a MPS vaccine induces a persistent germinal center reaction. One of the challenges of generating effective humoral response is generating robust germinal center B cell reaction. A single injection of the MPS vaccine against a self-peptide coupled to OVA elicited persistent germinal center B cell reaction for over a month. In comparison, a bolus vaccine strategy using the same adjuvant, CpG and GM-CSF elicited a transient germinal center reaction that quickly dissipated after a week. (A) A primary flow cytometry plot of Panel B, day 14 time point. (B) Left panel shows total cell number in the lymph nodes. Right panel shows cells having markers for activated B cells. (C) Fluorescent images show in increase in B cells undergoing activation in the germinal centers of lymph nodes of Vax treated mice compared to Bolus treated mice. B220 is a marker for B cells and GL7 is a marker for germinal center B cells. The images show that the level of GL7 is higher in Vax compared to Bolus at days 7, 14, and 25.

Figure 29A:
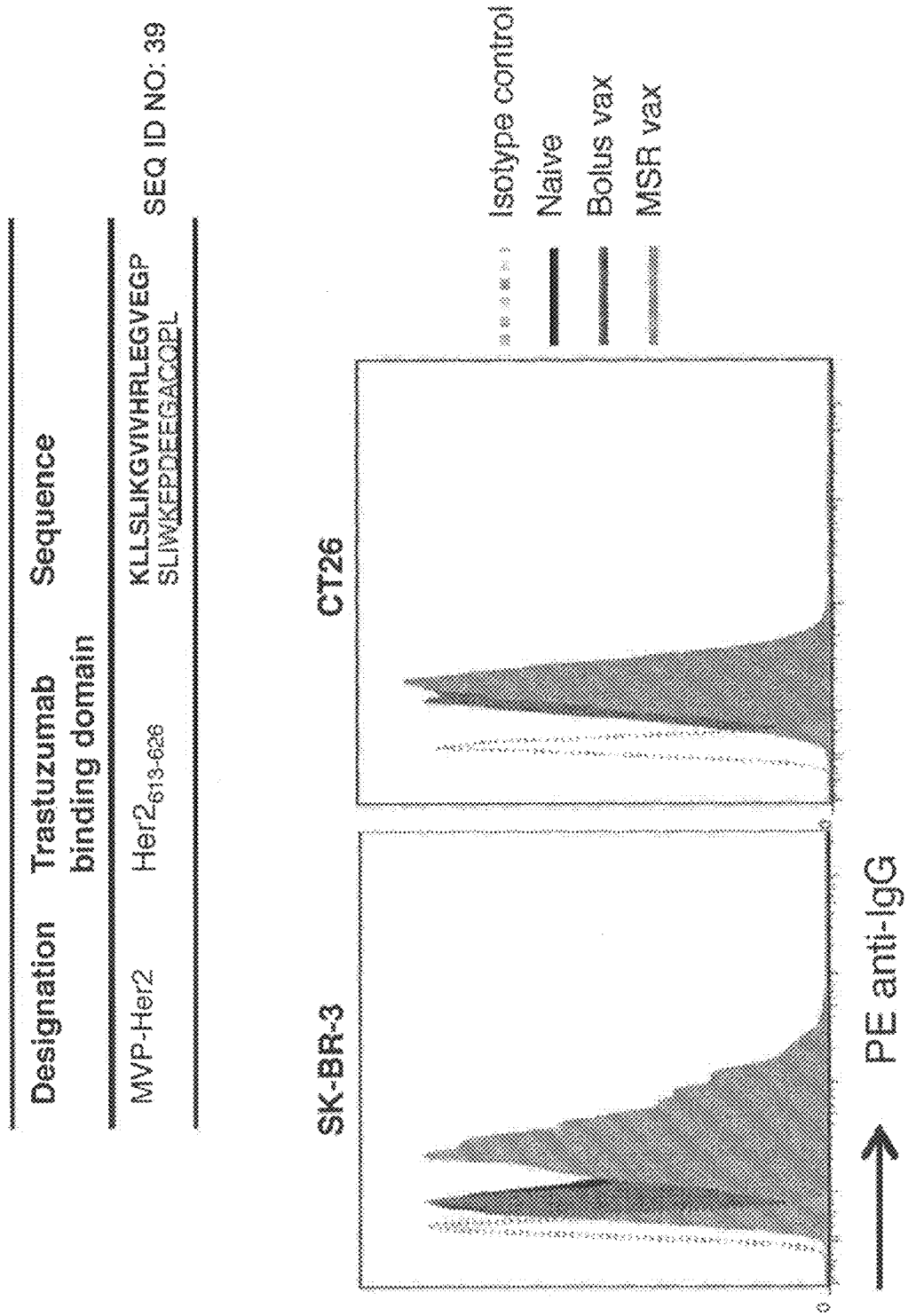
Figure 29B:
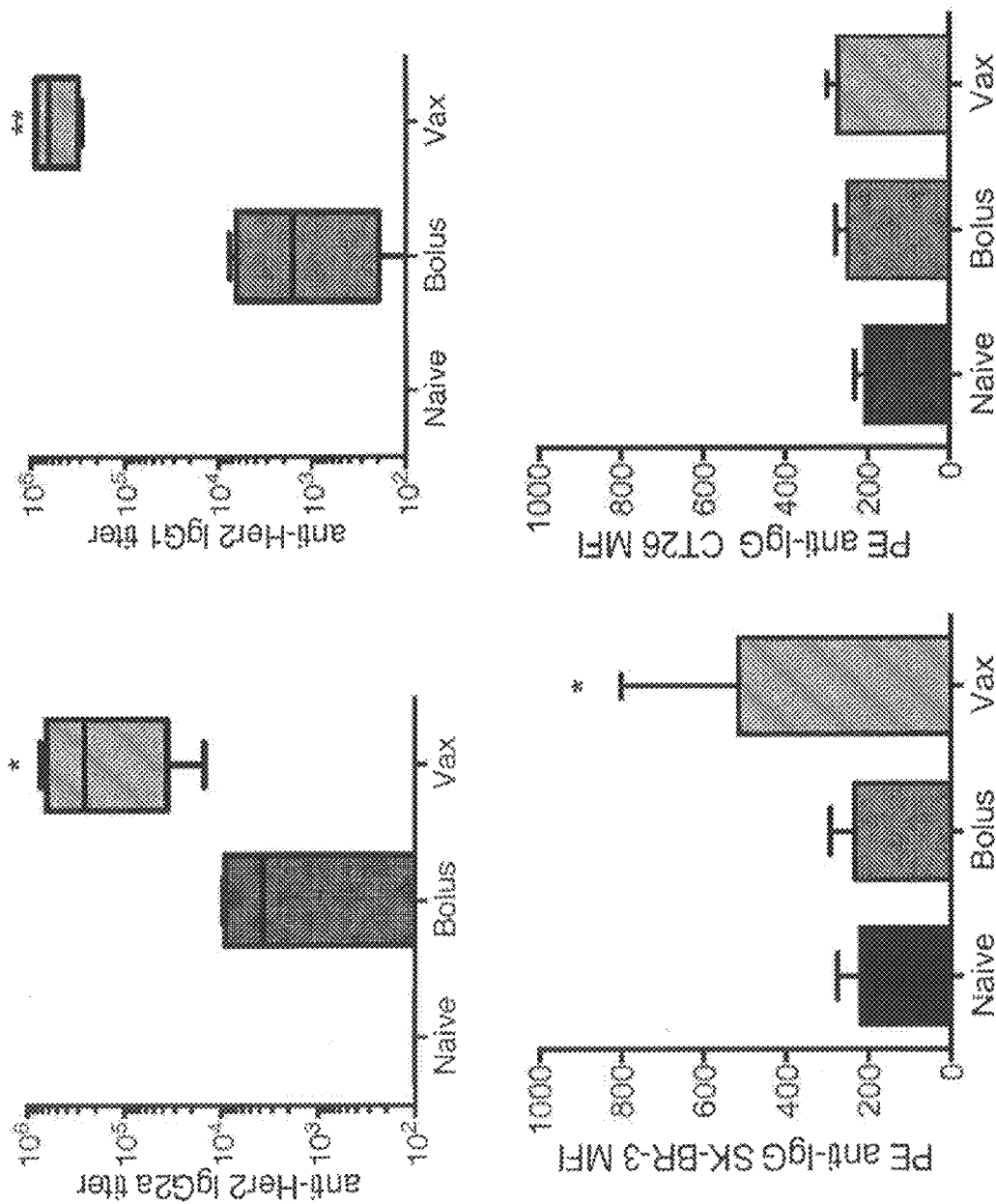

FIG. 29A table and a graph, and FIG. 29B is a set of graphs, showing that a MPS vaccine elicits high titer antibody against trastuzumab-binding region of Her2 and shows reactivity. Included herein are methods and compositions for generating antibodies. For example, the antibodies may be against the Herceptin® (trastuzumab) binding domain on the Her2 protein to bypass the need for multiple Herceptin administration and generate memory against Her2. In certain embodiments, a fusion peptide containing a CD4 epitope derived from measles linked to a short linear domain within the Herceptin binding domain on Her2 is used to generate an immune response. FIGS. 29A and B show that mice immunized with the MPS vaccine showed over an order of magnitude higher anti-Her2 titer response compared a bolus vaccine without the scaffold. Furthermore, the data shows that the anti-Her2 serum was able to recognize the Her2 protein on human Her2 positive breast cancer cells, whereas the serum from the bolus vaccinated mice did not show significant binding compared to control serum. In various embodiments, a vaccine comprising mesoporous silica rods and a polypeptide derived from Her2 is used to elicit an immune response against breast cancer cells, e.g., to treat breast cancer. SK-BR-3 cells are Her2+. CT26 cells are Her2-. PE=Phycoerythrin.

Figure 30:
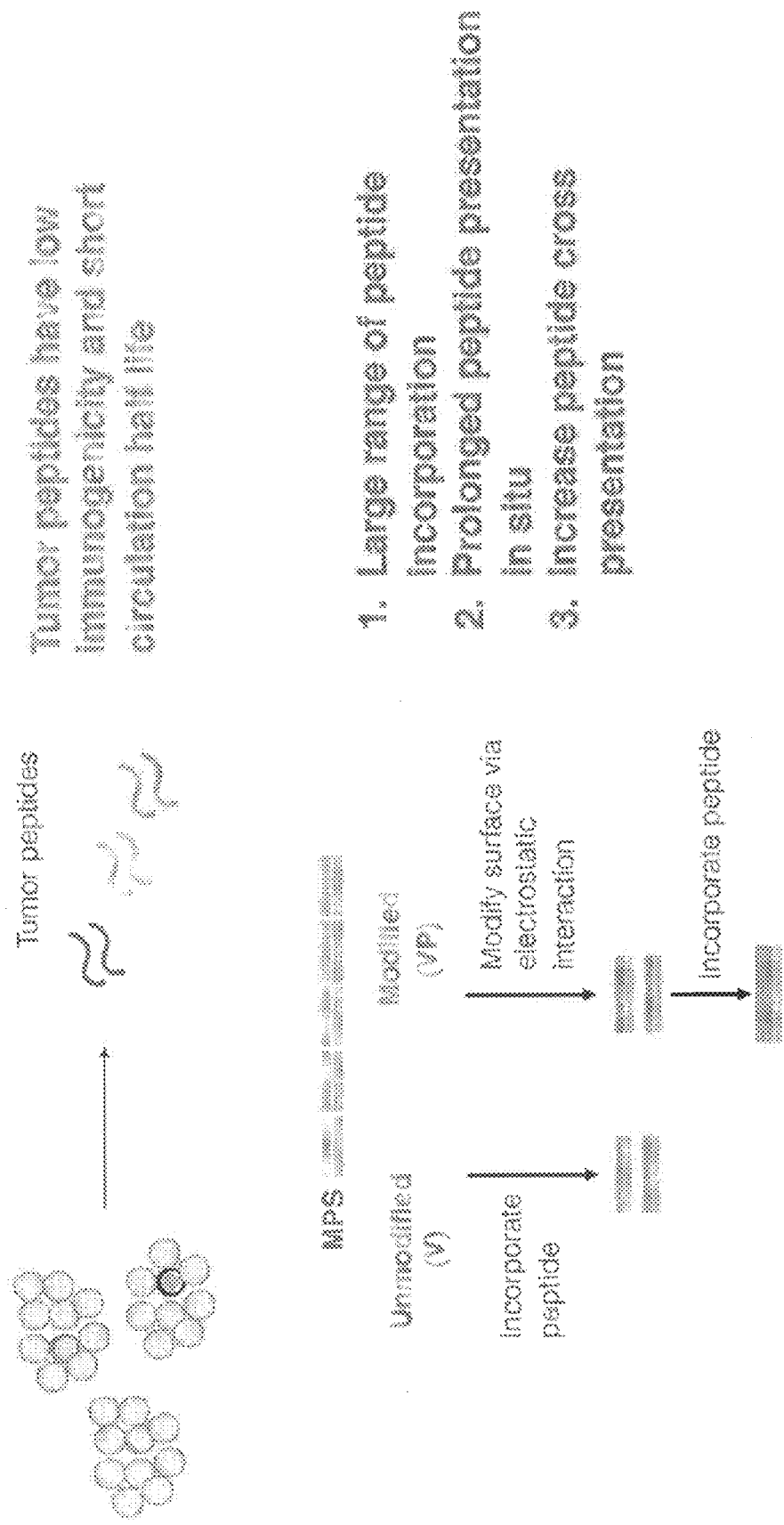

FIG. 30 is a cartoon showing that a surface modified vaccine enhances tumor peptide immunogenicity. In addition to antibody responses, anti-tumor responses may be driven by T cell responses against neoantigens, which are often in the form of peptides. However, generating effective response against these peptides is challenging since they are cleared very rapidly by the body and generally are not very immunogenic. Vaccines provided herein, such as vaccines comprising MPS rods, can address this problem. In some embodiments, tumor antigens are passively incorporated into the vaccine. In certain embodiments, the surface of a vaccine is modified using a simple electrostatic interaction that makes the scaffold (e.g., MPS rods) more sticky for the peptides to, such that the peptides remain in or on the scaffold longer and also to make the peptides more immunogenic. In various embodiments, such modification allows the incorporation of a wide range of peptides with different physical properties without using any chemistry. In embodiments, this is important since chemical modifications of peptides could potentially change the presentation capacity. In a non-limiting example, the surface modification comprises contacting the scaffold with PEI.

Figure 31A:
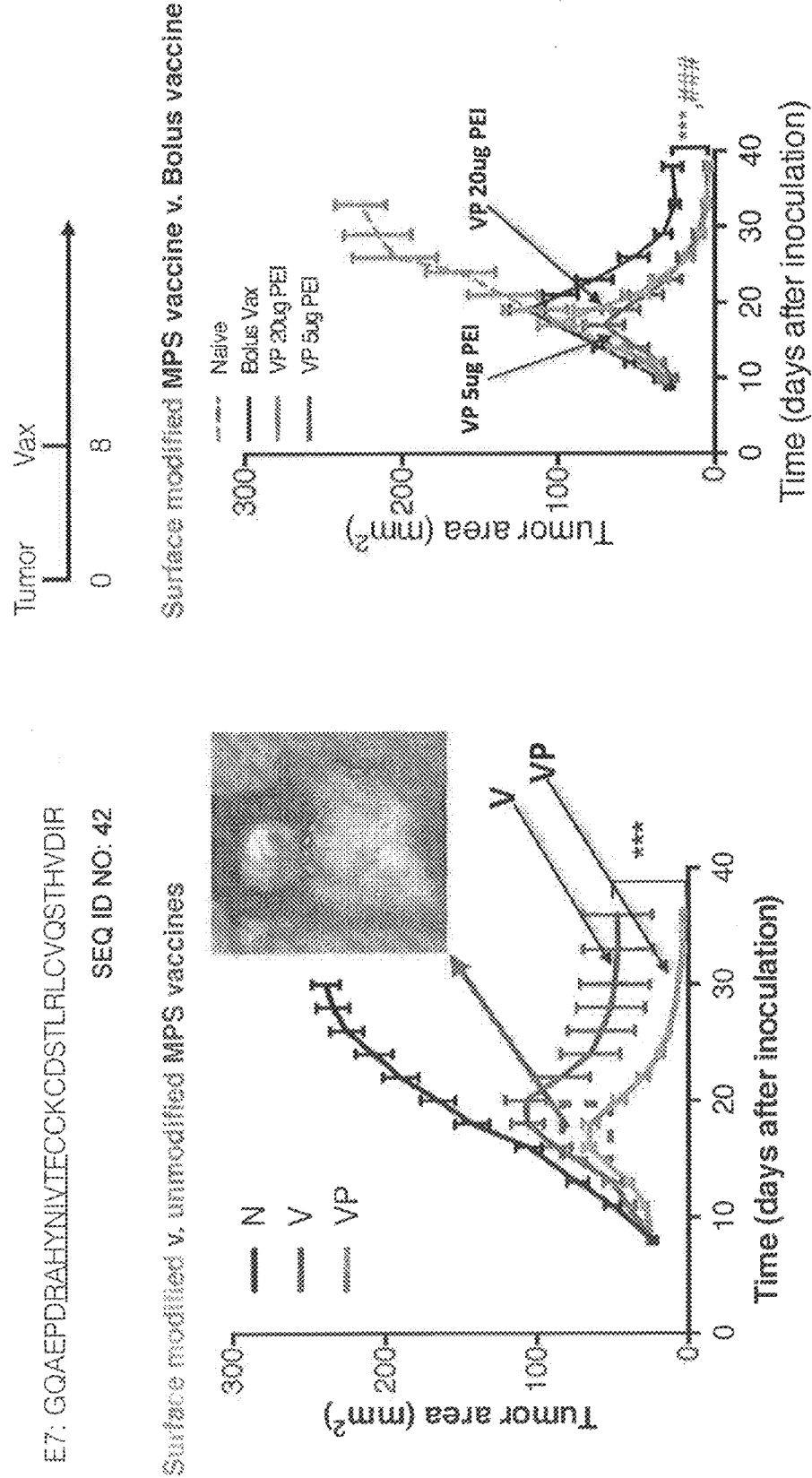
Figure 31B:
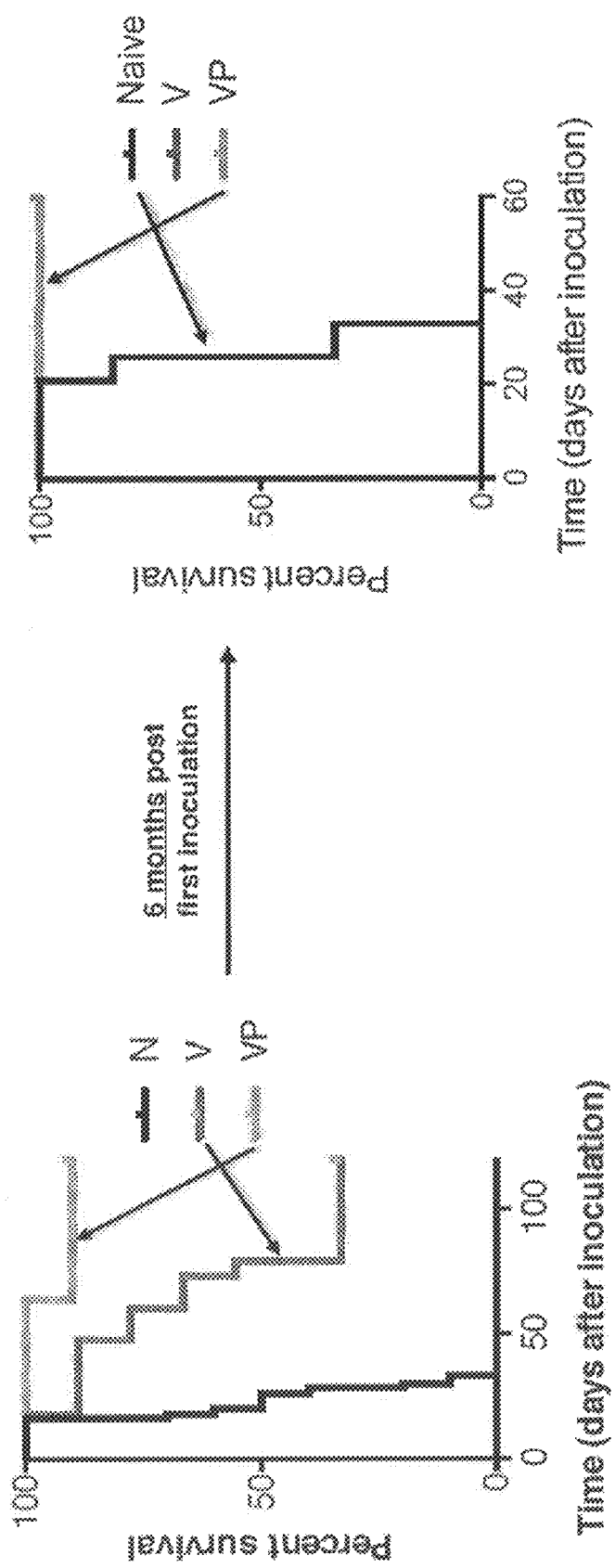

FIG. 31A is a sequence, timeline, set of graphs, and an image showing that a single injection of a surface modified MPS vaccine led to enhanced established tumor regression. FIG. 31B is a set of graphs showing a long term memory response post tumor rechallenge. A surface modified vaccine was tested using a peptide from the E7 oncoprotein from HPV, which is expressed in a number of tumors such as cervical cancer and oral cancer. As shown in FIG. 31A, the mice were inoculated with E7 expressing TC-1 cell line and immunized on day 8 with surface modified or unmodified vaccine. The surface modified vaccines showed much better tumor regression compared to the unmodified vaccine. Additionally, the surface modified MPS vaccine was compared with a bolus vaccine strategy and showed that the MPS vaccine induced complete tumor regression, whereas the bolus vaccine only resulted in partial regression. The image in this figure is depicting an example from a mouse undergoing treatment using the VP vaccine that had a large (1 cm×1 cm) tumor before regressing completely. As shown in FIG. 31B, over 80% of the mice treated with the surface modified MPS vaccine survived long term. The surviving mice were re-inoculated with the E7 expressing tumors after 6 months and showed that 100% of the mice were tumor free, suggesting there is long-term memory response generated by the vaccine.

Figure 32A:
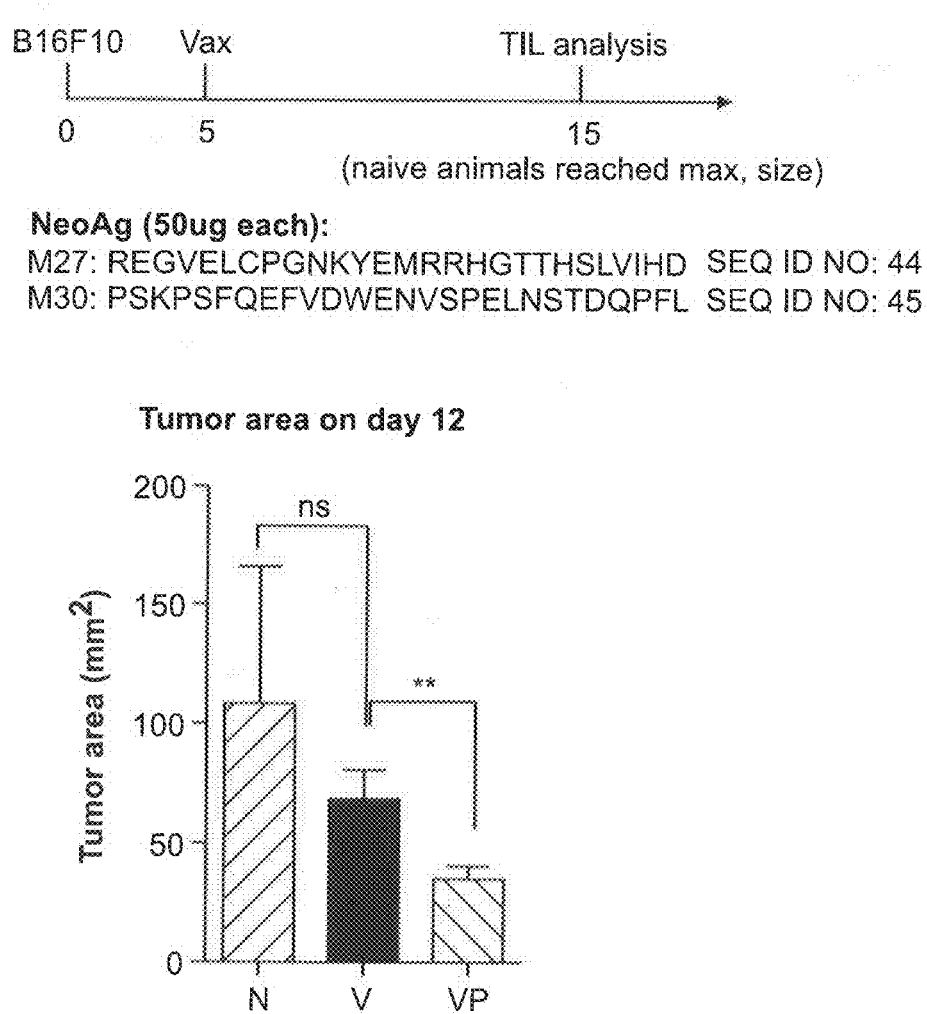

FIG. 32A is a timeline, set of sequences, and graph, and FIG. 32B is a set of graphs, showing that a surface modified MPS vaccine enhanced tumor control using a B16 neoantigen and effector lymphocyte phenotype in a tumor microenvironment in mice. A MPS vaccine (comprising PEI) was tested in the B16 model using recently discovered neoantigens (sequences shown in FIG. 32A). As shown in FIG. 32A, in a therapeutic subcutaneous model, the surface modified vaccine showed better tumor growth control compared to unmodified vaccine (lacking PEI). Furthermore, the tumor-infiltrating lymphocyte (TIL) population was analyzed on day 15 after inoculation, where the untreated mice had reached their maximum size. As shown in FIG. 32B, the surface modified vaccine generated more Granzyme B+, IFN+ and TNFa+ lymphocytes in the tumor. Looking more carefully at the CD8 and CD4 compartment, interesting, most of the response is coming from the CD4 lymphocytes. VP=surface modified vaccine. V=unmodified vaccine.

Figure 33A:
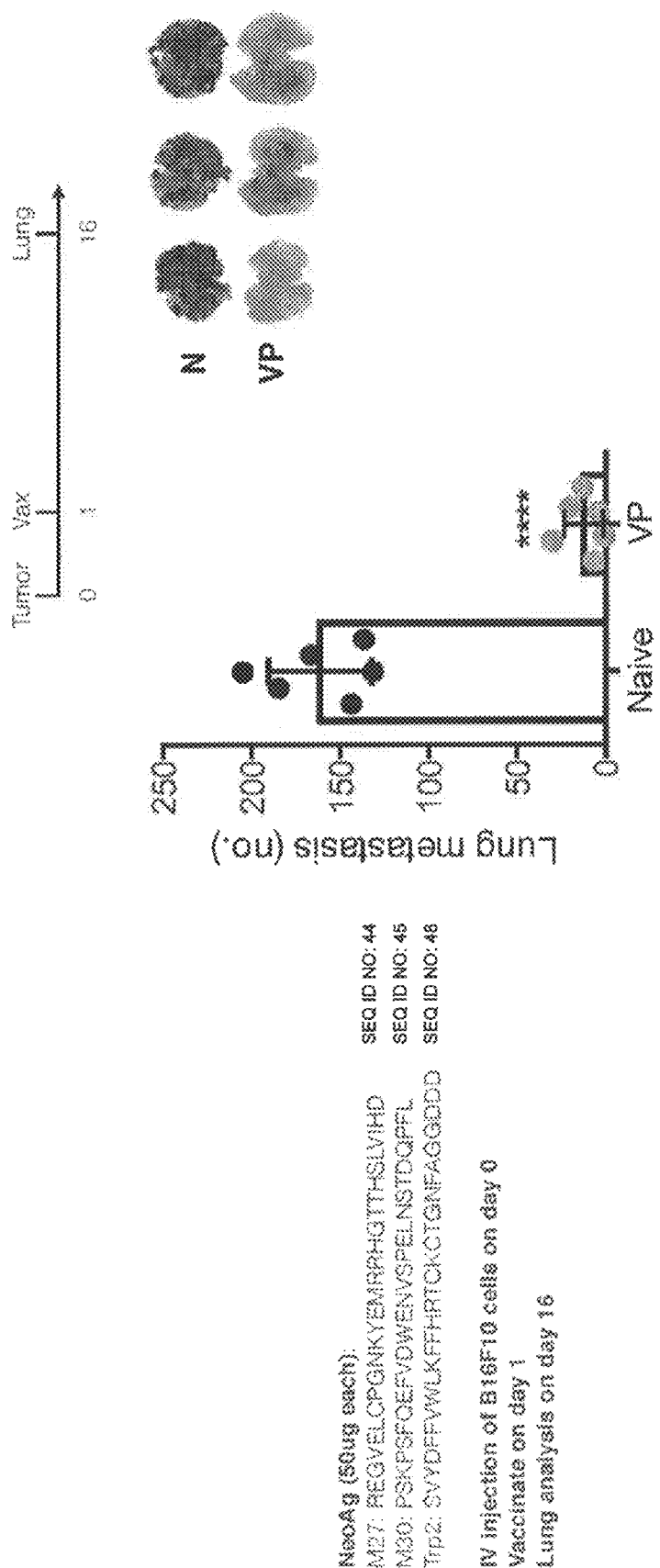
Figure 33B:
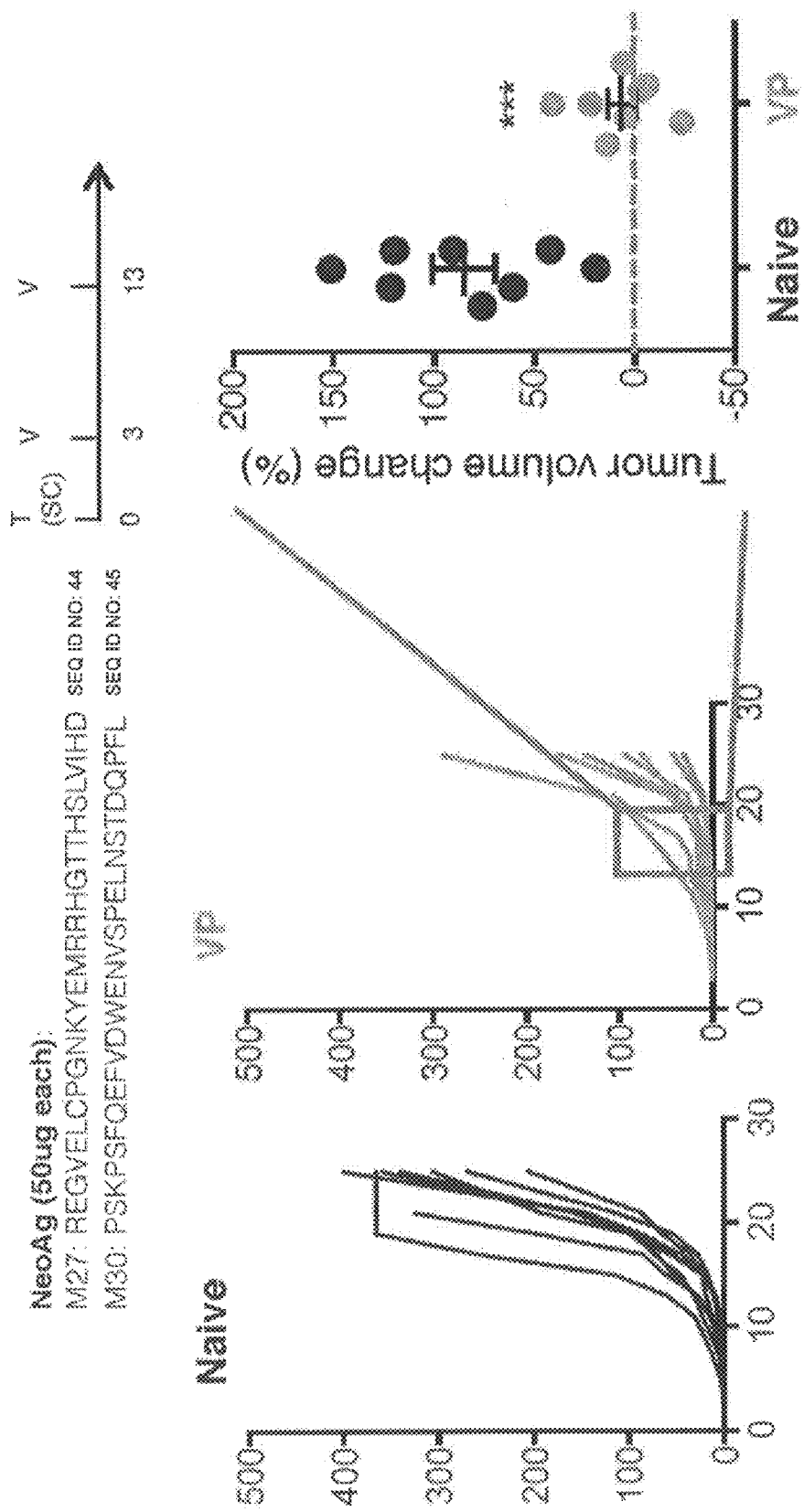

FIGS. 33A-C show therapeutic effects in a B16F10 subcutaneous mouse model using neoantigens. FIG. 33A is a set of exemplary neoantigen sequences, a timeline, images, and a graph showing that artificial lung metastasis decreased compared to naïve (untreated) mice. B16 cells were injected into the blood stream of C57 mice and treated with the VP vaccine after 24 hours. Lungs were excised on day 16 and the number of metastasis was counted in the lung. FIG. 33B is a set of exemplary sequences, a timeline, and graphs showing that a prime-boost treatment regimen (in which vaccine was injected more than once) in a therapeutic B16 model using M27 and M30 peptides. After the boost, there is a transient regression of established melanoma tumor for about 5 days. FIG. 33C is a set of exemplary sequences, a timeline, and graphs showing therapeutic synergy with anti-CTLA4 treatment. The surface modified vaccine in combination with anti-CTLA4 therapy was evaluated. Mice treated with anti-CTLA4 antibody alone did not show better tumor control compared to untreated animals. In comparison, mice treated with both the vaccine and anti-CTLA4 showed impressive tumor growth control.

Figure 34B:
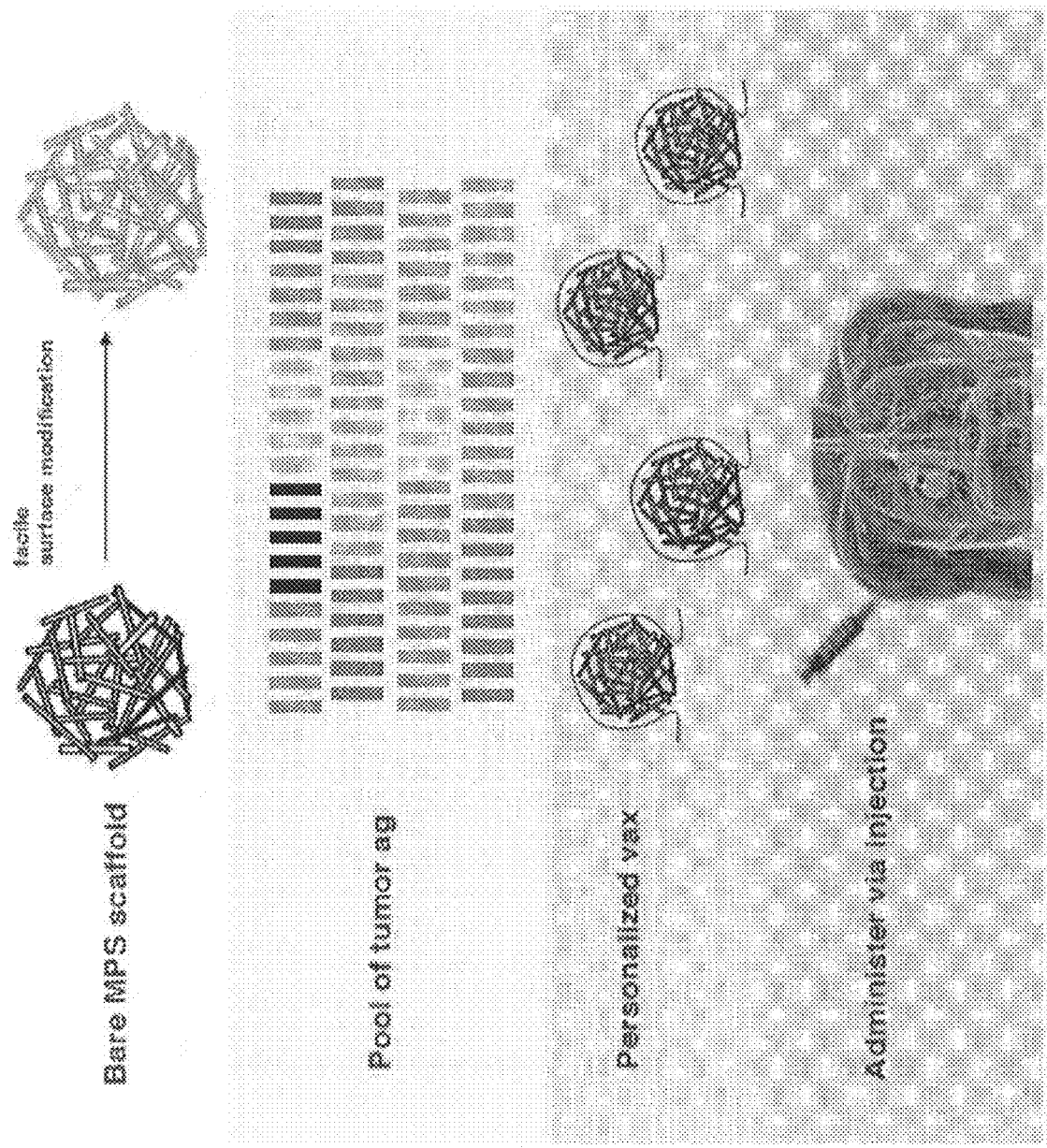

FIG. 34A is a table showing exemplary in vivo responses and FIG. 34B is a cartoon showing an exemplary process for administering a personalized tumor vaccine to a subject. As shown in FIG. 34A, a number of disease relevant antigens have been tested in protein form, peptide form, and small molecule form. The tested antigens include both T and B cell epitopes (T cell epitopes are those that can bind to MHC-I or MHC-II class molecules, B cell epitopes are domains that an antibody can recognize). T cell and B cell epitopes are not mutually exclusive. Positive responses have been seen using 4 independent tumor models. Included herein are vaccine platforms that are minimally invasive, highly versatile and effective biomaterial vaccine platform. As shown in FIG. 34B, because the MPS vaccine is assembled from individual particles, a library of different antigens (such as tumor antigens) can be incorporates into individual particles. Such particles can be mixed and matched, and readily upscaled to make individualized cancer vaccines. Each vaccine can contain multiple tumor antigens, and then administered into the patient via a simple injection. In non-limiting examples, a vaccine is administered as a single injection or in multiple injections (e.g., concurrently or over time). In various embodiments, an antigen can be purified, e.g., from tumor lysate or produced recombinantly (e.g., in cells that produce the antigen) or synthetically (via chemical synthesis without cells).

Figure 35:
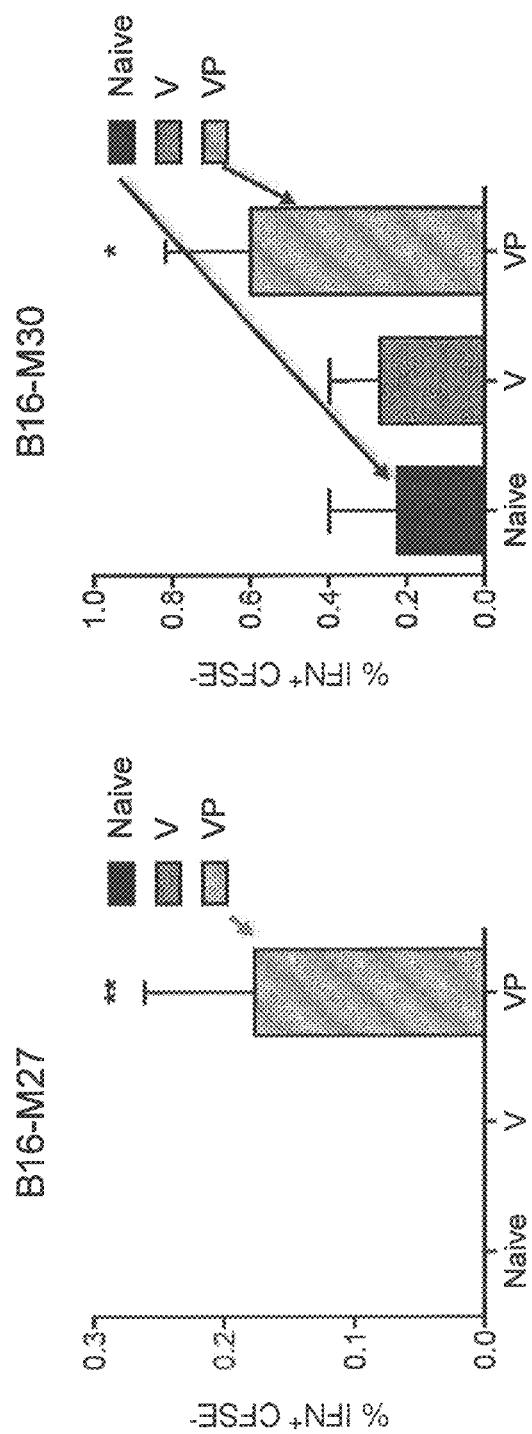

FIG. 35 is a pair of graphs showing a murine melanoma neoantigen specific T cell response. Animals were vaccinated with the MSR vaccine (V) or the MSR-PEI vaccine (VP) using 50 µg of the B16-M27 or B16-M30 neoantigen peptides, or left unvaccinated (Naive). After 14 days, mice were inoculated with $0.1\times10^6$ B16F10 cells. After 10 days, CD4 and CD8 T cells were harvested from the spleen and the tumor draining LN, stained with carboxyfluorescein succinimidyl ester (CFSE), and co-cultured with peptide pulsed splenic DCs. Proliferated and IFNγ secreting populations (IFN+CFSE−) were subsequently analyzed using flow cytometry.

DETAILED DESCRIPTION

Figure 1C:
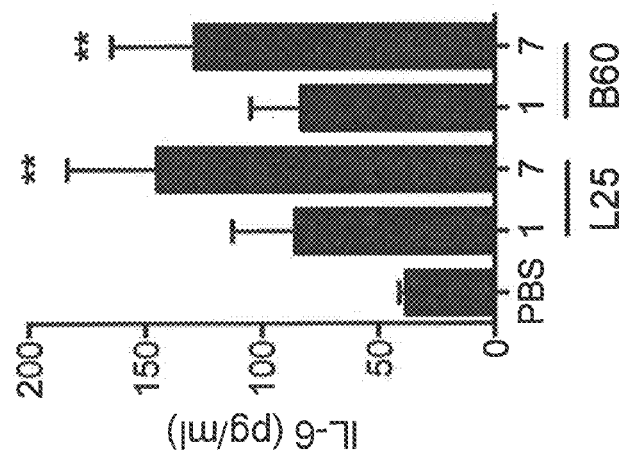
Figure 1B:
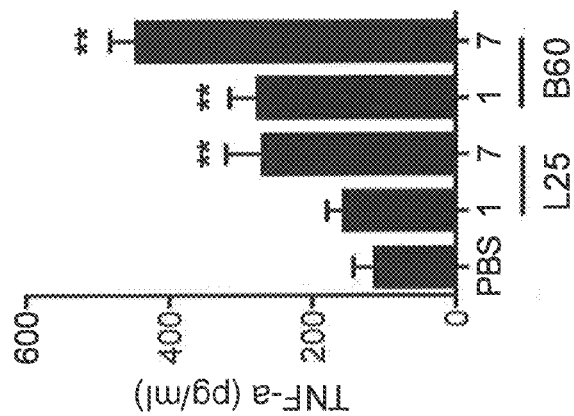
Figure 1A:
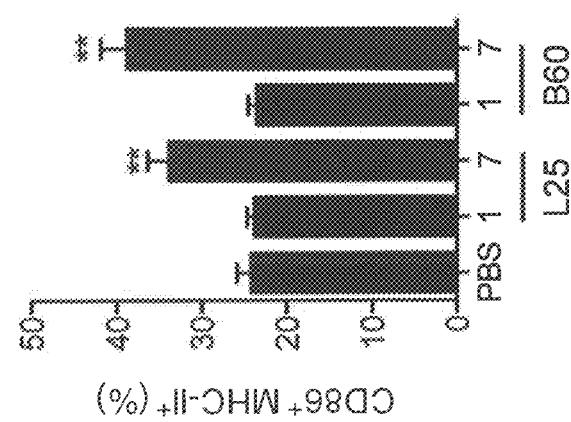
Figure 1E:
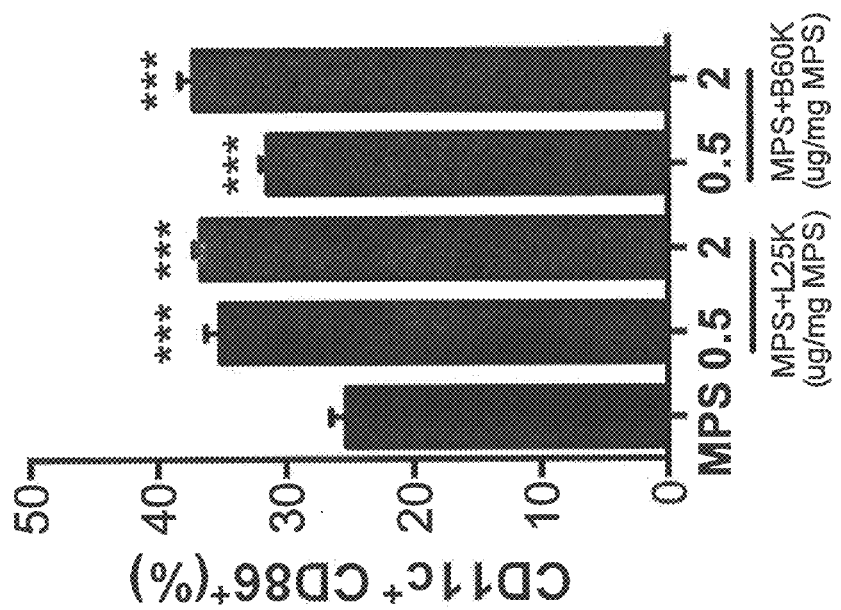
Figure 1D:
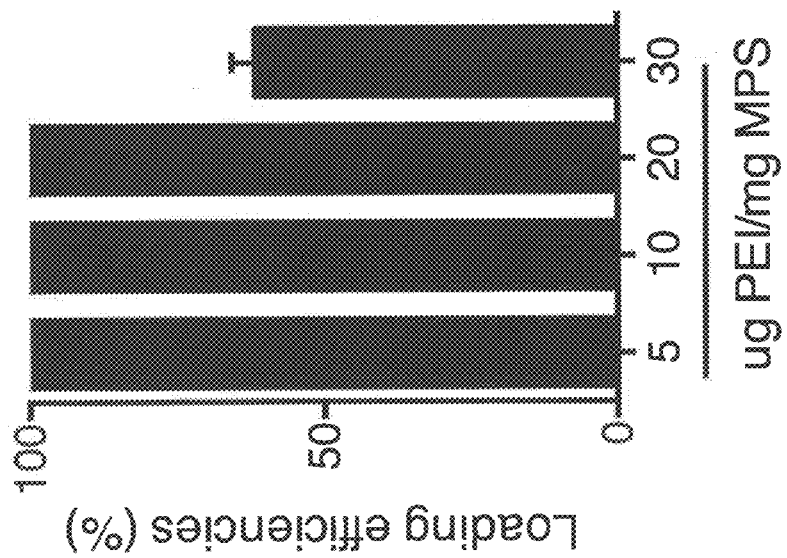
Figure 1G:
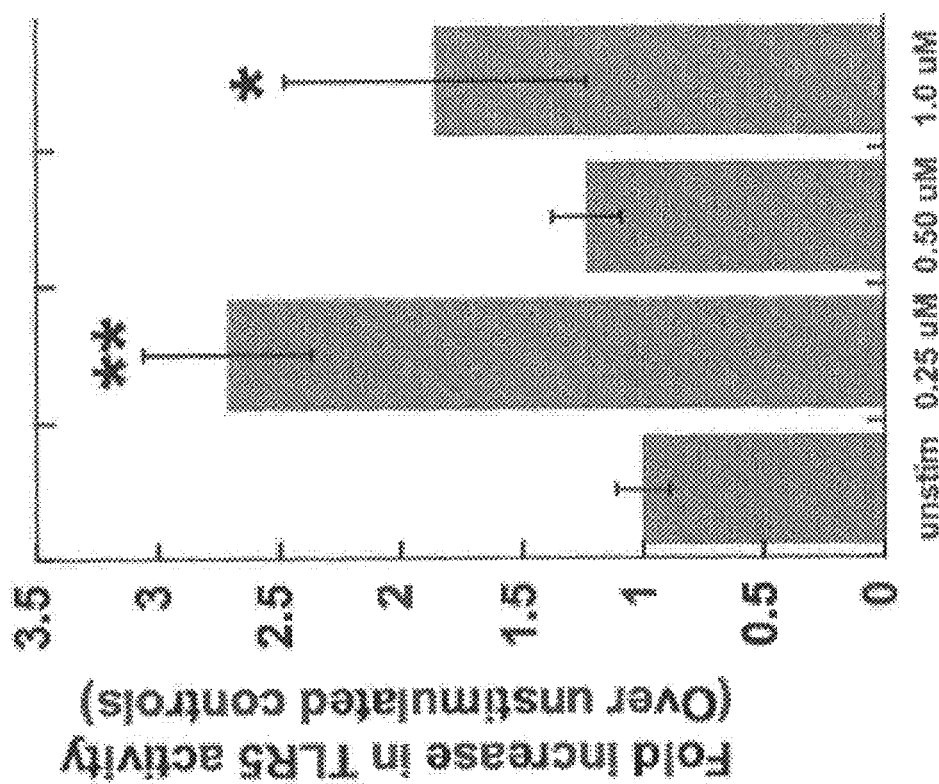
Figure 1F:
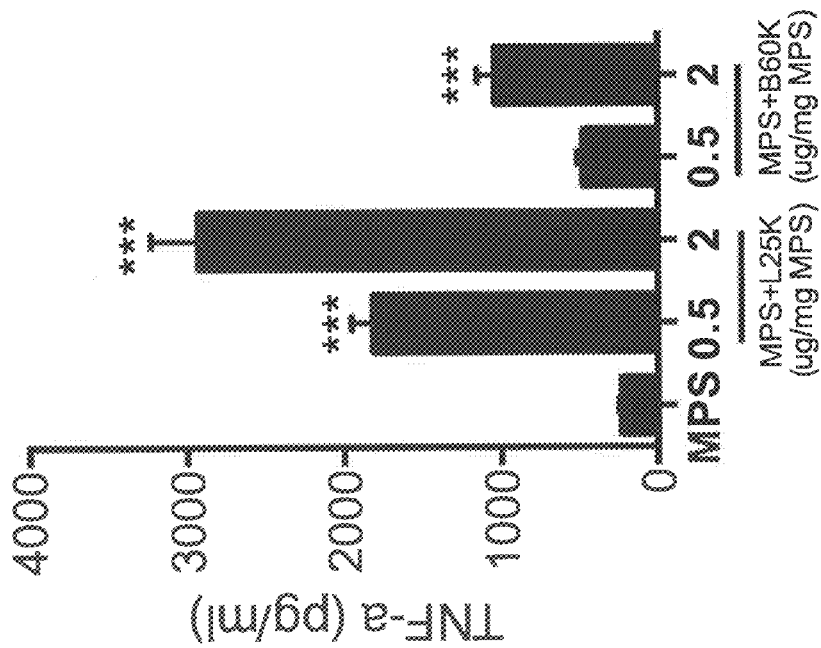
Figure 1I:
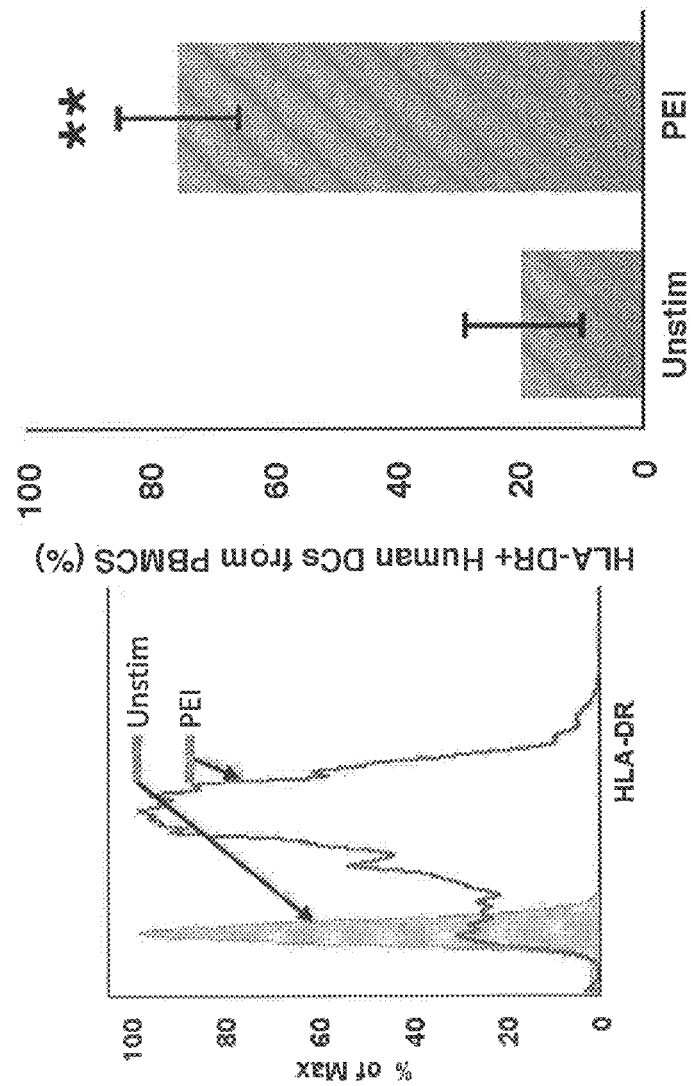
Figure 2A:
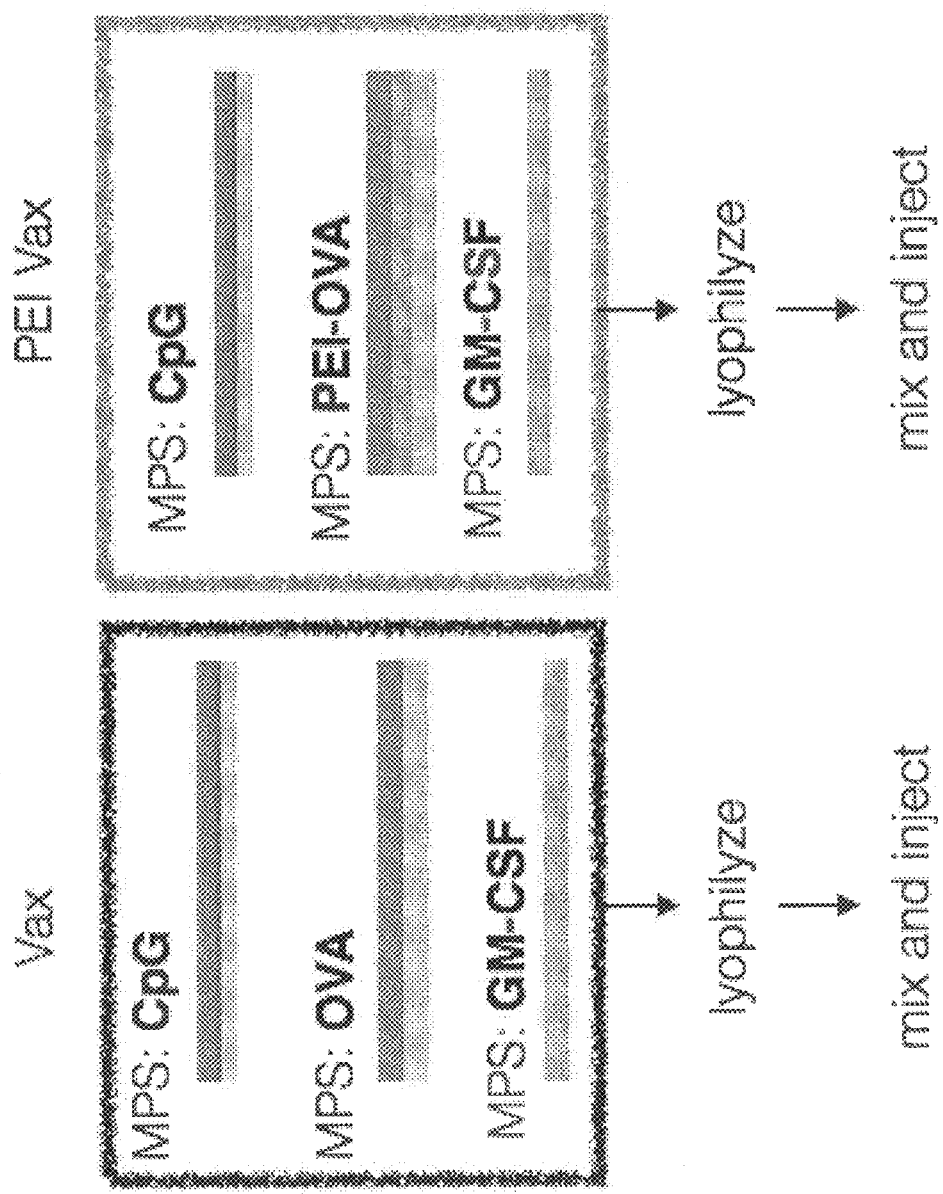
FIGS. 2A-H are graphs showing that PEI in MSR vaccine enhances BMDC activation and trafficking.
Figure 2B:
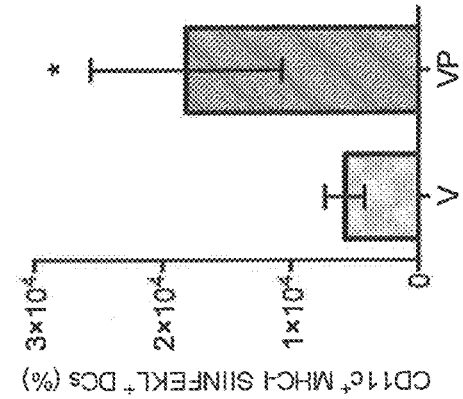
Figure 2C:
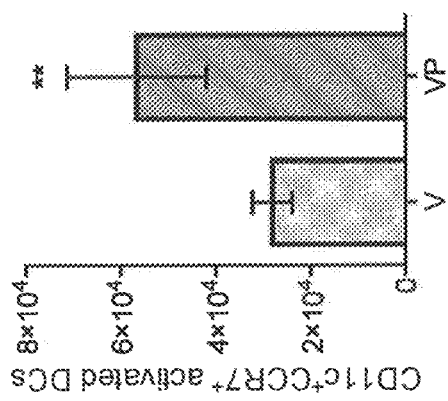
Figure 2D:
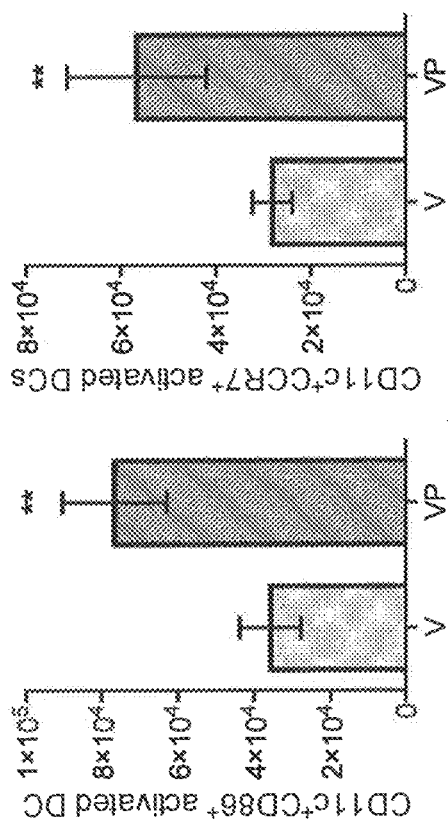
Figure 2E:
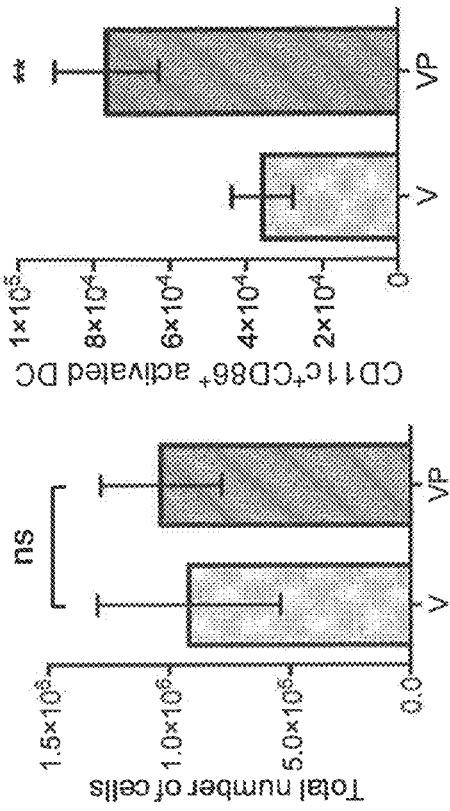
Figure 2F:
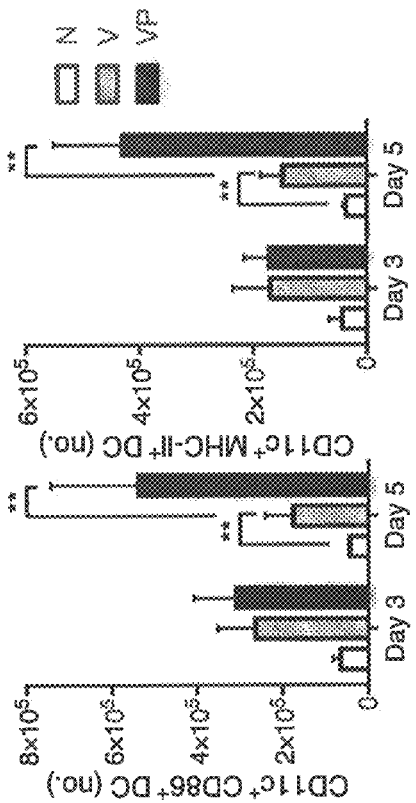
Figure 2G:
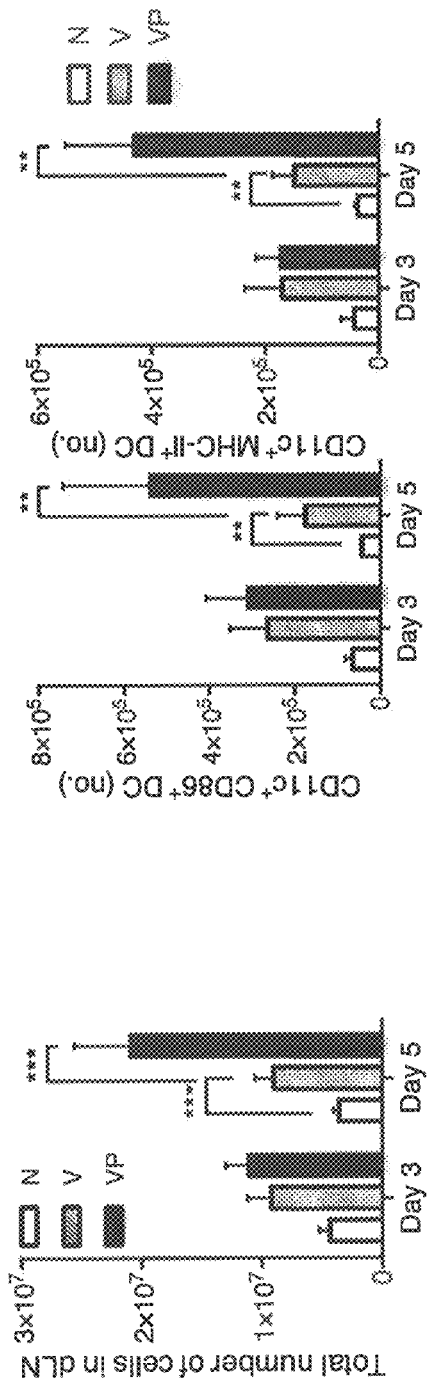
Figure 2H:
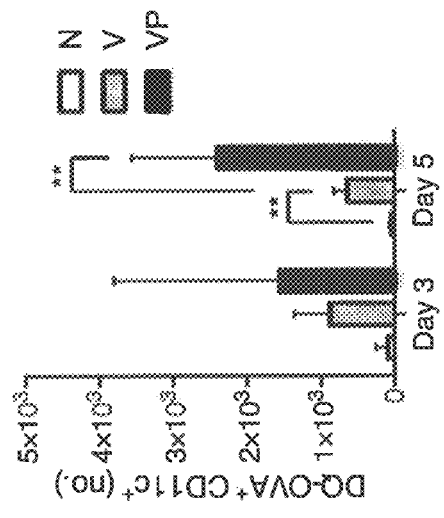
Figure 21:
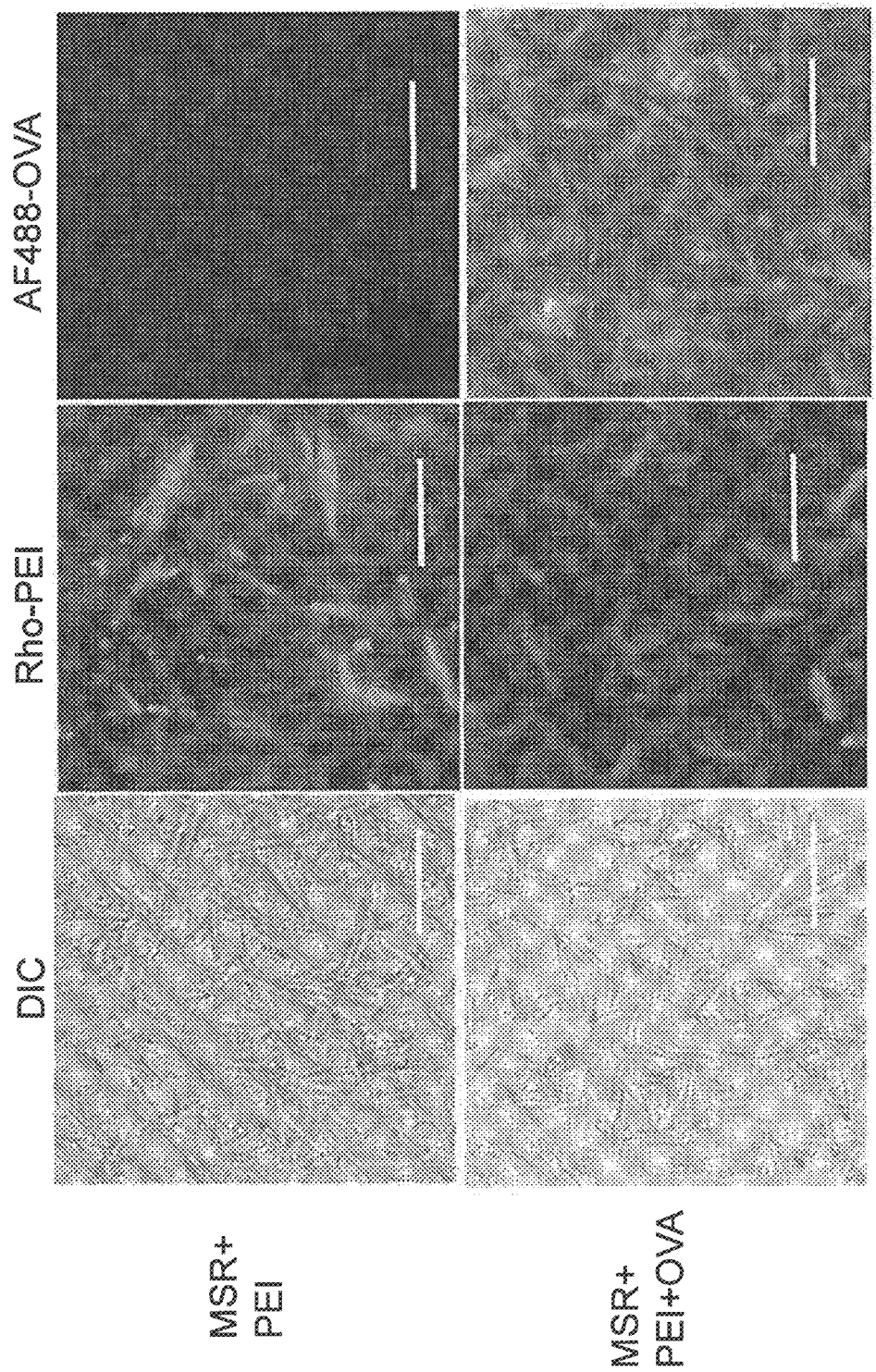
Figure 3C:
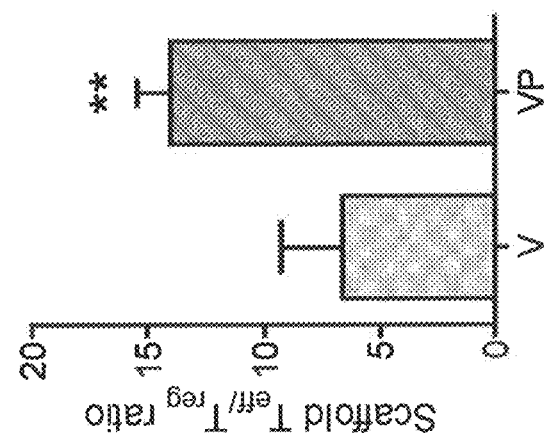
Figure 3A:
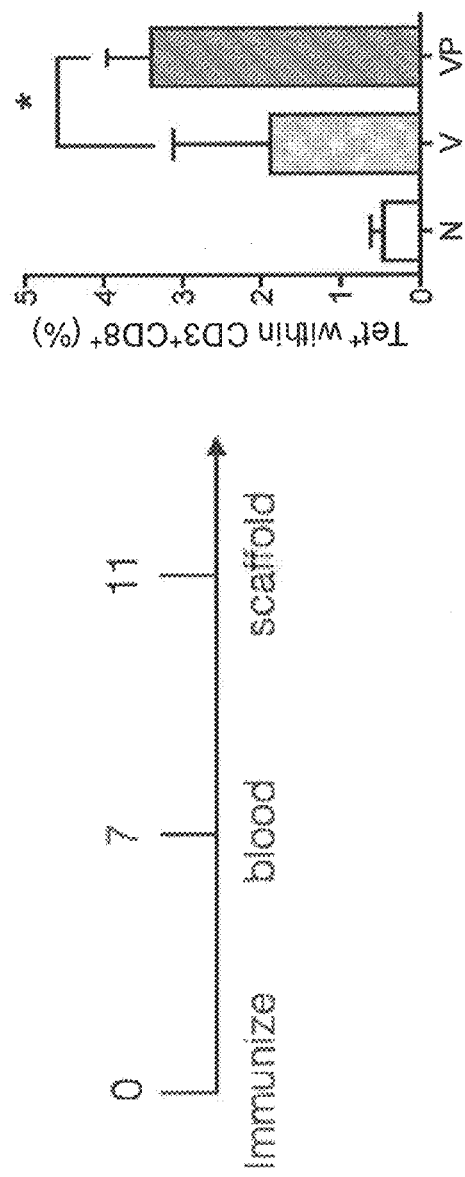
Figure 3B:
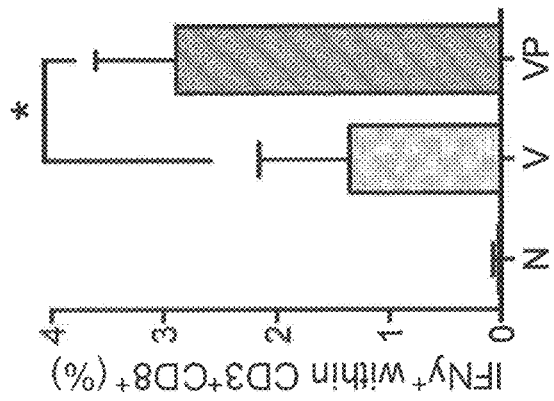
Figure 4A:
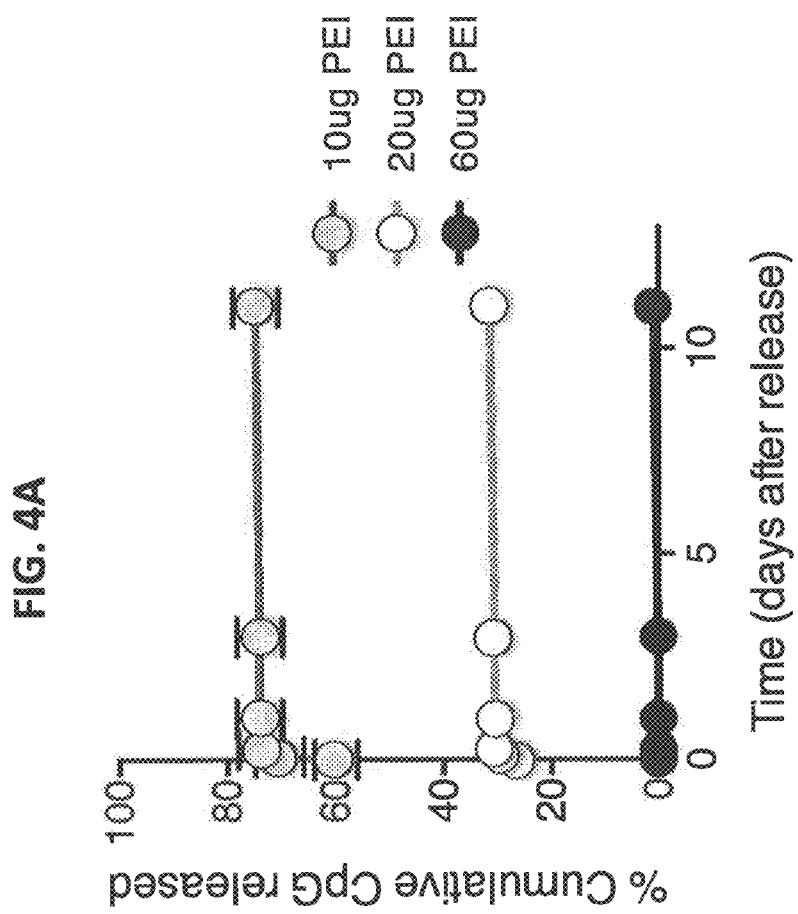
FIGS. 4A-C are graphs showing that a MSR PEI-CpG vaccine does not lead to enhanced CD8 T-cell responses. (A) Cumulative CpG release from MSR-PEI. (B) Percentage of IFN+ T cells in periphery blood after immunizing with the MSR vaccine (V), the MSR vaccine containing 1 µg GM-CSF, 100 µg OVA, and 100 µg CpG adsorbed to 10 µg PEI (V PC), and the MSR vaccine containing 1 µg GM-CSF, 100 µg ovalbumin (OVA) adsorbed to 10 µg PEI, and 100 µg CpG (V PO). Surprisingly, immune stimulation was a greater when antigen (OVA) was absorbed to (i.e., attached via an electrostatic interaction) PEI than when CpG-ODN is absorbed to PEI. (C) Percent tetramer+ T-cells in periphery blood after immunizing with the MSR vaccine containing 1 µg GM-CSF, 100 µg OVA and 100 µg CpG adsorbed to various amounts of B60 PEI.
Figure 4C:
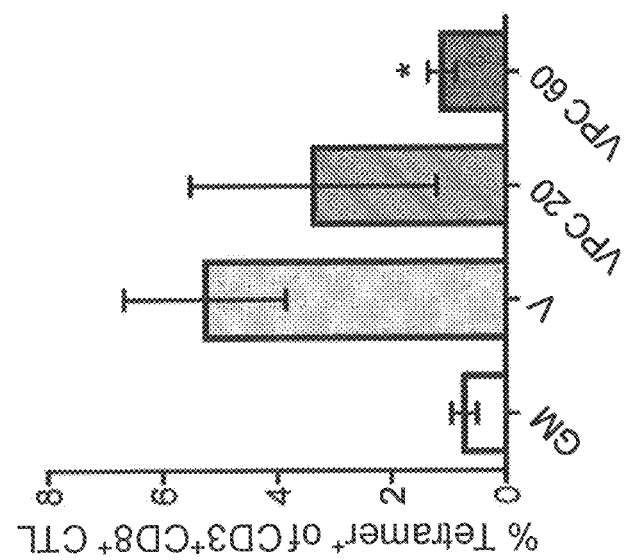
Figure 4B:
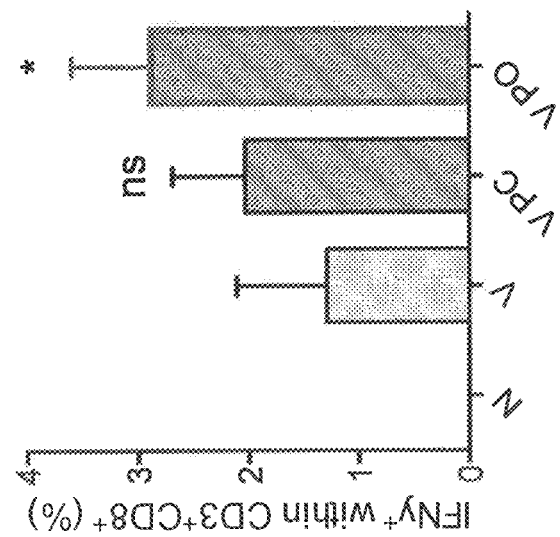
Figure 5A:
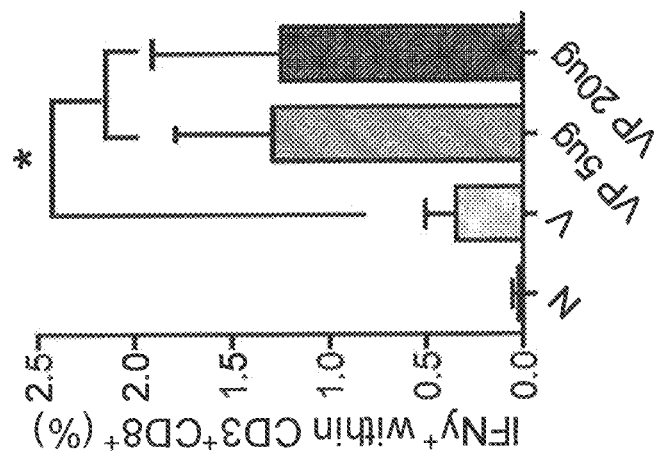
Figure 5B:
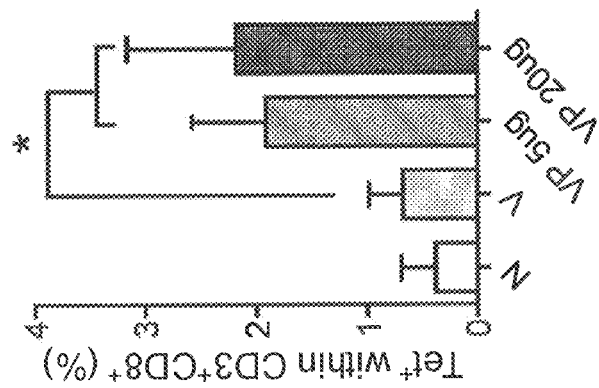
Figure 5C:
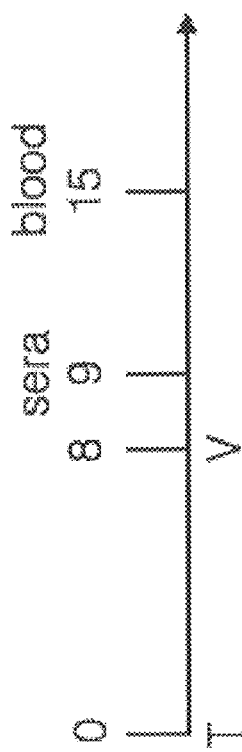
Figure 5F:
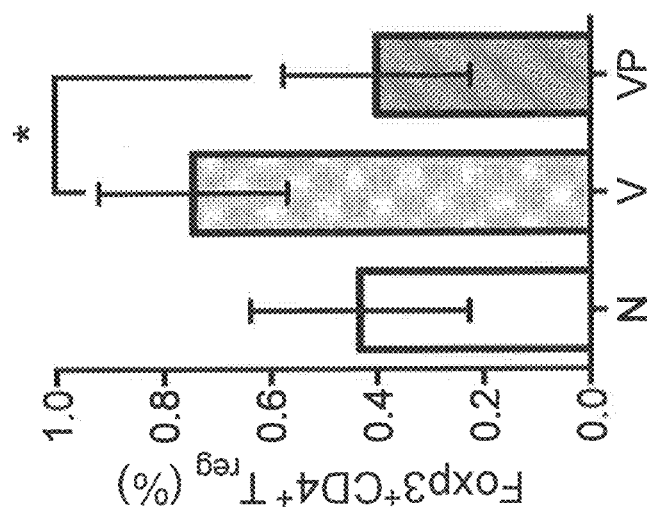
Figure 5E:
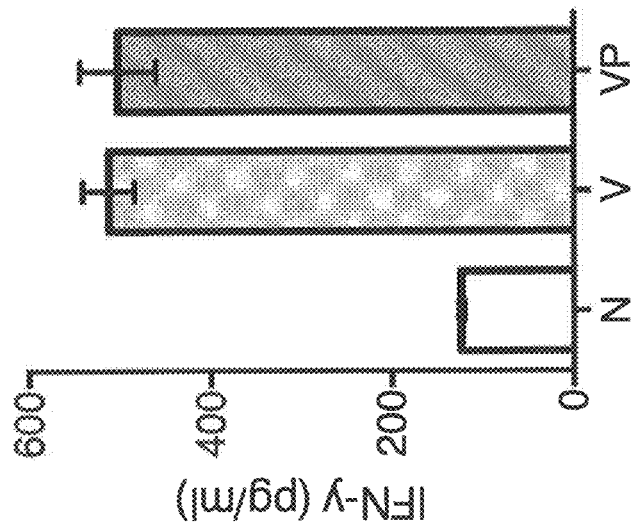
Figure 5D:
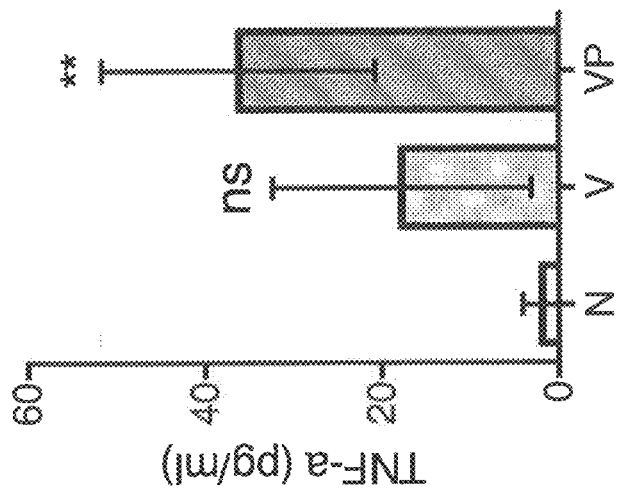

Aspects of the present subject matter relate to the discovery that polyethyleinemine (PEI) is useful as an adjuvant in biomaterial scaffold vaccines to enhance cytotoxic T lymphocyte responses and induce potent immunity against tumors. For example, injectable cryogels and injectable mesoporous silica rods containing PEI increase anti-tumor immunity significantly more (e.g., about 10%, 20%, 25%, 50%, 75%, 100%, 2-fold, 5-fold, 10-fold or more) than cryogels or mesoporous silica rods lacking PEI. Surprisingly, mesoporous silica rods comprising antigen attached to PEI were substantially more immunogenic than corresponding mesoporous silica rods comprising CpG-ODN attached to PEI (see, e.g., FIG. 4B). Additionally, mesoporous silica rods comprising antigen attached to PEI were more effective at reducing tumor size in vivo than corresponding mesoporous silica rods lacking PEI (see, e.g., FIG. 5G).

Immunotherapy

Immunotherapy has been established as an effective modality of cancer treatment. Cancer immunotherapy refers to any intervention that leverages the immune system to attack, reduce, or eliminate a malignancy. Leveraging the immune system has become a viable strategy for treating human cancers within the past five years. Recent progress in the understanding of the immune system—such as the discovery of key molecular players in the generation of immune responses, e.g., Toll-like receptors (TLRs) and their ligands—has enabled the development of platforms for precisely tuning the immune response so as to promoting anti-cancer immunity. Prominent examples of successful immunotherapies include immune checkpoint inhibitors for treatment of a number of advanced stage cancers, as well as Adoptive Cell Therapy (ACT) for certain hematological malignancies.

Although recent clinical successes with immunotherapies demonstrate their potential, drawbacks to current cancer immunotherapy strategies remain. For instance, therapeutics are commonly administered as soluble injections, typically necessitating high doses and frequent re-dosing to achieve biologically relevant concentrations in target tissues, which often results in systemic toxicities. Most soluble bolus-based vaccine formulations also fail to elicit sufficiently robust immune responses to achieve lasting therapeutic success, limiting their effective use for cancer.

Biomaterials are useful to overcome of these limitations and thus enhance the effectiveness of vaccines and other immunotherapies. Rationally designed biomaterial strategies to deliver immune modulatory drugs can potentially show improved safety profiles, while providing multifunctional and spatiotemporally controlled signals to immune cells to improve their anti-cancer activity. The generation of a productive anti-cancer immune response resulting in the elimination of cancer cells is dependent on a coordinated series of events that must take place in an iterative and self-sustaining manner Without wishing to be bound by any scientific theory, antigens (e.g., that have been obtained or released from cancer cells) are captured by DCs, the primary mediators of adaptive immunity. DC activation, which is associated with the upregulation of cell surface co-stimulatory molecules and cytokine production, is necessary for efficient downstream priming of a T-cell response, and may be promoted in the endogenous situation by factors released by dying cancer cells, which may be broadly termed "danger associated molecular patterns." DC activation facilitates efficient processing of the uptaken antigen and subsequent presentation of antigenic peptides on cell surface MHC molecules. In the draining lymph nodes, activated DCs present cancer antigens to naïve T-cells, resulting in the priming and activation of cancer antigen-specific T-cells, a subset of which will differentiate into long-lived memory cells. Activated T-cells, in particular, effector CD8+ cytotoxic T lymphocytes (CTLs), subsequently traffic to and infiltrate the tumor, recognize cancer cells presenting the cognate antigenic determinants, and kill the cancer cells.

Figure 6:
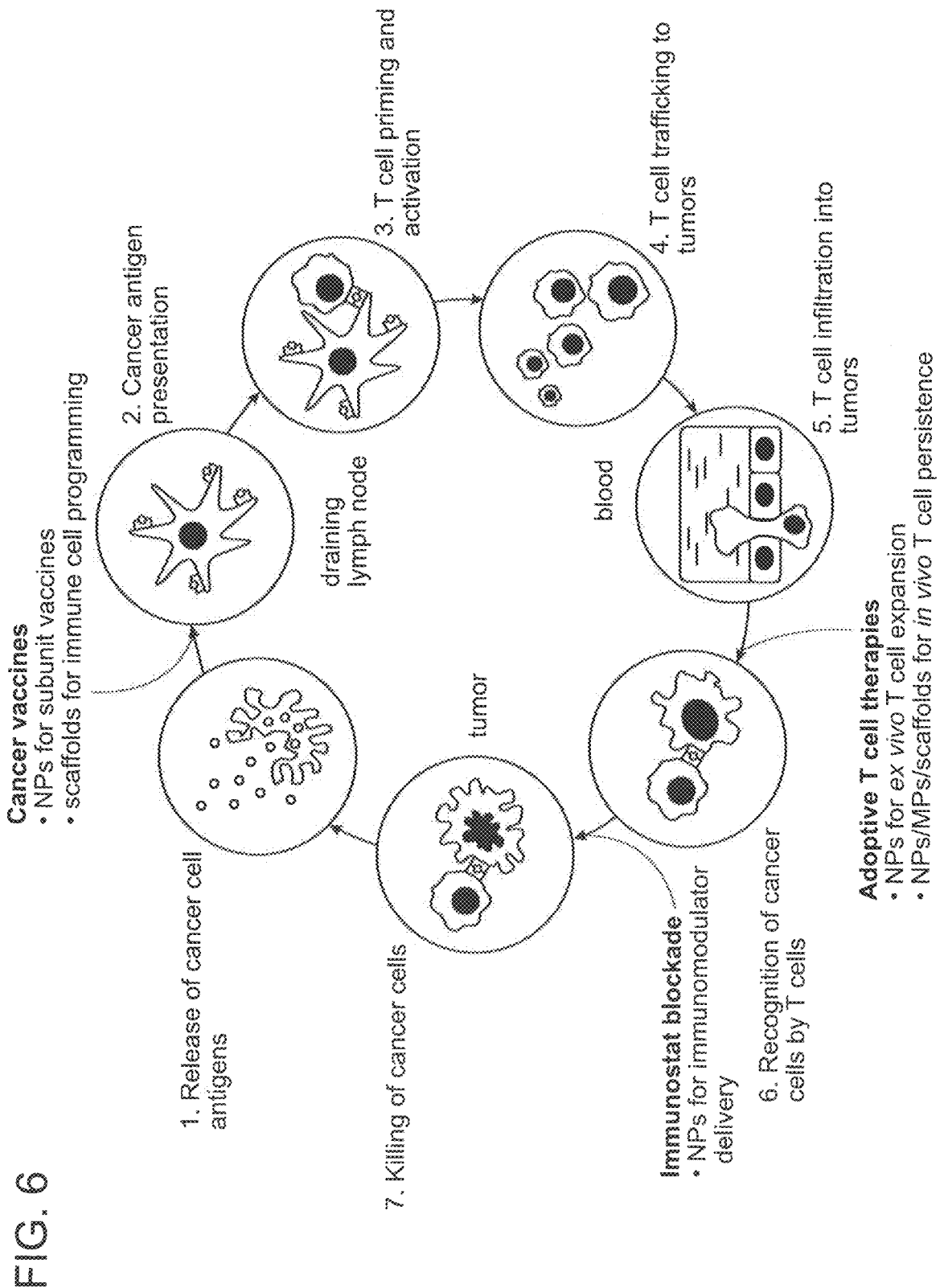
FIG. 6 is diagram illustrating non-limiting aspects relating to exemplary nanoparticle and scaffold-based cancer vaccines.
Figure 7:
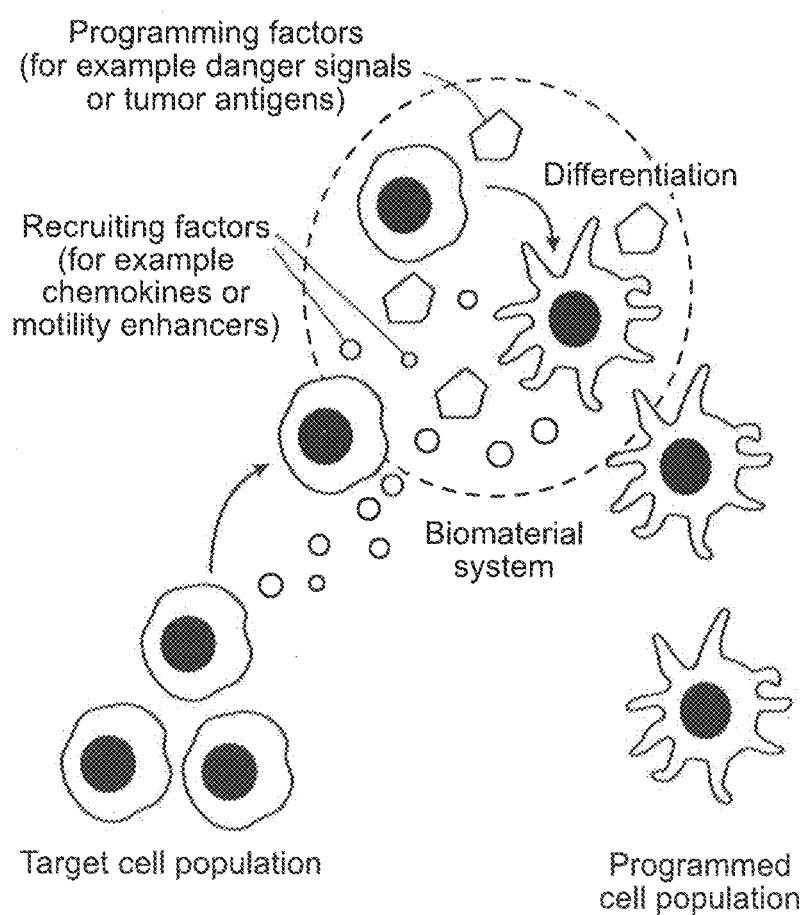
FIG. 7 is a diagram illustrating a non-limiting biomaterial system for programming immune cells.
Figure 8:
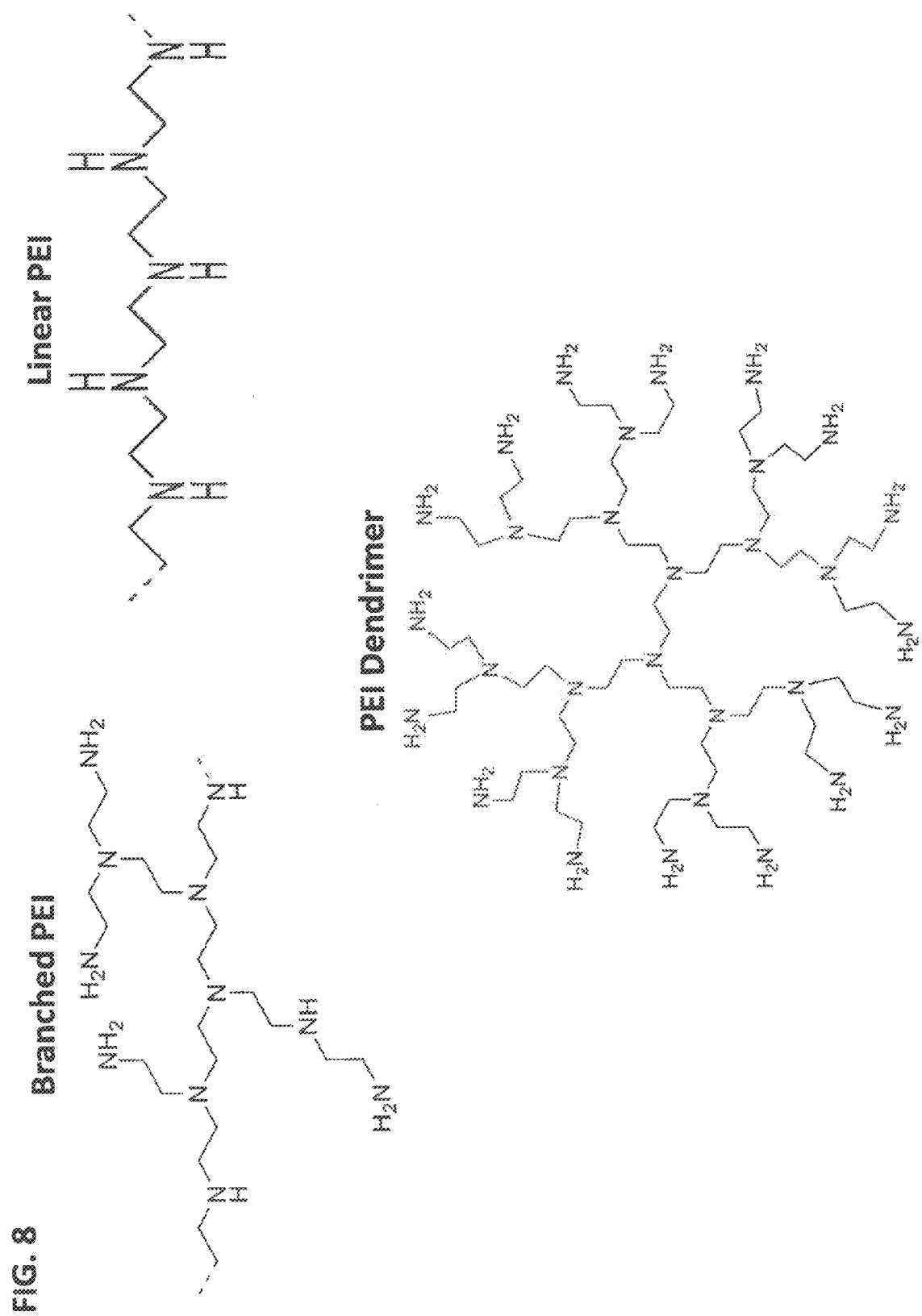
FIG. 8 is an illustration of non-limiting examples of branched, linear, and dendrimeric PEI. Dashed lines show where exemplary structures may continue. PEI is a cationic polymer, synthesized in various forms including linear, branched, or dendrimeric and high or low molecular weight species.
Figure 9A:
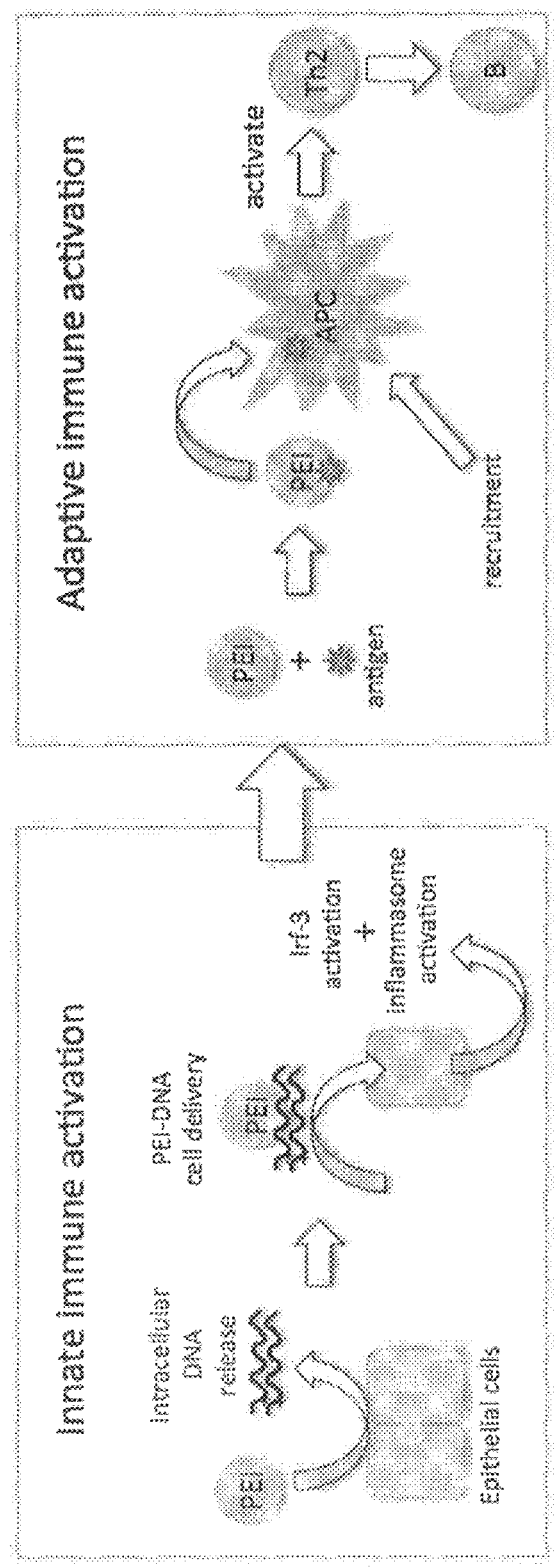
FIG. 9A is a series of cartoons showing non-limiting aspects of innate and adaptive immune activation with PEI.
Figure 9B:
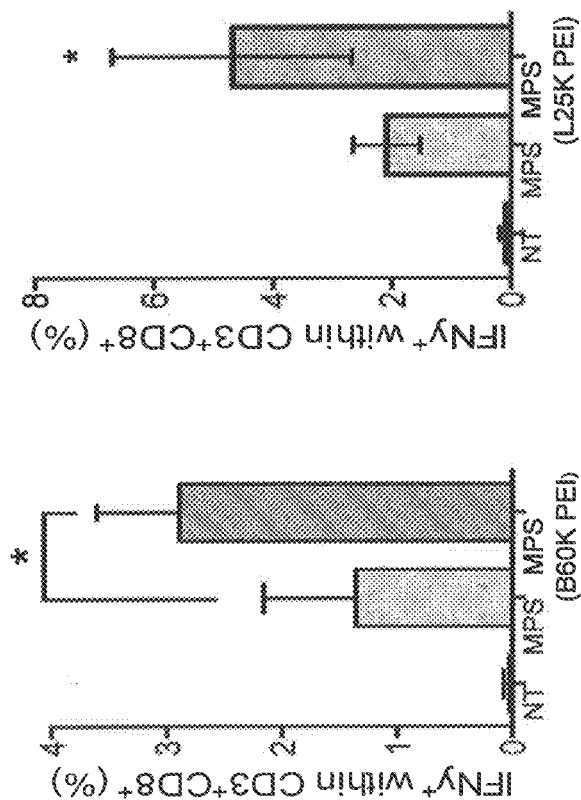
FIG. 9B is a set of graphs showing that MPS comprising PEI increases immune activation. B=B-cell; Th2=T-helper 2 cell.
Figure 10:
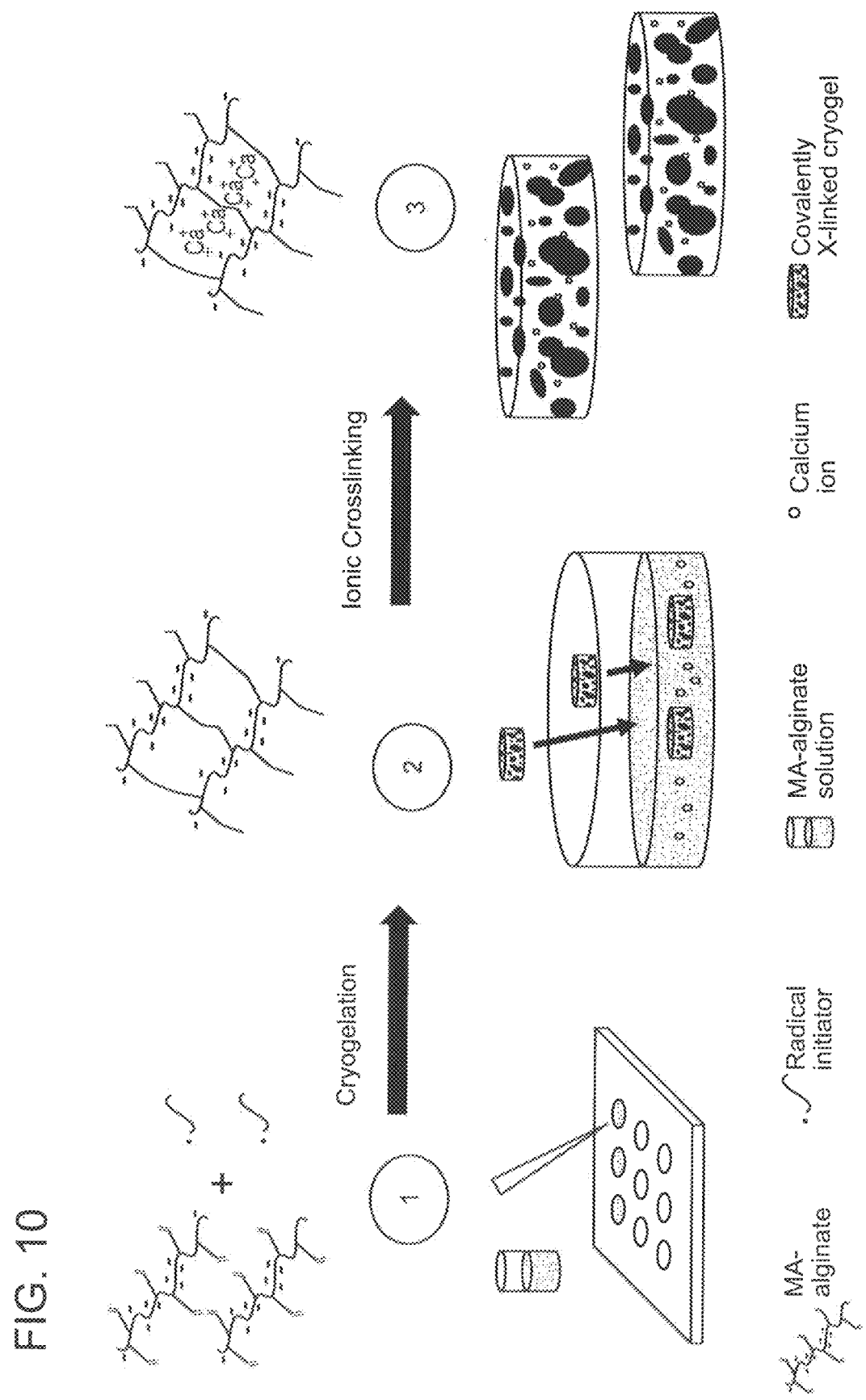
FIG. 10. Is a cartoon showing a non-limiting example of cryogel formation. Cryogels are macroporous scaffolds with shape-memory properties. Hydrogels are three dimensional (3D) networks that can absorb a large amount of water while maintaining their structural integrity. Hydrogels typically exhibit a nanoporous network structure, but it is advantageous to use hydrophilic networks with large interconnected pores (>10 µm) to allow cell infiltration and deployment, and provide an increased surface area for cell attachment and interaction. One technique to create macroporous hydrogel scaffolds is cryogelation. In an exemplary synthesis process, (i) Alginate (a naturally occurring, biocompatible polysaccharide) is chemically modified to allow radical polymerization, (ii) Methacrylated (MA)-alginate is added to ammonium persulfate (APS)/tetramethylethylenediamine (TEMED) initiator system before incubation at −20° C. to allow ice crystal formation, (iii) The process of cryogelation takes place via the following steps: phase separation with ice crystal formation, free-radical cross-linking, and polymerization followed by thawing of ice crystals (porogens) to form an interconnected macroporous cryogel network, and (iv) there is a calcium step. MA-alginate cryogels can undergo large levels of strain while being readily compressed to a fraction of their size and injected through a surgical needle for delivery. Once injected into the subcutaneous tissue, these scaffolds quickly recover their original memorized shape.

In cancer patients, the cancer-immunity cycle is blocked at one or more of these steps, dampening the anti-cancer immune response and allowing for immune escape. Cancer immunotherapies seek to promote anti-cancer immunity by augmenting specific steps in the cycle. Therapeutic vaccines provided herein target DCs to facilitate cancer antigen presentation (e.g., FIG. 6, step 2) in order to promote more robust T-cell priming and activation (e.g., FIG. 6, step 3) and subsequent CTL effector function.

PEI adjuvants viral glycoprotein antigens via the mucosal route, activating robust and protective immunity against influenza and herpes simplex virus-2 after a single intranasal administration of the relevant antigen co-formulated with PEI (Wegmann et al., Nat Biotechnol. 2012, 30(9): 883-888.).

Innate immune pathways are activated by the release of intracellular dsDNA that acts as a damage-associated molecular pattern triggering the Irf3 interferon pathway through cytoplasmic DNA sensors. Another innate immune pathway activated by PEI is the inflammasome, potentially either through the lysosomal destabilizing activity of PEI3, or through release of other damage-associated molecular patterns, such as uric acid. PEI triggers an influx of Antigen Presenting Cells (APCs) to the site of immunization and associates with antigen to form nanoparticles that are efficiently taken up by APCs. Sheppard et al. (2014) demonstrated that PEI also has systemic immune stimulating activity for viral glycoproteins (Sheppard et al., International Immunology, 2014, Vol. 26, No. 10, pp. 531-538). PEI has been tested in both subcutaneous and intraperitoneal models of immunization. Various forms of PEI act as potent systemic adjuvants that induce higher titers of antibody against natively folded antigen compared to alum (aluminum-based, clinical relevant adjuvant). Further characterization of branched 25 kDa PEI revealed that it drives a mixed Th1/Th2-type adaptive immune response if applied systemically, with robust antibody production in mice and rabbits. The mixed Th1/Th2 response induced by PEI is adequate for eliciting high titer antibody responses, and PEI was characterized by these researchers as being is unlikely to be optimal for co-induction of cytotoxic T-cells that require a Th1 cytokine environment. Co-formulation of PEI with the TLR ligand CpG ODN synergistically increases the magnitude of the adaptive immune response and biases the response toward Th1. Thus, PEI acts at multiple levels to deliver adjuvant activity for glycoprotein antigens. This is highly relevant for the biomaterial devices provided herein, such as devices comprising cryogels.

As shown in the figures herein, PEI induced DC maturation and pro-inflammatory cytokine production. PEI was loaded into the MSR/MPS scaffold and tough alginate cryogel scaffolds with high efficiency. MPS/MSR-PEI induced DC maturation and pro-inflammatory cytokine production. PEI also leads to an increased pro-inflammatory profile in cryogels.

Overcoming tolerogenic signals and the lack of co-stimulatory signals in the tumor microenvironment (TME) is a key challenge in cancer vaccine design. A key challenge in cancer vaccine design is to overcome the lack of co-stimulatory signals and presence of tolerogenic signals in the tumor microenvironment, without triggering systemic inflammatory toxicity, thereby extending the clinical scope of cancer vaccines to less immunogenic malignancies. Devices and biomaterials provided herein are useful for stimulating and/or eliciting an anti-cancer immune response. Exemplary methods comprise continuous in situ dendritic cell programming, comprising administering to a subject, a device comprising a scaffold composition, wherein the scaffold composition attracts a dendritic cell, introduces one or more immunogenic factors (e.g., including PEI alone or in combination with (a) an immunostimulatory compound; (b) a compound that attracts an immune cell to or into the delivery vehicle; (c) a compound that induces immunogenic cell death of a tumor cell; (d) a compound that inhibits T-cell or dendritic cell suppression; (e) a compound that inhibits an immune-inhibitory protein; or (f) an antigen, or any combination thereof) to the dendritic cell to promote dendritic cell activation, and induces the dendritic cell to migrate away from the scaffold composition. The devices may recruit and stimulate a heterogeneous population of dendritic cells (where each subset is specialized and contributes significantly to the generation of an immune response).

In some embodiments, a method of programming a dendritic cell in situ is carried out by introducing to a subject a device comprising scaffold composition and encapsulated recruitment composition. In certain embodiments, a pulse of recruitment composition may be released from the device within, e.g., 1-7 days of introduction of the device, leaving a residual amount of the recruitment composition in or on the device. The pulse may be followed by slow release of the residual amount over several weeks. The local concentration of the recruitment composition and the temporal pattern of release mediates recruitment, retention, and subsequent release of dendritic cells from the device. For example, the pulse may include at least 50, 60, 75, 90 or 95% of the amount of the recruitment composition associated with the device. An exemplary temporal release profile comprises a pulse characterized by the release of at least 60% of the amount of the recruitment composition associated with the device in about 1-5 days following the introduction of the device to a subject. Following the pulse, the residual amount is slowly released over an extended period of time (e.g., 1, 2, 3, 4, 5, 6, 7, 8, 9, 10, 12 days or 2, 3, 4, 5 or more weeks) following the pulse period. The recruitment compounds known in the art and/or disclosed herein may be used individually or in combination.

Aspects of the present subject matter also include increasing vaccine efficacy, comprising administering to a subject, a device comprising a scaffold composition and one or more compounds such as PEI (e.g., alone or in combination with (a) an immunostimulatory compound; (b) a compound that attracts an immune cell to or into the delivery vehicle; (c) a compound that induces immunogenic cell death of a tumor cell; (d) a compound that inhibits T-cell or dendritic cell suppression; (e) a compound that inhibits an immune-inhibitory protein; or (f) an antigen, or any combination thereof), the compounds being incorporated into or conjugated onto the scaffold composition, wherein the device attracts a dendritic cell, introduces the one or more compounds to the dendritic cell thereby activating the dendritic cell, and induces the dendritic cell to migrate away from the scaffold composition, thereby increasing the effectiveness of a vaccination procedure. The present subject matter also provides method comprise vaccinating a subject against cancer, comprising administering to a subject, a device comprising a scaffold composition and one or more compounds such as PEI (e.g., alone or in combination with (a) an immunostimulatory compound; (b) a compound that attracts an immune cell to or into the delivery vehicle; (c) a compound that induces immunogenic cell death of a tumor cell; (d) a compound that inhibits T-cell or dendritic cell suppression; (e) a compound that inhibits an immune-inhibitory protein; or (f) an antigen, or any combination thereof), wherein the scaffold composition attracts a dendritic cell, introduces the one or more compounds to the dendritic cell thereby activating the dendritic cell, and induces the dendritic cell to migrate away from the scaffold composition, thereby conferring upon a subject anti-tumor immunity, e.g., IL-12 production, and reduced tumor burden.

In various embodiments the cells that leave a device after encountering PEI, antigen, and/or other factors (and/or cells that contact the cells that leave the device) are activated to seek out tumor cells in the body to which an immune response is mounted. The activity of cells that leave the device differs from that prior to entering the device. In some embodiments, cells are recruited into the device and remain resident in the device for a period of time, e.g., minutes; 0.2, 0.5, 1, 2, 4, 6, 12, 24 hours; 2, 4, 6, days; 1-4 weeks; 2, 4, 6, 8, 10, or 12 months; or years, during which the cells are exposed to structural elements and bioactive compounds that lead to a change in the activity or level of activity of the cells. Optionally, an antigen corresponding to a target to which an immune response is desired is incorporated into or onto the scaffold structure. Cytokines may also be a component of the device to amplify immune activation and/or induce migration of the primed cells to lymph nodes. Various compounds that may be included in devices and scaffolds (e.g., PEI alone or in combination with (a) an immunostimulatory compound; (b) a compound that attracts an immune cell to or into the delivery vehicle; (c) a compound that induces immunogenic cell death of a tumor cell; (d) a compound that inhibits T-cell or dendritic cell suppression; (e) a compound that inhibits an immune-inhibitory protein; or (f) an antigen, or any combination thereof) are described herein. Encountering the antigen and other compounds in the device induces egress of the altered (re-educated or reprogrammed) cells, and the cells migrate out of the device and into surrounding tissues or remote target locations to seek out and mediate immunity against diseased cells such as tumor cells. For example, having ingested antigen, DCs become activated and migrate to lymph nodes, the spleen, and other anatomical locations, where they contact T-cells to further propagate an antigen-specific immune response, e.g., an anti-cancer response Immune cells such as T-cells, B-cells, or dendritic cells (DCs) of an individual may be recruited into the device, primed and activated to mount an immune response against an antigen-specific target.

In various embodiments, a biomaterial provided herein comprises 1) a cytokine such as granulocyte-macrophage colony-stimulating factor (GM-CSF), FMS-like tyrosine kinase 3 ligand (Flt3L), Chemokine (C-C Motif) Ligand 20 (CCL20), Interleukin 15 (IL-15), Chemokine (C Motif) Ligand 1 (XCL1), Chemokine (C-X-C Motif) Ligand 10 (CXCL10), Interferon Alpha 1 (IFN-alpha), Interferon Beta (IFN-beta), or Interleukin 12 (IL-12); 2) an immunostimulatory compound such as a TLR agonist, e.g., a CpG oligonucleotide, polyinosine-polycytidylic acid (poly (I:C)) PEI-poly (I:C), polyadenylic-polyuridylic acid (poly (A:U)), PEI-poly (A:U), double stranded ribonucleic acid (RNA), monophosphoryl lipid A (MPLA), imiquimod, CRX-527, and OM-174; 3) a small molecule immune suppression inhibitor such as LY2157299, GW788388, LY364947, 8268712, RepSox, SB525334, SD208, BP-1-102, S3I-M2001, STA-21, S3I-201, Stattic, Galiellalactone, INCB24360, NLG919, Norharmane, Rosmarinic Acid, 1-Methyltryptophan, and indoximod; and/or 4) an antibody that inhibits immune suppression. Non-liming examples of human amino acid sequences for isoforms of each of the cytokines listed above are publically available using the following accession numbers: GM-CSF—GenBank No: AAA52578.1 (SEQ ID NO: 3); Flt3L—UniProtKB/Swiss-Prot No: P49771.1 (SEQ ID NO: 4); CCL20—GenBank No: AAH20698.1 (SEQ ID NO: 5); IL-15—GenBank No: AAI00963.1 (SEQ ID NO: 6); XCL1—GenBank No: AAH69817.1 (SEQ ID NO: 7); CXCL10—GenBank No: EAX05693.1 (SEQ ID NO: 8); IFN-alpha—GenBank No: AAI12303.1 (SEQ ID NO: 9); IFN-beta—GenBank No: AAC41702.1 (SEQ ID NO: 10); and IL-12—NCBI Accession No. 1F45_A (Chain A) (SEQ ID NO: 11) and NCBI Accession No. 1F45_B (Chain B) (SEQ ID NO: 12).

In certain embodiments, an advantage of patient-specific immunization devices provided herein is reduced toxicity of immunomodulatory and/or chemotherapeutic agents, because the devices deliver agents locally at the tumor site and/or permits the use of lower concentrations of the agents. Inducers of immunogenic cell death, e.g., chemotherapeutic/tumor cytotoxic agents work together with the device-mediated immune modulation leading to improved tumor regression/reduction while reducing side effects. In one example, the cryogel or hydrogel includes PEI, an anthracycline or another immunogenic cell death inducer along with an immune cell enrichment composition, and an immunostimulatory agent (in the absence of tumor antigen prior to patient administration). In another example, the cryogel or hydrogel includes PEI, an immune cell enrichment composition, and a TLR ligand or a STING ligand, without an anthracycline or other immunogenic cell death inducer with the anthracycline or other immunogenic cell death being administered to the patient systemically.

In various embodiments in which a device or scaffold of the invention is administered without surgical implantation, the device or scaffold is injected using a needle. For example, the device or scaffold may be injected through a 16-gauge, an 18-gauge, a 20-gauge, a 22-gauge, a 24-gauge, a 26-gauge, a 28-gauge, a 30-gauge, a 32-gauge, or a 34-gauge needle.

As used herein, injection or other administration to a "tumor site" may mean placement of a device or scaffold of the invention such that (i) at least a portion of the device or scaffold is within the tumor, (ii) the entire device or scaffold is within the tumor, (iii) at least a portion of the device or scaffold contacts the tumor, or (iv) the device or scaffold is in the proximity of the tumor. In certain embodiments, the device or scaffold is administered such that it is peritumoral (i.e., in direct contact with or in close proximity to the tumor). Alternatively, the tumor capsule is punctured to deliver the device or scaffold directly into the tumor mass. In some embodiments, the tumor is not contacted with the device or scaffold. Various implementations of the present subject matter avoid puncturing or otherwise physically disrupting the tumor. Thus, aspects of the present invention relate to generating an immune response without physically interrupting or disrupting a tumor capsule. In non-limiting examples, the device or scaffold may be placed within 0 (i.e., touching the tumor) to 10 mm of a tumor. In various embodiments, the point of the device or scaffold that is closest to the tumor is about 0 (i.e., directly contacting tumor mass), 0.1, 0.5, 1, 2, 3, 4, 5, 6, 7, 8, 9, or 10 mm from the tumor mass boundary. In some embodiments, the point of the device or scaffold that is closest to the tumor is less than about 1, 2, 3, 4, 5, 6, 7, 8, 9, 10 mm from the tumor. In certain embodiments, the point of the device or scaffold that is closest to the tumor is at least about 1, 2, 3, or 5 mm and less than about 6, 7, 8, 9, or 10 mm from the tumor.

Various embodiments of the present subject matter obviate the need for patient-derived material (e.g., patient-derived tumor antigens). In various embodiments, devices and scaffolds do not contain a tumor antigen (from a subject or another source) at the time of administration. Anti-tumor vaccination may be achieved by inserting a device or scaffold into a tumor with, e.g., a needle, or by delivering a device or scaffold near a tumor without interrupting the tumor mass with the needle. Thus, embodiments of the present invention relate to devices and scaffolds that promote immune activation against a tumor in vivo without (i) containing a tumor antigen when administered or (ii) disrupting a tumor capsule.

Delivery of immunomodulatory factors (e.g., agents that modulate targets in the T-cell checkpoint) to the tumor site directly reduces the immunosuppressive local microenvironment at/near the tumor.

Exemplary Compounds for Delivery

Polyethylenimine

Polyethylenimine (PEI) or polyaziridine is a polymer with repeating unit composed of the amine group and two carbon aliphatic $CH_2CH_2$ spacer. Linear polyethyleneimines contain all secondary amines, in contrast to branched PEIs which contain primary, secondary and tertiary amino groups. Totally branched, dendrimeric forms are available. PEI is available at a variety of molecular weights, e.g., 1-60 kDa.

Branched PEI may be synthesized by the ring opening polymerization of aziridine (Zhuk et. al., Russian Chemical Reviews; Vol 34:7.1965). Depending on the reaction conditions different degree of branching can be achieved. Linear PEI is available by post-modification of other polymers like poly(2-oxazolines) (Tanaka et al., Macromolecules, 1983, 16 (6): 849-853) or N-substituted polyaziridines (Weyts et al., Polymer Bulletin, 1988, 19 (1): 13-19). Linear PEI may be synthesized by the hydrolysis of poly(2-ethyl-2-oxazoline) (Brissault et al., Bioconjugate Chemistry, 2003, 14: 581-587). Non-limiting examples of methods for synthesizing linear PEI are also described in U.S. Patent Application Publication No. 2010-0197888, published Aug. 5, 2010, the entire content of which is incorporated herein by reference. Branched 60 kDa PEI is commercially available from Sigma Aldrich (St. Louis, MO, USA), linear 25 kDa PEI is from Polysciences (Warrington, PA, USA). Branched 2 kDa PEI and Linear 2 kDa PEI is commercially from Sigma Aldrich.

Prior to the invention, PEI was used to condense plasmid DNA, as well as nucleic acids such as CpG and poly (I:C).

Chemotherapeutic Agents

Aspects of the present subject matter include compounds that induce immunogenic cell death. Such chemotherapeutic agents include members of the anthracycline class of compounds, e.g., doxorubicin, daunorubicin, epirubicin, idarubicin, and valrubicin as well as mitoxantrone, an anthracycline analog.

Chemotherapeutic agents may be used to generate antigen and prime the immune system. The anthracycline class of chemotherapeutic agents kill tumor cells in a way that causes priming of the immune system (immunogenic cell death). Anthracyclines are anticancer compounds that were originally derived from *Streptomyces* sp. Anthracyclines are red aromatic polyketides and occur in variety of forms due to the structural differences in the aglycone and the different attached sugar residues.

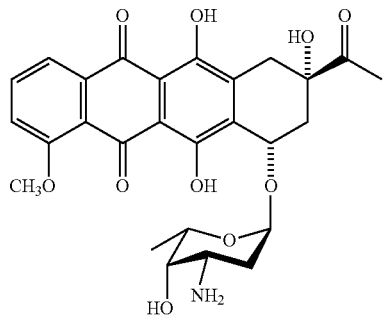

Daunorubicin, the prototypical anthracycline

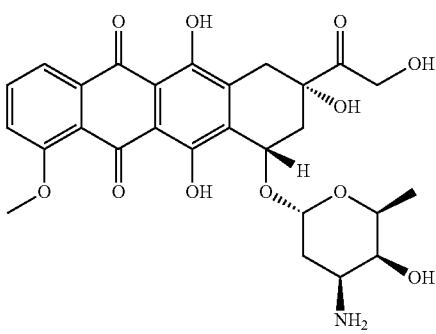

Doxorubicin

An exemplary chemotherapeutic agent that elicits immunogenic cell death is a tricyclic compound as shown below. In one embodiment, the present invention relates to a compound of formula (I):

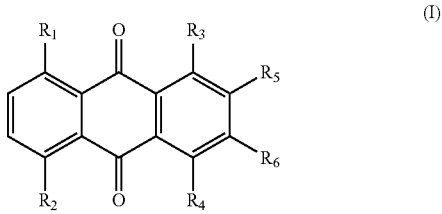

or a pharmaceutically acceptable salt, or solvate thereof, wherein $R_1$ and $R_2$ are independently selected from —$OCH_3$, —OH or —H; $R_3$ and $R_4$ are independently selected from —OH or —$NHCH_2CH_2NHCH_2CH_2OH$; $R_5$ and $R_6$ are selected from H or alternatively together form a six membered unsaturated carbocycle, substituted with $R_7$, $R_8$, and $R_9$; and $R_7$, $R_8$, and $R_9$ are independently selected from —OH, —C(=O)$CH_3$, —C(=O)$CH_2OC(O)$ $CH_2CH_2CH_2CH_3$, —C(=O)$CH_2OH$,

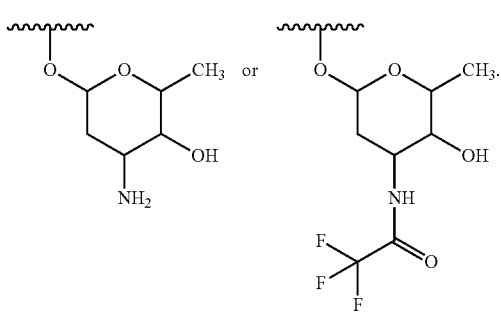 [SMILES: *OC1CC(N)C(O)C(C)O1 ; *OC1CC(NC(=O)C(F)(F)F)C(O)C(C)O1]

For example, one set of compounds of formula (I) includes those in which $R_3$ and $R_4$ are OH. Furthermore, this set of compounds can comprise a subset of compounds of formula (I), wherein $R_3$ and $R_4$ are OH and $R_1$ is H.

Another set of compounds of formula (I) includes those in which $R_1$ and $R_2$ are OH. This set of compounds can also comprise a subset of compounds of formula (I), wherein $R_1$ and $R_2$ are OH and $R_3$ and $R_4$ are $NHCH_2CH_2NHCH_2CH_2OH$. Another subset of compounds of formula (I) include those in which $R_1$ and $R_2$ are OH, $R_3$ and $R_4$ are $NHCH_2CH_2NHCH_2CH_2OH$, and $R_5$ and $R_6$ are H.

Another one embodiment, the present invention relates to a subset of compounds of formula (II):

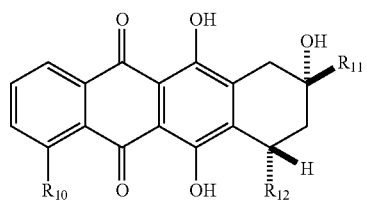

or a pharmaceutically acceptable salt, or solvate thereof, wherein $R_{10}$ is H or $-OCH_3$; $R_{11}$ is $-C(=O)$, $C(=O)CH_2OH$ or $-C(=O)CH_2OC(=O)CH_2CH_2CH_3$; and $R_{12}$ is

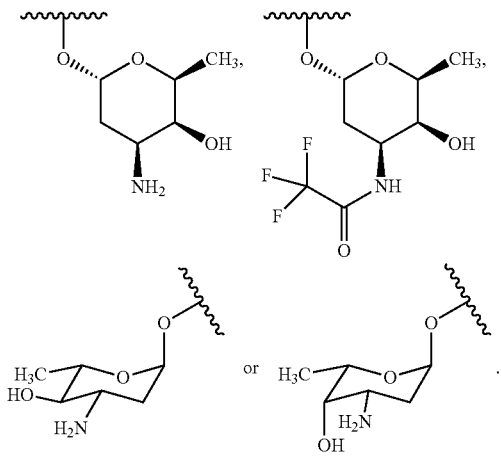

For example, one set of compounds of formula (II) includes those in which $R_{11}$ is $OCH_3$.

By "anthracycline" is meant a class of drugs that are commonly used as a chemotherapeutic agent. In embodiments, an anthracycline has a tricyclic core (e.g., Mitoxantrone) or a tetracyclic core. In embodiments, an anthracycline has a structure according to the following formula,

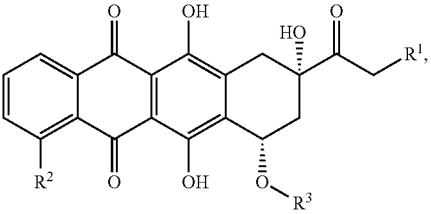

wherein
$R^1$ is $-H$, $-OH$, or $-O(C=O)(C_1-C_6$ alkyl);
$R^2$ is $-H$ or $-OCH_3$; and
$R^3$ is an amino sugar. Exemplary anthracyclines doxorubicin, daunorubicin, epirubicin, idarubicin, and vairubicin are described in Table 1. Still further exemplary anthracyclines include those described as Formulas I and II of U.S. Pat. No. 9,107,962, herein incorporated by reference in its entirety.

| Anthracycline | $R^1$ | $R^2$ | $R^3$ |
|---|---|---|---|
| daunorubicin | $-H$ | $-OCH_3$ | ![structure] |
| doxorubicin | $-OH$ | $-OCH_3$ | ![structure] |
| epirubicin | $-OH$ | $-OCH_3$ | ![structure] |
| idarubicin | $-H$ | $-H$ | ![structure] |
| valrubicin | $-O(C=O)(C_4H_9)$ | $-OCH_3$ | ![structure] |

Other classes of chemotherapeutic compounds that induce immunogenic cell death include alkylating agents such as platinum-containing anti-cancer drugs (e.g., cisplatin, oxaliplatin, and carboplatin), as well as (RS)—N,N-bis(2-chloroethyl)-1,3,2-oxazaphosphinan-2-amine 2-oxide (cyclophosphamide) and the related metabolite 4-hydroxy cyclophosphamide Immunogenic cell death may also be induced by cardiac glycosides such as oleandrin, ouabain, bufalin, digitoxin, digoxin, cinobufatalin, cinobufagin, and resibufogenin.

The activity of such inducers of immunogenic cell death results in antigen presenting cells being recruited to engulf dying tumor cells at the device injection site.

Inhibitors of Immune Response Suppression

Inhibitors of a tumor-generated immunosuppressive microenvironment are used to downregulate immunosuppression at the tumor site, potentiating the action of the agents listed above. Inhibitors may comprise, e.g., proteins, peptides, antibodies, small molecules, or RNA interference (RNAi) molecules that reduce the expression of a target protein.

Many inhibitory pathways exist within tumors that suppress tumor antigen presentation and the anti-tumor immune response. For example, TGF-β dampens tumor immunosurveillance and polarizes innate immune cells towards an immature differentiation status that prevents optimal anti-tumor immunity. Additionally, the STAT3 pathway promotes the production of immune inhibitory cytokines within the tumor, dampens anti-tumor T-helper 1-mediated immunity, and inhibits dendritic cell maturation. Also, Indoleamine-pyrrole 2,3-dioxygenase (IDO or INDO EC 1.13.11.52). IDO is an enzyme that in humans is encoded by the IDO1 gene and catalyzes the degradation of the essential amino acid L-tryptophan to N-formylkynurenine. IDO can deplete tryptophan in the tumor microenvironment, inhibiting the activity of T cells and dendritic cells. Small molecule inhibitors of these (TGF-β, STAT3, and IDO) and other immunosuppressive pathways have been developed and are being tested clinically. Examples of such inhibitors include TGF-β pathway inhibitors (LY2157299), STAT3 pathway inhibitors (BP-1-102), IDO pathway inhibitors (NLG919); PD-1 pathway inhibitors, CTLA-4 pathway inhibitors, LAG-3 pathway inhibitors, B7-H3 pathway inhibitors, and/or TIM3 pathway inhibitors.

In addition to protein inhibitors and antibody-based inhibitors, small molecule inhibitors are loaded into or onto the device and are delivered to the location of a tumor/tumor site to inhibit the local tumor-mediated immunosuppression. Small molecules are compounds that have a molecular mass of a less than 1000 daltons, e.g., 500 daltons or less, 250 daltons or less, 100 daltons or less. Exemplary small molecule immunomodulatory compounds, e.g., inhibitors of immune suppression, are described below. Many are generally hydrophobic.

TGF-β inhibitors

Non-limiting examples of TGF-β inhibitors include LY2157299, GW788388, LY364947, 8268712, RepSox, SB525334, and SD208.

LY2157299 has the following structure:

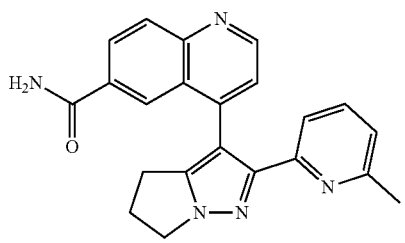 [SMILES: Cc1cccc(-c2nn3c(c2-c2ccnc4ccc(C(N)=O)cc24)CCC3)n1]

LY2157299 is also known as galunisertib and is described in Maier A, et al. (2015) Cell Oncol 38:131-144, the entire content of which is incorporated herein by reference. This compound has been used to treat solid tumors such as liver cancer (e.g. hepatocellular carcinoma) (clinicaltrials.gov/ct2/show/NCT02240433?term=LY2157299&rank=2) and has been used in combination with anti-PD-1 antibody from Bristol Meyers Squibb in advanced (metastatic and/or unresectable) glioblastoma, hepatocellular carcinoma and non-small cell lung cancer—news.bms.com/press-release/rd-news/bristol-myers-squibb-and-lilly-enter-clinical-collaboration-agreement-evaluate These and other non-limiting examples of TGF-β inhibitors are described in U.S. Pat. No. 7,265,225 issued Sep. 4, 2007; U.S. Pat. No. 7,834,029 issued Nov. 16, 2010; and U.S. Pat. No. 7,872,020 issued Jan. 8, 2011, the entire contents of each of which are incorporated herein by reference.

GW788388 has the following structure:

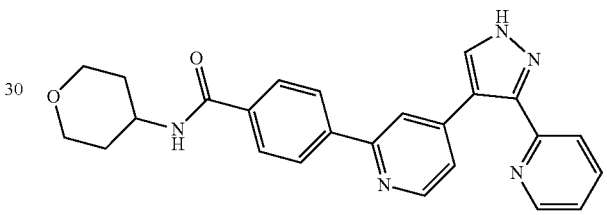

GW788388 is described in Gellibert et al (2006) Discovery of 4-{4-[3-(pyridin-2-yl)-1H-pyrazol-4-yl]pyridin-2-yl}-N-(tetrahydro-2H-pyran-4-yl)benzamide (GW788388): a potent, selective, and orally active transforming growth factor-β type I receptor inhibitor. J. Med. Chem. 49 2210, the entire content of which is incorporated herein by reference.

LY364947 has the following structure:

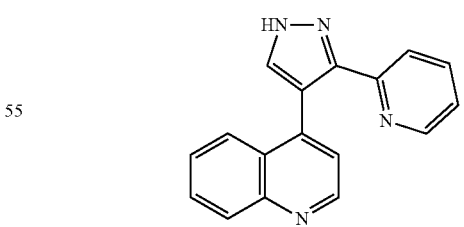

LY364947 is described in Sawyer et al (2003) Synthesis and activity of new aryl- and heteroaryl-substituted pyrazole inhibitors of the transforming growth factor-μ type I receptor kinase domain Journal of Medicinal Chemistry, 46(19), 3953-3956, the entire content of which is incorporated herein by reference.

R268712 has the following structure:

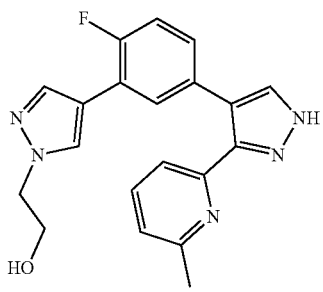 [SMILES: Cc1cccc(-c2n[nH]cc2-c2ccc(F)c(-c3cnn(CCO)c3)c2)n1]

R268712 is described in Terashima et al (2014) R-268712, an orally active transforming growth factor-β type I receptor inhibitor, prevents glomerular sclerosis in a Thy1 nephritis model. Eur. J. Pharmacol. 734:60, the entire content of which is incorporated herein by reference.

RepSox has the following structure:

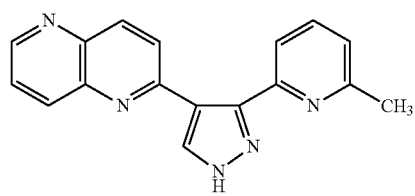 [SMILES: Cc1cccc(-c2n[nH]cc2-c2ccc3ncccc3n2)n1]

RepSox is also known as E-616452, SJN 2511, and ALK5 Inhibitor II. RepSox is described in Gellibert et al (2004) Identification of 1,5-naphthyridine derivatives as a novel series of potent and selective TGF-γ type I receptor inhibitors. J. Med. Chem. 47(18), 4494-4506, the entire content of which is incorporated herein by reference.

SB525334 has the following structure:

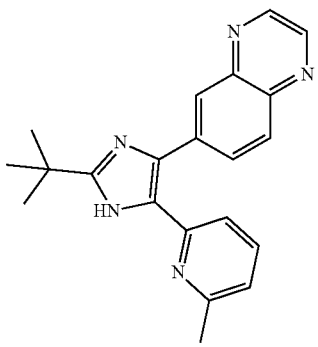 [SMILES: Cc1cccc(-c2[nH]c(C(C)(C)C)nc2-c2ccc3nccnc3c2)n1]

SB525334 is described in Grygielko et al (2005) Inhibition of gene markers of fibrosis with a novel inhibitor of transforming growth factor-β type I receptor kinase in puromycin-induced nephritis. J. Pharmacol. Exp. Ther. 313 943, the entire content of which is incorporated herein by reference.

SD208 has the following structure:

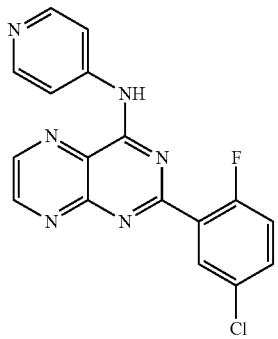 [SMILES: Fc1ccc(Cl)cc1-c1nc(Nc2ccncc2)c2nccnc2n1]

SD208 is described in Uhl et al (2004) SD-208, a novel transforming growth factor β feceptor I kinase inhibitor, inhibits growth and invasiveness and enhances immunogeneicity of murine and human glioma cells in vitro and in vivo. Cancer Res. 64(21), 7954-7961, the entire content of which is incorporated herein by reference.

Non-limiting examples of antibodies that antagonize TGF-β include metelimumab (also known as CAT-192) and fresolimumab (also known as GC1008). Fresolimumab is described in Gruner et al. (2008) "A cytokine-neutralizing antibody as a structural mimetic of 2 receptor interactions" Proceedings of the National Academy of Sciences 105 (51): 20251-20256, the entire content of which is incorporated herein by reference.

STAT3 Inhibitors

Non-limiting examples of STAT3 inhibitors include BP-1-102, S3I-M2001, STA-21, S3I-201, Stattic, Galiellalactone, a polypeptide having the sequence PY*LKTK (SEQ ID NO: 1) (where Y* represents phosphotyrosine), and a polypeptide having the sequence Y*LPQTV (SEQ ID NO: 2) (where Y* represents phosphotyrosine). Additional non-limiting examples of STAT3 inhibitors are described in Yue and Turkson Expert Opin Investig Drugs. 2009 January; 18(1): 45-56, the entire content of which is incorporated herein by reference.

S3I-M2001 has the following structure:

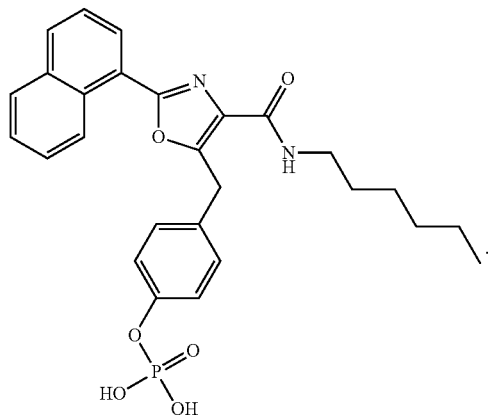 [SMILES: CCCCCCNC(=O)c1nc(-c2cccc3ccccc23)oc1Cc1ccc(OP(=O)(O)O)cc1]

S3I-M2001 is described in U.S. Pat. No. 8,609,639, issued Dec. 17, 2013, the entire content of which is incorporated herein by reference.

STA-21 has the following structure:

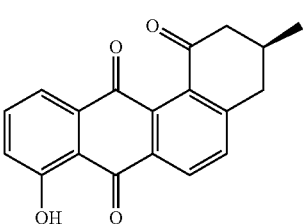 [SMILES: C[C@@H]1CC(=O)c2c(ccc3c2C(=O)c2cccc(O)c2C3=O)C1]

STA-21 is described in Miyoshi et al., J Invest Dermatol. 2011 January; 131(1):108-17, the entire content of which is incorporated herein by reference.

S3I-201 has the following structure:

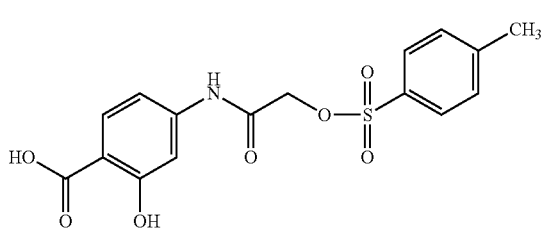 [SMILES: Cc1ccc(S(=O)(=O)OCC(=O)Nc2ccc(C(=O)O)c(O)c2)cc1]

S3I-201 is described in Siddiquee K, et al. Proc Natl Acad Sci USA, 2007, 104(18), 7391-7396, the entire content of which is incorporated herein by reference.

Stattic has the following structure:

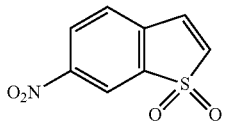

Stattic is described in Schust J, et al. Chem Biol, 2006, 13(11), 1235-1242, the entire content of which is incorporated herein by reference.

Galiellalactone has the following structure:

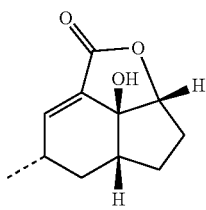

Galiellalactone is described in Don-Doncow et al., J Biol Chem. 2014 Jun. 6; 289(23):15969-78, the entire content of which is incorporated herein by reference.

BP-1-102 has the following structure:

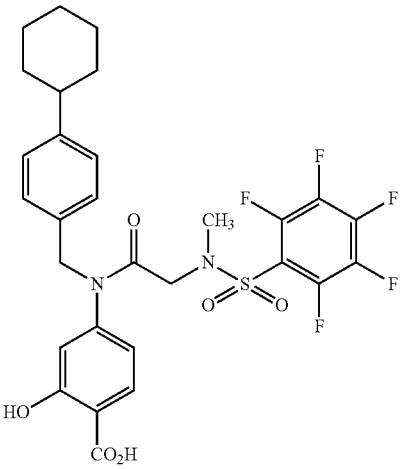 [SMILES: CN(CC(=O)N(Cc1ccc(C2CCCCC2)cc1)c1ccc(C(=O)O)c(O)c1)S(=O)(=O)c1c(F)c(F)c(F)c(F)c1F]

Signal transducer and activator of transcription 3 (STAT3) is a transcription factor which in humans is encoded by the STAT3 gene. The STAT3 inhibitor, BP-1-102 is active against tumors (e.g., solid tumors) such as human lung cancer and breast cancer in animals (PNAS 2012 109 (24) 9623-9628). Another small molecule STAT3 inhibitor is OPB-31121 (Cancer Lett. 2013 Jul. 10; 335(1):145-52. doi: 10.1016/j.canlet.2013.02.010. Epub 2013 Feb. 10).

Another non-limiting example is OPB-31121—clinicaltrials.gov/ct2/show/NCT00955812, clinicaltrials.gov/ct2/show/NCT01406574, OPB-31121 is an orally bioavailable inhibitor of STAT3, with antineoplastic activity. OPB-31121 inhibits the phosphorylation of STAT3, which prevents binding of STAT3 to DNA sequences on a variety of STAT3-responsive promoters and results in the inhibition of STAT3-mediated transcription and, potentially, the inhibition of tumor cell proliferation. STAT3 is constitutively activated in a variety of cancers, contributing to the loss of cell growth control and neoplastic transformation. OPB-31121 is described in Kim et al. (2013) OPB-31121, a novel small molecular inhibitor, disrupts the JAK2/STAT3 pathway and exhibits an antitumor activity in gastric cancer cells. Cancer Lett 335: 145-152, the entire content of which is incorporated herein by reference.

Other inhibitors are described in Miklossy et al., 2013 Nat. Rev. Drug Discov. 12:611-629, the entire content of which is incorporated herein by reference.

IDO Inhibitors

IDO is expressed by cancer cells in a range of tumor types. High IDO expression correlates with poor outcome in a number of cancers, such as ovarian cancer, endometrial cancer, colon cancer, and melanoma. Non-limiting examples of IDO inhibitors include INCB24360, INCB24360 analogues, NLG919 (also known as GDC-0919), Norharmane, Rosmarinic Acid, 1-Methyltryptophan, and indoximod.

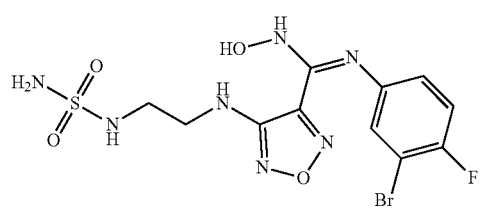 [SMILES: NS(=O)(=O)NCCNc1nonc1/C(=N\c1ccc(F)c(Br)c1)NO]

The structure of an INCB24360 analogue, which also inhibits IDO, has the following structure:

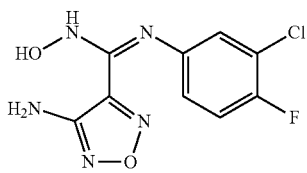 [SMILES: Nc1nonc1/C(=N\c1ccc(F)c(Cl)c1)NO]

This analogue is described in Yue et al. J Med Chem. 2009, 52(23), 7364-7367, the entire content of which is incorporated herein by reference.

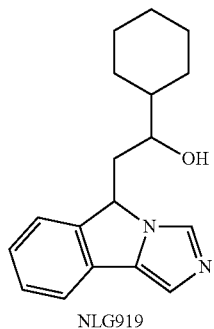 [SMILES: OC(CC1c2ccccc2-c2cncn21)C1CCCCC1]

NLG919

INCB24360, its analogue shown above, and NLG919 are IDO1 inhibitors. Selective inhibition of IDO1 effectively regulates mediators of antitumor immunity (Liu et al., Blood, 2010, 115: 3520-3530, incorporated herein by reference). These drugs are useful to inhibit tumor-mediated immune evasion or suppression and are optionally combined with immune checkpoint blockers such as antibody-based inhibitors, e.g., anti-PD1 (clinicaltrials.gov/ct2/show/NCT02327078, incorporated herein by reference).

Norharmane is another example of an IDO inhibitor, and has the following structure:

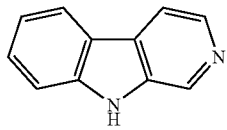 [SMILES: c1ccc2c(c1)[nH]c1cnccc12]

Norharmane is described in Chiarugi et al. (2000) Journal of Leukocyte Biology 68 (2): 260-6, the entire content of which is incorporated herein by reference.

Rosmarinic Acid is a further example of an IDO inhibitor, and has the following structure:

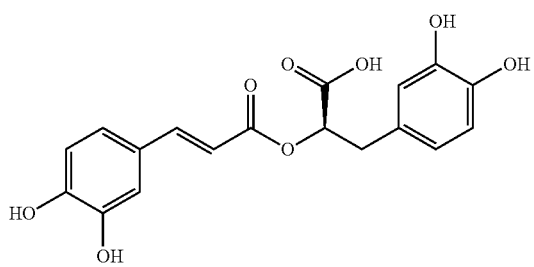 [SMILES: O=C(/C=C/c1ccc(O)c(O)c1)O[C@H](Cc1ccc(O)c(O)c1)C(=O)O]

Rosmarinic Acid is described in Lee et al. (2007) Biochemical Pharmacology 73 (9): 1412-21, the entire content of which is incorporated herein by reference.

1-Methyltryptophan is an additional example of an IDO inhibitor and has the following structure:

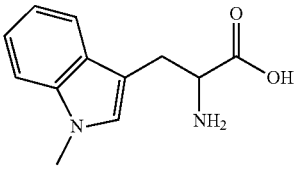 [SMILES: Cn1cc(CC(N)C(=O)O)c2ccccc21]

1-Methyltryptophan is described in Hou et al. (2007) Cancer Res. 67 (2): 792-801, the entire content of which is incorporated herein by reference.

The structure of indoximod is

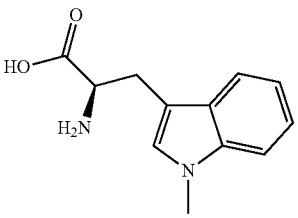 [SMILES: Cn1cc(C[C@@H](N)C(=O)O)c2ccccc21]

Indoximod is described in Soliman H H, Jackson E, Neuger T et al. A first in man phase I trial of the oral immunomodulator, indoximod, combined with docetaxel in patients with metastatic solid tumors. Oncotarget. 2014 Sep. 30; 5 (18):8136-46, the entire content of which is incorporated herein by reference.

Additional non-limiting examples of IDO inhibitors are described in U.S. Patent Application Publication No. US 2014315962 published Oct. 23, 2014, the entire content of which is incorporated herein by reference.

PD-1 Pathway Inhibitors

PD-1 limits the activity of T cells in peripheral tissues at the time of an inflammatory response to infection and to limit autoimmunity PD-1 blockade in vitro enhances T-cell proliferation and cytokine production in response to a challenge by specific antigen targets or by allogeneic cells in mixed lymphocyte reactions. A strong correlation between PD-1 expression and response was shown with blockade of PD-1 (Pardoll, Nature Reviews Cancer, 12: 252-264, 2012). PD-1 blockade can be accomplished by a variety of mechanisms including antibodies that bind PD-1 or its ligand, PD-L1. Examples of PD-1 and PD-L1 blockers are described in U.S. Pat. Nos. 7,488,802; 7,943,743; 8,008,449; 8,168,757; 8,217,149, and PCT Published Patent Application Nos: WO03042402, WO2008156712, WO2010077634, WO2010089411, WO2010036959, WO2011066342, WO2011159877, WO2011082400, WO2011161699, and WO2013181452, the entire contents of each of which are incorporated herein by reference. In certain embodiments the PD-1 blockers include anti-PD-L1 antibodies.

Non-limiting examples of PD-1 pathway inhibitors include AMP-224, Nivolumab (also known as MDX-1106; ONO-4538), Pembrolizumab, Pidilizumab, BMS 936559 (also known as MDX-1105), MPDL3280A (also known as Atezolizumab), MEDI4736, and MSB0010718C. Non-limiting examples of PD-1 pathway inhibitors are also described in Dolan and Gupta Cancer Control. 2014 July; 21(3):231-7 the entire content of which is incorporated herein by reference.

AMP-224, also known as B7-DCIg, is a PD-L2-Fc fusion soluble receptor. AMP-224 is being used in U.S. National Institutes of Health (NIH) clinical trial number NCT02298946. AMP-224 is described in U.S. Patent Application Publication No. 2011/0223188, published Sep. 15, 2011; U.S. Patent Application Publication No. 2013/0017199, published Jan. 17, 2013; and Smothers et al., Ann Oncol (2013) 24 (suppl 1): i7, the entire contents of each of which are incorporated herein by reference.

Nivolumab is also known as ONO-4538, BMS-936558, MDX1106, and Opdivo. Nivolumab is described in U.S. Pat. No. 8,008,449, issued Aug. 30, 2011; and Sundar R, Cho B C, Brahmer J R, Soo R A (2015). "Nivolumab in NSCLC: latest evidence and clinical potential" Ther Adv Med Oncol 7 (2): 85-96, the entire contents of each of which are incorporated herein by reference.

Pembrolizumab is also known as MK-3475, lambrolizumab, and Keytruda. Pembrolizumab is also described in U.S. Pat. No. 8,952,136, issued Feb. 10, 2015; U.S. Pat. No. 8,168,757, issued May 1, 2012; and Hamid et al., (2013) "Safety and tumor responses with lambrolizumab (anti-PD-1) in melanoma" New England Journal of Medicine 369 (2): 134-44, the entire contents of each of which are hereby incorporated herein by reference.

Pidilizumab also known as CT-011 and is described in U.S. Pat. No. 8,747,847, issued Jun. 10, 2014; Westin et al. (2014) "Safety and Activity of PD1 Blockade by Pidilizumab in Combination with Rituximab in Patients with Relapsed Follicular Lymphoma: a Single Group, Open-label, Phase 2 Trial" Lancet Oncol. 15: 69-77, the entire contents of each of which are incorporated herein by reference.

BMS 936559 is also known as MDX-1105. BMS 936559 is described in U.S. Pat. No. 7,943,743, issued May 17, 2011; and Brahmer, J. R. et al. Safety and activity of anti-PD-L1 antibody in patients with advanced cancer. N. Engl. J. Med. 366, 2455-2465 (2012), the entire contents of each of which are incorporated herein by reference.

MPDL3280A is also known as Atezolizumab. MPDL3280A has the CAS Registry number 1422185-06-5. MPDL3280A is described in McDermott et al., Atezolizumab, an Anti-Programmed Death-Ligand 1 Antibody, in Metastatic Renal Cell Carcinoma: Long-Term Safety, Clinical Activity, and Immune Correlates From a Phase Ia Study, J Clin Oncol. 2016 Jan. 11. pii: JCO637421 (Epub ahead of print) PMID: 26755520.

MEDI4736 is described in U.S. Pat. No. 8,779,108, issued Jul. 15, 2014; and Ibrahim et al., Semin Oncol. 2015 June; 42(3):474-83, the entire contents of each of which are incorporated herein by reference.

MSB0010718C is also known as Avelumab. The CAS Registry number for MSB0010718C is 1537032-82-8. MSB0010718C is described in Boyerinas B, Jochems C, Fantini M, Heery C R, Gulley J L, Tsang K Y, Schlom J. Cancer Immunol Res. 2015 October; 3(10):1148-57, the entire content of which is incorporated herein by reference.

CTLA-4 Inhibitors

Non-limiting examples of CTLA-4 inhibitors include tremelimumab and ipilimumab. See, e.g., Pardoll D M (April 2012). "The blockade of immune checkpoints in cancer immunotherapy". Nat. Rev. Cancer 12 (4): 252-64, the entire content of which is incorporated herein by reference.

Tremelimumab is also known as ticilimumab and CP-675,206. Tremelimumab is described in Antoni Ribas (28 Jun. 2012). "Tumor immunotherapy directed at PD-1". New England Journal of Medicine 366 (26): 2517-9, the entire content of which is incorporated herein by reference.

Ipilimumab is also known as Yervoy, MDX-010, and MDX-101. Ipilimumab is described in Antoni Ribas (28 Jun. 2012). "Tumor immunotherapy directed at PD-1". New England Journal of Medicine 366 (26): 2517-9, the entire content of which is incorporated herein by reference.

LAG-3 Inhibitors

A non-limiting example of a LAG-3 inhibitor is IMP321. IMP321 is soluble version of the immune checkpoint molecule LAG-3, used to increase an immune response to tumors. IMP321 is described in Brignone et al. (2007) "IMP321 (sLAG-3), an immunopotentiator for T cell responses against a HBsAg antigen in healthy adults: a single blind randomised controlled phase I study" J Immune Based Ther Vaccines 5 (1): 5, the entire content of which is incorporated herein by reference.

Non-limiting examples of soluble fractions of the LAG-3 protein which may be useful in embodiments of the invention are described in U.S. Pat. No. 5,955,300, issued Sep. 21, 1999, the entire content of which is incorporated herein by reference.

Non-limiting examples of anti-LAG-3 antibodies include BMS-986016 and GSK2831781.

GSK2831781 is described in U.S. Patent Application Publication No. 2014/0286935, published Sep. 25, 2014, the entire content of which is incorporated herein by reference.

BMS-986016 is described in PCT International Patent Application No. WO 2015/042246, published Mar. 26, 2015, the entire content of which is incorporated herein by reference.

Non-limiting examples of anti-LAG-3 antibodies are described in U.S. Patent Application Publication No. 2014/0286935, published Sep. 25, 2014; U.S. Patent Application Publication No. 2015/0307609, published Oct. 29, 2015; PCT International Patent Application Publication No. WO2008132601, published Nov. 6, 2008, the entire contents of each of which are incorporated herein by reference.

B7-H3 Inhibitors

A non-limiting example of a B7-H3 inhibitor is the antibody known as MGA271. MGA271 is described in Loo et al. (2012) Cancer Res. 2012 Jul. 15; 18(14):3834-45, the entire content of which is incorporated herein by reference.

Additional non-limiting examples of anti-B7-H3 inhibitors are described in U.S. Pat. No. 8,802,091, issued Aug. 12, 2014, the entire content of which is incorporated herein by reference.

TIM3 Inhibitors

Non-limiting examples of TIM3 inhibitors include the antibodies described in U.S. Pat. No. 8,841,418, issued Sep. 23, 2014; and U.S. Pat. No. 8,552,156, issued Oct. 8, 2013, the entire contents of each of which are incorporated herein by reference.

Immunostimulatory Compounds

As used herein and depending on context, the term "immunostimulatory compound" includes compounds that increase a subject's immune response to an antigen. Examples of immunostimulatory compounds include immune stimulants and immune cell activating compounds. Devices of the present subject matter may contain immunostimulatory compounds that help program the immune cells to recognize ligands and enhance antigen presentation.

An example of an immunostimulatory compound is PEI.

Immunostimulatory compound also include STING ligands, e.g., cyclic dinucleotides (such as a cyclic purine dinucleotide). In some embodiments, the cyclic dinucleotide is a compound comprising a 2'-5' and/or 3'-5' phosphodiester linkage between two purine (e.g., adenine and/or guanine) nucleotides. Non-limiting examples of STING ligands are described in PCT International Patent Application Publication No. WO 2015/077354, published May 28, 2015; U.S. Pat. No. 7,709,458, issued May 4, 2010; U.S. Pat. No. 7,592,326, issued Sep. 22, 2009; and U.S. Patent Application Publication No. 2014/0205653, published Jun. 19, 2014, the entire contents of each of which are hereby incorporated herein by reference. Cyclic-di-nucleotides (CDNs) include, but are not limited to, c-di-adenosine monophosphate (AMP), c-di-guanosine monophosphate (GMP), c-di-inosine monophosphate (IMP), c-AMP-GMP, c-AMP-IMP, and c-GMP-IMP, and analogs thereof including, but not limited to, phosphorothioate analogues, referred to herein as "thiophosphates". Phosphorothioates are a variant of normal nucleotides in which one of the nonbridging oxygens is replaced by a sulfur. The sulfurization of the internucleotide bond dramatically reduces the action of endo- and exonucleases, including 5' to 3' and 3' to 5' DNA Polymerase 1 exonuclease, nucleases 51 and P1, RNases, serum nucleases and snake venom phosphodiesterase. In addition, the potential for crossing the lipid bilayer increases. A phosphorothioate linkage in inherently chiral. The skilled artisan will recognize that the phosphates in this structure may each exist in R or S forms. Thus, Rp,Rp, Sp,Sp, and Rp,Sp forms are possible. In each case, preferred are substantially pure Rp,Rp and Rp,Sp diastereomers of these molecules. Examples of such CDN thiophosphate molecules include thiophosphate forms of Rp,Rp-c-di-adenosine monophosphate; Rp,Sp-c-di-adenosine monophosphate; Rp,Rp-c-di-guanosine monophosphate and Rp,Sp-c-di-guanosine monophosphate.

TLR agonists, such as TLR1, TLR2, TLR3, TLR4, TLR5, TLR6, TLR7, TLR8, TLR9, TLR10, TLR11, TLR12, and TLR13 agonists, are also immunostimulatory compounds. TLRs are a class of single transmembrane domain, non-catalytic, receptors that recognize structurally conserved molecules referred to as pathogen-associated molecular patterns (PAMPs). PAMPs are present on microbes and are distinguishable from host molecules. TLRs are present in all vertebrates. Thirteen TLRs (referred to as TLRs1-13, consecutively) have been identified in humans and mice. Humans comprise TLRs 1-10. Exemplary TLR agonists include pathogen associated molecular patterns (PAMPs), e.g., an infection-mimicking composition such as a bacterially-derived immunomodulator. TLR agonists include nucleic acid or lipid compositions [e.g., monophosphoryl lipid A (MPLA)].

A non-limiting example of a nucleic acid sequence that encodes human TLR1 is provided in GenBank Accession No. NM_003263.3 (GI:41350336) (SEQ ID NO: 267), incorporated herein by reference. An example of an amino acid sequence of human TLR1 is provided in GenBank Accession No. NP_003254.2 (GI:41350337) (SEQ ID NO: 268), incorporated herein by reference. Non-limiting examples of TLR1 agonists include triacyl lipopeptides.

A non-limiting example of a nucleic acid sequence that encodes human TLR2 is provided in GenBank Accession No. NM_003264.3 (GI:68160956) (SEQ ID NO: 269), incorporated herein by reference. An example of an amino acid sequence of human TLR2 is provided in GenBank Accession No. NP_003255.2 (GI:19718734) (SEQ ID NO: 270), incorporated herein by reference. Non-limiting examples of TLR2 agonists include bacterial peptidoglycans, glycolipids of bacterial peptidoglycans, lipopeptides of bacterial peptidoglycans, lipoproteins of bacterial peptidoglycans, lipoteichoic acid, heat shock protein 70, and zymosan.

A non-limiting example of a nucleic acid sequence that encodes human TLR3 is provided in GenBank Accession No. NM_003265.2 (GI:19718735) (SEQ ID NO: 271), incorporated herein by reference. An example of an amino acid sequence of human TLR3 is provided in GenBank Accession No. ABC86910.1 (GI:86161330) (SEQ ID NO: 272), incorporated herein by reference. Non-limiting examples of TLR3 agonists include double-stranded RNA, poly I:C, and poly (A:U).

A non-limiting example of a nucleic acid sequence that encodes human TLR4 is provided in GenBank Accession No. NM_138554.4 (GI:373432600) (SEQ ID NO: 273), incorporated herein by reference. An example of an amino acid sequence of human TLR4 is provided in GenBank Accession No. NP_612564.1 (GI:19924149) (SEQ ID NO: 274), incorporated herein by reference. Non-limiting examples of TLR4 agonists include lipopolysaccharide (LPS), monophosphoryl lipid A (MPLA), a heat shock protein, fibrinogen, heparin sulfate or a fragment thereof, hyaluronic acid or a fragment thereof, nickel, an opioid, α1-acid glycoprotein (AGP), RC-529, murine β-defensin 2, and complete Freund's adjuvant (CPA).

A non-limiting example of a nucleic acid sequence that encodes human TLR5 is provided in GenBank Accession No. NM_003268.5 (GI:281427130) (SEQ ID NO: 275), incorporated herein by reference. An example of an amino acid sequence of human TLR5 is provided in GenBank Accession No. NP_003259.2 (GI:16751843) (SEQ ID NO: 276), incorporated herein by reference. Non-limiting examples of TLR5 agonists include bacterial flagellin, and proflin from *Toxoplasma gondii*.

A non-limiting example of a nucleic acid sequence that encodes human TLR6 is provided in GenBank Accession No. NM_006068.4 (GI:318067953) (SEQ ID NO: 277), incorporated herein by reference. An example of an amino acid sequence of human TLR6 is provided in GenBank Accession No. NP_006059.2 (GI:20143971) (SEQ ID NO: 278), incorporated herein by reference. Non-limiting examples of TLR6 agonists include diacyl lipopeptides from *mycoplasma*.

A non-limiting example of a nucleic acid sequence of human TLR7 is provided in GenBank Accession No. NM_016562.3 (GI:67944638) (SEQ ID NO: 279), incorporated herein by reference. An example of an amino acid sequence of human TLR7 is provided in GenBank Accession No. NP_057646.1 (GI:7706093) (SEQ ID NO: 280), incorporated herein by reference. Non-limiting examples of TLR7 agonists include imidazoqinolines such as imidazoquinoline, guanosine analogues such as loxoribine, imiquimod, gardiquimod, resiquimod, bropirimine, and single-stranded RNA.

A non-limiting example of a nucleic acid sequence that encodes human TLR8 is provided in GenBank Accession No. NM_138636.4 (GI:257196253) (SEQ ID NO: 281), incorporated herein by reference. An example of an amino acid sequence of human TLR8 is provided in GenBank Accession No. NP_619542.1 (GI:20302168) (SEQ ID NO: 282), incorporated herein by reference. Non-limiting examples of TLR8 agonists include small synthetic compounds, single-stranded Viral RNA, and phagocytized bacterial RNA.

A non-limiting example of a nucleic acid sequence that encodes human TLR9, isoform A, is provided in NCBI Accession No. NM_017442 (SEQ ID NO: 283), incorporated herein by reference. An amino acid sequence of human TLR9, isoform A, is provided in NCBI Accession No. NP_059138 (SEQ ID NO: 284), incorporated herein by reference. Non-limiting examples of TLR9 oligonucleotides include CpG oligodeoxynucleotides.

A non-limiting example of a nucleic acid sequence that encodes human TLR10 is provided in GenBank Accession No. NM_030956.3 (GI:306140488) (SEQ ID NO: 285), incorporated herein by reference. An example of an amino acid sequence of human TLR10 is provided in GenBank Accession No. NP_112218.2 (GI:62865618) (SEQ ID NO: 286), incorporated herein by reference.

A non-limiting example of a nucleic acid sequence that encodes mouse TLR11 is provided in GenBank Accession No. NM_205819.3 (GI:408684412) (SEQ ID NO: 287), incorporated herein by reference. An example of an amino acid sequence of mouse TLR11 is provided in GenBank Accession No. NP_991388.2 (GI:408684413) (SEQ ID NO: 288), incorporated herein by reference. A non-limiting example of a TLR11 agonist includes proflin from *Toxoplasma gondii*.

A non-limiting example of a nucleic acid sequence that encodes mouse TLR12 is provided in GenBank Accession No. NM_205823.2 (GI:148539900) (SEQ ID NO: 289), incorporated herein by reference. An example of an amino acid sequence of mouse TLR12 is provided in GenBank Accession No. NP_991392.1 (GI:45430001) (SEQ ID NO: 290), incorporated herein by reference. A non-limiting example of a TLR12 agonist includes proflin from *Toxoplasma gondii*.

A non-limiting example of a nucleic acid sequence that encodes mouse TLR13 is provided in GenBank Accession No. NM_205820.1 (GI:45429998) (SEQ ID NO: 291), incorporated herein by reference. An example of an amino acid sequence of mouse TLR13 is provided in GenBank Accession No. NP_991389.1 (GI:45429999) (SEQ ID NO: 292), incorporated herein by reference. A non-limiting example of a TLR13 agonist includes the ribosomal RNA sequence "CGGAAAGACC." (SEQ ID NO: 34)

A representative list of TLR agonists (both synthetic and natural ligands), along with their corresponding receptors, is provided in Table 2 below.

TABLE 2

| Receptor | Ligand(s) | Cell types |
| --- | --- | --- |
| TLR 1 | multiple triacyl lipopeptides | monocytes/macrophages<br>a subset of dendritic cells<br>B lymphocytes |
| TLR 2 | multiple glycolipids<br>multiple lipopeptides<br>multiple lipoproteins<br>lipoteichoic acid<br>HSP70<br>zymosan (Beta-glucan)<br>Numerous others | monocytes/macrophages<br>neutrophils<br>Myeloid dendritic cells<br>Mast cells |
| TLR 3 | double-stranded RNA poly I:C | Dendritic cells<br>B lymphocytes |
| TLR 4 | lipopolysaccharide<br>several heat shock proteins<br>fibrinogen<br>heparan sulfate fragments<br>hyaluronic acid fragments<br>nickel<br>Various opioid drugs | monocytes/macrophages<br>neutrophils<br>Myeloid dendritic cells<br>Mast cells<br>B lymphocytes<br>Intestinal epithelium |

TABLE 2-continued

| Receptor | Ligand(s) | Cell types |
| --- | --- | --- |
| TLR 5 | Bacterial flagellin<br>profilin | monocyte/macrophages<br>a subset of dendritic cells<br>Intestinal epithelium |
| TLR 6 | multiple diacyl lipopeptides | monocytes/macrophages<br>Mast cells<br>B lymphocytes |
| TLR 7 | imidazoquinolines,<br>e.g., imiquimod (an<br>imidazoquinoline amine<br>analog to guanosine),<br>loxoribine (a guanosine<br>analogue), gardiquimod,<br>and resiquimod, bropirimine,<br>single-stranded RNA | monocytes/macrophages<br>Plasmacytoid dendritic cells<br>B lymphocytes |
| TLR 8 | small synthetic compounds;<br>single-stranded RNA | monocytes/macrophages<br>a subset of dendritic cells<br>Mast cells |
| TLR 9 | unmethylated CpG<br>Oligodeoxynucleotide DNA | monocytes/macrophages<br>Plasmacytoid dendritic cells<br>B lymphocytes |
| TLR 10 | unknown | |
| TLR 11 | Profilin | monocytes/macrophages<br>liver cells<br>kidney<br>urinary bladder epithelium |
| TLR 12 | Profilin | Neurons<br>plasmacytoid dendritic cells<br>conventional dendritic cells<br>macrophages |
| TLR 13 | bacterial ribosomal RNA<br>sequence "CGGAAAGACC"<br>(SEQ ID NO: 34) | monocytes/macrophages<br>conventional dendritic cells |

In various embodiments, the TLR ligand comprises a CpG oligonucleotide or a poly I:C poly nucleotide. Poly I:C is a mismatched double-stranded RNA with one strand being a polymer of inosinic acid, the other a polymer of cytidylic acid. Polyinosinic:polycytidylic acid (abbreviated poly I:C) is also an immunostimulant or adjuvant. In some embodiments, the polyI:C polynucleotide has a length of at least about, 0.1, 0.2, 0.3, 0.4, 0.5, 0.6, 0.7, 0.8, 0.9, 1, 1.2, 1.5, 2, 3, 4, 5, 6, 7, 8, 9, 1, 0.1-1, 0.2-1, 1-1.5, 0.5-1.5, 0.5-2, 1-5, 1.5-5, or 1.5-8 kilobases. In certain embodiments, the polyI:C polynucleotide has a length of about 0.1, 0.2, 0.3, 0.4, 0.5, 0.6, 0.7, 0.8, 0.9, 1, 1.2, 1.5, 2, 3, 4, 5, 6, 7, 8, 9, 1, 0.1-1, 0.2-1, 1-1.5, 0.5-1.5, 0.5-2, 1-5, 1.5-5, 1.5-8 or more kilobases. Optionally, it is used in the form of its sodium salt. Poly I:C interacts with TLR3 (i.e., poly I:C is a TLR 3 ligand), which is expressed in the membrane of B-cells, macrophages and dendritic cells. Optionally, CpG or poly I:C are condensed. For example, the adjuvant is condensed and then linked to an antigen; alternatively the adjuvant is linked to the antigen and then the conjugate is condensed. Exemplary condensing agents include poly-L-lysine (PLL), polyethylenimine (PEI), hexamine cobalt chloride, and TAT 47-57 peptide (YGRKKRRQRRR SEQ ID NO: 293).

Immunostimulatory compounds include imiquimod, CRX-527, and OM-174.

Imiquimod has the following structure:

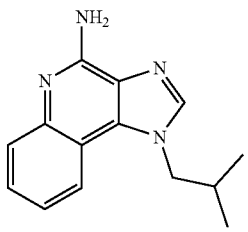 [SMILES: CC(C)Cn1cnc2c(N)nc3ccccc3c21]

This compound is described in U.S. Pat. No. 7,323,568 issued Jan. 29, 2008; U.S. Pat. No. 8,642,616 issued Feb. 4, 2004; Walter et al. (2013) Nat Commun 4: 1560; Bilu and Sauder (2003) Br. J. Dermatol. 149 Suppl 66: 5-8; and Miller et al. (1999) Int J Immunopharmacol 21 (1): 1-14, the entire contents of each of which are incorporated herein by reference.

Additional non-limiting examples of TLR agonists include CRX-527 and OM-174.

CRX-527 is described in Lembo et al., J Immunol. 2008 Jun. 1; 180(11):7574-81; and Hennessy et al., Nature Reviews Drug Discovery 9, 293-307 (April 2010), the entire content of which is hereby incorporated herein by reference. CRX-527 has the chemical name (2S)-2-[[(3R)-3-decanoyloxytetradecanoyl]amino]-3-[(2R,3R,4R,5S,6R)-3-[[(3R)-3-decanoyloxytetradecanoyl]amino]-4-[(3R)-3-decanoyloxytetradecanoyl]oxy-6-(hydroxymethyl)-5-phosphonooxyoxan-2-yl]oxypropanoic acid.

OM-174 has the chemical name [(3R)-1-[[(2R,3R,4R,5S,6R)-2-[[(2R,3S,4R,5R,6R)-3,4-dihydroxy-5-[[(3R)-3-hydroxytetradecanoyl]amino]-6-phosphonooxyoxan-2-yl]methoxy]-4-hydroxy-6-(hydroxymethyl)-5-phosphonooxyoxan-3-yl]amino]-1-oxotetradecan-3-yl]dodecanoate. OM-174 is described in Onier et al., Int J Cancer. 1999 May 31; 81(5):755-60; Isambert et al., BMC Cancer (2013) 13:172; and Hennessy et al., Nature Reviews Drug Discovery 9, 293-307 (April 2010), the entire content of each of which is hereby incorporated herein by reference.

Cytosine-Guanosine (CpG) Oligonucleotide (CpG-ODN) Sequences

CpG oligodeoxynucleotides (or CpG ODN) are short single-stranded synthetic deoxyribonucleic acid (DNA) molecules that contain a cytosine triphosphate deoxynucleotide ("C") followed by a guanine triphosphate deoxynucleotide ("G"). The "p" refers to the phosphodiester link between consecutive nucleotides, although some ODN have a modified phosphorothioate (PS) backbone instead. In some embodiments, the CpG oligodeoxynucleotide is at least about 15, 16, 17, 18, 19, 20, 25, 26, 27, 28, 29, 30, 15-30, 20-30, 20-25, or more nucleotides long.

CpG sites play a pivotal role in DNA methylation, which is one of several endogenous mechanisms cells use to silence gene expression. Methylation of CpG sites within promoter elements can lead to gene silencing. In the case of cancer, it is known that tumor suppressor genes are often silenced while oncogenes, or cancer-inducing genes, are expressed. CpG sites in the promoter regions of tumor suppressor genes (which prevent cancer formation) have been shown to be methylated while CpG sites in the promoter regions of oncogenes are hypomethylated or unmethylated in certain cancers. The TLR-9 receptor binds unmethylated CpG sites in DNA.

Various compositions described herein comprise CpG oligonucleotides. CpG oligonucleotides are isolated from endogenous sources or synthesized in vivo or in vitro. Exemplary sources of endogenous CpG oligonucleotides include, but are not limited to, microorganisms, bacteria, fungi, protozoa, viruses, molds, or parasites. Alternatively, endogenous CpG oligonucleotides are isolated from mammalian benign or malignant neoplastic tumors. Synthetic CpG oligonucleotides are synthesized in vivo following transfection or transformation of template DNA into a host organism. Alternatively, Synthetic CpG oligonucleotides are synthesized in vitro by polymerase chain reaction (PCR) or other art-recognized methods (Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

CpG oligonucleotides are presented for cellular uptake by dendritic cells. For example, naked CpG oligonucleotides are used. The term "naked" is used to describe an isolated endogenous or synthetic polynucleotide (or oligonucleotide) that is free of additional substituents. In another embodiment, CpG oligonucleotides are bound to one or more compounds to increase the efficiency of cellular uptake. Alternatively, or in addition, CpG oligonucleotides are bound to one or more compounds to increase the stability of the oligonucleotide within the scaffold and/or dendritic cell. CpG oligonucleotides are optionally condensed prior to cellular uptake. For example, CpG oligonucleotides may be condensed using polyethylimine (PEI), a cationic polymer that increases the efficiency of cellular uptake into dendritic cells to yield cationic nanoparticles. CpG oligonucleotides may also be condensed using other polycationic reagents to yield cationic nanoparticles. Additional non-limiting examples of polycationic reagents that may be used include poly-L-lysine (PLL) and polyamidoamine (PAMAM) dendrimers.

Vector systems that promote CpG internalization into DCs to enhance delivery and its localization to TLR9 have been developed. The amine-rich polycation, polyethylimine (PEI) has been extensively used to condense plasmid DNA, via association with DNA phosphate groups, resulting in small, positively charge condensates facilitating cell membrane association and DNA uptake into cells (Godbey W. T., Wu K. K., and Mikos, A. G. J. of Biomed Mater Res, 1999, 45, 268-275; Godbey W. T., Wu K. K., and Mikos, A. G. Proc Natl Acad Sci USA. 96(9), 5177-81. (1999); each herein incorporated by reference). An exemplary method for condensing CpG-ODN is described in U.S. Patent Application No. US 20130202707 A1 published Aug. 8, 2013, the entire content of which is incorporated herein by reference. Consequently, PEI has been utilized as a non-viral vector to enhance gene transfection and to fabricate PEI-DNA loaded PLG matrices that promoted long-term gene expression in host cells in situ (Huang Y C, Riddle F, Rice K G, and Mooney D J. Hum Gene Ther. 5, 609-17. (2005), herein incorporated by reference).

CpG oligonucleotides can be divided into multiple classes. For example, exemplary CpG-ODNs encompassed by compositions, methods and devices of the present invention are stimulatory, neutral, or suppressive. The term "stimulatory" describes a class of CpG-ODN sequences that activate TLR9. The term "neutral" describes a class of CpG-ODN sequences that do not activate TLR9. The term "suppressive" describes a class of CpG-ODN sequences that inhibit TLR9. The term "activate TLR9" describes a process by which TLR9 initiates intracellular signaling.

Stimulatory CpG-ODNs can further be divided into three types A, B and C, which differ in their immune-stimulatory activities. Type A stimulatory CpG ODNs are characterized by a phosphodiester central CpG-containing palindromic motif and a phosphorothioate 3' poly-G string. Following activation of TLR9, these CpG ODNs induce high IFN-α production from plasmacytoid dendritic cells (pDC). Type A CpG ODNs weakly stimulate TLR9-dependent NF-κB signaling.

Type B stimulatory CpG ODNs contain a full phosphorothioate backbone with one or more CpG dinucleotides. Following TLR9 activation, these CpG-ODNs strongly activate B cells. In contrast to Type A CpG-ODNs, Type B CpG-ODNS weakly stimulate IFN-α secretion.

Type C stimulatory CpG ODNs comprise features of Types A and B. Type C CpG-ODNs contain a complete phosphorothioate backbone and a CpG containing palindromic motif. Similar to Type A CpG ODNs, Type C CpG ODNs induce strong IFN-α production from pDC Similar to Type B CpG ODNs, Type C CpG ODNs induce strong B cell stimulation.

Exemplary stimulatory CpG ODNs comprise, but are not limited to, ODN 1585 (5'-ggGGTCAACGTTGAgggggg-3') (SEQ ID NO: 21), ODN 1668 (5'-tccatgacgttcctgatgct-3') (SEQ ID NO: 22), ODN 1826 (5'-tccatgacgttcctgacgtt-3') (SEQ ID NO: 23), ODN 2006 (5'-tcgtcgttttgtcgttttgtcgtt-3') (SEQ ID NO: 24), ODN 2006-G5 (5'-TCGTCGTTTTGTCGTTTTGTCGTTGGGGG-3') (SEQ ID NO: 25), ODN 2216 (5'-ggGGGACGA:TCGTCgggggg-3') (SEQ ID NO: 26), ODN 2336 (5'-gggGACGAC:GTCGTGgggggg-3') (SEQ ID NO: 27), ODN 2395 (5'-tcgtcgttttcggcgc:gcgccg-3') (SEQ ID NO: 28), ODN M362 (5'-tcgtcgtcgttc:gaacgacgttgat-3') (SEQ ID NO: 29) (all InvivoGen). The present invention also encompasses any humanized version of the preceding CpG ODNs. In one preferred embodiment, compositions, methods, and devices of the present invention comprise ODN 1826 (the sequence of which from 5' to 3' is tccatgacgttcctgacgtt, wherein CpG elements are underlined, SEQ ID NO: 23).

Neutral, or control, CpG ODNs that do not stimulate TLR9 are encompassed by the present invention. These ODNs comprise the same sequence as their stimulatory counterparts but contain GpC dinucleotides in place of CpG dinucleotides.

Exemplary neutral, or control, CpG ODNs encompassed by the present invention comprise, but are not limited to, ODN 1585 control, ODN 1668 control, ODN 1826 control, ODN 2006 control, ODN 2216 control, ODN 2336 control, ODN 2395 control, ODN M362 control (all InvivoGen). The present invention also encompasses any humanized version of the preceding CpG ODNs.

Immunostimulatory Antibodies

Additional non-limiting immunostimulatory compounds include immunostimulatory antibodies. Aspects of the present subject matter relate to the use of immunostimulatory antibodies to stimulate or active cells of the immune system. Providing stimulation to immune cells such as T cells and dendritic cells within the tumor microenvironment improves the anti-tumor immune response. In some embodiments, stimulation is provided using an immunostimulatory antibody that binds and agonizes a surface receptor on T cells or dendritic cells. In certain embodiments, T cell function is enhanced using one or more antibodies targeted to one or more co-stimulatory cell surface molecules, such as 4-1BB (CD137) and OX40 (CD134), leading to enhanced T cell proliferation and survival. In some embodiments, dendritic cell activation is facilitated with one or more agonistic CD40 antibodies. In general due to their immunostimulatory nature, these antibodies can lead to off target immune-related toxicities when applied systemically. Application of these antibodies at the site of action using a device or scaffold of the present subject matter circumvents this issue by focusing the dose at the desired site of action. Additionally, the clinical activity of immunostimulatory antibodies is improved by concentrating the dose thereof at the tumor site using a device or scaffold as disclosed herein.

CD137 Antibodies

CD137 is a surface molecule found on activated T cells that provides costimulation to these cells. Stimulation of CD137 results in increased T cell proliferation and protects T cells from activation induced cell death. CD137 has been shown in several preclinical models to lead to anti-tumor activity. BMS-66513 (urelumab), one non-limiting example of an anti-CD137 antibody, has been tested in several clinical trials and shown to lead to partial remissions in disease, but with liver toxicity, among other auto-immune sequalae (Ascierto et al., 2010, Seminars in Oncology). PF-05082566 is another example of an CD137 antibody in clinical development. PF-05082566 is described in Fisher et al. (2012) Cancer Immunol Immunother. 61(10):1721-33, the entire content of which is incorporated herein by reference. As indicated above, a variety of anti-CD137 antibodies, including those that are not be suitable for systemic delivery, may be used in devices and scaffolds of the present subject matter.

An exemplary non-limiting example of an amino acid sequence for CD137 is publically available as GenBank No: AAH06196.1 (SEQ ID NO: 35).

CD134 Antibodies

CD134 is expressed primarily on activated CD4+ and CD8+ T cells and provides co-stimulation when engaged. Engagement of CD134 with a ligand such as and anti-CD134 antibody promotes survival and expansion of T cells. Non-limiting examples of CD134 antibodies include 9B12 and MEDI6469. 9B12 is described in Curti et al. (2013) Cancer Res 73: 7189, the entire content of which is incorporated by reference. MEDI6469 is described in Leidner et al. Journal of Clinical Oncology, 2015 ASCO Annual Meeting (May 29-Jun. 2, 2015). Vol 33, No 15_suppl (May 20 Supplement), 2015: TPS6083, the entire content of which is incorporated herein by reference.

An exemplary non-limiting example of an amino acid sequence for CD134 is publically available as GenBank No: AAI05071.1 (SEQ ID NO: 36).

CD40 Antibodies

CD40 is a surface receptor found on antigen-presenting cells such as dendritic cells. Engagement of CD40 results in activation of antigen-presenting cells, a process important for their function. This activation of dendritic cells leads to upregulation of co-stimulatory receptors and production of pro-inflammatory cytokines, which lead to an enhanced ability to prime T cells. Agonistic anti-CD40 antibodies have shown limited activity in the clinic (Vonderheide and Glennie, 2013, Clinical Cancer Research). Non-limiting examples of CD40 antibodies include HCD122 (Lucatumumab), CP-870,893, SGN-40 huS2C6 (Dacetuzumab), and Chi Lob 7/4. These antibodies are in clinical development. As explained above, even antibodies that are not suitable for systemic use may be utilized in embodiments of the present subject matter with few or no adverse side effects. Lucatumumab is described in Fanale et al. (2014) Br J Haematol. 164(2):258-65, the entire content of which is incorporated herein by reference. CP-870,893 is described in Glaude et al. (2011) Cancer Immunol. Immunother. 60, 1009-1017 (2011), the entire content of which is incorporated herein by reference. Dacetuzumab is described in de Vos et al. (2014) Journal of Hematology & Oncology 20147:44, the entire content of which is incorporated herein by reference. Chi Lob 7/4 is described in Vonderheide and Glennie (2013) Clin Cancer Res. 19(5): 1035-1043., the entire content of which is incorporated herein by reference.

An exemplary non-limiting example of an amino acid sequence for CD40 is publically available as GenBank No: AAH12419.1 (SEQ ID NO: 37).

Inhibitors and Immune Checkpoint Blockade

Various implementations of the present subject matter relate to the administration of an inhibitor of T cell or dendritic cell suppression and scaffolds or devices comprising an inhibitor of T cell or dendritic cell suppression. Non-limiting examples of such inhibitors include TGF-β pathway inhibitors, STAT3 pathway inhibitors, and IDO pathway inhibitors, as well as immune checkpoint inhibitors such as PD-1 pathway inhibitors, CTLA-4 pathway inhibitors, LAG-3 pathway inhibitors, CD276 (also known as B7-H3) pathway inhibitors, and TIM3 pathway inhibitors.

Many inhibitory pathways exist within tumors that suppress tumor antigen presentation and the anti-tumor immune response. For example, TGF-β dampens tumor immunosurveillance and polarizes innate immune cells towards an immature differentiation status that prevents optimal anti-tumor immunity. Additionally, the STAT3 pathway promotes the production of immune inhibitory cytokines within the tumor, dampens anti-tumor T-helper 1-mediated immunity, and inhibits dendritic cell maturation. Small molecule inhibitors of these pathways and other immunosuppressive pathways described above are delivered to the tumor using the cryogel or hydrogel devices. Other approaches to alter the tumor microenvironment may also be utilized, e.g., antibodies against immune checkpoint proteins.

Cytotoxic T-lymphocyte associated antigen 4 (CTLA-4) is an immune checkpoint protein that down-regulates pathways of T-cell activation (Fong et al., Cancer Res. 69(2): 609-615, 2009; Weber Cancer Immunol. Immunother, 58:823-830, 2009). Blockade of CTLA-4 has been shown to augment T-cell activation and proliferation. Inhibitors of CTLA-4 include anti-CTLA-4 antibodies. Anti-CTLA-4 antibodies bind to CTLA-4 and block the interaction of CTLA-4 with its ligands CD80/CD86 expressed on antigen presenting cells and thereby blocking the negative down regulation of the immune responses elicited by the interaction of these molecules. Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CDLA-4 antibody is tremelimumab, (ticilimumab, CP-675,206). In one embodiment, the anti-CTLA-4 antibody is ipilimumab (also known as 10D1, MDX-D010) a fully human monoclonal IgG antibody that binds to CTLA-4. Ipilimumab is marketed under the name Yervoy™ and has been approved for the treatment of unresectable or metastatic melanoma.

Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207: 2187-94).

A ligand-receptor interaction that has been explored as a target for cancer treatment is the interaction between the transmembrane programmed cell death 1 protein (PDCD1, PD-1; also known as CD279) and its ligand, PD-1 ligand 1 (PD-L1, CD274). In normal physiology PD-L1 on the surface of a cell binds to PD1 on the surface of an immune cell, which inhibits the activity of the immune cell. Upregulation of PD-L1 on the cancer cell surface may allow them to evade the host immune system by inhibiting T cells that might otherwise attack the tumor cell. Antibodies that bind to either PD-1 or PD-L1 and therefore block the interaction may allow the T-cells to attack the tumor. An IgG4 PD1 antibody called Nivolumab has been described (Pardon, D M, 2012, Nature reviews. Cancer 12 (4): 252-64). Many of the immune checkpoints are initiated by ligand-receptor interactions; thus, hey can be readily blocked by antibodies or modulated by recombinant forms of ligands or receptors. Other examples of antibody-based blockers include Cytotoxic T-lymphocyte-associated antigen 4 (CTLA4)-specific antibodies.

In various embodiments, the antibody is a polyclonal antibody, a monoclonal antibody, a chimeric antibody, a humanized antibody, or a human antibody.

In some embodiments, the anti-PD-1 antibody is nivolumab, pembrolizumab, or pidilizumab. Nivolumab is described in Johnson et al. (2015) Ther Adv Med Oncol 7 (2): 97-106; and Sundar R et al. (2015) Ther Adv Med Oncol 7 (2): 85-96, the entire content of each of which is incorporated herein by reference. Pembrolizumab is described in Hamid et al. (2013) New England Journal of Medicine 369 (2): 134-44, the entire content of which is incorporated herein by reference. Pidilizumab is described in Westin et al. (2014) "Safety and Activity of PD1 Blockade by Pidilizumab in Combination with Rituximab in Patients with Relapsed Follicular Lymphoma: a Single Group, Open-label, Phase 2 Trial" doi:10.1016/51470-2045(13)70551-5, the entire content of which is incorporated herein by reference.

In certain embodiments, the anti-PD-L1 antibody is BMS-936559 or MPDL3280A. BMS-936559 is described in Brahmer J R et al. (2012) N Engl J Med. 2012; 366:2455, the entire content of which is incorporated herein by reference. MPDL3280A is described in Herbst R S et al. (2013) J Clin Oncol. 31 (suppl; abstr 3000); Soria J C et al. (2013) European Cancer Congress Amsterdam (abstr 3408); Hamid 0 et al. (2013) J Clin Onco 131 (suppl; abstr 9010); and Kohrt H et al. (2013) J Immunother Cancer. 2013; 1 (suppl 1):012, the entire content of each of which is incorporated herein by reference.

Additional anti-PD1 and anti-PD-L1 antibodies are described in U.S. Pat. No. 8,952,136 issued Feb. 10, 2015, the entire content of which is incorporated herein by reference.

In various embodiments, the anti-CTLA-4 antibody is ipilimumab. Ipilimumab is described in "Yervoy (ipilimumab) (package insert)" Princeton, NJ: Bristol-Myers Squibb Company; December 2013. Retrieved 29 Oct. 2014, the entire content of which is incorporated herein by reference.

Granulocyte Macrophage Colony Stimulating Factor (GM-CSF)

Granulocyte-macrophage colony-stimulating factor (GM-CSF) is a protein secreted by macrophages, T cells, mast cells, endothelial cells and fibroblasts. Specifically, GM-CSF is a cytokine that functions as a white blood cell growth factor. GM-CSF stimulates stem cells to produce granulocytes and monocytes. Monocytes exit the blood stream, migrate into tissue, and subsequently mature into macrophages.

Various scaffold devices described herein comprise and release GM-CSF polypeptides to attract host DCs to the device. Contemplated GM-CSF polypeptides are isolated from endogenous sources or synthesized in vivo or in vitro. Endogenous GM-CSF polypeptides are isolated from healthy human tissue. Synthetic GM-CSF polypeptides are synthesized in vivo following transfection or transformation of template DNA into a host organism or cell, e.g., a mammal or cultured human cell line. Alternatively, synthetic GM-CSF polypeptides are synthesized in vitro by polymerase chain reaction (PCR) or other art-recognized methods Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

GM-CSF polypeptides are modified to increase protein stability in vivo. Alternatively, GM-CSF polypeptides are engineered to be more or less immunogenic. Endogenous mature human GM-CSF polypeptides are glycosylated, reportedly, at amino acid residues 23 (leucine), 27 (asparagine), and 39 (glutamic acid) (see U.S. Pat. No. 5,073,627). GM-CSF polypeptides of the present invention are modified at one or more of these amino acid residues with respect to glycosylation state.

GM-CSF polypeptides are recombinant. Alternatively GM-CSF polypeptides are humanized derivatives of mammalian GM-CSF polypeptides. Exemplary mammalian species from which GM-CSF polypeptides are derived include, but are not limited to, mouse, rat, hamster, guinea pig, ferret, cat, dog, monkey, or primate. In a preferred embodiment, GM-CSF is a recombinant human protein (PeproTech, Catalog #300-03). Alternatively, GM-CSF is a recombinant murine (mouse) protein (PeproTech, Catalog #315-03). Finally, GM-CSF is a humanized derivative of a recombinant mouse protein.

Human Recombinant GM-CSF (PeproTech, Catalog #300-03) is encoded by the following polypeptide sequence (SEQ ID NO: 30):

```
MAPARSPSPS TQPWEHVNAI QEARRLLNLS RDTAAEMNET

VEVISEMFDL QEPTCLQTRL ELYKQGLRGS LTKLKGPLTM

MASHYKQHCP PTPETSCATQ IITFESFKEN LKDFLLVIPF

DCWEPVQE
```

Murine Recombinant GM-CSF (PeproTech, Catalog #315-03) is encoded by the following polypeptide sequence (SEQ ID NO: 31):

```
MAPTRSPITV TRPWKHVEAI KEALNLLDDM PVTLNEEVEV

VSNEFSFKKL TCVQTRLKIF EQGLRGNFTK LKGALNMTAS

YYQTYCPPTP ETDCETQVTT YADFIDSLKT FLTDIPFECK KPVQK
```

Human Endogenous GM-CSF is encoded by the following mRNA sequence (NCBI Accession No. NM_000758 and SEQ ID NO: 32):

```
  1 acacagagag aaaggctaaa gttctctgga ggatgtggct gcagagcctg ctgctcttgg
 61 gcactgtggc ctgcagcatc tctgcacccg cccgctcgcc cagccccagc acgcagccct
121 gggagcatgt gaatgccatc caggaggccc ggcgtctcct gaacctgagt agagacactg
181 ctgctgagat gaatgaaaca gtagaagtca tctcagaaat gttttgacctc caggagccga
241 cctgcctaca gacccgcctg gagctgtaca agcagggcct gcggggcagc ctcaccaagc
301 tcaagggccc cttgaccatg atggccagcc actacaagca gcactgccct ccaaccccgg
361 aaacttcctg tgcaacccag attatcacct ttgaaagttt caaagagaac ctgaaggact
421 ttctgcttgt catcccttt gactgctggg agccagtcca ggagtgagac cggccagatg
481 aggctggcca agccggggag ctgctctctc atgaaacaag agctagaaac tcaggatggt
541 catcttggag ggaccaaggg gtgggccaca gccatggtgg gagtggcctg gacctgccct
601 gggccacact gaccctgata caggcatggc agaagaatgg gaatattta tactgacaga
661 aatcagtaat atttatatat ttatattttt aaaatattta tttatttatt tatttaagtt
721 catattccat atttattcaa gatgttttac cgtaataatt attattaaaa atatgcttct
781 a
```

Human Endogenous GM-CSF is encoded by the following amino acid sequence (NCBI Accession No. NP_000749.2 and SEQ ID NO: 33):

MWLQSLLLLGTVACSISAPARSPSPSTQPWEHVNAIQEARRLLNLSRDTA

AEMNETVEVISEMFDLQEPTCLQTRLELYKQGLRGSLTKLKGPLTMMASH

YKQHCPPTPETSCATQIITFESFKENLKDFLLVIPFDCWEPVQE

Cancer Antigens

Compositions, methods, and devices of the present invention comprise cancer antigens with means to vaccinate and/or provide protective immunity to a subject to whom such a device was administered. In some embodiments, a cancer/tumor antigen is from a subject who is administered a device provided herein. In certain embodiments, a cancer/tumor antigen is from a different subject. In various embodiments, a tumor antigen is present in a tumor cell lysate. For example, the tumor cell lysate may comprise one or more lysed cells from a biopsy. In some embodiments, the tumor antigen is present on an attenuated live cancer cell. For example, the attenuated live cancer cell may be an irradiated cancer cell.

Exemplary cancer antigens encompassed by the compositions, methods, and devices of the present invention include, but are not limited to, tumor lysates extracted from biopsies, irradiated tumor cells, MAGE series of antigens (MAGE-1 is an example), MART-1/melana, tyrosinase, ganglioside, gp100, GD-2, 0-acetylated GD-3, GM-2, Mucin 1, Sos1, protein kinase C-binding protein, reverse transcriptase protein, AKAP protein, VRK1, KIAA1735, T7-1, T11-3, T11-9, *Homo sapiens* telomerase ferment (hTRT), Cytokeratin-19 (CYFRA21-1), squamous cell carcinoma antigen 1 (SCCA-1), Protein T4-A, squamous cell carcinoma antigen 2 (SCCA-2), ovarian carcinoma antigen CA125 (1A1-3B) (KIAA0049), CTCL tumor antigen se1-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, prostate-specific membrane antigen, 5T4 oncofetal trophoblast glycoprotein, Orf73 Kaposi's sarcoma-associated herpesvirus, MAGE-C1 (cancer/testis antigen CT7), MAGE-B1 Antigen (MAGE-XP Antigen), DAM10, MAGE-B2 Antigen (DAM6), MAGE-2 Antigen, MAGE-4a antigen, MAGE-4b antigen, colon cancer antigen NY-CO-45, lung cancer antigen NY-LU-12 variant A, cancer associated surface antigen, adenocarcinoma antigen ART1, paraneoplastic associated brain-testis-cancer antigen, onconeuronal antigen MA2, paraneoplastic neuronal antigen, neuro-oncological ventral antigen 2 (NOVA2), hepatocellular carcinoma antigen gene 520, tumor-associated antigen CO-029, tumor-associated antigen MAGE-X2, synovial sarcoma, X breakpoint 2, squamous cell carcinoma antigen recognized by T cell, seriologically defined colon cancer antigen 1, seriologically defined breast cancer antigen NY-BR-15, seriologically defined breast cancer antigen NY-BR-16, Wilms' Tumor protein (WT-1 peptide), Chromogranin A; parathyroid secretory protein 1, DUPAN-2, CA 19-9, CA 72-4, CA 195, or carcinoembryonic antigen (CEA).

Microbial Antigens

In some embodiments, the antigen is from a microbe such as a bacterium, virus, protozoan, archaean, or fungus. Various embodiments relate to vaccinating against or treating a bacterial, viral, or fungal infection. In various embodiments, a delivery vehicle comprising an antigen from a pathogen. For example, a pathogen includes but is not limited to a fungus, a bacterium (e.g., *Staphylococcus* species, *Staphylococcus aureus*, *Streptococcus* species, *Streptococcus pyogenes*, *Pseudomonas aeruginosa*, *Burkholderia cenocepacia*, *Mycobacterium* species, *Mycobacterium tuberculosis*, *Mycobacterium avium*, *Salmonella* species, *Salmonella typhi*, *Salmonella typhimurium*, *Neisseria* species, *Brucella* species, *Bordetella* species, *Borrelia* species, *Campylobacter* species, *Chlamydia* species, *Chlamydophila* species, *Clostrium* species, *Clostrium botulinum*, *Clostridium difficile*, *Clostridium tetani*, *Helicobacter* species, *Helicobacter pylori*, *Mycoplasma pneumonia*, *Corynebacterium* species, *Neisseria gonorrhoeae*, *Neisseria meningitidis*, *Enterococcus* species, *Escherichia* species, *Escherichia coli*, *Listeria* species, *Francisella* species, *Vibrio* species, *Vibrio cholera*, *Legionella* species, or *Yersinia pestis*), a virus (e.g., adenovirus, Epstein-Barr virus, Hepatitis A virus, Hepatitis B virus, Hepatitis C virus, Herpes simplex virus type 1, 2, or 8, human immunodeficiency virus, influenza virus, measles, Mumps, human papillomavirus, poliovirus, rabies, respiratory syncytial virus, rubella virus, or varicella-zoster virus), a parasite or a protozoa (e.g., *Entamoeba histolytica*, *Plasmodium*, *Giardia lamblia*, *Trypanosoma brucei*, or a parasitic protozoa such as malaria-causing *Plasmodium*). For example, a pathogen antigen is derived from a pathogen cell or particle described herein.

Antibodies

The term "antibody" is used in the broadest sense and specifically covers monoclonal antibodies (including full length monoclonal antibodies), polyclonal antibodies, multispecific antibodies (e.g., bispecific antibodies), monovalent antibodies, multivalent antibodies, and antibody fragments so long as they exhibit the desired biological activity (e.g., Fab and/or single-armed antibodies).

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F (ab')₂; diabodies; linear antibodies; single-chain antibody molecules (e.g., scFv); and multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three hypervariable regions (HVRs) of each variable domain interact to define an antigen binding site on the surface of the VH-VL dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

A "Fab" fragment contains a variable and constant domain of the light chain and a variable domain and the first constant domain (CHI) of the heavy chain. F(ab') 2 antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the VH and VL domains of an antibody, wherein these domains are present in a single polypeptide chain Generally the Fv polypeptide further comprises a polypeptide linker between the VH and L domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-31S (1994), the entire content of which is incorporated herein by reference.

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, BP 404,097; WO 93/11161; and Hollinger et al., Proc. Natl. Acad. Sci. USA, 90:6444-6448 (1993), the entire content of which is incorporated herein by reference.

The expression "linear antibodies" refers to the antibodies described in Zapata et al., Protein Eng., 8 (10): 1057-1062 (1995), the entire content of which is incorporated herein by reference. Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

RNA Interference

As used herein, "RNA interference inducing compound" or "RNAi compound" refers to a compound capable of inducing RNA interference or "RNAi" of protein expression, depending on the context. RNAi involves mRNA degradation, but many of the biochemical mechanisms underlying this interference are unknown. The use of RNAi has been described in Fire et al., 1998, Carthew et al., 2001, and Elbashir et al., 2001, the contents of which are incorporated herein by reference.

Isolated RNA molecules can mediate RNAi. That is, the isolated RNA molecules of the present invention mediate degradation or block expression of mRNA that is the transcriptional product of the gene, which is also referred to as a target gene. For convenience, such mRNA may also be referred to herein as mRNA to be degraded. The terms RNA, RNA molecule (s), RNA segment(s) and RNA fragment(s) may be used interchangeably to refer to RNA that mediates RNA interference. These terms include double-stranded RNA, small interfering RNA (siRNA), hairpin RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise nonstandard nucleotides, including non-naturally occurring nucleotides or deoxyribonucleotides. Collectively, all such altered RNAi molecules are referred to as analogs or analogs of naturally-occurring RNA. RNA of the present invention need only be sufficiently similar to natural RNA that it has the ability to mediate RNAi.

As used herein the phrase "mediate RNAi" refers to and indicates the ability to distinguish which mRNA molecules are to be afflicted with the RNAi machinery or process. RNA that mediates RNAi interacts with the RNAi machinery such that it directs the machinery to degrade particular mRNAs or to otherwise reduce the expression of the target protein. In one embodiment, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or blocking expression of the target mRNA.

As noted above, the RNA molecules of the present invention in general comprise an RNA portion and some additional portion, for example a deoxyribonucleotide portion. In some embodiments, an RNAi molecules comprises about 10, 11, 12, 13, 14, 15, 16, 17, 18, 19, 20, 21, 22, or 23 nucleotides, about 16 to 29 nucleotides, about 18 to 23 nucleotides, or about 21-23 nucleotides. In various embodiments, a device or scaffold comprises one or more RNAi molecules that mediate RNAi of one or more genes that inhibit T cell or dendritic cell suppression. In some embodiments, the target gene is an immune checkpoint gene. In some embodiments, the target gene is an immune suppression gene. In certain embodiments, the target gene encodes a TGF-β, STAT3, IDO, PD-1, PD-1 ligand 1, CTLA-4, LAG-3, or TIM3 protein. Non-limiting examples of nucleotide sequences for each of these targets are as follows: TGF-β (GenBank No: M60316.1, SEQ ID NO: 13); STAT3 (NCBI Reference Sequence No: NM_139276.2, SEQ ID NO: 14); IDO1 (NCBI Reference Sequence No: NM_002164.5, SEQ ID NO: 15); PD-1 (NCBI Reference Sequence No: NM_005018.2, SEQ ID NO: 16); PD-L1 (NCBI Reference Sequence No: NM_014143.3, SEQ ID NO: 17); CTLA-4 (NCBI Reference Sequence No: NM_001037631.2, SEQ ID NO: 18); LAG-3 (GenBank No: X51985.3, SEQ ID NO: 19); and TIM3 (GenBank No: AF450242.1, SEQ ID NO: 20). These sequences are not limiting, as additional variants and isoforms of each protein may be targeted.

In various embodiments, an RNAi molecule may be present in a device or scaffold with a transfection agent. For example, the RNAi molecule may be condensed with polyethylimine (PEI), poly-L-lysine (PLL), or a polyamidoamine (PAMAM) dendrimer. See, e.g., Huang et al. (2005) Human Gene Therapy 16:609-617. Additional non-limiting examples of transfection agents include liposomes (e.g., lipofectamine)

Dendritic Cells

Dendritic cells (DCs) are immune cells within the mammalian immune system and are derived from hematopoietic bone marrow progenitor cells. More specifically, dendritic cells can be categorized into lymphoid (or plasmacytoid) dendritic cell (pDC) and myeloid dendritic cell (mDC) subdivisions having arisen from a lymphoid (or plasmacytoid) or myeloid precursor cell, respectively. From the progenitor cell, regardless of the progenitor cell type, an immature dendritic cell is born. Immature dendritic cells are characterized by high endocytic activity and low T-cell activation potential. Thus, immature dendritic cells constitutively sample their immediate surrounding environment for pathogens. Exemplary pathogens include, but are not limited to, a virus or a bacteria. Sampling is accomplished by pattern recognition receptors (PRRs) such as the toll-like receptors (TLRs). Dendritic cells activate and mature once a pathogen is recognized by a pattern recognition receptor, such as a toll-like receptor.

Mature dendritic cells not only phagocytose pathogens and break them down, but also, degrade their proteins, and present pieces of these proteins, also referred to as antigens, on their cell surfaces using MHC (Major Histocompatibility Complex) molecules (Classes I, II, and III). Mature dendritic cells also upregulate cell-surface receptors that serve as co-receptors for T-cell activation. Exemplary co-receptors include, but are not limited to, CD80, CD86, and CD40. Simultaneously, mature dendritic cells upregulate chemotactic receptors, such as CCR7, that allows the cell to migrate through the blood stream or the lymphatic system to the spleen or lymph node, respectively.

Dendritic cells are present in external tissues that are in contact with the external environment such as the skin (dendritic cells residing in skin are also referred to as Langerhans cells). Alternatively, dendritic cells are present in internal tissues that are in contact with the external environment such as linings of the nose, lungs, stomach, and intestines. Finally, immature dendritic cells reside in the blood stream. Once activated, dendritic cells from all off these tissues migrate to lymphoid tissues where they present antigens and interact with T-cells and B-cells to initiate an immune response. One signaling system of particular importance for the present invention involves the chemokine receptor CCR7 expressed on the surface of dendritic cells and the chemokine receptor ligand CCL19 secreted by lymph node structures to attract migrating mature dendritic cells toward high concentrations of immune cells. Exemplary immune cells activated by contact with mature dendritic cells include, but are not limited to, helper T-cells, killer T-cells, and B-cells. Although multiple cell types within the immune system present antigens, including macrophages and B lymphocytes, dendritic cells are the most potent activators of all antigen-presenting cells.

Dendritic cells earned their name from the characteristic cell shape comprising multiple dendrites extending from the cell body. The functional benefit of this cell shape is a significantly increased cell surface and contact area to the surroundings compared to the cell volume. Immature dendritic cells sometimes lack the characteristic dendrite formations and are referred to as veiled cells. Veiled cells possess large cytoplasmic veils rather than dendrites.

Plasmacytoid dendritic cells (pDCs) are innate immune cells that circulate in the blood and are found in peripheral lymphoid organs. They constitute <0.4% of peripheral blood mononuclear cells (PBMC). In humans these cells express the surface markers CD123, BDCA-2(CD303) and BDCA-4(CD304), but do not express high levels of CD11c or CD14, which distinguishes them from conventional dendritic cells or monocytes, respectively. Mouse pDC express CD11c, B220, BST-2 (mPDCA) and Siglec-H and are negative for CD11b. As components of the innate immune system, these cells express intracellular Toll-like receptors 7 and 9 which detect ssRNA and CpG DNA motifs, respectively. Upon stimulation and subsequent activation, these cells produce large amounts of type I interferon (mainly IFN-α (alpha) and IFN-β (beta)), which are critical pleiotropic anti-viral compounds mediating a wide range of effects. The CD8-subset presents antigen using the class II pathway to CD4+ helper T cells. The CD8+ subset presents antigens using the class I pathway. The peptide/MHC class I molecules are presented to CD8+ T cells which go on to become cytotoxic T lymphocytes (CTL). The CD8 cell surface protein in the mouse corresponds to the CD141 cell surface protein in the human CD8/CD141-positive cells express TLR3 and are preferentially activated by TLR3 agonists.

Materials Systems

Scaffold compositions may comprise biodegradable and/or non-biodegradable materials. Exemplary non-biodegradable materials include, but are not limited to, metal, plastic polymer, or silk polymer. In various embodiments, a scaffold composition comprises biocompatible material that is non-toxic or non-immunogenic. In some embodiments, a scaffold composition comprises an inflammatory material, e.g., mesoporous silica. In certain embodiments, the scaffold composition degrades at a predetermined rate based on a physical parameter selected from the group consisting of temperature, pH, hydration status, and porosity, the crosslink density, type, and chemistry or the susceptibility of main chain linkages to degradation or it degrades at a predetermined rate based on a ratio of chemical polymers. For example, a high molecular weight polymer comprised of solely lactide typically degrades over a period of years, e.g., 1-2 years, while a low molecular weight polymer comprised of a 50:50 mixture of lactide and glycolide typically degrades in a matter of weeks, e.g., 1, 2, 3, 4, 6, 10 weeks. A calcium cross-linked gels composed of high molecular weight, high guluronic acid alginate typically degrade over several months (1, 2, 4, 6, 8, 10, 12 months) to years (1, 2, 5 years) in vivo, while a gel comprised of low molecular weight alginate, and/or alginate that has been partially oxidized, will degrade in a matter of weeks.

In certain embodiments, one or more compounds disclosed herein are covalently or non-covalently linked or attached to the scaffold composition. In various embodiments, one or more compounds disclosed herein is incorporated into, present within the structure or pores of, on incorporated into a scaffold composition.

In various embodiments, any type of cryogel or hydrogel is suitable as a delivery device.

A hydrogel (also called aquagel) is a network of polymer chains that are hydrophilic, and are sometimes found as a colloidal gel in which water is the dispersion medium. Hydrogels are highly absorbent (they can contain over 99% water) natural or synthetic polymers that possess a degree of flexibility very similar to natural tissue, due to their significant water content. Unlike conventional hydrogels, a unique characteristic of the devices described herein is that when an appropriate shear stress is applied, the deformable hydrogel is dramatically and reversibly compressed (up to 95% of its volume), resulting in injectable macroporous preformed scaffolds. This property allows the devices to be delivered via syringe with high precision to target sites.

Aspects of the present subject matter relate to click-hydrogels and click-cryogels. A click hydrogel or cryogel is a gel in which cross-linking between hydrogel or cryogel polymers is facilitated by click reactions between the polymers. Each polymer may contain one of more functional groups useful in a click reaction. Given the high level of specificity of the functional group pairs in a click reaction, active compounds can be added to the preformed device prior to or contemporaneously with formation of the hydrogel device by click chemistry. Non-limiting examples of click reactions that may be used to form click-hydrogels include Copper I catalyzed azide-alkyne cycloaddition, strain-promoted assize-alkyne cycloaddition, thiol-ene photocoupling, Diels-Alder reactions, inverse electron demand Diels-Alder reactions, tetrazole-alkene photo-click reactions, oxime reactions, thiol-Michael addition, and aldehyde-hydrazide coupling. Non-limiting aspects of click hydrogels are described in Jiang et al. (2014) Biomaterials, 35:4969-4985, the entire content of which is incorporated herein by reference.

In various embodiments, a click alginate is utilized (see, e.g., PCT International Patent Application Publication No. WO 2015/154078 published Oct. 8, 2015, hereby incorporated by reference in its entirety).

Exemplary click-hydrogel devices and scaffold materials include a hydrogel comprising a first polymer and a second polymer, where the first polymer is connected to the second polymer by linkers of formula (A):

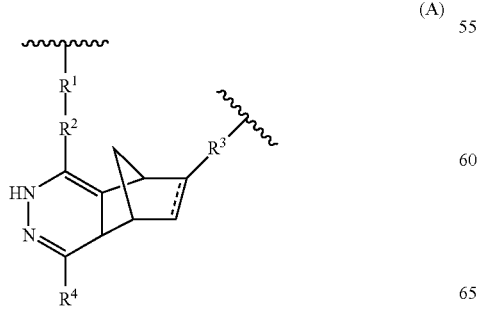

(A)

wherein bond ═══ is a single or a double bond;

$R^1$ is —$C_0$-$C_6$alkyl-$NR^{2N}$—, —$C_0$-$C_6$alkyl-O—, or —$C_0$-$C_3$alkyl-C(O)—;

$R^2$ is a bond, aryl, or heteroaryl, wherein aryl and heteroaryl are optionally substituted with halogen, hydroxy, $C_1$-$C_6$alkyl, $C_1$-$C_6$alkoxy, ($C_1$-$C_6$alkyl)amino, or di($C_1$-$C_6$alkyl)amino;

$R^3$ is —$C_0$-$C_6$alkyl-$NR^{2N}$—, —$C_0$-$C_6$alkyl-O—, or —$C_0$-$C_3$alkyl-C(O)—; and R4 is hydrogen, $C_1$-$C_6$alkyl, aryl, or heteroaryl, wherein aryl and heteroaryl are optionally substituted with halogen, hydroxy, $C_1$-$C_6$alkyl, $C_1$-$C_6$alkoxy, ($C_1$-$C_6$alkyl)amino, or di($C_1$-$C_6$alkyl) amino.

$R^{2N}$ is independently hydrogen, $C_1$-$C_6$ alkyl, aryl, heteroaryl, $R^2N$, or $R^2$, wherein $C_1$-$C_6$ alkyl, aryl and heteroaryl are optionally substituted with halogen, hydroxy, $C_1$-$C_6$ alkyl, $C_1$-$C_6$ alkoxy, ($C_1$-$C_6$ alkyl) amino, or di($C_1$-$C_6$ alkyl)amino In one embodiment, the hydrogel of the disclosure is wherein the linkers of formula (A) are of the form of formula (I):

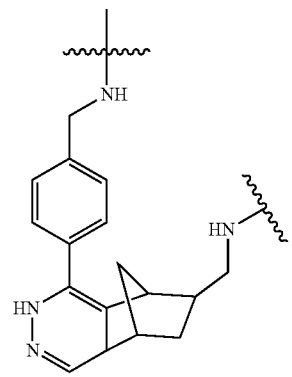

(I)

or by formula (II):

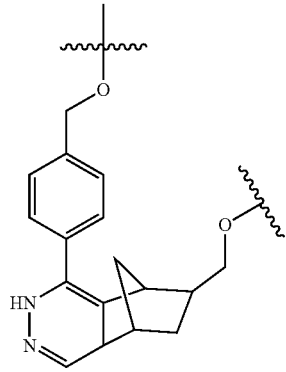

(II)

or by formula (III):

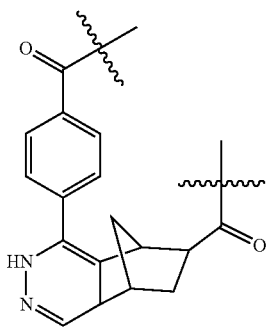

wherein the linkers of formula (I), (II), or (III) are optionally substituted at any suitable position.

Another embodiment provides the linkers of formula (A) according to any preceding embodiment, wherein $R^1$ is
a. —$NR^{2N}$—, —$C_1$-$C_6$ alkyl-$NR^{2N}$—, —O—, —$C_1$-$C_6$ alkyl-O—, —C(O)—, or —$C_1$-$C_3$alkyl-C(O)—;
b. —$C_0$-$C_6$ alkyl-$NR^{2N}$—;
c. —$C_1$-$C_6$ alkyl-$NR^{2N}$—;
d. —$C_1$-$C_3$ alkyl-$NR^{2N}$—;
e. -methyl-NH— or -pentyl-NH—;
f. —$C_0$-$C_6$ alkyl-O—;
g. —$C_1$-$C_6$ alkyl-O—;
h. —$C_1$-$C_3$ alkyl-O—;
i. -methyl-O— or -pentyl-O—;
j. —$C_0$-$C_3$ alkyl-C(O)—;
k. —C(O)—;
l. -methyl-C(O)—;
m. the same as $R^3$.

$R^{2N}$ is independently hydrogen, $C_1$-$C_6$ alkyl, aryl, heteroaryl, $R^2N$, or $R^2$, wherein $C_1$-$C_6$ alkyl, aryl and heteroaryl are optionally substituted with halogen, hydroxy, $C_1$-$C_6$ alkyl, $C_1$-$C_6$ alkoxy, ($C_1$-$C_6$ alkyl)amino, or di($C_1$-$C_6$ alkyl)amino Another embodiment provides the linkers of formula (A) according to any preceding embodiment, wherein $R^2$ is a bond.

In one embodiment, the linkers of formula (A) according to any preceding embodiment are those wherein $R^2$ is
a. aryl or heteroaryl, each optionally substituted;
b. optionally substituted aryl;
c. phenyl;
d. optionally substituted heteroaryl; or
e. pyridyl, pyrimidyl, or pyrazinyl.

Another embodiment provides the linkers of formula (A) according to any preceding embodiment, wherein $R^3$ is
a. —$NR^{2N}$—, —$C_1$-$C_6$ alkyl-$NR^{2N}$—, —O—, —$C_1$-$C_6$ alkyl-O—, —C(O)—, or —$C_1$-$C_3$alkyl-C(O)—;
b. —$C_0$-$C_6$ alkyl-$NR^{2N}$—;
c. —$C_1$-$C_6$ alkyl-$NR^{2N}$—;
d. —$C_1$-$C_3$ alkyl-$NR^{2N}$—;
e. -methyl-NH— or -pentyl-NH—;
f. —$C_0$-$C_6$ alkyl-O—;
g. —$C_1$-$C_6$ alkyl-O—;
h. —$C_1$-$C_3$ alkyl-O—;
i. -methyl-O— or -pentyl-O—;
j. —$C_0$-$C_3$ alkyl-C(O)—;
k. —C(O)—;
l. -methyl-C(O)—; or
m. the same as $R^1$.

$R^{2N}$ is independently hydrogen, $C_1$-$C_6$ alkyl, aryl, heteroaryl, $R^2N$, or $R^2$, wherein $C_1$-$C_6$ alkyl, aryl and heteroaryl are optionally substituted with halogen, hydroxy, $C_1$-$C_6$ alkyl, $C_1$-$C_6$ alkoxy, ($C_1$-$C_6$ alkyl) amino, or di($C_1$-$C_6$ alkyl)amino In one embodiment, the linkers of formula (A) according to any preceding embodiment are those wherein $R^4$ is hydrogen.

In one embodiment, the linkers of formula (A) according to any preceding embodiment are those wherein $R^4$ is
a. $C_1$-$C_6$ alkyl, aryl, or heteroaryl, wherein aryl and heteroaryl are optionally substituted;
b. aryl or heteroaryl, wherein aryl and heteroaryl are optionally substituted;
c. optionally substituted aryl;
d. phenyl;
e. optionally substituted heteroaryl; or
f. pyridyl, pyrimidyl, or pyrazinyl.

Another embodiment provides the linkers of formula (A) according to any preceding embodiment, wherein $R_4$ is $C_1$-$C_6$ alkyl, $C_1$-$C_3$ alkyl, or methyl.

In some embodiments, the hydrogel comprises a plurality of linkers of formula (A); or formula (I), formula (II), or formula (III).

The invention also includes a hydrogel comprising an interconnected network of a plurality of polymers, e.g., including a first polymer and a second polymer. For example, the polymers are connected via a plurality of linkers of formula (A), or of formula (I), formula (II), or formula (III).

Some embodiments of the disclosure provide hydrogels wherein the first polymer and the second polymer are independently soluble polymers. In other embodiments, the first polymer and the second polymer are independently water-soluble polymers.

In some cases, the concentration of crosslinks per hydrogel (e.g., where each crosslink comprises formula I) is at least about 10% (w/w), e.g., at least about 10%, about 15%, about 20%, about 30%, about 40%, about 50%, about 60%, about 70%, about 80%, about 90%, about 95%, about 97%, about 99%, or about 100% (w/w).

The first polymer and the second polymer can be the same or different. In some embodiments, the first polymer and the second polymer are the same type of polymer. In other embodiments, the first polymer and/or the second polymer comprise a polysaccharide. For example, the first polymer and the second polymer can both comprise a polysaccharide. In some embodiments, the first polymer and/or the second polymer are independently selected from the group consisting of alginate, chitosan, polyethylene glycol (PEG), gelatin, hyaluronic acid, collagen, chondroitin, agarose, polyacrylamide, and heparin. In some embodiments, the first polymer and the second polymer are the same polymer independently selected from the group consisting of alginate, chitosan, polyethylene glycol (PEG), gelatin, hyaluronic acid, collagen, chondroitin, agarose, polyacrylamide, and heparin.

Such scaffolds and scaffold materials, as well as methods for producing such scaffolds, are described in PCT International Patent Application Publication No. WO 2015/154078 published Oct. 8, 2015, the entire content of which is incorporated herein by reference. For example, a click hydrogel may be prepared in a process: a) providing a first polymer comprising a first click reaction moiety and a second polymer comprising a second click reaction moiety. In non-limiting examples, the first click reaction moiety and the second click reaction moiety may be react with each other in a copper I catalyzed azide-alkyne cycloaddition, strain-promoted assize-alkyne cycloaddition, thiol-ene photocoupling, a Diels-Alder reaction, a inverse electron demand Diels-Alder reaction, a tetrazole-alkene photo-click reaction, a oxime reaction, a thiol-Michael addition, or via aldehyde-hydrazide coupling. In an embodiment, the first click reaction moiety is a diene moiety and the second click reaction moiety is a dienophile moiety. In an embodiment, the first click reaction moiety is a tetrazine moiety and the second click reaction moiety is a norbornene moiety. As used herein, the terms "tetrazine" and "tetrazine moiety" include molecules that comprise 1,2,4,5-tetrazine substituted with suitable spacer for linking to the polymer (e.g., alkylamines like methylamine or pentylamine), and optionally further substituted with one or more substituents at any available position. Exemplary tetrazine moieties suitable for the compositions and methods of the disclosure are described in Karver et al. Bioconjugate Chem. 22(2011): 2263-2270, and WO 2014/065860, both incorporated herein by reference). As used herein, the terms "norbornene" and "norbornene moieties" include but are not limited to norbornadiene and norbornene groups further comprising suitable spacer for linking to the polymer (e.g., alkylamines like methylamine or pentylamine), and optionally further substituted with one or more substituents at any available position. Such moieties include, for example, norbornene-5-methylamine and norbornadienemethylamine Accordingly, some embodiments feature a cell-compatible and optionally, cell-adhesive, highly crosslinked hydrogel (e.g., cryogel) polymer composition comprising open interconnected pores, wherein the hydrogel (e.g., cryogel) is characterized by shape memory following deformation by compression or dehydration. The device has a high density of open interconnected pores. Also, the hydrogel (e.g., cryogel) comprises a crosslinked gelatin polymer or a crosslinked alginate polymer.

In some embodiments, a cryogel system can deliver (along with antigen-carrying tumor cells) GM-CSF and a specific TLR agonist (such as CpG-ODN), while creating a space for DC infiltration and trafficking. GM-CSF is a cytokine that acts as a DC enhancement/recruitment factor, and CpG ODN is an adjuvant that is a specific TLR agonist (DC activation factor).

MA-alginate cryogel devices can function as a vaccine platform by creating a local immunogenic niche. Overall, the cryogel creates a local immunogenic niche in which the encounter of DCs and tumor cells is tightly controlled, favoring the induction of a potent and durable anti-tumor immune response. The cryogel vaccine can be engineered to coordinate the delivery of both adjuvant and antigen in space and time, potentially enhancing overall vaccine performance by more closely matching factor delivery with the kinetics of DC-T-cell priming and activation. The vaccine platform is designed to provide appropriate DC co-stimulation through creating a local space where DCs can interface with tumor cells in the presence of immunomodulatory factors. Specifically, the macropores create a physical space for DCs and tumor cells to interact in the presence of the released immunomodulatory factors, without the tolerogenic milieu present in the tumor bed. Unlike bolus delivery of tumor cells and adjuvant, the cells and immunomodulatory agents are localized into a small volume, and the delivery of factors in space and time can be quantitatively controlled. As the immunomodulatory factors are released locally, few systemic effects are anticipated, in contrast to systemically delivered agents, such as immune checkpoint blocking antibodies.

Examples of polymer compositions from which the cryogel or hydrogel is fabricated are described throughout the present disclosure, and include alginate, hyaluronic acid, gelatin, heparin, dextran, carob gum, PEG, PEG derivatives including PEG-co-PGA and PEG-peptide conjugates. The techniques can be applied to any biocompatible polymers, e.g. collagen, chitosan, carboxymethylcellulose, pullulan, polyvinyl alcohol (PVA), Poly(2-hydroxyethyl methacrylate) (PHEMA), Poly(N-isopropylacrylamide) (PNIPAAm), or Poly(acrylic acid) (PAAc). For example, the composition comprises an alginate-based hydrogel/cryogel. In another example, the composition comprises a gelatin-based hydrogel/cryogel.

Cryogels are a class of materials with a highly porous interconnected structure that are produced using a cryotropic gelation (or cryogelation) technique. Cryogels also have a highly porous structure. Typically, active compounds are added to the cryogel device after the freeze-formation of the pore/wall structure of the cryogel. Cryogels are characterized by high porosity, e.g., at least about 50, 55, 60, 65, 70, 75, 80, 85, 90, or 95% pores with thin pore walls that are characterized by high density of polymer crosslinking. The walls of cryogels are typically dense and highly crosslinked, enabling them to be compressed through a needle into a subject without permanent deformation or substantial structural damage. In various embodiments, the pore walls comprise at least about 10, 15, 20, 25, 30, 35, 40, 10-40% or more polymer. In some embodiments, a polymer concentration of about 0.5-4% (before the cryogelation) is used, and the concentration increases substantially by the completion of cryogelation. Non-limiting aspects of cryogel gelation and the increase of polymer concentration after cryogelation are discussed in Béduer et al. (2015) Advanced Healthcare Materials Volume 4, Issue 2, pages 301-312, the entire content of which is incorporated herein by reference. In various implementations, cryogelation comprises a technique in which polymerization-crosslinking reactions are conducted in quasi-frozen reaction solution. Non-limiting examples of cryogelation techniques are described in U.S. Patent Application Publication No. 2014/0227327, published Aug. 14, 2014, the entire content of which is incorporated herein by reference. An advantage of cryogels compared to conventional macroporous hydrogels obtained by phase separation is their high reversible deformability. Cryogels may be extremely soft but can be deformed and reform their shape. They are very tough, and can withstand high levels of deformations, such as elongation and torsion; they can also be squeezed under mechanical force to drain out their solvent content. In various embodiments, improved deformability properties of alginate cryogels originate from the high crosslinking density of the unfrozen liquid channels of the reaction system.

Examples of polymer compositions from which the cryogel is fabricated include alginate, hyaluronic acid, gelatin, heparin, dextran, carob gum, PEG, PEG derivatives including PEG-co-PGA and PEG-peptide conjugates. The techniques can be applied to any biocompatible polymers, e.g. collagen, chitosan, carboxymethylcellulose, pullulan, polyvinyl alcohol (PVA), Poly(2-hydroxyethyl methacrylate) (PHEMA), Poly(N-isopropylacrylamide) (PNIPAAm), or Poly(acrylic acid) (PAAc). For example, the composition comprises an alginate-based hydrogel/cryogel. In another example, the composition comprises a gelatin-based hydrogel/cryogel.

In some embodiments, the invention also features gelatin scaffolds, e.g., gelatin hydrogels such as gelatin cryogels, which are a cell-responsive platform for biomaterial-based therapy. Gelatin is a mixture of polypeptides that is derived from collagen by partial hydrolysis. These gelatin scaffolds have distinct advantages over other types of scaffolds and hydrogels/cryogels. For example, the gelatin scaffolds of the invention support attachment, proliferation, and survival of cells and are degraded by cells, e.g., by the action of enzymes such as matrix metalloproteinases (MMPs) (e.g., recombinant matrix metalloproteinase-2 and -9).

Prefabricated gelatin cryogels rapidly reassume their original shape ("shape memory") when injected subcutaneously into a subject (e.g., a mammal such as a human, dog, cat, pig, or horse) and elicit little or no harmful host immune response (e.g., immune rejection) following injection.

In some embodiments, the hydrogel (e.g., cryogel) comprises polymers that are modified, e.g., sites on the polymer molecule are modified with a methacrylic acid group (methacrylate (MA)) or an acrylic acid group (acrylate). Exemplary modified hydrogels/cryogels are MA-alginate (methacrylated alginate) or MA-gelatin. In the case of MA-alginate or MA-gelatin, 50% corresponds to the degree of methacrylation of alginate or gelatin. This means that every other repeat unit contains a methacrylated group. The degree of methacrylation can be varied from 1% to 90%. Above 90%, the chemical modification may reduce solubility of the polymer water-solubility.

Polymers can also be modified with acrylated groups instead of methacrylated groups. The product would then be referred to as an acrylated-polymer. The degree of methacrylation (or acrylation) can be varied for most polymers. However, some polymers (e.g. PEG) maintain their water-solubility properties even at 100% chemical modification. After crosslinking, polymers normally reach near complete methacrylate group conversion indicating approximately 100% of cross-linking efficiency. For example, the polymers in the hydrogel are 50-100% crosslinked (covalent bonds). The extent of crosslinking correlates with the durability of the hydrogel. Thus, a high level of crosslinking (90-100%) of the modified polymers is desirable.

For example, the highly crosslinked hydrogel/cryogel polymer composition is characterized by at least 50% polymer crosslinking (e.g., 75%, 80%, 85%, 90%, 95%, 98%). The high level of crosslinking confers mechanical robustness to the structure. However, the % crosslinking is generally less than 100%. The composition is formed using a free radical polymerization process and a cryogelation process. For example, the cryogel is formed by cryopolymerization of methacrylated gelatin or methacrylated alginate. In some cases, the cryogel comprises a methacrylated gelatin macromonomer or a methacrylated alginate macromonomer concentration of 1.5% (w/v) or less (e.g., 1.5%, 1.4%, 1.3%, 1.2%, 1.1%, 1% 0.9%, 0.8%, 0.7%, 0.6%, 0.5%, 0.4%, 0.3%, 0.2% or less). For example, the methacrylated gelatin or alginate macromonomer concentration is about 1% (w/v).

In some embodiments, crosslinked gelatin hydrogels/cryogels are formed by modification of gelatin with pendant methacrylate groups. For example, crosslinking occurs via radical polymerization. In some examples, 2-6% (e.g., 3-4%) of the amino acid composition of gelatin is lysine. In some cases, lysine in the gelatin is converted to reactive methacrylate groups. In some cases, 70-90% (e.g., 80%) of the lysine in the gelatin is converted to reactive methacrylate groups. These reactive methacrylate groups on the gelatin are then crosslinked, e.g., by radical polymerization. In some embodiments, the gelatin polymers of the invention (e.g., crosslinked by radical polymerization) contain a greater number of crosslinks compared to a gelatin polymer incubated at room temperature without radical polymerization (e.g., without modification by methacrylate).

The cryogel comprises at least 75% pores, e.g., 80%, 85%, 90%, 91%, 92%, 93%, 94%, 95%, 96%, 97%, 98%, or 99% or more pores. The pores are interconnected. Interconnectivity is important to the function of the composition, as without interconnectivity, water would become trapped within the gel. Interconnectivity of the pores permits passage of water (and other compositions such as cells and compounds) in and out of the structure. In a fully hydrated state, the composition comprises at least 90% water (e.g., between 90-99%, at least 92%, 95%, 97%, 99%, or more) water. For example, at least 90% (e.g., at least 92%, 95%, 97%, 99%, or more) of the volume of the cryogel is made of liquid (e.g., water) contained in the pores. In a compressed or dehydrated hydrogel, up to 50%, 60%, 70% of that water is absent, e.g., the cryogel comprises less than 25% (20%, 15%, 10%, 5%, or less) water.

The cryogels of the invention comprises pores large enough for a cell to travel through. For example, the cryogel contains pores of 20-500 μm in diameter, e.g., 20-300 μm, 30-150 μm, 50-500 μm, 50-450 μm, 100-400 μm, 200-500 μm. In some cases, the hydrated pore size is 1-500. μm (e.g., 10-400 μm, 20-300 μm, 50-250 μm).

In some embodiments, injectable hydrogels or cryogels are further functionalized by addition of a functional group chosen from the group consisting of: amino, vinyl, aldehyde, thiol, silane, carboxyl, azide, alkyne. Alternatively or in addition, the cryogel is further functionalized by the addition of a further cross-linker agent (e.g. multiple arms polymers, salts, aldehydes, etc.). The solvent can be aqueous, and in particular acidic or alkaline. The aqueous solvent can comprise a water-miscible solvent (e.g. methanol, ethanol, DMF, DMSO, acetone, dioxane, etc).

For cryogels, the cryo-crosslinking may take place in a mold and the cryogels (which may be injected) can be degradable. The pore size can be controlled by the selection of the main solvent used, the incorporation of a porogen, the freezing temperature and rate applied, the cross-linking conditions (e.g. polymer concentration), and also the type and molecule weight of the polymer used. The shape of the cryogel may be dictated by a mold and can thus take on any shape desired by the fabricator, e.g., various sizes and shapes (disc, cylinders, squares, strings, etc.) are prepared by cryogenic polymerization. Injectable cryogels can be prepared in the micrometer-scale to millimeter-scale. Exemplary volumes vary from a few hundred $\mu m^3$ (e.g., 100-500 $\mu m^3$) to over 100 $mm^3$. An exemplary scaffold composition is between 100 $\mu m^3$ to 100 $mm^3$ in size (e.g., between 1 $mm^3$ and 10 $mm^3$ in size). In some applications, the cryogels are hydrated, loaded with compounds and loaded into a syringe or other delivery apparatus. For example, the syringes are prefilled and refrigerated until use. In another example, the cryogel is dehydrated, e.g., lyophilized, optionally with a compound (such as PEI) loaded in the gel and stored dry or refrigerated. Prior to administration, a cryogel-loaded syringe or apparatus may be contacted with a solution containing compounds to be delivered. For example, the barrel of the cryogel pre-loaded syringe is filled with a physiologically-compatible solution, e.g., phosphate-buffered saline (PBS). In some embodiments, the cryogel may be administered to a desired anatomical site followed by the volume of solution, optionally containing other ingredients, e.g., PEI alone or together with one or more compounds disclosed herein. The cryogel is then rehydrated and regains its shape integrity in situ. The volume of PBS or other physiologic solution administered following cryogel placement is generally about 10 times the volume of the cryogel itself. The cryogel also has the advantage that, upon compression, the cryogel composition maintains structural integrity and shape memory properties. For example, the cryogel is injectable through a hollow needle. For example, the cryogel returns to its original geometry after traveling through a needle (e.g., a 16 gauge (G) needle, e.g., having a 1.65 mm inner diameter). Other exemplary needle sizes are 16-gauge, an 18-gauge, a 20-gauge, a 22-gauge, a 24-gauge, a 26-gauge, a 28-gauge, a 30-gauge, a 32-gauge, or a 34-gauge needle. Injectable cryogels have been designed to pass through a hollow structure, e.g., very fine needles, such as 18-30 G needles. The injectable cryogels may be molded to a desired shape, in the form of rods, square, disc, spheres, cubes, fibers, foams. In some cases, the cryogel comprises the shape of a disc, cylinder, square, rectangle, or string. For example, the cryogel composition is between 100 $\mu m^3$ to 100 $mm^3$ in size, e.g., between 1 $mm^3$ to 50 $mm^3$ in size. For example, the cryogel composition is between 1 mm in diameter to 50 mm in diameter (e.g., around 5 mm). Optionally, the thickness of the cryogel is between 0.2 mm to 50 mm (e.g., around 2 mm).

In some examples, the scaffold composition comprises a cell adhesion composition chemically linked, e.g., covalently attached, to a polymer. For example, the cell adhesion composition comprises a peptide comprising an RGD amino acid sequence. In non-limiting examples, the hydrogel or cryogel composition (e.g., gelatin) has cell-adhesive properties. In some cases, the scaffold composition is not modified with a cell adhesive molecule, such as arginine-glycine-aspartate (RGD).

Three exemplary cryogel materials systems are described below.

a) Methacrylated gelatin cryogel (CryoGelMA)—An exemplary cryogel utilized methacrylated gelatin and the results are described in detail in U.S. Patent Application Publication No. 2014-0227327, published Aug. 14, 2014, the entire contents of which are incorporated herein by reference.

b) Methacrylated alginate cryogel (CryoMAAlginate)—An exemplary cryogel utilized methacrylated alginate and the results are described in detail in U.S. Patent Application Publication No. 2014-0227327, published Aug. 14, 2014, the entire contents of which are incorporated herein by reference.

c) Click Alginate cryogel with Laponite nanoplatelets (CryoClick)—The base material is click alginate (PCT International Patent Application Publication No. WO 2015/154078 published Oct. 8, 2015, hereby incorporated by reference in its entirety). In some examples, the base material contains laponite (commercially available silicate clay used in many consumer products such as cosmetics). Laponite has a large surface area and highly negative charge density which allows it to adsorb positively charged moieties on a variety of proteins and other biologically active molecules by an electrostatic interaction, allowing drug loading. When placed in an environment with a low concentration of drug, adsorbed drug releases from the laponite in a sustained manner. This system allows release of a more flexible array of immunomodulators compared to the base material alone.

Various embodiments of the present subject matter include delivery vehicles comprising a pore-forming scaffold composition. For example, pores (such as macropores) are formed in situ within a hydrogel following hydrogel injection into a subject. Pores that are formed in situ via degradation of a sacrificial porogen hydrogel within the surrounding hydrogel (bulk hydrogel) facilitate recruitment and trafficking of cells, as well as the release of compounds, such as PEI, an immunostimulatory compound; a compound that attracts an immune cell to or into the delivery vehicle; a compound that induces immunogenic cell death of a tumor cell; a compound that inhibits T-cell or dendritic cell suppression; a compound that inhibits an immune-inhibitory protein; or an antigen, or any combination thereof. In some embodiments, the sacrificial porogen hydrogel, the bulk hydrogel, or both the sacrificial porogen hydrogel and the bulk hydrogel comprises PEI, an immunostimulatory compound, a compound that attracts an immune cell to or into the delivery vehicle, a compound that induces immunogenic cell death of a tumor cell, a compound that inhibits T-cell or dendritic cell suppression, a compound that inhibits an immune-inhibitory protein, and/or an antigen, or any combination thereof.

In various embodiments, the pore-forming composition becomes macroporous over time when resident in the body of a recipient animal such as a mammalian subject. For example, the pore-forming composition may comprise a sacrificial porogen hydrogel and a bulk hydrogel, wherein the sacrificial porogen hydrogel degrades at least 10% faster (e.g., at least 15%, at least 20%, at least 25%, at least 30%, at least 35%, at least 40%, at least 45%, or at least 50% faster) than the bulk hydrogel. The sacrificial porogen hydrogel may degrade leaving macropores in its place. In certain embodiments, the macropores are open interconnected macropores. In some embodiments, the sacrificial porogen hydrogel may degrade more rapidly than the bulk hydrogel, because the sacrificial porogen hydrogel (i) is more soluble in water (comprises a lower solubility index), (ii) is cross-linked to protease-mediated degradation motifs as described in U.S. Patent Application Publication No. 2005-0119762, published Jun. 2, 2005 (incorporated herein by reference), (iii) comprises a shorter polymer that degrades more quickly compared to that of a longer bulk hydrogel polymer, (iv) is modified to render it more hydrolytically degradable than the bulk hydrogel (e.g., by oxidation), and/or (v) is more enzymatically degradable compared to the bulk hydrogel.

In various embodiments, a device or scaffold is loaded (e.g., soaked with) with one or more active compounds after polymerization. In certain embodiments, device or scaffold polymer forming material is mixed with one or more active compounds before polymerization. In some embodiments, a device or scaffold polymer forming material is mixed with one or more active compounds before polymerization, and hen is loaded with more of the same or one or more additional active compounds after polymerization.

In some embodiments, pore size or total pore volume of a device or scaffold is selected to influence the release of compounds from the device or scaffold. Exemplary porosities (e.g., nanoporous, microporous, and macroporous scaffolds and devices) and total pore volumes (e.g., about 5, 10, 15, 20, 25, 30, 35, 40, 45, 50, 55, 60, 65, 70, 75, 80, 85, 90, or 95%) are described herein. Increased pore size and total pore volume increases the amount of compounds that can be delivered into or near a tumor. In some embodiments, a pore size or total pore volume is selected to increase the speed at which active ingredients exit the device or scaffold. In various embodiments, an active ingredient may be incorporated into the scaffold material of a hydrogel or cryogel, e.g., to achieve continuous release of the active ingredient from the scaffold or device over a longer period of time compared to active ingredient that may diffuse from a pore cavity.

Porosity influences recruitment the cells into devices and scaffolds and the release of substances from devices and scaffolds. Pores may be, e.g., nanoporous, microporous, or macroporous. For example, the diameter of nanopores is less than about 10 nm. Micropores are in the range of about 100 nm to about 20 μm in diameter. Macropores are greater than about 20 μm (e.g., greater than about 100 μm or greater than about 400 μm). Exemplary macropore sizes include 50 μm, 100 μm, 150 μm, 200 μm, 250 μm, 300 μm, 350 μm, 400 μm, 450 μm, 500 μm, 550 μm, and 600 μm. Macropores are those of a size that permit a eukaryotic cell to traverse into or out of the composition. In one example, a macroporous composition has pores of about 400 μm to 500 μm in diameter. The preferred pore size depends on the application.

In various embodiments, the device is manufactured in one stage in which one layer or compartment is made and infused or coated with one or more compounds. Exemplary bioactive compositions comprise polypeptides or polynucleotides. In certain alternative embodiments, the device is manufactured in two or more (3, 4, 5, 6, . . . 10 or more) stages in which one layer or compartment is made and infused or coated with one or more compounds followed by the construction of a second, third, fourth or more layers, which are in turn infused or coated with one or more compounds in sequence. In some embodiments, each layer or compartment is identical to the others or distinguished from one another by the number or mixture of bioactive compositions as well as distinct chemical, physical and biological properties. Polymers that may be formulated for specific applications by controlling the molecular weight, rate of degradation, and method of scaffold formation. Coupling reactions can be used to covalently attach bioactive epitopes, such as the cell adhesion sequence RGD to the polymer backbone.

In some embodiments, one or more compounds is added to the scaffold compositions using a known method including surface absorption, physical immobilization, e.g., using a phase change to entrap the substance in the scaffold material. For example, an immunostimulatory compound is mixed with the scaffold composition while it is in an aqueous or liquid phase, and after a change in environmental conditions (e.g., pH, temperature, ion concentration), the liquid gels or solidifies thereby entrapping the bioactive substance. In some embodiments, covalent coupling, e.g., using alkylating or acylating agents, is used to provide a stable, long term presentation of a compound on the scaffold in a defined conformation. Exemplary reagents for covalent coupling of such substances are provided in the table below.

Methods to Covalently Couple Peptides/Proteins to Polymers

| Functional Group of Polymer | Coupling reagents and cross-linker | Reacting groups on proteins/peptides |
|---|---|---|
| —OH | Cyanogen bromide (CNBr) Cyanuric chloride 4-(4,6-Dimethoxy-1,3,5-triazin-2-yl)-4-methyl-morpholinium chloride (DMT-MM) | —NH$_2$ |
| —NH$_2$ | Diisocyanate compounds Diisothoncyanate compounds Glutaraldehyde Succinic anhydride | —NH$_2$ —OH |

-continued

| Functional Group of Polymer | Coupling reagents and cross-linker | Reacting groups on proteins/peptides |
|---|---|---|
| —NH$_2$ | Nitrous Acid Hydrazine + nitrous acid | —NH$_2$ —SH —Ph—OH |
| —NH$_2$ | Carbodiimide compounds (e.g., EDC, DCC)[a] DMT-MM | —COOH |
| —COOH | Thionyl chloride N-hydroxysuccinimide N-hydroxysulfosuccinimide + EDC | —NH$_2$ |
| —SH | Disulfide compound | —SH |

[a]EDC: 1-ethyl-3-(3-dimethylaminopropyl) carbodiimide hydrochloride;
DCC: dicyclohexylcarbodiimide Mesoporous Silica Rods Various embodiments of the present subject matter include the use of delivery vehicles comprising mesoporous silica rods. Injectable mesoporous silica rods randomly self-assemble to form a 3D scaffold structure in vivo. The 3D scaffold structure comprises micro spaces that allow for immune cell (e.g., dendritic cell) infiltration and/or trafficking. As with other scaffold compositions disclosed herein, the mesoporous silica rods may comprise, e.g., PEI alone or together with an immunostimulatory compound; a compound that attracts an immune cell to or into the delivery vehicle; a compound that induces immunogenic cell death of a tumor cell; a compound that inhibits T-cell or dendritic cell suppression; a compound that inhibits an immune-inhibitory protein; or an antigen, or any combination thereof. In some embodiments, the mesoporous silica rod itself serves as an immunostimulatory compound.

In some embodiments, the rods or scaffold comprising the rods comprises pores of between 1-50 nm in diameter, e.g., pores comprising within the range about 1-50, 2-50, 3-50, 4-50, 5-50, 6-50, 7-50, 8-50, 9-10, 10-50, 15-50, 25-50, 1-25, 2-25, 3-25, 4-25, 5-25, 6-25, 7-25, 8-25, 9-25, 10-25, or 15-25 nm. In various embodiments, the length of the mesoporous silica rods ranges from 5 μm to 500 μm. In one example, the rods comprise a length of 5-25 μm, e.g., 10-20 μm. In other examples, the rods comprise length of 50 μm to 250 μm or 80 μm to 120 μm. In certain embodiments, the mesoporous silica rods comprise a length of about 25-100, 25-250, 25-500, 50-250, or 50-500 μm, or a length of at least about 5, 10, 15, 20, 25, 30, 35, 40, 45, 50, 75, or 100 μm but no more than about 500 μm.

Linkage of PEI with Other Compounds

In various embodiments, PEI is covalently linked with another compound such as an antigen and/or another immunostimulatory agent. Covalent conjugation with covalent bonds or a linker facilitates the delivery of both molecules (e.g., PEI and antigen) to the same cell. Non-limiting examples of linkers include peptide linkers, e.g., varying from 1 to 10 or more amino acids, click chemistry linkers, and variety of others known in the art. Other examples include carbamate, maleimide, a triazole ring, disulfide, thioester, amide, ester bond or carbodiimide linkage (a few atoms to up to as many as desirable). Additional coupling reactive chemistries can be employed to link PEI to the antigen, e.g., NHS-esters (amine-amine), imidoesters (amine-amine), hydrazide (aldehyde-hydrazide), maleimides (sulfhydryl-sulfhydryl), azide alkyne Huisgen cycloaddition, and streptavidin-biotin conjugation, as well as click chemistries. In some cases, the linker is cleavable. For example, the linker is cleavable by enzymes, nucleophilic/basic reagents, reducing/oxidizing agents (e.g., inside a cell), photo-irradiation, thermal, electrophilic/acidic reagents, or organometallic/metal reagents. In some embodiments, PEI is linked to another compound via a linker and/or bond formed by a click reaction. Covalent coupling increases the likelihood that a cell that uptakes the PEI will also uptake the antigen.

Aspects of the present subject matter relate to immunoconjugates in which PEI is conjugated, e.g., covalently linked, to an antigen or another immunomodulatory agent, e.g. directly via a covalent bond or optionally via a linker or a spacer. Covalent bonds may have various lengths. Non-limiting examples of covalent bond lengths include lengths from about 1 angstrom to 3 angstroms. In various embodiments, the linker or spacer is sufficiently short as to promote the association of PEI and the antigen or immunomodulatory agent conjugate with a single cell or to limit the association of PEI and the antigen or the immunomodulatory agent with a single cell. For example, the linker or spacer may be less than about 1, 2, 3, 4, 5, 6, 7, 8, 9, 10, 11, 12, 13, 14, 15, 20, 25, 30, 35, 40, 50, 1-5, 5-10, 5-15, 5-25, 10-30 or 5-50 angstroms long. Thus, in some embodiments, the antigen is no farther than 1, 2, 3, 4, 5, 6, 7, 8, 9, 10, 11, 12, 13, 14, 15, 20, 25, 30, 35, 40, 50, 1-5, 5-10, 5-15, 5-25, 10-30 or 5-50 angstroms from the immunomodulatory agent. In some embodiments, the antigen and immunomodulatory agent are directly linked via a covalent bond [without spacer linker compound(s)]. In certain embodiments, the linker or spacer is an amino acid, or a polypeptide comprising about 2, 3, 4, 5, 6, 7, 8, 9, or 10 amino acids. In some embodiments, the polypeptide comprises about 2, 3, 4, 5, 6, 7, 8, 9, or 10 glycines. Contacting a single cell with an PEI-containing or other immunoconjugate of the present subject matter reduces the off target effects that might result from delivering the components of the immunoconjugate to different cells.

Aspects of the present subject matter provide a PEI molecule that is covalently linked to an antigen. In some embodiments, a PEI is covalently linked to more than one antigen molecule, e.g., a linear PEI is covalently linked at each of its ends or a branched PEI covalently linked at multiple branch ends. In some embodiments, a single PEI molecule is covalently linked to at least about 2, 3, 4, 5, 6, 7, 8, 9, or 10 antigen molecules. "Covalently linked" molecules include molecules linked by one covalent bond, or linked by more than one covalent bond (e.g., 2, 3, 4, 5, 6, 7, 8, 9, 10, 11, 12, 13, 14, 15, 16, 17, 18, 19, 20, or more), e.g., linked by a linker or spacer. In some cases, PEI and the antigen are covalently attached by a bond, e.g., a carbamate, amide, maleimide, a triazole ring, disulfide, thioester, or ester bond. In some embodiments PEI and the antigen are linked by a bond that has been formed by a click reaction. In some cases, PEI and the antigen are covalently attached by a linker or spacer. In some cases, PEI and the antigen are connected by a carbodiimide linkage. An exemplary linker includes a stretch of 2, 3, 4, 5, or more glycines, optionally also including 1 or more serines. In some embodiments, PEI is covalently linked to an antigen via a bifunctional maleimide (amine-sulfhydryl), carbodiimide (amine-carboxylic acid) or photo-click (norbornene-thiol) linker. In some examples, one or more, e.g., a plurality of, (e.g., 2, 3, 4, 5, 6, 7, 8, 9, 10, or more) antigens are mixed together, e.g., coupled to PEI, e.g., to form an immunogenic cocktail, to provide broader antigenic coverage than with one antigen alone.

In some embodiments, PEI is linked with another compound (e.g. an antigen or another immunostimulatory compound) via a bioorthogonal chemical reaction, such as a bioorthogonal click reaction. By "biorthogonal" is meant a functional group or chemical reaction that can occur inside a living cell, tissue, or organism without interfering with native biological or biochemical processes. However, the present subject matter does not require that conjugation of PEI with another compound occur in the presence of or inside a living cell, tissue, or organism. A bioorthogonal functional group or reaction is not toxic to cells. For example, a bioorthogonal reaction may function in biological conditions, e.g., biological pH, aqueous environments, and temperatures within living organisms or cells. For example, a bioorthogonal reaction must occur rapidly to ensure that covalent ligation between two functional groups occurs before metabolism and/or elimination of one or more of the functional groups from the organism. In other examples, the covalent bond formed between the two functional groups must be inert to biological reactions in living cells, tissues, and organisms.

A bioorthogonal functional group and the target recognition molecule comprise a complementary functional group, where the bioorthogonal functional group is capable of chemically reacting with the complementary functional group to form a covalent bond.

Exemplary bioorthogonal functional group/complementary functional group pairs include azide with phosphine; azide with cyclooctyne; nitrone with cyclooctyne; nitrile oxide with norbornene; oxanorbornadiene with azide; trans-cyclooctene with s-tetrazine; quadricyclane with bis(dithiobenzil)nickel(II). For example, the bioorthogonal functional group is capable of reacting by click chemistry with the complementary functional group. In some cases, the bioorthogonal functional group comprises transcyclooctene (TOC) or norbornene (NOR), and the complementary functional group comprises a tetrazine (Tz). In some examples, the bioorthogonal functional group comprises dibenzocyclooctyne (DBCO), and the complementary functional group comprises an azide (Az). In other examples, the bioorthogonal functional group comprises a Tz, and the complementary functional group comprises transcyclooctene (TOC) or norbornene (NOR). Alternatively or in addition, the bioorthogonal functional group comprises an Az, and the complementary functional group comprises dibenzocyclooctyne (DBCO).

For example, the target comprises a bioorthogonal functional group and the target recognition molecule comprises a complementary functional group, where the bioorthogonal functional group is capable of chemically reacting with the complementary functional group to form a covalent bond, e.g., using a reaction type described in the table below, e.g., via click chemistry.

Exemplary bioorthogonal functional group/complementary functional group pairs are shown in the table below.

| Functional group | Paired with Functional group | Reaction type (Reference) |
| --- | --- | --- |
| Azide | phosphine | Staudinger ligation (Saxon et al. Science 287(2000): 2007-10) |
| Azide | Cyclooctyne, e.g., dibenzocyclooctyne, or one of the cyclooctynes shown below:<br><br>OCT<br><br>ALO<br><br>MOFO<br><br>DIBO<br><br>DIFO<br><br>DIBAC<br><br>BARAC | Copper-free click chemistry (Jewett et al. J. Am. Chem. Soc. 132.11(2010): 3688-90; Sletten et al. Organic Letters 10.14(2008): 3097-9; Lutz. 47.12(2008): 2182) |

| Functional group | Paired with Functional group | Reaction type (Reference) |
|---|---|---|
| | DIMAC (structure shown) | |
| Nitrone | cyclooctyne | Nitrone Dipole Cycloaddition (Ning et al. 49.17(2010): 3065) |
| Nitrile oxide | norbornene | Norbornene Cycloaddition (Gutsmiedl et al. Organic Letters 11.11(2009): 2405-8) |
| Oxanorbornadiene | azide | Oxanorbornadiene Cycloaddition (Van Berkel et al. 8.13(2007): 1504-8) |
| Trans-cyclooctene | s-tetrazine | Tetrazine ligation (Hansell et al. J. Am. Chem. Soc. 133.35(2011): 13828-31) |
| Nitrile | 1,2,4,5-tetrazine | [4 + 1] cycloaddition (Stackman et al. Organic and Biomol. Chem. 9.21(2011): 7303) |
| quadricyclane | Bis(dithiobenzil)nickel(II) | Quadricyclane Ligation (Sletten et al. J. Am. Chem. Soc. 133.44(2011): 17570-3) |
| Ketone or aldehyde | Hydrazines, hydrazones, oximes, amines, ureas, thioureas, etc. | Non-aldol carbonyl chemistry (Khomyakova EA, et al. Nucleosides Nucleotides Nucleic Acids. 30(7-8) (2011) 577-84 |
| Thiol | maleimide | Michael addition (Zhou et al. 2007 18(2): 323-32.) |
| Dienes | dieoniphiles | Diels Alder (Rossin et al. Nucl Med. (2013) 54(11): 1989-95) |
| Tetrazene | Norbornene | Norbornene click chemistry (Knight et al. Org Biomol Chem. 2013 Jun 21; 11(23): 3817-25.) |

In some examples, a target molecule comprises a bioorthogonal functional group such as a trans-cyclooctene (TCO), dibenzycyclooctyne (DBCO), norbornene, tetrazine (Tz), or azide (Az). In other example, a target recognition molecule (e.g., on the device) comprises a bioorthogonal functional group such as a trans-cyclooctene (TCO), dibenzycyclooctyne (DBCO), norbornene, tetrazine (Tz), or azide (Az). TCO reacts specifically in a click chemistry reaction with a tetrazine (Tz) moiety. DBCO reacts specifically in a click chemistry reaction with an azide (Az) moiety. Norbornene reacts specifically in a click chemistry reaction with a tetrazine (Tz) moiety. For example, TCO is paired with a tetrazine moiety as target/target recognition molecules. For example, DBCO is paired with an azide moiety as target/target recognition molecules. For example, norbornene is paired with a tetrazine moiety as target/target recognition molecules.

The exemplary click chemistry reactions have high specificity, efficient kinetics, and occur in vivo under physiological conditions. See, e.g., Baskin et al. Proc. Natl. Acad. Sci. USA 104(2007):16793; Oneto et al. Acta biomaterilia (2014); Neves et al. Bioconjugate chemistry 24(2013):934; Koo et al. Angewandte Chemie 51(2012):11836; and Rossin et al. Angewandte Chemie 49(2010):3375.

As described above, click chemistry reactions are particularly effective for conjugating biomolecules. They also proceed in biological conditions with high yield. Exemplary click chemistry reactions are (a) Azide-Alkyne Cycloaddition, (b) Copper-Free Azide Alkyne Cycloaddition, and (c) Staudinger Ligation shown in the schemes below.

A) Azide-alkyne cycloaddition

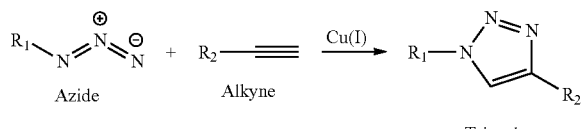

B) Copper-free azide-alkyne cycloaddition

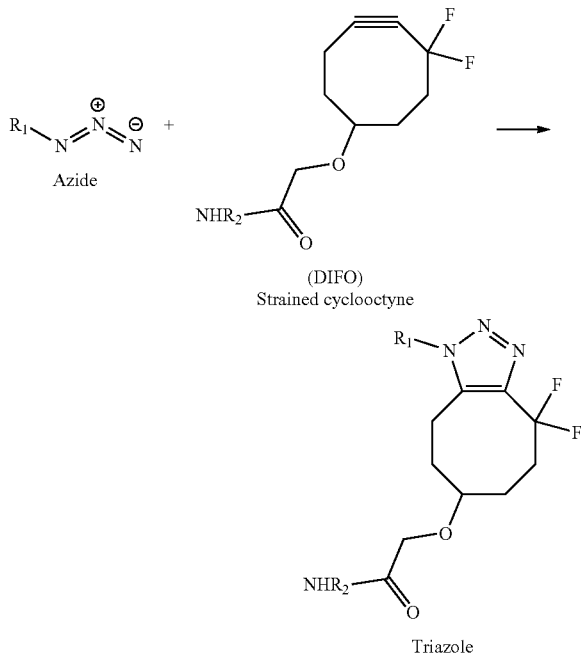

C) Staudinger ligation

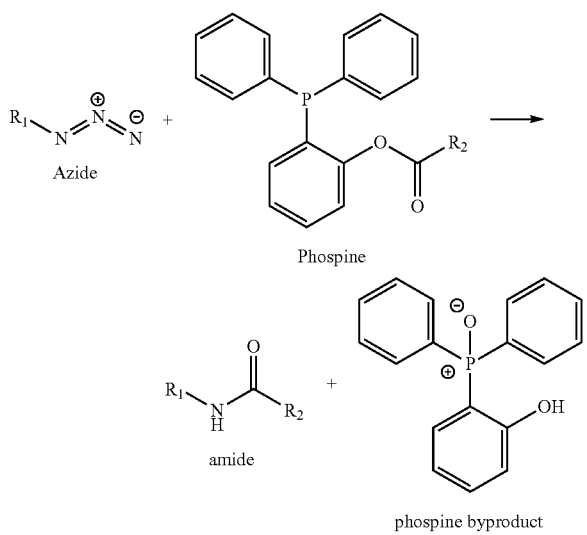

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means ±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

Polynucleotides, polypeptides, or other agents may be purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also may define a degree of sterility that is safe for administration to a human subject, e.g., lacking infectious or toxic agents.

Similarly, by "substantially pure" with respect to a nucleotide or polypeptide means a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

As used herein, an "expression vector" is a DNA or RNA vector that is capable of transforming a cell and of effecting expression of one or more specified polynucleotides. Preferably, the expression vector is also capable of replicating within the host cell. Expression vectors may be, e.g., eukaryotic, and are typically viruses or plasmids. Expression vectors of the present invention contain regulatory sequences such as transcription control sequences, translation control sequences, origins of replication, and other regulatory sequences that are compatible with the host cell (e.g., a cell of a subject such as a tumor cell, immune cell, or cells surrounding a device or scaffold after it is administered) and that control the expression of polynucleotides of the present invention. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in a cell or cells of a subject. Such regulatory sequences may be obtained from, e.g., viruses or eukaryotic organisms, or may be chemically synthesized. A variety of such transcription control sequences are known to those skilled in the art. Particularly preferred transcription control sequences are promoters active in directing transcription in the cells of a subject, either constitutively and/or in one or more specific tissues. In various embodiments, an expression vector is expressed transiently.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: Mesoporous Silica (MPS) Vaccine to Enhance Anti-Tumor Immunity

Biomaterials have shown substantial potential to integrate synergistically with current cancer vaccine strategies and enhance their effectiveness. We recently developed an injectable biomaterial vaccine via spontaneous assembly of mesoporous silica (MPS) microparticles into a 3D scaffold in vivo. When formulated with GM-CSF and CpG, the MPS vaccine modulates host dendritic cell (DC) activation and trafficking. Here we demonstrate that a single injection of the MPS vaccine induced persistent germinal center activity, e.g., in a draining lymph node, for over 30 days. Consequently, when immunized with a small linear Her2/neu peptide within the Trastuzumab binding domain, the MPS vaccine elicited over 2 orders of magnitude higher IgG1 and IgG2a antibody titer compared to a bolus vaccine, and the antibody exhibited reactivity on the native Her2 structure on breast cancer cells. To further enhance CTL responses against tumor antigens, we co-presented the antigen with polyethylenimine (PEI) in the MPS vaccine. PEI increased antigen cross-presentation in murine DCs, and TNF-a and IL-6 production in both murine and human DCs in vitro. Compared to the MPS vaccine, the MPS-PEI vaccine enhanced activated DCs in the vaccine and the vaccine dLN by ~2 fold. Systemically, the MPS-PEI vaccine induced ~2.5 fold higher IFN-y producing antigen specific circulating $CD8^+$ T cells compared to the MPS vaccine. Impressively, using a HPV-E7 expressing tumor model, we demonstrated that a single injection of the MPS-PEI vaccine completely eradicated large established tumors in over 80% of mice Finally, when immunized with a pool of recently sequenced B16 melanoma neoantigen peptides, the MPS-PEI vaccine induced therapeutic tumor growth control and synergy with anti-CTLA4 therapy. These findings indicate that the MPS vaccine serves as a facile multifunctional and multi-epitope platform to modulate host immune cell function and augment personalized anti-tumor immunity.

Example 2: D, L-Lactide and Glycolide (PLG) Scaffolds Comprising PEI

Coating PLG scaffolds with polyethylenimine (PEI) enhances dendritic cell (DC) activation. Application of PEI to PLG systems prior to antigen adsorption enhances anti-tumor responses in cancer vaccine models.

PEI-loaded scaffolds promoted 3-4 fold increases in TLR5 activity over controls in vitro (FIG. 19A). In addition, murine DCs seeded onto PEI-PLG scaffolds produced over 3 times more IL-12 and almost 30 times more IFN-alpha than cells seeded onto scaffolds without PEI. (FIG. 19B). These results suggest that PEI modified PLG may locally activate DCs and other antigen presenting cells APCs, potentially via the TLR5 pathway.

Antigens from B16-F10 melanoma tumor lysates were adsorbed onto PEI-PLG systems to create cancer vaccines. Implantation of PEI-antigen coated vaccines into mice induced the local production of immunostimulatory cytokines in situ, including G-CSF, MIP-a, RANTES, KC, IL-2, MIP-1b, IL-12 (FIG. 20A). In addition, PEI-antigen loaded scaffolds inhibited potentially suppressive cytokines such as IL-10 and GM-CSF induced by PLG systems not coated with PEI (FIG. 20A). PEI-modified PLG vaccines also resulted in an 11-22 fold increase in activated DCs recruited to the scaffold site as indicated by MHC-II and CD86 expression (FIG. 20B).

When utilized as a prophylactic vaccine in a lethal B16-F10 melanoma model, PEI-antigen scaffolds protected 50% of mice from tumor development whereas antigen loaded scaffolds without PEI coatings only protected 10% of mice (FIG. 20C). This positive vaccine efficacy extended to the therapeutic setting, where PEI-antigen vaccines were able to significantly slow tumor growth relative to blank controls that had no impact on tumor growth (FIGS. 21A and 21B). This efficacy correlated to the magnitude of activated T cell infiltrates in tumor masses as PEI-antigen presenting PLG vaccines produced 15-32 times more activated T cells at the tumor site relative to systems that did not use PEI-antigen coatings (FIG. 21C). These data indicate that PEI-antigen coating of PLG systems enhances antigen presentation and activation by dendritic cells to produce specific, anti-tumor efficacy.

We also investigated whether PEI-PLG systems could promote the activation of human DCs in vitro. Seeding human peripheral blood mononuclear cell (PBMC)-derived DCs onto PEI-PLG scaffolds significantly enhanced DC expression of the activation markers HLA-DR and CD83 relative to controls (FIG. 22). Interestingly, the magnitude of DC activation by PEI-loaded scaffolds was similar to the activation levels induced by CpG-ODN and P(I:C) adjuvants. Additionally, PBMCs seeded onto PEI-scaffolds induced significantly higher levels of IL-6, IL-2 and TNF-alpha production compared to controls and scaffolds containing CpG-ODN and P(I:C) adjuvants.

Materials and Methods

Cell Lines

B16-F10 melanoma cells were obtained from American Type Culture Collection (catalog: ATCC CRL-6475) in 2010 and 2012. Upon receipt, the cells were cultured to passage three, aliquoted and frozen in liquid nitrogen. For tumor experiments, B16-F10 cells were thawed and cultured in DMEM (Life Technologies, Inc.), containing 10% fetal bovine serum (Life Technologies, Inc.), 100 units/ml penicillin, and 100 µg/ml streptomycin. The cells were maintained at 37° C. in a humidified 5% $CO_2$/95% air atmosphere and early passage cells (between 4 and 9) were utilized for experiments.

DC Isolation and Culture

Known methods, e.g., a protocol developed by Lutz et al, was used for generation of primary bone-marrow-derived dendritic cells (BMDCs) (Lutz 1999 J Immunol Methods 223(1):77-92). Briefly, bone marrow cells were flushed from the femurs of C57BL/6 mice and cultured in 100-mm bacteriological petri dishes (Falcon number 1029/Becton Dickinson). Cell culture medium RPMI-1640 (R10) (Sigma) was supplemented with 1% Penicillin-Streptomycin (Invitrogen), 2 mM 1-Glutamine (Invitrogen), 50 µM 2-mercaptoethanol (Sigma) and 10% heat-inactivated fetal bovine serum (FBS, Invitrogen). At day 0, bone marrow leukocytes were seeded at $2 \times 10^6$ cells per 100-mm dish in 10 ml R10 medium containing 20 ng/ml granulocyte-macrophage colony-stimulating factor (GM-CSF) (Peprotech). At day 3 another 10 ml R10 medium containing 20 ng/mL GM-CSF was added to the plates. At days 6 and 8, half of the culture supernatant was collected and centrifuged, the cell pellet was resuspended in 10 ml fresh R10 containing 20 ng/mL GM-CSF, and placed back into the original plate. We used the non-adherent cell population in the culture supernatant between days 8 and 12 for all our experiments.

For human lymphocytes isolation, peripheral blood mononuclear cells (PBMCs) were obtained from patients. Dendritic cells were generated from adherent PBMCs with GM-CSF and IL-4 cultures.

PLG Vaccine Fabrication

A 85:15, 120 kDa copolymer of D,L-lactide and glycolide (PLG) (Alkermes, Cambridge, MA) was utilized in a gas-foaming process to form porous PLG matrices (Harris et al. 1998 J. Biomed. Mater. Res. 42, 396-402). To coat PLG polymer with PEI, 40 µM PLG microspheres (phosphorex) were incubated with solutions of branched 60K and linear 25K polyethylenimine in $ddH_2O$ to a final wt % of 4% PEI. PEI-PLG microspheres were frozen and lyophilized and stored at 4° C. until antigen adsorption. To incorporate antigen or tumor lysates containing antigens, onto PEI-PLG spheres protein antigens were vortexed and incubated in ddH20 at room temperature for 15 min to allow for adsorption and freeze dried. To create melanoma antigens, biopsies of B16-F10 tumors that had grown subcutaneously in the backs of C57BL/6J mice (Jackson Laboratory, Bar Harbor Maine), were digested in collagenase (250 U/ml) (Worthington, Lakewood, NJ) and suspended at a concentration equivalent to $10^7$ cells per ml after filtration through 40 µm cell strainers. GM-CSF is incorporated into PLG microspheres using standard double emulsion process. The tumor cell suspension was subjected to 4 cycles of rapid freeze in liquid nitrogen and thaw (37° C.) and then centrifuged at 400 rpm for 10 min The supernatant (1 ml) containing tumor lysates was collected and lyophilized. To incorporate CpG-ODNs or poly (I:C) into PLG scaffolds, CpG-ODN 1826 (for mouse studies), HMW P(I:C) and CpG-ODN 2216 (for human DC studies) (Invivogen, San Diego, CA) was first condensed with poly(ethylenimine) (PEI, Mn ~60,000, Sigma Aldrich) by dropping CpG-ODN 1826 solutions into a PEI solution, while vortexing the mixture. The charge ratio between PEI and CpG-ODN (NH3+:PO4−) was kept constant at 7 during condensation. The condensate solutions were then vortexed with 60 µl of 50% (wt/vol) sucrose solution, lyophilized and mixed with dry sucrose to a final weight of 150 mg.

PLG microspheres with or without PEI coatings were then mixed with the sucrose containing PEI-CpG-ODN condensate, PEI-P(I:C) or tumor lysate and compression molded. The resulting disc was allowed to equilibrate within a high-pressure $CO_2$ environment, and a rapid reduction in pressure causes the polymer particles to expand and fuse into an interconnected structure. The sucrose was leached from the scaffolds by immersion in water, yielding scaffolds that were 80-90% porous.

Vaccine Assays

For prohylactic vaccination, animals were vaccinated with B16-lysate loaded PLG vaccines with or without PEI-coatings 14 days prior to a tumor challenge of $10^5$ B16-F10 melanoma cells (ATCC, Manassas, NJ). For therapeutic vaccination, animals were challenged with a subcutaneous injection of $10^5$ B16-F10 melanoma cells (ATCC, Manassas, NJ) in the back of the neck. At day 9 after tumor challenge, PLG vaccines with or without PEI coating were used to incorporate melanoma tumor lysate antigens. Animals were monitored for the onset of tumor growth (approximately 1 $mm^3$) and sacrificed for humane reasons when tumors grew to 20-25 mm (longest diameter).

In Vitro Cell Activation and Cytokine Production

PLG vaccines were seeded with 5×10⁶ human PBMCs or murine cells as indicated and directly placed into RPMI media supplemented with 10% FBS. At the indicated timepoints, scaffolds were mechanically agitated to release cells for analysis of cell surface markers and media was collected to assess cytokine production. Flow cytommetric stainings and analyses were conducted using APC-CD11c antibodies in conjuction with FITC-MHCII and APC-CD86 to determine murine DC activation. Human cell activation was analyzed using FITC-HLA-DR and APC-CD83 stains. All antibodies were obtained from eBioscience, San Diego, CA Cells were gated according to single positive FITC, APC and PE stainings, using isotype controls. The percentage of cells staining positive for each surface antigen was recorded. The production of inflammatory cytokines was analyzed using ELISAs for murine IL12 or IFN-a or by using human IL-2, TNF-a and 11-6 ELISAs.

To assess TLR activation by PEI coated scaffolds, HEK293 cells co-transfected with hTLR5 gene and harboring an NF-κB-dependent secreted embryonic alkaline phosphatase reporter plasmid (Invivogen) were seeded on PLG scaffolds (PLG) or scaffolds containing either linear (L25) or branched PEI (B60). After 36 hours in 3-dimensional PLG cultures, secreted alkaline phosphatase was developed using Quantiblue® reagent (Invivogen) and values normalized to unstimulated cells.

In Vivo DC and T Cell Infiltration and Activation and Cytokine Production

PLG vaccines were excised at indicated timepoints and the ingrown tissue was digested into single cell suspensions using a collagenase solution (Worthington, 250 U/ml) that was agitated at 37° C. for 45 minutes. The cell suspensions were then poured through a 40 μm cell strainer to isolate cells from scaffold particles and the cells were pelleted and washed with cold PBS and counted using a Z2 coulter counter (Beckman Coulter). On the indicated days, B16-F10 tumors were also removed from mice, and digested in 1 mg/mL collagenase II (250 U/ml) (Worthington, Lakewood, NJ) and 0.1 mg/mL DNase for 1 hour at 37° C., and dissociated cells were filtered through a 40-μm filter. Negative T cell separation was performed using a murine, pan T cell separation kit (Miltenyi Biotec, San Diego, CA), which primarily removes innate immune cells and APCs along with debris and necrotic cells from suspension.

To assess DCs isolated from the vaccine site, isolated cells were directly stained with antibodies for phenotype characterization by fluorescence-activated cell sorting (FACS) analysis. APC conjugated CD11c stains were performed in conjunction with FITC conjugated MHC-II and PE-conjugated CD86 stains and analyzed with flow cytometry to mark DC activation. Tumor infiltrating leukocytes were costained with PE-Cy7 CD3e, APC CD8a for T cell identification along with the activation marker FITC-anti-IFNγ and PE-anti-CD107a. All antibodies were obtained from eBioscience, San Diego, CA Cells were gated according to single positive FITC, APC and PE stainings, using isotype controls. The percentage of cells staining positive for each surface antigen was recorded.

To determine in vivo concentrations of inflammatory cytokines at the matrix implant site, adjacent tissue was excised and digested with tissue protein extraction reagent (Pierce). After centrifugation, the concentrations of cytokines in the supernatant were then analyzed with ELISA (R&D systems) and Bio-Plex Pro™ Mouse Cytokine 23-plex Assay (Biorad), according to the manufacturers instructions. Local cytokine analysis at the vaccine site was performed in wild-type C57BL/6J mice, Batf3-/-mice, and CD8 T cell knockout mice.

Statistical Analysis

All values in the present study were expressed as mean±S.D. Statistical significance of differences between the groups were analyzed by a two-tailed, Student's t test and a P value of less than 0.05 was considered significant.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A device comprising:
   a polymeric scaffold composition comprising mesoporous silica rods surface modified with a coating of polyethylenimine (PEI); and
   a tumor antigen attached to the PEI,
   wherein (i) the PEI does not interact with the tumor antigen to form a nanoparticle, and (ii) the PEI is not attached to CpG-ODN, poly(I:C), or poly(A:U), and
   wherein the polymeric scaffold composition comprises open interconnected macropores having diameters of about 10 μm to about 600 μm.

2. The device of claim 1, wherein said tumor antigen comprises a tumor neoantigen.

3. The device of claim 2, wherein said PEI is attached to said tumor antigen via an electrostatic interaction.

4. The device of claim 2, wherein said PEI is attached to said tumor antigen via a covalent bond.

5. The device of claim 1, wherein
   (i) said PEI is branched or linear;
   (ii) the device comprises both branched PEI and linear PEI;
   (iii) said PEI comprises branched dendrimeric PEI;
   (iv) said PEI comprises at least about 2 primary, secondary, and/or tertiary amino groups;
   (v) said PEI comprises a molecular weight of at least about 1 kilodaltons (kDa); and/or
   (vi) said PEI comprises linear PEI having a molecular weight of about 25 kDa or branched PEI having a molecular weight of about 60 kDa.

6. The device of claim 1, further comprising
   (a) an immunostimulatory compound;
   (b) a compound that attracts an immune cell to or into the delivery vehicle;
   (c) a compound that induces immunogenic cell death of a tumor cell;
   (d) a compound that inhibits T-cell or dendritic cell suppression;
   (e) a compound that inhibits an immune-inhibitory protein,
   or any combination thereof.

7. The device of claim 1, wherein said tumor antigen comprises a tumor antigen peptide.

8. A method of treating cancer in a subject in need thereof, comprising administering the device of claim 1 to said subject.

9. The method of claim 8, wherein said device stimulates activation of dendritic cells or elicits a cytotoxic T cell-mediated immune response against a tumor antigen.

10. The device of claim 1, wherein said polymeric scaffold composition is anionic or cationic.

* * * * *